(12) United States Patent
Kudo et al.

(10) Patent No.: US 10,882,869 B2
(45) Date of Patent: Jan. 5, 2021

(54) CONDENSED HETEROCYCLIC COMPOUNDS AND PESTICIDES

(71) Applicant: NISSAN CHEMICAL CORPORATION, Chuo-ku (JP)

(72) Inventors: Takao Kudo, Funabashi (JP); Yukihiro Maizuru, Funabashi (JP); Ayano Tanaka, Funabashi (JP); Kenkichi Noto, Funabashi (JP); Hiroto Matsui, Shiraoka (JP); Masaki Kobayashi, Shiraoka (JP)

(73) Assignee: NISSAN CHEMICAL CORPORATION, Chuo-ku (JP)

( * ) Notice: Subject to any disclaimer, the term of this patent is extended or adjusted under 35 U.S.C. 154(b) by 0 days.

(21) Appl. No.: 16/545,594

(22) Filed: Aug. 20, 2019

(65) Prior Publication Data

US 2019/0375765 A1    Dec. 12, 2019

Related U.S. Application Data

(62) Division of application No. 15/550,165, filed as application No. PCT/JP2016/054171 on Feb. 12, 2016, now Pat. No. 10,464,950.

(30) Foreign Application Priority Data

Feb. 12, 2015 (JP) ................. 2015-025604
Jul. 2, 2015 (JP) ................. 2015-133816

(51) Int. Cl.
| | | |
|---|---|---|
| C07D 471/04 | (2006.01) | |
| C07D 519/00 | (2006.01) | |
| A01N 43/90 | (2006.01) | |
| A61K 31/437 | (2006.01) | |
| A61K 31/5025 | (2006.01) | |
| A61K 31/519 | (2006.01) | |
| C07D 513/04 | (2006.01) | |

(52) U.S. Cl.
CPC .......... *C07D 519/00* (2013.01); *A01N 43/90* (2013.01); *A61K 31/437* (2013.01); *A61K 31/5025* (2013.01); *A61K 31/519* (2013.01); *C07D 471/04* (2013.01); *C07D 513/04* (2013.01)

(58) Field of Classification Search
CPC .................................................. C07D 471/04
See application file for complete search history.

(56) References Cited

U.S. PATENT DOCUMENTS

| | | |
|---|---|---|
| 2012/0196891 A1 | 8/2012 | Iwakoshi |
| 2013/0090353 A1 | 4/2013 | Iwakoshi et al. |
| 2013/0252981 A1 | 9/2013 | Takahashi et al. |
| 2015/0094329 A1 | 4/2015 | Nokura et al. |
| 2015/0166573 A1 | 6/2015 | Takahashi et al. |
| 2015/0181880 A1 | 7/2015 | Takahashi et al. |
| 2015/0191474 A1 | 7/2015 | Takahashi et al. |
| 2015/0246911 A1 | 9/2015 | Takahashi et al. |
| 2015/0313234 A1 | 11/2015 | Takahashi et al. |
| 2016/0002260 A1 | 1/2016 | Tanabe et al. |
| 2016/0021886 A1 | 1/2016 | Yonemura et al. |
| 2016/0227779 A1 | 8/2016 | Alig et al. |
| 2016/0368915 A1 | 12/2016 | Tanabe et al. |
| 2017/0073342 A1 | 3/2017 | Fischer et al. |
| 2017/0135348 A1 | 5/2017 | Tanabe et al. |

FOREIGN PATENT DOCUMENTS

| | | |
|---|---|---|
| EP | 2 274 983 A1 | 1/2011 |
| EP | 2 955 178 A1 | 12/2015 |
| EP | 2 955 179 A1 | 12/2015 |
| EP | 2 963 022 A1 | 1/2016 |
| GB | 2 282 808 A | 4/1995 |
| WO | WO 2009/131237 A1 | 10/2009 |
| WO | WO 2010/125985 A1 | 11/2010 |
| WO | WO 2011/043404 A1 | 4/2011 |
| WO | WO 2011/162364 A1 | 12/2011 |
| WO | WO 2012/074135 A1 | 6/2012 |
| WO | WO 2012/086848 A1 | 6/2012 |
| WO | WO 2013/018928 A1 | 2/2013 |
| WO | WO 2013/180193 A1 | 12/2013 |
| WO | WO 2013/180194 A1 | 12/2013 |
| WO | WO 2013/191112 A1 | 12/2013 |
| WO | WO 2013/191113 A1 | 12/2013 |
| WO | WO 2013/191188 A1 | 12/2013 |
| WO | WO 2013/191189 A1 | 12/2013 |
| WO | WO 2014/104407 A1 | 7/2014 |
| WO | WO 2014/123205 A1 | 8/2014 |
| WO | WO 2014/123206 A1 | 8/2014 |
| WO | WO 2014/132971 A1 | 9/2014 |
| WO | WO 2014/132972 A1 | 9/2014 |
| WO | WO 2014/142292 A1 | 9/2014 |
| WO | WO 2014/148451 A1 | 9/2014 |

(Continued)

OTHER PUBLICATIONS

International Search Report dated Apr. 5, 2016 in PCT/JP2016/054171 filed Feb. 12, 2016.

*Primary Examiner* — Brian E McDowell
(74) *Attorney, Agent, or Firm* — Oblon, McClelland, Maier & Neustadt, L.L.P.

(57) ABSTRACT

A condensed heterocyclic compound represented by the following formula or its salt or an N-oxide thereof:

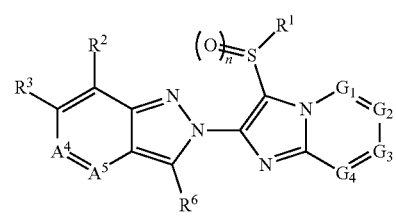

wherein $G_1$ is $C(Y1)$; $G_2$ is $C(Y2)$; $G_3$ is $C(Y3)$; $G_4$ is $C(Y4)$; $A^4$ is a nitrogen atom or $C(R^4)$; $A^5$ is a nitrogen atom or $C(R^5)$; and n is an integer of 0, 1 or 2.

8 Claims, No Drawings

(56) References Cited

FOREIGN PATENT DOCUMENTS

| WO | WO 2014/157600 A1 | 10/2014 |
|---|---|---|
| WO | WO 2015/000715 A1 | 1/2015 |
| WO | WO 2015/002211 A1 | 1/2015 |
| WO | WO 2015/059088 A1 | 4/2015 |
| WO | WO 2015/071180 A1 | 5/2015 |
| WO | WO 2015/087458 A1 | 6/2015 |
| WO | WO 2015/091945 A1 | 6/2015 |
| WO | WO 2015/121136 A1 | 8/2015 |
| WO | WO 2015/133603 A1 | 9/2015 |
| WO | WO 2015/198859 A1 | 12/2015 |
| WO | WO 2016/005263 A1 | 1/2016 |
| WO | WO 2016/142327 A1 | 9/2016 |
| WO | WO 2016/162318 | 10/2016 |
| WO | WO 2017/061497 | 4/2017 |

CONDENSED HETEROCYCLIC COMPOUNDS AND PESTICIDES

CROSS REFERENCES TO RELATED APPLICATIONS

This application is a divisional of U.S. patent application Ser. No. 15/550,165, filed on Aug. 10, 2017, which is a National Stage of PCT/JP2016/054171, filed on Feb. 12, 2016, and claims priority to Japanese Patent Application No. 2015-025604, filed on Feb. 12, 2015, and Japanese Patent Application No. 2015-133816, filed on Jul. 2, 2015, all of which are incorporated herein by reference in their entireties.

TECHNICAL FIELD

The present invention relates to a novel condensed heterocyclic compound and its salt, and a pesticide containing the compound as an active ingredient.

BACKGROUND ART

For example, Patent Documents 1 to 31 disclose condensed heterocyclic compounds, however, they failed to disclose the condensed heterocyclic compounds of the present invention. Usefulness of the compounds as pesticides, especially, as insecticides, acaricides or parasiticides against internal or external parasites in or on a mammal or bird is not known at all.

PRIOR ART DOCUMENTS

Patent Documents

Patent Document 1: WO20161005263
Patent Document 2: WO2015/198859
Patent Document 3: WO2015/133603
Patent Document 4: WO20151121136
Patent Document 5: WO2015/091945
Patent Document 6: WO2015/087458
Patent Document 7: WO20151071180
Patent Document 8: WO2015/059088
Patent Document 9: WO2015/002211
Patent Document 10: WO2015/000715
Patent Document 11: WO2014/157600
Patent Document 12: WO2014/148451
Patent Document 13: WO2014/142292
Patent Document 14: WO2014/132972
Patent Document 15: WO2014/132971
Patent Document 16: WO2014/123206
Patent Document 17: WO2014/123205
Patent Document 18: WO2014/104407
Patent Document 19: WO2013/180194
Patent Document 20: WO2013/180193
Patent Document 21: WO2013/191113
Patent Document 22: WO2013/191189
Patent Document 23: WO2013/191112
Patent Document 24: WO2013/191188
Patent Document 25: WO2013/018928
Patent Document 26: WO2012/086848
Patent Document 27: WO2012/074135
Patent Document 28: WO2011/162364
Patent Document 29: WO2011/043404
Patent Document 30: WO2010/125985
Patent Document 31: WO2009/131237

DISCLOSURE OF INVENTION

Technical Problem

With the advance of development of pesticides targeted at various pest insects such as agricultural pest insects, forest pest insects or hygienic pest insects, various pesticides have been put into practical use.

However, recently, control of pest insects with conventional insecticides or fungicides has become difficult in more and more cases, as pest insects acquire resistance to them over many years of their use. Problems of the high toxicity of some conventional pesticides and of the disturbance of the ecosystem by some conventional pesticides which remain in the environment for a long period are becoming apparent. Under these circumstances, development of novel pesticides with high pesticidal activity, low toxicity and low persistence is always expected.

It is an object of the present invention to provide a novel pesticide which has excellent pesticidal activities, which has low toxicity, for example, which has little harmful effect on non-target organisms such as mammals, fishes and useful insects, and which has low persistence.

Solution to Problems

The present inventors have conducted extensive studies to achieve the above object and as a result, found that a novel condensed heterocyclic compound represented by the following formula (1) of the present invention is a very useful compound which has excellent pesticidal activities particularly insecticidal and acaricidal activities, and which has little harmful effect on non-target organisms such as mammals, fishes and useful insects, and accomplished the present invention.

That is, the present invention relates to the following [1] to [167].

[1] A condensed heterocyclic compound represented by the formula (1) or its salt or an N-oxide thereof:

wherein D substituted with $—S(O)_n R^1$ is a ring represented by any one of D1, D2 and D3:

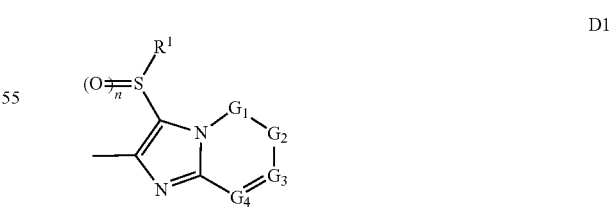

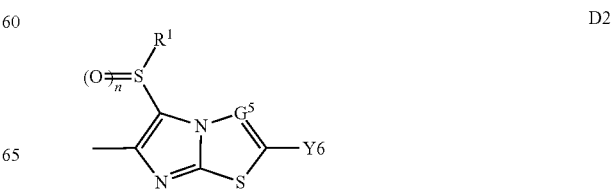

-continued

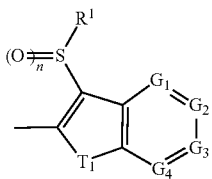

D3

Q is a ring represented by any one of Q1, Q2, Q3 and Q4:

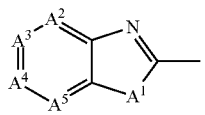

Q1

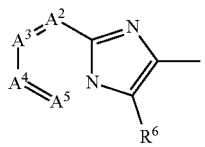

Q2

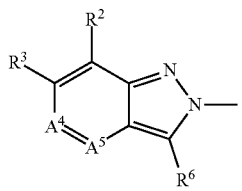

Q3

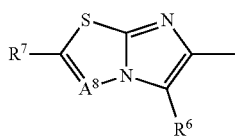

Q4

$G_1$ is a nitrogen atom or C(Y1),
$G_2$ is a nitrogen atom or C(Y2),
$G_3$ is a nitrogen atom or C(Y3),
$G_4$ is a nitrogen atom or C(Y4),
$G_5$ is a nitrogen atom or C(Y5),
$T_1$ is $N(T_{1a})$, an oxygen atom or a sulfur atom,
$A^1$ is $N(A^{1a})$, an oxygen atom or a sulfur atom,
$A^2$ is a nitrogen atom or $C(R^2)$,
$A^3$ is a nitrogen atom or $C(R^3)$,
$A^4$ is a nitrogen atom or $C(R^4)$,
$A^5$ is a nitrogen atom or $C(R^5)$,
$A^8$ is a nitrogen atom or $C(R^8)$,
$R^1$ is $C_1$-$C_6$ alkyl, $C_1$-$C_6$ haloalkyl, ($C_1$-$C_6$) alkyl optionally substituted with $R^{1a}$, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_3$-$C_6$ cycloalkyl ($C_1$-$C_6$) alkyl, $C_3$-$C_6$ halocycloalkyl ($C_1$-$C_6$) alkyl or hydroxy ($C_1$-$C_6$) alkyl,
$R^{1a}$ is $C_1$-$C_8$ alkoxy, $C_1$-$C_8$ haloalkoxy, $C_1$-$C_8$ alkoxycarbonyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or cyano,
$R^2$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_3$-$C_6$ cycloalkyl, $C_3$-$C_6$ halocycloalkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)$R_{20a}$, —C(O)OH, hydroxy, —NH$_2$, —NHR$^{20g}$, —N(R$^{20h}$)R$^{20g}$, mercapto, cyano or nitro, $R^3$ is a hydrogen atom, a halogen atom, $C_1$-$C_6$ alkyl, $C_1$-$C_6$ haloalkyl, $C_2$-$C_6$ haloalkenyl, $C_2$-$C_6$ haloalkynyl, $C_1$-$C_8$ alkoxy, $C_1$-$C_8$ haloalkoxy, $C_3$-$C_6$ cycloalkyl, $C_3$-$C_6$ halocycloalkyl, $C_1$-$C_6$ alkylthio, $C_1$-$C_6$ haloalkylthio, ($C_1$-$C_6$) alkylthio optionally substituted with $R^{3a}$, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)R$^{30a}$, —C(O)OH, hydroxy, —OC(O)R$^{30e}$, —OS(O)$_2$R$^{30f}$, —NH$_2$, —NHR$^{30g}$, —N(R$^{30h}$)R$^{30g}$, mercapto, —SC(O)R$^{30i}$, —SF$_5$, cyano, nitro, phenyl, phenyl optionally substituted with $R^{3b}$, heterocyclyl or heterocyclyl optionally substituted with $R^{3b}$,
$R^{3a}$ is $C_1$-$C_8$ alkoxycarbonyl,
$R^{3b}$ is a halogen atom, $C_1$-$C_6$ alkyl, $C_1$-$C_6$ haloalkyl, $C_1$-$C_8$ alkoxy, $C_1$-$C_8$ haloalkoxy, cyano or nitro,
$R^4$ is a hydrogen atom, a halogen atom, $C_1$-$C_6$ alkyl, $C_1$-$C_6$ haloalkyl, $C_2$-$C_6$ haloalkenyl, $C_2$-$C_6$ haloalkynyl, $C_1$-$C_8$ alkoxy, $C_1$-$C_8$ haloalkoxy, $C_3$-$C_6$ cycloalkyl, $C_3$-$C_6$ halocycloalkyl, $C_1$-$C_6$ alkylthio, $C_1$-$C_6$ haloalkylthio, ($C_1$-$C_6$) alkylthio optionally substituted with $R^{4a}$, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)R$^{40a}$, —C(O)OH, hydroxy, —OC(O)R$^{40e}$, —OS(O)$_2$R$^{40f}$, —NH$_2$, —NHR$^{40g}$, —N(R$^{40h}$)R$^{40g}$, mercapto, —SC(O)R$^{40i}$, —SF$_5$, cyano, nitro, phenyl, phenyl optionally substituted with $R^{4b}$, heterocyclyl or heterocyclyl optionally substituted with $R^{4b}$,
$R^{4a}$ is $C_1$-$C_8$ alkoxycarbonyl,
$R^{4b}$ is a halogen atom, $C_1$-$C_6$ alkyl, $C_1$-$C_6$ haloalkyl, $C_1$-$C_8$ alkoxy, $C_1$-$C_8$ haloalkoxy, cyano or nitro,
$R^5$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_3$-$C_6$ cycloalkyl, $C_3$-$C_6$ halocycloalkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)R$^{50a}$, —C(O)OH, hydroxy, —NH$_2$, —NHR$^{50g}$, —N(R$^{50h}$)R$^{50g}$, mercapto, cyano or nitro,
$R^6$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_3$-$C_6$ cycloalkyl, $C_3$-$C_6$ halocycloalkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)R$^{60a}$, —C(O)OH, hydroxy, —NH$_2$, —NHR$^{60g}$, —N(R$^{60h}$)R$^{60g}$, mercapto, cyano or nitro,
$R^7$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, mercapto, —SF$_5$, cyano or nitro,
$R^8$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy or cyano,
$A^{1a}$ is a hydrogen atom, $C_1$-$C_6$ alkyl, $C_1$-$C_6$ haloalkyl, ($C_1$-$C_6$) alkyl optionally substituted with $A^{1a-a}$, ($C_1$-$C_6$) haloalkyl optionally substituted with $A^{1a-a}$, $C_2$-$C_6$ alkenyl, $C_2$-$C_6$ haloalkenyl, $C_2$-$C_6$ alkynyl, $C_2$-$C_6$ haloalkynyl, $C_1$-$C_8$ alkoxy, $C_1$-$C_8$ haloalkoxy, $C_3$-$C_6$ cycloalkyl, $C_3$-$C_6$ halocycloalkyl, $C_3$-$C_6$ cycloalkyl ($C_1$-$C_6$) alkyl, $C_3$-$C_6$ halocycloalkyl ($C_1$-$C_6$) alkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, C(O)R$^{10a}$, hydroxy or cyano,
$A^{1a-a}$ is $C_1$-$C_6$ alkoxy, $C_1$-$C_6$ haloalkoxy, $C_1$-$C_6$ alkoxycarbonyl, $C_1$-$C_6$ haloalkoxycarbonyl, $C_1$-$C_6$ alkylcarbonyl, $C_1$-$C_6$ haloalkylcarbonyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, hydroxy or cyano,
$T_{1a}$ is a hydrogen atom, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_8$ alkoxy, $C_1$-$C_8$ haloalkoxy, $C_3$-$C_6$ cycloalkyl, $C_3$-$C_6$ halocycloalkyl, $C_3$-$C_6$ cycloalkyl ($C_1$-$C_6$) alkyl or $C_3$-$C_6$ halocycloalkyl ($C_1$-$C_6$) alkyl, each of Y1, Y2, Y3 and Y4 is independently a hydrogen atom, a halogen atom, $C_1$-$C_6$ alkyl, $C_1$-$C_6$ haloalkyl, ($C_1$-$C_6$) alkyl optionally substituted with $Y^a$, ($C_1$-$C_6$) haloalkyl optionally substituted with $Y^a$, $C_2$-$C_6$ alkenyl, $C_2$-$C_6$ haloalkenyl, ($C_2$-$C_6$) alkenyl optionally substituted with $Y^a$, $C_2$-$C_6$ alkynyl, $C_2$-$C_6$ haloalkynyl, ($C_2$-$C_6$) alkynyl optionally substituted with $Y^b$, $C_1$-$C_8$ alkoxy, $C_1$-$C_8$ haloalkoxy, ($C_1$-$C_8$) alkoxy optionally substituted with $Y^a$, $C_2$-$C_6$ alkenyloxy, $C_2$-$C_6$ haloalkenyloxy, ($C_2$-$C_6$) alkenyloxy optionally substituted with $Y^a$, $C_2$-$C_6$ alkynyloxy, $C_2$-$C_6$ haloalkynyloxy, ($C_2$-$C_6$) alkynyloxy optionally substituted with $Y^a$, $C_3$-$C_6$ cycloalkyl, $C_3$-$C_6$ halocycloalkyl, $C_3$-$C_6$ cycloalkyl ($C_1$-$C_6$) alkyl, $C_3$-$C_6$ halocycloalkyl ($C_1$-$C_6$) alkyl, $C_1$-$C_6$ alkylthio, $C_1$-$C_6$ haloalkylthio, ($C_1$-$C_6$) alkylthio optionally substituted with $Y^a$, $C_2$-$C_6$ alkenylthio, $C_2$-$C_6$ haloalkenylthio, $C_2$-$C_6$ alkynylthio, $C_2$-$C_6$ haloalkynylthio, $C_1$-$C_6$ alkylsulfinyl, $C_1$-$C_6$ haloalkylsulfinyl, ($C_1$-$C_6$) alkylsulfinyl optionally substituted with $Y^a$, $C_2$-$C_6$ alkenylsulfinyl, $C_2$-$C_6$ haloalkenylsulfinyl, $C_2$-$C_6$ alkynylsulfinyl, $C_2$-$C_6$ haloalkynylsulfinyl, $C_1$-$C_6$ alkylsulfonyl, $C_1$-$C_6$ haloalkylsulfonyl, ($C_1$-$C_6$) alkylsulfonyl optionally substituted with $Y^a$, $C_2$-$C_6$ alkenylsulfonyl, $C_2$-$C_6$ haloalkenylsulfonyl, $C_2$-$C_6$ alkynylsulfonyl, $C_2$-$C_6$ haloalkynylsulfonyl, —C(O)$R^{90a}$, —C(O)NH$R^{90b}$, —C(O)N($R^{90c}$)$R^{90b}$, —C(O)OH, —C(=NO$R^{90d}$)$R^{90a}$, —C(O)NH$_2$, hydroxy, —OC(O)$R^{90e}$, —OS(O)$_2R^{90f}$, —NH$_2$, —NH$R^{90g}$, —N($R^{90h}$)$R^{90g}$, mercapto, —SC(O)$R^{90i}$, —S(O)$_2$NH$R^{90j}$, —S(O)N($R^{90k}$)$R^{90j}$, —SF$_5$, cyano, nitro, phenyl, phenyl optionally substituted with $Y^c$, heterocyclyl or heterocyclyl optionally substituted with $Y^c$, each of Y5 and Y6 is independently a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, mercapto, —SF$_5$, cyano or nitro, $Y^a$ is $C_1$-$C_8$ alkoxy, $C_1$-$C_8$ haloalkoxy, $C_1$-$C_8$ alkoxycarbonyl, $C_1$-$C_8$ haloalkoxycarbonyl, $C_1$-$C_6$ alkylcarbonyl, $C_1$-$C_6$ haloalkylcarbonyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, hydroxy or cyano, $Y^b$ is $C_1$-$C_6$ alkyl, $C_3$-$C_6$ cycloalkyl, trimethylsilyl or phenyl, $Y^c$ is a halogen atom, $C_1$-$C_6$ alkyl, $C_1$-$C_6$ haloalkyl, $C_1$-$C_8$ alkoxy, $C_1$-$C_8$ haloalkoxy, cyano or nitro, each of $R^{10a}$, $R^{20a}$, $R^{30a}$, $R^{30e}$, $R^{40a}$, $R^{40e}$, $R^{50a}$, $R^{60a}$ and $R^{90a}$ is independently a hydrogen atom, $C_1$-$C_6$ alkyl, $C_1$-$C_6$ haloalkyl, $C_1$-$C_8$ alkoxy or $C_1$-$C_8$ haloalkoxy, each of $R^{20g}$, $R^{20h}$, $R^{30f}$, $R^{30g}$, $R^{30h}$, $R^{30i}$, $R^{40f}$, $R^{40g}$, $R^{40h}$, $R^{40i}$, $R^{50g}$, $R^{50h}$, $R^{60g}$, $R^{60h}$, $R^{90b}$, $R^{90c}$, $R^{90i}$, $R^{90j}$ and $R^{90k}$ is independently $C_1$-$C_6$ alkyl or $C_1$-$C_6$ haloalkyl, $R^{90d}$ is a hydrogen atom, $C_1$-$C_6$ alkyl or $C_1$-$C_6$ haloalkyl, $R^{90e}$ is a hydrogen atom, $C_1$-$C_6$ alkyl, $C_1$-$C_6$ haloalkyl, $C_1$-$C_6$ alkoxy, $C_1$-$C_8$ haloalkoxy, $C_1$-$C_6$ alkylamino, $C_1$-$C_6$ haloalkylamino, di($C_1$-$C_6$) alkylamino or di($C_1$-$C_6$) haloalkylamino, $R^{90f}$ is $C_1$-$C_6$ alkyl, $C_1$-$C_6$ haloalkyl, $C_1$-$C_6$ alkylamino, $C_1$-$C_6$ haloalkylamino, di($C_1$-$C_6$) alkylamino or di($C_1$-$C_6$) haloalkylamino, each of $R^{90g}$ and $R^{90h}$ is independently $C_1$-$C_6$ alkyl, $C_1$-$C_6$ haloalkyl, $C_1$-$C_6$ alkylcarbonyl, $C_1$-$C_6$ haloalkylcarbonyl, $C_1$-$C_6$ alkoxycarbonyl, $C_1$-$C_6$ haloalkoxycarbonyl, $C_1$-$C_6$ alkylaminocarbonyl, $C_1$-$C_6$ haloalkylaminocarbonyl, $C_1$-$C_6$ alkylaminothiocarbonyl, $C_1$-$C_6$ haloalkylaminothiocarbonyl, phenylcarbonyl, $C_1$-$C_6$ alkylsulfonyl, $C_1$-$C_6$ haloalkylsulfonyl, $C_1$-$C_6$ alkylaminosulfonyl or di($C_1$-$C_6$) alkylaminosulfonyl, and n is an integer of 0, 1 or 2.

[2] The condensed heterocyclic compound or its salt or an N-oxide thereof according to the above [1], wherein D substituted with —S(O)$_n$$R^1$ is a ring represented by D1, $G_1$ is C(Y1),
$G_2$ is C(Y2),
$G_3$ is C(Y3),
$G_4$ is C(Y4),
$A^2$ is C($R^2$),
$A^3$ is C($R^3$), $R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl ($C_1$-$C_6$) alkyl or $C_3$-$C_6$ halocycloalkyl ($C_1$-$C_6$) alkyl, $R^2$ is a hydrogen atom, a halogen atom, $C_1$-$C_6$ alkyl or $C_1$-$C_6$ haloalkyl, $R^3$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, ($C_1$-$C_6$) alkylthio optionally substituted with $R^{3a}$, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, $R^4$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, ($C_1$-$C_6$) alkylthio optionally substituted with $R^{4a}$, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, each of $R^5$, $R^6$ and $R^8$ is independently a hydrogen atom, a halogen atom, $C_1$-$C_6$ alkyl or $C_1$-$C_6$ haloalkyl, $R^7$ is a hydrogen atom, a halogen atom or $C_1$-$C_6$ haloalkyl, $A^{1a}$ is a hydrogen atom, $C_1$-$C_6$ alkyl, ($C_1$-$C_6$) alkyl optionally substituted with $A^{1a-a}$, $C_2$-$C_6$ alkenyl, $C_2$-$C_6$ alkynyl, $C_1$-$C_6$ alkoxy, $C_3$-$C_6$ cycloalkyl or C(O)$R^{10a}$, $A^{1a-a}$ is $C_1$-$C_6$ alkoxy, $C_1$-$C_6$ alkylthio, $C_1$-$C_6$ alkylsulfinyl, $C_1$-$C_6$ alkylsulfonyl or cyano, $R^{10a}$ is a hydrogen atom, $C_1$-$C_6$ alkyl or $C_1$-$C_6$ alkoxy, each of Y1, Y2, Y3 and Y4 is independently a hydrogen atom, a halogen atom, $C_1$-$C_6$ alkyl, $C_1$-$C_6$ haloalkyl, $C_2$-$C_6$ alkenyl, $C_2$-$C_6$ alkynyl, ($C_2$-$C_6$) alkynyl optionally substituted with $Y^b$, $C_1$-$C_6$ alkoxy, $C_1$-$C_6$ haloalkoxy, $C_1$-$C_6$ alkylthio, $C_1$-$C_6$ haloalkylthio, ($C_1$-$C_6$) alkylthio optionally substituted with $Y^a$, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)$R^{90a}$, —C(O)NH$R^{90b}$, —C(O)N($R^{90c}$)$R^{90b}$, —C(O)OH, hydroxy, —OC(O)$R^{90e}$, —OS(O)$_2R^{90f}$, —NH$_2$, —NH$R^{90g}$, —N($R^{90h}$)$R^{90g}$, mercapto, —SC(O)$R^{90i}$, —S(O)$_2$NH$R^{90j}$, —S(O)$_2$N($R^{90k}$)$R^{90j}$, —SF$_5$, cyano, nitro, phenyl, phenyl optionally substituted with $Y^c$, heterocyclyl or heterocyclyl optionally substituted with $Y^c$, and $Y^a$ is $C_1$-$C_8$ alkoxycarbonyl.

[3] The condensed heterocyclic compound or its salt or an N-oxide thereof according to the above [1], wherein D substituted with —S(O)$_n$$R^1$ is a ring represented by D2,
Q is a ring represented by Q1,
$A^1$ is N($A^{1e}$),
$A^2$ is C($R^2$),
$A^3$ is C($R^3$),
$A^4$ is C($R^4$),
$A^5$ is a nitrogen atom, $R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl ($C_1$-$C_6$) alkyl or $C_3$-$C_6$ halocycloalkyl ($C_1$-$C_6$) alkyl, $R^2$ is a hydrogen atom, a halogen atom, $C_1$-$C_6$ alkyl or $C_1$-$C_6$ haloalkyl, R$^3$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, (C$_1$-C$_6$) alkylthio optionally substituted with R$^{3a}$, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, R$^4$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, (C$_1$-C$_6$) alkylthio optionally substituted with R$^4$, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, A$^{1a}$ is a hydrogen atom, C$_1$-C$_6$ alkyl, (C$_1$-C$_6$) alkyl optionally substituted with A$^{1a\text{-}a}$, C$_2$-C$_6$ alkenyl, C$_2$-C$_6$ alkynyl, C$_1$-C$_8$ alkoxy, C$_3$-C$_6$ cycloalkyl or C(O)R$^{10a}$, A$^{1a\text{-}a}$ is C$_1$-C$_8$ alkoxy, C$_1$-C$_6$ alkylthio, C$_1$-C$_6$ alkylsulfinyl, C$_1$-C$_6$ alkylsulfonyl or cyano, R$^{10a}$ is a hydrogen atom, C$_1$-C$_6$ alkyl or C$_1$-C$_8$ alkoxy, Y5 is a hydrogen atom, a halogen atom, C$_1$-C$_6$ alkyl or C$_1$-C$_6$ haloalkyl, and Y6 is a hydrogen atom, a halogen atom or C$_1$-C$_6$ haloalkyl.

[4] The condensed heterocyclic compound or its salt or an N-oxide thereof according to the above [1], wherein D substituted with —S(O)$_n$R$^1$ is a ring represented by D3, Q is a ring represented by Q1, G$_1$ is C(Y1), G$_2$ is C(Y2), G$_3$ is C(Y3), G$_4$ is C(Y4), T$_1$ is N(T$_{1a}$) or a sulfur atom, A$^1$ is N(A$^{1a}$)

A$^2$ is C(R$^2$),

A$^3$ is C(R$^3$),

A$^4$ is C(R$^4$),

A$^5$ is a nitrogen atom,

R$^1$ is C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_2$-C$_6$ haloalkynyl, C$_3$-C$_6$ cycloalkyl (C$_1$-C$_6$) alkyl or C$_3$-C$_6$ halocycloalkyl (C$_1$-C$_6$) alkyl, R$^2$ is a hydrogen atom, a halogen atom, C$_1$-C$_6$ alkyl or C$_1$-C$_6$ haloalkyl, R$^3$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, (C$_1$-C$_6$) alkylthio optionally substituted with R$^{3a}$, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, R$^4$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, (C$_1$-C$_6$) alkylthio optionally substituted with R$^{4a}$, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, A$^{1a}$ is a hydrogen atom, C$_1$-C$_6$ alkyl, (C$_1$-C$_6$) alkyl optionally substituted with A$^{1a\text{-}a}$, C$_2$-C$_6$ alkenyl, C$_2$-C$_6$ alkynyl, C$_1$-C$_6$ alkoxy, C$_3$-C$_6$ cycloalkyl or C(O)R$^{10a}$, A$^{1a\text{-}a}$ is C$_1$-C$_8$ alkoxy, C$_1$-C$_6$ alkylthio, C$_1$-C$_6$ alkylsulfinyl, C$_1$-C$_6$ alkylsulfonyl or cyano, R$^{10a}$ is a hydrogen atom, C$_1$-C$_6$ alkyl or C$_1$-C$_8$ alkoxy, T$_{1a}$ is a hydrogen atom or C$_1$-C$_6$ alkyl, and each of Y1, Y2, Y3 and Y4 is independently a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, cyano or nitro.

[5] The condensed heterocyclic compound or its salt or an N-oxide thereof according to the above [2], wherein Q is a ring represented by Q1, A$^1$ is N(A$^{1a}$), R$^1$ is C$_1$-C$_6$ alkyl, R$^3$ is a hydrogen atom, a halogen atom, C$_1$-C$_6$ haloalkyl, C$_1$-C$_6$ haloalkylthio, (C$_1$-C$_6$) alkylthio optionally substituted with R$^{3a}$, C$_1$-C$_6$ haloalkylsulfinyl or C$_1$-C$_6$ haloalkylsulfonyl, R$^4$ is a hydrogen atom, a halogen atom, C$_1$-C$_6$ haloalkyl, C$_1$-C$_6$ haloalkylthio, (C$_1$-C$_6$) alkylthio optionally substituted with R$^{4a}$, C$_1$-C$_6$ haloalkylsulfinyl or C$_1$-C$_6$ haloalkylsulfonyl, and A$^{1a}$ is a hydrogen atom or C$_1$-C$_6$ alkyl.

[6] The condensed heterocyclic compound or its salt or an N-oxide thereof according to the above [5], wherein A$^4$ is C(R$^4$), and A$^5$ is a nitrogen atom.

[7] The condensed heterocyclic compound or its salt or an N-oxide thereof according to the above [5] or [6], wherein A$^4$ is C(R$^4$), A$^5$ is a nitrogen atom, R$^2$ is a hydrogen atom, R$^4$ is a hydrogen atom or C$_1$-C$_6$ haloalkyl, Y1 is a hydrogen atom, C$_1$-C$_6$ alkyl or C$_1$-C$_6$ haloalkyl, Y2 is a hydrogen atom, a halogen atom, C$_1$-C$_6$ alkyl, C$_1$-C$_6$ haloalkyl, C$_2$-C$_6$ alkenyl, (C$_2$-C$_6$) alkynyl optionally substituted with Y$^b$, C$_1$-C$_6$ alkoxy, C$_1$-C$_6$ alkylthio, C$_1$-C$_6$ haloalkylthio, (C$_1$-C$_6$) alkylthio optionally substituted with Y$^a$, C$_1$-C$_6$ alkylsulfinyl, C$_1$-C$_6$ alkylsulfonyl, —NH$_2$, —NHR$^{90g}$, nitro, phenyl, phenyl optionally substituted with Y$^c$, thiophen-2-yl, pyridin-3-yl or pyridin-4-yl, Y3 is a hydrogen atom, a halogen atom, C$_1$-C$_6$ alkyl, C$_1$-C$_6$ haloalkyl, C$_1$-C$_6$ alkoxy, C$_1$-C$_6$ alkylthio, (C$_1$-C$_6$) alkylthio optionally substituted with Y$^a$, C$_1$-C$_6$ alkylsulfinyl, C$_1$-C$_6$ alkylsulfonyl, —C(O)R$^{90a}$, —C(O)N(R$^{90c}$)R$^{90b}$, —C(O)OH, cyano or nitro, Y4 is a hydrogen atom, a halogen atom, C$_1$-C$_6$ alkyl, C$_1$-C$_6$ haloalkyl, C$_1$-C$_8$ alkoxy, C$_1$-C$_6$ alkylthio, C$_1$-C$_6$ alkylsulfonyl, —N(R$^{90h}$)R$^{90g}$ or cyano, Y$^a$ is C$_1$-C$_8$ alkoxycarbonyl, Y$^b$ is C$_3$-C$_6$ cycloalkyl or trimethylsilyl, Y$^c$ is a halogen atom or C$_1$-C$_6$ haloalkyl, R$^{90a}$ is C$_1$-C$_6$ alkoxy, each of R$^{90b}$ and R$^{90c}$ is independently C$_1$-C$_6$ alkyl, R$^{90g}$ is C$_1$-C$_6$ alkyl, C$_1$-C$_6$ haloalkylcarbonyl, C$_1$-C$_8$ alkoxycarbonyl or phenylcarbonyl, and R$^{9h}$ is C$_1$-C$_6$ alkyl.

[8] The condensed heterocyclic compound or its salt or an N-oxide thereof according to the above [5], wherein A$^4$ is a nitrogen atom, and A$^5$ is C(R$^5$).

[9] The condensed heterocyclic compound or its salt or an N-oxide thereof according to the above [5] or [8], wherein A$^4$ is a nitrogen atom, A$^5$ is C(R$^5$), R$^2$ is a hydrogen atom, R$^3$ is C$_1$-C$_6$ haloalkyl, R$^5$ is a hydrogen atom or C$_1$-C$_6$ alkyl, Y1 is a hydrogen atom, Y2 is a hydrogen atom, a halogen atom or C$_1$-C$_6$ haloalkyl, Y3 is a hydrogen atom, a halogen atom, C$_1$-C$_6$ haloalkyl or cyano, and Y4 is a hydrogen atom, a halogen atom or C$_1$-C$_8$ alkoxy.

[10] The condensed heterocyclic compound or its salt or an N-oxide thereof according to the above [2], wherein Q is a ring represented by Q2, A$^4$ is a nitrogen atom or C(R$^4$), A$^5$ is a nitrogen atom or C(R$^5$), (excluding a case where both A$^4$ and A$^5$ are nitrogen atoms)

R$^1$ is C$_1$-C$_6$ alkyl,

R² is a hydrogen atom,
R³ is a hydrogen atom, a halogen atom, $C_1$-$C_6$ haloalkyl, $C_1$-$C_6$ haloalkylthio, ($C_1$-$C_6$) alkylthio optionally substituted with $R^{3a}$, $C_1$-$C_6$ haloalkylsulfinyl or $C_1$-$C_6$ haloalkylsulfonyl, and
R⁴ is a hydrogen atom, a halogen atom, $C_1$-$C_6$ haloalkyl, $C_1$-$C_6$ haloalkylthio, ($C_1$-$C_6$) alkylthio optionally substituted with $R^{4a}$, $C_1$-$C_6$ haloalkylsulfinyl or $C_1$-$C_6$ haloalkylsulfonyl.

[11] The condensed heterocyclic compound or its salt or an N-oxide thereof according to the above [10], wherein
A⁴ is C(R⁴), and
A⁵ is C(R⁵).

[12] The condensed heterocyclic compound or its salt or an N-oxide thereof according to the above [10], wherein
A⁴ is C(R⁴), and
A⁵ is a nitrogen atom.

[13] The condensed heterocyclic compound or its salt or an N-oxide thereof according to the above [10], wherein
A⁴ is a nitrogen atom, and
A⁵ is C(R⁵).

[14] The condensed heterocyclic compound or its salt or an N-oxide thereof according to the above [10] or [13], wherein
A⁴ is a nitrogen atom,
A⁵ is C(R⁵),
R³ is $C_1$-$C_6$ haloalkyl,
R⁵ is a hydrogen atom or $C_1$-$C_6$ alkyl,
R⁶ is a hydrogen atom, a halogen atom or $C_1$-$C_6$ alkyl,
each of Y1 and Y4 is a hydrogen atom,
Y2 is a hydrogen atom, a halogen atom or $C_1$-$C_6$ haloalkyl, and
Y3 is a hydrogen atom or $C_1$-$C_6$ haloalkyl.

[15] The condensed heterocyclic compound or its salt or an N-oxide thereof according to the above [2], wherein
Q is a ring represented by Q3,
A⁴ is a nitrogen atom or C(R⁴),
A⁵ is a nitrogen atom or C(R⁵),
(excluding a case where both A⁴ and A⁵ are nitrogen atoms),
R¹ is $C_1$-$C_6$ alkyl,
R² is a hydrogen atom,
R³ is a hydrogen atom, a halogen atom, $C_1$-$C_6$ haloalkyl, $C_1$-$C_6$ haloalkylthio, ($C_1$-$C_6$)alkylthio optionally substituted with $R^{3a}$, $C_1$-$C_6$ haloalkylsulfinyl or $C_1$-$C_6$ haloalkylsulfonyl, and
R⁴ is a hydrogen atom, a halogen atom, $C_1$-$C_6$ haloalkyl, $C_1$-$C_6$ haloalkylthio, ($C_1$-$C_6$) alkylthio optionally substituted with $R^{4a}$, $C_1$-$C_6$ haloalkylsulfinyl or $C_1$-$C_6$ haloalkylsulfonyl.

[16] The condensed heterocyclic compound or its salt or an N-oxide thereof according to the above [15], wherein
A⁴ is C(R⁴), and
A⁵ is C(R⁵).

[17] The condensed heterocyclic compound or its salt or an N-oxide thereof according to the above [15], wherein
A⁴ is C(R⁴), and
A⁵ is a nitrogen atom.

[18] The condensed heterocyclic compound or its salt or an N-oxide thereof according to the above [15], wherein
A⁴ is a nitrogen atom, and
A⁵ is C(R⁵).

[19] The condensed heterocyclic compound or its salt or an N-oxide thereof according to the above [15] or [18], wherein
A⁴ is a nitrogen atom,
A⁵ is C(R⁵),
R³ is $C_1$-$C_6$ haloalkyl,
R⁵ is a hydrogen atom,
R⁶ is a hydrogen atom,
Y1 is a hydrogen atom,
each of Y2 and Y3 is independently a hydrogen atom, a halogen atom or $C_1$-$C_6$ haloalkyl, and
Y4 is a hydrogen atom or a halogen atom.

[20] The condensed heterocyclic compound or its salt or an N-oxide thereof according to the above [2], wherein Q is a ring represented by Q4.

[21] The condensed heterocyclic compound or its salt or an N-oxide thereof according to the above [20], wherein
A⁸ is a nitrogen atom.

[22] The condensed heterocyclic compound or its salt or an N-oxide thereof according to the above [20], wherein
A⁸ is C(R⁸).

[23] The condensed heterocyclic compound or its salt or an N-oxide thereof according to the above [20], [21] or [22], wherein
R¹ is $C_1$-$C_6$ alkyl,
R⁶ is a hydrogen atom,
R⁷ is $C_1$-$C_6$ haloalkyl,
R⁸ is a hydrogen atom or $C_1$-$C_6$ alkyl,
each of Y1 and Y4 is a hydrogen atom,
Y2 is a hydrogen atom, a halogen atom or $C_1$-$C_6$ haloalkyl, and
Y3 is a hydrogen atom or $C_1$-$C_6$ haloalkyl.

[24] The condensed heterocyclic compound or its salt or an N-oxide thereof according to the above [3], wherein
R¹ is $C_1$-$C_6$ alkyl,
R² is a hydrogen atom,
R³ is $C_1$-$C_6$ haloalkyl,
R⁴ is a hydrogen atom,
$A^{1a}$ is $C_1$-$C_6$ alkyl,
Y5 is a hydrogen atom, and
Y6 is $C_1$-$C_6$ haloalkyl.

[25] The condensed heterocyclic compound or its salt or an N-oxide thereof according to the above [4], wherein
R¹ is $C_1$-$C_6$ alkyl,
R² is a hydrogen atom,
R³ is $C_1$-$C_6$ haloalkyl,
R⁴ is a hydrogen atom,
$A^{1a}$ is $C_1$-$C_6$ alkyl,
$T_{1a}$ is $C_1$-$C_6$ alkyl,
each of Y1, Y3 and Y4 is a hydrogen atom, and
Y2 is $C_1$-$C_6$ haloalkyl.

[26] The condensed heterocyclic compound or its salt or an N-oxide thereof according to the above [2], wherein
A¹ is N($A^{1a}$) or an oxygen atom,
R² is a hydrogen atom,
R³ is $C_1$-$C_6$ haloalkyl, $C_1$-$C_6$ haloalkylthio, $C_1$-$C_6$ haloalkylsulfinyl or $C_1$-$C_6$ haloalkylsulfonyl,
R⁴ is a hydrogen atom,
R⁵ is a hydrogen atom or $C_1$-$C_6$ alkyl,
R⁶ is a hydrogen atom,
$A^{1a}$ is $C_1$-$C_6$ alkyl,
each of Y1 and Y4 is a hydrogen atom, and
each of Y2 and Y3 is independently a hydrogen atom or $C_1$-$C_6$ haloalkyl.

[27] The condensed heterocyclic compound or its salt or an N-oxide thereof according to the above [1] or [2], wherein the formula (1) is the following formula (1-A-A1), (1-A-B1), (1-A-C1), (1-A-D1), (1-A-E1), (1-A-F1), (1-A-G1), (1-A-H1), (1-A-I1), (1-A-J1), (1-A-K1), (1-A-L1), (1-A-M1) or (1-A-N1):

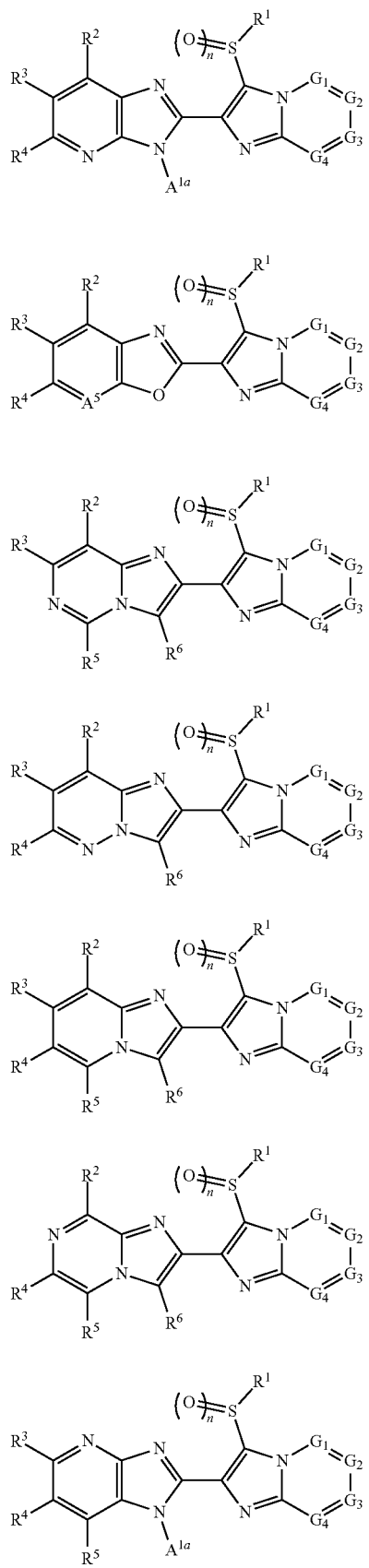
[28] The condensed heterocyclic compound or its salt or an N-oxide thereof according to the above [1] or [3], wherein the formula (1) is the following formula (1-B-A1):

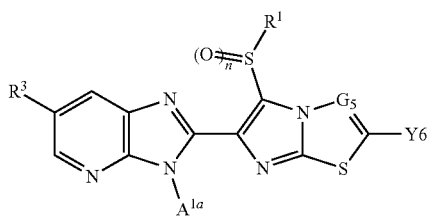

(1-B-A1)

[29] The condensed heterocyclic compound or its salt or an N-oxide thereof according to the above [1] or [4], wherein the formula (1) is the following formula (1-C-A1):

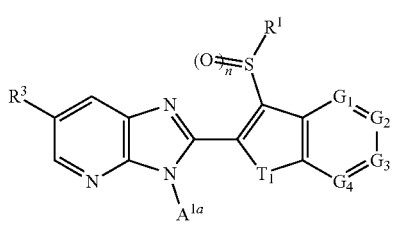

(1-C-A1)

[30] The condensed heterocyclic compound or its salt or an N-oxide thereof according to the above [1], wherein the formula (1) is the following formula (1-d-A1):

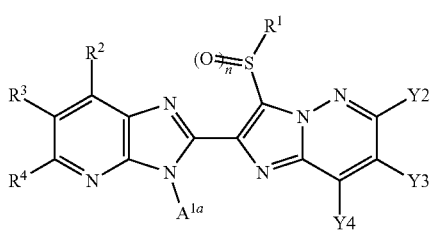

(1-d-A1)

wherein $R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl, $R^3$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, $A^{1a}$ is a hydrogen atom, $C_1$-$C_6$ alkyl, $C_2$-$C_6$ alkenyl or $C_2$-$C_6$ alkynyl, and each of $R^2$, $R^4$, Y2, Y3 and Y4 is independently a hydrogen atom, a halogen atom, $C_1$-$C_6$ alkyl or $C_1$-$C_6$ haloalkyl.

[31] The condensed heterocyclic compound or its salt or an N-oxide thereof according to the above [30], wherein each of $R^1$ and $A^{1a}$ is independently $C_1$-$C_6$ alkyl, each of $R^3$ and Y3 is independently $C_1$-$C_6$ haloalkyl, and each of $R^2$, $R^4$, Y2 and Y4 is a hydrogen atom.

[32] The condensed heterocyclic compound or its salt or an N-oxide thereof according to the above [1], wherein the formula (1) is the following formula (1-e-A1):

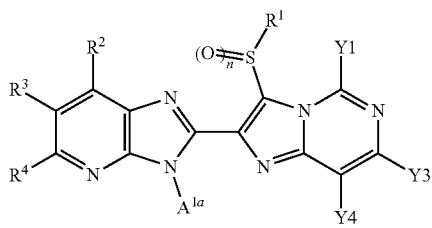

(1-e-A1)

wherein $R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl, $R^3$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, $A^{1a}$ is a hydrogen atom, $C_1$-$C_6$ alkyl, $C_2$-$C_6$ alkenyl or $C_2$-$C_6$ alkynyl, and each of $R^2$, $R^4$, Y1, Y3 and Y4 is independently a hydrogen atom, a halogen atom, $C_1$-$C_6$ alkyl or $C_1$-$C_6$ haloalkyl.

[33] The condensed heterocyclic compound or its salt or an N-oxide thereof according to the above [32], wherein each of $R^1$ and $A^{1a}$ is independently $C_1$-$C_6$ alkyl, each of $R^3$ and Y3 is independently $C_1$-$C_6$ haloalkyl, and each of $R^2$, $R^4$, Y1 and Y4 is a hydrogen atom.

[34] The condensed heterocyclic compound or its salt or an N-oxide thereof according to the above [1], wherein the formula (1) is the following formula (1-f-A1):

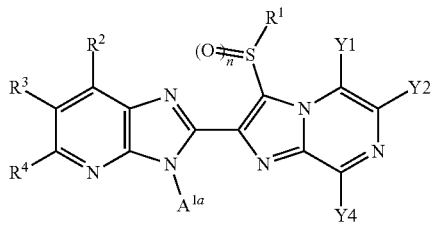

(1-f-A1)

wherein $R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl, $R^3$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, $A^{1a}$ is a hydrogen atom, $C_1$-$C_6$ alkyl, $C_2$-$C_6$ alkenyl or $C_2$-$C_6$ alkynyl, and each of $R^2$, $R^4$, Y1, Y2 and Y4 is independently a hydrogen atom, a halogen atom, $C_1$-$C_6$ alkyl or $C_1$-$C_6$ haloalkyl.

[35] The condensed heterocyclic compound or its salt or an N-oxide thereof according to the above [34], wherein each of $R^1$ and $A^{1a}$ is independently $C_1$-$C_6$ alkyl, $R^3$ is $C_1$-$C_6$ haloalkyl, each of $R^2$, $R^4$, Y1 and Y4 is a hydrogen atom, and Y2 is a hydrogen atom or a halogen atom.

[36] The condensed heterocyclic compound or its salt or an N-oxide thereof according to the above [1], wherein the formula (1) is the following formula (1-g-A1):

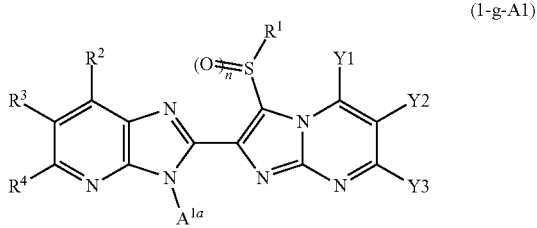

(1-g-A1)

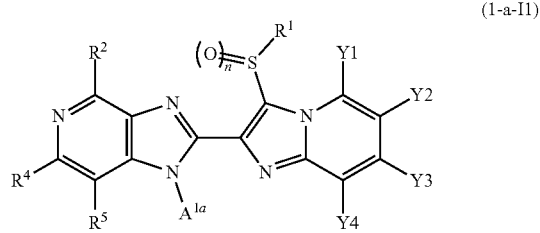

(1-a-I1)

wherein
$R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl, $R^3$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, $A^{1a}$ is a hydrogen atom, $C_1$-$C_6$ alkyl, $C_2$-$C_6$ alkenyl or $C_2$-$C_6$ alkynyl, and each of $R^2$, $R^4$, Y1, Y2 and Y3 is independently a hydrogen atom, a halogen atom, $C_1$-$C_6$ alkyl or $C_1$-$C_6$ haloalkyl.

[37] The condensed heterocyclic compound or its salt or an N-oxide thereof according to the above [36], wherein
each of $R^1$ and $A^{1a}$ is independently $C_1$-$C_6$ alkyl,
$R^3$ is $C_1$-$C_6$ haloalkyl,
each of $R^2$, $R^4$, Y1 and Y3 is a hydrogen atom, and
Y2 is a halogen atom or $C_1$-$C_6$ haloalkyl.

[38] The condensed heterocyclic compound or its salt or an N-oxide thereof according to the above [1], wherein the formula (1) is the following formula (1-a-G1):

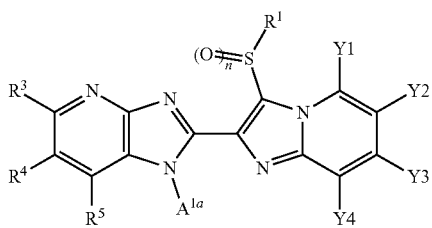

(1-a-G1)

wherein
$R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl, $R^3$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, $A^{1a}$ is a hydrogen atom, $C_1$-$C_6$ alkyl, $C_2$-$C_6$ alkenyl or $C_2$-$C_6$ alkynyl, and each of $R^4$, $R^5$, Y1, Y2, Y3 and Y4 is independently a hydrogen atom, a halogen atom, $C_1$-$C_6$ alkyl or $C_1$-$C_6$ haloalkyl.

[39] The condensed heterocyclic compound or its salt or an N-oxide thereof according to the above [38], wherein
each of $R^1$ and $A^{1a}$ is independently $C_1$-$C_6$ alkyl,
each of $R^3$ and Y3 is independently $C_1$-$C_6$ haloalkyl, and
each of $R^4$, $R^5$, Y1, Y2 and Y4 is a hydrogen atom.

[40] The condensed heterocyclic compound or its salt or an N-oxide thereof according to the above [1], wherein the formula (1) is the following formula (1-a-I1):

wherein
$R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl, $R^4$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, $A^{1a}$ is a hydrogen atom, $C_1$-$C_6$ alkyl, $C_2$-$C_6$ alkenyl or $C_2$-$C_6$ alkynyl, and each of $R^2$, $R^5$, Y1, Y2, Y3 and Y4 is independently a hydrogen atom, a halogen atom, $C_1$-$C_6$ alkyl or $C_1$-$C_6$ haloalkyl.

[41] The condensed heterocyclic compound or its salt or an N-oxide thereof according to the above [40], wherein
each of $R^1$ and $A^{1a}$ is independently $C_1$-$C_6$ alkyl,
$R^4$ is $C_1$-$C_6$ haloalkyl,
Y2 is a hydrogen atom or $C_1$-$C_6$ haloalkyl,
Y3 is a hydrogen atom, a halogen atom or $C_1$-$C_6$ haloalkyl, and
each of $R^2$, $R^5$, Y1 and Y4 is a hydrogen atom.

[42] The condensed heterocyclic compound or its salt or an N-oxide thereof according to the above [1], wherein the formula (1) is the following formula (1-a-F1):

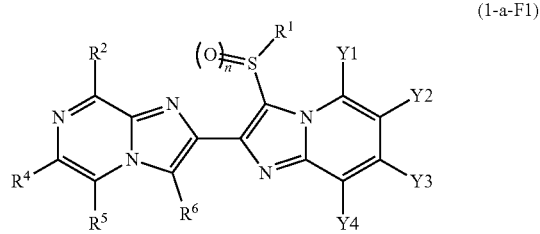

(1-a-F1)

wherein
$R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl or $C_2$-$C_6$ haloalkynyl, $R^4$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl, and each of $R^2$, $R^5$, $R^6$, Y1, Y2, Y3 and Y4 is independently a hydrogen atom, a halogen atom, $C_1$-$C_6$ akyl or $C_1$-$C_6$ haloalkyl.

[43] The condensed heterocyclic compound or its salt or an N-oxide thereof according to the above [42], wherein
$R^1$ is $C_1$-$C_6$ alkyl,
$R^4$ is $C_1$-$C_6$ haloalkyl,
each of Y2 and Y3 is independently a hydrogen atom or $C_1$-$C_6$ haloalkyl, and
each of $R^2$, $R^5$, $R^6$, Y1 and Y4 is a hydrogen atom.

[44] The condensed heterocyclic compound or its salt or an N-oxide thereof according to the above [1], wherein the formula (1) is the following formula (1-a-O1):

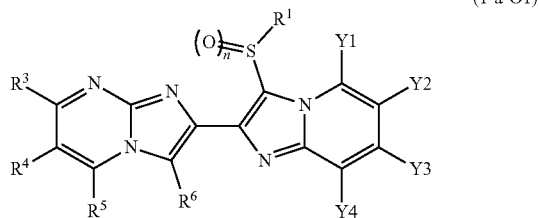
(1-a-O1)

wherein
R$^1$ is C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl or C$_3$-C$_6$ haloalkynyl,
R$^4$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, and
each of R$^3$, R$^5$, R$^6$, Y1, Y2, Y3 and Y4 is independently a hydrogen atom, a halogen atom, C$_1$-C$_6$ akyl or C$_1$-C$_6$ haloalkyl.

[45] The condensed heterocyclic compound or its salt or an N-oxide thereof according to the above [44], wherein
R$^1$ is C$_1$-C$_6$ alkyl,
R$^4$ is C$_1$-C$_6$ haloalkyl,
each of R$^6$ and Y2 is independently a halogen atom, and
each of R$^3$, R$^5$, Y1, Y3 and Y4 is a hydrogen atom.

[46] The condensed heterocyclic compound or its salt or an N-oxide thereof according to the above [1] or [2], wherein the formula (1) is the following formula (1-a-b1):

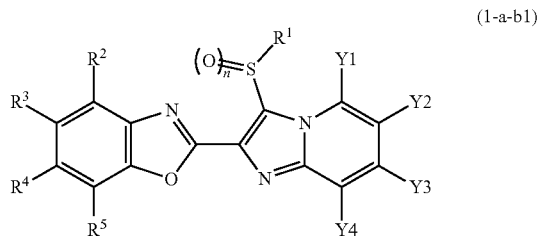
(1-a-b1)

wherein
R$^1$ is C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl or C$_2$-C$_6$ haloalkynyl,
each of R$^3$ and R$^4$ is independently a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, and
each of R$^2$, R$^5$, Y1, Y2, Y3 and Y4 is independently a hydrogen atom, a halogen atom, C$_1$-C$_6$ alkyl or C$_1$-C$_6$ haloalkyl.

[47] The condensed heterocyclic compound or its salt or an N-oxide thereof according to the above [46], wherein
R$^1$ is C$_1$-C$_6$ alkyl,
R$^3$ is C$_1$-C$_6$ haloalkylthio, C$_1$-C$_6$ haloalkylsulfinyl or C$_1$-C$_6$ haloalkylsulfonyl,
each of Y2 and Y3 is independently a hydrogen atom or C$_1$-C$_6$ haloalkyl, and
each of R$^2$, R$^4$, R$^5$, Y1 and Y4 is a hydrogen atom.

[48] The condensed heterocyclic compound or its salt or an N-oxide thereof according to the above [1] or [2], wherein the formula (1) is the following formula (1-a-b2):

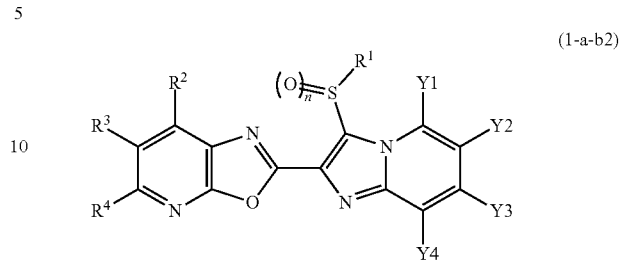
(1-a-b2)

wherein
R$^1$ is C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl or C$_2$-C$_6$ haloalkynyl,
each of R$^3$ and R$^4$ is independently a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, and
each of R$^2$, Y1, Y2, Y3 and Y4 is independently a hydrogen atom, a halogen atom, C$_1$-C$_6$ alkyl or C$_1$-C$_6$ haloalkyl.

[49] The condensed heterocyclic compound or its salt or an N-oxide thereof according to the above [48], wherein
R$^1$ is C$_1$-C$_6$ alkyl,
each of R$^3$ and Y3 is independently C$_1$-C$_6$ haloalkyl, and
each of R$^2$, R$^4$, Y1, Y2 and Y4 is a hydrogen atom.

[50] The condensed heterocyclic compound or its salt or an N-oxide thereof according to the above [1] or [2], wherein the formula (1) is the following formula (1-a-m2):

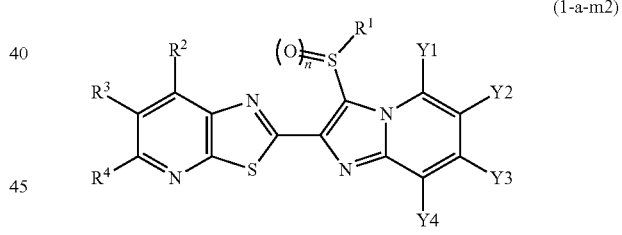
(1-a-m2)

wherein
R$^1$ is C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl or C$_2$-C$_6$ haloalkynyl,
R$^3$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl, and
each of R$^2$, R$^4$, Y1, Y2, Y3 and Y4 is independently a hydrogen atom, a halogen atom, C$_1$-C$_6$ alkyl or C$_1$-C$_6$ haloalkyl.

[51] The condensed heterocyclic compound or its salt or an N-oxide thereof according to the above [50], wherein
R$^1$ is C$_1$-C$_6$ alkyl,
each of R$^3$ and Y3 is independently C$_1$-C$_6$ haloalkyl, and
each of R$^2$, R$^4$, Y1, Y2 and Y4 is a hydrogen atom.

[52] The condensed heterocyclic compound or its salt or an N-oxide thereof according to the above [1], [2] or [5], wherein the formula (1) is the following formula (1-a-p1):

(1-a-p1)

wherein
$R^1$ is $C_1$-$C_6$ alkyl,
$R^3$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl,
$R^4$ is a hydrogen atom, a halogen atom or $C_1$-$C_6$ haloalkyl,
$A^{1a}$ is a hydrogen atom or $C_1$-$C_6$ alkyl, and
each of $R^2$, $R^5$, Y1, Y2, Y3 and Y4 is independently a hydrogen atom, a halogen atom, $C_1$-$C_6$ alkyl or $C_1$-$C_6$ haloalkyl.

[53] The condensed heterocyclic compound or its salt or an N-oxide thereof according to the above [52], wherein
each of $R^2$ and $R^5$ is independently a hydrogen atom or a halogen atom,
each of $R^3$ and $R^4$ is independently a hydrogen atom or $C_1$-$C_6$ haloalkyl,
Y3 is $C_1$-$C_6$ haloalkyl, and
each of Y1, Y2 and Y4 is a hydrogen atom.

[54] The condensed heterocyclic compound or its salt or an N-oxide thereof according to the above [1], [2] or [5], wherein the formula (1) is the following formula (1-a-q1):

(1-a-q1)

wherein
$R^1$ is $C_1$-$C_6$ alkyl,
$R^3$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl,
$A^{1a}$ is a hydrogen atom or $C_1$-$C_6$ alkyl, and
each of $R^2$, Y1, Y2, Y3 and Y4 is independently a hydrogen atom, a halogen atom, $C_1$-$C_6$ alkyl or $C_1$-$C_6$ haloalkyl.

[55] The condensed heterocyclic compound or its salt or an N-oxide thereof according to the above [54], wherein
each of $R^3$ and Y2 is independently $C_1$-$C_6$ haloalkyl,
$A^{1a}$ is $C_1$-$C_6$ alkyl, and
each of $R^2$, Y1, Y3 and Y4 is a hydrogen atom.

[56] The condensed heterocyclic compound or its salt or an N-oxide thereof according to the above [1], [2], [10] or [11], wherein the formula (1) is the following formula (1-a-E1):

(1-a-E1)

wherein
$R^1$ is $C_1$-$C_6$ alkyl,
$R^2$ is a hydrogen atom,
$R^3$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl,
$R^4$ is a hydrogen atom, a halogen atom or $C_1$-$C_6$ haloalkyl, and
each of $R^5$, $R^6$, Y1, Y2, Y3 and Y4 is independently a hydrogen atom, a halogen atom, $C_1$-$C_6$ alkyl or $C_1$-$C_6$ haloalkyl.

[57] The condensed heterocyclic compound or its salt or an N-oxide thereof according to the above [56], wherein
each of $R^3$, $R^4$, Y2 and Y3 is independently a hydrogen atom or $C_1$-$C_6$ haloalkyl, and
each of $R^5$, $R^6$, Y1 and Y4 is a hydrogen atom.

[58] The condensed heterocyclic compound or its salt or an N-oxide thereof according to the above [1], [2], [10] or [12], wherein the formula (1) is the following formula (1-a-D1):

(1-a-D1)

wherein
$R^1$ is $C_1$-$C_6$ alkyl,
$R^2$ is a hydrogen atom,
$R^3$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl,
$R^4$ is a hydrogen atom, a halogen atom or $C_1$-$C_6$ haloalkyl, and
each of $R^6$, Y1, Y2, Y3 and Y4 is independently a hydrogen atom, a halogen atom, $C_1$-$C_6$ alkyl or $C_1$-$C_6$ haloalkyl.

[59] The condensed heterocyclic compound or its salt or an N-oxide thereof according to the above [58], wherein
$R^3$ is $C_1$-$C_6$ haloalkyl,
Y2 is a hydrogen atom, a halogen atom or $C_1$-$C_6$ haloalkyl,
Y3 is a hydrogen atom or $C_1$-$C_6$ haloalkyl, and
each of $R^4$, $R^6$, Y1 and Y4 is a hydrogen atom.

[60] The condensed heterocyclic compound or its salt or an N-oxide thereof according to the above [1], [2], [15] or [16], wherein the formula (1) is the following formula (1-a-j1):

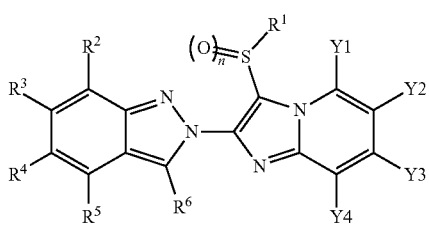

(1-a-j1)

wherein
$R^1$ is $C_1$-$C_6$ alkyl,
$R^2$ is a hydrogen atom,
$R^3$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl, $R^4$ is a hydrogen atom, a halogen atom or $C_1$-$C_6$ haloalkyl, and
each of $R^5$, $R^6$, Y1, Y2, Y3 and Y4 is independently a hydrogen atom, a halogen atom, $C_1$-$C_6$ alkyl or $C_1$-$C_6$ haloalkyl.

[61] The condensed heterocyclic compound or its salt or an N-oxide thereof according to the above [60], wherein
each of $R^3$ and Y3 is independently $C_1$-$C_6$ haloalkyl, and
each of $R^4$, $R^5$, $R^6$, Y1, Y2 and Y4 is a hydrogen atom.

[62] The condensed heterocyclic compound or its salt or an N-oxide thereof according to the above [1], [2], [15] or [17], wherein the formula (1) is the following formula (1-a-j2):

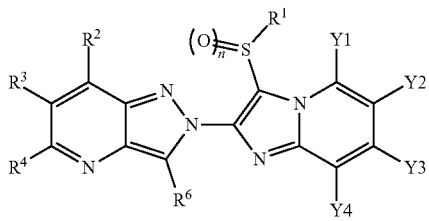

(1-a-j2)

wherein
$R^1$ is $C_1$-$C_6$ alkyl,
$R^2$ is a hydrogen atom,
$R^3$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl,
$R^4$ is a hydrogen atom, a halogen atom or $C_1$-$C_6$ haloalkyl, and
each of $R^6$, Y1, Y2, Y3 and Y4 is independently a hydrogen atom, a halogen atom, $C_1$-$C_6$ alkyl or $C_1$-$C_6$ haloalkyl.

[63] The condensed heterocyclic compound or its salt or an N-oxide thereof according to the above [62], wherein
$R^3$ is $C_1$-$C_6$ haloalkyl,
Y2 is a hydrogen atom or a halogen atom,
Y3 is a hydrogen atom or $C_1$-$C_6$ haloalkyl, and
each of $R^4$, $R^6$, Y1 and Y4 is a hydrogen atom.

[64] The condensed heterocyclic compound or its salt or an N-oxide thereof according to the above [1], wherein
D substituted with —S(O)$_n$R$^1$ is a ring represented by either D1 or D2,
Q is a ring represented by either Q1 or Q2,
$R^{1a}$ is $C_1$-$C_8$ alkoxycarbonyl,
$R^2$ is a hydrogen atom, a halogen atom, $C_1$-$C_6$ alkyl, $C_1$-$C_6$ haloalkyl, $C_1$-$C_8$ alkoxy or $C_1$-$C_8$ haloalkoxy,
each of $R^3$ and $R^4$ is independently a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, mercapto, cyano or nitro,
$R^5$ is a hydrogen atom, a halogen atom, $C_1$-$C_6$ alkyl or $C_1$-$C_6$ haloalkyl,
$R^6$ is a hydrogen atom, a halogen atom or $C_1$-$C_6$ alkyl,
$A^{1a}$ is a hydrogen atom, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl ($C_1$-$C_6$) alkyl or $C_3$-$C_6$ halocycloalkyl ($C_1$-$C_6$) alkyl, and
each of Y1, Y2, Y3, Y4, Y5 and Y6 is independently a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, cyano or nitro.

[65] The condensed heterocyclic compound or its salt or an N-oxide thereof according to the above [2], wherein
D substituted with —S(O)$_n$R$^1$ is a ring represented by D1,
$G_1$ is C(Y1),
$G_2$ is C(Y2),
$G_3$ is C(Y3),
$G_4$ is C(Y4),
$A^1$ is N($A^{1a}$) or an oxygen atom,
$A^2$ is C($R^2$),
$A^3$ is C($R^3$),
each of $R^1$ and $A^{1a}$ is independently $C_1$-$C_6$ alkyl,
$R^3$ is $C_1$-$C_6$ haloalkyl, $C_1$-$C_6$ haloalkylthio, $C_1$-$C_6$ haloalkylsulfinyl or $C_1$-$C_6$ haloalkylsulfonyl,
$R^5$ is a hydrogen atom or $C_1$-$C_6$ alkyl,
each of Y2 and Y3 is independently a hydrogen atom or $C_1$-$C_6$ haloalkyl, and
each of $R^2$, $R^4$, $R^6$, Y1 and Y4 is a hydrogen atom.

[66] The condensed heterocyclic compound or its salt or an N-oxide thereof according to the above [3], wherein
D substituted with —S(O)$_n$R$^1$ is a ring represented by D2,
Q is a ring represented by Q1,
$G_5$ is C(Y5),
$A^1$ is N($A^{1a}$),
$A^2$ is C($R^2$),
$A^3$ is C($R^3$),
$A^4$ is C($R^4$),
$A^5$ is a nitrogen atom,
each of $R^1$ and $A^{1a}$ is independently $C_1$-$C_6$ alkyl,
each of $R^2$, $R^4$ and Y5 is a hydrogen atom, and
each of $R^3$ and Y6 is independently $C_1$-$C_6$ haloalkyl.

[67] The condensed heterocyclic compound or its salt or an N-oxide thereof according to any one of the above [1] to [66], wherein
$R^1$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl ($C_1$-$C_6$) alkyl or $C_3$-$C_6$ halocycloalkyl ($C_1$-$C_6$) alkyl.

[68] The condensed heterocyclic compound or its salt or an N-oxide thereof according to any one of the above [1] to [66], wherein
$R^1$ is $C_1$-$C_6$ alkyl, $C_1$-$C_6$ haloalkyl or $C_3$-$C_6$ cycloalkyl ($C_1$-$C_6$) alkyl.

[69] The condensed heterocyclic compound or its salt or an N-oxide thereof according to any one of the above [1] to [66], wherein
$R^1$ is $C_1$-$C_6$ alkyl or $C_1$-$C_6$ haloalkyl.

[70] The condensed heterocyclic compound or its salt or an N-oxide thereof according to any one of the above [1] to [66], wherein
$R^1$ is $C_1$-$C_6$ alkyl.

[71] The condensed heterocyclic compound or its salt or an N-oxide thereof according to any one of the above [1] to [66], wherein
$R^1$ is $C_1$-$C_6$ haloalkyl.
[72] The condensed heterocyclic compound or its salt or an N-oxide thereof according to any one of the above [1] to [71], wherein
$R^{1a}$ is $C_1$-$C_8$ alkoxy, $C_1$-$C_8$ alkoxycarbonyl or cyano.
[73] The condensed heterocyclic compound or its salt or an N-oxide thereof according to any one of the above [1] to [71], wherein
$R^{1a}$ is $C_1$-$C_8$ alkoxycarbonyl.
[74] The condensed heterocyclic compound or its salt or an N-oxide thereof according to any one of the above [1] to [73], wherein
$R^2$ is a hydrogen atom, a halogen atom, $C_1$-$C_6$ alkyl or $C_1$-$C_6$ haloalkyl.
[75] The condensed heterocyclic compound or its salt or an N-oxide thereof according to any one of the above [1] to [73], wherein
$R^2$ is a hydrogen atom.
[76] The condensed heterocyclic compound or its salt or an N-oxide thereof according to any one of the above [1] to [75], wherein
$R^3$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, ($C_1$-$C_6$) alkylthio optionally substituted with $R^{3a}$, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl.
[77] The condensed heterocyclic compound or its salt or an N-oxide thereof according to any one of the above [1] to [75], wherein
$R^3$ is a hydrogen atom, a halogen atom, $C_1$-$C_6$ haloalkyl, $C_1$-$C_6$ alkylthio, ($C_1$-$C_6$) alkylthio optionally substituted with $R^{3a}$, $C_1$-$C_6$ haloalkylthio, $C_1$-$C_6$ haloalkylsulfinyl or $C_1$-$C_6$ haloalkylsulfonyl.
[78] The condensed heterocyclic compound or its salt or an N-oxide thereof according to any one of the above [1] to [75], wherein
$R^3$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl.
[79] The condensed heterocyclic compound or its salt or an N-oxide thereof according to any one of the above [1] to [75], wherein
$R^3$ is $C_1$-$C_6$ haloalkylthio, $C_1$-$C_6$ haloalkylsulfinyl or $C_1$-$C_6$ haloalkylsulfonyl.
[80] The condensed heterocyclic compound or its salt or an N-oxide thereof according to any one of the above [1] to [75], wherein
$R^3$ is a halogen atom.
[81] The condensed heterocyclic compound or its salt or an N-oxide thereof according to any one of the above [1] to [75], wherein
$R^3$ is $C_1$-$C_6$ haloalkyl.
[82] The condensed heterocyclic compound or its salt or an N-oxide thereof according to any one of the above [1] to [75], wherein
$R^3$ is $C_1$-$C_6$ haloalkylthio.
[83] The condensed heterocyclic compound or its salt or an N-oxide thereof according to any one of the above [1] to [75], wherein
$R^3$ is $C_1$-$C_6$ haloalkylsulfinyl.
[84] The condensed heterocyclic compound or its salt or an N-oxide thereof according to any one of the above [1] to [75], wherein
$R^3$ is $C_1$-$C_6$ haloalkylsulfonyl.
[85] The condensed heterocyclic compound or its salt or an N-oxide thereof according to any one of the above [1] to [84], wherein
$R^4$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_1$-$C_6$ alkylthio, $C_1$-$C_6$ haloalkylthio, ($C_1$-$C_6$) alkylthio optionally substituted with $R^{4a}$, $C_1$-$C_6$ alkylsulfinyl, $C_1$-$C_6$ haloalkylsulfinyl, $C_1$-$C_6$ alkylsulfonyl or $C_1$-$C_6$ haloalkylsulfonyl.
[86] The condensed heterocyclic compound or its salt or an N-oxide thereof according to any one of the above [1] to [84], wherein
$R^4$ is a hydrogen atom, a halogen atom, $C_1$-$C_6$ haloalkyl, $C_1$-$C_6$ alkylthio, ($C_1$-$C_6$) alkylthio optionally substituted with $R^{4a}$, $C_1$-$C_6$ haloalkylthio, $C_1$-$C_6$ haloalkylsulfinyl or $C_1$-$C_6$ haloalkylsulfonyl.
[87] The condensed heterocyclic compound or its salt or an N-oxide thereof according to any one of the above [1] to [84], wherein
$R^4$ is a hydrogen atom, a halogen atom, $C_1$-$C_6$ haloalkyl, $C_1$-$C_6$ haloalkylthio, $C_1$-$C_6$ haloalkylsulfinyl or $C_1$-$C_6$ haloalkylsulfonyl.
[88] The condensed heterocyclic compound or its salt or an N-oxide thereof according to any one of the above [1] to [84], wherein
$R^4$ is a hydrogen atom.
[89] The condensed heterocyclic compound or its salt or an N-oxide thereof according to any one of the above [1] to [84], wherein
$R^4$ is a halogen atom.
[90] The condensed heterocyclic compound or its salt or an N-oxide thereof according to any one of the above [1] to [84], wherein
$R^4$ is $C_1$-$C_6$ haloalkylthio, $C_1$-$C_6$ haloalkylsulfinyl or $C_1$-$C_6$ haloalkylsulfonyl.
[91] The condensed heterocyclic compound or its salt or an N-oxide thereof according to any one of the above [1] to [84], wherein
$R^4$ is $C_1$-$C_6$ haloalkyl.
[92] The condensed heterocyclic compound or its salt or an N-oxide thereof according to any one of the above [1] to [91], wherein
$R^5$ is a hydrogen atom, a halogen atom, $C_1$-$C_6$ alkyl or $C_1$-$C_6$ haloalkyl.
[93] The condensed heterocyclic compound or its salt or an N-oxide thereof according to any one of the above [1] to [91], wherein
$R^5$ is a halogen atom.
[94] The condensed heterocyclic compound or its salt or an N-oxide thereof according to any one of the above [1] to [91], wherein
$R^5$ is a hydrogen atom.
[95] The condensed heterocyclic compound or its salt or an N-oxide thereof according to any one of the above [1] to [91], wherein
$R^5$ is $C_1$-$C_6$ alkyl.
[96] The condensed heterocyclic compound or its salt or an N-oxide thereof according to any one of the above [1] to [95], wherein
$R^6$ is a hydrogen atom, a halogen atom, $C_1$-$C_6$ alkyl or $C_1$-$C_6$ haloalkyl.
[97] The condensed heterocyclic compound or its salt or an N-oxide thereof according to any one of the above [1] to [95], wherein
$R^6$ is a hydrogen atom.

[98] The condensed heterocyclic compound or its salt or an N-oxide thereof according to any one of the above [1] to [95], wherein
$R^6$ is a halogen atom.
[99] The condensed heterocyclic compound or its salt or an N-oxide thereof according to any one of the above [1] to [95], wherein
$R^6$ is $C_1$-$C_6$ alkyl.
[100] The condensed heterocyclic compound or its salt or an N-oxide thereof according to any one of the above [1] to [99], wherein
$R^7$ is a hydrogen atom, a halogen atom or $C_1$-$C_6$ haloalkyl.
[101] The condensed heterocyclic compound or its salt or an N-oxide thereof according to any one of the above [1] to [99], wherein
$R^7$ is $C_1$-$C_6$ haloalkyl.
[102] The condensed heterocyclic compound or its salt or an N-oxide thereof according to any one of the above [1] to [101], wherein
$R^8$ is a hydrogen atom, a halogen atom, $C_1$-$C_6$ alkyl or $C_1$-$C_6$ haloalkyl.
[103] The condensed heterocyclic compound or its salt or an N-oxide thereof according to any one of the above [1] to [101], wherein
$R^8$ is $C_1$-$C_6$ alkyl.
[104] The condensed heterocyclic compound or its salt or an N-oxide thereof according to any one of the above [1] to [103], wherein
$A^{1a}$ is a hydrogen atom, $C_1$-$C_6$ alkyl, ($C_1$-$C_6$) alkyl optionally substituted with $A^{1\ a-a}$, $C_2$-$C_6$ alkenyl, $C_2$-$C_6$ alkynyl, $C_1$-$C_8$ alkoxy, $C_3$-$C_6$ cycloalkyl or $C(O)R^{10a}$.
[105] The condensed heterocyclic compound or its salt or an N-oxide thereof according to any one of the above [1] to [103], wherein
$A^{1a}$ is a hydrogen atom, $C_1$-$C_6$ alkyl, $C_2$-$C_6$ alkenyl, $C_2$-$C_6$ alkynyl or $C_3$-$C_6$ cycloalkyl.
[106] The condensed heterocyclic compound or its salt or an N-oxide thereof according to any one of the above [1] to [103], wherein
$A^{1a}$ is a hydrogen atom.
[107] The condensed heterocyclic compound or its salt or an N-oxide thereof according to any one of the above [1] to [103], wherein
$A^{1a}$ is $C_1$-$C_6$ alkyl.
[108] The condensed heterocyclic compound or its salt or an N-oxide thereof according to any one of the above [1] to [107], wherein
each of Y1, Y2, Y3 and Y4 is independently a hydrogen atom, a halogen atom, $C_1$-$C_6$ alkyl, $C_1$-$C_6$ haloalkyl, $C_2$-$C_6$ alkenyl, $C_2$-$C_6$ alkynyl, ($C_2$-$C_6$) alkynyl optionally substituted with $Y^b$, $C_1$-$C_6$ alkoxy, $C_1$-$C_6$ haloalkoxy, $C_1$-$C_6$ alkylthio, $C_1$-$C_6$ haloalkylthio, ($C_1$-$C_6$) alkylthio optionally substituted with $Y^a$, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —C(O)$R^{90a}$, —C(O)NH$R^{90b}$, —C(O)N($R^{90c}$)$R^{90b}$, —C(O)OH, hydroxy, —OC(O)$R^{90e}$, —OS(O)$_2R^{90f}$, —NH$_2$, —NH$R^{90g}$, —N($R^{90h}$)$R^{90g}$, mercapto, —SC(O)$R^{90i}$, —S(O)$_2$NH$R^{90j}$, —S(O)$_2$N($R^{90k}$)$R^{90j}$, —SF$_5$, cyano, nitro, phenyl, phenyl optionally substituted with $Y^c$, heterocyclyl or heterocyclyl optionally substituted with $Y^c$.
[109] The condensed heterocyclic compound or its salt or an N-oxide thereof according to any one of the above [1] to [107], wherein
each of Y1, Y2, Y3 and Y4 is independently a hydrogen atom, a halogen atom, $C_1$-$C_6$ alkyl, $C_1$-$C_6$ haloalkyl, $C_2$-$C_6$ alkenyl, ($C_2$-$C_6$) alkynyl optionally substituted with $Y^b$, $C_1$-$C_6$ alkoxy, $C_1$-$C_6$ alkylthio, $C_1$-$C_6$ haloalkylthio, ($C_1$-$C_6$) alkylthio optionally substituted with $Y^a$, $C_1$-$C_6$ alkylsulfinyl, $C_1$-$C_6$ alkylsulfonyl, —C(O)$R^{90a}$, —C(O)N($R^{90c}$)$R^{90b}$, —C(O)OH, —NH$_2$, —NH$R^{90g}$, —N($R^{90h}$)$R^{90g}$, mercapto, cyano, nitro, phenyl, phenyl optionally substituted with $Y^c$, heterocyclyl or heterocyclyl optionally substituted with $Y^c$.
[110] The condensed heterocyclic compound or its salt or an N-oxide thereof according to any one of the above [1] to [109], wherein
Y1 is a hydrogen atom, a halogen atom, $C_1$-$C_6$ alkyl or $C_1$-$C_6$ haloalkyl.
[111] The condensed heterocyclic compound or its salt or an N-oxide thereof according to any one of the above [1] to [109], wherein
Y1 is a hydrogen atom.
[112] The condensed heterocyclic compound or its salt or an N-oxide thereof according to any one of the above [1] to [109], wherein
Y1 is a halogen atom.
[113] The condensed heterocyclic compound or its salt or an N-oxide thereof according to any one of the above [1] to [109], wherein
Y1 is $C_1$-$C_6$ alkyl.
[114] The condensed heterocyclic compound or its salt or an N-oxide thereof according to any one of the above [1] to [109], wherein
Y1 is $C_1$-$C_6$ haloalkyl.
[115] The condensed heterocyclic compound or its salt or an N-oxide thereof according to any one of the above [1] to [114], wherein
Y2 is a hydrogen atom, a halogen atom, $C_1$-$C_6$ alkyl, $C_1$-$C_6$ haloalkyl, $C_2$-$C_6$ alkenyl, ($C_2$-$C_6$) alkynyl optionally substituted with $Y^{1*}$, $C_1$-$C_6$ alkoxy, $C_1$-$C_6$ alkylthio, $C_1$-$C_6$ haloalkylthio, ($C_1$-$C_6$) alkylthio optionally substituted with $Y^a$, $C_1$-$C_6$ alkylsulfinyl, $C_1$-$C_6$ alkylsulfonyl, —NH$_2$, —NH$R^{90g}$, nitro, phenyl, phenyl optionally substituted with $Y^c$ or heterocyclyl.
[116] The condensed heterocyclic compound or its salt or an N-oxide thereof according to any one of the above [1] to [114], wherein
Y2 is a hydrogen atom, a halogen atom, $C_1$-$C_6$ alkyl or $C_1$-$C_6$ haloalkyl.
[117] The condensed heterocyclic compound or its salt or an N-oxide thereof according to any one of the above [1] to [114], wherein
Y2 is a hydrogen atom.
[118] The condensed heterocyclic compound or its salt or an N-oxide thereof according to any one of the above [1] to [114], wherein
Y2 is a halogen atom.
[119] The condensed heterocyclic compound or its salt or an N-oxide thereof according to any one of the above [1] to [114], wherein
Y2 is $C_1$-$C_6$ alkyl.
[120] The condensed heterocyclic compound or its salt or an N-oxide thereof according to any one of the above [1] to [114], wherein
Y2 is $C_1$-$C_6$ haloalkyl.
[121] The condensed heterocyclic compound or its salt or an N-oxide thereof according to any one of the above [1] to [120], wherein
Y3 is a hydrogen atom, a halogen atom, $C_1$-$C_6$ alkyl, $C_1$-$C_6$ haloalkyl, $C_1$-$C_6$ alkoxy, $C_1$-$C_6$ alkylthio, ($C_1$-$C_6$) alkylthio optionally substituted with $Y^a$, $C_1$-$C_6$ alkylsulfinyl, $C_1$-$C_6$ alkylsulfonyl, —C(O)$R^{90a}$, —C(O)N($R^{90c}$)$R^{90b}$, —C(O)OH, cyano or nitro.

[122] The condensed heterocyclic compound or its salt or an N-oxide thereof according to any one of the above [1] to [120], wherein
Y3 is a hydrogen atom, a halogen atom, $C_1$-$C_6$ alkyl or $C_1$-$C_6$ haloalkyl.

[123] The condensed heterocyclic compound or its salt or an N-oxide thereof according to any one of the above [1] to [120], wherein
Y3 is a hydrogen atom.

[124] The condensed heterocyclic compound or its salt or an N-oxide thereof according to any one of the above [1] to [120], wherein
Y3 is a halogen atom.

[125] The condensed heterocyclic compound or its salt or an N-oxide thereof according to any one of the above [1] to [120], wherein
Y3 is $C_1$-$C_6$ alkyl.

[126] The condensed heterocyclic compound or its salt or an N-oxide thereof according to any one of the above [1] to [120], wherein
Y3 is $C_1$-$C_6$ haloalkyl.

[127] The condensed heterocyclic compound or its salt or an N-oxide thereof according to any one of the above [1] to [126], wherein
Y4 is a hydrogen atom, a halogen atom, $C_1$-$C_6$ alkyl, $C_1$-$C_6$ haloalkyl, $C_1$-$C_6$ alkoxy, $C_1$-$C_6$ alkylthio, $C_1$-$C_6$ alkylsulfonyl, —N($R^{90h}$)$R^{90g}$ or cyano.

[128] The condensed heterocyclic compound or its salt or an N-oxide thereof according to any one of the above [1] to [126], wherein
Y4 is $C_1$-$C_8$ alkoxy, $C_1$-$C_6$ alkylthio, $C_1$-$C_6$ alkylsulfonyl, —N($R^{90h}$)$R^{90g}$ or cyano.

[129] The condensed heterocyclic compound or its salt or an N-oxide thereof according to any one of the above [1] to [126], wherein
Y4 is a hydrogen atom, a halogen atom, $C_1$-$C_6$ alkyl or $C_1$-$C_6$ haloalkyl.

[130] The condensed heterocyclic compound or its salt or an N-oxide thereof according to any one of the above [1] to [126], wherein
Y4 is a hydrogen atom.

[131] The condensed heterocyclic compound or its salt or an N-oxide thereof according to any one of the above [1] to [126], wherein
Y4 is a halogen atom.

[132] The condensed heterocyclic compound or its salt or an N-oxide thereof according to any one of the above [1] to [126], wherein
Y4 is $C_1$-$C_6$ alkyl.

[133] The condensed heterocyclic compound or its salt or an N-oxide thereof according to any one of the above [1] to [126], wherein
Y4 is $C_1$-$C_6$ haloalkyl.

[134] The condensed heterocyclic compound or its salt or an N-oxide thereof according to any one of the above [1] to [133], wherein
$Y^1$ is $C_1$-$C_8$ alkoxycarbonyl or $C_1$-$C_6$ alkylcarbonyl.

[135] The condensed heterocyclic compound or its salt or an N-oxide thereof according to any one of the above [1] to [133], wherein
$Y^a$ is $C_1$-$C_8$ alkoxycarbonyl.

[136] The condensed heterocyclic compound or its salt or an N-oxide thereof according to any one of the above [1] to [135], wherein
$Y^b$ is $C_1$-$C_6$ alkyl, $C_3$-$C_6$ cycloalkyl, trimethylsilyl or phenyl.

[137] The condensed heterocyclic compound or its salt or an N-oxide thereof according to any one of the above [1] to [135], wherein
$Y^b$ is $C_3$-$C_6$ cycloalkyl or trimethylsilyl.

[138] The condensed heterocyclic compound or its salt or an N-oxide thereof according to any one of the above [1] to [135], wherein
$Y^b$ is $C_3$-$C_6$ cycloalkyl.

[139] The condensed heterocyclic compound or its salt or an N-oxide thereof according to any one of the above [1] to [135], wherein
$Y^b$ is trimethylsilyl.

[140] The condensed heterocyclic compound or its salt or an N-oxide thereof according to any one of the above [1] to [139], wherein
$Y^c$ is a halogen atom, $C_1$-$C_6$ alkyl, $C_1$-$C_6$ haloalkyl, $C_1$-$C_8$ alkoxy, $C_1$-$C_8$ haloalkoxy, cyano or nitro.

[141] The condensed heterocyclic compound or its salt or an N-oxide thereof according to any one of the above [1] to [139], wherein
$Y^c$ is a halogen atom or $C_1$-$C_6$ haloalkyl.

[142] The condensed heterocyclic compound or its salt or an N-oxide thereof according to any one of the above [1] to [139], wherein
$Y^c$ is a halogen atom.

[143] The condensed heterocyclic compound or its salt or an N-oxide thereof according to any one of the above [1] to [139], wherein
$Y^c$ is $C_1$-$C_6$ haloalkyl.

[140] The condensed heterocyclic compound or its salt or an N-oxide thereof according to any one of the above [1] to [143], wherein
each of $R^{10a}$, $R^{20a}$, $R^{30a}$, $R^{30e}$, $R^{40a}$, $R^{40e}$, $R^{50a}$, $R^{60a}$ and $R^{90a}$ is independently a hydrogen atom, $C_1$-$C_6$ alkyl, $C_1$-$C_6$ haloalkyl, $C_1$-$C_8$ alkoxy or $C_1$-$C_8$ haloalkoxy.

[145] The condensed heterocyclic compound or its salt or an N-oxide thereof according to any one of the above [1] to [143], wherein
each of $R^{10a}$, $R^{20a}$, $R^{30a}$, $R^{30e}$, $R^{40a}$, $R^{40e}$, $R^{50a}$, $R^{60a}$ and $R^{90a}$ is independently a hydrogen atom, $C_1$-$C_6$ alkyl or $C_1$-$C_8$ alkoxy.

[146] The condensed heterocyclic compound or its salt or an N-oxide thereof according to any one of the above [1] to [143], wherein
each of $R^{10a}$, $R^{20a}$, $R^{30a}$, $R^{30e}$, $R^{40a}$, $R^{40e}$, $R^{50a}$, $R^{60a}$ and $R^{90a}$ is a hydrogen atom.

[147] The condensed heterocyclic compound or its salt or an N-oxide thereof according to any one of the above [1] to [143], wherein
each of $R^{10a}$, $R^{20a}$, $R^{30a}$, $R^{30e}$, $R^{40a}$, $R^{40e}$, $R^{50a}$, $R^{60a}$ and $R^{90a}$ is independently $C_1$-$C_6$ alkyl.

[148] The condensed heterocyclic compound or its salt or an N-oxide thereof according to any one of the above [1] to [143], wherein
each of $R^{10a}$, $R^{20a}$, $R^{30a}$, $R^{30e}$, $R^{40a}$, $R^{40e}$, $R^{50a}$, $R^{60a}$ and $R^{90a}$ is independently $C_1$-$C_8$ alkoxy.

[149] The condensed heterocyclic compound or its salt or an N-oxide thereof according to any one of the above [1] to [148], wherein
each of $R^{20g}$, $R^{20h}$, $R^{30f}$, $R^{30g}$, $R^{30h}$, $R^{30i}$, $R^{40f}$, $R^{40g}$, $R^{40h}$, $R^{40i}$, $R^{50g}$, $R^{50h}$, $R^{60g}$, $R^{60h}$, $R^{90b}$, $R^{90c}$, $R^{90i}$, $R^{90j}$ and $R^{90k}$ is independently $C_1$-$C_6$ alkyl or $C_1$-$C_6$ haloalkyl.

[150] The condensed heterocyclic compound or its salt or an N-oxide thereof according to any one of the above [1] to [148], wherein each of $R^{20g}$, $R^{20h}$, $R^{30f}$, $R^{30g}$, $R^{30h}$, $R^{30i}$, $R^{40f}$, $R^{40g}$, $R^{40h}$, $R^{40i}$, $R^{50g}$, $R^{50h}$, $R^{60g}$, $R^{60h}$, $R^{90b}$, $R^{90c}$, $R^{90i}$, $R^{90j}$ and $R^{90k}$ is independently $C_1$-$C_6$ alkyl.

[151] The condensed heterocyclic compound or its salt or an N-oxide thereof according to any one of the above [1] to [150], wherein each of $R^{90g}$ and $R^{90h}$ is independently $C_1$-$C_6$ alkyl, $C_1$-$C_6$ haloalkyl, $C_1$-$C_6$ alkylcarbonyl, $C_1$-$C_6$ haloalkylcarbonyl, $C_1$-$C_8$ alkoxycarbonyl, $C_1$-$C_8$ haloalkoxycarbonyl, $C_1$-$C_6$ alkylaminocarbonyl, $C_1$-$C_6$ haloalkylaminocarbonyl, $C_1$-$C_6$ alkylaminothiocarbonyl, $C_1$-$C_6$ haloalkylaminothiocarbonyl, phenylcarbonyl, $C_1$-$C_6$ alkylsulfonyl, $C_1$-$C_6$ haloalkylsulfonyl, $C_1$-$C_6$ alkylaminosulfonyl or di($C_1$-$C_6$) alkylaminosulfonyl.

[152] The condensed heterocyclic compound or its salt or an N-oxide thereof according to any one of the above [1] to [151], wherein $R^{90g}$ is $C_1$-$C_6$ alkyl, $C_1$-$C_6$ haloalkylcarbonyl, $C_1$-$C_8$ alkoxycarbonyl or phenylcarbonyl.

[153] The condensed heterocyclic compound or its salt or an N-oxide thereof according to any one of the above [1] to [151], wherein $R^{90g}$ is $C_1$-$C_6$ alkyl.

[154] The condensed heterocyclic compound or its salt or an N-oxide thereof according to any one of the above [1] to [151], wherein $R^{90g}$ is $C_1$-$C_6$ haloalkylcarbonyl.

[155] The condensed heterocyclic compound or its salt or an N-oxide thereof according to any one of the above [1] to [151], wherein $R^{90g}$ is $C_1$-$C_8$ alkoxycarbonyl.

[156] The condensed heterocyclic compound or its salt or an N-oxide thereof according to any one of the above [1] to [151], wherein $R^{90g}$ is phenylcarbonyl.

[157] The condensed heterocyclic compound or its salt or an N-oxide thereof according to any one of the above [1] to [156], wherein $R^{90h}$ is $C_1$-$C_6$ alkyl.

[158] The condensed heterocyclic compound or its salt or an N-oxide thereof according to any one of the above [1] to [157], wherein $T_1$ is a sulfur atom.

[159] The condensed heterocyclic compound or its salt or an N-oxide thereof according to any one of the above [1] to [157], wherein $T_1$ is $N(T_{1a})$.

[160] The condensed heterocyclic compound or its salt or an N-oxide thereof according to any one of the above [1] to [159], wherein $T_{1a}$ is a hydrogen atom.

[161] The condensed heterocyclic compound or its salt or an N-oxide thereof according to any one of the above [1] to [159], wherein $T_{1a}$ is $C_1$-$C_6$ alkyl.

[162] A pesticide containing one or more members selected from the condensed heterocyclic compounds and their salts as defined in the above [1] to [161] as active ingredient(s).

[163] An agricultural chemical containing one or more members selected from the condensed heterocyclic compounds and their salts as defined in the above [1] to [161] as active ingredient(s).

[164] A parasiticide against internal or external parasites in or on a mammal or bird, containing one or more members selected from the condensed heterocyclic compounds and their salts as defined in the above [1] to [161] as active ingredient(s).

[165] The parasiticide according to the above [164], wherein the external parasites are Siphonaptera or ticks.

[166] An insecticide or acaricide containing one or more members selected from the condensed heterocyclic compounds and their salts as defined in the above [1] to [161] as active ingredient(s).

[167] A seed treatment agent containing one or more members selected from the condensed heterocyclic compounds and their salts as defined in the above [1] to [161] as active ingredient(s).

[168] The seed treatment agent according to the above [167], which is used to treat seeds by dipping.

[169] A soil treatment agent containing one or more members selected from the condensed hetercyclic compounds as defined in the above [1] to [161] as active ingredient(s).

[170] The soil treatment agent according to the above [169], which is used to treat soil by irrigation.

Advantageous Effects of Invention

The compounds of the present invention have excellent insecticidal and acaricidal activities on many agricultural pest insects, spider mites, internal or external parasites in or on a mammal or bird and have sufficient controlling effect on pest insects which have acquired resistance to conventional insecticides. The compounds of the present invention have little harmful effect on mammals, fish and beneficial insects, show low persistence and are environmentally friendly. Thus, the present invention can provide useful novel pesticides.

DESCRIPTION OF EMBODIMENTS

The compounds of the present invention can have geometrical isomers such as E-isomers and Z-isomers, depending on the types of substituents in them, and the present invention covers both E-isomers and Z-isomers and mixtures containing them in any ratios.

The compounds of the present invention can have optically active isomers due to the presence of one or more asymmetric carbon atoms or asymmetric sulfur atoms, and the present invention covers any optically active isomers and any racemates.

Further, the compounds of the present invention can have tautomers depending on the type of substituents in them, and the present invention covers all tautomers and mixtures containing them in any ratios.

Some of the compounds of the present invention can be converted, by ordinary methods, to salts with hydrogen halides such as hydrofluoric acid, hydrochloric acid, hydrobromic acid and hydroiodic acid, with inorganic acids such as nitric acid, sulfuric acid, phosphoric acid, chloric acid and perchloric acid, with sulfonic acids such as methanesulfonic acid, ethanesulfonic acid, trifluoromethanesulfonic acid, benzenesulfonic acid and p-toluenesulfonic acid, with carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid, with amino acids such as glutamic acid and aspartic acid, with alkali metals such as lithium, sodium and potassium, with alkaline earth metals such as calcium, barium and magnesium, with aluminum, and with quaternary ammonium such as tetramethylammonium, tetrabutylammonium and benzyltrimethylammonium.

In the present invention, the N-oxide is a compound having a nitrogen atom constituting the ring in the heterocyclic group oxidized. A heterocyclic group which may constitute an N-oxide may, for example, be a condensed ring containing a pyridine ring, a condensed ring containing a pyrazine ring, a condensed ring containing a pyridazine ring or a condensed ring containing a pyrimidine ring.

Next, specific examples of each substituent used herein will be given below. n-denotes normal, i-iso, s-secondary, and tert-tertiary.

As a "halogen atom" in the compounds of the present invention, a fluorine atom, a chlorine atom, a bromine atom or an iodine atom may be mentioned. Herein, the expression "halo" also means such a halogen atom.

The expression "$C_a$-$C_b$ alkyl" herein means a linear or branched hydrocarbon group containing from a to b carbon atoms such as methyl, ethyl, n-propyl, i-propyl, n-butyl, i-butyl, s-butyl, tert-butyl, n-pentyl, 1,1-dimethylpropyl or n-hexyl, and those within the designated carbon number range are selected.

The expression "$C_a$-$C_b$ haloalkyl" herein means a linear or branched hydrocarbon group containing from a to b carbon atoms in which hydrogen atom(s) on carbon atom(s) are optionally substituted with halogen atom(s) which may be identical with or different from one another if two or more halogen atoms are present, such as fluoromethyl, chloromethyl, bromomethyl, iodomethyl, difluoromethyl, dichloromethyl, trifluoromethyl, chlorodifluoromethyl, trichloromethyl, bromodifluoromethyl, 1-fluoroethyl, 2-fluoroethyl, 2-chloroethyl, 2-bromoethyl, 2,2-difluoroethyl, 2,2,2-trifluoroethyl, 2-chloro-2,2-difluoroethyl, 2,2,2-trichloroethyl, 2-bromo-2,2-difluoroethyl, 1,1,2,2-tetrafluoroethyl, 2-chloro-1,1,2-trifluoroethyl, 2-chloro-1,1,2,2-tetrafluoroethyl, pentafluoroethyl, 2,2-difluoropropyl, 3,3,3-trifluoropropyl, 3-bromo-3,3-difluoropropyl, 2,2,3,3-tetrafluoropropyl, 2,2,3,3,3-pentafluoropropyl, 1,1,2,3,3,3-hexafluoropropyl, heptafluoropropyl, 2,2,2-trifluoro-1-(methyl)ethyl, 2,2,2-trifluoro-1-(trifluoromethyl)ethyl, 1,2,2,2-tetrafluoro-1-(trifluoromethyl)ethyl, 2,2,3,4,4,4-hexafluorobutyl, 2,2,3,3,4,4,4-heptafluorobutyl and nonafluorobutyl, and those within the designated carbon number range are selected.

The expression "$C_a$-$C_b$ alkenyl" herein means a linear or branched unsaturated hydrocarbon group containing from a to b carbon atoms and having one or more double bonds in the molecule, such as vinyl, 1-propenyl, 2-propenyl, 1-methylethenyl, 2-butenyl, 2-methyl-2-propenyl, 3-methyl-2-butenyl or 1,1-dimethyl-2-propenyl, and those within the designated carbon number range are selected.

The expression "$C_a$-$C_b$ haloalkenyl" herein means a linear or branched unsaturated hydrocarbon group containing from a to b carbon atoms and having one or more double bonds in the molecule, in which hydrogen atom(s) on carbon atom(s) are optionally substituted with halogen atom(s) which may be identical with or different from one another if two or more halogen atoms are present, such as 2,2-dichlorovinyl, 2-fluoro-2-propenyl, 2-chloro-2-propenyl, 3-chloro-2-propenyl, 2-bromo-2-propenyl, 3,3-difluoro-2-propenyl, 2,3-dichloro-2-propenyl, 3,3-dichloro-2-propenyl, 2,3,3-trifluoro-2-propenyl, 2,3,3-trichloro-2-propenyl, 1-(trifluoromethyl)ethenyl, 4,4-difluoro-3-butenyl, 3,4,4-trifluoro-3-butenyl or 3-chloro-4,4,4-trifluoro-2-butenyl, and those within the designated carbon number range are selected.

The expression "$C_a$-$C_b$ alkynyl" herein means a linear or branched unsaturated hydrocarbon group containing from a to b carbon atoms and having one or more triple bonds in the molecule, such as ethynyl, propargyl, 2-butynyl, 3-butynyl, 1-pentynyl, 1-hexynyl or 4,4,4-trifluoro-2-butynyl, and those within the designated carbon number range are selected.

The expression "$C_a$-$C_b$ haloalkynyl" herein means a linear or branched unsaturated hydrocarbon group containing from a to b carbon atoms and having one or more triple bonds in the molecule, in which hydrogen atom(s) on carbon atom(s) are optionally substituted with halogen atom(s) which may be identical with or different from one another if two or more halogen atoms are present, such as 2-chloroethynyl, 2-bromoethynyl, 2-iodoethynyl, 3-chloro-2-propynyl, 3-bromo-2-propynyl or 3-iodo-2-propynyl, and those within the designated carbon number range are selected.

The expression "$C_a$-$C_b$ cycloalkyl" herein means a cyclic hydrocarbon group containing from a to b carbon atoms in the form of a 3- to 6-membered monocyclic or polycyclic ring which may optionally be substituted with an alkyl group as long as the number of carbon atoms does not exceed the designated carbon number range, such as cyclopropyl, 1-methylcyclopropyl, 2-methylcyclopropyl, 2,2-dimethylcyclopropyl, cyclobutyl, cyclopentyl or cyclohexyl, and those within the designated carbon number range are selected.

The expression "$C_a$-$C_b$ halocycloalkyl" herein means a cyclic hydrocarbon group containing from a to b carbon atoms in the form of a 3- to 6-membered monocyclic or polycyclic ring which may optionally be substituted with an alkyl group as long as the number of carbon atoms does not exceed the designated carbon number range, in which hydrogen atom(s) on carbon atom(s) in a ring moiety and/or in a side chain are optionally substituted with halogen atom(s) which may be identical with or different from one another if two or more halogen atoms are present, such as 2,2-difluorocyclopropyl, 2,2-dichlorocyclopropyl, 2,2-dibromocyclopropyl, 2,2-difluoro-1-methylcyclopropyl, 2,2-dichloro-1-methylcyclopropyl, 2,2-dibromo-1-methylcyclopropyl or 2,2,3,3-tetrafluorocyclobutyl, and those within the designated carbon number range are selected.

The expression "$C_a$-$C_b$ alkoxy" herein means an alkyl-O— group in which the alkyl is a previously mentioned alkyl group containing from a to b carbon atoms, such as methoxy, ethoxy, n-propyloxy, i-propyloxy, n-butyloxy, i-butyloxy, s-butyloxy, tert-butyloxy or 2-ethylhexyloxy, and those within the designated carbon number range are selected.

The expression "$C_a$-$C_b$ haloalkoxy" herein means a haloalkyl-O— group in which the haloalkyl is a previously mentioned haloalkyl group containing from a to b carbon atoms, such as difluoromethoxy, trifluoromethoxy, chlorodifluoromethoxy, bromodifluoromethoxy, 2-fluoroethoxy, 2-chloroethoxy, 2,2,2-trifluoroethoxy, 1,1,2,2,-tetrafluoroethoxy, 2-chloro-1,1,2-trifluoroethoxy or 1,1,2,3,3,3-hexafluoropropyloxy, and those within the designated carbon number range are selected.

The expression "$C_a$-$C_b$ alkenyloxy" herein means an alkenyl-O— group in which the alkenyl is a previously mentioned alkenyl group containing from a to b carbon atoms, such as 2-propenyloxy, 2-butenyloxy, 2-methyl-2-propenyloxy or 3-methyl-2-butenyloxy, and those within the designated carbon number range are selected.

The expression "$C_a$-$C_b$ haloalkenyloxy" herein means a haloalkenyl-O— group in which the haloalkenyl is a previously mentioned haloalkenyl group containing from a to b carbon atoms, such as 3,3-difluoroallyloxy or 3,3-dichloroallyloxy, and those within the designated carbon number range are selected.

The expression "$C_a$-$C_b$ alkynyloxy" herein means an alkynyl-O— group in which the alkynyl is a previously mentioned alkynyl group containing from a to b carbon atoms, such as ethynyloxy, propargyloxy, 2-butynyloxy, 1-pentynyloxy or 1-hexynyloxy, and those within the designated carbon number range are selected.

The expression "$C_a$-$C_b$ haloalkynyloxy" herein means a haloalkynyl-O— group in which the haloalkynyl is a previously mentioned haloalkynyl group containing from a to b carbon atoms, such as 3-chloro-2-propynyloxy, 3-bromo-2-propynyloxy or 3-iodo-2-propynyloxy, and those within the designated carbon number range are selected.

The expression "$C_a$-$C_b$ alkylthio" herein means an alkyl-S— group in which the alkyl is a previously mentioned alkyl group containing from a to b carbon atoms, such as methylthio, ethylthio, n-propylthio, i-propylthio, n-butylthio, i-butylthio, s-butylthio or tert-butylthio, and those within the designated carbon number range are selected.

The expression "$C_a$-$C_b$ haloalkylthio" herein means a haloalkyl-S— group in which the haloalkyl is a previously mentioned haloalkyl group containing from a to b carbon atoms, such as difluoromethylthio, trifluoromethylthio, chlorodifluoromethylthio, bromodifluoromethylthio, 2,2,2-trifluoroethylthio, 1,1,2,2-tetrafluoroethylthio, 2-chloro-1,1,2-trifluoroethylthio, pentafluoroethylthio, 1,1,2,3,3,3-hexafluoropropylthio, heptafluoropropylthio, 1,2,2,2-tetrafluoro-1-(trifluoromethyl)ethylthio or nonafluorobutylthio, and those within the designated carbon number range are selected.

The expression "$C_a$-$C_b$ alkenylthio" herein means an alkenyl-S— group in which the alkenyl is a previously mentioned alkenyl group containing from a to b carbon atoms, such as 2-propenylthio, 2-butenylthio, 2-methyl-2-propenylthio or 3-methyl-2-butenylthio, and those within the designated carbon number range are selected.

The expression "$C_a$-$C_b$ haloalkenylthio" herein means a haloalkenyl-S— group in which the haloalkenyl is a previously mentioned haloalkenyl group containing from a to b carbon atoms, such as 2-fluoro-2-propenylthio, 2-chloro-2-propenylthio, 3,3-difluoro-2-propenylthio, 3,3-dichloro-2-propenylthio, 2,3,3-trifluoro-2-propenylthio, 4,4-difluoro-3-butenylthio or 3,4,4-trifluoro-3-butenylthio, and those within the designated carbon number range are selected.

The expression "$C_a$-$C_b$ alkynylthio" herein means an alkynyl-S— group in which the alkynyl is a previously mentioned alkynyl group containing from a to b carbon atoms, such as propynylthio, butynyithio, pentynylthio or hexynylthio, and those within the designated carbon number range are selected.

The expression "$C_a$-$C_b$ haloalkynylthio" herein means a haloalkynyl-S— group in which the haloalkynyl is a previously mentioned haloalkynyl group containing from a to b carbon atoms, such as 3-chloro-2-propynylthio, 3-bromo-2-propynylthio or 3-iodo-2-propynylthio, and those within the designated carbon number range are selected.

The expression "$C_a$-$C_b$ alkylsulfinyl" herein means an alkyl-S(O)— group in which the alkyl is a previously mentioned alkyl group containing from a to b carbon atoms, such as methylsulfinyl, ethylsufinyl, n-propylsulfinyl, i-propylsulfinyl, n-butylsulfinyl, i-butylsulfinyl, s-butylsulfinyl or tert-butylsulfinyl, and those within the designated carbon number range are selected.

The expression "$C_a$-$C_b$ haloalkylsulfinyl" herein means a haloalkyl-S(O)— group in which the haloalkyl is a previously mentioned haloalkyl group containing from a to b carbon atoms, such as difluoromethylsulfinyl, trifluoromethylsulfinyl, chlorodifluoromethylsufinyl, bromodifluoromethylsulfinyl, 2,2,2-trifluoroethylsulfinyl, 1,2,2,2-tetrafluoro-1-(trifluoromethyl)ethylsulfinyl or nonafluorobutylsulfinyl, and those within the designated carbon number range are selected.

The expression "$C_a$-$C_b$ alkenylsulfinyl" herein means an alkenyl-S(O)— group in which the alkenyl is a previously mentioned alkenyl group containing from a to b carbon atoms, such as 2-propenylsulfinyl, 2-butenylsulfinyl, 2-methyl-2-propenylsulfinyl or 3-methyl-2-butenylsulfinyl, and those within the designated carbon number range are selected.

The expression "$C_a$-$C_b$ haloalkenylsulfinyl" herein means a haloalkenyl-S(O)— group in which the haloalkenyl is a previously mentioned haloalkenyl group containing from a to b carbon atoms, such as 2-fluoro-2-propenylsulfinyl, 2-chloro-2-propenylsulfinyl, 3,3-difluoro-2-propenylsufinyl, 3,3-dichloro-2-propenylsulfinyl, 4,4-difluoro-3-butenylsulfinyl or 3,4,4-trifluoro-3-butenylsulfinyl, and those within the designated carbon number range are selected.

The expression "$C_a$-$C_b$ alkynylsulfinyl" herein means an alkynyl-S(O)— group in which the alkynyl is a previously mentioned alkynyl group containing from a to b carbon atoms, such as 2-propynylsulfinyl or 2-butynylsulfinyl, and those within the designated carbon number range are selected.

The expression "$C_a$-$C_b$ haloalkynylsulfinyl" herein means a haloalkynyl-S(O)— group in which the haloalkynyl is a previously mentioned haloalkynyl group containing from a to b carbon atoms, such as 3-chloro-2-propynylsulfinyl, 3-bromo-2-propynylsulfinyl or 3-iodo-2-propynylsulfinyl, and those within the designated carbon number range are selected.

The expression "$C_a$-$C_b$ alkylsulfonyl" herein means an alkyl-$SO_2$— group in which the alkyl is a previously mentioned alkyl group containing from a to b carbon atoms, such as methylsulfonyl, ethylsulfonyl, n-propylsulfonyl, i-propylsulfonyl, n-butylsulfonyl, i-butylsulfonyl, s-butylsulfonyl or tert-butylsulfonyl, and those within the designated carbon number range are selected.

The expression "$C_a$-$C_b$ haloalkylsulfonyl" herein means a haloalkyl-$SO_2$— group in which the haloalkyl is a previously mentioned haloalkyl group containing from a to b carbon atoms, such as difluoromethylsulfonyl, trifluoromethylsulfonyl, chlorodifluoromethylsulfonyl, bromodifluoromethylsulfonyl, 2,2,2-trifluoroethylsulfonyl, 1,1,2,2-tetrafluoroethylsulfonyl or 2-chloro-1,1,2-trifluoroethylsulfonyl, and those within the designated carbon number range are selected.

The expression "$C_a$-$C_b$ alkenylsulfonyl" herein means an alkenyl-$SO_2$— group in which the alkenyl is a previously mentioned alkenyl group containing from a to b carbon atoms, such as 2-propenylsulfonyl, 2-butenylsulfonyl, 2-methyl-2-propenylsulfonyl or 3-methyl-2-butenylsulfonyl, and those within the designated carbon number range are selected.

The expression "$C_a$-$C_b$ haloalkenylsulfonyl" herein means a haloalkenyl-$SO_2$— group in which the haloalkenyl is a previously mentioned haloalkenyl group containing from a to b carbon atoms, such as 2-fluoro-2-propenylsulfonyl, 2-chloro-2-propenylsulfonyl, 3,3-difluoro-2-propenylsulfonyl, 3,3-dichloro-2-propenylsulfonyl, 4,4-difluoro-3-butenylsulfonyl or 3,4,4-trifluoro-3-butenylsulfonyl, and those within the designated carbon number range are selected.

The expression "$C_a$-$C_b$ alkynylsulfonyl" herein means an alkynyl-$SO_2$— group in which the alkynyl is a previously mentioned alkynyl group containing from a to b carbon atoms, such as 2-propynylsulfonyl or 2-butynylsulfonyl, and those within the designated carbon number range are selected.

The expression "$C_a$-$C_b$ haloalkynylsulfonyl" herein means a haloalkynyl-$SO_2$— group in which the haloalkynyl is a previously mentioned haloalkynyl group containing from a to b carbon atoms, such as 3-chloro-2-propynylsulfonyl, 3-bromo-2-propynylsulfonyl or 3-iodo-2-propynylsulfonyl, and those within the designated carbon number range are selected.

The expression "$C_a$-$C_b$ alkylamino" herein means an amino group in which either hydrogen atom is replaced with a previously mentioned alkyl group containing from a to b carbon atoms, such as methylamino, ethylamino, n-propylamino, i-propylamino, n-butylamino, i-butylamino or tert-butylamino, and those within the designated carbon number range are selected.

The expression "$C_a$-$C_b$ haloalkylamino" herein means an amino group in which either hydrogen atom is replaced with a previously mentioned haloalkyl group containing from a to b carbon atoms, such as 2,2,2-trifluoroethylamino, 2-chloro-2,2-difluoroethylamino or 3,3,3-trifluoropropylamino, and those within the designated carbon number range are selected.

The expression "di($C_a$-$C_b$) alkylamino" herein means an amino group in which both hydrogen atoms are replaced with previously mentioned alkyl groups containing from a to b carbon atoms which may be identical with or different from each other, such as dimethylamino, ethyl(methyl)amino, diethylamino, n-propyl(methyl)amino, i-propyl(methyl)amino, di(n-propyl)amino or di(n-butyl)amino, and those within the designated carbon number range are selected.

The expression "di($C_a$-$C_b$) haloalkylamino" herein means an amino group in which both hydrogen atoms are replaced with previously mentioned haloalkyl groups containing from a to b carbon atoms which may be identical with or different from each other, such as bis(2,2,2-trifluoroethyl)amino, and those within the designated carbon number range are selected.

The expression "$C_a$-$C_b$ alkylcarbonyl" herein means an alkyl-C(O)— group in which the alkyl means a previously mentioned alkyl group containing from a to b carbon atoms, such as acetyl, propionyl, butyryl, isobutyryl, valeryl, isovaleryl, 2-methylbutanoyl, pivaloyl, hexanoyl or heptanoyl, and those within the designated carbon number range are selected.

The expression "$C_a$-$C_b$ haloalkylcarbonyl" herein means a haloalkyl-C(O)— group in which the haloalkyl means a previously mentioned haloalkyl group containing from a to b carbon atoms, such as fluoroacetyl, chloroacetyl, difluoroacetyl, dichloroacetyl, trifluoroacetyl, chlorodifluoroacetyl, bromodifluoroacetyl, trichloroacetyl, pentafluoropropionyl, heptafluorobutanoyl or 3-chloro-2,2-dimethylpropanoyl, and those within the designated carbon number range are selected.

The expression "$C_a$-$C_b$ alkoxycarbonyl" herein means an alkyl-O—C(O)— group in which the alkyl means a previously mentioned alkyl group containing from a to b carbon atoms, such as methoxycarbonyl, ethoxycarbonyl, n-propyloxycarbonyl, i-propyloxycarbonyl, n-butoxycarbonyl, i-butoxycarbonyl, s-butoxycarbonyl, tert-butoxycarbonyl or 2-ethylhexyloxycarbonyl, and those within the designated carbon number range are selected.

The expression "$C_a$-$C_b$ haloalkoxycarbonyl" herein means a haloalkyl-O—C(O)— group in which the haloalkyl means a previously mentioned haloalkyl group containing from a to b carbon atoms, such as chloromethoxycarbonyl, 2-chloroethoxycarbonyl, 2,2-difluoroethoxycarbonyl, 2,2,2-trifluoroethoxycarbonyl or 2,2,2-trichloroethoxycarbonyl, and those within the designated carbon number range are selected.

The expression "$C_a$-$C_b$ alkylaminocarbonyl" herein means a carbamoyl group in which either hydrogen atom is replaced with a previously mentioned alkyl group containing from a to b carbon atoms, such as methylcarbamoyl, ethylcarbamoyl, n-propylcarbamoyl, i-propylcarbamoyl, n-butylcarbamoyl, i-butylcarbamoyl, s-butylcarbamoyl or tert-butylcarbamoyl, and those within the designated carbon number range are selected.

The expression "$C_a$-$C_b$ haloalkylaminocarbonyl" herein means a carbamoyl group in which either hydrogen atom is replaced with a previously mentioned haloalkyl group containing from a to b carbon atoms, such as 2-fluoroethylcarbamonyl, 2-chloroethylcarbamoyl, 2,2-difluoroethylcarbamoyl or 2-trifluoroethylcarbamoyl, and those within the designated carbon number range are selected.

The expression "$C_a$-$C_b$ alkylaminothiocarbonyl" herein means an amino-C(=S)— group in which either hydrogen atom is replaced with a previously mentioned alkyl group containing from a to b carbon atoms, such as methylthiocarbamoyl, ethylthiocarbamoyl, n-propylthiocarbamoyl, i-propylthiocarbamoyl, n-butylthiocarbamoyl, i-butylthiocarbamoyl, s-butylthiocarbamoyl or tert-butylthiocarbamoyl, and those within the designated carbon number range are selected.

The expression "$C_a$-$C_b$ haloalkylaminothiocarbonyl" herein means an amino-C(=S)— group in which either hydrogen atom is replaced with a previously mentioned haloalkyl group containing from a to b carbon atoms, such as 2-fluoroethylthiocarbamoyl, 2-chloroethylthiocarbamoyl, 2,2-difluoroethylthiocarbamoyl or 2-trifluoroethylthiocarbamoyl, and those within the designated carbon number range are selected.

The expression "$C_a$-$C_b$ alkylaminosulfonyl" herein means a sulfamoyl group in which either hydrogen atom is replaced with a previously mentioned alkyl group containing from a to b carbon atoms, such as methylsulfamoyl, ethylsulfamoyl, n-propylsulfamoyl, i-propylsulfamoyl, n-butylsulfamoyl, i-butylsulfamoyl, s-butylsulfamoyl or tert-butylsulfamoyl, and those within the designated carbon number range are selected.

The expression "di($C_a$-$C_b$) alkylaminosulfonyl" herein means a sulfamoyl group in which both hydrogen atoms are replaced with previously mentioned alkyl groups containing from a to b carbon atoms which may be identical with or different from each other, such as N,N-dimethylsulfamoyl, N-ethyl-N-methylsulfamoyl, N,N-diethylsulfamoyl, N,N-di(n-propyl)sulfamoyl or N,N-di(n-butyl)sulfamoyl, and those within the designated carbon number range are selected.

The expression "heterocyclyl" herein may, for example, be specifically thiophen-2-yl, thiophen-3-yl, furan-2-yl, furan-3-yl, pyrrol-1-yl, pyrrol-2-yl, pyrrol-3-yl, oxazol-2-yl, oxazol-4-yl, oxazol-5-yl, isoxazol-3-yl, isoxazol-4-yl, isoxazol-5-yl, isoxazolin-3-yl, isoxazolin-4-yl, isoxazolin-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, pyrazol-5-yl, imidazol-1-yl, imidazol-2-yl, imidazol-4-yl, 1,3,4-oxadiazol-2-yl, 1,2,4-oxadiazol-3-yl, 1,2,4-oxadiazol-5-yl, 1,3,4-thiadiazol-2-yl, 1,2,4-thiadiazol-3-yl, 1,2,4-thiadiazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,3-triazol-1-yl, 1,2,3-triazol-2-yl, 1,2,3-triazol-4-yl, 1,2,3,4-tetrazol-1-yl, 1,2,3,4-tetrazol-2-yl, 1,2,3,4- tetrazol-5-yl, pyridin-2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, benzothiophen-2-yl, benzothiophen-3-yl, benzothiophen-4-yl, benzothiophen-5-yl, benzothiophen-6-yl, benzothiophen-7-yl, benzofuran-2-yl, benzofuran-3-yl, benzofuran-4-yl, benzofuran-5-yl, benzofuran-6-yl, benzofuran-7-yl, indol-1-yl, indol-2-yl, indol-3-yl, indol-4-yl, indol-5-yl, indol-6-yl, indol-7-yl, benzothiazol-2-yl, benzothiazol-4-yl, benzothiazol-5-yl, benzothiazol-6-yl, benzothiazol-7-yl, benzimidazol-1-yl, benzimidazol-2-yl, benzimidazol-4-yl, benzimidazol-5-yl, benzimidazol-6-yl, benzimidazol-7-yl, benzisoxazol-3-yl, benzisoxazol-4-yl, benzisoxazol-5-yl, benzisoxazol-6-yl, benzisoxazol-7-yl, benzisothiazol-3-yl, benzisothiazol-4-yl, benzisothiazol-5-yl, benzisothiazol-6-yl, benzisothiazol-7-yl, indazol-1-yl, indazol-3-yl, indazol-4-yl, indazol-5-yl, indazol-6-yl, indazol-7-yl, benzoxazol-2-yl, benzoxazol-4-yl, benzoxazol-5-yl, benzoxazol-6-yl, benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, quinoxalin-2-yl, quinoxalin-3-yl, quinoxalin-5-yl, quinoxalin-6-yl, quinoxalin-7-yl, quinoxalin-8-yl, phthalazin-1-yl, phthalazin-4-yl, phthalazin-5-yl, phthalazin-6-yl, phthalazin-7-yl, phthalazin-8-yl, cinnolin-3-yl, cinnolin-4-yl, cinnolin-5-yl, cinnolin-6-yl, cinnolin-7-yl, cinnolin-8-yl, quinazolin-2-yl, quinazolin-4-yl, quinazolin-5-yl, quinazolin-6-yl, quinazolin-7-yl or quinazolin-8-yl.

The expression such as "$C_a$-$C_b$ cycloalkyl ($C_d$-$C_e$) alkyl", "$C_a$-$C_b$ halocycloalkyl ($C_d$-$C_e$) alkyl" or "hydroxy ($C_d$-$C_e$) alkyl" herein means a previously mentioned alkyl group containing from d to e carbon atoms in which hydrogen atom(s) on carbon atom(s) are optionally substituted with an optional previously mentioned $C_a$-$C_b$ cycloalkyl, $C_a$-$C_b$ halocycloalkyl or hydroxy, and those within the designated carbon number range are selected.

The expression such as "($C_a$-$C_b$) alkyl optionally substituted with $R^{1a}$", "($C_1$-$C_6$) alkyl optionally substituted with $A^{1a-a}$" or "($C_1$-$C_6$) alkyl optionally substituted with $Y^a$" herein means a previously mentioned alkyl group having from a to b carbon atoms in which hydrogen atom(s) on carbon(s) are optionally substituted with optional $R^{1a}$ $A^{1a-a}$ or $Y^a$, and those within the designated carbon number range are selected. When there are two or more $R^{1a}$'s, $A^{1a-a}$'s or $Y^a$'s on ($C_a$-$C_b$) alkyl, each $R^{1a}$, $A^{1a-a}$ or $Y^a$ may be identical with or different from one another.

The expression such as "($C_a$-$C_b$) haloalkyl optionally substituted with $A^{1a-a}$" or "($C_a$-$C_b$) haloalkyl optionally substituted with $Y^a$" herein means a previously mentioned haloalkyl group having from a to b carbon atoms in which hydrogen atom(s) or halogen atom(s) on carbon atom(s) are optionally substituted with optional $A^{1a-a}$ or $Y^a$, and those within the designated carbon number range are selected. When there are two or more $A^{1a-a}$'s or $Y^a$'s on ($C_a$-$C_b$) haloalkyl, each $A^{1a-a}$ or $Y^a$ may be identical with or different from one another.

The expression such as "($C_a$-$C_b$) alkenyl optionally substituted with $Y^a$" herein means a previously mentioned alkenyl group having from a to b carbon atoms in which hydrogen atom(s) on carbon atom(s) are optionally substituted with optional $Y^a$, and those within the designated carbon number range are selected. When there are two or more $Y^a$'s on ($C_a$-$C_b$) alkenyl, each $Y^a$ may be identical with or different from one another.

The expression such as "($C_a$-$C_b$) alkynyl optionally substituted with $Y^b$" herein means a previously mentioned alkynyl group having from a to b carbon atoms in which hydrogen atom(s) on carbon atom(s) are optionally substituted with optional $Y^b$, and those within the designated carbon number range are selected. When there are two or more $Y^b$'s on ($C_a$-$C_b$) alkynyl, each $Y^b$ may be identical with or different from one another.

The expression such as "($C_a$-$C_b$) alkoxy optionally substituted with $Y^a$" herein means a previously mentioned alkoxy group having from a to b carbon atoms in which hydrogen atom(s) on carbon atom(s) are optionally substituted with optional $Y^a$, and those within the designated carbon number range are selected. When there are two or more $Y^a$'s on ($C_a$-$C_b$) alkoxy, each $Y^a$ may be identical with or different from one another.

The expression such as "($C_a$-$C_b$) alkenyloxy optionally substituted with $Y^a$" herein means a previously mentioned alkenyloxy group having from a to b carbon atoms in which hydrogen atom(s) on carbon atom(s) are optionally substituted with optional $Y^a$, and those within the designated carbon number range are selected. When there are two or more $Y^a$'s on ($C_a$-$C_b$) alkenyloxy, each $Y^a$ may be identical with or different from one another.

The expression such as "($C_a$-$C_b$) alkynyloxy optionally substituted with $Y^a$" herein means a previously mentioned alkynyloxy group having from a to b carbon atoms in which hydrogen atom(s) on carbon atom(s) are optionally substituted with optional $Y^a$, and those within the designated carbon number range are selected. When there are two or more $Y^a$'s on ($C_a$-$C_b$) alkynyloxy, each $Y^a$ may be identical with or different from one another.

The expression "($C_a$-$C_b$) alkylthio optionally substituted with $R^{3a}$", "($C_a$-$C_b$) alkylthio optionally substituted with $R^{4a}$" or "($C_a$-$C_b$) alkylthio optionally substituted with $Y^a$" herein means a previously mentioned alkylthio group having from a to b carbon atoms in which hydrogen atom(s) on carbon atom(s) are optionally substituted with optional $R^{3a}$, $R^{4a}$ or $Y^a$, and those within the designated carbon number range are selected. When there are two or more $R^{3a}$'s, $R^{4a}$'s or $Y^a$'s on ($C_a$-$C_b$) alkylthio, each $R^{3a}$, $R^{4a}$ or $Y^a$ may be identical with or different from one another.

The expression such as "($C_a$-$C_b$) alkylsulfinyl optionally substituted with $Y^a$" herein means a previously mentioned alkylsulfinyl group having from a to b carbon atoms in which hydrogen atom(s) on carbon atom(s) are optionally substituted with optional $Y^a$, and those within the designated carbon number range are selected. When there are two or more $Y^a$'s on ($C_a$-$C_b$) alkylsulfinyl, each $Y^a$ may be identical with or different from one another.

The expression such as "($C_a$-$C_b$) alkylsulfonyl optionally substituted with $Y^a$" herein means a previously mentioned alkylsulfonyl group having from a to b carbon atoms in which hydrogen atom(s) on carbon atom(s) are optionally substituted with optional $Y^a$, and those within the designated carbon number range are selected. When there are two or more $Y^a$'s on ($C_a$-$C_b$) alkylsulfonyl, each $Y^a$ may be identical with or different from one another.

The expression "phenyl optionally substituted with $R^{3b}$", "phenyl optionally substituted with $R^{4b}$" or "phenyl optionally substituted with $Y^c$" herein means a previously mentioned phenyl in which hydrogen atom(s) on carbon atom(s) are optionally substituted with optional $R^{3b}$, $R^{4b}$ or $Y^c$. When there are two or more $R^{3b}$'s, $R^{4b}$'s or $Y^c$'s on phenyl, each $R^{3b}$, $R^{4b}$ or $Y^c$ may be identical with or different from one another.

The expression such as "heterocyclyl optionally substituted with $R^{3b}$", "heterocyclyl optionally substituted with $R^{4b}$" or "heterocyclyl optionally substituted with $Y^c$" herein means a heterocyclic group in which hydrogen atom(s) on carbon atom(s) or nitrogen atom(s) are optionally substituted with optional $R^{3b}$, $R^{4b}$ or $Y^c$. When there are two or more $R^{3b}$'s, $R^{4b}$'s or $Y^c$'s, each $R^{3b}$, $R^{4b}$ or $Y^c$ may be identical with or different from one another.

Now, a process for producing the compound of the present invention represented by the above formula (1) will be described below.

The compounds of the present invention may be produced, for example, by the following Processes 1 to 17.

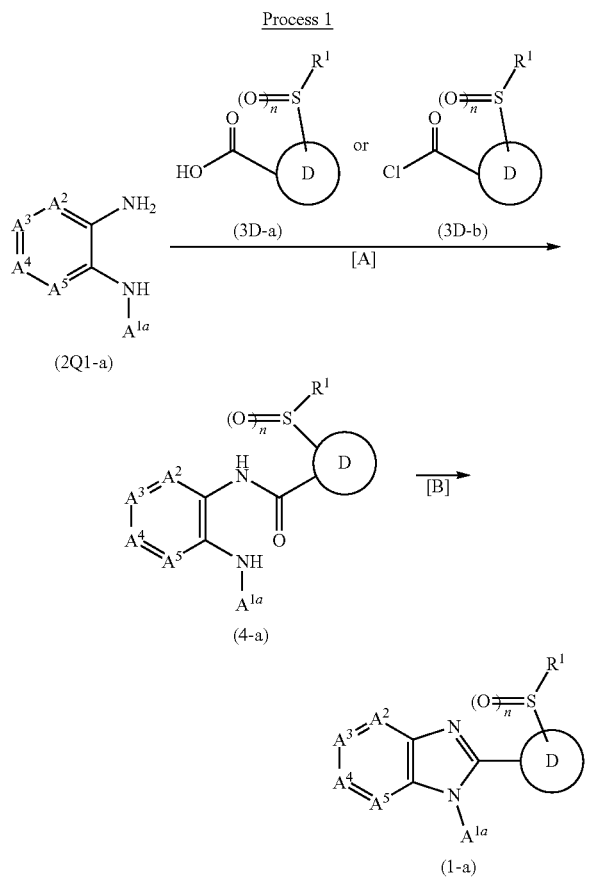

A compound represented by the formula (2Q1-a) (wherein $A^{1a}$, $A^2$, $A^3$, $A^4$ and $A^5$ are the same as defined above) and a compound represented by the formula (3D-a) (wherein $R^1$, D and n are the same as defined above) are reacted in a solvent or without solvent, as the case requires, in the presence of a dehydration condensation agent, and as the case requires, in the presence of a catalyst to produce a compound represented by the formula (4-a) (wherein $R^1$, $A^{1a}$, $A^2$, $A^3$, $A^4$, $A^5$, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a dehydration condensation agent. The dehydration condensation agent to be used may, for example, be 1H-benzotriazol-1-yloxytris(dimethylamino)phosphonium hexafluorophosphate, N,N'-dicyclohexylcarbodiimide, 1-ethyl-3-(3-dimethylaminopropyl)carbodiimide hydrochloride or 2-chloro-1-methylpyridinium iodide. The equivalent amount of the hehydration condensation agent used is from 0.1 to 100 equivalent amount, preferably from 1 to 20 equivalent amount based on the compound represented by the formula (2Q1-a).

The reaction may be carried out in the presence of a catalyst. The catalyst to be used may, for example, be 1-hydroxybenzotriazole or 4-(dimethylamino)pyridine. The equivalent amount of the catalyst used is from 0.005 to 20 quivalent amount, preferably from 0.1 to 5 equivalent amount based on the compound represented by the formula (2Q1-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (3D-a) may be used in an amount of from 0.5 to 50 equivilant amount, preferably from 1 to 20 equivalent amount based on the compound (2Q1-a).

Further, the compound represented by the formula (4-a) may be produced by reacting the compound represented by the formula (2Q1-a) and a compound represented by the formula (3D-b) (wherein $R^1$, D and n are the same as defined above) in a solvent or without solvent, and as the case requires, in the presence of a base. In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The equivalent amount of the base used is from 0.1 to 100 equivalent amount, preferably from 1 to 20 equivalent amount based on the compound represented by the formula (2Q1-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (3D-b) may be used in an amount of from 0.5 to 50 equivalent amount, preferably from 1 to 20 equivalent amount based on the compound (2Q1-a).

Then, the compound represented by the formula (4-a) is subjected to dehydration condensation in a solvent or without solvent, as the case requires, in the presence of an acid, and as the case requires, in the presence of a dehydration agent to produce a compound represented by the formula (1-a) (wherein $R^1$, $A^{1a}$, $A^2$, $A^3$, $A^4$, $A^5$, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of an acid. The acid to be used may, for example, be p-toluenesulfonic acid, polyphosphoric acid, acetic acid or propionic acid. The equivalent amount of the acid used is from 0.1 to 1,000 equivalent amount, preferably from 1 to 500 equivalent amount based on the compound represented by the formula (4-a).

The reaction may be carried out in the presence of a dehydration agent. The dehydration agent to be used may, for example, be phosphorus oxychloride or acetic anhydride. The equivalent amount of the dehydration agent used is from 0.5 to 50 equivalent amount, preferably from 1 to 20 equivalent amount based on the compound represented by the formula (4-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Some of compounds represented by the formula (2Q1-a) are known compounds, and some of them are commercially available. The rest of them may be prepared, for example, in accordance with the after-mentioned Reaction Scheme 4.

The compound represented by the formula (3D-a) may be prepared, for example, in accordance with the after-mentioned Reaction Scheme 1 or Reaction Scheme 2.

The compound represented by the formula (3D-b) may be prepared, for example, in accordance with the after-mentioned Reaction Scheme 1.

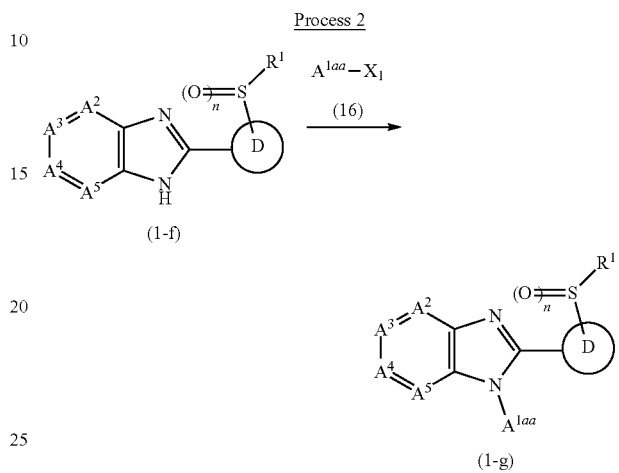

A compound represented by the formula (1-f) (wherein $R^1$, $A^2$, $A^3$, $A^4$, $A^5$, D and n are the same as defined above) and a compound represented by the formula (16) (wherein $A^{1aa}$ is $C_1$-$C_6$ alkyl, and $X_1$ is a leaving group such as a halogen atom, $C_1$-$C_4$ alkylsulfonate (such as methanesulfonyloxy), $C_1$-$C_4$ haloalkylsulfonate (such as trifluoromethanesulfonyloxy) or arylsulfonate (such as benzenesulfonyloxy or p-toluenesulfonyloxy)) are reacted in a solvent or without solvent, and as the case requires, in the presence of a base, to produce a compound represented by the formula (1-g) (wherein $R^1$, $A^{1aa}$, $A^2$, $A^3$, $A^4$, $A^5$, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The equivalent amount of the base used is from 0.1 to 100 equivalent amount, preferably from 1 to 20 equivalent amount based on the compound represented by the formula (1-f).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (16) may be used in an amount of from 0.5 to 50 equivalent amount, preferably from 1 to 20 equivalent amount based on the compound (1-f).

The compound represented by the formula (1-f) may be prepared in accordance with Process 1.

Some of the compounds represented by the formula (16) are known compounds, and some of them are commercially available.

the formula (2Q1-a) and a compound represented by the formula (17-b) (wherein $G_1$, $G_2$, $G_3$ and $G_4$ are the same as defined above) in accordance with the method disclosed in step [A] of Process 1.

Then, the compound represented by the formula (18-a) is subjected to dehydration condensation in accordance with the method disclosed in step [B] of Process 1 to produce a compound represented by the formula (19-a) (wherein $A^{1a}$, $A^2$, $A^3$, $A^4$, $A^5$, $G_1$, $G_2$, $G_3$ and $G_4$ are the same as defined above).

Then, the compound represented by the formula (19-a) is reacted with a compound represented by the formula (9) (wherein $R^1$ is the same as defined above) and a halogenating agent in a solvent or without solvent to produce a compound represented by the formula (1-h) (wherein $R^1$, $A^{1a}$, $A^2$, $A^3$, $A^4$, $A^5$, $G_1$, $G_2$, $G_3$ and $G_4$ are the same as defined above). In a case where a solvent is used, the solvent used may be any solvent which is inert to the reaction, and

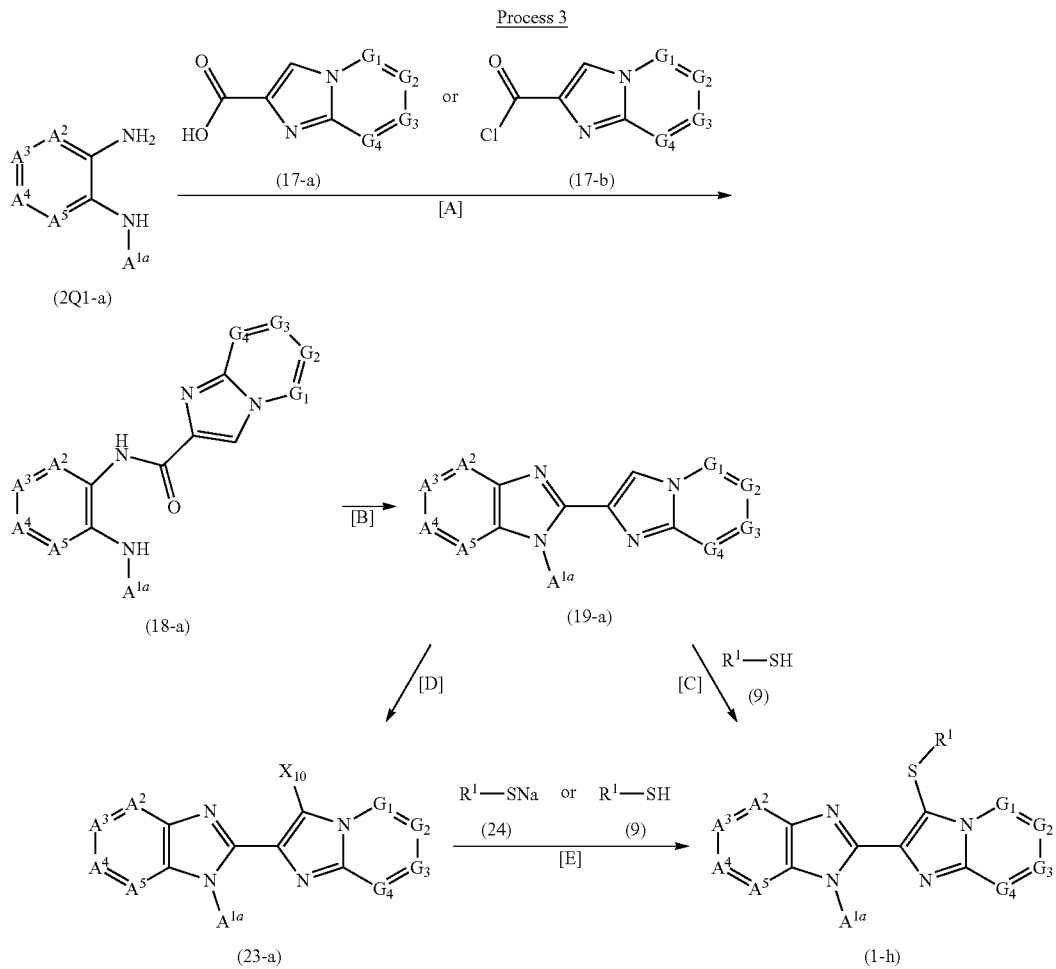

The compound represented by the formula (2Q1-a) and a compound represented by the formula (17-a) (wherein $G_1$, $G_2$, $G_3$ and $G_4$ are the same as defined above) are reacted in accordance with the method disclosed in step [A] of Process 1 to produce a compound represented by the formula (18-a) (wherein $A^{1a}$, $A^2$, $A^3$, $A^4$, $A^5$, $G_1$, $G_2$, $G_3$ and $G_4$ are the same as defined above).

Further, the compound represented by the formula (18-a) may be produced by reacting the compound represented by for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The halogenating agent may, for example, be chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin. The equivalent amount of the halogenating agent used is from 0.5 to 50 equivalent amount, preferably from 1 to 20 equivalent amount based on the compound represented by the formula (19-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (9) may be used in an amount of from 0.5 to 50 equivalent amount, preferably from 1 to 20 equivalent amount based on the compound (19-a).

Further, the compound represented by the formula (19-a) and a halogenating agent are reacted in a solvent or without solvent to produce a compound represented by the formula (23-a) (wherein $A^{1a}$, $A^2$, $A^3$, $A^4$, $A^5$, $G_1$, $G_2$, $G_3$ and $G_4$ are the same as defined above, and $X_{10}$ is a chlorine atom, a bromine atom or an iodine atom). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The halogenating agent may, for example, be chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin. The equivalent amount of the halogenating agent used is from 0.5 to 50 equivalent amount, preferably from 1 to 20 equivalent amount based on the compound represented by the formula (19-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Then, the compound represented by the formula (23-a) and a compound represented by the formula (24) (wherein $R^1$ is the same as defined above) are reacted in a solvent or without solvent, and as the case requires, in the presence of a base, to produce a compound represented by the formula (1-h) (wherein $R^1$, $A^{1a}$, $A^2$, $A^3$, $A^4$, $A^5$, $G_1$, $G_2$, $G_3$ and $G_4$ are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The equivalent amount of the base used is from 0.1 to 100 equivalent amount, preferably from 1 to 20 equivalent amount based on the compound represented by the formula (23-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (24) may be used in an amount of from 0.5 to 50 equivalent amount, preferably from 1 to 20 equivalent amount based on the compound (23-a).

Further, the compound represented by the formula (1-h) may be produced by reacting the compound represented by the formula (23-a) and the compound represented by the formula (9) in a solvent or without solvent, as the case requires, in the presence of a base, as the case requires, in the presence of a palladium catalyst, and as the case requires, in the presence of a ligand. In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The equivalent amount of the base used is from 0.1 to 100 equivalent amount, preferably from 1 to 20 equivalent amount based on the compound represented by the formula (23-a).

The reaction may be carried out in the presence of a palladium catalyst. The palladium catalyst to be used may, for example, be palladium-carbon, palladium(II) chloride, palladium(II) acetate, bis(triphenylphosphine) palladium(II) dichloride, tetrakis(triphenylphosphine) palladium(0), bis(dibenzylideneacetone) palladium(0) or tris(dibenzylideneacetone) dipalladium(0). The equivalent amount of the palladium catalyst used may be from 0.005 to 20 equivalent amount, preferably from 0.01 to 5 equivalent amount based on the compound (23-a).

The reaction may be carried out in the presence of a ligand. The ligand to be used may, for example, be 4,5'-bis(diphenylphosphino)-9,9'-dimethylxanthene or 1,10-phenanthroline. The equivalent amount of the ligand used may be from 0.005 to 20 equivalent amount, preferably from 0.01 to 5 equivalent amount based on the compound (23-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (9) may be used in an amount of from 0.5 to 50 equivalent amount, preferably from 1 to 20 equivalent amount based on the compound (23-a).

Some of the compounds represented by the formula (17-a) are known compounds, and some of them are commercially available.

Some of the compounds represented by the formula (17-b) are known compounds, and some of them are commercially available.

Some of the compounds represented by the formula (9) are known compounds, and some of them are commercially available.

Some of the compounds represented by the formula (24) are known compounds, and some of them are commercially available.

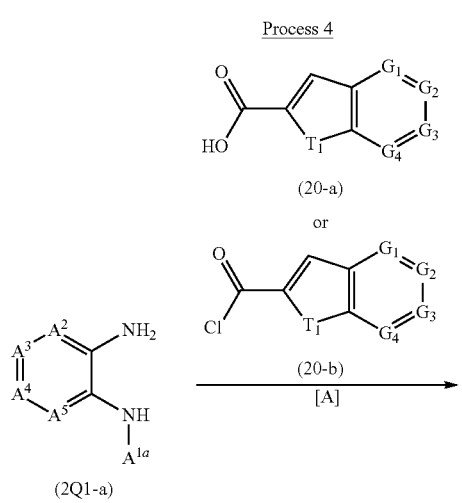

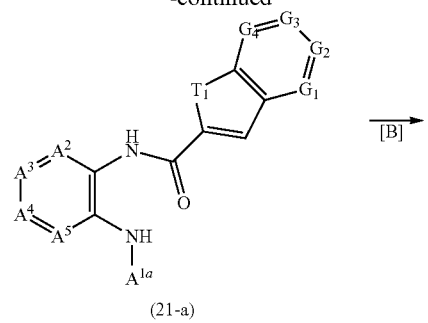

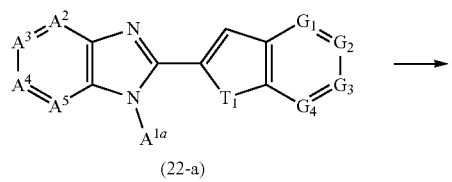

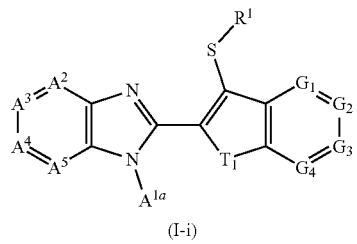

The compound represented by the formula (2Q1-a) is reacted with a compound represented by the formula (20-a) (wherein $T_1$, $G_1$, $G_2$, $G_3$ and $G_4$ are the same as defined above) in accordance with the method disclosed in step [A] of Process 1 to produce a compound represented by the formula (21-a) (wherein $A^{1a}$, $A^2$, $A^3$, $A^4$, $A^5$, $T_1$, $G_1$, $G_2$, $G_3$ and $G_4$ are the same as defined above).

Further, the compound represented by the formula (21-a) may be produced by reacting the compound represented by the formula (2Q1-a) and a compound represented by the formula (20-b) (wherein $T_1$, $G_1$, $G_2$, $G_3$ and $G_4$ are the same as defined above) in accordance with the method disclosed in step [A] of Process 1.

Then, the compound represented by the formula (21-a) is subjected to hydration condensation in accordance with the method disclosed in step [B] of Process 1 to produce a compound represented by the formula (22-a) (wherein $A^{1a}$, $A^2$, $A^3$, $A^4$, $A^5$, $T_1$, $G_1$, $G_2$, $G_3$ and $G_4$ are the same as defined above).

Then, the compound represented by the formula (22-a) is reacted in accordance with the method disclosed in step [C] of Process 3 or the method disclosed in steps [D] and [E] of Process 3 to produce a compound represented by the formula (1-i) (wherein $R^1$, $A^{1a}$, $A^2$, $A^3$, $A^4$, $A^5$, $T_1$, $G_1$, $G_2$, $G_3$ and $G_4$ are the same as defined above).

Some of the compounds represented by the formula (20-a) are known compounds, and some of them are commercially available.

Some of the compounds represented by the formula (20-b) are known compounds, and some of them are commercially available.

Process 5

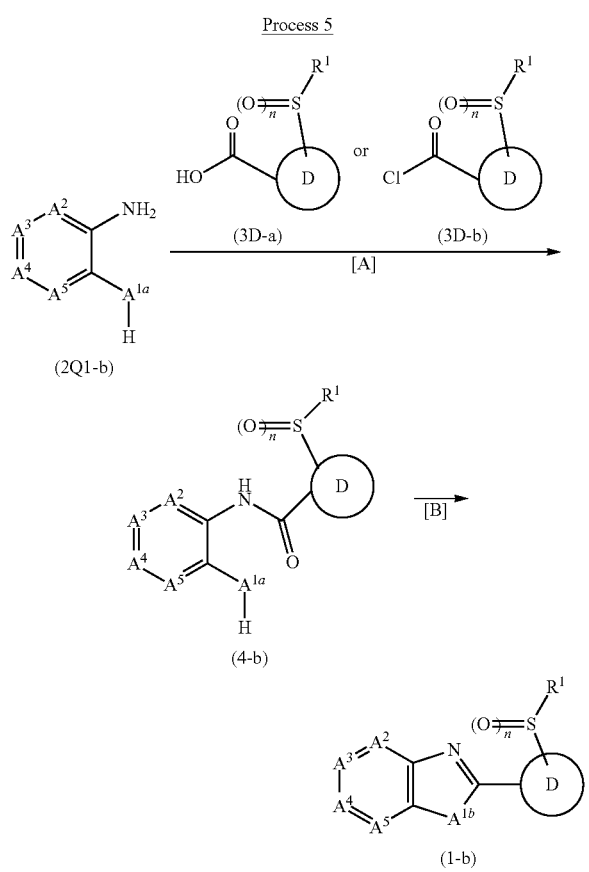

A compound represented by the formula (2Q1-b) (wherein $A^2$, $A^3$, $A^4$ and $A^5$ are the same as defined above, and $A^{1b}$ is an oxygen atom or a sulfur atom) and a compound represented by the formula (3D-a) are reacted in accordance with the method disclosed in step [A] of Process 1 to produce a compound represented by the formula (4-b) (wherein $A^{1b}$, $R^1$, $A^2$, $A^3$, $A^4$, $A^5$, D and n are the same as defined above).

Further, the compound represented by the formula (4-b) may be produced by reacting the compound represented by the formula (2Q1-b) and the compound represented by the formula (3D-b) in accordance with the method disclosed in step [A] of Process 1.

Then, the compound represented by the formula (4-b) is reacted in a solvent or without solvent, as the case requires, in the presence of an acid, and as the case requires, in the presence of a dehydration condensation agent to produce a compound represented by the formula (1-b) (wherein $A^{1b}$, $R^1$, $A^2$, $A^3$, $A^4$, $A^5$, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of an acid. The acid to be used may, for example, be p-toluenesulfonic acid, polyphosphoric acid, acetic acid or propionic acid. The equivalent amount of the acid used is from 0.1 to 1,000 equivalent amount, preferably from 1 to 500 equivalent amount based on the compound represented by the formula (4-b).

The reaction may be carried out in the presence of a dehydration condensation agent. The dehydration condensation agent to be used may, for example, be a mixture of triphenylphosphine and bis(2-methoxyethyl) azodicarboxylate.

The equivalent amount of triphenylphosphine used is from 0.5 to 50 equivalent amount, preferably from 1 to 20 equivalent amount based on the compound represented by the formula (4-b).

The equivalent amount of bis(2-methoxyethyl) azodicarboxylate used is from 0.5 to 50 equivalent amount, preferably from 1 to 20 equivalent amount based on the compound represented by the formula (4-b).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Some of the compounds represented by the formula (2Q1-b) are known compounds, and some of them are commercially available.

Process 6

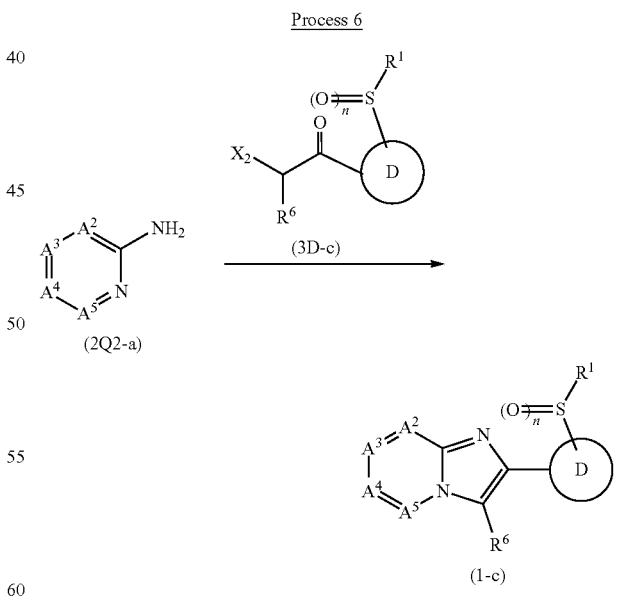

A compound represented by the formula (2Q2-a) (wherein $A^2$, $A^3$, $A^4$ and $A^5$ are the same as defined above) and a compound represented by the formula (3D-c) (wherein $R^1$, $R^6$, D and n are the same as defined above, and $X_2$ is a chlorine atom, a bromine atom or an iodine atom) are reacted in the presence of a solvent or without solvent, and as the case requires, in the presence of a base to produce a compound represented by the formula (1-c) (wherein $R^1$, $R^6$, $A^2$, $A^3$, $A^4$, $A^5$, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The equivalent amount of the base used is from 0.1 to 100 equivalent amount, preferably from 1 to 20 equivalent amount based on the compound represented by the formula (2Q2-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Some of the compounds represented by the formula (2Q2-a) are known compounds, and some of them are commercially available. The rest of them may be prepared, for example, in accordance with the after-mentioned Reaction Scheme 5.

The compound represented by the formula (3D-c) may be prepared, for example, in accordance with the after-mentioned Reaction Scheme 1.

A compound represented by the formula (1-j) (wherein $R^1$, $A^2$, $A^3$, $A^4$, $A^5$, D and n are the same as defined above) and a halogenating agent are reacted in a solvent or without solvent to produce a compound represented by the formula (1-k) (wherein $R^1$, $A^2$, $A^3$, $A^4$, $A^5$, D and n are the same as defined above, and $X_4$ is a chlorine atom, a bromine atom or an iodine atom). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The halogenating agent may, for example, be chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin. The equivalent amount of the halogenating agent used is from 0.5 to 50 equivalent amount, preferably from 1 to 20 equivalent amount based on the compound represented by the formula (1-j).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

The compound represented by the formula (1-j) may be prepared in accordance with the method disclosed in Process 6.

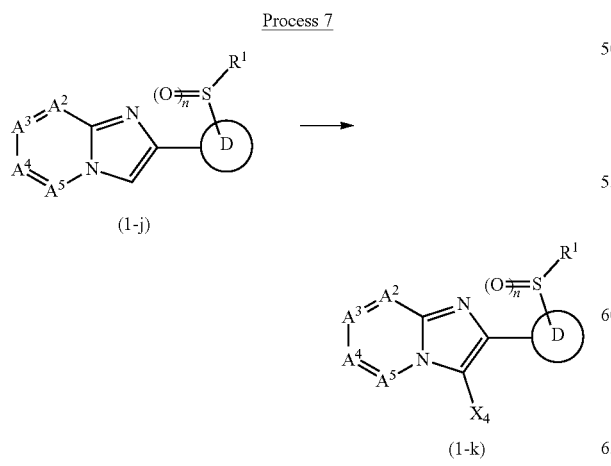

Process 7

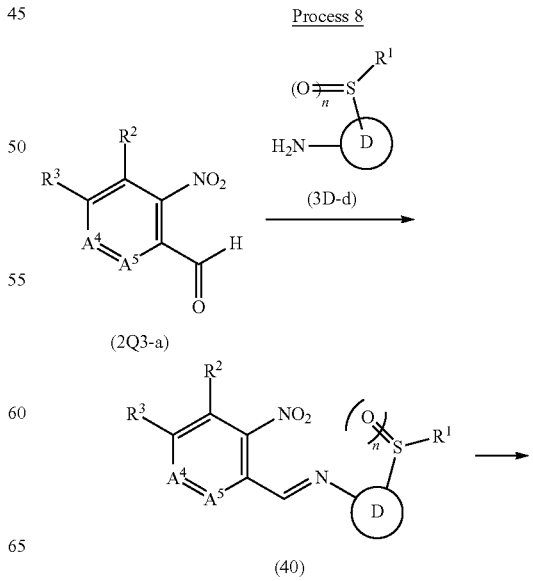

Process 8

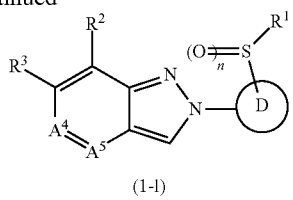

(1-I)

A compound represented by the formula (2Q3-a) (wherein R², R³, A⁴ and A⁵ are the same as defined above) and a compound represented by the formula (3D-d) (wherein R¹, D and n are the same as defined above) are reacted in a solvent or without solvent, and as the case requires, in the presence of an acid to produce a compound represented by the formula (40) (wherein R¹, R², R³, A⁴, A⁵, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of an acid. The acid to be used may, for example, be acetic acid, formic acid or p-toluenesulfonic acid. The equivalent amount of the acid used is from 0.1 to 100 equivalent amount, preferably from 1 to 20 equivalent amount based on the compound represented by the formula (2Q3-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (3D-d) may be used in an amount of from 0.5 to 50 equivalent amount, preferably from 1 to 20 equivalent amount based on the compound (2Q3-a).

Then, the compound represented by the formula (40) and a phosphite are reacted in a solvent or without solvent to produce a compound represented by the formula (1-I) (wherein R¹, R², R³, A⁴, A⁵, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The phosphite may, for example, be trimethyl phosphite or triethyl phosphite. The equivalent amount of the phophite used is from 0.5 to 50 equivalent amount, preferably from 1 to 20 equivalent amount based on the compound represented by the formula (40).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Some of the compounds represented by the formula (2Q3-a) are known compounds, and some of them are commercially available. The rest of them may be prepared from known compounds in accordance with conventional methods disclosed in literature, for example, in accordance with the reaction conditions disclosed in Journal of Medicinal Chemistry, 2008, Vol. 50, p. 2468, WO2011/075628 or the like.

Some of the compounds represented by the formula (3D-d) are known compounds, and some of them are commercially available. The rest of them may be prepared, for example, in accordance with the after-mentioned Reaction Scheme 6.

Process 9

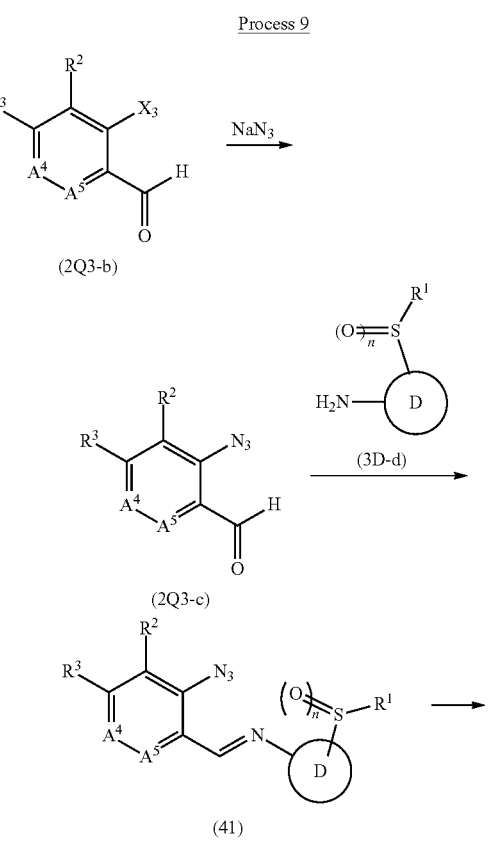

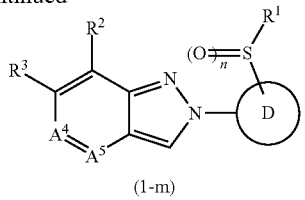

(1-m)

A compound represented by the formula (2Q3-b) (wherein $R^2$, $R^3$, $A^4$ and $A^5$ are the same as defined above, and $X_3$ is a fluorine atom, a chlorine atom, a bromine atom or an iodine atom) and sodium azide are reacted in a solvent or without solvent to produce a compound represented by the formula (2Q3-c) (wherein $R^2$, $R^3$, $A^4$ and $A^5$ are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, sodium azide may be used in an amount of from 0.5 to 50 equivalent amount, preferably from 1 to 20 equivalent amount based on the compound (2Q3-b).

Then, the compound represented by the formula (2Q3-c) and the compound represented by the formula (3D-d) are reacted in a solvent or without solvent, as the case requires, in the presence of a base, and as the case requires, in the presence of a catalyst to produce a compound represented by the formula (41) (wherein $R^1$, $R^2$, $R^3$, $A^4$, $A^5$, D and n are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The equivalent amount of the base used is from 0.1 to 100 equivalent amount, preferably from 1 to 20 equivalent amount based on the compound represented by the formula (2Q3-c).

The reaction may be carried out in the presence of a catalyst. The catalyst to be used may, for example, be titanium tetrachloride. The equivalent amount of the catalyst used is from 0.005 to 20 equivalent amount, preferably from 0.1 to 5 equivalent amount based on the compound represented by the formula (2Q3-c).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (3D-d) may be used in an amount of from 0.5 to 50 equivalent amount, preferably from 1 to 20 equivalent amount based on the compound (2Q3-c).

Then, the compound represented by the formula (41) is cyclized in a solvent or without solvent to produce a compound represented by the formula (1-m) (wherein $R^1$, $R^2$, $R^3$, $A^4$, $A^5$, D and n are the same as defined above).

In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Some of the compounds represented by the formula (2Q3-b) are known compounds, and some of them are commercially available. The rest of them may be prepared, for example, in accordance with the after-mentioned Reaction Scheme 7.

Process 10

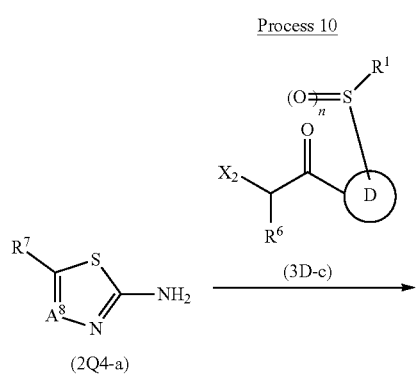

(2Q4-a) + (3D-c) → (1-n)

A compound represented by the formula (2Q4-a) (wherein $R^7$ and $A^8$ are the same as defined above) is reacted with the compound represented by the formula (3D-c) in accordance with the method disclosed in Process 6 to produce a compound represented by the formula (1-n) (wherein $R^1$, $R^6$, $R^7$, $A^8$, D and n are the same as defined above).

Some of the compounds represented by the formula (2Q4-a) are known compounds, and some of them are commercially available. The rest of them may be prepared from known compounds in accordance with conventional methods disclosed in literature, for example, in accordance with the reaction conditions disclosed in Journal of Fluorine Chemistry, 2012, Vol. 133, p. 115, CN101768135, CN101885708 or the like.

Process 11

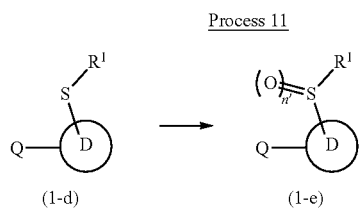

(1-d) → (1-e)

A compound represented by the formula (1-d) (wherein $R^1$, Q and D are the same as defined above) and an oxidizing agent are reacted in a solvent or without solvent, and as the case requires, in the presence of a catalyst to produce a compound represented by the formula (1-e) (wherein $R^1$, Q and D are the same as defined above, and n' is an integer of 1 or 2). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, acetic acid, or a mixture thereof may be mentioned.

The oxidizing agent may, for example, be a peracid such as m-chloroperbenzoic acid or peracetic acid, hydrogen peroxide or OXONE (registered trademark by E. I. duPont, potassium peroxymonosulfate). The equivalent amount of the oxidizing agent used is from 0.1 to 100 equivalent amount, preferably from 1 to 20 equivalent amount based on the compound represented by the formula (1-d).

The reaction may be carried out in the presence of a catalyst. The catalyst used may, for example, be sodium tungstate. The equivalent amount of the catalyst used is from 0.005 to 20 equivalent amount, preferably from 0.1 to 5 equivalent amount based on the compound represented by the formula (1-d).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

The compound represented by the formula (1-d) may be prepared in accordance with the methods in Processes 1 to 10 or the following Processes 14 to 17.

Process 12

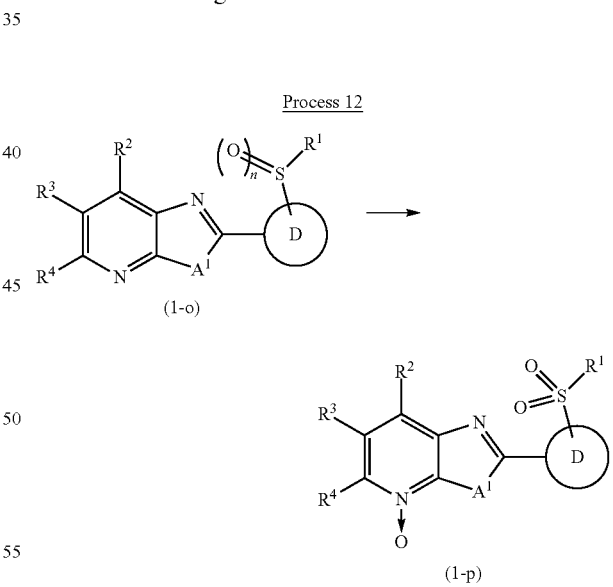

(1-o) → (1-p)

A compound represented by the formula (1-o) (wherein $R^1$, $R^2$, $R^3$, $R^4$, $A^1$, D and n are the same as defined above) is reacted with an oxidizing agent in accordance with the method disclosed in Process 11 to produce a compound represented by the formula (1-p) (wherein $R^1$, $R^2$, $R^3$, $R^4$, $A^1$ and D are the same as defined above).

The compound represented by the formula (1-o) may be prepared in accordance with the method disclosed in Processes 1 to 5.

Process 13

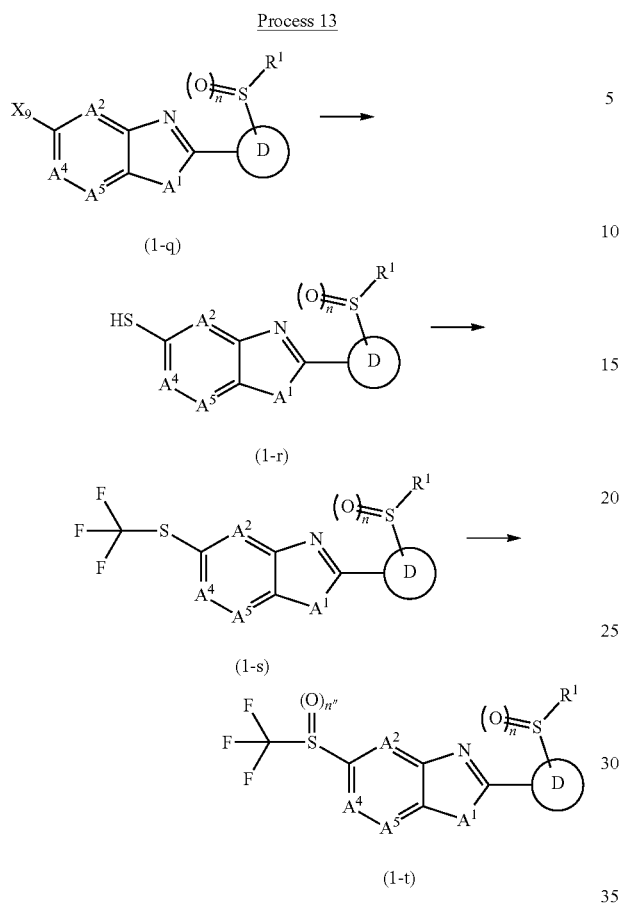

(1-q)

(1-r)

(1-s)

(1-t)

Process 14

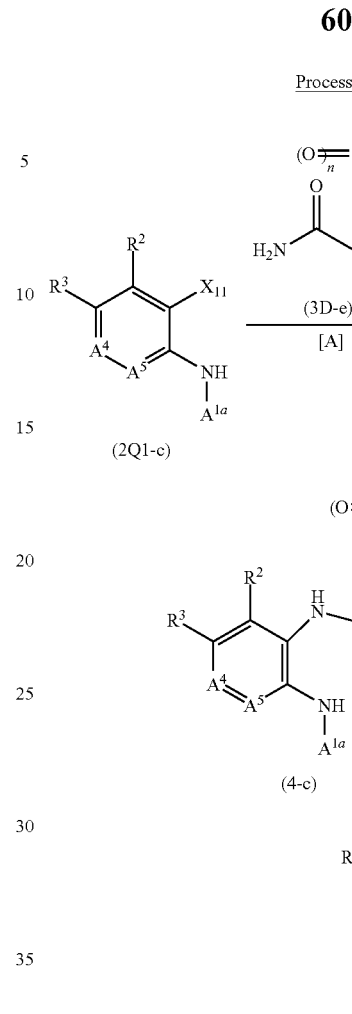

(2Q1-c)

(4-c)

(1-u)

A compound represented by the formula (1-q) (wherein $R^1$, $A^1$, $A^2$, $A^4$, $A^5$, D and n are the same as defined above, and X is a chlorine atom, a bromine atom or an iodine atom) is reacted with a thiolating agent such as 2-ethylhexyl 3-mercaptopropionate, sodium hydrogen sulfide or sodium sulfide, for example, in accordance with the method disclosed in Organic Lett. 2007, Vol. 9, p. 3687, Tetrahedron 1998, Vol. 44, p. 1187, WO2011/159839 or the like to produce a compound represented by the formula (1-r) (wherein $R^1$, $A^1$, $A^2$, $A^4$, $A^5$, D and n are the same as defined above).

Then, the compound represented by the formula (1-r) is reacted with a trifluoromethylating agent such as Umemoto reagent (5-(trifluoromethyl)dibenzothiophenium trifluoromethanesulfonate) or Togni reagent (1-trifluoromethyl-3,3-dimethyl-1,2-benziodoxole), for example, in accordance with the method disclosed in WO2013/043962, WO2013/040863, WO2012/082566 or the like, to produce a compound represented by the formula (1-s) (wherein $R^1$, $A^1$, $A^2$, $A^4$, $A^5$, D and n are the same as defined above).

Then, the compound represented by the formula (1-s) is reacted with an oxidizing agent in accordance with the method disclosed in Process 11 to produce a compound represented by the formula (1-t) (wherein $R^1$, $A^1$, $A^2$, $A^4$, $A^5$, D and n are the same as defined above, and n" is an integer of 1 or 2).

The compound represented by the formula (1-q) may be prepared in accordance with the method disclosed in Processes 1 to 5.

A compound represented by the formula (2Q1-c) (wherein $A^{1a}$, $A^4$, $A^5$, $R^2$ and $R^3$ are the same as defined above, and $X_{11}$ is a chlorine atom, a bromine atom or an iodine atom) and a compound represented by the formula (3D-e) (wherein $R^1$, D and n are the same as defined above) are reacted in a solvent or without solvent, as the case requires, in the presence of a copper catalyst, as the case requires, in the presence of a base, and as the case requires, in the presence of a ligand. In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a copper catalyst. The copper catalyst to be used may, for example, be copper(I) iodide. The equivalent amount of the copper catalyst used is from 0.005 to 20 equivalent amount, preferably from 0.01 to 5 equivalent amount based on the compound (2Q1-c).

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate, cesium carbonate or potassium phosphate. The equivalent amount of the base used is from 0.1 to 100 equivalent amount, preferably from 1 to 20 equivalent amount based on the compound represented by the formula (2Q1-c).

The reaction may be carried out in the presence of a ligand. The ligand to be used may, for example, be 1,10-phenanthroline, 1,2-diaminoethane or N,N'-dimethylethylenediamine. The equivalent amount of the ligand used is from 0.005 to 20 equivalent amount, preferably from 0.01 to 5 equivalent amount based on the compound (2Q1-c).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (3D-e) may be used in an amount of from 0.5 to 50 equivalent amount, preferably from 1 to 20 equivalent amount based on the compound (2Q1-c).

Then, the compound represented by the formula (4-c) is subjected to dehydration condensation in accordance with the method disclosed in step [B] of Process 1 to produce a compound represented by the formula (1-u) (wherein $A^{1a}$, $A^4$, $A^5$, $R^1$, $R^2$, $R^3$, D and n are the same as defined above).

Some of the compounds represented by the formula (2Q1-c) are known compounds, and some of them are commercially available. The rest of them may be prepared, for example, in accordance with the after-mentioned Reaction Scheme 4.

The compound represented by the formula (3D-e) may be prepared, for example, in accordance with the after-mentioned Reaction Scheme 8.

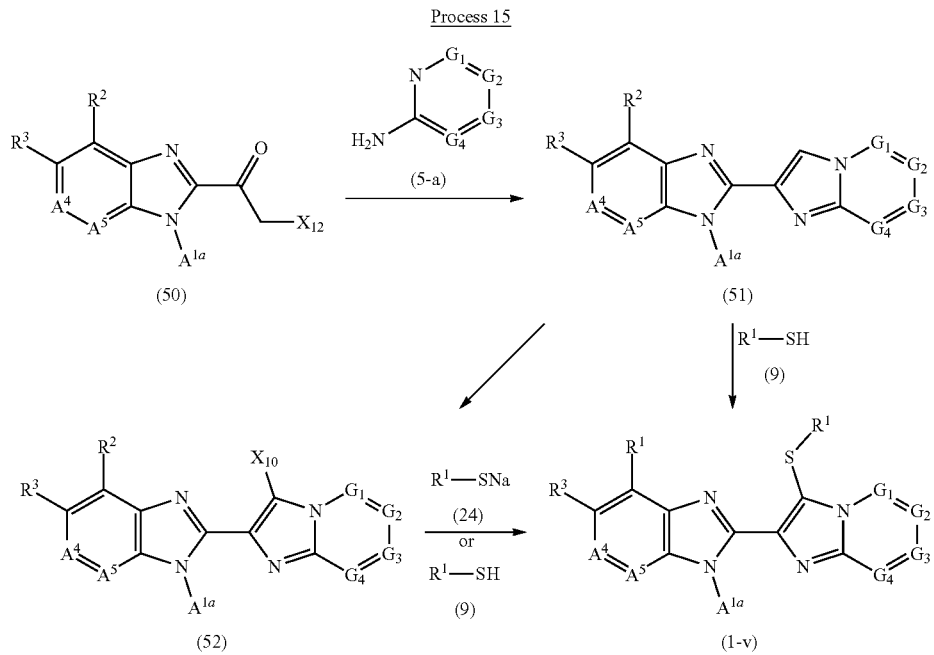

A compound represented by the formula (50) (wherein $R^2$, $R^3$, $A^{1a}$, $A^4$ and $A^5$ are the same as defined above, and $X_{12}$ is a chlorine atom, a bromine atom or an iodine atom) and a compound represented by the formula (5-a) (wherein $G_1$, $G_2$, $G_3$ and $G_4$ are the same as defined above) are reacted in accordance with the method disclosed in Process 6 to produce a compound represented by the formula (51) (wherein $R^2$, $R^3$, $A^{1a}$, $A^4$, $A^5$, $G_1$, $G_2$, $G_3$ and $G_4$ are the same as defined above).

Then, the compound represented by the formula (51) and the compound represented by the formula (9) are reacted in accordance with the method disclosed in step [C] of Process 3 to produce a compound represented by the formula (1-v) (wherein $R^1$, $R^2$, $R^3$, $A^{1a}$, $A^4$, $A^5$, $G_1$, $G_2$, $G_3$ and $G_4$ are the same as defined above).

Further, the compound represented by the formula (51) and a halogenating agent are reacted in accordance with the method disclosed in step [D] of Process 3 to produce a compound represented by the formula (52) (wherein $R^2$, $R^3$, $A^{1a}$, $A^4$, $A^5$, $G_1$, $G_2$, $G_3$, $G_4$ and $X_{10}$ are the same as defined above).

Then, the compound represented by the formula (52) and a compound represented by the formula (24) are reacted in accordance with the method disclosed in step [E] of Process 3 to produce a compound represented by the formula (1-v).

Further, the compound represented by the formula (1-v) may be produced by reacting the compound represented by the formula (52) and the compound represented by the formula (9) in accordance with the method disclosed in step [E] of Process 3.

The compound represented by the formula (50) may be prepared, for example, in accordance with the after-mentioned Reaction Scheme 9.

Some of the compounds represented by the formula (5-a) are known compounds, and some of them are commercially available.

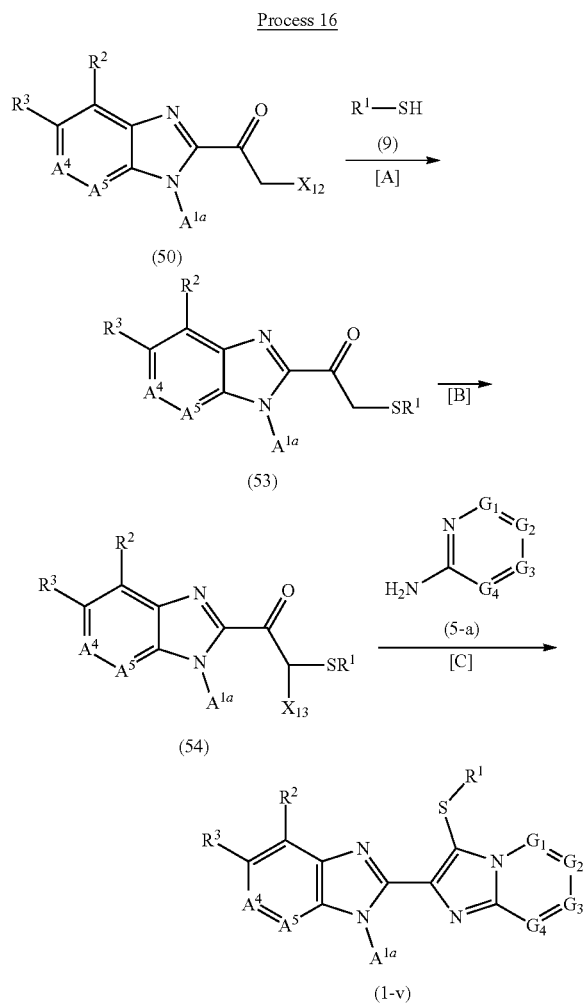

The compound represented by the formula (50) and the compound represented by the formula (9) are reacted in a solvent or without solvent, and as the case requires, in the presence of a base to produce a compound represented by the formula (53) (wherein $R^1$, $R^2$, $R^3$, $A^{1a}$, $A^4$ and $A^5$ are the same as defined above). In a case where a solvent is used, the solvent used may be any solvent which is inert to the reaction, and for example, water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The equivalent amount of the base used is from 0.1 to 100 equivalent amount, preferably from 1 to 20 equivalent amount based on the compound represented by the formula (50).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the equivalent amount of the reaction substrate, the compound (9) may be used in an amount of from 0.5 to 50 equivalent amount, preferably from 1 to 20 equivalent amount based on the compound (50).

Then, the compound represented by the formula (53) and a halogenating agent are reacted in a solvent or without solvent, as the case requires, in the presence of a silylating agent, as the case requires, in the presence of a base, as the case requires, in the presence of an acid to produce a compound represented by the formula (54) (wherein $R^1$, $R^2$, $R^3$, $A^{1a}$, $A^4$ and $A^5$ are the same as defined above, and $X_{13}$ is a chlorine atom, a bromine atom or an iodine atom). In a case where a solvent is used, the solvent used may be any solvent which is inert to the reaction, and for example, water, an aliphatic acid such as acetic acid, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N, N-dimethylacetamide, N-methylpyrrolidone or N,N'-dimethylimidazolidinone, a sulfoxide such as dimethyl sulfoxide, a nitrogen-containing aromatic compound such as pyridine or quinoline, or a mixture thereof may be mentioned.

The halogenating agent may, for example, be chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin or trimethylphenylammonium tribromide. The equivalent amount of the halogenating agent used is from 0.5 to 50 equivalent amount, preferably from 1 to 20 equivalent amount based on the compound represented by the formula (53).

The reaction may be carried out in the presence of a silylating agent. The silylating agent to be used may, for example, be trimethylsilyl trifluoromethanesulfonate. The equivalent amount of the silylating agent used is from 0.005 to 20 equivalent amount, preferably from 0.01 to 5 equivalent amount based on the compound represented by the formula (53).

The reaction may be carried out in the presence of a base. The base to be used may, for example, be an organic base such as pyridine, 2,6-lutidine, 4-dimethylaminopyridine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate, cesium carbonate or potassium phosphate. The equivalent amount of the base used is from 0.1 to 100 equivalent amount, preferably from 1 to 20 equivalent amount based on the compound represented by the formula (53).

The reaction may be carried out in the presence of an acid. The acid to be used may, for example, be hydrobromic acid or an acetic acid solution of hydrogen bromide. The equivalent amount of the acid used is from 0.1 to 100 equivalent amount, preferably from 1 to 20 equivalent amount based on the compound represented by the formula (53).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Then, the compound represented by the formula (54) and the compound represented by the formula (5-a) are reacted in accordance with the method disclosed in Process 6 to produce a compound represented by the formula (1-v).

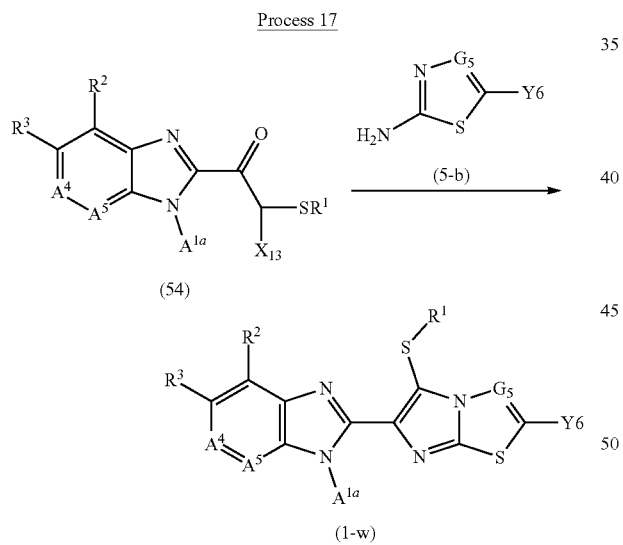

The compound represented by the formula (54) and a compound represented by the formula (5-b) (wherein $G_5$ and Y6 are the same as defined above) are reacted in accordance with the method disclosed in Process 6 to produce a compound represented by the formula (1-w) (wherein $R^1$, $R^2$, $R^3$, $A^{1a}$, $A^4$, $A^5$, $G_5$ and Y6 are the same as defined above).

In Processes 1 to 17, the reaction mixture after the reaction can be worked up by an ordinary procedure such as direct concentration, concentration of a solution in an organic solvent after washing with water, pouring into ice-water or extraction with an organic solvent followed by concentration to obtain the desired compound of the present invention. Further, if necessary, the desired product may be isolated or purified by an optional purification method such as recrystallization, column chromatography, thin layer chromatography or liquid chromatography. Otherwise, the compound of the present invention may be subjected to the next step without isolation and purification. In some cases, the dehydration condensation reaction as the subsequent step proceeds in step [A] of Process 1, in step [A] of Process 3, in step [A] of Process 4, in step [A] of Process 5 and in step [A] of Process 14, and thus step [B] may be omitted.

Among the compounds represented by the formulae (3D-a) and (3D-b) used in Processes 1 and 5, compounds represented by the formulae (3D-a1) and (3D-b1) wherein n is an integer of 0, and among the compounds represented by the formula (3D-c) used in Processes 6 and 10, a compound represented by the formula (3D-c1) wherein n is an integer of 1 or 2 and a compound represented by the formula (3D-c2) wherein n is an integer of 0, may be produced, for example, in accordance with the following Reaction Scheme 1.

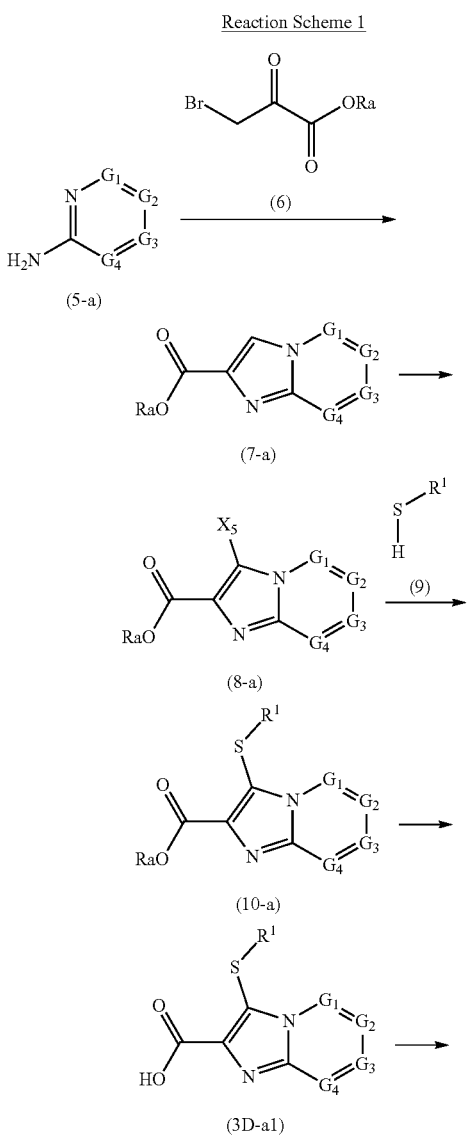

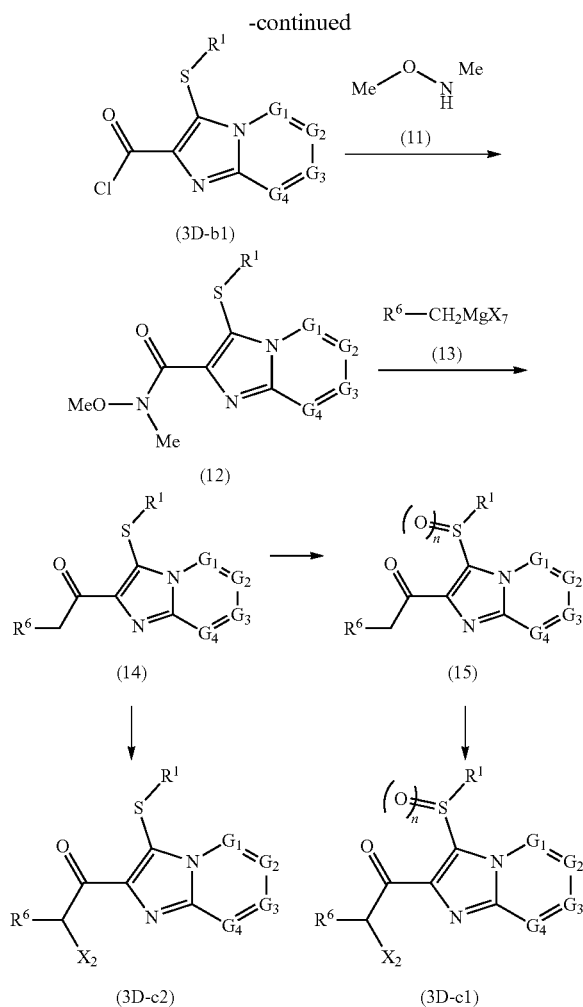

The compound represented by the formula (5-a) is reacted with a compound represented by the formula (6) (wherein Ra is $C_1$-$C_6$ alkyl) in accordance with the method disclosed in Process 6 to produce a compound represented by the formula (7-a) (wherein $G_1$, $G_2$, $G_3$ and $G_4$ are the same as defined above, and Ra is $C_1$-$C_6$ alkyl).

Then, the compound represented by the formula (7-a) is reacted with a halogenating agent in accordance with the method disclosed in Process 7 to produce a compound represented by the formula (8-a) (wherein $G_1$, $G_2$, $G_3$ and $G_4$ are the same as defined above, Ra is $C_1$-$C_6$ alkyl, and $X_5$ is a chlorine atom, a bromine atom or an iodine atom).

Then, the compound represented by the formula (8-a) is reacted with a compound represented by the formula (9) (wherein $R^1$ is the same as defined above) in accordance with the method disclosed in step [E] of Process 3 to produce a compound represented by the formula (10-a) (wherein $G_1$, $G_2$, $G_3$, $G_4$ and $R^1$ are the same as defined above, and Ra is $C_1$-$C_6$ alkyl).

Then, the compound represented by the formula (10-a) is hydrolyzed in accordance with conventional methods disclosed in literature to produce a compound represented by the formula (3D-a1) (wherein $G_1$, $G_2$, $G_3$, $G_4$ and $R^1$ are the same as defined above).

Then, the compound represented by the formula (3D-a1) is reacted with a chlorinating agent in accordance with conventional methods disclosed in literature to produce a compound represented by the formula (3D-b1) (wherein $G_1$, $G_2$, $G_3$, $G_4$ and $R^1$ are the same as defined above).

Then, the compound represented by the formula (3D-b1) and N,O-dimethylhydroxylamine represented by the formula (11) or its hydrochloride are reacted, as the case requires, in the presence of a base to produce a compound represented by the formula (12) (wherein $G_1$, $G_2$, $G_3$, $G_4$ and $R^1$ are the same as defined above).

Then, the compound represented by the formula (12) and a Grignard reagent represented by the formula (13) (wherein $R^6$ is the same as defined above, and $X_7$ is a chlorine atom, a bromine atom or an iodine atom) are reacted in accordance with conventional methods disclosed in literature to produce a compound represented by the formula (14) (wherein $G_1$, $G_2$, $G_3$, $G_4$, $R^1$ and $R^6$ are the same as defined above).

Then, the compound represented by the formula (14) and an oxidizing agent are reacted in accordance with the method disclosed in Process 11 to produce a compound represented by the formula (15) (wherein $G_1$, $G_2$, $G_3$, $G_4$, $R^1$, $R^6$ and n' are the same as defined above).

Then, the compound represented by the formula (15) is reacted with a halogenating agent in accordance with the method disclosed in step [B] of Process 16 to produce a compound represented by the formula (3D-c1) (wherein $G_1$, $G_2$, $G_3$, $G_4$, $R^1$, $R^6$, $X_2$ and n' are the same as defined above).

Further, the compound represented by the formula (14) is reacted with a halogenating agent in accordance with the method disclosed in step [B] of Process 16 to produce a compound represented by the formula (3D-c2) (wherein $G_1$, $G_2$, $G_3$, $G_4$, $R^1$, $R^6$ and $X_2$ are the same as defined above).

Some of the compounds represented by the formula (5-a) are known compounds, and some of them are commercially available.

Some of the compounds represented by the formula (6) are known compounds, and some of them are commercially available.

Some of the compounds represented by the formula (13) are known compounds, and some of them are commercially available.

Among the compounds represented by the formula (3D-a) used in Process 1, a compound represented by the formula (3D-a2) wherein n is an integer of 0 may be produced, for example, in accordance with the following Reaction Scheme 2.

Reaction Scheme 2

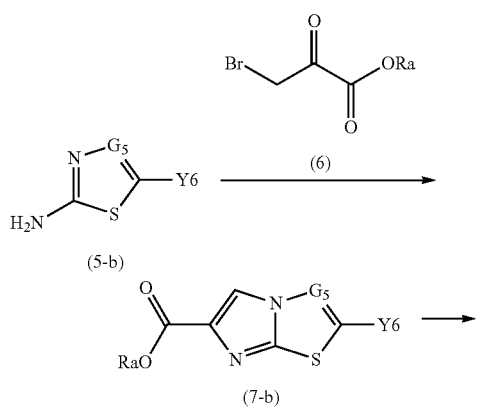

-continued

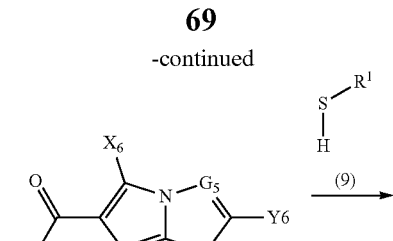

(8-b)

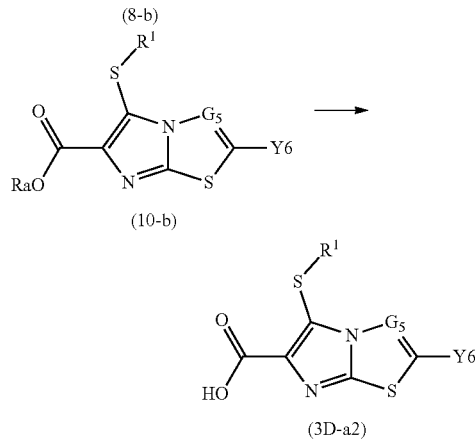

(10-b)

(3D-a2)

The compound represented by the formula (5-b) is reacted with the compound represented by the formula (6) in accordance with the method disclosed in Process 6 to produce a compound represented by the formula (7-b) (wherein $G_5$, Y6 and Ra are the same as defined above).

Then, the compound represented by the formula (7-b) is reacted with a halogenating agent in accordance with the method disclosed in Process 7 to produce a compound represented by the formula (8-b) (wherein $G_5$, Y6 and Ra are the same as defined above, and $X_6$ is a chlorine atom, a bromine atom or an iodine atom).

Then, the compound represented by the formula (8-b) is reacted with the compound represented by the formula (9) in accordance with the method disclosed in step [E] of Process 3 to produce a compound represented by the formula (10-b) (wherein $G_5$, Y6, $R^1$ and Ra are the same as defined above).

Then, the compound represented by the formula (10-b) is hydrolyzed in accordance with conventional methods disclosed in literature to produce a compound represented by the formula (3D-a2) (wherein $G_5$, Y6 and $R^1$ are the same as defined above).

Some of the compounds represented by the formula (5-b) are known compounds, and some of them are commercially available.

The compound represented by the formula (10-a) used in Reaction Scheme 1 may be produced, for example, in accordance with the following Reaction Scheme 3.

Reaction Scheme 3

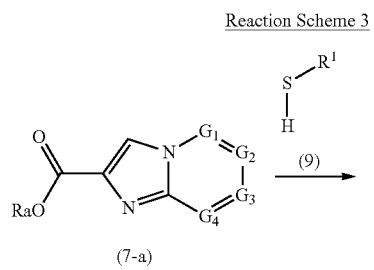

(7-a)

-continued

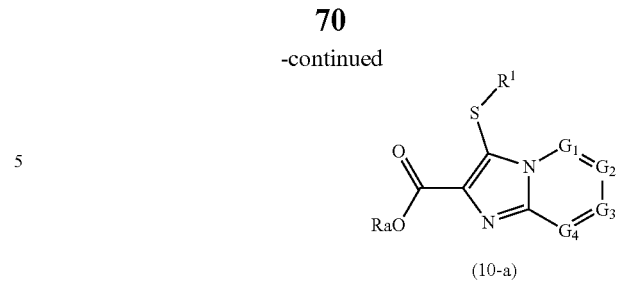

(10-a)

The compound represented by the formula (7-a) is reacted with the compound represented by the formula (9) and a halogenating agent in accordance with the method disclosed in step [C] of Process 3 to produce a compound represented by the formula (10-a).

Among the compounds represented by the formula (2Q1-a) used in Process 1, a compound represented by the formula (2Q1-a-1) may be produced, for example, in accordance with the following Reaction Scheme 4.

Reaction Scheme 4

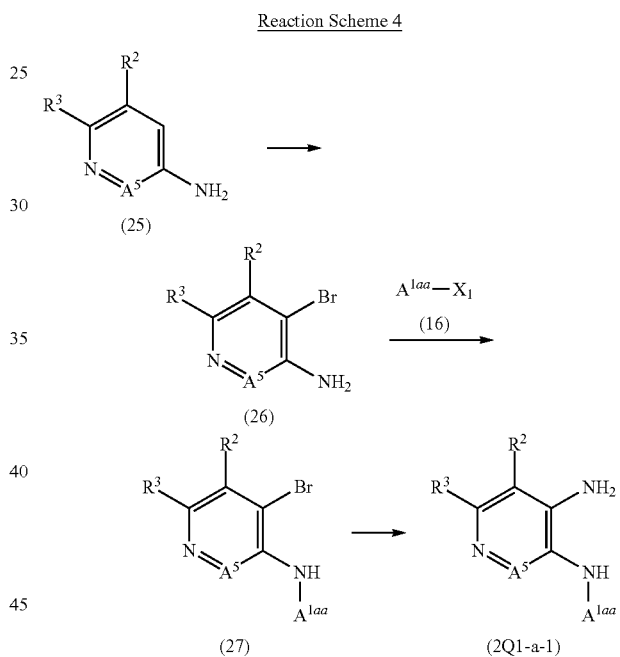

A compound represented by the formula (25) (wherein $R^2$, $R^3$ and $A^5$ are the same as defined above) is reacted with a brominating agent such as N-bromosuccinimide, for example, in accordance with the method disclosed in WO2007/093901 to produce a compound represented by the formula (26) (wherein $R^2$, $R^3$ and $A^5$ are the same as defined above).

Then, the compound represented by the formula (26) is reacted with the compound represented by the formula (16) in accordance with the method disclosed in Process 2 to produce a compound represented by the formula (27) (wherein $R^2$, $R^3$, $A^{1aa}$ and $A^5$ are the same as defined above).

Then, the compound represented by the formula (27) is reacted with an aminating agent such as ammonia, aqueous ammonia or lithium amide in accordance with the method disclosed in e.g. WO2012/086848 to produce a compound represented by the formula (2Q1-a-1) (wherein $R^2$, $R^3$, $A^{1aa}$ and $A^5$ are the same as defined above).

Some of the compounds represented by the formula (25) are known compounds, and some of them are commercially available.

Among the compounds represented by the formula (2Q2-a) used in Process 6, a compound represented by the formula (2Q2-a-1) may be produced, for example, in accordance with the following Reaction Scheme 5.

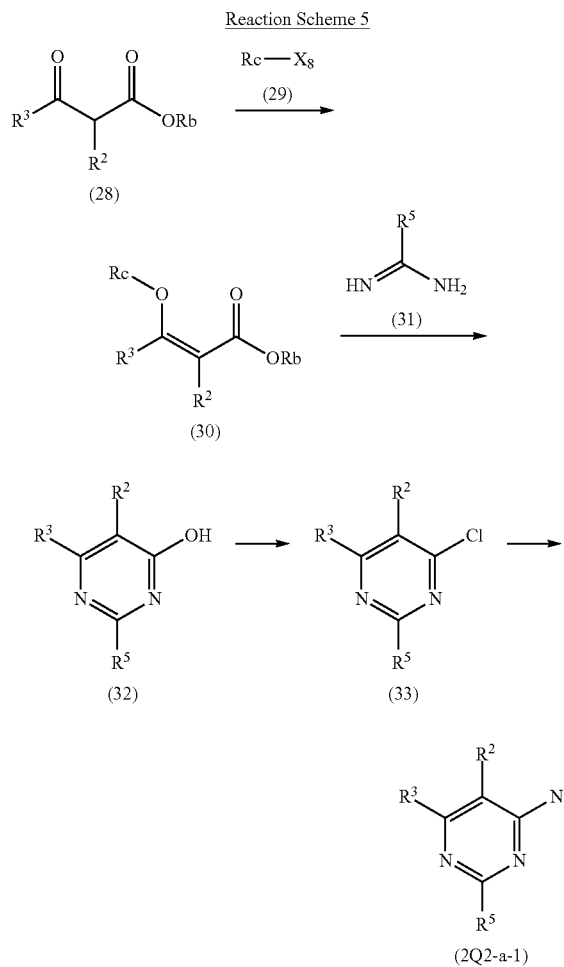

A compound represented by the formula (28) (wherein $R^2$ and $R^3$ are the same as defined above, and Rb is $C_1$-$C_6$ alkyl) is reacted with a compound represented by the formula (29) (wherein Rc is $C_1$-$C_6$ alkyl, and $X_8$ is a favorable leaving group such as a halogen atom, $C_1$-$C_4$ alkylsulfonate (such as methanesufonyloxy), $C_1$-$C_4$ haloalkylsulfonate (such as trifluoromethanesulfonyloxy) or arylsulfonate (such as benzenesulfonyloxy or p-toluenesulfonyloxy)) for example in accordance with the method disclosed in e.g. Journal of Fluorine Chemistry, 1989, Vol. 44, p. 361, Journal of Heterocyclic Chemistry, 1993, Vol. 33, p. 49, or Synthesis 2000, p. 1078 to produce a compound represented by the formula (30) (wherein $R^2$, $R^3$, Rb and Rc are the same as defined above).

Then, the compound represented by the formula (30) is reacted with a compound represented by the formula (31) (wherein $R^5$ is the same as defined above) in accordance with e.g. Bioorganic & Medicinal Chemistry Letters, 2011, Vol. 21, p. 1601 to produce a compound represented by the formula (32) (wherein $R^2$, $R^3$ and $R^5$ are the same as defined above).

Then, the compound represented by the formula (32) is reacted with a chlorinating agent such as phosphorus oxychloride, thionyl chloride or oxalyl chloride for example in accordance with e.g. WO2012/061337 or WO2005/033084 to produce a compound represented by the formula (33) (wherein $R^2$, $R^3$ and $R^5$ are the same as defined above).

Then, the compound represented by the formula (33) is reacted with aqueous ammonia for example in accordance with the method disclosed in e.g. WO2012/061337 or WO2005/033084 to produce a compound represented by the formula (2Q2-a-1).

Some of the compounds represented by the formula (28) are known compounds, and some of them are commercially available.

Some of the compounds represented by the formula (29) are known compounds, and some of them are commercially available.

Some of the compounds represented by the formula (31) are known compounds, and some of them are commercially available.

The compound represented by the formula (3D-d) used in Process 8 may be produced, for example, in accordance with the following Reaction Scheme 6.

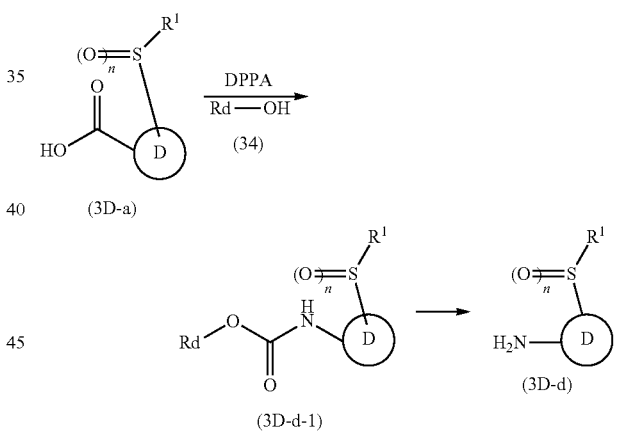

The compound represented by the formula (3D-a) is reacted with diphenylphosphoryl azide (DPPA) and a compound represented by the formula (34) (wherein Rd is $C_1$-$C_6$ alkyl) for example in accordance with the method disclosed in e.g. WO2012/174312 or WO2013/018021 to produce a compound represented by the formula (3D-d-1) (wherein $R^1$, Rd, D and n are the same as defined above).

Then, the compound represented by the formula (3D-d-1) is reacted with an acid for example in accordance with the method disclosed in e.g. WO2012/174312 or WO2003/018021 to produce a compound represented by the formula (3D-d).

Among the compounds represented by the formula (2Q3-b) used in Process 9, a compound represented by the formula (2Q3-b-1) may be produced, for example, in accordance with the following Reaction Scheme 7.

Reaction Scheme 7

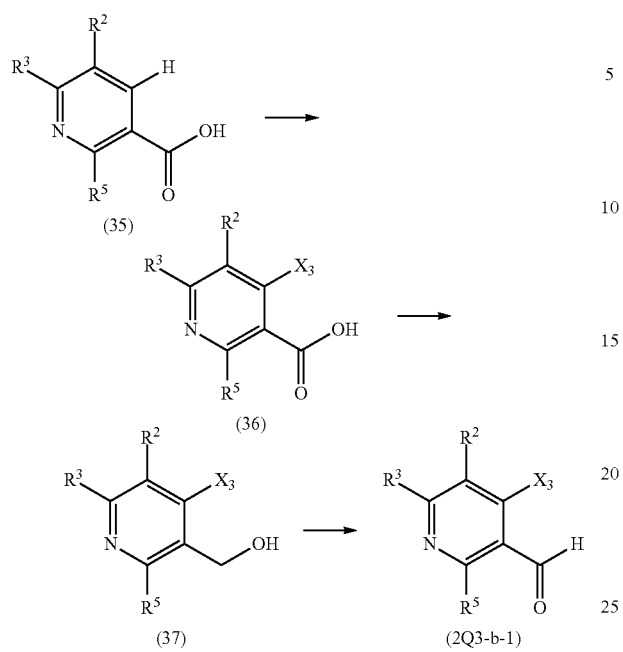

A compound represented by the formula (35) (wherein $R^2$, $R^3$ and $R^5$ are the same as defined above) is halogenated by using a halogenating agent for example in accordance with the method disclosed in e.g. WO2013/064460 or WO2013/064461 to produce a compound represented by the formula (36) (wherein $R^2$, $R^3$, $R^5$ and $X_3$ are the same as defined above).

Then, the compound represented by the formula (36) is reduced for example in accordance with the method disclosed in e.g. WO2013/064460 or WO2013/064461 to produce a compound represented by the formula (37) (wherein $R^2$, $R^3$, $R^5$ and $X_3$ are the same as defined above).

Then, the compound represented by the formula (37) is oxidized for example in accordance with the method disclosed in e.g. WO2013/064460 or WO2013/064461 to produce a compound represented by the formula (2Q3-b-1) (wherein $R^2$, $R^3$, $R^5$ and $X_3$ are the same as defined above).

Some of the compounds represented by the formula (35) are known compounds, and some of them are commercially available. The rest of them may be prepared from known compounds in accordance with conventional methods disclosed in literature, for example, in accordance with the reaction conditions disclosed in e.g. WO2000/039094.

Among the compounds represented by the formula (3D-e) used in Process 14, a compound represented by the formula (3D-e1) wherein n is an integer of 0 may be produced, for example, in accordance with the following Reaction Shceme 8.

Reaction Shceme 8

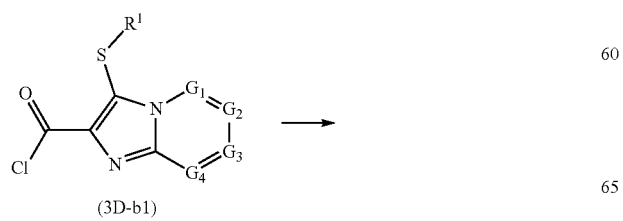

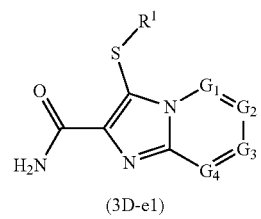

The compound represented by the formula (3D-b1) is reacted with aqueous ammonia for example in accordance with the method disclosed in e.g. JP-A-2009-108046 to produce a compound represented by the formula (3D-e1) (wherein $R^1$, $G_1$, $G_2$, $G_3$ and $G_4$ are the same as defined above).

The compound represented by the formula (50) used in Processes 15 and 16 may be produced, for example, in accordance with the following Reaction Scheme 9.

Reaction Scheme 9

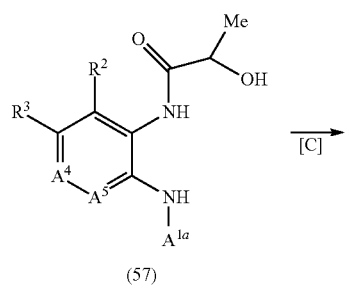

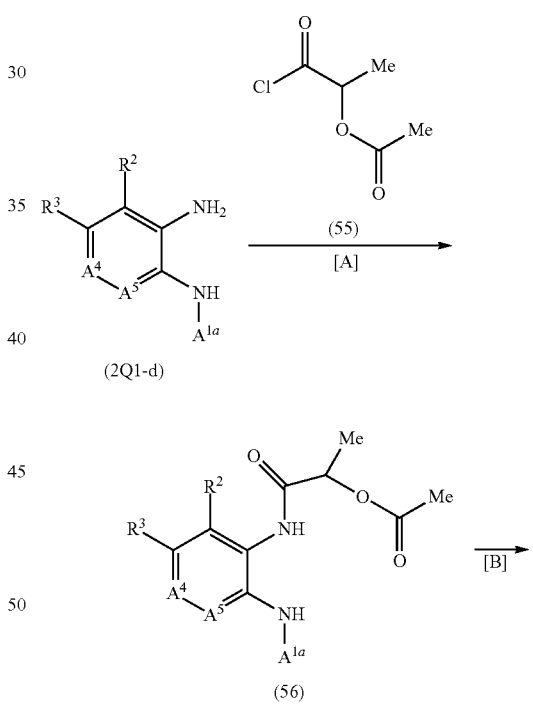

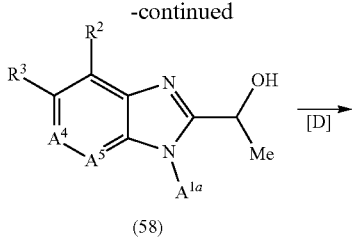

(58)

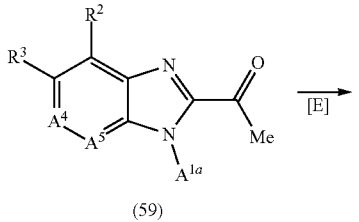

(59)

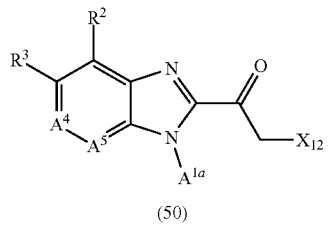

(50)

A compound represented by the formula (2Q1-d) is reacted with compound represented by the formula (55) in accordance with the method disclosed in step [A] of Process 1 to produce a compound represented by the formula (56) (wherein $R^2$, $R^3$, $A^{1a}$, $A^4$ and $A^5$ are the same as defined above).

Then, the compound represented by the formula (56) is subjected to deacetylation for example in accordance with the method disclosed in e.g. Synthesis, 1991, p. 465 to produce a compound represented by the formula (57) (wherein $R^2$, $R^3$, $A^{1a}$, $A^4$ and $A^5$ are the same as defined above).

Then, the compound represented by the formula (57) is subjected to dehydration condensation in accordance with the method disclosed in step [B] of Process 1 to produce a compound represented by the formula (58) (wherein $R^2$, $R^3$, $A^{1a}$, $A^4$ and $A^5$ are the same as defined above).

Then, the compound represented by the formula (58) and an oxidizing agent are reacted for example in accordance with the method disclosed in e.g. Journal of Medicinal Chemistry, 1998, Vol. 31, p. 545 to produce a compound represented by the formula (59) (wherein $R^2$, $R^3$, $A^{1a}$, $A^4$ and $A^5$ are the same as defined above).

Then, the compound represented by the formula (59) and a halogenating agent are reacted in accordance with the method disclosed in step [B] of Process 16 or in accordance with the method disclosed in e.g. Journal of Medicinal Chemistry, 1988, Vol. 31, p. 656 or Journal of Medicinal Chemistry, 2005, Vol. 48, p. 7658 to produce a compound represented by the formula (50).

The compound represented by the formula (55) is a known compound and is commercially available. Further, the compound represented by the formula (55) has optically active isomers due to the presence of an asymmetric carbon atom, and the present invention covers any optical isomers and any racemates.

In each reaction, after the reaction, an ordinary post treatment is carried out to obtain respective production intermediates to be raw material compounds in Processes 1 to 17.

Further, each production intermediate produced by the above methods may be used for the reaction in the subsequent step as it is without isolation nor purification. In some cases, the dehydration condensation reaction as the subsequent step proceeds, in step [B] of Reaction Scheme 9, and thus step [C] may be omitted.

As the condensed heterocyclic compounds represented by the formula (1) of the present invention, which can be produced by the above methods, compounds represented by the following Tables 1 to 5 may be mentioned. However, the compounds shown in the following Tables 1 to 5 merely exemplify the present invention, and the present invention is by no means restricted thereto.

In Tables, Me represents methyl, and similarly, Et represents ethyl, $^n$Pr represents normal propyl, and $^i$Pr represents isopropyl.

TABLE 1

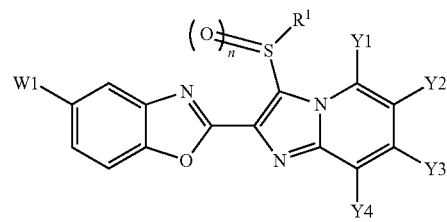

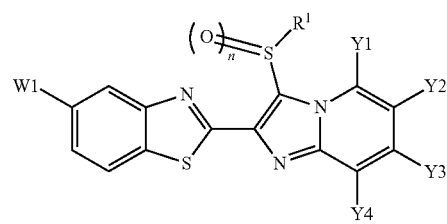

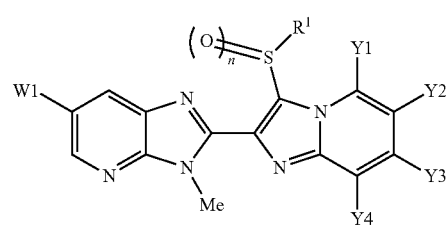

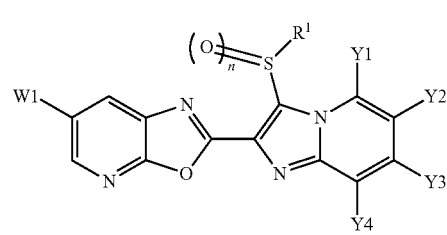

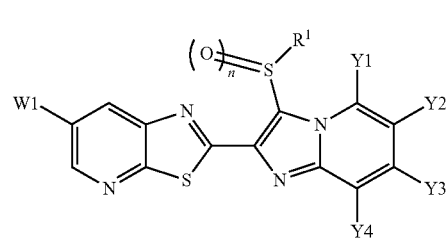

TABLE 1-continued
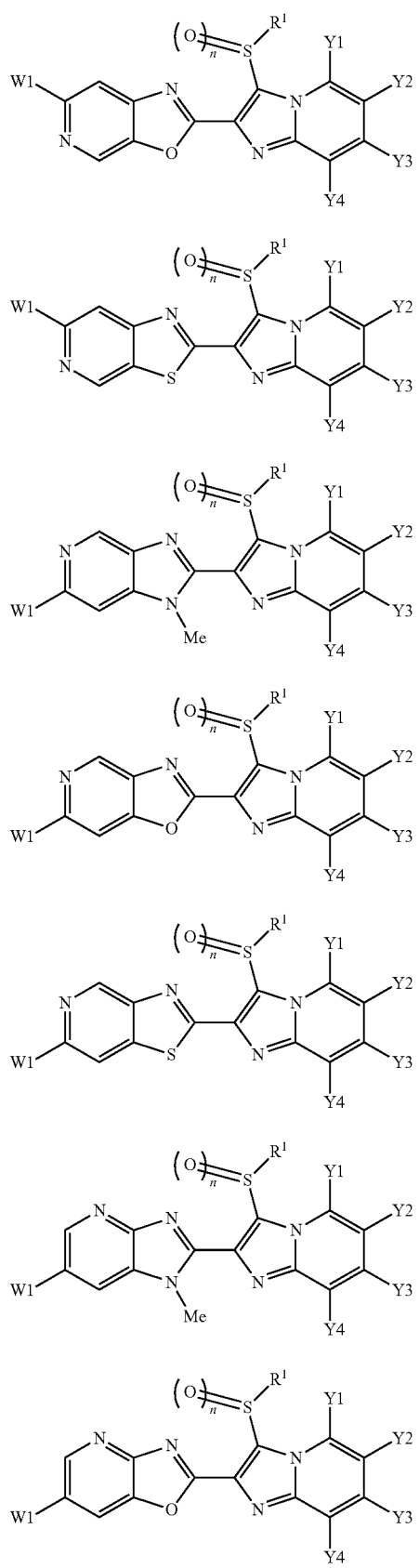
TABLE 1-continued
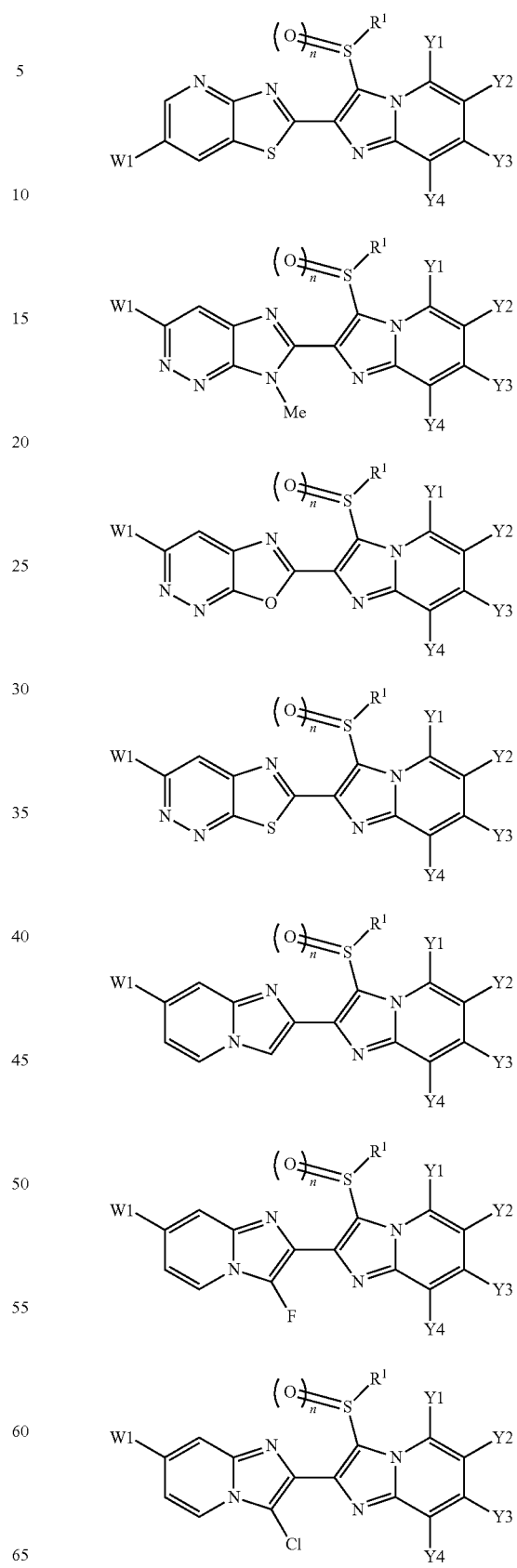

TABLE 1-continued
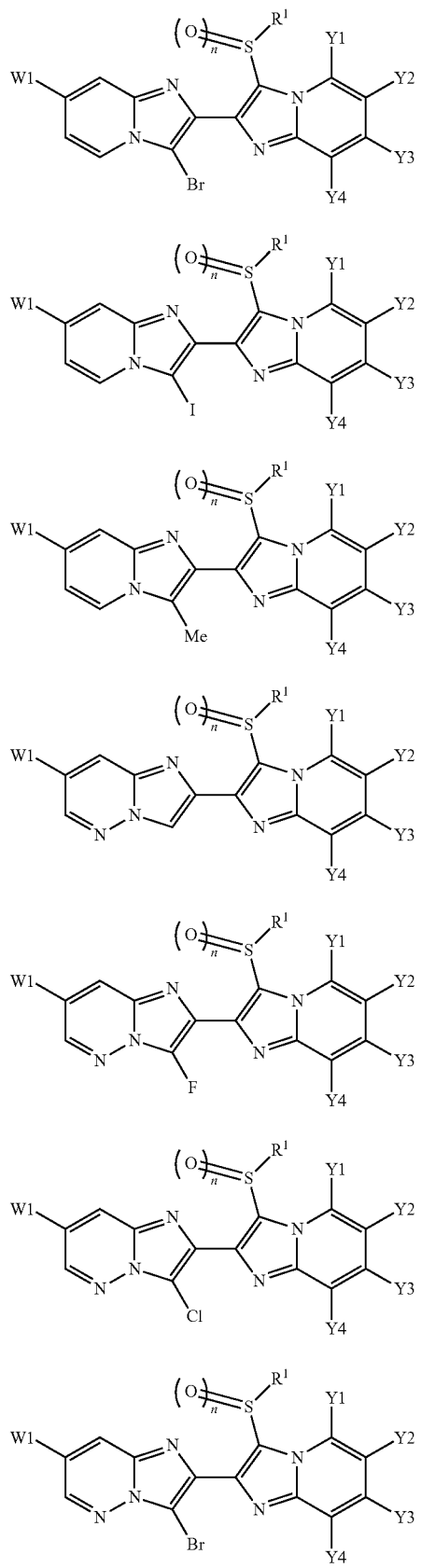
TABLE 1-continued
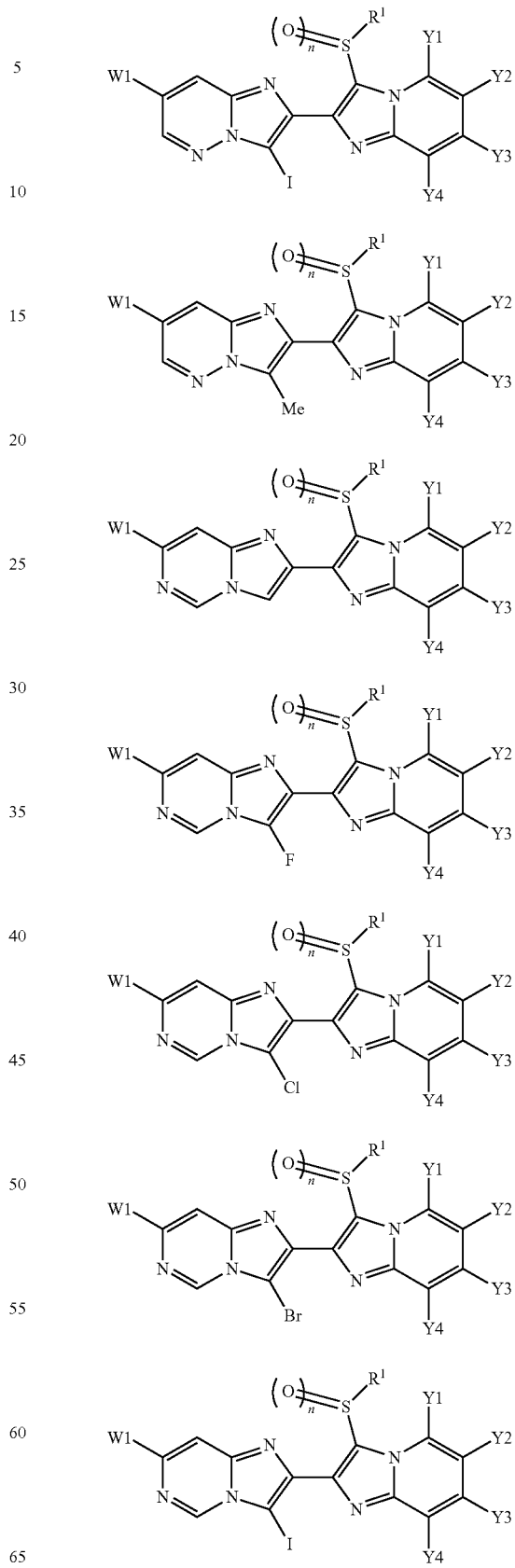

TABLE 1-continued
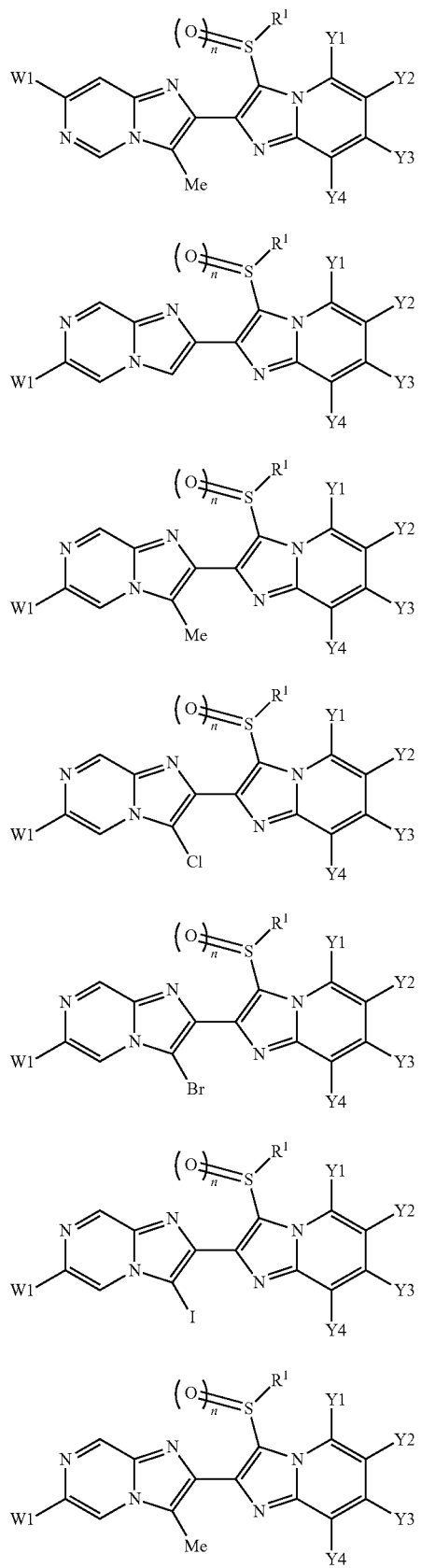
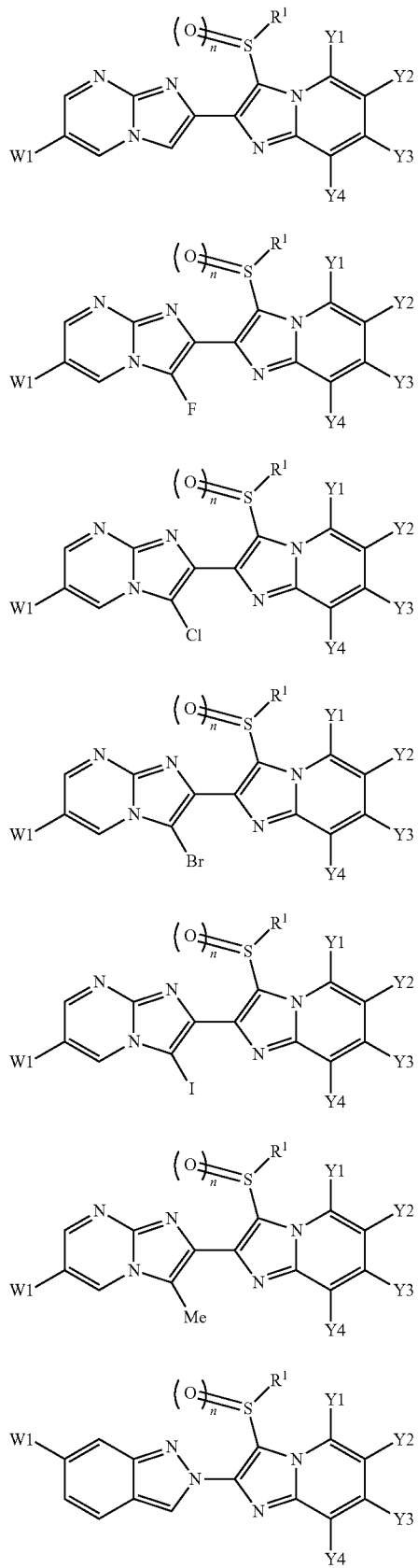

TABLE 1-continued
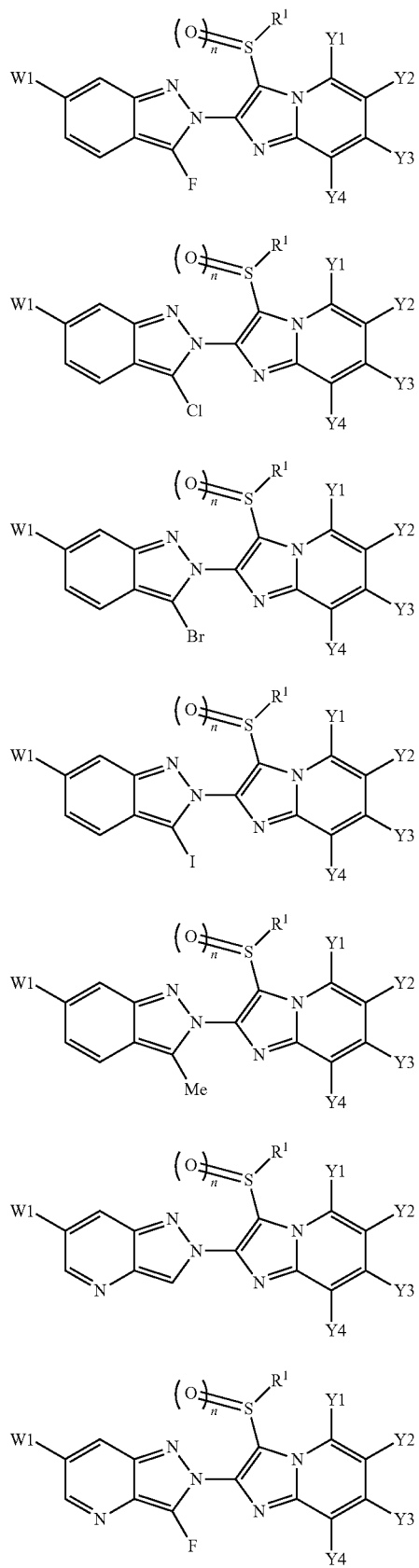
TABLE 1-continued
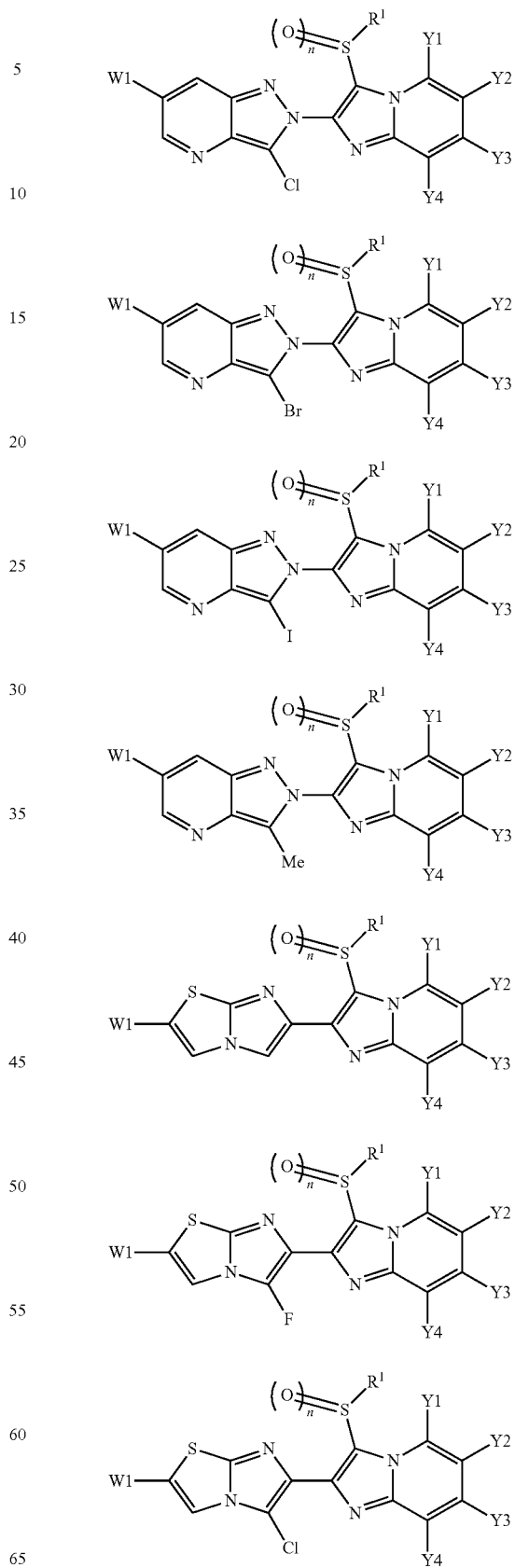

TABLE 1-continued

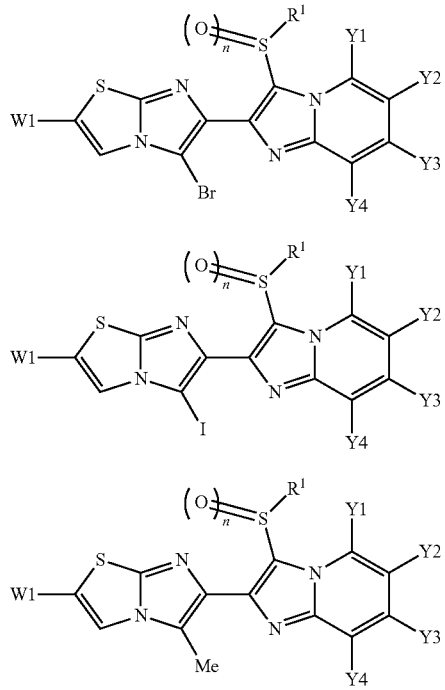

| W1 | R¹ | Y1 | Y2 | Y3 | Y4 | n |
|---|---|---|---|---|---|---|
| $CF_3$ | Me | H | H | H | H | 0 |
| $CF_3$ | Me | H | H | H | H | 1 |
| $CF_3$ | Me | H | H | H | H | 2 |
| $CF_3$ | Me | F | H | H | H | 0 |
| $CF_3$ | Me | F | H | H | H | 1 |
| $CF_3$ | Me | F | H | H | H | 2 |
| $CF_3$ | Me | Cl | H | H | H | 0 |
| $CF_3$ | Me | Cl | H | H | H | 1 |
| $CF_3$ | Me | Cl | H | H | H | 2 |
| $CF_3$ | Me | Br | H | H | H | 0 |
| $CF_3$ | Me | Br | H | H | H | 1 |
| $CF_3$ | Me | Br | H | H | H | 2 |
| $CF_3$ | Me | I | H | H | H | 0 |
| $CF_3$ | Me | I | H | H | H | 1 |
| $CF_3$ | Me | I | H | H | H | 2 |
| $CF_3$ | Me | Me | H | H | H | 0 |
| $CF_3$ | Me | Me | H | H | H | 1 |
| $CF_3$ | Me | Me | H | H | H | 2 |
| $CF_3$ | Me | $CF_3$ | H | H | H | 0 |
| $CF_3$ | Me | $CF_3$ | H | H | H | 1 |
| $CF_3$ | Me | $CF_3$ | H | H | H | 2 |
| $CF_3$ | Me | H | F | H | H | 0 |
| $CF_3$ | Me | H | F | H | H | 1 |
| $CF_3$ | Me | H | F | H | H | 2 |
| $CF_3$ | Me | H | Cl | H | H | 0 |
| $CF_3$ | Me | H | Cl | H | H | 1 |
| $CF_3$ | Me | H | Cl | H | H | 2 |
| $CF_3$ | Me | H | Br | H | H | 0 |
| $CF_3$ | Me | H | Br | H | H | 1 |
| $CF_3$ | Me | H | Br | H | H | 2 |
| $CF_3$ | Me | H | I | H | H | 0 |
| $CF_3$ | Me | H | I | H | H | 1 |
| $CF_3$ | Me | H | I | H | H | 2 |
| $CF_3$ | Me | H | Me | H | H | 0 |
| $CF_3$ | Me | H | Me | H | H | 1 |
| $CF_3$ | Me | H | Me | H | H | 2 |
| $CF_3$ | Me | H | $CF_3$ | H | H | 0 |
| $CF_3$ | Me | H | $CF_3$ | H | H | 1 |
| $CF_3$ | Me | H | $CF_3$ | H | H | 2 |
| $CF_3$ | Me | H | $CF_2CF_3$ | H | H | 0 |
| $CF_3$ | Me | H | $CF_2CF_3$ | H | H | 1 |
| $CF_3$ | Me | H | $CF_2CF_3$ | H | H | 2 |
| $CF_3$ | Me | H | $CF(CF_3)_2$ | H | H | 0 |
| $CF_3$ | Me | H | $CF(CF_3)_2$ | H | H | 1 |
| $CF_3$ | Me | H | $CF(CF_3)_2$ | H | H | 2 |
| $CF_3$ | Me | H | SMe | H | H | 0 |
| $CF_3$ | Me | H | SMe | H | H | 1 |
| $CF_3$ | Me | H | SMe | H | H | 2 |
| $CF_3$ | Me | H | SOMe | H | H | 0 |
| $CF_3$ | Me | H | SOMe | H | H | 1 |
| $CF_3$ | Me | H | SOMe | H | H | 2 |
| $CF_3$ | Me | H | $SO_2Me$ | H | H | 0 |
| $CF_3$ | Me | H | $SO_2Me$ | H | H | 1 |
| $CF_3$ | Me | H | $SO_2Me$ | H | H | 2 |
| $CF_3$ | Me | H | OMe | H | H | 0 |
| $CF_3$ | Me | H | OMe | H | H | 1 |
| $CF_3$ | Me | H | OMe | H | H | 2 |
| $CF_3$ | Me | H | $OCF_3$ | H | H | 0 |
| $CF_3$ | Me | H | $OCF_3$ | H | H | 1 |
| $CF_3$ | Me | H | $OCF_3$ | H | H | 2 |
| $CF_3$ | Me | H | $NO_2$ | H | H | 0 |
| $CF_3$ | Me | H | $NO_2$ | H | H | 1 |
| $CF_3$ | Me | H | $NO_2$ | H | H | 2 |
| $CF_3$ | Me | H | CN | H | H | 0 |
| $CF_3$ | Me | H | CN | H | H | 1 |
| $CF_3$ | Me | H | CN | H | H | 2 |
| $CF_3$ | Me | H | H | F | H | 0 |
| $CF_3$ | Me | H | H | F | H | 1 |
| $CF_3$ | Me | H | H | F | H | 2 |
| $CF_3$ | Me | H | H | Cl | H | 0 |
| $CF_3$ | Me | H | H | Cl | H | 1 |
| $CF_3$ | Me | H | H | Cl | H | 2 |
| $CF_3$ | Me | H | H | Br | H | 0 |
| $CF_3$ | Me | H | H | Br | H | 1 |
| $CF_3$ | Me | H | H | Br | H | 2 |
| $CF_3$ | Me | H | H | I | H | 0 |
| $CF_3$ | Me | H | H | I | H | 1 |
| $CF_3$ | Me | H | H | I | H | 2 |
| $CF_3$ | Me | H | H | Me | H | 0 |
| $CF_3$ | Me | H | H | Me | H | 1 |
| $CF_3$ | Me | H | H | Me | H | 2 |
| $CF_3$ | Me | H | H | $CF_3$ | H | 0 |
| $CF_3$ | Me | H | H | $CF_3$ | H | 1 |
| $CF_3$ | Me | H | H | $CF_3$ | H | 2 |
| $CF_3$ | Me | H | H | $CF_2CF_3$ | H | 0 |
| $CF_3$ | Me | H | H | $CF_2CF_3$ | H | 1 |
| $CF_3$ | Me | H | H | $CF_2CF_3$ | H | 2 |
| $CF_3$ | Me | H | H | $CF(CF_3)_2$ | H | 0 |
| $CF_3$ | Me | H | H | $CF(CF_3)_2$ | H | 1 |
| $CF_3$ | Me | H | H | $CF(CF_3)_2$ | H | 2 |
| $CF_3$ | Me | H | H | SMe | H | 0 |
| $CF_3$ | Me | H | H | SMe | H | 1 |
| $CF_3$ | Me | H | H | SMe | H | 2 |
| $CF_3$ | Me | H | H | SOMe | H | 0 |
| $CF_3$ | Me | H | H | SOMe | H | 1 |
| $CF_3$ | Me | H | H | SOMe | H | 2 |
| $CF_3$ | Me | H | H | $SO_2Me$ | H | 0 |
| $CF_3$ | Me | H | H | $SO_2Me$ | H | 1 |
| $CF_3$ | Me | H | H | $SO_2Me$ | H | 2 |
| $CF_3$ | Me | H | H | OMe | H | 0 |
| $CF_3$ | Me | H | H | OMe | H | 1 |
| $CF_3$ | Me | H | H | OMe | H | 2 |
| $CF_3$ | Me | H | H | $OCF_3$ | H | 0 |
| $CF_3$ | Me | H | H | $OCF_3$ | H | 1 |
| $CF_3$ | Me | H | H | $OCF_3$ | H | 2 |
| $CF_3$ | Me | H | H | $NO_2$ | H | 0 |
| $CF_3$ | Me | H | H | $NO_2$ | H | 1 |
| $CF_3$ | Me | H | H | $NO_2$ | H | 2 |
| $CF_3$ | Me | H | H | CN | H | 0 |
| $CF_3$ | Me | H | H | CN | H | 1 |
| $CF_3$ | Me | H | H | CN | H | 2 |
| $CF_3$ | Me | H | H | H | F | 0 |
| $CF_3$ | Me | H | H | H | F | 1 |
| $CF_3$ | Me | H | H | H | F | 2 |
| $CF_3$ | Me | H | H | H | Cl | 0 |
| $CF_3$ | Me | H | H | H | Cl | 1 |
| $CF_3$ | Me | H | H | H | Cl | 2 |
| $CF_3$ | Me | H | H | H | Br | 0 |
| $CF_3$ | Me | H | H | H | Br | 1 |
| $CF_3$ | Me | H | H | H | Br | 2 |
| $CF_3$ | Me | H | H | H | I | 0 |
| $CF_3$ | Me | H | H | H | I | 1 |
| $CF_3$ | Me | H | H | H | I | 2 |
| $CF_3$ | Me | H | H | H | Me | 0 |

TABLE 1-continued

| | | | | | | |
|---|---|---|---|---|---|---|
| CF₃ | Me | H | H | H | Me | 1 |
| CF₃ | Me | H | H | H | Me | 2 |
| CF₃ | Me | H | H | H | CF₃ | 0 |
| CF₃ | Me | H | H | H | CF₃ | 1 |
| CF₃ | Me | H | H | H | CF₃ | 2 |
| CF₃ | Me | H | H | H | CF₂CF₃ | 0 |
| CF₃ | Me | H | H | H | CF₂CF₃ | 1 |
| CF₃ | Me | H | H | H | CF₂CF₃ | 2 |
| CF₃ | Me | H | H | H | CF(CF₃)₂ | 0 |
| CF₃ | Me | H | H | H | CF(CF₃)₂ | 1 |
| CF₃ | Me | H | H | H | CF(CF₃)₂ | 2 |
| CF₃ | Me | H | H | H | SMe | 0 |
| CF₃ | Me | H | H | H | SMe | 1 |
| CF₃ | Me | H | H | H | SMe | 2 |
| CF₃ | Me | H | H | H | SOMe | 0 |
| CF₃ | Me | H | H | H | SOMe | 1 |
| CF₃ | Me | H | H | H | SOMe | 2 |
| CF₃ | Me | H | H | H | SO₂Me | 0 |
| CF₃ | Me | H | H | H | SO₂Me | 1 |
| CF₃ | Me | H | H | H | SO₂Me | 2 |
| CF₃ | Me | H | H | H | OMe | 0 |
| CF₃ | Me | H | H | H | OMe | 1 |
| CF₃ | Me | H | H | H | OMe | 2 |
| CF₃ | Me | H | H | H | OCF₃ | 0 |
| CF₃ | Me | H | H | H | OCF₃ | 1 |
| CF₃ | Me | H | H | H | OCF₃ | 2 |
| CF₃ | Me | H | H | H | NO₂ | 0 |
| CF₃ | Me | H | H | H | NO₂ | 1 |
| CF₃ | Me | H | H | H | NO₂ | 2 |
| CF₃ | Me | H | H | H | CN | 0 |
| CF₃ | Me | H | H | H | CN | 1 |
| CF₃ | Me | H | H | H | CN | 2 |
| CF₃ | Me | H | F | H | F | 0 |
| CF₃ | Me | H | F | H | F | 1 |
| CF₃ | Me | H | F | H | F | 2 |
| CF₃ | Me | H | Cl | H | Cl | 0 |
| CF₃ | Me | H | Cl | H | Cl | 1 |
| CF₃ | Me | H | Cl | H | Cl | 2 |
| CF₃ | Me | H | Br | H | Br | 0 |
| CF₃ | Me | H | Br | H | Br | 1 |
| CF₃ | Me | H | Br | H | Br | 2 |
| CF₃ | Me | H | I | H | I | 0 |
| CF₃ | Me | H | I | H | I | 1 |
| CF₃ | Me | H | I | H | I | 2 |
| CF₃ | Me | H | F | H | Cl | 0 |
| CF₃ | Me | H | F | H | Cl | 1 |
| CF₃ | Me | H | F | H | Cl | 2 |
| CF₃ | Me | H | F | H | Br | 0 |
| CF₃ | Me | H | F | H | Br | 1 |
| CF₃ | Me | H | F | H | Br | 2 |
| CF₃ | Me | H | F | H | I | 0 |
| CF₃ | Me | H | F | H | I | 1 |
| CF₃ | Me | H | F | H | I | 2 |
| CF₃ | Me | H | Cl | H | F | 0 |
| CF₃ | Me | H | Cl | H | F | 1 |
| CF₃ | Me | H | Cl | H | F | 2 |
| CF₃ | Me | H | Cl | H | Br | 0 |
| CF₃ | Me | H | Cl | H | Br | 1 |
| CF₃ | Me | H | Cl | H | Br | 2 |
| CF₃ | Me | H | Cl | H | I | 0 |
| CF₃ | Me | H | Cl | H | I | 1 |
| CF₃ | Me | H | Cl | H | I | 2 |
| CF₃ | Me | H | Br | H | F | 0 |
| CF₃ | Me | H | Br | H | F | 1 |
| CF₃ | Me | H | Br | H | F | 2 |
| CF₃ | Me | H | Br | H | Cl | 0 |
| CF₃ | Me | H | Br | H | Cl | 1 |
| CF₃ | Me | H | Br | H | Cl | 2 |
| CF₃ | Me | H | Br | H | I | 0 |
| CF₃ | Me | H | Br | H | I | 1 |
| CF₃ | Me | H | Br | H | I | 2 |
| CF₃ | Me | H | I | H | F | 0 |
| CF₃ | Me | H | I | H | F | 1 |
| CF₃ | Me | H | I | H | F | 2 |
| CF₃ | Me | H | I | H | Cl | 0 |
| CF₃ | Me | H | I | H | Cl | 1 |
| CF₃ | Me | H | I | H | Cl | 2 |
| CF₃ | Me | H | I | H | Br | 0 |
| CF₃ | Me | H | I | H | Br | 1 |
| CF₃ | Me | H | I | H | Br | 2 |
| CF₃ | Me | H | F | H | CN | 0 |
| CF₃ | Me | H | F | H | CN | 1 |
| CF₃ | Me | H | F | H | CN | 2 |
| CF₃ | Me | H | Cl | H | CN | 0 |
| CF₃ | Me | H | Cl | H | CN | 1 |
| CF₃ | Me | H | Cl | H | CN | 2 |
| CF₃ | Me | H | Br | H | CN | 0 |
| CF₃ | Me | H | Br | H | CN | 1 |
| CF₃ | Me | H | Br | H | CN | 2 |
| CF₃ | Me | H | I | H | CN | 0 |
| CF₃ | Me | H | I | H | CN | 1 |
| CF₃ | Me | H | I | H | CN | 2 |
| CF₃ | Me | H | CF₃ | H | F | 0 |
| CF₃ | Me | H | CF₃ | H | F | 1 |
| CF₃ | Me | H | CF₃ | H | F | 2 |
| CF₃ | Me | H | CF₃ | H | Cl | 0 |
| CF₃ | Me | H | CF₃ | H | Cl | 1 |
| CF₃ | Me | H | CF₃ | H | Cl | 2 |
| CF₃ | Me | H | CF₃ | H | Br | 0 |
| CF₃ | Me | H | CF₃ | H | Br | 1 |
| CF₃ | Me | H | CF₃ | H | Br | 2 |
| CF₃ | Me | H | CF₃ | H | I | 0 |
| CF₃ | Me | H | CF₃ | H | I | 1 |
| CF₃ | Me | H | CF₃ | H | I | 2 |
| CF₃ | Me | H | CF₃ | H | CN | 0 |
| CF₃ | Me | H | CF₃ | H | CN | 1 |
| CF₃ | Me | H | CF₃ | H | CN | 2 |
| CF₃ | Me | H | F | F | H | 0 |
| CF₃ | Me | H | F | F | H | 1 |
| CF₃ | Me | H | F | F | H | 2 |
| CF₃ | Me | H | Cl | Cl | H | 0 |
| CF₃ | Me | H | Cl | Cl | H | 1 |
| CF₃ | Me | H | Cl | Cl | H | 2 |
| CF₃ | Me | H | Br | Br | H | 0 |
| CF₃ | Me | H | Br | Br | H | 1 |
| CF₃ | Me | H | Br | Br | H | 2 |
| CF₃ | Me | H | I | I | H | 0 |
| CF₃ | Me | H | I | I | H | 1 |
| CF₃ | Me | H | I | I | H | 2 |
| CF₃ | Me | H | F | Cl | H | 0 |
| CF₃ | Me | H | F | Cl | H | 1 |
| CF₃ | Me | H | F | Cl | H | 2 |
| CF₃ | Me | H | F | Br | H | 0 |
| CF₃ | Me | H | F | Br | H | 1 |
| CF₃ | Me | H | F | Br | H | 2 |
| CF₃ | Me | H | F | I | H | 0 |
| CF₃ | Me | H | F | I | H | 1 |
| CF₃ | Me | H | F | I | H | 2 |
| CF₃ | Me | H | Cl | F | H | 0 |
| CF₃ | Me | H | Cl | F | H | 1 |
| CF₃ | Me | H | Cl | F | H | 2 |
| CF₃ | Me | H | Cl | Br | H | 0 |
| CF₃ | Me | H | Cl | Br | H | 1 |
| CF₃ | Me | H | Cl | Br | H | 2 |
| CF₃ | Me | H | Cl | I | H | 0 |
| CF₃ | Me | H | Cl | I | H | 1 |
| CF₃ | Me | H | Cl | I | H | 2 |
| CF₃ | Me | H | Br | F | H | 0 |
| CF₃ | Me | H | Br | F | H | 1 |
| CF₃ | Me | H | Br | F | H | 2 |
| CF₃ | Me | H | Br | Cl | H | 0 |
| CF₃ | Me | H | Br | Cl | H | 1 |
| CF₃ | Me | H | Br | Cl | H | 2 |
| CF₃ | Me | H | Br | I | H | 0 |
| CF₃ | Me | H | Br | I | H | 1 |
| CF₃ | Me | H | Br | I | H | 2 |
| CF₃ | Me | H | I | F | H | 0 |
| CF₃ | Me | H | I | F | H | 1 |
| CF₃ | Me | H | I | F | H | 2 |
| CF₃ | Me | H | I | Cl | H | 0 |
| CF₃ | Me | H | I | Cl | H | 1 |
| CF₃ | Me | H | I | Cl | H | 2 |
| CF₃ | Me | H | I | Br | H | 0 |
| CF₃ | Me | H | I | Br | H | 1 |
| CF₃ | Me | H | I | Br | H | 2 |
| CF₃ | Me | H | F | CN | H | 0 |
| CF₃ | Me | H | F | CN | H | 1 |
| CF₃ | Me | H | F | CN | H | 2 |
| CF₃ | Me | H | Cl | CN | H | 0 |
| CF₃ | Me | H | Cl | CN | H | 1 |

TABLE 1-continued

| | | | | | | |
|---|---|---|---|---|---|---|
| CF₃ | Me | H | Cl | CN | H | 2 |
| CF₃ | Me | H | Br | CN | H | 0 |
| CF₃ | Me | H | Br | CN | H | 1 |
| CF₃ | Me | H | Br | CN | H | 2 |
| CF₃ | Me | H | I | CN | H | 0 |
| CF₃ | Me | H | I | CN | H | 1 |
| CF₃ | Me | H | I | CN | H | 2 |
| CF₃ | Me | H | CF₃ | F | H | 0 |
| CF₃ | Me | H | CF₃ | F | H | 1 |
| CF₃ | Me | H | CF₃ | F | H | 2 |
| CF₃ | Me | H | CF₃ | Cl | H | 0 |
| CF₃ | Me | H | CF₃ | Cl | H | 1 |
| CF₃ | Me | H | CF₃ | Cl | H | 2 |
| CF₃ | Me | H | CF₃ | Br | H | 0 |
| CF₃ | Me | H | CF₃ | Br | H | 1 |
| CF₃ | Me | H | CF₃ | Br | H | 2 |
| CF₃ | Me | H | CF₃ | I | H | 0 |
| CF₃ | Me | H | CF₃ | I | H | 1 |
| CF₃ | Me | H | CF₃ | I | H | 2 |
| CF₃ | Me | H | CF₃ | CN | H | 0 |
| CF₃ | Me | H | CF₃ | CN | H | 1 |
| CF₃ | Me | H | CF₃ | CN | H | 2 |
| CF₃ | Et | H | H | H | H | 0 |
| CF₃ | Et | H | H | H | H | 1 |
| CF₃ | Et | H | H | H | H | 2 |
| CF₃ | Et | F | H | H | H | 0 |
| CF₃ | Et | F | H | H | H | 1 |
| CF₃ | Et | F | H | H | H | 2 |
| CF₃ | Et | Cl | H | H | H | 0 |
| CF₃ | Et | Cl | H | H | H | 1 |
| CF₃ | Et | Cl | H | H | H | 2 |
| CF₃ | Et | Br | H | H | H | 0 |
| CF₃ | Et | Br | H | H | H | 1 |
| CF₃ | Et | Br | H | H | H | 2 |
| CF₃ | Et | I | H | H | H | 0 |
| CF₃ | Et | I | H | H | H | 1 |
| CF₃ | Et | I | H | H | H | 2 |
| CF₃ | Et | Me | H | H | H | 0 |
| CF₃ | Et | Me | H | H | H | 1 |
| CF₃ | Et | Me | H | H | H | 2 |
| CF₃ | Et | CF₃ | H | H | H | 0 |
| CF₃ | Et | CF₃ | H | H | H | 1 |
| CF₃ | Et | CF₃ | H | H | H | 2 |
| CF₃ | Et | H | F | H | H | 0 |
| CF₃ | Et | H | F | H | H | 1 |
| CF₃ | Et | H | F | H | H | 2 |
| CF₃ | Et | H | Cl | H | H | 0 |
| CF₃ | Et | H | Cl | H | H | 1 |
| CF₃ | Et | H | Cl | H | H | 2 |
| CF₃ | Et | H | Br | H | H | 0 |
| CF₃ | Et | H | Br | H | H | 1 |
| CF₃ | Et | H | Br | H | H | 2 |
| CF₃ | Et | H | I | H | H | 0 |
| CF₃ | Et | H | I | H | H | 1 |
| CF₃ | Et | H | I | H | H | 2 |
| CF₃ | Et | H | Me | H | H | 0 |
| CF₃ | Et | H | Me | H | H | 1 |
| CF₃ | Et | H | Me | H | H | 2 |
| CF₃ | Et | H | CF₃ | H | H | 0 |
| CF₃ | Et | H | CF₃ | H | H | 1 |
| CF₃ | Et | H | CF₃ | H | H | 2 |
| CF₃ | Et | H | CF₂CF₃ | H | H | 0 |
| CF₃ | Et | H | CF₂CF₃ | H | H | 1 |
| CF₃ | Et | H | CF₂CF₃ | H | H | 2 |
| CF₃ | Et | H | CF(CF₃)₂ | H | H | 0 |
| CF₃ | Et | H | CF(CF₃)₂ | H | H | 1 |
| CF₃ | Et | H | CF(CF₃)₂ | H | H | 2 |
| CF₃ | Et | H | SMe | H | H | 0 |
| CF₃ | Et | H | SMe | H | H | 1 |
| CF₃ | Et | H | SMe | H | H | 2 |
| CF₃ | Et | H | SOMe | H | H | 0 |
| CF₃ | Et | H | SOMe | H | H | 1 |
| CF₃ | Et | H | SOMe | H | H | 2 |
| CF₃ | Et | H | SO₂Me | H | H | 0 |
| CF₃ | Et | H | SO₂Me | H | H | 1 |
| CF₃ | Et | H | SO₂Me | H | H | 2 |
| CF₃ | Et | H | OMe | H | H | 0 |
| CF₃ | Et | H | OMe | H | H | 1 |
| CF₃ | Et | H | OMe | H | H | 2 |
| CF₃ | Et | H | OCF₃ | H | H | 0 |
| CF₃ | Et | H | OCF₃ | H | H | 1 |
| CF₃ | Et | H | OCF₃ | H | H | 2 |
| CF₃ | Et | H | NO₂ | H | H | 0 |
| CF₃ | Et | H | NO₂ | H | H | 1 |
| CF₃ | Et | H | NO₂ | H | H | 2 |
| CF₃ | Et | H | CN | H | H | 0 |
| CF₃ | Et | H | CN | H | H | 1 |
| CF₃ | Et | H | CN | H | H | 2 |
| CF₃ | Et | H | H | F | H | 0 |
| CF₃ | Et | H | H | F | H | 1 |
| CF₃ | Et | H | H | F | H | 2 |
| CF₃ | Et | H | H | Cl | H | 0 |
| CF₃ | Et | H | H | Cl | H | 1 |
| CF₃ | Et | H | H | Cl | H | 2 |
| CF₃ | Et | H | H | Br | H | 0 |
| CF₃ | Et | H | H | Br | H | 1 |
| CF₃ | Et | H | H | Br | H | 2 |
| CF₃ | Et | H | H | I | H | 0 |
| CF₃ | Et | H | H | I | H | 1 |
| CF₃ | Et | H | H | I | H | 2 |
| CF₃ | Et | H | H | Me | H | 0 |
| CF₃ | Et | H | H | Me | H | 1 |
| CF₃ | Et | H | H | Me | H | 2 |
| CF₃ | Et | H | H | CF₃ | H | 0 |
| CF₃ | Et | H | H | CF₃ | H | 1 |
| CF₃ | Et | H | H | CF₃ | H | 2 |
| CF₃ | Et | H | H | CF₂CF₃ | H | 0 |
| CF₃ | Et | H | H | CF₂CF₃ | H | 1 |
| CF₃ | Et | H | H | CF₂CF₃ | H | 2 |
| CF₃ | Et | H | H | CF(CF₃)₂ | H | 0 |
| CF₃ | Et | H | H | CF(CF₃)₂ | H | 1 |
| CF₃ | Et | H | H | CF(CF₃)₂ | H | 2 |
| CF₃ | Et | H | H | SMe | H | 0 |
| CF₃ | Et | H | H | SMe | H | 1 |
| CF₃ | Et | H | H | SMe | H | 2 |
| CF₃ | Et | H | H | SOMe | H | 0 |
| CF₃ | Et | H | H | SOMe | H | 1 |
| CF₃ | Et | H | H | SOMe | H | 2 |
| CF₃ | Et | H | H | SO₂Me | H | 0 |
| CF₃ | Et | H | H | SO₂Me | H | 1 |
| CF₃ | Et | H | H | SO₂Me | H | 2 |
| CF₃ | Et | H | H | OMe | H | 0 |
| CF₃ | Et | H | H | OMe | H | 1 |
| CF₃ | Et | H | H | OMe | H | 2 |
| CF₃ | Et | H | H | OCF₃ | H | 0 |
| CF₃ | Et | H | H | OCF₃ | H | 1 |
| CF₃ | Et | H | H | OCF₃ | H | 2 |
| CF₃ | Et | H | H | NO₂ | H | 0 |
| CF₃ | Et | H | H | NO₂ | H | 1 |
| CF₃ | Et | H | H | NO₂ | H | 2 |
| CF₃ | Et | H | H | CN | H | 0 |
| CF₃ | Et | H | H | CN | H | 1 |
| CF₃ | Et | H | H | CN | H | 2 |
| CF₃ | Et | H | H | H | F | 0 |
| CF₃ | Et | H | H | H | F | 1 |
| CF₃ | Et | H | H | H | F | 2 |
| CF₃ | Et | H | H | H | Cl | 0 |
| CF₃ | Et | H | H | H | Cl | 1 |
| CF₃ | Et | H | H | H | Cl | 2 |
| CF₃ | Et | H | H | H | Br | 0 |
| CF₃ | Et | H | H | H | Br | 1 |
| CF₃ | Et | H | H | H | Br | 2 |
| CF₃ | Et | H | H | H | I | 0 |
| CF₃ | Et | H | H | H | I | 1 |
| CF₃ | Et | H | H | H | I | 2 |
| CF₃ | Et | H | H | H | Me | 0 |
| CF₃ | Et | H | H | H | Me | 1 |
| CF₃ | Et | H | H | H | Me | 2 |
| CF₃ | Et | H | H | H | CF₃ | 0 |
| CF₃ | Et | H | H | H | CF₃ | 1 |
| CF₃ | Et | H | H | H | CF₃ | 2 |
| CF₃ | Et | H | H | H | CF₂CF₃ | 0 |
| CF₃ | Et | H | H | H | CF₂CF₃ | 1 |
| CF₃ | Et | H | H | H | CF₂CF₃ | 2 |
| CF₃ | Et | H | H | H | CF(CF₃)₂ | 0 |
| CF₃ | Et | H | H | H | CF(CF₃)₂ | 2 |
| CF₃ | Et | H | H | H | SMe | 0 |
| CF₃ | Et | H | H | H | SMe | 1 |
| CF₃ | Et | H | H | H | SMe | 2 |

TABLE 1-continued

| | | | | | | |
|---|---|---|---|---|---|---|
| CF₃ | Et | H | H | H | SOMe | 0 |
| CF₃ | Et | H | H | H | SOMe | 1 |
| CF₃ | Et | H | H | H | SOMe | 2 |
| CF₃ | Et | H | H | H | SO₂Me | 0 |
| CF₃ | Et | H | H | H | SO₂Me | 1 |
| CF₃ | Et | H | H | H | SO₂Me | 2 |
| CF₃ | Et | H | H | H | OMe | 0 |
| CF₃ | Et | H | H | H | OMe | 1 |
| CF₃ | Et | H | H | H | OMe | 2 |
| CF₃ | Et | H | H | H | OCF₃ | 0 |
| CF₃ | Et | H | H | H | OCF₃ | 1 |
| CF₃ | Et | H | H | H | OCF₃ | 2 |
| CF₃ | Et | H | H | H | NO₂ | 0 |
| CF₃ | Et | H | H | H | NO₂ | 1 |
| CF₃ | Et | H | H | H | NO₂ | 2 |
| CF₃ | Et | H | H | H | CN | 0 |
| CF₃ | Et | H | H | H | CN | 1 |
| CF₃ | Et | H | H | H | CN | 2 |
| CF₃ | Et | H | F | H | F | 0 |
| CF₃ | Et | H | F | H | F | 1 |
| CF₃ | Et | H | F | H | F | 2 |
| CF₃ | Et | H | Cl | H | Cl | 0 |
| CF₃ | Et | H | Cl | H | Cl | 1 |
| CF₃ | Et | H | Cl | H | Cl | 2 |
| CF₃ | Et | H | Br | H | Br | 0 |
| CF₃ | Et | H | Br | H | Br | 1 |
| CF₃ | Et | H | Br | H | Br | 2 |
| CF₃ | Et | H | I | H | I | 0 |
| CF₃ | Et | H | I | H | I | 1 |
| CF₃ | Et | H | I | H | I | 2 |
| CF₃ | Et | H | F | H | Cl | 0 |
| CF₃ | Et | H | F | H | Cl | 1 |
| CF₃ | Et | H | F | H | Cl | 2 |
| CF₃ | Et | H | F | H | Br | 0 |
| CF₃ | Et | H | F | H | Br | 1 |
| CF₃ | Et | H | F | H | Br | 2 |
| CF₃ | Et | H | F | H | I | 0 |
| CF₃ | Et | H | F | H | I | 1 |
| CF₃ | Et | H | F | H | I | 2 |
| CF₃ | Et | H | Cl | H | F | 0 |
| CF₃ | Et | H | Cl | H | F | 1 |
| CF₃ | Et | H | Cl | H | F | 2 |
| CF₃ | Et | H | Cl | H | Br | 0 |
| CF₃ | Et | H | Cl | H | Br | 1 |
| CF₃ | Et | H | Cl | H | Br | 2 |
| CF₃ | Et | H | Cl | H | I | 0 |
| CF₃ | Et | H | Cl | H | I | 1 |
| CF₃ | Et | H | Cl | H | I | 2 |
| CF₃ | Et | H | Br | H | F | 0 |
| CF₃ | Et | H | Br | H | F | 1 |
| CF₃ | Et | H | Br | H | F | 2 |
| CF₃ | Et | H | Br | H | Cl | 0 |
| CF₃ | Et | H | Br | H | Cl | 1 |
| CF₃ | Et | H | Br | H | Cl | 2 |
| CF₃ | Et | H | Br | H | I | 0 |
| CF₃ | Et | H | Br | H | I | 1 |
| CF₃ | Et | H | Br | H | I | 2 |
| CF₃ | Et | H | I | H | F | 0 |
| CF₃ | Et | H | I | H | F | 1 |
| CF₃ | Et | H | I | H | F | 2 |
| CF₃ | Et | H | I | H | Cl | 0 |
| CF₃ | Et | H | I | H | Cl | 1 |
| CF₃ | Et | H | I | H | Cl | 2 |
| CF₃ | Et | H | I | H | Br | 0 |
| CF₃ | Et | H | I | H | Br | 1 |
| CF₃ | Et | H | I | H | Br | 2 |
| CF₃ | Et | H | F | H | CN | 0 |
| CF₃ | Et | H | F | H | CN | 1 |
| CF₃ | Et | H | F | H | CN | 2 |
| CF₃ | Et | H | Cl | H | CN | 0 |
| CF₃ | Et | H | Cl | H | CN | 1 |
| CF₃ | Et | H | Cl | H | CN | 2 |
| CF₃ | Et | H | Br | H | CN | 0 |
| CF₃ | Et | H | Br | H | CN | 1 |
| CF₃ | Et | H | Br | H | CN | 2 |
| CF₃ | Et | H | I | H | CN | 0 |
| CF₃ | Et | H | I | H | CN | 1 |
| CF₃ | Et | H | I | H | CN | 2 |
| CF₃ | Et | H | CF₃ | H | F | 0 |
| CF₃ | Et | H | CF₃ | H | F | 1 |
| CF₃ | Et | H | CF₃ | H | F | 2 |
| CF₃ | Et | H | CF₃ | H | Cl | 0 |
| CF₃ | Et | H | CF₃ | H | Cl | 1 |
| CF₃ | Et | H | CF₃ | H | Cl | 2 |
| CF₃ | Et | H | CF₃ | H | Br | 0 |
| CF₃ | Et | H | CF₃ | H | Br | 1 |
| CF₃ | Et | H | CF₃ | H | Br | 2 |
| CF₃ | Et | H | CF₃ | H | I | 0 |
| CF₃ | Et | H | CF₃ | H | I | 1 |
| CF₃ | Et | H | CF₃ | H | I | 2 |
| CF₃ | Et | H | CF₃ | H | CN | 0 |
| CF₃ | Et | H | CF₃ | H | CN | 1 |
| CF₃ | Et | H | CF₃ | H | CN | 2 |
| CF₃ | Et | H | F | F | H | 0 |
| CF₃ | Et | H | F | F | H | 1 |
| CF₃ | Et | H | F | F | H | 2 |
| CF₃ | Et | H | Cl | Cl | H | 0 |
| CF₃ | Et | H | Cl | Cl | H | 1 |
| CF₃ | Et | H | Cl | Cl | H | 2 |
| CF₃ | Et | H | Br | Br | H | 0 |
| CF₃ | Et | H | Br | Br | H | 1 |
| CF₃ | Et | H | Br | Br | H | 2 |
| CF₃ | Et | H | I | I | H | 0 |
| CF₃ | Et | H | I | I | H | 1 |
| CF₃ | Et | H | I | I | H | 2 |
| CF₃ | Et | H | F | Cl | H | 0 |
| CF₃ | Et | H | F | Cl | H | 1 |
| CF₃ | Et | H | F | Cl | H | 2 |
| CF₃ | Et | H | F | Br | H | 0 |
| CF₃ | Et | H | F | Br | H | 1 |
| CF₃ | Et | H | F | Br | H | 2 |
| CF₃ | Et | H | F | I | H | 0 |
| CF₃ | Et | H | F | I | H | 1 |
| CF₃ | Et | H | F | I | H | 2 |
| CF₃ | Et | H | Cl | F | H | 0 |
| CF₃ | Et | H | Cl | F | H | 1 |
| CF₃ | Et | H | Cl | F | H | 2 |
| CF₃ | Et | H | Cl | Br | H | 0 |
| CF₃ | Et | H | Cl | Br | H | 1 |
| CF₃ | Et | H | Cl | Br | H | 2 |
| CF₃ | Et | H | Cl | I | H | 0 |
| CF₃ | Et | H | Cl | I | H | 1 |
| CF₃ | Et | H | Cl | I | H | 2 |
| CF₃ | Et | H | Br | F | H | 0 |
| CF₃ | Et | H | Br | F | H | 1 |
| CF₃ | Et | H | Br | F | H | 2 |
| CF₃ | Et | H | Br | Cl | H | 0 |
| CF₃ | Et | H | Br | Cl | H | 1 |
| CF₃ | Et | H | Br | Cl | H | 2 |
| CF₃ | Et | H | Br | I | H | 0 |
| CF₃ | Et | H | Br | I | H | 1 |
| CF₃ | Et | H | Br | I | H | 2 |
| CF₃ | Et | H | I | F | H | 0 |
| CF₃ | Et | H | I | F | H | 1 |
| CF₃ | Et | H | I | F | H | 2 |
| CF₃ | Et | H | I | Cl | H | 0 |
| CF₃ | Et | H | I | Cl | H | 1 |
| CF₃ | Et | H | I | Cl | H | 2 |
| CF₃ | Et | H | I | Br | H | 0 |
| CF₃ | Et | H | I | Br | H | 1 |
| CF₃ | Et | H | I | Br | H | 2 |
| CF₃ | Et | H | F | CN | H | 0 |
| CF₃ | Et | H | F | CN | H | 1 |
| CF₃ | Et | H | F | CN | H | 2 |
| CF₃ | Et | H | Cl | CN | H | 0 |
| CF₃ | Et | H | Cl | CN | H | 1 |
| CF₃ | Et | H | Cl | CN | H | 2 |
| CF₃ | Et | H | Br | CN | H | 0 |
| CF₃ | Et | H | Br | CN | H | 1 |
| CF₃ | Et | H | Br | CN | H | 2 |
| CF₃ | Et | H | I | CN | H | 0 |
| CF₃ | Et | H | I | CN | H | 1 |
| CF₃ | Et | H | I | CN | H | 2 |
| CF₃ | Et | H | CF₃ | F | H | 0 |
| CF₃ | Et | H | CF₃ | F | H | 1 |
| CF₃ | Et | H | CF₃ | F | H | 2 |
| CF₃ | Et | H | CF₃ | Cl | H | 0 |
| CF₃ | Et | H | CF₃ | Cl | H | 1 |
| CF₃ | Et | H | CF₃ | Cl | H | 2 |
| CF₃ | Et | H | CF₃ | Br | H | 0 |

TABLE 1-continued

| | | | | | | |
|---|---|---|---|---|---|---|
| CF$_3$ | Et | H | CF$_3$ | Br | H | 1 |
| CF$_3$ | Et | H | CF$_3$ | Br | H | 2 |
| CF$_3$ | Et | H | CF$_3$ | I | H | 0 |
| CF$_3$ | Et | H | CF$_3$ | I | H | 1 |
| CF$_3$ | Et | H | CF$_3$ | I | H | 2 |
| CF$_3$ | Et | H | CF$_3$ | CN | H | 0 |
| CF$_3$ | Et | H | CF$_3$ | CN | H | 1 |
| CF$_3$ | Et | H | CF$_3$ | CN | H | 2 |
| CF$_3$ | $^n$Pr | H | H | H | H | 0 |
| CF$_3$ | $^n$Pr | H | H | H | H | 1 |
| CF$_3$ | $^n$Pr | H | H | H | H | 2 |
| CF$_3$ | $^n$Pr | F | H | H | H | 0 |
| CF$_3$ | $^n$Pr | F | H | H | H | 1 |
| CF$_3$ | $^n$Pr | F | H | H | H | 2 |
| CF$_3$ | $^n$Pr | Cl | H | H | H | 0 |
| CF$_3$ | $^n$Pr | Cl | H | H | H | 1 |
| CF$_3$ | $^n$Pr | Cl | H | H | H | 2 |
| CF$_3$ | $^n$Pr | Br | H | H | H | 0 |
| CF$_3$ | $^n$Pr | Br | H | H | H | 1 |
| CF$_3$ | $^n$Pr | Br | H | H | H | 2 |
| CF$_3$ | $^n$Pr | I | H | H | H | 0 |
| CF$_3$ | $^n$Pr | I | H | H | H | 1 |
| CF$_3$ | $^n$Pr | I | H | H | H | 2 |
| CF$_3$ | $^n$Pr | Me | H | H | H | 0 |
| CF$_3$ | $^n$Pr | Me | H | H | H | 1 |
| CF$_3$ | $^n$Pr | Me | H | H | H | 2 |
| CF$_3$ | $^n$Pr | CF$_3$ | H | H | H | 0 |
| CF$_3$ | $^n$Pr | CF$_3$ | H | H | H | 1 |
| CF$_3$ | $^n$Pr | CF$_3$ | H | H | H | 2 |
| CF$_3$ | $^n$Pr | H | F | H | H | 0 |
| CF$_3$ | $^n$Pr | H | F | H | H | 1 |
| CF$_3$ | $^n$Pr | H | F | H | H | 2 |
| CF$_3$ | $^n$Pr | H | Cl | H | H | 0 |
| CF$_3$ | $^n$Pr | H | Cl | H | H | 1 |
| CF$_3$ | $^n$Pr | H | Cl | H | H | 2 |
| CF$_3$ | $^n$Pr | H | Br | H | H | 0 |
| CF$_3$ | $^n$Pr | H | Br | H | H | 1 |
| CF$_3$ | $^n$Pr | H | Br | H | H | 2 |
| CF$_3$ | $^n$Pr | H | I | H | H | 0 |
| CF$_3$ | $^n$Pr | H | I | H | H | 1 |
| CF$_3$ | $^n$Pr | H | I | H | H | 2 |
| CF$_3$ | $^n$Pr | H | Me | H | H | 0 |
| CF$_3$ | $^n$Pr | H | Me | H | H | 1 |
| CF$_3$ | $^n$Pr | H | Me | H | H | 2 |
| CF$_3$ | $^n$Pr | H | CF$_3$ | H | H | 0 |
| CF$_3$ | $^n$Pr | H | CF$_3$ | H | H | 1 |
| CF$_3$ | $^n$Pr | H | CF$_3$ | H | H | 2 |
| CF$_3$ | $^n$Pr | H | CF$_2$CF$_3$ | H | H | 0 |
| CF$_3$ | $^n$Pr | H | CF$_2$CF$_3$ | H | H | 1 |
| CF$_3$ | $^n$Pr | H | CF$_2$CF$_3$ | H | H | 2 |
| CF$_3$ | $^n$Pr | H | CF(CF$_3$)$_2$ | H | H | 0 |
| CF$_3$ | $^n$Pr | H | CF(CF$_3$)$_2$ | H | H | 1 |
| CF$_3$ | $^n$Pr | H | CF(CF$_3$)$_2$ | H | H | 2 |
| CF$_3$ | $^n$Pr | H | SMe | H | H | 0 |
| CF$_3$ | $^n$Pr | H | SMe | H | H | 1 |
| CF$_3$ | $^n$Pr | H | SMe | H | H | 2 |
| CF$_3$ | $^n$Pr | H | SOMe | H | H | 0 |
| CF$_3$ | $^n$Pr | H | SOMe | H | H | 1 |
| CF$_3$ | $^n$Pr | H | SOMe | H | H | 2 |
| CF$_3$ | $^n$Pr | H | SO$_2$Me | H | H | 0 |
| CF$_3$ | $^n$Pr | H | SO$_2$Me | H | H | 1 |
| CF$_3$ | $^n$Pr | H | SO$_2$Me | H | H | 2 |
| CF$_3$ | $^n$Pr | H | OMe | H | H | 0 |
| CF$_3$ | $^n$Pr | H | OMe | H | H | 1 |
| CF$_3$ | $^n$Pr | H | OMe | H | H | 2 |
| CF$_3$ | $^n$Pr | H | OCF$_3$ | H | H | 0 |
| CF$_3$ | $^n$Pr | H | OCF$_3$ | H | H | 1 |
| CF$_3$ | $^n$Pr | H | OCF$_3$ | H | H | 2 |
| CF$_3$ | $^n$Pr | H | NO$_2$ | H | H | 0 |
| CF$_3$ | $^n$Pr | H | NO$_2$ | H | H | 1 |
| CF$_3$ | $^n$Pr | H | NO$_2$ | H | H | 2 |
| CF$_3$ | $^n$Pr | H | CN | H | H | 0 |
| CF$_3$ | $^n$Pr | H | CN | H | H | 1 |
| CF$_3$ | $^n$Pr | H | CN | H | H | 2 |
| CF$_3$ | $^n$Pr | H | H | F | H | 0 |
| CF$_3$ | $^n$Pr | H | H | F | H | 1 |
| CF$_3$ | $^n$Pr | H | H | F | H | 2 |
| CF$_3$ | $^n$Pr | H | H | Cl | H | 0 |
| CF$_3$ | $^n$Pr | H | H | Cl | H | 1 |
| CF$_3$ | $^n$Pr | H | H | Cl | H | 2 |
| CF$_3$ | $^n$Pr | H | H | Br | H | 0 |
| CF$_3$ | $^n$Pr | H | H | Br | H | 1 |
| CF$_3$ | $^n$Pr | H | H | Br | H | 2 |
| CF$_3$ | $^n$Pr | H | H | I | H | 0 |
| CF$_3$ | $^n$Pr | H | H | I | H | 1 |
| CF$_3$ | $^n$Pr | H | H | I | H | 2 |
| CF$_3$ | $^n$Pr | H | H | Me | H | 0 |
| CF$_3$ | $^n$Pr | H | H | Me | H | 1 |
| CF$_3$ | $^n$Pr | H | H | Me | H | 2 |
| CF$_3$ | $^n$Pr | H | H | CF$_3$ | H | 0 |
| CF$_3$ | $^n$Pr | H | H | CF$_3$ | H | 1 |
| CF$_3$ | $^n$Pr | H | H | CF$_3$ | H | 2 |
| CF$_3$ | $^n$Pr | H | H | CF$_2$CF$_3$ | H | 0 |
| CF$_3$ | $^n$Pr | H | H | CF$_2$CF$_3$ | H | 1 |
| CF$_3$ | $^n$Pr | H | H | CF$_2$CF$_3$ | H | 2 |
| CF$_3$ | $^n$Pr | H | H | CF(CF$_3$)$_2$ | H | 0 |
| CF$_3$ | $^n$Pr | H | H | CF(CF$_3$)$_2$ | H | 1 |
| CF$_3$ | $^n$Pr | H | H | CF(CF$_3$)$_2$ | H | 2 |
| CF$_3$ | $^n$Pr | H | H | SMe | H | 0 |
| CF$_3$ | $^n$Pr | H | H | SMe | H | 1 |
| CF$_3$ | $^n$Pr | H | H | SMe | H | 2 |
| CF$_3$ | $^n$Pr | H | H | SOMe | H | 0 |
| CF$_3$ | $^n$Pr | H | H | SOMe | H | 1 |
| CF$_3$ | $^n$Pr | H | H | SOMe | H | 2 |
| CF$_3$ | $^n$Pr | H | H | SO$_2$Me | H | 0 |
| CF$_3$ | $^n$Pr | H | H | SO$_2$Me | H | 1 |
| CF$_3$ | $^n$Pr | H | H | SO$_2$Me | H | 2 |
| CF$_3$ | $^n$Pr | H | H | OMe | H | 0 |
| CF$_3$ | $^n$Pr | H | H | OMe | H | 1 |
| CF$_3$ | $^n$Pr | H | H | OMe | H | 2 |
| CF$_3$ | $^n$Pr | H | H | OCF$_3$ | H | 0 |
| CF$_3$ | $^n$Pr | H | H | OCF$_3$ | H | 1 |
| CF$_3$ | $^n$Pr | H | H | OCF$_3$ | H | 2 |
| CF$_3$ | $^n$Pr | H | H | NO$_2$ | H | 0 |
| CF$_3$ | $^n$Pr | H | H | NO$_2$ | H | 1 |
| CF$_3$ | $^n$Pr | H | H | NO$_2$ | H | 2 |
| CF$_3$ | $^n$Pr | H | H | CN | H | 0 |
| CF$_3$ | $^n$Pr | H | H | CN | H | 1 |
| CF$_3$ | $^n$Pr | H | H | CN | H | 2 |
| CF$_3$ | $^n$Pr | H | H | H | F | 0 |
| CF$_3$ | $^n$Pr | H | H | H | F | 1 |
| CF$_3$ | $^n$Pr | H | H | H | F | 2 |
| CF$_3$ | $^n$Pr | H | H | H | Cl | 0 |
| CF$_3$ | $^n$Pr | H | H | H | Cl | 1 |
| CF$_3$ | $^n$Pr | H | H | H | Cl | 2 |
| CF$_3$ | $^n$Pr | H | H | H | Br | 0 |
| CF$_3$ | $^n$Pr | H | H | H | Br | 1 |
| CF$_3$ | $^n$Pr | H | H | H | Br | 2 |
| CF$_3$ | $^n$Pr | H | H | H | I | 0 |
| CF$_3$ | $^n$Pr | H | H | H | I | 1 |
| CF$_3$ | $^n$Pr | H | H | H | I | 2 |
| CF$_3$ | $^n$Pr | H | H | H | Me | 0 |
| CF$_3$ | $^n$Pr | H | H | H | Me | 1 |
| CF$_3$ | $^n$Pr | H | H | H | Me | 2 |
| CF$_3$ | $^n$Pr | H | H | H | CF$_3$ | 0 |
| CF$_3$ | $^n$Pr | H | H | H | CF$_3$ | 1 |
| CF$_3$ | $^n$Pr | H | H | H | CF$_3$ | 2 |
| CF$_3$ | $^n$Pr | H | H | H | CF$_2$CF$_3$ | 0 |
| CF$_3$ | $^n$Pr | H | H | H | CF$_2$CF$_3$ | 1 |
| CF$_3$ | $^n$Pr | H | H | H | CF$_2$CF$_3$ | 2 |
| CF$_3$ | $^n$Pr | H | H | H | CF(CF$_3$)$_2$ | 0 |
| CF$_3$ | $^n$Pr | H | H | H | CF(CF$_3$)$_2$ | 1 |
| CF$_3$ | $^n$Pr | H | H | H | CF(CF$_3$)$_2$ | 2 |
| CF$_3$ | $^n$Pr | H | H | H | SMe | 0 |
| CF$_3$ | $^n$Pr | H | H | H | SMe | 1 |
| CF$_3$ | $^n$Pr | H | H | H | SMe | 2 |
| CF$_3$ | $^n$Pr | H | H | H | SOMe | 0 |
| CF$_3$ | $^n$Pr | H | H | H | SOMe | 1 |
| CF$_3$ | $^n$Pr | H | H | H | SOMe | 2 |
| CF$_3$ | $^n$Pr | H | H | H | SO$_2$Me | 0 |
| CF$_3$ | $^n$Pr | H | H | H | SO$_2$Me | 1 |
| CF$_3$ | $^n$Pr | H | H | H | SO$_2$Me | 2 |
| CF$_3$ | $^n$Pr | H | H | H | OMe | 0 |
| CF$_3$ | $^n$Pr | H | H | H | OMe | 1 |
| CF$_3$ | $^n$Pr | H | H | H | OMe | 2 |
| CF$_3$ | $^n$Pr | H | H | H | OCF$_3$ | 0 |
| CF$_3$ | $^n$Pr | H | H | H | OCF$_3$ | 1 |
| CF$_3$ | $^n$Pr | H | H | H | OCF$_3$ | 2 |
| CF$_3$ | $^n$Pr | H | H | H | NO$_2$ | 0 |
| CF$_3$ | $^n$Pr | H | H | H | NO$_2$ | 1 |

TABLE 1-continued

| | | | | | | |
|---|---|---|---|---|---|---|
| CF₃ | ⁿPr | H | H | H | NO₂ | 2 |
| CF₃ | ⁿPr | H | H | H | CN | 0 |
| CF₃ | ⁿPr | H | H | H | CN | 1 |
| CF₃ | ⁿPr | H | H | H | CN | 2 |
| CF₃ | ⁿPr | H | F | H | F | 0 |
| CF₃ | ⁿPr | H | F | H | F | 1 |
| CF₃ | ⁿPr | H | F | H | F | 2 |
| CF₃ | ⁿPr | H | Cl | H | Cl | 0 |
| CF₃ | ⁿPr | H | Cl | H | Cl | 1 |
| CF₃ | ⁿPr | H | Cl | H | Cl | 2 |
| CF₃ | ⁿPr | H | Br | H | Br | 0 |
| CF₃ | ⁿPr | H | Br | H | Br | 1 |
| CF₃ | ⁿPr | H | Br | H | Br | 2 |
| CF₃ | ⁿPr | H | I | H | I | 0 |
| CF₃ | ⁿPr | H | I | H | I | 1 |
| CF₃ | ⁿPr | H | I | H | I | 2 |
| CF₃ | ⁿPr | H | F | H | Cl | 0 |
| CF₃ | ⁿPr | H | F | H | Cl | 1 |
| CF₃ | ⁿPr | H | F | H | Cl | 2 |
| CF₃ | ⁿPr | H | F | H | Br | 0 |
| CF₃ | ⁿPr | H | F | H | Br | 1 |
| CF₃ | ⁿPr | H | F | H | Br | 2 |
| CF₃ | ⁿPr | H | F | H | I | 0 |
| CF₃ | ⁿPr | H | F | H | I | 1 |
| CF₃ | ⁿPr | H | F | H | I | 2 |
| CF₃ | ⁿPr | H | Cl | H | F | 0 |
| CF₃ | ⁿPr | H | Cl | H | F | 1 |
| CF₃ | ⁿPr | H | Cl | H | F | 2 |
| CF₃ | ⁿPr | H | Cl | H | Br | 0 |
| CF₃ | ⁿPr | H | Cl | H | Br | 1 |
| CF₃ | ⁿPr | H | Cl | H | Br | 2 |
| CF₃ | ⁿPr | H | Cl | H | I | 0 |
| CF₃ | ⁿPr | H | Cl | H | I | 1 |
| CF₃ | ⁿPr | H | Cl | H | I | 2 |
| CF₃ | ⁿPr | H | Br | H | F | 0 |
| CF₃ | ⁿPr | H | Br | H | F | 1 |
| CF₃ | ⁿPr | H | Br | H | F | 2 |
| CF₃ | ⁿPr | H | Br | H | Cl | 0 |
| CF₃ | ⁿPr | H | Br | H | Cl | 1 |
| CF₃ | ⁿPr | H | Br | H | Cl | 2 |
| CF₃ | ⁿPr | H | Br | H | I | 0 |
| CF₃ | ⁿPr | H | Br | H | I | 1 |
| CF₃ | ⁿPr | H | Br | H | I | 2 |
| CF₃ | ⁿPr | H | I | H | F | 0 |
| CF₃ | ⁿPr | H | I | H | F | 1 |
| CF₃ | ⁿPr | H | I | H | F | 2 |
| CF₃ | ⁿPr | H | I | H | Cl | 0 |
| CF₃ | ⁿPr | H | I | H | Cl | 1 |
| CF₃ | ⁿPr | H | I | H | Cl | 2 |
| CF₃ | ⁿPr | H | I | H | Br | 0 |
| CF₃ | ⁿPr | H | I | H | Br | 1 |
| CF₃ | ⁿPr | H | I | H | Br | 2 |
| CF₃ | ⁿPr | H | F | H | CN | 0 |
| CF₃ | ⁿPr | H | F | H | CN | 1 |
| CF₃ | ⁿPr | H | F | H | CN | 2 |
| CF₃ | ⁿPr | H | Cl | H | CN | 0 |
| CF₃ | ⁿPr | H | Cl | H | CN | 1 |
| CF₃ | ⁿPr | H | Cl | H | CN | 2 |
| CF₃ | ⁿPr | H | Br | H | CN | 0 |
| CF₃ | ⁿPr | H | Br | H | CN | 1 |
| CF₃ | ⁿPr | H | Br | H | CN | 2 |
| CF₃ | ⁿPr | H | I | H | CN | 0 |
| CF₃ | ⁿPr | H | I | H | CN | 1 |
| CF₃ | ⁿPr | H | I | H | CN | 2 |
| CF₃ | ⁿPr | H | CF₃ | H | F | 0 |
| CF₃ | ⁿPr | H | CF₃ | H | F | 1 |
| CF₃ | ⁿPr | H | CF₃ | H | F | 2 |
| CF₃ | ⁿPr | H | CF₃ | H | Cl | 0 |
| CF₃ | ⁿPr | H | CF₃ | H | Cl | 1 |
| CF₃ | ⁿPr | H | CF₃ | H | Cl | 2 |
| CF₃ | ⁿPr | H | CF₃ | H | Br | 0 |
| CF₃ | ⁿPr | H | CF₃ | H | Br | 1 |
| CF₃ | ⁿPr | H | CF₃ | H | Br | 2 |
| CF₃ | ⁿPr | H | CF₃ | H | I | 0 |
| CF₃ | ⁿPr | H | CF₃ | H | I | 1 |
| CF₃ | ⁿPr | H | CF₃ | H | I | 2 |
| CF₃ | ⁿPr | H | CF₃ | H | CN | 0 |
| CF₃ | ⁿPr | H | CF₃ | H | CN | 1 |
| CF₃ | ⁿPr | H | CF₃ | H | CN | 2 |
| CF₃ | ⁿPr | H | F | F | H | 0 |
| CF₃ | ⁿPr | H | F | F | H | 1 |
| CF₃ | ⁿPr | H | F | F | H | 2 |
| CF₃ | ⁿPr | H | Cl | Cl | H | 0 |
| CF₃ | ⁿPr | H | Cl | Cl | H | 1 |
| CF₃ | ⁿPr | H | Cl | Cl | H | 2 |
| CF₃ | ⁿPr | H | Br | Br | H | 0 |
| CF₃ | ⁿPr | H | Br | Br | H | 1 |
| CF₃ | ⁿPr | H | Br | Br | H | 2 |
| CF₃ | ⁿPr | H | I | I | H | 0 |
| CF₃ | ⁿPr | H | I | I | H | 1 |
| CF₃ | ⁿPr | H | I | I | H | 2 |
| CF₃ | ⁿPr | H | F | Cl | H | 0 |
| CF₃ | ⁿPr | H | F | Cl | H | 1 |
| CF₃ | ⁿPr | H | F | Cl | H | 2 |
| CF₃ | ⁿPr | H | F | Br | H | 0 |
| CF₃ | ⁿPr | H | F | Br | H | 1 |
| CF₃ | ⁿPr | H | F | Br | H | 2 |
| CF₃ | ⁿPr | H | F | I | H | 0 |
| CF₃ | ⁿPr | H | F | I | H | 1 |
| CF₃ | ⁿPr | H | F | I | H | 2 |
| CF₃ | ⁿPr | H | Cl | F | H | 0 |
| CF₃ | ⁿPr | H | Cl | F | H | 1 |
| CF₃ | ⁿPr | H | Cl | F | H | 2 |
| CF₃ | ⁿPr | H | Cl | Br | H | 0 |
| CF₃ | ⁿPr | H | Cl | Br | H | 1 |
| CF₃ | ⁿPr | H | Cl | Br | H | 2 |
| CF₃ | ⁿPr | H | Cl | I | H | 0 |
| CF₃ | ⁿPr | H | Cl | I | H | 1 |
| CF₃ | ⁿPr | H | Cl | I | H | 2 |
| CF₃ | ⁿPr | H | Br | F | H | 0 |
| CF₃ | ⁿPr | H | Br | F | H | 1 |
| CF₃ | ⁿPr | H | Br | F | H | 2 |
| CF₃ | ⁿPr | H | Br | Cl | H | 0 |
| CF₃ | ⁿPr | H | Br | Cl | H | 1 |
| CF₃ | ⁿPr | H | Br | Cl | H | 2 |
| CF₃ | ⁿPr | H | Br | I | H | 0 |
| CF₃ | ⁿPr | H | Br | I | H | 1 |
| CF₃ | ⁿPr | H | Br | I | H | 2 |
| CF₃ | ⁿPr | H | I | F | H | 0 |
| CF₃ | ⁿPr | H | I | F | H | 1 |
| CF₃ | ⁿPr | H | I | F | H | 2 |
| CF₃ | ⁿPr | H | I | Cl | H | 0 |
| CF₃ | ⁿPr | H | I | Cl | H | 1 |
| CF₃ | ⁿPr | H | I | Cl | H | 2 |
| CF₃ | ⁿPr | H | I | Br | H | 0 |
| CF₃ | ⁿPr | H | I | Br | H | 1 |
| CF₃ | ⁿPr | H | I | Br | H | 2 |
| CF₃ | ⁿPr | H | F | CN | H | 0 |
| CF₃ | ⁿPr | H | F | CN | H | 1 |
| CF₃ | ⁿPr | H | F | CN | H | 2 |
| CF₃ | ⁿPr | H | Cl | CN | H | 0 |
| CF₃ | ⁿPr | H | Cl | CN | H | 1 |
| CF₃ | ⁿPr | H | Cl | CN | H | 2 |
| CF₃ | ⁿPr | H | Br | CN | H | 0 |
| CF₃ | ⁿPr | H | Br | CN | H | 1 |
| CF₃ | ⁿPr | H | Br | CN | H | 2 |
| CF₃ | ⁿPr | H | I | CN | H | 0 |
| CF₃ | ⁿPr | H | I | CN | H | 1 |
| CF₃ | ⁿPr | H | I | CN | H | 2 |
| CF₃ | ⁿPr | H | CF₃ | F | H | 0 |
| CF₃ | ⁿPr | H | CF₃ | F | H | 1 |
| CF₃ | ⁿPr | H | CF₃ | F | H | 2 |
| CF₃ | ⁿPr | H | CF₃ | Cl | H | 0 |
| CF₃ | ⁿPr | H | CF₃ | Cl | H | 1 |
| CF₃ | ⁿPr | H | CF₃ | Cl | H | 2 |
| CF₃ | ⁿPr | H | CF₃ | Br | H | 0 |
| CF₃ | ⁿPr | H | CF₃ | Br | H | 1 |
| CF₃ | ⁿPr | H | CF₃ | Br | H | 2 |
| CF₃ | ⁿPr | H | CF₃ | I | H | 0 |
| CF₃ | ⁿPr | H | CF₃ | I | H | 1 |
| CF₃ | ⁿPr | H | CF₃ | I | H | 2 |
| CF₃ | ⁿPr | H | CF₃ | CN | H | 0 |
| CF₃ | ⁿPr | H | CF₃ | CN | H | 1 |
| CF₃ | ⁿPr | H | CF₃ | CN | H | 2 |
| CF₃ | ⁱPr | H | H | H | H | 0 |
| CF₃ | ⁱPr | H | H | H | H | 1 |
| CF₃ | ⁱPr | H | H | H | H | 2 |
| CF₃ | ⁱPr | F | H | H | H | 0 |
| CF₃ | ⁱPr | F | H | H | H | 1 |
| CF₃ | ⁱPr | F | H | H | H | 2 |

TABLE 1-continued

| | | | | | | |
|---|---|---|---|---|---|---|
| CF$_3$ | $^i$Pr | Cl | H | H | H | 0 |
| CF$_3$ | $^i$Pr | Cl | H | H | H | 1 |
| CF$_3$ | $^i$Pr | Cl | H | H | H | 2 |
| CF$_3$ | $^i$Pr | Br | H | H | H | 0 |
| CF$_3$ | $^i$Pr | Br | H | H | H | 1 |
| CF$_3$ | $^i$Pr | Br | H | H | H | 2 |
| CF$_3$ | $^i$Pr | I | H | H | H | 0 |
| CF$_3$ | $^i$Pr | I | H | H | H | 1 |
| CF$_3$ | $^i$Pr | I | H | H | H | 2 |
| CF$_3$ | $^i$Pr | Me | H | H | H | 0 |
| CF$_3$ | $^i$Pr | Me | H | H | H | 1 |
| CF$_3$ | $^i$Pr | Me | H | H | H | 2 |
| CF$_3$ | $^i$Pr | CF$_3$ | H | H | H | 0 |
| CF$_3$ | $^i$Pr | CF$_3$ | H | H | H | 1 |
| CF$_3$ | $^i$Pr | CF$_3$ | H | H | H | 2 |
| CF$_3$ | $^i$Pr | H | F | H | H | 0 |
| CF$_3$ | $^i$Pr | H | F | H | H | 1 |
| CF$_3$ | $^i$Pr | H | F | H | H | 2 |
| CF$_3$ | $^i$Pr | H | Cl | H | H | 0 |
| CF$_3$ | $^i$Pr | H | Cl | H | H | 1 |
| CF$_3$ | $^i$Pr | H | Cl | H | H | 2 |
| CF$_3$ | $^i$Pr | H | Br | H | H | 0 |
| CF$_3$ | $^i$Pr | H | Br | H | H | 1 |
| CF$_3$ | $^i$Pr | H | Br | H | H | 2 |
| CF$_3$ | $^i$Pr | H | I | H | H | 0 |
| CF$_3$ | $^i$Pr | H | I | H | H | 1 |
| CF$_3$ | $^i$Pr | H | I | H | H | 2 |
| CF$_3$ | $^i$Pr | H | Me | H | H | 0 |
| CF$_3$ | $^i$Pr | H | Me | H | H | 1 |
| CF$_3$ | $^i$Pr | H | Me | H | H | 2 |
| CF$_3$ | $^i$Pr | H | CF$_3$ | H | H | 0 |
| CF$_3$ | $^i$Pr | H | CF$_3$ | H | H | 1 |
| CF$_3$ | $^i$Pr | H | CF$_3$ | H | H | 2 |
| CF$_3$ | $^i$Pr | H | CF$_2$CF$_3$ | H | H | 0 |
| CF$_3$ | $^i$Pr | H | CF$_2$CF$_3$ | H | H | 1 |
| CF$_3$ | $^i$Pr | H | CF$_2$CF$_3$ | H | H | 2 |
| CF$_3$ | $^i$Pr | H | CF(CF$_3$)$_2$ | H | H | 0 |
| CF$_3$ | $^i$Pr | H | CF(CF$_3$)$_2$ | H | H | 1 |
| CF$_3$ | $^i$Pr | H | CF(CF$_3$)$_2$ | H | H | 2 |
| CF$_3$ | $^i$Pr | H | SMe | H | H | 0 |
| CF$_3$ | $^i$Pr | H | SMe | H | H | 1 |
| CF$_3$ | $^i$Pr | H | SMe | H | H | 2 |
| CF$_3$ | $^i$Pr | H | SOMe | H | H | 0 |
| CF$_3$ | $^i$Pr | H | SOMe | H | H | 1 |
| CF$_3$ | $^i$Pr | H | SOMe | H | H | 2 |
| CF$_3$ | $^i$Pr | H | SO$_2$Me | H | H | 0 |
| CF$_3$ | $^i$Pr | H | SO$_2$Me | H | H | 1 |
| CF$_3$ | $^i$Pr | H | SO$_2$Me | H | H | 2 |
| CF$_3$ | $^i$Pr | H | OMe | H | H | 0 |
| CF$_3$ | $^i$Pr | H | OMe | H | H | 1 |
| CF$_3$ | $^i$Pr | H | OMe | H | H | 2 |
| CF$_3$ | $^i$Pr | H | OCF$_3$ | H | H | 0 |
| CF$_3$ | $^i$Pr | H | OCF$_3$ | H | H | 1 |
| CF$_3$ | $^i$Pr | H | OCF$_3$ | H | H | 2 |
| CF$_3$ | $^i$Pr | H | NO$_2$ | H | H | 0 |
| CF$_3$ | $^i$Pr | H | NO$_2$ | H | H | 1 |
| CF$_3$ | $^i$Pr | H | NO$_2$ | H | H | 2 |
| CF$_3$ | $^i$Pr | H | CN | H | H | 0 |
| CF$_3$ | $^i$Pr | H | CN | H | H | 1 |
| CF$_3$ | $^i$Pr | H | CN | H | H | 2 |
| CF$_3$ | $^i$Pr | H | H | F | H | 0 |
| CF$_3$ | $^i$Pr | H | H | F | H | 1 |
| CF$_3$ | $^i$Pr | H | H | F | H | 2 |
| CF$_3$ | $^i$Pr | H | H | Cl | H | 0 |
| CF$_3$ | $^i$Pr | H | H | Cl | H | 1 |
| CF$_3$ | $^i$Pr | H | H | Cl | H | 2 |
| CF$_3$ | $^i$Pr | H | H | Br | H | 0 |
| CF$_3$ | $^i$Pr | H | H | Br | H | 1 |
| CF$_3$ | $^i$Pr | H | H | Br | H | 2 |
| CF$_3$ | $^i$Pr | H | H | I | H | 0 |
| CF$_3$ | $^i$Pr | H | H | I | H | 1 |
| CF$_3$ | $^i$Pr | H | H | I | H | 2 |
| CF$_3$ | $^i$Pr | H | H | Me | H | 0 |
| CF$_3$ | $^i$Pr | H | H | Me | H | 1 |
| CF$_3$ | $^i$Pr | H | H | Me | H | 2 |
| CF$_3$ | $^i$Pr | H | H | CF$_3$ | H | 0 |
| CF$_3$ | $^i$Pr | H | H | CF$_3$ | H | 1 |
| CF$_3$ | $^i$Pr | H | H | CF$_3$ | H | 2 |
| CF$_3$ | $^i$Pr | H | H | CF$_2$CF$_3$ | H | 0 |
| CF$_3$ | $^i$Pr | H | H | CF$_2$CF$_3$ | H | 1 |
| CF$_3$ | $^i$Pr | H | H | CF$_2$CF$_3$ | H | 2 |
| CF$_3$ | $^i$Pr | H | H | CF(CF$_3$)$_2$ | H | 0 |
| CF$_3$ | $^i$Pr | H | H | CF(CF$_3$)$_2$ | H | 1 |
| CF$_3$ | $^i$Pr | H | H | CF(CF$_3$)$_2$ | H | 2 |
| CF$_3$ | $^i$Pr | H | H | SMe | H | 0 |
| CF$_3$ | $^i$Pr | H | H | SMe | H | 1 |
| CF$_3$ | $^i$Pr | H | H | SMe | H | 2 |
| CF$_3$ | $^i$Pr | H | H | SOMe | H | 0 |
| CF$_3$ | $^i$Pr | H | H | SOMe | H | 1 |
| CF$_3$ | $^i$Pr | H | H | SOMe | H | 2 |
| CF$_3$ | $^i$Pr | H | H | SO$_2$Me | H | 0 |
| CF$_3$ | $^i$Pr | H | H | SO$_2$Me | H | 1 |
| CF$_3$ | $^i$Pr | H | H | SO$_2$Me | H | 2 |
| CF$_3$ | $^i$Pr | H | H | OMe | H | 0 |
| CF$_3$ | $^i$Pr | H | H | OMe | H | 1 |
| CF$_3$ | $^i$Pr | H | H | OMe | H | 2 |
| CF$_3$ | $^i$Pr | H | H | OCF$_3$ | H | 0 |
| CF$_3$ | $^i$Pr | H | H | OCF$_3$ | H | 1 |
| CF$_3$ | $^i$Pr | H | H | OCF$_3$ | H | 2 |
| CF$_3$ | $^i$Pr | H | H | NO$_2$ | H | 0 |
| CF$_3$ | $^i$Pr | H | H | NO$_2$ | H | 1 |
| CF$_3$ | $^i$Pr | H | H | NO$_2$ | H | 2 |
| CF$_3$ | $^i$Pr | H | H | CN | H | 0 |
| CF$_3$ | $^i$Pr | H | H | CN | H | 1 |
| CF$_3$ | $^i$Pr | H | H | CN | H | 2 |
| CF$_3$ | $^i$Pr | H | H | H | F | 0 |
| CF$_3$ | $^i$Pr | H | H | H | F | 1 |
| CF$_3$ | $^i$Pr | H | H | H | F | 2 |
| CF$_3$ | $^i$Pr | H | H | H | Cl | 0 |
| CF$_3$ | $^i$Pr | H | H | H | Cl | 1 |
| CF$_3$ | $^i$Pr | H | H | H | Cl | 2 |
| CF$_3$ | $^i$Pr | H | H | H | Br | 0 |
| CF$_3$ | $^i$Pr | H | H | H | Br | 1 |
| CF$_3$ | $^i$Pr | H | H | H | Br | 2 |
| CF$_3$ | $^i$Pr | H | H | H | I | 0 |
| CF$_3$ | $^i$Pr | H | H | H | I | 1 |
| CF$_3$ | $^i$Pr | H | H | H | I | 2 |
| CF$_3$ | $^i$Pr | H | H | H | Me | 0 |
| CF$_3$ | $^i$Pr | H | H | H | Me | 1 |
| CF$_3$ | $^i$Pr | H | H | H | Me | 2 |
| CF$_3$ | $^i$Pr | H | H | H | CF$_3$ | 0 |
| CF$_3$ | $^i$Pr | H | H | H | CF$_3$ | 1 |
| CF$_3$ | $^i$Pr | H | H | H | CF$_3$ | 2 |
| CF$_3$ | $^i$Pr | H | H | H | CF$_2$CF$_3$ | 0 |
| CF$_3$ | $^i$Pr | H | H | H | CF$_2$CF$_3$ | 1 |
| CF$_3$ | $^i$Pr | H | H | H | CF$_2$CF$_3$ | 2 |
| CF$_3$ | $^i$Pr | H | H | H | CF(CF$_3$)$_2$ | 0 |
| CF$_3$ | $^i$Pr | H | H | H | CF(CF$_3$)$_2$ | 1 |
| CF$_3$ | $^i$Pr | H | H | H | CF(CF$_3$)$_2$ | 2 |
| CF$_3$ | $^i$Pr | H | H | H | SMe | 0 |
| CF$_3$ | $^i$Pr | H | H | H | SMe | 1 |
| CF$_3$ | $^i$Pr | H | H | H | SMe | 2 |
| CF$_3$ | $^i$Pr | H | H | H | SOMe | 0 |
| CF$_3$ | $^i$Pr | H | H | H | SOMe | 1 |
| CF$_3$ | $^i$Pr | H | H | H | SOMe | 2 |
| CF$_3$ | $^i$Pr | H | H | H | SO$_2$Me | 0 |
| CF$_3$ | $^i$Pr | H | H | H | SO$_2$Me | 1 |
| CF$_3$ | $^i$Pr | H | H | H | SO$_2$Me | 2 |
| CF$_3$ | $^i$Pr | H | H | H | OMe | 0 |
| CF$_3$ | $^i$Pr | H | H | H | OMe | 1 |
| CF$_3$ | $^i$Pr | H | H | H | OMe | 2 |
| CF$_3$ | $^i$Pr | H | H | H | OCF$_3$ | 0 |
| CF$_3$ | $^i$Pr | H | H | H | OCF$_3$ | 1 |
| CF$_3$ | $^i$Pr | H | H | H | OCF$_3$ | 2 |
| CF$_3$ | $^i$Pr | H | H | H | NO$_2$ | 0 |
| CF$_3$ | $^i$Pr | H | H | H | NO$_2$ | 1 |
| CF$_3$ | $^i$Pr | H | H | H | NO$_2$ | 2 |
| CF$_3$ | $^i$Pr | H | H | H | CN | 0 |
| CF$_3$ | $^i$Pr | H | H | H | CN | 1 |
| CF$_3$ | $^i$Pr | H | H | H | CN | 2 |
| CF$_3$ | $^i$Pr | H | F | H | F | 0 |
| CF$_3$ | $^i$Pr | H | F | H | F | 1 |
| CF$_3$ | $^i$Pr | H | F | H | F | 2 |
| CF$_3$ | $^i$Pr | H | Cl | H | Cl | 0 |
| CF$_3$ | $^i$Pr | H | Cl | H | Cl | 1 |
| CF$_3$ | $^i$Pr | H | Cl | H | Cl | 2 |
| CF$_3$ | $^i$Pr | H | Br | H | Br | 0 |
| CF$_3$ | $^i$Pr | H | Br | H | Br | 1 |
| CF$_3$ | $^i$Pr | H | Br | H | Br | 2 |
| CF$_3$ | $^i$Pr | H | I | H | I | 0 |

TABLE 1-continued

| | | | | | | |
|---|---|---|---|---|---|---|
| CF₃ | ⁱPr | H | I | H | I | 1 |
| CF₃ | ⁱPr | H | I | H | I | 2 |
| CF₃ | ⁱPr | H | F | H | Cl | 0 |
| CF₃ | ⁱPr | H | F | H | Cl | 1 |
| CF₃ | ⁱPr | H | F | H | Cl | 2 |
| CF₃ | ⁱPr | H | F | H | Br | 0 |
| CF₃ | ⁱPr | H | F | H | Br | 1 |
| CF₃ | ⁱPr | H | F | H | Br | 2 |
| CF₃ | ⁱPr | H | F | H | I | 0 |
| CF₃ | ⁱPr | H | F | H | I | 1 |
| CF₃ | ⁱPr | H | F | H | I | 2 |
| CF₃ | ⁱPr | H | Cl | H | F | 0 |
| CF₃ | ⁱPr | H | Cl | H | F | 1 |
| CF₃ | ⁱPr | H | Cl | H | F | 2 |
| CF₃ | ⁱPr | H | Cl | H | Br | 0 |
| CF₃ | ⁱPr | H | Cl | H | Br | 1 |
| CF₃ | ⁱPr | H | Cl | H | Br | 2 |
| CF₃ | ⁱPr | H | Cl | H | I | 0 |
| CF₃ | ⁱPr | H | Cl | H | I | 1 |
| CF₃ | ⁱPr | H | Cl | H | I | 2 |
| CF₃ | ⁱPr | H | Br | H | F | 0 |
| CF₃ | ⁱPr | H | Br | H | F | 1 |
| CF₃ | ⁱPr | H | Br | H | F | 2 |
| CF₃ | ⁱPr | H | Br | H | Cl | 0 |
| CF₃ | ⁱPr | H | Br | H | Cl | 1 |
| CF₃ | ⁱPr | H | Br | H | Cl | 2 |
| CF₃ | ⁱPr | H | Br | H | I | 0 |
| CF₃ | ⁱPr | H | Br | H | I | 1 |
| CF₃ | ⁱPr | H | Br | H | I | 2 |
| CF₃ | ⁱPr | H | I | H | F | 0 |
| CF₃ | ⁱPr | H | I | H | F | 1 |
| CF₃ | ⁱPr | H | I | H | F | 2 |
| CF₃ | ⁱPr | H | I | H | Cl | 0 |
| CF₃ | ⁱPr | H | I | H | Cl | 1 |
| CF₃ | ⁱPr | H | I | H | Cl | 2 |
| CF₃ | ⁱPr | H | I | H | Br | 0 |
| CF₃ | ⁱPr | H | I | H | Br | 1 |
| CF₃ | ⁱPr | H | I | H | Br | 2 |
| CF₃ | ⁱPr | H | F | H | CN | 0 |
| CF₃ | ⁱPr | H | F | H | CN | 1 |
| CF₃ | ⁱPr | H | F | H | CN | 2 |
| CF₃ | ⁱPr | H | Cl | H | CN | 0 |
| CF₃ | ⁱPr | H | Cl | H | CN | 1 |
| CF₃ | ⁱPr | H | Cl | H | CN | 2 |
| CF₃ | ⁱPr | H | Br | H | CN | 0 |
| CF₃ | ⁱPr | H | Br | H | CN | 1 |
| CF₃ | ⁱPr | H | Br | H | CN | 2 |
| CF₃ | ⁱPr | H | I | H | CN | 0 |
| CF₃ | ⁱPr | H | I | H | CN | 1 |
| CF₃ | ⁱPr | H | I | H | CN | 2 |
| CF₃ | ⁱPr | H | CF₃ | H | F | 0 |
| CF₃ | ⁱPr | H | CF₃ | H | F | 1 |
| CF₃ | ⁱPr | H | CF₃ | H | F | 2 |
| CF₃ | ⁱPr | H | CF₃ | H | Cl | 0 |
| CF₃ | ⁱPr | H | CF₃ | H | Cl | 1 |
| CF₃ | ⁱPr | H | CF₃ | H | Cl | 2 |
| CF₃ | ⁱPr | H | CF₃ | H | Br | 0 |
| CF₃ | ⁱPr | H | CF₃ | H | Br | 1 |
| CF₃ | ⁱPr | H | CF₃ | H | Br | 2 |
| CF₃ | ⁱPr | H | CF₃ | H | I | 0 |
| CF₃ | ⁱPr | H | CF₃ | H | I | 1 |
| CF₃ | ⁱPr | H | CF₃ | H | I | 2 |
| CF₃ | ⁱPr | H | CF₃ | H | CN | 0 |
| CF₃ | ⁱPr | H | CF₃ | H | CN | 1 |
| CF₃ | ⁱPr | H | CF₃ | H | CN | 2 |
| CF₃ | ⁱPr | H | F | F | H | 0 |
| CF₃ | ⁱPr | H | F | F | H | 1 |
| CF₃ | ⁱPr | H | F | F | H | 2 |
| CF₃ | ⁱPr | H | Cl | Cl | H | 0 |
| CF₃ | ⁱPr | H | Cl | Cl | H | 1 |
| CF₃ | ⁱPr | H | Cl | Cl | H | 2 |
| CF₃ | ⁱPr | H | Br | Br | H | 0 |
| CF₃ | ⁱPr | H | Br | Br | H | 1 |
| CF₃ | ⁱPr | H | Br | Br | H | 2 |
| CF₃ | ⁱPr | H | I | I | H | 0 |
| CF₃ | ⁱPr | H | I | I | H | 1 |
| CF₃ | ⁱPr | H | I | I | H | 2 |
| CF₃ | ⁱPr | H | F | Cl | H | 0 |
| CF₃ | ⁱPr | H | F | Cl | H | 1 |
| CF₃ | ⁱPr | H | F | Cl | H | 2 |
| CF₃ | ⁱPr | H | F | Br | H | 0 |
| CF₃ | ⁱPr | H | F | Br | H | 1 |
| CF₃ | ⁱPr | H | F | Br | H | 2 |
| CF₃ | ⁱPr | H | F | I | H | 0 |
| CF₃ | ⁱPr | H | F | I | H | 1 |
| CF₃ | ⁱPr | H | F | I | H | 2 |
| CF₃ | ⁱPr | H | Cl | F | H | 0 |
| CF₃ | ⁱPr | H | Cl | F | H | 1 |
| CF₃ | ⁱPr | H | Cl | F | H | 2 |
| CF₃ | ⁱPr | H | Cl | Br | H | 0 |
| CF₃ | ⁱPr | H | Cl | Br | H | 1 |
| CF₃ | ⁱPr | H | Cl | Br | H | 2 |
| CF₃ | ⁱPr | H | Cl | I | H | 0 |
| CF₃ | ⁱPr | H | Cl | I | H | 1 |
| CF₃ | ⁱPr | H | Cl | I | H | 2 |
| CF₃ | ⁱPr | H | Br | F | H | 0 |
| CF₃ | ⁱPr | H | Br | F | H | 1 |
| CF₃ | ⁱPr | H | Br | F | H | 2 |
| CF₃ | ⁱPr | H | Br | Cl | H | 0 |
| CF₃ | ⁱPr | H | Br | Cl | H | 1 |
| CF₃ | ⁱPr | H | Br | Cl | H | 2 |
| CF₃ | ⁱPr | H | Br | I | H | 0 |
| CF₃ | ⁱPr | H | Br | I | H | 1 |
| CF₃ | ⁱPr | H | Br | I | H | 2 |
| CF₃ | ⁱPr | H | I | F | H | 0 |
| CF₃ | ⁱPr | H | I | F | H | 1 |
| CF₃ | ⁱPr | H | I | F | H | 2 |
| CF₃ | ⁱPr | H | I | Cl | H | 0 |
| CF₃ | ⁱPr | H | I | Cl | H | 1 |
| CF₃ | ⁱPr | H | I | Cl | H | 2 |
| CF₃ | ⁱPr | H | I | Br | H | 0 |
| CF₃ | ⁱPr | H | I | Br | H | 1 |
| CF₃ | ⁱPr | H | I | Br | H | 2 |
| CF₃ | ⁱPr | H | F | CN | H | 0 |
| CF₃ | ⁱPr | H | F | CN | H | 1 |
| CF₃ | ⁱPr | H | F | CN | H | 2 |
| CF₃ | ⁱPr | H | Cl | CN | H | 0 |
| CF₃ | ⁱPr | H | Cl | CN | H | 1 |
| CF₃ | ⁱPr | H | Cl | CN | H | 2 |
| CF₃ | ⁱPr | H | Br | CN | H | 0 |
| CF₃ | ⁱPr | H | Br | CN | H | 1 |
| CF₃ | ⁱPr | H | Br | CN | H | 2 |
| CF₃ | ⁱPr | H | I | CN | H | 0 |
| CF₃ | ⁱPr | H | I | CN | H | 1 |
| CF₃ | ⁱPr | H | I | CN | H | 2 |
| CF₃ | ⁱPr | H | CF₃ | F | H | 0 |
| CF₃ | ⁱPr | H | CF₃ | F | H | 1 |
| CF₃ | ⁱPr | H | CF₃ | F | H | 2 |
| CF₃ | ⁱPr | H | CF₃ | Cl | H | 0 |
| CF₃ | ⁱPr | H | CF₃ | Cl | H | 1 |
| CF₃ | ⁱPr | H | CF₃ | Cl | H | 2 |
| CF₃ | ⁱPr | H | CF₃ | Br | H | 0 |
| CF₃ | ⁱPr | H | CF₃ | Br | H | 1 |
| CF₃ | ⁱPr | H | CF₃ | Br | H | 2 |
| CF₃ | ⁱPr | H | CF₃ | I | H | 0 |
| CF₃ | ⁱPr | H | CF₃ | I | H | 1 |
| CF₃ | ⁱPr | H | CF₃ | I | H | 2 |
| CF₃ | ⁱPr | H | CF₃ | CN | H | 0 |
| CF₃ | ⁱPr | H | CF₃ | CN | H | 1 |
| CF₃ | ⁱPr | H | CF₃ | CN | H | 2 |
| CF₃ | CH₂CF₃ | H | H | H | H | 0 |
| CF₃ | CH₂CF₃ | H | H | H | H | 1 |
| CF₃ | CH₂CF₃ | H | H | H | H | 2 |
| CF₃ | CH₂CF₃ | F | H | H | H | 0 |
| CF₃ | CH₂CF₃ | F | H | H | H | 1 |
| CF₃ | CH₂CF₃ | F | H | H | H | 2 |
| CF₃ | CH₂CF₃ | Cl | H | H | H | 0 |
| CF₃ | CH₂CF₃ | Cl | H | H | H | 1 |
| CF₃ | CH₂CF₃ | Cl | H | H | H | 2 |
| CF₃ | CH₂CF₃ | Br | H | H | H | 0 |
| CF₃ | CH₂CF₃ | Br | H | H | H | 1 |
| CF₃ | CH₂CF₃ | Br | H | H | H | 2 |
| CF₃ | CH₂CF₃ | I | H | H | H | 0 |
| CF₃ | CH₂CF₃ | I | H | H | H | 1 |
| CF₃ | CH₂CF₃ | I | H | H | H | 2 |
| CF₃ | CH₂CF₃ | Me | H | H | H | 0 |
| CF₃ | CH₂CF₃ | Me | H | H | H | 1 |
| CF₃ | CH₂CF₃ | Me | H | H | H | 2 |
| CF₃ | CH₂CF₃ | CF₃ | H | H | H | 0 |
| CF₃ | CH₂CF₃ | CF₃ | H | H | H | 1 |

TABLE 1-continued

| | | | | | | |
|---|---|---|---|---|---|---|
| CF₃ | CH₂CF₃ | CF₃ | H | H | H | 2 |
| CF₃ | CH₂CF₃ | H | F | H | H | 0 |
| CF₃ | CH₂CF₃ | H | F | H | H | 1 |
| CF₃ | CH₂CF₃ | H | F | H | H | 2 |
| CF₃ | CH₂CF₃ | H | Cl | H | H | 0 |
| CF₃ | CH₂CF₃ | H | Cl | H | H | 1 |
| CF₃ | CH₂CF₃ | H | Cl | H | H | 2 |
| CF₃ | CH₂CF₃ | H | Br | H | H | 0 |
| CF₃ | CH₂CF₃ | H | Br | H | H | 1 |
| CF₃ | CH₂CF₃ | H | Br | H | H | 2 |
| CF₃ | CH₂CF₃ | H | I | H | H | 0 |
| CF₃ | CH₂CF₃ | H | I | H | H | 1 |
| CF₃ | CH₂CF₃ | H | I | H | H | 2 |
| CF₃ | CH₂CF₃ | H | Me | H | H | 0 |
| CF₃ | CH₂CF₃ | H | Me | H | H | 1 |
| CF₃ | CH₂CF₃ | H | Me | H | H | 2 |
| CF₃ | CH₂CF₃ | H | CF₃ | H | H | 0 |
| CF₃ | CH₂CF₃ | H | CF₃ | H | H | 1 |
| CF₃ | CH₂CF₃ | H | CF₃ | H | H | 2 |
| CF₃ | CH₂CF₃ | H | CF₂CF₃ | H | H | 0 |
| CF₃ | CH₂CF₃ | H | CF₂CF₃ | H | H | 1 |
| CF₃ | CH₂CF₃ | H | CF₂CF₃ | H | H | 2 |
| CF₃ | CH₂CF₃ | H | CF(CF₃)₂ | H | H | 0 |
| CF₃ | CH₂CF₃ | H | CF(CF₃)₂ | H | H | 1 |
| CF₃ | CH₂CF₃ | H | CF(CF₃)₂ | H | H | 2 |
| CF₃ | CH₂CF₃ | H | SMe | H | H | 0 |
| CF₃ | CH₂CF₃ | H | SMe | H | H | 1 |
| CF₃ | CH₂CF₃ | H | SMe | H | H | 2 |
| CF₃ | CH₂CF₃ | H | SOMe | H | H | 0 |
| CF₃ | CH₂CF₃ | H | SOMe | H | H | 1 |
| CF₃ | CH₂CF₃ | H | SOMe | H | H | 2 |
| CF₃ | CH₂CF₃ | H | SO₂Me | H | H | 0 |
| CF₃ | CH₂CF₃ | H | SO₂Me | H | H | 1 |
| CF₃ | CH₂CF₃ | H | SO₂Me | H | H | 2 |
| CF₃ | CH₂CF₃ | H | OMe | H | H | 0 |
| CF₃ | CH₂CF₃ | H | OMe | H | H | 1 |
| CF₃ | CH₂CF₃ | H | OMe | H | H | 2 |
| CF₃ | CH₂CF₃ | H | OCF₃ | H | H | 0 |
| CF₃ | CH₂CF₃ | H | OCF₃ | H | H | 1 |
| CF₃ | CH₂CF₃ | H | OCF₃ | H | H | 2 |
| CF₃ | CH₂CF₃ | H | NO₂ | H | H | 0 |
| CF₃ | CH₂CF₃ | H | NO₂ | H | H | 1 |
| CF₃ | CH₂CF₃ | H | NO₂ | H | H | 2 |
| CF₃ | CH₂CF₃ | H | CN | H | H | 0 |
| CF₃ | CH₂CF₃ | H | CN | H | H | 1 |
| CF₃ | CH₂CF₃ | H | CN | H | H | 2 |
| CF₃ | CH₂CF₃ | H | H | F | H | 0 |
| CF₃ | CH₂CF₃ | H | H | F | H | 1 |
| CF₃ | CH₂CF₃ | H | H | F | H | 2 |
| CF₃ | CH₂CF₃ | H | H | Cl | H | 0 |
| CF₃ | CH₂CF₃ | H | H | Cl | H | 1 |
| CF₃ | CH₂CF₃ | H | H | Cl | H | 2 |
| CF₃ | CH₂CF₃ | H | H | Br | H | 0 |
| CF₃ | CH₂CF₃ | H | H | Br | H | 1 |
| CF₃ | CH₂CF₃ | H | H | Br | H | 2 |
| CF₃ | CH₂CF₃ | H | H | I | H | 0 |
| CF₃ | CH₂CF₃ | H | H | I | H | 1 |
| CF₃ | CH₂CF₃ | H | H | I | H | 2 |
| CF₃ | CH₂CF₃ | H | H | Me | H | 0 |
| CF₃ | CH₂CF₃ | H | H | Me | H | 1 |
| CF₃ | CH₂CF₃ | H | H | Me | H | 2 |
| CF₃ | CH₂CF₃ | H | H | CF₃ | H | 0 |
| CF₃ | CH₂CF₃ | H | H | CF₃ | H | 1 |
| CF₃ | CH₂CF₃ | H | H | CF₃ | H | 2 |
| CF₃ | CH₂CF₃ | H | H | CF₂CF₃ | H | 0 |
| CF₃ | CH₂CF₃ | H | H | CF₂CF₃ | H | 1 |
| CF₃ | CH₂CF₃ | H | H | CF₂CF₃ | H | 2 |
| CF₃ | CH₂CF₃ | H | H | CF(CF₃)₂ | H | 0 |
| CF₃ | CH₂CF₃ | H | H | CF(CF₃)₂ | H | 1 |
| CF₃ | CH₂CF₃ | H | H | CF(CF₃)₂ | H | 2 |
| CF₃ | CH₂CF₃ | H | H | SMe | H | 0 |
| CF₃ | CH₂CF₃ | H | H | SMe | H | 1 |
| CF₃ | CH₂CF₃ | H | H | SMe | H | 2 |
| CF₃ | CH₂CF₃ | H | H | SOMe | H | 0 |
| CF₃ | CH₂CF₃ | H | H | SOMe | H | 1 |
| CF₃ | CH₂CF₃ | H | H | SOMe | H | 2 |
| CF₃ | CH₂CF₃ | H | H | SO₂Me | H | 0 |
| CF₃ | CH₂CF₃ | H | H | SO₂Me | H | 1 |
| CF₃ | CH₂CF₃ | H | H | SO₂Me | H | 2 |
| CF₃ | CH₂CF₃ | H | H | OMe | H | 0 |
| CF₃ | CH₂CF₃ | H | H | OMe | H | 1 |
| CF₃ | CH₂CF₃ | H | H | OMe | H | 2 |
| CF₃ | CH₂CF₃ | H | H | OCF₃ | H | 0 |
| CF₃ | CH₂CF₃ | H | H | OCF₃ | H | 1 |
| CF₃ | CH₂CF₃ | H | H | OCF₃ | H | 2 |
| CF₃ | CH₂CF₃ | H | H | NO₂ | H | 0 |
| CF₃ | CH₂CF₃ | H | H | NO₂ | H | 1 |
| CF₃ | CH₂CF₃ | H | H | NO₂ | H | 2 |
| CF₃ | CH₂CF₃ | H | H | CN | H | 0 |
| CF₃ | CH₂CF₃ | H | H | CN | H | 1 |
| CF₃ | CH₂CF₃ | H | H | CN | H | 2 |
| CF₃ | CH₂CF₃ | H | H | H | F | 0 |
| CF₃ | CH₂CF₃ | H | H | H | F | 1 |
| CF₃ | CH₂CF₃ | H | H | H | F | 2 |
| CF₃ | CH₂CF₃ | H | H | H | Cl | 0 |
| CF₃ | CH₂CF₃ | H | H | H | Cl | 1 |
| CF₃ | CH₂CF₃ | H | H | H | Cl | 2 |
| CF₃ | CH₂CF₃ | H | H | H | Br | 0 |
| CF₃ | CH₂CF₃ | H | H | H | Br | 1 |
| CF₃ | CH₂CF₃ | H | H | H | Br | 2 |
| CF₃ | CH₂CF₃ | H | H | H | I | 0 |
| CF₃ | CH₂CF₃ | H | H | H | I | 1 |
| CF₃ | CH₂CF₃ | H | H | H | I | 2 |
| CF₃ | CH₂CF₃ | H | H | H | Me | 0 |
| CF₃ | CH₂CF₃ | H | H | H | Me | 1 |
| CF₃ | CH₂CF₃ | H | H | H | Me | 2 |
| CF₃ | CH₂CF₃ | H | H | H | CF₃ | 0 |
| CF₃ | CH₂CF₃ | H | H | H | CF₃ | 1 |
| CF₃ | CH₂CF₃ | H | H | H | CF₃ | 2 |
| CF₃ | CH₂CF₃ | H | H | H | CF₂CF₃ | 0 |
| CF₃ | CH₂CF₃ | H | H | H | CF₂CF₃ | 1 |
| CF₃ | CH₂CF₃ | H | H | H | CF₂CF₃ | 2 |
| CF₃ | CH₂CF₃ | H | H | H | CF(CF₃)₂ | 0 |
| CF₃ | CH₂CF₃ | H | H | H | CF(CF₃)₂ | 1 |
| CF₃ | CH₂CF₃ | H | H | H | CF(CF₃)₂ | 2 |
| CF₃ | CH₂CF₃ | H | H | H | SMe | 0 |
| CF₃ | CH₂CF₃ | H | H | H | SMe | 1 |
| CF₃ | CH₂CF₃ | H | H | H | SMe | 2 |
| CF₃ | CH₂CF₃ | H | H | H | SOMe | 0 |
| CF₃ | CH₂CF₃ | H | H | H | SOMe | 1 |
| CF₃ | CH₂CF₃ | H | H | H | SOMe | 2 |
| CF₃ | CH₂CF₃ | H | H | H | SO₂Me | 0 |
| CF₃ | CH₂CF₃ | H | H | H | SO₂Me | 1 |
| CF₃ | CH₂CF₃ | H | H | H | SO₂Me | 2 |
| CF₃ | CH₂CF₃ | H | H | H | OMe | 0 |
| CF₃ | CH₂CF₃ | H | H | H | OMe | 1 |
| CF₃ | CH₂CF₃ | H | H | H | OMe | 2 |
| CF₃ | CH₂CF₃ | H | H | H | OCF₃ | 0 |
| CF₃ | CH₂CF₃ | H | H | H | OCF₃ | 1 |
| CF₃ | CH₂CF₃ | H | H | H | OCF₃ | 2 |
| CF₃ | CH₂CF₃ | H | H | H | NO₂ | 0 |
| CF₃ | CH₂CF₃ | H | H | H | NO₂ | 1 |
| CF₃ | CH₂CF₃ | H | H | H | NO₂ | 2 |
| CF₃ | CH₂CF₃ | H | H | H | CN | 0 |
| CF₃ | CH₂CF₃ | H | H | H | CN | 1 |
| CF₃ | CH₂CF₃ | H | H | H | CN | 2 |
| CF₃ | CH₂CF₃ | H | F | H | F | 0 |
| CF₃ | CH₂CF₃ | H | F | H | F | 1 |
| CF₃ | CH₂CF₃ | H | F | H | F | 2 |
| CF₃ | CH₂CF₃ | H | Cl | H | Cl | 0 |
| CF₃ | CH₂CF₃ | H | Cl | H | Cl | 1 |
| CF₃ | CH₂CF₃ | H | Cl | H | Cl | 2 |
| CF₃ | CH₂CF₃ | H | Br | H | Br | 0 |
| CF₃ | CH₂CF₃ | H | Br | H | Br | 1 |
| CF₃ | CH₂CF₃ | H | Br | H | Br | 2 |
| CF₃ | CH₂CF₃ | H | I | H | I | 0 |
| CF₃ | CH₂CF₃ | H | I | H | I | 1 |
| CF₃ | CH₂CF₃ | H | I | H | I | 2 |
| CF₃ | CH₂CF₃ | H | F | H | Cl | 0 |
| CF₃ | CH₂CF₃ | H | F | H | Cl | 1 |
| CF₃ | CH₂CF₃ | H | F | H | Cl | 2 |
| CF₃ | CH₂CF₃ | H | F | H | Br | 0 |
| CF₃ | CH₂CF₃ | H | F | H | Br | 1 |
| CF₃ | CH₂CF₃ | H | F | H | Br | 2 |
| CF₃ | CH₂CF₃ | H | F | H | I | 0 |
| CF₃ | CH₂CF₃ | H | F | H | I | 1 |
| CF₃ | CH₂CF₃ | H | F | H | I | 2 |
| CF₃ | CH₂CF₃ | H | Cl | H | F | 0 |
| CF₃ | CH₂CF₃ | H | Cl | H | F | 1 |
| CF₃ | CH₂CF₃ | H | Cl | H | F | 2 |

TABLE 1-continued

| | | | | | | |
|---|---|---|---|---|---|---|
| CF$_3$ | CH$_2$CF$_3$ | H | Cl | H | Br | 0 |
| CF$_3$ | CH$_2$CF$_3$ | H | Cl | H | Br | 1 |
| CF$_3$ | CH$_2$CF$_3$ | H | Cl | H | Br | 2 |
| CF$_3$ | CH$_2$CF$_3$ | H | Cl | H | I | 0 |
| CF$_3$ | CH$_2$CF$_3$ | H | Cl | H | I | 1 |
| CF$_3$ | CH$_2$CF$_3$ | H | Cl | H | I | 2 |
| CF$_3$ | CH$_2$CF$_3$ | H | Br | H | F | 0 |
| CF$_3$ | CH$_2$CF$_3$ | H | Br | H | F | 1 |
| CF$_3$ | CH$_2$CF$_3$ | H | Br | H | F | 2 |
| CF$_3$ | CH$_2$CF$_3$ | H | Br | H | Cl | 0 |
| CF$_3$ | CH$_2$CF$_3$ | H | Br | H | Cl | 1 |
| CF$_3$ | CH$_2$CF$_3$ | H | Br | H | Cl | 2 |
| CF$_3$ | CH$_2$CF$_3$ | H | Br | H | I | 0 |
| CF$_3$ | CH$_2$CF$_3$ | H | Br | H | I | 1 |
| CF$_3$ | CH$_2$CF$_3$ | H | Br | H | I | 2 |
| CF$_3$ | CH$_2$CF$_3$ | H | I | H | F | 0 |
| CF$_3$ | CH$_2$CF$_3$ | H | I | H | F | 1 |
| CF$_3$ | CH$_2$CF$_3$ | H | I | H | F | 2 |
| CF$_3$ | CH$_2$CF$_3$ | H | I | H | Cl | 0 |
| CF$_3$ | CH$_2$CF$_3$ | H | I | H | Cl | 1 |
| CF$_3$ | CH$_2$CF$_3$ | H | I | H | Cl | 2 |
| CF$_3$ | CH$_2$CF$_3$ | H | I | H | Br | 0 |
| CF$_3$ | CH$_2$CF$_3$ | H | I | H | Br | 1 |
| CF$_3$ | CH$_2$CF$_3$ | H | I | H | Br | 2 |
| CF$_3$ | CH$_2$CF$_3$ | H | F | H | CN | 0 |
| CF$_3$ | CH$_2$CF$_3$ | H | F | H | CN | 1 |
| CF$_3$ | CH$_2$CF$_3$ | H | F | H | CN | 2 |
| CF$_3$ | CH$_2$CF$_3$ | H | Cl | H | CN | 0 |
| CF$_3$ | CH$_2$CF$_3$ | H | Cl | H | CN | 1 |
| CF$_3$ | CH$_2$CF$_3$ | H | Cl | H | CN | 2 |
| CF$_3$ | CH$_2$CF$_3$ | H | Br | H | CN | 0 |
| CF$_3$ | CH$_2$CF$_3$ | H | Br | H | CN | 1 |
| CF$_3$ | CH$_2$CF$_3$ | H | Br | H | CN | 2 |
| CF$_3$ | CH$_2$CF$_3$ | H | I | H | CN | 0 |
| CF$_3$ | CH$_2$CF$_3$ | H | I | H | CN | 1 |
| CF$_3$ | CH$_2$CF$_3$ | H | I | H | CN | 2 |
| CF$_3$ | CH$_2$CF$_3$ | H | CF$_3$ | H | F | 0 |
| CF$_3$ | CH$_2$CF$_3$ | H | CF$_3$ | H | F | 1 |
| CF$_3$ | CH$_2$CF$_3$ | H | CF$_3$ | H | F | 2 |
| CF$_3$ | CH$_2$CF$_3$ | H | CF$_3$ | H | Cl | 0 |
| CF$_3$ | CH$_2$CF$_3$ | H | CF$_3$ | H | Cl | 1 |
| CF$_3$ | CH$_2$CF$_3$ | H | CF$_3$ | H | Cl | 2 |
| CF$_3$ | CH$_2$CF$_3$ | H | CF$_3$ | H | Br | 0 |
| CF$_3$ | CH$_2$CF$_3$ | H | CF$_3$ | H | Br | 1 |
| CF$_3$ | CH$_2$CF$_3$ | H | CF$_3$ | H | Br | 2 |
| CF$_3$ | CH$_2$CF$_3$ | H | CF$_3$ | H | I | 0 |
| CF$_3$ | CH$_2$CF$_3$ | H | CF$_3$ | H | I | 1 |
| CF$_3$ | CH$_2$CF$_3$ | H | CF$_3$ | H | I | 2 |
| CF$_3$ | CH$_2$CF$_3$ | H | CF$_3$ | H | CN | 0 |
| CF$_3$ | CH$_2$CF$_3$ | H | CF$_3$ | H | CN | 1 |
| CF$_3$ | CH$_2$CF$_3$ | H | CF$_3$ | H | CN | 2 |
| CF$_3$ | CH$_2$CF$_3$ | H | F | F | H | 0 |
| CF$_3$ | CH$_2$CF$_3$ | H | F | F | H | 1 |
| CF$_3$ | CH$_2$CF$_3$ | H | F | F | H | 2 |
| CF$_3$ | CH$_2$CF$_3$ | H | Cl | Cl | H | 0 |
| CF$_3$ | CH$_2$CF$_3$ | H | Cl | Cl | H | 1 |
| CF$_3$ | CH$_2$CF$_3$ | H | Cl | Cl | H | 2 |
| CF$_3$ | CH$_2$CF$_3$ | H | Br | Br | H | 0 |
| CF$_3$ | CH$_2$CF$_3$ | H | Br | Br | H | 1 |
| CF$_3$ | CH$_2$CF$_3$ | H | Br | Br | H | 2 |
| CF$_3$ | CH$_2$CF$_3$ | H | I | I | H | 0 |
| CF$_3$ | CH$_2$CF$_3$ | H | I | I | H | 1 |
| CF$_3$ | CH$_2$CF$_3$ | H | I | I | H | 2 |
| CF$_3$ | CH$_2$CF$_3$ | H | F | Cl | H | 0 |
| CF$_3$ | CH$_2$CF$_3$ | H | F | Cl | H | 1 |
| CF$_3$ | CH$_2$CF$_3$ | H | F | Cl | H | 2 |
| CF$_3$ | CH$_2$CF$_3$ | H | F | Br | H | 0 |
| CF$_3$ | CH$_2$CF$_3$ | H | F | Br | H | 1 |
| CF$_3$ | CH$_2$CF$_3$ | H | F | Br | H | 2 |
| CF$_3$ | CH$_2$CF$_3$ | H | F | I | H | 0 |
| CF$_3$ | CH$_2$CF$_3$ | H | F | I | H | 1 |
| CF$_3$ | CH$_2$CF$_3$ | H | F | I | H | 2 |
| CF$_3$ | CH$_2$CF$_3$ | H | Cl | F | H | 0 |
| CF$_3$ | CH$_2$CF$_3$ | H | Cl | F | H | 1 |
| CF$_3$ | CH$_2$CF$_3$ | H | Cl | F | H | 2 |
| CF$_3$ | CH$_2$CF$_3$ | H | Cl | Br | H | 0 |
| CF$_3$ | CH$_2$CF$_3$ | H | Cl | Br | H | 1 |
| CF$_3$ | CH$_2$CF$_3$ | H | Cl | Br | H | 2 |
| CF$_3$ | CH$_2$CF$_3$ | H | Cl | I | H | 0 |
| CF$_3$ | CH$_2$CF$_3$ | H | Cl | I | H | 1 |
| CF$_3$ | CH$_2$CF$_3$ | H | Cl | I | H | 2 |
| CF$_3$ | CH$_2$CF$_3$ | H | Br | F | H | 0 |
| CF$_3$ | CH$_2$CF$_3$ | H | Br | F | H | 1 |
| CF$_3$ | CH$_2$CF$_3$ | H | Br | F | H | 2 |
| CF$_3$ | CH$_2$CF$_3$ | H | Br | Cl | H | 0 |
| CF$_3$ | CH$_2$CF$_3$ | H | Br | Cl | H | 1 |
| CF$_3$ | CH$_2$CF$_3$ | H | Br | Cl | H | 2 |
| CF$_3$ | CH$_2$CF$_3$ | H | Br | I | H | 0 |
| CF$_3$ | CH$_2$CF$_3$ | H | Br | I | H | 1 |
| CF$_3$ | CH$_2$CF$_3$ | H | Br | I | H | 2 |
| CF$_3$ | CH$_2$CF$_3$ | H | I | F | H | 0 |
| CF$_3$ | CH$_2$CF$_3$ | H | I | F | H | 1 |
| CF$_3$ | CH$_2$CF$_3$ | H | I | F | H | 2 |
| CF$_3$ | CH$_2$CF$_3$ | H | I | Cl | H | 0 |
| CF$_3$ | CH$_2$CF$_3$ | H | I | Cl | H | 1 |
| CF$_3$ | CH$_2$CF$_3$ | H | I | Cl | H | 2 |
| CF$_3$ | CH$_2$CF$_3$ | H | I | Br | H | 0 |
| CF$_3$ | CH$_2$CF$_3$ | H | I | Br | H | 1 |
| CF$_3$ | CH$_2$CF$_3$ | H | I | Br | H | 2 |
| CF$_3$ | CH$_2$CF$_3$ | H | F | CN | H | 0 |
| CF$_3$ | CH$_2$CF$_3$ | H | F | CN | H | 1 |
| CF$_3$ | CH$_2$CF$_3$ | H | F | CN | H | 2 |
| CF$_3$ | CH$_2$CF$_3$ | H | Cl | CN | H | 0 |
| CF$_3$ | CH$_2$CF$_3$ | H | Cl | CN | H | 1 |
| CF$_3$ | CH$_2$CF$_3$ | H | Cl | CN | H | 2 |
| CF$_3$ | CH$_2$CF$_3$ | H | Br | CN | H | 0 |
| CF$_3$ | CH$_2$CF$_3$ | H | Br | CN | H | 1 |
| CF$_3$ | CH$_2$CF$_3$ | H | Br | CN | H | 2 |
| CF$_3$ | CH$_2$CF$_3$ | H | I | CN | H | 0 |
| CF$_3$ | CH$_2$CF$_3$ | H | I | CN | H | 1 |
| CF$_3$ | CH$_2$CF$_3$ | H | I | CN | H | 2 |
| CF$_3$ | CH$_2$CF$_3$ | H | CF$_3$ | F | H | 0 |
| CF$_3$ | CH$_2$CF$_3$ | H | CF$_3$ | F | H | 1 |
| CF$_3$ | CH$_2$CF$_3$ | H | CF$_3$ | F | H | 2 |
| CF$_3$ | CH$_2$CF$_3$ | H | CF$_3$ | Cl | H | 0 |
| CF$_3$ | CH$_2$CF$_3$ | H | CF$_3$ | Cl | H | 1 |
| CF$_3$ | CH$_2$CF$_3$ | H | CF$_3$ | Cl | H | 2 |
| CF$_3$ | CH$_2$CF$_3$ | H | CF$_3$ | Br | H | 0 |
| CF$_3$ | CH$_2$CF$_3$ | H | CF$_3$ | Br | H | 1 |
| CF$_3$ | CH$_2$CF$_3$ | H | CF$_3$ | Br | H | 2 |
| CF$_3$ | CH$_2$CF$_3$ | H | CF$_3$ | I | H | 0 |
| CF$_3$ | CH$_2$CF$_3$ | H | CF$_3$ | I | H | 1 |
| CF$_3$ | CH$_2$CF$_3$ | H | CF$_3$ | I | H | 2 |
| CF$_3$ | CH$_2$CF$_3$ | H | CF$_3$ | CN | H | 0 |
| CF$_3$ | CH$_2$CF$_3$ | H | CF$_3$ | CN | H | 1 |
| CF$_3$ | CH$_2$CF$_3$ | H | CF$_3$ | CN | H | 2 |
| CF$_2$CF$_3$ | Me | H | H | H | H | 0 |
| CF$_2$CF$_3$ | Me | H | H | H | H | 1 |
| CF$_2$CF$_3$ | Me | H | H | H | H | 2 |
| CF$_2$CF$_3$ | Me | F | H | H | H | 0 |
| CF$_2$CF$_3$ | Me | F | H | H | H | 1 |
| CF$_2$CF$_3$ | Me | F | H | H | H | 2 |
| CF$_2$CF$_3$ | Me | Cl | H | H | H | 0 |
| CF$_2$CF$_3$ | Me | Cl | H | H | H | 1 |
| CF$_2$CF$_3$ | Me | Cl | H | H | H | 2 |
| CF$_2$CF$_3$ | Me | Br | H | H | H | 0 |
| CF$_2$CF$_3$ | Me | Br | H | H | H | 1 |
| CF$_2$CF$_3$ | Me | Br | H | H | H | 2 |
| CF$_2$CF$_3$ | Me | I | H | H | H | 0 |
| CF$_2$CF$_3$ | Me | I | H | H | H | 1 |
| CF$_2$CF$_3$ | Me | I | H | H | H | 2 |
| CF$_2$CF$_3$ | Me | Me | H | H | H | 0 |
| CF$_2$CF$_3$ | Me | Me | H | H | H | 1 |
| CF$_2$CF$_3$ | Me | Me | H | H | H | 2 |
| CF$_2$CF$_3$ | Me | CF$_3$ | H | H | H | 0 |
| CF$_2$CF$_3$ | Me | CF$_3$ | H | H | H | 1 |
| CF$_2$CF$_3$ | Me | CF$_3$ | H | H | H | 2 |
| CF$_2$CF$_3$ | Me | H | F | H | H | 0 |
| CF$_2$CF$_3$ | Me | H | F | H | H | 1 |
| CF$_2$CF$_3$ | Me | H | F | H | H | 2 |
| CF$_2$CF$_3$ | Me | H | Cl | H | H | 0 |
| CF$_2$CF$_3$ | Me | H | Cl | H | H | 1 |
| CF$_2$CF$_3$ | Me | H | Cl | H | H | 2 |
| CF$_2$CF$_3$ | Me | H | Br | H | H | 0 |
| CF$_2$CF$_3$ | Me | H | Br | H | H | 1 |
| CF$_2$CF$_3$ | Me | H | Br | H | H | 2 |
| CF$_2$CF$_3$ | Me | H | I | H | H | 0 |
| CF$_2$CF$_3$ | Me | H | I | H | H | 1 |
| CF$_2$CF$_3$ | Me | H | I | H | H | 2 |
| CF$_2$CF$_3$ | Me | H | Me | H | H | 0 |

TABLE 1-continued

| | | | | | | |
|---|---|---|---|---|---|---|
| CF₂CF₃ | Me | H | Me | H | H | 1 |
| CF₂CF₃ | Me | H | Me | H | H | 2 |
| CF₂CF₃ | Me | H | CF₃ | H | H | 0 |
| CF₂CF₃ | Me | H | CF₃ | H | H | 1 |
| CF₂CF₃ | Me | H | CF₃ | H | H | 2 |
| CF₂CF₃ | Me | H | CF₂CF₃ | H | H | 0 |
| CF₂CF₃ | Me | H | CF₂CF₃ | H | H | 1 |
| CF₂CF₃ | Me | H | CF₂CF₃ | H | H | 2 |
| CF₂CF₃ | Me | H | CF(CF₃)₂ | H | H | 0 |
| CF₂CF₃ | Me | H | CF(CF₃)₂ | H | H | 1 |
| CF₂CF₃ | Me | H | CF(CF₃)₂ | H | H | 2 |
| CF₂CF₃ | Me | H | SMe | H | H | 0 |
| CF₂CF₃ | Me | H | SMe | H | H | 1 |
| CF₂CF₃ | Me | H | SMe | H | H | 2 |
| CF₂CF₃ | Me | H | SOMe | H | H | 0 |
| CF₂CF₃ | Me | H | SOMe | H | H | 1 |
| CF₂CF₃ | Me | H | SOMe | H | H | 2 |
| CF₂CF₃ | Me | H | SO₂Me | H | H | 0 |
| CF₂CF₃ | Me | H | SO₂Me | H | H | 1 |
| CF₂CF₃ | Me | H | SO₂Me | H | H | 2 |
| CF₂CF₃ | Me | H | OMe | H | H | 0 |
| CF₂CF₃ | Me | H | OMe | H | H | 1 |
| CF₂CF₃ | Me | H | OMe | H | H | 2 |
| CF₂CF₃ | Me | H | OCF₃ | H | H | 0 |
| CF₂CF₃ | Me | H | OCF₃ | H | H | 1 |
| CF₂CF₃ | Me | H | OCF₃ | H | H | 2 |
| CF₂CF₃ | Me | H | NO₂ | H | H | 0 |
| CF₂CF₃ | Me | H | NO₂ | H | H | 1 |
| CF₂CF₃ | Me | H | NO₂ | H | H | 2 |
| CF₂CF₃ | Me | H | CN | H | H | 0 |
| CF₂CF₃ | Me | H | CN | H | H | 1 |
| CF₂CF₃ | Me | H | CN | H | H | 2 |
| CF₂CF₃ | Me | H | H | F | H | 0 |
| CF₂CF₃ | Me | H | H | F | H | 1 |
| CF₂CF₃ | Me | H | H | F | H | 2 |
| CF₂CF₃ | Me | H | H | Cl | H | 0 |
| CF₂CF₃ | Me | H | H | Cl | H | 1 |
| CF₂CF₃ | Me | H | H | Cl | H | 2 |
| CF₂CF₃ | Me | H | H | Br | H | 0 |
| CF₂CF₃ | Me | H | H | Br | H | 1 |
| CF₂CF₃ | Me | H | H | Br | H | 2 |
| CF₂CF₃ | Me | H | H | I | H | 0 |
| CF₂CF₃ | Me | H | H | I | H | 1 |
| CF₂CF₃ | Me | H | H | I | H | 2 |
| CF₂CF₃ | Me | H | H | Me | H | 0 |
| CF₂CF₃ | Me | H | H | Me | H | 1 |
| CF₂CF₃ | Me | H | H | Me | H | 2 |
| CF₂CF₃ | Me | H | H | CF₃ | H | 0 |
| CF₂CF₃ | Me | H | H | CF₃ | H | 1 |
| CF₂CF₃ | Me | H | H | CF₃ | H | 2 |
| CF₂CF₃ | Me | H | H | CF₂CF₃ | H | 0 |
| CF₂CF₃ | Me | H | H | CF₂CF₃ | H | 1 |
| CF₂CF₃ | Me | H | H | CF₂CF₃ | H | 2 |
| CF₂CF₃ | Me | H | H | CF(CF₃)₂ | H | 0 |
| CF₂CF₃ | Me | H | H | CF(CF₃)₂ | H | 1 |
| CF₂CF₃ | Me | H | H | CF(CF₃)₂ | H | 2 |
| CF₂CF₃ | Me | H | H | SMe | H | 0 |
| CF₂CF₃ | Me | H | H | SMe | H | 1 |
| CF₂CF₃ | Me | H | H | SMe | H | 2 |
| CF₂CF₃ | Me | H | H | SOMe | H | 0 |
| CF₂CF₃ | Me | H | H | SOMe | H | 1 |
| CF₂CF₃ | Me | H | H | SOMe | H | 2 |
| CF₂CF₃ | Me | H | H | SO₂Me | H | 0 |
| CF₂CF₃ | Me | H | H | SO₂Me | H | 1 |
| CF₂CF₃ | Me | H | H | SO₂Me | H | 2 |
| CF₂CF₃ | Me | H | H | OMe | H | 0 |
| CF₂CF₃ | Me | H | H | OMe | H | 1 |
| CF₂CF₃ | Me | H | H | OMe | H | 2 |
| CF₂CF₃ | Me | H | H | OCF₃ | H | 0 |
| CF₂CF₃ | Me | H | H | OCF₃ | H | 1 |
| CF₂CF₃ | Me | H | H | OCF₃ | H | 2 |
| CF₂CF₃ | Me | H | H | NO₂ | H | 0 |
| CF₂CF₃ | Me | H | H | NO₂ | H | 1 |
| CF₂CF₃ | Me | H | H | NO₂ | H | 2 |
| CF₂CF₃ | Me | H | H | CN | H | 0 |
| CF₂CF₃ | Me | H | H | CN | H | 1 |
| CF₂CF₃ | Me | H | H | CN | H | 2 |
| CF₂CF₃ | Me | H | H | H | F | 0 |
| CF₂CF₃ | Me | H | H | H | F | 1 |
| CF₂CF₃ | Me | H | H | H | F | 2 |
| CF₂CF₃ | Me | H | H | H | Cl | 0 |
| CF₂CF₃ | Me | H | H | H | Cl | 1 |
| CF₂CF₃ | Me | H | H | H | Cl | 2 |
| CF₂CF₃ | Me | H | H | H | Br | 0 |
| CF₂CF₃ | Me | H | H | H | Br | 1 |
| CF₂CF₃ | Me | H | H | H | Br | 2 |
| CF₂CF₃ | Me | H | H | H | I | 0 |
| CF₂CF₃ | Me | H | H | H | I | 1 |
| CF₂CF₃ | Me | H | H | H | I | 2 |
| CF₂CF₃ | Me | H | H | H | Me | 0 |
| CF₂CF₃ | Me | H | H | H | Me | 1 |
| CF₂CF₃ | Me | H | H | H | Me | 2 |
| CF₂CF₃ | Me | H | H | H | CF₃ | 0 |
| CF₂CF₃ | Me | H | H | H | CF₃ | 1 |
| CF₂CF₃ | Me | H | H | H | CF₃ | 2 |
| CF₂CF₃ | Me | H | H | H | CF₂CF₃ | 0 |
| CF₂CF₃ | Me | H | H | H | CF₂CF₃ | 1 |
| CF₂CF₃ | Me | H | H | H | CF₂CF₃ | 2 |
| CF₂CF₃ | Me | H | H | H | CF(CF₃)₂ | 0 |
| CF₂CF₃ | Me | H | H | H | CF(CF₃)₂ | 1 |
| CF₂CF₃ | Me | H | H | H | CF(CF₃)₂ | 2 |
| CF₂CF₃ | Me | H | H | H | SMe | 0 |
| CF₂CF₃ | Me | H | H | H | SMe | 1 |
| CF₂CF₃ | Me | H | H | H | SMe | 2 |
| CF₂CF₃ | Me | H | H | H | SOMe | 0 |
| CF₂CF₃ | Me | H | H | H | SOMe | 1 |
| CF₂CF₃ | Me | H | H | H | SOMe | 2 |
| CF₂CF₃ | Me | H | H | H | SO₂Me | 0 |
| CF₂CF₃ | Me | H | H | H | SO₂Me | 1 |
| CF₂CF₃ | Me | H | H | H | SO₂Me | 2 |
| CF₂CF₃ | Me | H | H | H | OMe | 0 |
| CF₂CF₃ | Me | H | H | H | OMe | 1 |
| CF₂CF₃ | Me | H | H | H | OMe | 2 |
| CF₂CF₃ | Me | H | H | H | OCF₃ | 0 |
| CF₂CF₃ | Me | H | H | H | OCF₃ | 1 |
| CF₂CF₃ | Me | H | H | H | OCF₃ | 2 |
| CF₂CF₃ | Me | H | H | H | NO₂ | 0 |
| CF₂CF₃ | Me | H | H | H | NO₂ | 1 |
| CF₂CF₃ | Me | H | H | H | NO₂ | 2 |
| CF₂CF₃ | Me | H | H | H | CN | 0 |
| CF₂CF₃ | Me | H | H | H | CN | 1 |
| CF₂CF₃ | Me | H | H | H | CN | 2 |
| CF₂CF₃ | Me | H | F | H | F | 0 |
| CF₂CF₃ | Me | H | F | H | F | 1 |
| CF₂CF₃ | Me | H | F | H | F | 2 |
| CF₂CF₃ | Me | H | Cl | H | Cl | 0 |
| CF₂CF₃ | Me | H | Cl | H | Cl | 1 |
| CF₂CF₃ | Me | H | Cl | H | Cl | 2 |
| CF₂CF₃ | Me | H | Br | H | Br | 0 |
| CF₂CF₃ | Me | H | Br | H | Br | 1 |
| CF₂CF₃ | Me | H | Br | H | Br | 2 |
| CF₂CF₃ | Me | H | I | H | I | 0 |
| CF₂CF₃ | Me | H | I | H | I | 1 |
| CF₂CF₃ | Me | H | I | H | I | 2 |
| CF₂CF₃ | Me | H | F | H | Cl | 0 |
| CF₂CF₃ | Me | H | F | H | Cl | 1 |
| CF₂CF₃ | Me | H | F | H | Cl | 2 |
| CF₂CF₃ | Me | H | F | H | Br | 0 |
| CF₂CF₃ | Me | H | F | H | Br | 1 |
| CF₂CF₃ | Me | H | F | H | Br | 2 |
| CF₂CF₃ | Me | H | F | H | I | 0 |
| CF₂CF₃ | Me | H | F | H | I | 1 |
| CF₂CF₃ | Me | H | F | H | I | 2 |
| CF₂CF₃ | Me | H | Cl | H | F | 0 |
| CF₂CF₃ | Me | H | Cl | H | F | 1 |
| CF₂CF₃ | Me | H | Cl | H | F | 2 |
| CF₂CF₃ | Me | H | Cl | H | Br | 0 |
| CF₂CF₃ | Me | H | Cl | H | Br | 1 |
| CF₂CF₃ | Me | H | Cl | H | Br | 2 |
| CF₂CF₃ | Me | H | Cl | H | I | 0 |
| CF₂CF₃ | Me | H | Cl | H | I | 1 |
| CF₂CF₃ | Me | H | Cl | H | I | 2 |
| CF₂CF₃ | Me | H | Br | H | F | 0 |
| CF₂CF₃ | Me | H | Br | H | F | 1 |
| CF₂CF₃ | Me | H | Br | H | F | 2 |
| CF₂CF₃ | Me | H | Br | H | Cl | 0 |
| CF₂CF₃ | Me | H | Br | H | Cl | 1 |
| CF₂CF₃ | Me | H | Br | H | Cl | 2 |
| CF₂CF₃ | Me | H | Br | H | I | 0 |
| CF₂CF₃ | Me | H | Br | H | I | 1 |

TABLE 1-continued

| | | | | | | |
|---|---|---|---|---|---|---|
| CF$_2$CF$_3$ | Me | H | Br | H | I | 2 |
| CF$_2$CF$_3$ | Me | H | I | H | F | 0 |
| CF$_2$CF$_3$ | Me | H | I | H | F | 1 |
| CF$_2$CF$_3$ | Me | H | I | H | F | 2 |
| CF$_2$CF$_3$ | Me | H | I | H | Cl | 0 |
| CF$_2$CF$_3$ | Me | H | I | H | Cl | 1 |
| CF$_2$CF$_3$ | Me | H | I | H | Cl | 2 |
| CF$_2$CF$_3$ | Me | H | I | H | Br | 0 |
| CF$_2$CF$_3$ | Me | H | I | H | Br | 1 |
| CF$_2$CF$_3$ | Me | H | I | H | Br | 2 |
| CF$_2$CF$_3$ | Me | H | F | H | CN | 0 |
| CF$_2$CF$_3$ | Me | H | F | H | CN | 1 |
| CF$_2$CF$_3$ | Me | H | F | H | CN | 2 |
| CF$_2$CF$_3$ | Me | H | Cl | H | CN | 0 |
| CF$_2$CF$_3$ | Me | H | Cl | H | CN | 1 |
| CF$_2$CF$_3$ | Me | H | Cl | H | CN | 2 |
| CF$_2$CF$_3$ | Me | H | Br | H | CN | 0 |
| CF$_2$CF$_3$ | Me | H | Br | H | CN | 1 |
| CF$_2$CF$_3$ | Me | H | Br | H | CN | 2 |
| CF$_2$CF$_3$ | Me | H | I | H | CN | 0 |
| CF$_2$CF$_3$ | Me | H | I | H | CN | 1 |
| CF$_2$CF$_3$ | Me | H | I | H | CN | 2 |
| CF$_2$CF$_3$ | Me | H | CF$_3$ | H | F | 0 |
| CF$_2$CF$_3$ | Me | H | CF$_3$ | H | F | 1 |
| CF$_2$CF$_3$ | Me | H | CF$_3$ | H | F | 2 |
| CF$_2$CF$_3$ | Me | H | CF$_3$ | H | Cl | 0 |
| CF$_2$CF$_3$ | Me | H | CF$_3$ | H | Cl | 1 |
| CF$_2$CF$_3$ | Me | H | CF$_3$ | H | Cl | 2 |
| CF$_2$CF$_3$ | Me | H | CF$_3$ | H | Br | 0 |
| CF$_2$CF$_3$ | Me | H | CF$_3$ | H | Br | 1 |
| CF$_2$CF$_3$ | Me | H | CF$_3$ | H | Br | 2 |
| CF$_2$CF$_3$ | Me | H | CF$_3$ | H | I | 0 |
| CF$_2$CF$_3$ | Me | H | CF$_3$ | H | I | 1 |
| CF$_2$CF$_3$ | Me | H | CF$_3$ | H | I | 2 |
| CF$_2$CF$_3$ | Me | H | CF$_3$ | H | CN | 0 |
| CF$_2$CF$_3$ | Me | H | CF$_3$ | H | CN | 1 |
| CF$_2$CF$_3$ | Me | H | CF$_3$ | H | CN | 2 |
| CF$_2$CF$_3$ | Me | H | F | F | H | 0 |
| CF$_2$CF$_3$ | Me | H | F | F | H | 1 |
| CF$_2$CF$_3$ | Me | H | F | F | H | 2 |
| CF$_2$CF$_3$ | Me | H | Cl | Cl | H | 0 |
| CF$_2$CF$_3$ | Me | H | Cl | Cl | H | 1 |
| CF$_2$CF$_3$ | Me | H | Cl | Cl | H | 2 |
| CF$_2$CF$_3$ | Me | H | Br | Br | H | 0 |
| CF$_2$CF$_3$ | Me | H | Br | Br | H | 1 |
| CF$_2$CF$_3$ | Me | H | Br | Br | H | 2 |
| CF$_2$CF$_3$ | Me | H | I | I | H | 0 |
| CF$_2$CF$_3$ | Me | H | I | I | H | 1 |
| CF$_2$CF$_3$ | Me | H | I | I | H | 2 |
| CF$_2$CF$_3$ | Me | H | F | Cl | H | 0 |
| CF$_2$CF$_3$ | Me | H | F | Cl | H | 1 |
| CF$_2$CF$_3$ | Me | H | F | Cl | H | 2 |
| CF$_2$CF$_3$ | Me | H | F | Br | H | 0 |
| CF$_2$CF$_3$ | Me | H | F | Br | H | 1 |
| CF$_2$CF$_3$ | Me | H | F | Br | H | 2 |
| CF$_2$CF$_3$ | Me | H | F | I | H | 0 |
| CF$_2$CF$_3$ | Me | H | F | I | H | 1 |
| CF$_2$CF$_3$ | Me | H | F | I | H | 2 |
| CF$_2$CF$_3$ | Me | H | Cl | F | H | 0 |
| CF$_2$CF$_3$ | Me | H | Cl | F | H | 1 |
| CF$_2$CF$_3$ | Me | H | Cl | F | H | 2 |
| CF$_2$CF$_3$ | Me | H | Cl | Br | H | 0 |
| CF$_2$CF$_3$ | Me | H | Cl | Br | H | 1 |
| CF$_2$CF$_3$ | Me | H | Cl | Br | H | 2 |
| CF$_2$CF$_3$ | Me | H | Cl | I | H | 0 |
| CF$_2$CF$_3$ | Me | H | Cl | I | H | 1 |
| CF$_2$CF$_3$ | Me | H | Cl | I | H | 2 |
| CF$_2$CF$_3$ | Me | H | Br | F | H | 0 |
| CF$_2$CF$_3$ | Me | H | Br | F | H | 1 |
| CF$_2$CF$_3$ | Me | H | Br | F | H | 2 |
| CF$_2$CF$_3$ | Me | H | Br | Cl | H | 0 |
| CF$_2$CF$_3$ | Me | H | Br | Cl | H | 1 |
| CF$_2$CF$_3$ | Me | H | Br | Cl | H | 2 |
| CF$_2$CF$_3$ | Me | H | Br | I | H | 0 |
| CF$_2$CF$_3$ | Me | H | Br | I | H | 1 |
| CF$_2$CF$_3$ | Me | H | Br | I | H | 2 |
| CF$_2$CF$_3$ | Me | H | I | F | H | 0 |
| CF$_2$CF$_3$ | Me | H | I | F | H | 1 |
| CF$_2$CF$_3$ | Me | H | I | F | H | 2 |
| CF$_2$CF$_3$ | Me | H | I | Cl | H | 0 |
| CF$_2$CF$_3$ | Me | H | I | Cl | H | 1 |
| CF$_2$CF$_3$ | Me | H | I | Cl | H | 2 |
| CF$_2$CF$_3$ | Me | H | I | Br | H | 0 |
| CF$_2$CF$_3$ | Me | H | I | Br | H | 1 |
| CF$_2$CF$_3$ | Me | H | I | Br | H | 2 |
| CF$_2$CF$_3$ | Me | H | F | CN | H | 0 |
| CF$_2$CF$_3$ | Me | H | F | CN | H | 1 |
| CF$_2$CF$_3$ | Me | H | F | CN | H | 2 |
| CF$_2$CF$_3$ | Me | H | Cl | CN | H | 0 |
| CF$_2$CF$_3$ | Me | H | Cl | CN | H | 1 |
| CF$_2$CF$_3$ | Me | H | Cl | CN | H | 2 |
| CF$_2$CF$_3$ | Me | H | Br | CN | H | 0 |
| CF$_2$CF$_3$ | Me | H | Br | CN | H | 1 |
| CF$_2$CF$_3$ | Me | H | Br | CN | H | 2 |
| CF$_2$CF$_3$ | Me | H | I | CN | H | 0 |
| CF$_2$CF$_3$ | Me | H | I | CN | H | 1 |
| CF$_2$CF$_3$ | Me | H | I | CN | H | 2 |
| CF$_2$CF$_3$ | Me | H | CF$_3$ | F | H | 0 |
| CF$_2$CF$_3$ | Me | H | CF$_3$ | F | H | 1 |
| CF$_2$CF$_3$ | Me | H | CF$_3$ | F | H | 2 |
| CF$_2$CF$_3$ | Me | H | CF$_3$ | Cl | H | 0 |
| CF$_2$CF$_3$ | Me | H | CF$_3$ | Cl | H | 1 |
| CF$_2$CF$_3$ | Me | H | CF$_3$ | Cl | H | 2 |
| CF$_2$CF$_3$ | Me | H | CF$_3$ | Br | H | 0 |
| CF$_2$CF$_3$ | Me | H | CF$_3$ | Br | H | 1 |
| CF$_2$CF$_3$ | Me | H | CF$_3$ | Br | H | 2 |
| CF$_2$CF$_3$ | Me | H | CF$_3$ | I | H | 0 |
| CF$_2$CF$_3$ | Me | H | CF$_3$ | I | H | 1 |
| CF$_2$CF$_3$ | Me | H | CF$_3$ | I | H | 2 |
| CF$_2$CF$_3$ | Me | H | CF$_3$ | CN | H | 0 |
| CF$_2$CF$_3$ | Me | H | CF$_3$ | CN | H | 1 |
| CF$_2$CF$_3$ | Me | H | CF$_3$ | CN | H | 2 |
| CF$_2$CF$_3$ | Et | H | H | H | H | 0 |
| CF$_2$CF$_3$ | Et | H | H | H | H | 1 |
| CF$_2$CF$_3$ | Et | H | H | H | H | 2 |
| CF$_2$CF$_3$ | Et | F | H | H | H | 0 |
| CF$_2$CF$_3$ | Et | F | H | H | H | 1 |
| CF$_2$CF$_3$ | Et | F | H | H | H | 2 |
| CF$_2$CF$_3$ | Et | Cl | H | H | H | 0 |
| CF$_2$CF$_3$ | Et | Cl | H | H | H | 1 |
| CF$_2$CF$_3$ | Et | Cl | H | H | H | 2 |
| CF$_2$CF$_3$ | Et | Br | H | H | H | 0 |
| CF$_2$CF$_3$ | Et | Br | H | H | H | 1 |
| CF$_2$CF$_3$ | Et | Br | H | H | H | 2 |
| CF$_2$CF$_3$ | Et | I | H | H | H | 0 |
| CF$_2$CF$_3$ | Et | I | H | H | H | 1 |
| CF$_2$CF$_3$ | Et | I | H | H | H | 2 |
| CF$_2$CF$_3$ | Et | Me | H | H | H | 0 |
| CF$_2$CF$_3$ | Et | Me | H | H | H | 1 |
| CF$_2$CF$_3$ | Et | Me | H | H | H | 2 |
| CF$_2$CF$_3$ | Et | CF$_3$ | H | H | H | 0 |
| CF$_2$CF$_3$ | Et | CF$_3$ | H | H | H | 1 |
| CF$_2$CF$_3$ | Et | CF$_3$ | H | H | H | 2 |
| CF$_2$CF$_3$ | Et | H | F | H | H | 0 |
| CF$_2$CF$_3$ | Et | H | F | H | H | 1 |
| CF$_2$CF$_3$ | Et | H | F | H | H | 2 |
| CF$_2$CF$_3$ | Et | H | Cl | H | H | 0 |
| CF$_2$CF$_3$ | Et | H | Cl | H | H | 1 |
| CF$_2$CF$_3$ | Et | H | Cl | H | H | 2 |
| CF$_2$CF$_3$ | Et | H | Br | H | H | 0 |
| CF$_2$CF$_3$ | Et | H | Br | H | H | 1 |
| CF$_2$CF$_3$ | Et | H | Br | H | H | 2 |
| CF$_2$CF$_3$ | Et | H | I | H | H | 0 |
| CF$_2$CF$_3$ | Et | H | I | H | H | 1 |
| CF$_2$CF$_3$ | Et | H | I | H | H | 2 |
| CF$_2$CF$_3$ | Et | H | Me | H | H | 0 |
| CF$_2$CF$_3$ | Et | H | Me | H | H | 1 |
| CF$_2$CF$_3$ | Et | H | Me | H | H | 2 |
| CF$_2$CF$_3$ | Et | H | CF$_3$ | H | H | 0 |
| CF$_2$CF$_3$ | Et | H | CF$_3$ | H | H | 1 |
| CF$_2$CF$_3$ | Et | H | CF$_3$ | H | H | 2 |
| CF$_2$CF$_3$ | Et | H | CF$_2$CF$_3$ | H | H | 0 |
| CF$_2$CF$_3$ | Et | H | CF$_2$CF$_3$ | H | H | 1 |
| CF$_2$CF$_3$ | Et | H | CF$_2$CF$_3$ | H | H | 2 |
| CF$_2$CF$_3$ | Et | H | CF(CF$_3$)$_2$ | H | H | 0 |
| CF$_2$CF$_3$ | Et | H | CF(CF$_3$)$_2$ | H | H | 1 |
| CF$_2$CF$_3$ | Et | H | CF(CF$_3$)$_2$ | H | H | 2 |
| CF$_2$CF$_3$ | Et | H | SMe | H | H | 0 |
| CF$_2$CF$_3$ | Et | H | SMe | H | H | 1 |
| CF$_2$CF$_3$ | Et | H | SMe | H | H | 2 |

TABLE 1-continued

| | | | | | | |
|---|---|---|---|---|---|---|
| CF₂CF₃ | Et | H | SOMe | H | H | 0 |
| CF₂CF₃ | Et | H | SOMe | H | H | 1 |
| CF₂CF₃ | Et | H | SOMe | H | H | 2 |
| CF₂CF₃ | Et | H | SO₂Me | H | H | 0 |
| CF₂CF₃ | Et | H | SO₂Me | H | H | 1 |
| CF₂CF₃ | Et | H | SO₂Me | H | H | 2 |
| CF₂CF₃ | Et | H | OMe | H | H | 0 |
| CF₂CF₃ | Et | H | OMe | H | H | 1 |
| CF₂CF₃ | Et | H | OMe | H | H | 2 |
| CF₂CF₃ | Et | H | OCF₃ | H | H | 0 |
| CF₂CF₃ | Et | H | OCF₃ | H | H | 1 |
| CF₂CF₃ | Et | H | OCF₃ | H | H | 2 |
| CF₂CF₃ | Et | H | NO₂ | H | H | 0 |
| CF₂CF₃ | Et | H | NO₂ | H | H | 1 |
| CF₂CF₃ | Et | H | NO₂ | H | H | 2 |
| CF₂CF₃ | Et | H | CN | H | H | 0 |
| CF₂CF₃ | Et | H | CN | H | H | 1 |
| CF₂CF₃ | Et | H | CN | H | H | 2 |
| CF₂CF₃ | Et | H | H | F | H | 0 |
| CF₂CF₃ | Et | H | H | F | H | 1 |
| CF₂CF₃ | Et | H | H | F | H | 2 |
| CF₂CF₃ | Et | H | H | Cl | H | 0 |
| CF₂CF₃ | Et | H | H | Cl | H | 1 |
| CF₂CF₃ | Et | H | H | Cl | H | 2 |
| CF₂CF₃ | Et | H | H | Br | H | 0 |
| CF₂CF₃ | Et | H | H | Br | H | 1 |
| CF₂CF₃ | Et | H | H | Br | H | 2 |
| CF₂CF₃ | Et | H | H | I | H | 0 |
| CF₂CF₃ | Et | H | H | I | H | 1 |
| CF₂CF₃ | Et | H | H | I | H | 2 |
| CF₂CF₃ | Et | H | H | Me | H | 0 |
| CF₂CF₃ | Et | H | H | Me | H | 1 |
| CF₂CF₃ | Et | H | H | Me | H | 2 |
| CF₂CF₃ | Et | H | H | CF₃ | H | 0 |
| CF₂CF₃ | Et | H | H | CF₃ | H | 1 |
| CF₂CF₃ | Et | H | H | CF₃ | H | 2 |
| CF₂CF₃ | Et | H | H | CF₂CF₃ | H | 0 |
| CF₂CF₃ | Et | H | H | CF₂CF₃ | H | 1 |
| CF₂CF₃ | Et | H | H | CF₂CF₃ | H | 2 |
| CF₂CF₃ | Et | H | H | CF(CF₃)₂ | H | 0 |
| CF₂CF₃ | Et | H | H | CF(CF₃)₂ | H | 1 |
| CF₂CF₃ | Et | H | H | CF(CF₃)₂ | H | 2 |
| CF₂CF₃ | Et | H | H | SMe | H | 0 |
| CF₂CF₃ | Et | H | H | SMe | H | 1 |
| CF₂CF₃ | Et | H | H | SMe | H | 2 |
| CF₂CF₃ | Et | H | H | SOMe | H | 0 |
| CF₂CF₃ | Et | H | H | SOMe | H | 1 |
| CF₂CF₃ | Et | H | H | SOMe | H | 2 |
| CF₂CF₃ | Et | H | H | SO₂Me | H | 0 |
| CF₂CF₃ | Et | H | H | SO₂Me | H | 1 |
| CF₂CF₃ | Et | H | H | SO₂Me | H | 2 |
| CF₂CF₃ | Et | H | H | OMe | H | 0 |
| CF₂CF₃ | Et | H | H | OMe | H | 1 |
| CF₂CF₃ | Et | H | H | OMe | H | 2 |
| CF₂CF₃ | Et | H | H | OCF₃ | H | 0 |
| CF₂CF₃ | Et | H | H | OCF₃ | H | 1 |
| CF₂CF₃ | Et | H | H | OCF₃ | H | 2 |
| CF₂CF₃ | Et | H | H | NO₂ | H | 0 |
| CF₂CF₃ | Et | H | H | NO₂ | H | 1 |
| CF₂CF₃ | Et | H | H | NO₂ | H | 2 |
| CF₂CF₃ | Et | H | H | CN | H | 0 |
| CF₂CF₃ | Et | H | H | CN | H | 1 |
| CF₂CF₃ | Et | H | H | CN | H | 2 |
| CF₂CF₃ | Et | H | H | H | F | 0 |
| CF₂CF₃ | Et | H | H | H | F | 1 |
| CF₂CF₃ | Et | H | H | H | F | 2 |
| CF₂CF₃ | Et | H | H | H | Cl | 0 |
| CF₂CF₃ | Et | H | H | H | Cl | 1 |
| CF₂CF₃ | Et | H | H | H | Cl | 2 |
| CF₂CF₃ | Et | H | H | H | Br | 0 |
| CF₂CF₃ | Et | H | H | H | Br | 1 |
| CF₂CF₃ | Et | H | H | H | Br | 2 |
| CF₂CF₃ | Et | H | H | H | I | 0 |
| CF₂CF₃ | Et | H | H | H | I | 1 |
| CF₂CF₃ | Et | H | H | H | I | 2 |
| CF₂CF₃ | Et | H | H | H | Me | 0 |
| CF₂CF₃ | Et | H | H | H | Me | 1 |
| CF₂CF₃ | Et | H | H | H | Me | 2 |
| CF₂CF₃ | Et | H | H | H | CF₃ | 0 |
| CF₂CF₃ | Et | H | H | H | CF₃ | 1 |
| CF₂CF₃ | Et | H | H | H | CF₃ | 2 |
| CF₂CF₃ | Et | H | H | H | CF₂CF₃ | 0 |
| CF₂CF₃ | Et | H | H | H | CF₂CF₃ | 1 |
| CF₂CF₃ | Et | H | H | H | CF₂CF₃ | 2 |
| CF₂CF₃ | Et | H | H | H | CF(CF₃)₂ | 0 |
| CF₂CF₃ | Et | H | H | H | CF(CF₃)₂ | 1 |
| CF₂CF₃ | Et | H | H | H | CF(CF₃)₂ | 2 |
| CF₂CF₃ | Et | H | H | H | SMe | 0 |
| CF₂CF₃ | Et | H | H | H | SMe | 1 |
| CF₂CF₃ | Et | H | H | H | SMe | 2 |
| CF₂CF₃ | Et | H | H | H | SOMe | 0 |
| CF₂CF₃ | Et | H | H | H | SOMe | 1 |
| CF₂CF₃ | Et | H | H | H | SOMe | 2 |
| CF₂CF₃ | Et | H | H | H | SO₂Me | 0 |
| CF₂CF₃ | Et | H | H | H | SO₂Me | 1 |
| CF₂CF₃ | Et | H | H | H | SO₂Me | 2 |
| CF₂CF₃ | Et | H | H | H | OMe | 0 |
| CF₂CF₃ | Et | H | H | H | OMe | 1 |
| CF₂CF₃ | Et | H | H | H | OMe | 2 |
| CF₂CF₃ | Et | H | H | H | OCF₃ | 0 |
| CF₂CF₃ | Et | H | H | H | OCF₃ | 1 |
| CF₂CF₃ | Et | H | H | H | OCF₃ | 2 |
| CF₂CF₃ | Et | H | H | H | NO₂ | 0 |
| CF₂CF₃ | Et | H | H | H | NO₂ | 1 |
| CF₂CF₃ | Et | H | H | H | NO₂ | 2 |
| CF₂CF₃ | Et | H | H | H | CN | 0 |
| CF₂CF₃ | Et | H | H | H | CN | 1 |
| CF₂CF₃ | Et | H | H | H | CN | 2 |
| CF₂CF₃ | Et | H | F | H | F | 0 |
| CF₂CF₃ | Et | H | F | H | F | 1 |
| CF₂CF₃ | Et | H | F | H | F | 2 |
| CF₂CF₃ | Et | H | Cl | H | Cl | 0 |
| CF₂CF₃ | Et | H | Cl | H | Cl | 1 |
| CF₂CF₃ | Et | H | Cl | H | Cl | 2 |
| CF₂CF₃ | Et | H | Br | H | Br | 0 |
| CF₂CF₃ | Et | H | Br | H | Br | 1 |
| CF₂CF₃ | Et | H | Br | H | Br | 2 |
| CF₂CF₃ | Et | H | I | H | I | 0 |
| CF₂CF₃ | Et | H | I | H | I | 1 |
| CF₂CF₃ | Et | H | I | H | I | 2 |
| CF₂CF₃ | Et | H | F | H | Cl | 0 |
| CF₂CF₃ | Et | H | F | H | Cl | 1 |
| CF₂CF₃ | Et | H | F | H | Cl | 2 |
| CF₂CF₃ | Et | H | F | H | Br | 0 |
| CF₂CF₃ | Et | H | F | H | Br | 1 |
| CF₂CF₃ | Et | H | F | H | Br | 2 |
| CF₂CF₃ | Et | H | F | H | I | 0 |
| CF₂CF₃ | Et | H | F | H | I | 1 |
| CF₂CF₃ | Et | H | F | H | I | 2 |
| CF₂CF₃ | Et | H | Cl | H | F | 0 |
| CF₂CF₃ | Et | H | Cl | H | F | 1 |
| CF₂CF₃ | Et | H | Cl | H | F | 2 |
| CF₂CF₃ | Et | H | Cl | H | Br | 0 |
| CF₂CF₃ | Et | H | Cl | H | Br | 1 |
| CF₂CF₃ | Et | H | Cl | H | Br | 2 |
| CF₂CF₃ | Et | H | Cl | H | I | 0 |
| CF₂CF₃ | Et | H | Cl | H | I | 1 |
| CF₂CF₃ | Et | H | Cl | H | I | 2 |
| CF₂CF₃ | Et | H | Br | H | F | 0 |
| CF₂CF₃ | Et | H | Br | H | F | 1 |
| CF₂CF₃ | Et | H | Br | H | F | 2 |
| CF₂CF₃ | Et | H | Br | H | Cl | 0 |
| CF₂CF₃ | Et | H | Br | H | Cl | 1 |
| CF₂CF₃ | Et | H | Br | H | Cl | 2 |
| CF₂CF₃ | Et | H | Br | H | I | 0 |
| CF₂CF₃ | Et | H | Br | H | I | 1 |
| CF₂CF₃ | Et | H | Br | H | I | 2 |
| CF₂CF₃ | Et | H | I | H | F | 0 |
| CF₂CF₃ | Et | H | I | H | F | 1 |
| CF₂CF₃ | Et | H | I | H | F | 2 |
| CF₂CF₃ | Et | H | I | H | Cl | 0 |
| CF₂CF₃ | Et | H | I | H | Cl | 1 |
| CF₂CF₃ | Et | H | I | H | Cl | 2 |
| CF₂CF₃ | Et | H | I | H | Br | 0 |
| CF₂CF₃ | Et | H | I | H | Br | 2 |
| CF₂CF₃ | Et | H | F | H | CN | 0 |
| CF₂CF₃ | Et | H | F | H | CN | 1 |
| CF₂CF₃ | Et | H | F | H | CN | 2 |
| CF₂CF₃ | Et | H | Cl | H | CN | 0 |

TABLE 1-continued

| | | | | | | |
|---|---|---|---|---|---|---|
| CF$_2$CF$_3$ | Et | H | Cl | H | CN | 1 |
| CF$_2$CF$_3$ | Et | H | Cl | H | CN | 2 |
| CF$_2$CF$_3$ | Et | H | Br | H | CN | 0 |
| CF$_2$CF$_3$ | Et | H | Br | H | CN | 1 |
| CF$_2$CF$_3$ | Et | H | Br | H | CN | 2 |
| CF$_2$CF$_3$ | Et | H | I | H | CN | 0 |
| CF$_2$CF$_3$ | Et | H | I | H | CN | 1 |
| CF$_2$CF$_3$ | Et | H | I | H | CN | 2 |
| CF$_2$CF$_3$ | Et | H | CF$_3$ | H | F | 0 |
| CF$_2$CF$_3$ | Et | H | CF$_3$ | H | F | 1 |
| CF$_2$CF$_3$ | Et | H | CF$_3$ | H | F | 2 |
| CF$_2$CF$_3$ | Et | H | CF$_3$ | H | Cl | 0 |
| CF$_2$CF$_3$ | Et | H | CF$_3$ | H | Cl | 1 |
| CF$_2$CF$_3$ | Et | H | CF$_3$ | H | Cl | 2 |
| CF$_2$CF$_3$ | Et | H | CF$_3$ | H | Br | 0 |
| CF$_2$CF$_3$ | Et | H | CF$_3$ | H | Br | 1 |
| CF$_2$CF$_3$ | Et | H | CF$_3$ | H | Br | 2 |
| CF$_2$CF$_3$ | Et | H | CF$_3$ | H | I | 0 |
| CF$_2$CF$_3$ | Et | H | CF$_3$ | H | I | 1 |
| CF$_2$CF$_3$ | Et | H | CF$_3$ | H | I | 2 |
| CF$_2$CF$_3$ | Et | H | CF$_3$ | H | CN | 0 |
| CF$_2$CF$_3$ | Et | H | CF$_3$ | H | CN | 1 |
| CF$_2$CF$_3$ | Et | H | CF$_3$ | H | CN | 2 |
| CF$_2$CF$_3$ | Et | H | F | F | H | 0 |
| CF$_2$CF$_3$ | Et | H | F | F | H | 1 |
| CF$_2$CF$_3$ | Et | H | F | F | H | 2 |
| CF$_2$CF$_3$ | Et | H | Cl | Cl | H | 0 |
| CF$_2$CF$_3$ | Et | H | Cl | Cl | H | 1 |
| CF$_2$CF$_3$ | Et | H | Cl | Cl | H | 2 |
| CF$_2$CF$_3$ | Et | H | Br | Br | H | 0 |
| CF$_2$CF$_3$ | Et | H | Br | Br | H | 1 |
| CF$_2$CF$_3$ | Et | H | Br | Br | H | 2 |
| CF$_2$CF$_3$ | Et | H | I | I | H | 0 |
| CF$_2$CF$_3$ | Et | H | I | I | H | 1 |
| CF$_2$CF$_3$ | Et | H | I | I | H | 2 |
| CF$_2$CF$_3$ | Et | H | F | Cl | H | 0 |
| CF$_2$CF$_3$ | Et | H | F | Cl | H | 1 |
| CF$_2$CF$_3$ | Et | H | F | Cl | H | 2 |
| CF$_2$CF$_3$ | Et | H | F | Br | H | 0 |
| CF$_2$CF$_3$ | Et | H | F | Br | H | 1 |
| CF$_2$CF$_3$ | Et | H | F | Br | H | 2 |
| CF$_2$CF$_3$ | Et | H | F | I | H | 0 |
| CF$_2$CF$_3$ | Et | H | F | I | H | 1 |
| CF$_2$CF$_3$ | Et | H | F | I | H | 2 |
| CF$_2$CF$_3$ | Et | H | Cl | F | H | 0 |
| CF$_2$CF$_3$ | Et | H | Cl | F | H | 1 |
| CF$_2$CF$_3$ | Et | H | Cl | F | H | 2 |
| CF$_2$CF$_3$ | Et | H | Cl | Br | H | 0 |
| CF$_2$CF$_3$ | Et | H | Cl | Br | H | 1 |
| CF$_2$CF$_3$ | Et | H | Cl | Br | H | 2 |
| CF$_2$CF$_3$ | Et | H | Cl | I | H | 0 |
| CF$_2$CF$_3$ | Et | H | Cl | I | H | 1 |
| CF$_2$CF$_3$ | Et | H | Cl | I | H | 2 |
| CF$_2$CF$_3$ | Et | H | Br | F | H | 0 |
| CF$_2$CF$_3$ | Et | H | Br | F | H | 1 |
| CF$_2$CF$_3$ | Et | H | Br | F | H | 2 |
| CF$_2$CF$_3$ | Et | H | Br | Cl | H | 0 |
| CF$_2$CF$_3$ | Et | H | Br | Cl | H | 1 |
| CF$_2$CF$_3$ | Et | H | Br | Cl | H | 2 |
| CF$_2$CF$_3$ | Et | H | Br | I | H | 0 |
| CF$_2$CF$_3$ | Et | H | Br | I | H | 1 |
| CF$_2$CF$_3$ | Et | H | Br | I | H | 2 |
| CF$_2$CF$_3$ | Et | H | I | F | H | 0 |
| CF$_2$CF$_3$ | Et | H | I | F | H | 1 |
| CF$_2$CF$_3$ | Et | H | I | F | H | 2 |
| CF$_2$CF$_3$ | Et | H | I | Cl | H | 0 |
| CF$_2$CF$_3$ | Et | H | I | Cl | H | 1 |
| CF$_2$CF$_3$ | Et | H | I | Cl | H | 2 |
| CF$_2$CF$_3$ | Et | H | I | Br | H | 0 |
| CF$_2$CF$_3$ | Et | H | I | Br | H | 1 |
| CF$_2$CF$_3$ | Et | H | I | Br | H | 2 |
| CF$_2$CF$_3$ | Et | H | F | CN | H | 0 |
| CF$_2$CF$_3$ | Et | H | F | CN | H | 1 |
| CF$_2$CF$_3$ | Et | H | F | CN | H | 2 |
| CF$_2$CF$_3$ | Et | H | Cl | CN | H | 0 |
| CF$_2$CF$_3$ | Et | H | Cl | CN | H | 1 |
| CF$_2$CF$_3$ | Et | H | Cl | CN | H | 2 |
| CF$_2$CF$_3$ | Et | H | Br | CN | H | 0 |
| CF$_2$CF$_3$ | Et | H | Br | CN | H | 1 |
| CF$_2$CF$_3$ | Et | H | Br | CN | H | 2 |
| CF$_2$CF$_3$ | Et | H | I | CN | H | 0 |
| CF$_2$CF$_3$ | Et | H | I | CN | H | 1 |
| CF$_2$CF$_3$ | Et | H | I | CN | H | 2 |
| CF$_2$CF$_3$ | Et | H | CF$_3$ | F | H | 0 |
| CF$_2$CF$_3$ | Et | H | CF$_3$ | F | H | 1 |
| CF$_2$CF$_3$ | Et | H | CF$_3$ | F | H | 2 |
| CF$_2$CF$_3$ | Et | H | CF$_3$ | Cl | H | 0 |
| CF$_2$CF$_3$ | Et | H | CF$_3$ | Cl | H | 1 |
| CF$_2$CF$_3$ | Et | H | CF$_3$ | Cl | H | 2 |
| CF$_2$CF$_3$ | Et | H | CF$_3$ | Br | H | 0 |
| CF$_2$CF$_3$ | Et | H | CF$_3$ | Br | H | 1 |
| CF$_2$CF$_3$ | Et | H | CF$_3$ | Br | H | 2 |
| CF$_2$CF$_3$ | Et | H | CF$_3$ | I | H | 0 |
| CF$_2$CF$_3$ | Et | H | CF$_3$ | I | H | 1 |
| CF$_2$CF$_3$ | Et | H | CF$_3$ | I | H | 2 |
| CF$_2$CF$_3$ | Et | H | CF$_3$ | CN | H | 0 |
| CF$_2$CF$_3$ | Et | H | CF$_3$ | CN | H | 1 |
| CF$_2$CF$_3$ | Et | H | CF$_3$ | CN | H | 2 |
| CF$_2$CF$_3$ | "Pr | H | H | H | H | 0 |
| CF$_2$CF$_3$ | "Pr | H | H | H | H | 1 |
| CF$_2$CF$_3$ | "Pr | H | H | H | H | 2 |
| CF$_2$CF$_3$ | "Pr | F | H | H | H | 0 |
| CF$_2$CF$_3$ | "Pr | F | H | H | H | 1 |
| CF$_2$CF$_3$ | "Pr | F | H | H | H | 2 |
| CF$_2$CF$_3$ | "Pr | Cl | H | H | H | 0 |
| CF$_2$CF$_3$ | "Pr | Cl | H | H | H | 1 |
| CF$_2$CF$_3$ | "Pr | Cl | H | H | H | 2 |
| CF$_2$CF$_3$ | "Pr | Br | H | H | H | 0 |
| CF$_2$CF$_3$ | "Pr | Br | H | H | H | 1 |
| CF$_2$CF$_3$ | "Pr | Br | H | H | H | 2 |
| CF$_2$CF$_3$ | "Pr | I | H | H | H | 0 |
| CF$_2$CF$_3$ | "Pr | I | H | H | H | 1 |
| CF$_2$CF$_3$ | "Pr | I | H | H | H | 2 |
| CF$_2$CF$_3$ | "Pr | Me | H | H | H | 0 |
| CF$_2$CF$_3$ | "Pr | Me | H | H | H | 1 |
| CF$_2$CF$_3$ | "Pr | Me | H | H | H | 2 |
| CF$_2$CF$_3$ | "Pr | CF$_3$ | H | H | H | 0 |
| CF$_2$CF$_3$ | "Pr | CF$_3$ | H | H | H | 1 |
| CF$_2$CF$_3$ | "Pr | CF$_3$ | H | H | H | 2 |
| CF$_2$CF$_3$ | "Pr | H | F | H | H | 0 |
| CF$_2$CF$_3$ | "Pr | H | F | H | H | 1 |
| CF$_2$CF$_3$ | "Pr | H | F | H | H | 2 |
| CF$_2$CF$_3$ | "Pr | H | Cl | H | H | 0 |
| CF$_2$CF$_3$ | "Pr | H | Cl | H | H | 1 |
| CF$_2$CF$_3$ | "Pr | H | Cl | H | H | 2 |
| CF$_2$CF$_3$ | "Pr | H | Br | H | H | 0 |
| CF$_2$CF$_3$ | "Pr | H | Br | H | H | 1 |
| CF$_2$CF$_3$ | "Pr | H | Br | H | H | 2 |
| CF$_2$CF$_3$ | "Pr | H | I | H | H | 0 |
| CF$_2$CF$_3$ | "Pr | H | I | H | H | 1 |
| CF$_2$CF$_3$ | "Pr | H | I | H | H | 2 |
| CF$_2$CF$_3$ | "Pr | H | Me | H | H | 0 |
| CF$_2$CF$_3$ | "Pr | H | Me | H | H | 1 |
| CF$_2$CF$_3$ | "Pr | H | Me | H | H | 2 |
| CF$_2$CF$_3$ | "Pr | H | CF$_3$ | H | H | 0 |
| CF$_2$CF$_3$ | "Pr | H | CF$_3$ | H | H | 1 |
| CF$_2$CF$_3$ | "Pr | H | CF$_3$ | H | H | 2 |
| CF$_2$CF$_3$ | "Pr | H | CF$_2$CF$_3$ | H | H | 0 |
| CF$_2$CF$_3$ | "Pr | H | CF$_2$CF$_3$ | H | H | 1 |
| CF$_2$CF$_3$ | "Pr | H | CF$_2$CF$_3$ | H | H | 2 |
| CF$_2$CF$_3$ | "Pr | H | CF(CF$_3$)$_2$ | H | H | 0 |
| CF$_2$CF$_3$ | "Pr | H | CF(CF$_3$)$_2$ | H | H | 1 |
| CF$_2$CF$_3$ | "Pr | H | CF(CF$_3$)$_2$ | H | H | 2 |
| CF$_2$CF$_3$ | "Pr | H | SMe | H | H | 0 |
| CF$_2$CF$_3$ | "Pr | H | SMe | H | H | 1 |
| CF$_2$CF$_3$ | "Pr | H | SMe | H | H | 2 |
| CF$_2$CF$_3$ | "Pr | H | SOMe | H | H | 0 |
| CF$_2$CF$_3$ | "Pr | H | SOMe | H | H | 1 |
| CF$_2$CF$_3$ | "Pr | H | SOMe | H | H | 2 |
| CF$_2$CF$_3$ | "Pr | H | SO$_2$Me | H | H | 0 |
| CF$_2$CF$_3$ | "Pr | H | SO$_2$Me | H | H | 1 |
| CF$_2$CF$_3$ | "Pr | H | SO$_2$Me | H | H | 2 |
| CF$_2$CF$_3$ | "Pr | H | OMe | H | H | 0 |
| CF$_2$CF$_3$ | "Pr | H | OMe | H | H | 1 |
| CF$_2$CF$_3$ | "Pr | H | OMe | H | H | 2 |
| CF$_2$CF$_3$ | "Pr | H | OCF$_3$ | H | H | 0 |
| CF$_2$CF$_3$ | "Pr | H | OCF$_3$ | H | H | 1 |
| CF$_2$CF$_3$ | "Pr | H | OCF$_3$ | H | H | 2 |
| CF$_2$CF$_3$ | "Pr | H | NO$_2$ | H | H | 0 |
| CF$_2$CF$_3$ | "Pr | H | NO$_2$ | H | H | 1 |

TABLE 1-continued

| | | | | | | |
|---|---|---|---|---|---|---|
| CF₂CF₃ | ⁿPr | H | NO₂ | H | H | 2 |
| CF₂CF₃ | ⁿPr | H | CN | H | H | 0 |
| CF₂CF₃ | ⁿPr | H | CN | H | H | 1 |
| CF₂CF₃ | ⁿPr | H | CN | H | H | 2 |
| CF₂CF₃ | ⁿPr | H | H | F | H | 0 |
| CF₂CF₃ | ⁿPr | H | H | F | H | 1 |
| CF₂CF₃ | ⁿPr | H | H | F | H | 2 |
| CF₂CF₃ | ⁿPr | H | H | Cl | H | 0 |
| CF₂CF₃ | ⁿPr | H | H | Cl | H | 1 |
| CF₂CF₃ | ⁿPr | H | H | Cl | H | 2 |
| CF₂CF₃ | ⁿPr | H | H | Br | H | 0 |
| CF₂CF₃ | ⁿPr | H | H | Br | H | 1 |
| CF₂CF₃ | ⁿPr | H | H | Br | H | 2 |
| CF₂CF₃ | ⁿPr | H | H | I | H | 0 |
| CF₂CF₃ | ⁿPr | H | H | I | H | 1 |
| CF₂CF₃ | ⁿPr | H | H | I | H | 2 |
| CF₂CF₃ | ⁿPr | H | H | Me | H | 0 |
| CF₂CF₃ | ⁿPr | H | H | Me | H | 1 |
| CF₂CF₃ | ⁿPr | H | H | Me | H | 2 |
| CF₂CF₃ | ⁿPr | H | H | CF₃ | H | 0 |
| CF₂CF₃ | ⁿPr | H | H | CF₃ | H | 1 |
| CF₂CF₃ | ⁿPr | H | H | CF₃ | H | 2 |
| CF₂CF₃ | ⁿPr | H | H | CF₂CF₃ | H | 0 |
| CF₂CF₃ | ⁿPr | H | H | CF₂CF₃ | H | 1 |
| CF₂CF₃ | ⁿPr | H | H | CF₂CF₃ | H | 2 |
| CF₂CF₃ | ⁿPr | H | H | CF(CF₃)₂ | H | 0 |
| CF₂CF₃ | ⁿPr | H | H | CF(CF₃)₂ | H | 1 |
| CF₂CF₃ | ⁿPr | H | H | CF(CF₃)₂ | H | 2 |
| CF₂CF₃ | ⁿPr | H | H | SMe | H | 0 |
| CF₂CF₃ | ⁿPr | H | H | SMe | H | 1 |
| CF₂CF₃ | ⁿPr | H | H | SMe | H | 2 |
| CF₂CF₃ | ⁿPr | H | H | SOMe | H | 0 |
| CF₂CF₃ | ⁿPr | H | H | SOMe | H | 1 |
| CF₂CF₃ | ⁿPr | H | H | SOMe | H | 2 |
| CF₂CF₃ | ⁿPr | H | H | SO₂Me | H | 0 |
| CF₂CF₃ | ⁿPr | H | H | SO₂Me | H | 1 |
| CF₂CF₃ | ⁿPr | H | H | SO₂Me | H | 2 |
| CF₂CF₃ | ⁿPr | H | H | OMe | H | 0 |
| CF₂CF₃ | ⁿPr | H | H | OMe | H | 1 |
| CF₂CF₃ | ⁿPr | H | H | OMe | H | 2 |
| CF₂CF₃ | ⁿPr | H | H | OCF₃ | H | 0 |
| CF₂CF₃ | ⁿPr | H | H | OCF₃ | H | 1 |
| CF₂CF₃ | ⁿPr | H | H | OCF₃ | H | 2 |
| CF₂CF₃ | ⁿPr | H | H | NO₂ | H | 0 |
| CF₂CF₃ | ⁿPr | H | H | NO₂ | H | 1 |
| CF₂CF₃ | ⁿPr | H | H | NO₂ | H | 2 |
| CF₂CF₃ | ⁿPr | H | H | CN | H | 0 |
| CF₂CF₃ | ⁿPr | H | H | CN | H | 1 |
| CF₂CF₃ | ⁿPr | H | H | CN | H | 2 |
| CF₂CF₃ | ⁿPr | H | H | H | F | 0 |
| CF₂CF₃ | ⁿPr | H | H | H | F | 1 |
| CF₂CF₃ | ⁿPr | H | H | H | F | 2 |
| CF₂CF₃ | ⁿPr | H | H | H | Cl | 0 |
| CF₂CF₃ | ⁿPr | H | H | H | Cl | 1 |
| CF₂CF₃ | ⁿPr | H | H | H | Cl | 2 |
| CF₂CF₃ | ⁿPr | H | H | H | Br | 0 |
| CF₂CF₃ | ⁿPr | H | H | H | Br | 1 |
| CF₂CF₃ | ⁿPr | H | H | H | Br | 2 |
| CF₂CF₃ | ⁿPr | H | H | H | I | 0 |
| CF₂CF₃ | ⁿPr | H | H | H | I | 1 |
| CF₂CF₃ | ⁿPr | H | H | H | I | 2 |
| CF₂CF₃ | ⁿPr | H | H | H | Me | 0 |
| CF₂CF₃ | ⁿPr | H | H | H | Me | 1 |
| CF₂CF₃ | ⁿPr | H | H | H | Me | 2 |
| CF₂CF₃ | ⁿPr | H | H | H | CF₃ | 0 |
| CF₂CF₃ | ⁿPr | H | H | H | CF₃ | 1 |
| CF₂CF₃ | ⁿPr | H | H | H | CF₃ | 2 |
| CF₂CF₃ | ⁿPr | H | H | H | CF₂CF₃ | 0 |
| CF₂CF₃ | ⁿPr | H | H | H | CF₂CF₃ | 1 |
| CF₂CF₃ | ⁿPr | H | H | H | CF₂CF₃ | 2 |
| CF₂CF₃ | ⁿPr | H | H | H | CF(CF₃)₂ | 0 |
| CF₂CF₃ | ⁿPr | H | H | H | CF(CF₃)₂ | 1 |
| CF₂CF₃ | ⁿPr | H | H | H | CF(CF₃)₂ | 2 |
| CF₂CF₃ | ⁿPr | H | H | H | SMe | 0 |
| CF₂CF₃ | ⁿPr | H | H | H | SMe | 1 |
| CF₂CF₃ | ⁿPr | H | H | H | SMe | 2 |
| CF₂CF₃ | ⁿPr | H | H | H | SOMe | 0 |
| CF₂CF₃ | ⁿPr | H | H | H | SOMe | 1 |
| CF₂CF₃ | ⁿPr | H | H | H | SOMe | 2 |
| CF₂CF₃ | ⁿPr | H | H | H | SO₂Me | 0 |
| CF₂CF₃ | ⁿPr | H | H | H | SO₂Me | 1 |
| CF₂CF₃ | ⁿPr | H | H | H | SO₂Me | 2 |
| CF₂CF₃ | ⁿPr | H | H | H | OMe | 0 |
| CF₂CF₃ | ⁿPr | H | H | H | OMe | 1 |
| CF₂CF₃ | ⁿPr | H | H | H | OMe | 2 |
| CF₂CF₃ | ⁿPr | H | H | H | OCF₃ | 0 |
| CF₂CF₃ | ⁿPr | H | H | H | OCF₃ | 1 |
| CF₂CF₃ | ⁿPr | H | H | H | OCF₃ | 2 |
| CF₂CF₃ | ⁿPr | H | H | H | NO₂ | 0 |
| CF₂CF₃ | ⁿPr | H | H | H | NO₂ | 1 |
| CF₂CF₃ | ⁿPr | H | H | H | NO₂ | 2 |
| CF₂CF₃ | ⁿPr | H | H | H | CN | 0 |
| CF₂CF₃ | ⁿPr | H | H | H | CN | 1 |
| CF₂CF₃ | ⁿPr | H | H | H | CN | 2 |
| CF₂CF₃ | ⁿPr | H | F | H | F | 0 |
| CF₂CF₃ | ⁿPr | H | F | H | F | 1 |
| CF₂CF₃ | ⁿPr | H | F | H | F | 2 |
| CF₂CF₃ | ⁿPr | H | Cl | H | Cl | 0 |
| CF₂CF₃ | ⁿPr | H | Cl | H | Cl | 1 |
| CF₂CF₃ | ⁿPr | H | Cl | H | Cl | 2 |
| CF₂CF₃ | ⁿPr | H | Br | H | Br | 0 |
| CF₂CF₃ | ⁿPr | H | Br | H | Br | 1 |
| CF₂CF₃ | ⁿPr | H | Br | H | Br | 2 |
| CF₂CF₃ | ⁿPr | H | I | H | I | 0 |
| CF₂CF₃ | ⁿPr | H | I | H | I | 1 |
| CF₂CF₃ | ⁿPr | H | I | H | I | 2 |
| CF₂CF₃ | ⁿPr | H | F | H | Cl | 0 |
| CF₂CF₃ | ⁿPr | H | F | H | Cl | 1 |
| CF₂CF₃ | ⁿPr | H | F | H | Cl | 2 |
| CF₂CF₃ | ⁿPr | H | F | H | Br | 0 |
| CF₂CF₃ | ⁿPr | H | F | H | Br | 1 |
| CF₂CF₃ | ⁿPr | H | F | H | Br | 2 |
| CF₂CF₃ | ⁿPr | H | F | H | I | 0 |
| CF₂CF₃ | ⁿPr | H | F | H | I | 1 |
| CF₂CF₃ | ⁿPr | H | F | H | I | 2 |
| CF₂CF₃ | ⁿPr | H | Cl | H | F | 0 |
| CF₂CF₃ | ⁿPr | H | Cl | H | F | 1 |
| CF₂CF₃ | ⁿPr | H | Cl | H | F | 2 |
| CF₂CF₃ | ⁿPr | H | Cl | H | Br | 0 |
| CF₂CF₃ | ⁿPr | H | Cl | H | Br | 1 |
| CF₂CF₃ | ⁿPr | H | Cl | H | Br | 2 |
| CF₂CF₃ | ⁿPr | H | Cl | H | I | 0 |
| CF₂CF₃ | ⁿPr | H | Cl | H | I | 1 |
| CF₂CF₃ | ⁿPr | H | Cl | H | I | 2 |
| CF₂CF₃ | ⁿPr | H | Br | H | F | 0 |
| CF₂CF₃ | ⁿPr | H | Br | H | F | 1 |
| CF₂CF₃ | ⁿPr | H | Br | H | F | 2 |
| CF₂CF₃ | ⁿPr | H | Br | H | Cl | 0 |
| CF₂CF₃ | ⁿPr | H | Br | H | Cl | 1 |
| CF₂CF₃ | ⁿPr | H | Br | H | Cl | 2 |
| CF₂CF₃ | ⁿPr | H | Br | H | I | 0 |
| CF₂CF₃ | ⁿPr | H | Br | H | I | 1 |
| CF₂CF₃ | ⁿPr | H | Br | H | I | 2 |
| CF₂CF₃ | ⁿPr | H | I | H | F | 0 |
| CF₂CF₃ | ⁿPr | H | I | H | F | 1 |
| CF₂CF₃ | ⁿPr | H | I | H | F | 2 |
| CF₂CF₃ | ⁿPr | H | I | H | Cl | 0 |
| CF₂CF₃ | ⁿPr | H | I | H | Cl | 1 |
| CF₂CF₃ | ⁿPr | H | I | H | Cl | 2 |
| CF₂CF₃ | ⁿPr | H | I | H | Br | 0 |
| CF₂CF₃ | ⁿPr | H | I | H | Br | 1 |
| CF₂CF₃ | ⁿPr | H | I | H | Br | 2 |
| CF₂CF₃ | ⁿPr | H | F | H | CN | 0 |
| CF₂CF₃ | ⁿPr | H | F | H | CN | 1 |
| CF₂CF₃ | ⁿPr | H | F | H | CN | 2 |
| CF₂CF₃ | ⁿPr | H | Cl | H | CN | 0 |
| CF₂CF₃ | ⁿPr | H | Cl | H | CN | 1 |
| CF₂CF₃ | ⁿPr | H | Cl | H | CN | 2 |
| CF₂CF₃ | ⁿPr | H | Br | H | CN | 0 |
| CF₂CF₃ | ⁿPr | H | Br | H | CN | 1 |
| CF₂CF₃ | ⁿPr | H | Br | H | CN | 2 |
| CF₂CF₃ | ⁿPr | H | I | H | CN | 0 |
| CF₂CF₃ | ⁿPr | H | I | H | CN | 1 |
| CF₂CF₃ | ⁿPr | H | I | H | CN | 2 |
| CF₂CF₃ | ⁿPr | H | CF₃ | H | F | 0 |
| CF₂CF₃ | ⁿPr | H | CF₃ | H | F | 1 |
| CF₂CF₃ | ⁿPr | H | CF₃ | H | F | 2 |
| CF₂CF₃ | ⁿPr | H | CF₃ | H | Cl | 0 |
| CF₂CF₃ | ⁿPr | H | CF₃ | H | Cl | 1 |
| CF₂CF₃ | ⁿPr | H | CF₃ | H | Cl | 2 |

TABLE 1-continued

| | | | | | | |
|---|---|---|---|---|---|---|
| CF₂CF₃ | ⁿPr | H | CF₃ | H | Br | 0 |
| CF₂CF₃ | ⁿPr | H | CF₃ | H | Br | 1 |
| CF₂CF₃ | ⁿPr | H | CF₃ | H | Br | 2 |
| CF₂CF₃ | ⁿPr | H | CF₃ | H | I | 0 |
| CF₂CF₃ | ⁿPr | H | CF₃ | H | I | 1 |
| CF₂CF₃ | ⁿPr | H | CF₃ | H | I | 2 |
| CF₂CF₃ | ⁿPr | H | CF₃ | H | CN | 0 |
| CF₂CF₃ | ⁿPr | H | CF₃ | H | CN | 1 |
| CF₂CF₃ | ⁿPr | H | CF₃ | H | CN | 2 |
| CF₂CF₃ | ⁿPr | H | F | F | H | 0 |
| CF₂CF₃ | ⁿPr | H | F | F | H | 1 |
| CF₂CF₃ | ⁿPr | H | F | F | H | 2 |
| CF₂CF₃ | ⁿPr | H | Cl | Cl | H | 0 |
| CF₂CF₃ | ⁿPr | H | Cl | Cl | H | 1 |
| CF₂CF₃ | ⁿPr | H | Cl | Cl | H | 2 |
| CF₂CF₃ | ⁿPr | H | Br | Br | H | 0 |
| CF₂CF₃ | ⁿPr | H | Br | Br | H | 1 |
| CF₂CF₃ | ⁿPr | H | Br | Br | H | 2 |
| CF₂CF₃ | ⁿPr | H | I | I | H | 0 |
| CF₂CF₃ | ⁿPr | H | I | I | H | 1 |
| CF₂CF₃ | ⁿPr | H | I | I | H | 2 |
| CF₂CF₃ | ⁿPr | H | F | Cl | H | 0 |
| CF₂CF₃ | ⁿPr | H | F | Cl | H | 1 |
| CF₂CF₃ | ⁿPr | H | F | Cl | H | 2 |
| CF₂CF₃ | ⁿPr | H | F | Br | H | 0 |
| CF₂CF₃ | ⁿPr | H | F | Br | H | 1 |
| CF₂CF₃ | ⁿPr | H | F | Br | H | 2 |
| CF₂CF₃ | ⁿPr | H | F | I | H | 0 |
| CF₂CF₃ | ⁿPr | H | F | I | H | 1 |
| CF₂CF₃ | ⁿPr | H | F | I | H | 2 |
| CF₂CF₃ | ⁿPr | H | Cl | F | H | 0 |
| CF₂CF₃ | ⁿPr | H | Cl | F | H | 1 |
| CF₂CF₃ | ⁿPr | H | Cl | F | H | 2 |
| CF₂CF₃ | ⁿPr | H | Cl | Br | H | 0 |
| CF₂CF₃ | ⁿPr | H | Cl | Br | H | 1 |
| CF₂CF₃ | ⁿPr | H | Cl | Br | H | 2 |
| CF₂CF₃ | ⁿPr | H | Cl | I | H | 0 |
| CF₂CF₃ | ⁿPr | H | Cl | I | H | 1 |
| CF₂CF₃ | ⁿPr | H | Cl | I | H | 2 |
| CF₂CF₃ | ⁿPr | H | Br | F | H | 0 |
| CF₂CF₃ | ⁿPr | H | Br | F | H | 1 |
| CF₂CF₃ | ⁿPr | H | Br | F | H | 2 |
| CF₂CF₃ | ⁿPr | H | Br | Cl | H | 0 |
| CF₂CF₃ | ⁿPr | H | Br | Cl | H | 1 |
| CF₂CF₃ | ⁿPr | H | Br | Cl | H | 2 |
| CF₂CF₃ | ⁿPr | H | Br | I | H | 0 |
| CF₂CF₃ | ⁿPr | H | Br | I | H | 1 |
| CF₂CF₃ | ⁿPr | H | Br | I | H | 2 |
| CF₂CF₃ | ⁿPr | H | I | F | H | 0 |
| CF₂CF₃ | ⁿPr | H | I | F | H | 1 |
| CF₂CF₃ | ⁿPr | H | I | F | H | 2 |
| CF₂CF₃ | ⁿPr | H | I | Cl | H | 0 |
| CF₂CF₃ | ⁿPr | H | I | Cl | H | 1 |
| CF₂CF₃ | ⁿPr | H | I | Cl | H | 2 |
| CF₂CF₃ | ⁿPr | H | I | Br | H | 0 |
| CF₂CF₃ | ⁿPr | H | I | Br | H | 1 |
| CF₂CF₃ | ⁿPr | H | I | Br | H | 2 |
| CF₂CF₃ | ⁿPr | H | F | CN | H | 0 |
| CF₂CF₃ | ⁿPr | H | F | CN | H | 1 |
| CF₂CF₃ | ⁿPr | H | F | CN | H | 2 |
| CF₂CF₃ | ⁿPr | H | Cl | CN | H | 0 |
| CF₂CF₃ | ⁿPr | H | Cl | CN | H | 1 |
| CF₂CF₃ | ⁿPr | H | Cl | CN | H | 2 |
| CF₂CF₃ | ⁿPr | H | Br | CN | H | 0 |
| CF₂CF₃ | ⁿPr | H | Br | CN | H | 1 |
| CF₂CF₃ | ⁿPr | H | Br | CN | H | 2 |
| CF₂CF₃ | ⁿPr | H | I | CN | H | 0 |
| CF₂CF₃ | ⁿPr | H | I | CN | H | 1 |
| CF₂CF₃ | ⁿPr | H | I | CN | H | 2 |
| CF₂CF₃ | ⁿPr | H | CF₃ | F | H | 0 |
| CF₂CF₃ | ⁿPr | H | CF₃ | F | H | 1 |
| CF₂CF₃ | ⁿPr | H | CF₃ | F | H | 2 |
| CF₂CF₃ | ⁿPr | H | CF₃ | Cl | H | 0 |
| CF₂CF₃ | ⁿPr | H | CF₃ | Cl | H | 1 |
| CF₂CF₃ | ⁿPr | H | CF₃ | Cl | H | 2 |
| CF₂CF₃ | ⁿPr | H | CF₃ | Br | H | 0 |
| CF₂CF₃ | ⁿPr | H | CF₃ | Br | H | 1 |
| CF₂CF₃ | ⁿPr | H | CF₃ | Br | H | 2 |
| CF₂CF₃ | ⁿPr | H | CF₃ | I | H | 0 |
| CF₂CF₃ | ⁿPr | H | CF₃ | I | H | 1 |
| CF₂CF₃ | ⁿPr | H | CF₃ | I | H | 2 |
| CF₂CF₃ | ⁿPr | H | CF₃ | CN | H | 0 |
| CF₂CF₃ | ⁿPr | H | CF₃ | CN | H | 1 |
| CF₂CF₃ | ⁿPr | H | CF₃ | CN | H | 2 |
| CF₂CF₃ | ⁱPr | H | H | H | H | 0 |
| CF₂CF₃ | ⁱPr | H | H | H | H | 1 |
| CF₂CF₃ | ⁱPr | H | H | H | H | 2 |
| CF₂CF₃ | ⁱPr | F | H | H | H | 0 |
| CF₂CF₃ | ⁱPr | F | H | H | H | 1 |
| CF₂CF₃ | ⁱPr | F | H | H | H | 2 |
| CF₂CF₃ | ⁱPr | Cl | H | H | H | 0 |
| CF₂CF₃ | ⁱPr | Cl | H | H | H | 1 |
| CF₂CF₃ | ⁱPr | Cl | H | H | H | 2 |
| CF₂CF₃ | ⁱPr | Br | H | H | H | 0 |
| CF₂CF₃ | ⁱPr | Br | H | H | H | 1 |
| CF₂CF₃ | ⁱPr | Br | H | H | H | 2 |
| CF₂CF₃ | ⁱPr | I | H | H | H | 0 |
| CF₂CF₃ | ⁱPr | I | H | H | H | 1 |
| CF₂CF₃ | ⁱPr | I | H | H | H | 2 |
| CF₂CF₃ | ⁱPr | Me | H | H | H | 0 |
| CF₂CF₃ | ⁱPr | Me | H | H | H | 1 |
| CF₂CF₃ | ⁱPr | Me | H | H | H | 2 |
| CF₂CF₃ | ⁱPr | CF₃ | H | H | H | 0 |
| CF₂CF₃ | ⁱPr | CF₃ | H | H | H | 1 |
| CF₂CF₃ | ⁱPr | CF₃ | H | H | H | 2 |
| CF₂CF₃ | ⁱPr | H | F | H | H | 0 |
| CF₂CF₃ | ⁱPr | H | F | H | H | 1 |
| CF₂CF₃ | ⁱPr | H | F | H | H | 2 |
| CF₂CF₃ | ⁱPr | H | Cl | H | H | 0 |
| CF₂CF₃ | ⁱPr | H | Cl | H | H | 1 |
| CF₂CF₃ | ⁱPr | H | Cl | H | H | 2 |
| CF₂CF₃ | ⁱPr | H | Br | H | H | 0 |
| CF₂CF₃ | ⁱPr | H | Br | H | H | 1 |
| CF₂CF₃ | ⁱPr | H | Br | H | H | 2 |
| CF₂CF₃ | ⁱPr | H | I | H | H | 0 |
| CF₂CF₃ | ⁱPr | H | I | H | H | 1 |
| CF₂CF₃ | ⁱPr | H | I | H | H | 2 |
| CF₂CF₃ | ⁱPr | H | Me | H | H | 0 |
| CF₂CF₃ | ⁱPr | H | Me | H | H | 1 |
| CF₂CF₃ | ⁱPr | H | Me | H | H | 2 |
| CF₂CF₃ | ⁱPr | H | CF₃ | H | H | 0 |
| CF₂CF₃ | ⁱPr | H | CF₃ | H | H | 1 |
| CF₂CF₃ | ⁱPr | H | CF₃ | H | H | 2 |
| CF₂CF₃ | ⁱPr | H | CF₂CF₃ | H | H | 0 |
| CF₂CF₃ | ⁱPr | H | CF₂CF₃ | H | H | 1 |
| CF₂CF₃ | ⁱPr | H | CF₂CF₃ | H | H | 2 |
| CF₂CF₃ | ⁱPr | H | CF(CF₃)₂ | H | H | 0 |
| CF₂CF₃ | ⁱPr | H | CF(CF₃)₂ | H | H | 1 |
| CF₂CF₃ | ⁱPr | H | CF(CF₃)₂ | H | H | 2 |
| CF₂CF₃ | ⁱPr | H | SMe | H | H | 0 |
| CF₂CF₃ | ⁱPr | H | SMe | H | H | 1 |
| CF₂CF₃ | ⁱPr | H | SMe | H | H | 2 |
| CF₂CF₃ | ⁱPr | H | SOMe | H | H | 0 |
| CF₂CF₃ | ⁱPr | H | SOMe | H | H | 1 |
| CF₂CF₃ | ⁱPr | H | SOMe | H | H | 2 |
| CF₂CF₃ | ⁱPr | H | SO₂Me | H | H | 0 |
| CF₂CF₃ | ⁱPr | H | SO₂Me | H | H | 1 |
| CF₂CF₃ | ⁱPr | H | SO₂Me | H | H | 2 |
| CF₂CF₃ | ⁱPr | H | OMe | H | H | 0 |
| CF₂CF₃ | ⁱPr | H | OMe | H | H | 1 |
| CF₂CF₃ | ⁱPr | H | OMe | H | H | 2 |
| CF₂CF₃ | ⁱPr | H | OCF₃ | H | H | 0 |
| CF₂CF₃ | ⁱPr | H | OCF₃ | H | H | 1 |
| CF₂CF₃ | ⁱPr | H | OCF₃ | H | H | 2 |
| CF₂CF₃ | ⁱPr | H | NO₂ | H | H | 0 |
| CF₂CF₃ | ⁱPr | H | NO₂ | H | H | 1 |
| CF₂CF₃ | ⁱPr | H | NO₂ | H | H | 2 |
| CF₂CF₃ | ⁱPr | H | CN | H | H | 0 |
| CF₂CF₃ | ⁱPr | H | CN | H | H | 1 |
| CF₂CF₃ | ⁱPr | H | CN | H | H | 2 |
| CF₂CF₃ | ⁱPr | H | H | F | H | 0 |
| CF₂CF₃ | ⁱPr | H | H | F | H | 1 |
| CF₂CF₃ | ⁱPr | H | H | F | H | 2 |
| CF₂CF₃ | ⁱPr | H | H | Cl | H | 0 |
| CF₂CF₃ | ⁱPr | H | H | Cl | H | 1 |
| CF₂CF₃ | ⁱPr | H | H | Cl | H | 2 |
| CF₂CF₃ | ⁱPr | H | H | Br | H | 0 |
| CF₂CF₃ | ⁱPr | H | H | Br | H | 1 |
| CF₂CF₃ | ⁱPr | H | H | Br | H | 2 |
| CF₂CF₃ | ⁱPr | H | H | I | H | 0 |

TABLE 1-continued

| | | | | | | |
|---|---|---|---|---|---|---|
| CF$_2$CF$_3$ | $^i$Pr | H | H | I | H | 1 |
| CF$_2$CF$_3$ | $^i$Pr | H | H | I | H | 2 |
| CF$_2$CF$_3$ | $^i$Pr | H | H | Me | H | 0 |
| CF$_2$CF$_3$ | $^i$Pr | H | H | Me | H | 1 |
| CF$_2$CF$_3$ | $^i$Pr | H | H | Me | H | 2 |
| CF$_2$CF$_3$ | $^i$Pr | H | H | CF$_3$ | H | 0 |
| CF$_2$CF$_3$ | $^i$Pr | H | H | CF$_3$ | H | 1 |
| CF$_2$CF$_3$ | $^i$Pr | H | H | CF$_3$ | H | 2 |
| CF$_2$CF$_3$ | $^i$Pr | H | H | CF$_2$CF$_3$ | H | 0 |
| CF$_2$CF$_3$ | $^i$Pr | H | H | CF$_2$CF$_3$ | H | 1 |
| CF$_2$CF$_3$ | $^i$Pr | H | H | CF$_2$CF$_3$ | H | 2 |
| CF$_2$CF$_3$ | $^i$Pr | H | H | CF(CF$_3$)$_2$ | H | 0 |
| CF$_2$CF$_3$ | $^i$Pr | H | H | CF(CF$_3$)$_2$ | H | 1 |
| CF$_2$CF$_3$ | $^i$Pr | H | H | CF(CF$_3$)$_2$ | H | 2 |
| CF$_2$CF$_3$ | $^i$Pr | H | H | SMe | H | 0 |
| CF$_2$CF$_3$ | $^i$Pr | H | H | SMe | H | 1 |
| CF$_2$CF$_3$ | $^i$Pr | H | H | SMe | H | 2 |
| CF$_2$CF$_3$ | $^i$Pr | H | H | SOMe | H | 0 |
| CF$_2$CF$_3$ | $^i$Pr | H | H | SOMe | H | 1 |
| CF$_2$CF$_3$ | $^i$Pr | H | H | SOMe | H | 2 |
| CF$_2$CF$_3$ | $^i$Pr | H | H | SO$_2$Me | H | 0 |
| CF$_2$CF$_3$ | $^i$Pr | H | H | SO$_2$Me | H | 1 |
| CF$_2$CF$_3$ | $^i$Pr | H | H | SO$_2$Me | H | 2 |
| CF$_2$CF$_3$ | $^i$Pr | H | H | OMe | H | 0 |
| CF$_2$CF$_3$ | $^i$Pr | H | H | OMe | H | 1 |
| CF$_2$CF$_3$ | $^i$Pr | H | H | OMe | H | 2 |
| CF$_2$CF$_3$ | $^i$Pr | H | H | OCF$_3$ | H | 0 |
| CF$_2$CF$_3$ | $^i$Pr | H | H | OCF$_3$ | H | 1 |
| CF$_2$CF$_3$ | $^i$Pr | H | H | OCF$_3$ | H | 2 |
| CF$_2$CF$_3$ | $^i$Pr | H | H | NO$_2$ | H | 0 |
| CF$_2$CF$_3$ | $^i$Pr | H | H | NO$_2$ | H | 1 |
| CF$_2$CF$_3$ | $^i$Pr | H | H | NO$_2$ | H | 2 |
| CF$_2$CF$_3$ | $^i$Pr | H | H | CN | H | 0 |
| CF$_2$CF$_3$ | $^i$Pr | H | H | CN | H | 1 |
| CF$_2$CF$_3$ | $^i$Pr | H | H | CN | H | 2 |
| CF$_2$CF$_3$ | $^i$Pr | H | H | H | F | 0 |
| CF$_2$CF$_3$ | $^i$Pr | H | H | H | F | 1 |
| CF$_2$CF$_3$ | $^i$Pr | H | H | H | F | 2 |
| CF$_2$CF$_3$ | $^i$Pr | H | H | H | Cl | 0 |
| CF$_2$CF$_3$ | $^i$Pr | H | H | H | Cl | 1 |
| CF$_2$CF$_3$ | $^i$Pr | H | H | H | Cl | 2 |
| CF$_2$CF$_3$ | $^i$Pr | H | H | H | Br | 0 |
| CF$_2$CF$_3$ | $^i$Pr | H | H | H | Br | 1 |
| CF$_2$CF$_3$ | $^i$Pr | H | H | H | Br | 2 |
| CF$_2$CF$_3$ | $^i$Pr | H | H | H | I | 0 |
| CF$_2$CF$_3$ | $^i$Pr | H | H | H | I | 1 |
| CF$_2$CF$_3$ | $^i$Pr | H | H | H | I | 2 |
| CF$_2$CF$_3$ | $^i$Pr | H | H | H | Me | 0 |
| CF$_2$CF$_3$ | $^i$Pr | H | H | H | Me | 1 |
| CF$_2$CF$_3$ | $^i$Pr | H | H | H | Me | 2 |
| CF$_2$CF$_3$ | $^i$Pr | H | H | H | CF$_3$ | 0 |
| CF$_2$CF$_3$ | $^i$Pr | H | H | H | CF$_3$ | 1 |
| CF$_2$CF$_3$ | $^i$Pr | H | H | H | CF$_3$ | 2 |
| CF$_2$CF$_3$ | $^i$Pr | H | H | H | CF$_2$CF$_3$ | 0 |
| CF$_2$CF$_3$ | $^i$Pr | H | H | H | CF$_2$CF$_3$ | 1 |
| CF$_2$CF$_3$ | $^i$Pr | H | H | H | CF$_2$CF$_3$ | 2 |
| CF$_2$CF$_3$ | $^i$Pr | H | H | H | CF(CF$_3$)$_2$ | 0 |
| CF$_2$CF$_3$ | $^i$Pr | H | H | H | CF(CF$_3$)$_2$ | 1 |
| CF$_2$CF$_3$ | $^i$Pr | H | H | H | CF(CF$_3$)$_2$ | 2 |
| CF$_2$CF$_3$ | $^i$Pr | H | H | H | SMe | 0 |
| CF$_2$CF$_3$ | $^i$Pr | H | H | H | SMe | 1 |
| CF$_2$CF$_3$ | $^i$Pr | H | H | H | SMe | 2 |
| CF$_2$CF$_3$ | $^i$Pr | H | H | H | SOMe | 0 |
| CF$_2$CF$_3$ | $^i$Pr | H | H | H | SOMe | 1 |
| CF$_2$CF$_3$ | $^i$Pr | H | H | H | SOMe | 2 |
| CF$_2$CF$_3$ | $^i$Pr | H | H | H | SO$_2$Me | 0 |
| CF$_2$CF$_3$ | $^i$Pr | H | H | H | SO$_2$Me | 1 |
| CF$_2$CF$_3$ | $^i$Pr | H | H | H | SO$_2$Me | 2 |
| CF$_2$CF$_3$ | $^i$Pr | H | H | H | OMe | 0 |
| CF$_2$CF$_3$ | $^i$Pr | H | H | H | OMe | 1 |
| CF$_2$CF$_3$ | $^i$Pr | H | H | H | OMe | 2 |
| CF$_2$CF$_3$ | $^i$Pr | H | H | H | OCF$_3$ | 0 |
| CF$_2$CF$_3$ | $^i$Pr | H | H | H | OCF$_3$ | 1 |
| CF$_2$CF$_3$ | $^i$Pr | H | H | H | OCF$_3$ | 2 |
| CF$_2$CF$_3$ | $^i$Pr | H | H | H | NO$_2$ | 0 |
| CF$_2$CF$_3$ | $^i$Pr | H | H | H | NO$_2$ | 1 |
| CF$_2$CF$_3$ | $^i$Pr | H | H | H | NO$_2$ | 2 |
| CF$_2$CF$_3$ | $^i$Pr | H | H | H | CN | 0 |
| CF$_2$CF$_3$ | $^i$Pr | H | H | H | CN | 1 |
| CF$_2$CF$_3$ | $^i$Pr | H | H | H | CN | 2 |
| CF$_2$CF$_3$ | $^i$Pr | H | F | H | F | 0 |
| CF$_2$CF$_3$ | $^i$Pr | H | F | H | F | 1 |
| CF$_2$CF$_3$ | $^i$Pr | H | F | H | F | 2 |
| CF$_2$CF$_3$ | $^i$Pr | H | Cl | H | Cl | 0 |
| CF$_2$CF$_3$ | $^i$Pr | H | Cl | H | Cl | 1 |
| CF$_2$CF$_3$ | $^i$Pr | H | Cl | H | Cl | 2 |
| CF$_2$CF$_3$ | $^i$Pr | H | Br | H | Br | 0 |
| CF$_2$CF$_3$ | $^i$Pr | H | Br | H | Br | 1 |
| CF$_2$CF$_3$ | $^i$Pr | H | Br | H | Br | 2 |
| CF$_2$CF$_3$ | $^i$Pr | H | I | H | I | 0 |
| CF$_2$CF$_3$ | $^i$Pr | H | I | H | I | 1 |
| CF$_2$CF$_3$ | $^i$Pr | H | I | H | I | 2 |
| CF$_2$CF$_3$ | $^i$Pr | H | F | H | Cl | 0 |
| CF$_2$CF$_3$ | $^i$Pr | H | F | H | Cl | 1 |
| CF$_2$CF$_3$ | $^i$Pr | H | F | H | Cl | 2 |
| CF$_2$CF$_3$ | $^i$Pr | H | F | H | Br | 0 |
| CF$_2$CF$_3$ | $^i$Pr | H | F | H | Br | 1 |
| CF$_2$CF$_3$ | $^i$Pr | H | F | H | Br | 2 |
| CF$_2$CF$_3$ | $^i$Pr | H | F | H | I | 0 |
| CF$_2$CF$_3$ | $^i$Pr | H | F | H | I | 1 |
| CF$_2$CF$_3$ | $^i$Pr | H | F | H | I | 2 |
| CF$_2$CF$_3$ | $^i$Pr | H | Cl | H | F | 0 |
| CF$_2$CF$_3$ | $^i$Pr | H | Cl | H | F | 1 |
| CF$_2$CF$_3$ | $^i$Pr | H | Cl | H | F | 2 |
| CF$_2$CF$_3$ | $^i$Pr | H | Cl | H | Br | 0 |
| CF$_2$CF$_3$ | $^i$Pr | H | Cl | H | Br | 1 |
| CF$_2$CF$_3$ | $^i$Pr | H | Cl | H | Br | 2 |
| CF$_2$CF$_3$ | $^i$Pr | H | Cl | H | I | 0 |
| CF$_2$CF$_3$ | $^i$Pr | H | Cl | H | I | 1 |
| CF$_2$CF$_3$ | $^i$Pr | H | Cl | H | I | 2 |
| CF$_2$CF$_3$ | $^i$Pr | H | Br | H | F | 0 |
| CF$_2$CF$_3$ | $^i$Pr | H | Br | H | F | 1 |
| CF$_2$CF$_3$ | $^i$Pr | H | Br | H | F | 2 |
| CF$_2$CF$_3$ | $^i$Pr | H | Br | H | Cl | 0 |
| CF$_2$CF$_3$ | $^i$Pr | H | Br | H | Cl | 1 |
| CF$_2$CF$_3$ | $^i$Pr | H | Br | H | Cl | 2 |
| CF$_2$CF$_3$ | $^i$Pr | H | Br | H | I | 0 |
| CF$_2$CF$_3$ | $^i$Pr | H | Br | H | I | 1 |
| CF$_2$CF$_3$ | $^i$Pr | H | Br | H | I | 2 |
| CF$_2$CF$_3$ | $^i$Pr | H | I | H | F | 0 |
| CF$_2$CF$_3$ | $^i$Pr | H | I | H | F | 1 |
| CF$_2$CF$_3$ | $^i$Pr | H | I | H | F | 2 |
| CF$_2$CF$_3$ | $^i$Pr | H | I | H | Cl | 0 |
| CF$_2$CF$_3$ | $^i$Pr | H | I | H | Cl | 1 |
| CF$_2$CF$_3$ | $^i$Pr | H | I | H | Cl | 2 |
| CF$_2$CF$_3$ | $^i$Pr | H | I | H | Br | 0 |
| CF$_2$CF$_3$ | $^i$Pr | H | I | H | Br | 1 |
| CF$_2$CF$_3$ | $^i$Pr | H | I | H | Br | 2 |
| CF$_2$CF$_3$ | $^i$Pr | H | F | H | CN | 0 |
| CF$_2$CF$_3$ | $^i$Pr | H | F | H | CN | 1 |
| CF$_2$CF$_3$ | $^i$Pr | H | F | H | CN | 2 |
| CF$_2$CF$_3$ | $^i$Pr | H | Cl | H | CN | 0 |
| CF$_2$CF$_3$ | $^i$Pr | H | Cl | H | CN | 1 |
| CF$_2$CF$_3$ | $^i$Pr | H | Cl | H | CN | 2 |
| CF$_2$CF$_3$ | $^i$Pr | H | Br | H | CN | 0 |
| CF$_2$CF$_3$ | $^i$Pr | H | Br | H | CN | 1 |
| CF$_2$CF$_3$ | $^i$Pr | H | Br | H | CN | 2 |
| CF$_2$CF$_3$ | $^i$Pr | H | I | H | CN | 0 |
| CF$_2$CF$_3$ | $^i$Pr | H | I | H | CN | 1 |
| CF$_2$CF$_3$ | $^i$Pr | H | I | H | CN | 2 |
| CF$_2$CF$_3$ | $^i$Pr | H | CF$_3$ | H | F | 0 |
| CF$_2$CF$_3$ | $^i$Pr | H | CF$_3$ | H | F | 1 |
| CF$_2$CF$_3$ | $^i$Pr | H | CF$_3$ | H | F | 2 |
| CF$_2$CF$_3$ | $^i$Pr | H | CF$_3$ | H | Cl | 0 |
| CF$_2$CF$_3$ | $^i$Pr | H | CF$_3$ | H | Cl | 1 |
| CF$_2$CF$_3$ | $^i$Pr | H | CF$_3$ | H | Cl | 2 |
| CF$_2$CF$_3$ | $^i$Pr | H | CF$_3$ | H | Br | 0 |
| CF$_2$CF$_3$ | $^i$Pr | H | CF$_3$ | H | Br | 1 |
| CF$_2$CF$_3$ | $^i$Pr | H | CF$_3$ | H | Br | 2 |
| CF$_2$CF$_3$ | $^i$Pr | H | CF$_3$ | H | I | 0 |
| CF$_2$CF$_3$ | $^i$Pr | H | CF$_3$ | H | I | 1 |
| CF$_2$CF$_3$ | $^i$Pr | H | CF$_3$ | H | I | 2 |
| CF$_2$CF$_3$ | $^i$Pr | H | CF$_3$ | H | CN | 0 |
| CF$_2$CF$_3$ | $^i$Pr | H | CF$_3$ | H | CN | 1 |
| CF$_2$CF$_3$ | $^i$Pr | H | CF$_3$ | H | CN | 2 |
| CF$_2$CF$_3$ | $^i$Pr | H | F | F | H | 0 |
| CF$_2$CF$_3$ | $^i$Pr | H | F | F | H | 1 |
| CF$_2$CF$_3$ | $^i$Pr | H | F | F | H | 2 |
| CF$_2$CF$_3$ | $^i$Pr | H | Cl | Cl | H | 0 |
| CF$_2$CF$_3$ | $^i$Pr | H | Cl | Cl | H | 1 |

TABLE 1-continued

| | | | | | | |
|---|---|---|---|---|---|---|
| CF₂CF₃ | ⁱPr | H | Cl | Cl | H | 2 |
| CF₂CF₃ | ⁱPr | H | Br | Br | H | 0 |
| CF₂CF₃ | ⁱPr | H | Br | Br | H | 1 |
| CF₂CF₃ | ⁱPr | H | Br | Br | H | 2 |
| CF₂CF₃ | ⁱPr | H | I | I | H | 0 |
| CF₂CF₃ | ⁱPr | H | I | I | H | 1 |
| CF₂CF₃ | ⁱPr | H | I | I | H | 2 |
| CF₂CF₃ | ⁱPr | H | F | Cl | H | 0 |
| CF₂CF₃ | ⁱPr | H | F | Cl | H | 1 |
| CF₂CF₃ | ⁱPr | H | F | Cl | H | 2 |
| CF₂CF₃ | ⁱPr | H | F | Br | H | 0 |
| CF₂CF₃ | ⁱPr | H | F | Br | H | 1 |
| CF₂CF₃ | ⁱPr | H | F | Br | H | 2 |
| CF₂CF₃ | ⁱPr | H | F | I | H | 0 |
| CF₂CF₃ | ⁱPr | H | F | I | H | 1 |
| CF₂CF₃ | ⁱPr | H | F | I | H | 2 |
| CF₂CF₃ | ⁱPr | H | Cl | F | H | 0 |
| CF₂CF₃ | ⁱPr | H | Cl | F | H | 1 |
| CF₂CF₃ | ⁱPr | H | Cl | F | H | 2 |
| CF₂CF₃ | ⁱPr | H | Cl | Br | H | 0 |
| CF₂CF₃ | ⁱPr | H | Cl | Br | H | 1 |
| CF₂CF₃ | ⁱPr | H | Cl | Br | H | 2 |
| CF₂CF₃ | ⁱPr | H | Cl | I | H | 0 |
| CF₂CF₃ | ⁱPr | H | Cl | I | H | 1 |
| CF₂CF₃ | ⁱPr | H | Cl | I | H | 2 |
| CF₂CF₃ | ⁱPr | H | Br | F | H | 0 |
| CF₂CF₃ | ⁱPr | H | Br | F | H | 1 |
| CF₂CF₃ | ⁱPr | H | Br | F | H | 2 |
| CF₂CF₃ | ⁱPr | H | Br | Cl | H | 0 |
| CF₂CF₃ | ⁱPr | H | Br | Cl | H | 1 |
| CF₂CF₃ | ⁱPr | H | Br | Cl | H | 2 |
| CF₂CF₃ | ⁱPr | H | Br | I | H | 0 |
| CF₂CF₃ | ⁱPr | H | Br | I | H | 1 |
| CF₂CF₃ | ⁱPr | H | Br | I | H | 2 |
| CF₂CF₃ | ⁱPr | H | I | F | H | 0 |
| CF₂CF₃ | ⁱPr | H | I | F | H | 1 |
| CF₂CF₃ | ⁱPr | H | I | F | H | 2 |
| CF₂CF₃ | ⁱPr | H | I | Cl | H | 0 |
| CF₂CF₃ | ⁱPr | H | I | Cl | H | 1 |
| CF₂CF₃ | ⁱPr | H | I | Cl | H | 2 |
| CF₂CF₃ | ⁱPr | H | I | Br | H | 0 |
| CF₂CF₃ | ⁱPr | H | I | Br | H | 1 |
| CF₂CF₃ | ⁱPr | H | I | Br | H | 2 |
| CF₂CF₃ | ⁱPr | H | F | CN | H | 0 |
| CF₂CF₃ | ⁱPr | H | F | CN | H | 1 |
| CF₂CF₃ | ⁱPr | H | F | CN | H | 2 |
| CF₂CF₃ | ⁱPr | H | Cl | CN | H | 0 |
| CF₂CF₃ | ⁱPr | H | Cl | CN | H | 1 |
| CF₂CF₃ | ⁱPr | H | Cl | CN | H | 2 |
| CF₂CF₃ | ⁱPr | H | Br | CN | H | 0 |
| CF₂CF₃ | ⁱPr | H | Br | CN | H | 1 |
| CF₂CF₃ | ⁱPr | H | Br | CN | H | 2 |
| CF₂CF₃ | ⁱPr | H | I | CN | H | 0 |
| CF₂CF₃ | ⁱPr | H | I | CN | H | 1 |
| CF₂CF₃ | ⁱPr | H | I | CN | H | 2 |
| CF₂CF₃ | ⁱPr | H | CF₃ | F | H | 0 |
| CF₂CF₃ | ⁱPr | H | CF₃ | F | H | 1 |
| CF₂CF₃ | ⁱPr | H | CF₃ | F | H | 2 |
| CF₂CF₃ | ⁱPr | H | CF₃ | Cl | H | 0 |
| CF₂CF₃ | ⁱPr | H | CF₃ | Cl | H | 1 |
| CF₂CF₃ | ⁱPr | H | CF₃ | Cl | H | 2 |
| CF₂CF₃ | ⁱPr | H | CF₃ | Br | H | 0 |
| CF₂CF₃ | ⁱPr | H | CF₃ | Br | H | 1 |
| CF₂CF₃ | ⁱPr | H | CF₃ | Br | H | 2 |
| CF₂CF₃ | ⁱPr | H | CF₃ | I | H | 0 |
| CF₂CF₃ | ⁱPr | H | CF₃ | I | H | 1 |
| CF₂CF₃ | ⁱPr | H | CF₃ | I | H | 2 |
| CF₂CF₃ | ⁱPr | H | CF₃ | CN | H | 0 |
| CF₂CF₃ | ⁱPr | H | CF₃ | CN | H | 1 |
| CF₂CF₃ | ⁱPr | H | CF₃ | CN | H | 2 |
| CF₂CF₃ | CH₂CF₃ | H | H | H | H | 0 |
| CF₂CF₃ | CH₂CF₃ | H | H | H | H | 1 |
| CF₂CF₃ | CH₂CF₃ | H | H | H | H | 2 |
| CF₂CF₃ | CH₂CF₃ | F | H | H | H | 0 |
| CF₂CF₃ | CH₂CF₃ | F | H | H | H | 1 |
| CF₂CF₃ | CH₂CF₃ | F | H | H | H | 2 |
| CF₂CF₃ | CH₂CF₃ | Cl | H | H | H | 0 |
| CF₂CF₃ | CH₂CF₃ | Cl | H | H | H | 1 |
| CF₂CF₃ | CH₂CF₃ | Cl | H | H | H | 2 |
| CF₂CF₃ | CH₂CF₃ | Br | H | H | H | 0 |
| CF₂CF₃ | CH₂CF₃ | Br | H | H | H | 1 |
| CF₂CF₃ | CH₂CF₃ | Br | H | H | H | 2 |
| CF₂CF₃ | CH₂CF₃ | I | H | H | H | 0 |
| CF₂CF₃ | CH₂CF₃ | I | H | H | H | 1 |
| CF₂CF₃ | CH₂CF₃ | I | H | H | H | 2 |
| CF₂CF₃ | CH₂CF₃ | Me | H | H | H | 0 |
| CF₂CF₃ | CH₂CF₃ | Me | H | H | H | 1 |
| CF₂CF₃ | CH₂CF₃ | Me | H | H | H | 2 |
| CF₂CF₃ | CH₂CF₃ | CF₃ | H | H | H | 0 |
| CF₂CF₃ | CH₂CF₃ | CF₃ | H | H | H | 1 |
| CF₂CF₃ | CH₂CF₃ | CF₃ | H | H | H | 2 |
| CF₂CF₃ | CH₂CF₃ | H | F | H | H | 0 |
| CF₂CF₃ | CH₂CF₃ | H | F | H | H | 1 |
| CF₂CF₃ | CH₂CF₃ | H | F | H | H | 2 |
| CF₂CF₃ | CH₂CF₃ | H | Cl | H | H | 0 |
| CF₂CF₃ | CH₂CF₃ | H | Cl | H | H | 1 |
| CF₂CF₃ | CH₂CF₃ | H | Cl | H | H | 2 |
| CF₂CF₃ | CH₂CF₃ | H | Br | H | H | 0 |
| CF₂CF₃ | CH₂CF₃ | H | Br | H | H | 1 |
| CF₂CF₃ | CH₂CF₃ | H | Br | H | H | 2 |
| CF₂CF₃ | CH₂CF₃ | H | I | H | H | 0 |
| CF₂CF₃ | CH₂CF₃ | H | I | H | H | 1 |
| CF₂CF₃ | CH₂CF₃ | H | I | H | H | 2 |
| CF₂CF₃ | CH₂CF₃ | H | Me | H | H | 0 |
| CF₂CF₃ | CH₂CF₃ | H | Me | H | H | 1 |
| CF₂CF₃ | CH₂CF₃ | H | Me | H | H | 2 |
| CF₂CF₃ | CH₂CF₃ | H | CF₃ | H | H | 0 |
| CF₂CF₃ | CH₂CF₃ | H | CF₃ | H | H | 1 |
| CF₂CF₃ | CH₂CF₃ | H | CF₃ | H | H | 2 |
| CF₂CF₃ | CH₂CF₃ | H | CF₂CF₃ | H | H | 0 |
| CF₂CF₃ | CH₂CF₃ | H | CF₂CF₃ | H | H | 1 |
| CF₂CF₃ | CH₂CF₃ | H | CF₂CF₃ | H | H | 2 |
| CF₂CF₃ | CH₂CF₃ | H | CF(CF₃)₂ | H | H | 0 |
| CF₂CF₃ | CH₂CF₃ | H | CF(CF₃)₂ | H | H | 1 |
| CF₂CF₃ | CH₂CF₃ | H | CF(CF₃)₂ | H | H | 2 |
| CF₂CF₃ | CH₂CF₃ | H | SMe | H | H | 0 |
| CF₂CF₃ | CH₂CF₃ | H | SMe | H | H | 1 |
| CF₂CF₃ | CH₂CF₃ | H | SMe | H | H | 2 |
| CF₂CF₃ | CH₂CF₃ | H | SOMe | H | H | 0 |
| CF₂CF₃ | CH₂CF₃ | H | SOMe | H | H | 1 |
| CF₂CF₃ | CH₂CF₃ | H | SOMe | H | H | 2 |
| CF₂CF₃ | CH₂CF₃ | H | SO₂Me | H | H | 0 |
| CF₂CF₃ | CH₂CF₃ | H | SO₂Me | H | H | 1 |
| CF₂CF₃ | CH₂CF₃ | H | SO₂Me | H | H | 2 |
| CF₂CF₃ | CH₂CF₃ | H | OMe | H | H | 0 |
| CF₂CF₃ | CH₂CF₃ | H | OMe | H | H | 1 |
| CF₂CF₃ | CH₂CF₃ | H | OMe | H | H | 2 |
| CF₂CF₃ | CH₂CF₃ | H | OCF₃ | H | H | 0 |
| CF₂CF₃ | CH₂CF₃ | H | OCF₃ | H | H | 1 |
| CF₂CF₃ | CH₂CF₃ | H | OCF₃ | H | H | 2 |
| CF₂CF₃ | CH₂CF₃ | H | NO₂ | H | H | 0 |
| CF₂CF₃ | CH₂CF₃ | H | NO₂ | H | H | 1 |
| CF₂CF₃ | CH₂CF₃ | H | NO₂ | H | H | 2 |
| CF₂CF₃ | CH₂CF₃ | H | CN | H | H | 0 |
| CF₂CF₃ | CH₂CF₃ | H | CN | H | H | 1 |
| CF₂CF₃ | CH₂CF₃ | H | CN | H | H | 2 |
| CF₂CF₃ | CH₂CF₃ | H | H | F | H | 0 |
| CF₂CF₃ | CH₂CF₃ | H | H | F | H | 1 |
| CF₂CF₃ | CH₂CF₃ | H | H | F | H | 2 |
| CF₂CF₃ | CH₂CF₃ | H | H | Cl | H | 0 |
| CF₂CF₃ | CH₂CF₃ | H | H | Cl | H | 1 |
| CF₂CF₃ | CH₂CF₃ | H | H | Cl | H | 2 |
| CF₂CF₃ | CH₂CF₃ | H | H | Br | H | 0 |
| CF₂CF₃ | CH₂CF₃ | H | H | Br | H | 1 |
| CF₂CF₃ | CH₂CF₃ | H | H | Br | H | 2 |
| CF₂CF₃ | CH₂CF₃ | H | H | I | H | 0 |
| CF₂CF₃ | CH₂CF₃ | H | H | I | H | 1 |
| CF₂CF₃ | CH₂CF₃ | H | H | I | H | 2 |
| CF₂CF₃ | CH₂CF₃ | H | H | Me | H | 0 |
| CF₂CF₃ | CH₂CF₃ | H | H | Me | H | 1 |
| CF₂CF₃ | CH₂CF₃ | H | H | Me | H | 2 |
| CF₂CF₃ | CH₂CF₃ | H | H | CF₃ | H | 0 |
| CF₂CF₃ | CH₂CF₃ | H | H | CF₃ | H | 1 |
| CF₂CF₃ | CH₂CF₃ | H | H | CF₃ | H | 2 |
| CF₂CF₃ | CH₂CF₃ | H | H | CF₂CF₃ | H | 0 |
| CF₂CF₃ | CH₂CF₃ | H | H | CF₂CF₃ | H | 1 |
| CF₂CF₃ | CH₂CF₃ | H | H | CF₂CF₃ | H | 2 |
| CF₂CF₃ | CH₂CF₃ | H | H | CF(CF₃)₂ | H | 0 |
| CF₂CF₃ | CH₂CF₃ | H | H | CF(CF₃)₂ | H | 1 |
| CF₂CF₃ | CH₂CF₃ | H | H | CF(CF₃)₂ | H | 2 |

TABLE 1-continued

| | | | | | | |
|---|---|---|---|---|---|---|
| CF₂CF₃ | CH₂CF₃ | H | H | SMe | H | 0 |
| CF₂CF₃ | CH₂CF₃ | H | H | SMe | H | 1 |
| CF₂CF₃ | CH₂CF₃ | H | H | SMe | H | 2 |
| CF₂CF₃ | CH₂CF₃ | H | H | SOMe | H | 0 |
| CF₂CF₃ | CH₂CF₃ | H | H | SOMe | H | 1 |
| CF₂CF₃ | CH₂CF₃ | H | H | SOMe | H | 2 |
| CF₂CF₃ | CH₂CF₃ | H | H | SO₂Me | H | 0 |
| CF₂CF₃ | CH₂CF₃ | H | H | SO₂Me | H | 1 |
| CF₂CF₃ | CH₂CF₃ | H | H | SO₂Me | H | 2 |
| CF₂CF₃ | CH₂CF₃ | H | H | OMe | H | 0 |
| CF₂CF₃ | CH₂CF₃ | H | H | OMe | H | 1 |
| CF₂CF₃ | CH₂CF₃ | H | H | OMe | H | 2 |
| CF₂CF₃ | CH₂CF₃ | H | H | OCF₃ | H | 0 |
| CF₂CF₃ | CH₂CF₃ | H | H | OCF₃ | H | 1 |
| CF₂CF₃ | CH₂CF₃ | H | H | OCF₃ | H | 2 |
| CF₂CF₃ | CH₂CF₃ | H | H | NO₂ | H | 0 |
| CF₂CF₃ | CH₂CF₃ | H | H | NO₂ | H | 1 |
| CF₂CF₃ | CH₂CF₃ | H | H | NO₂ | H | 2 |
| CF₂CF₃ | CH₂CF₃ | H | H | CN | H | 0 |
| CF₂CF₃ | CH₂CF₃ | H | H | CN | H | 1 |
| CF₂CF₃ | CH₂CF₃ | H | H | CN | H | 2 |
| CF₂CF₃ | CH₂CF₃ | H | H | H | F | 0 |
| CF₂CF₃ | CH₂CF₃ | H | H | H | F | 1 |
| CF₂CF₃ | CH₂CF₃ | H | H | H | F | 2 |
| CF₂CF₃ | CH₂CF₃ | H | H | H | Cl | 0 |
| CF₂CF₃ | CH₂CF₃ | H | H | H | Cl | 1 |
| CF₂CF₃ | CH₂CF₃ | H | H | H | Cl | 2 |
| CF₂CF₃ | CH₂CF₃ | H | H | H | Br | 0 |
| CF₂CF₃ | CH₂CF₃ | H | H | H | Br | 1 |
| CF₂CF₃ | CH₂CF₃ | H | H | H | Br | 2 |
| CF₂CF₃ | CH₂CF₃ | H | H | H | I | 0 |
| CF₂CF₃ | CH₂CF₃ | H | H | H | I | 1 |
| CF₂CF₃ | CH₂CF₃ | H | H | H | I | 2 |
| CF₂CF₃ | CH₂CF₃ | H | H | H | Me | 0 |
| CF₂CF₃ | CH₂CF₃ | H | H | H | Me | 1 |
| CF₂CF₃ | CH₂CF₃ | H | H | H | Me | 2 |
| CF₂CF₃ | CH₂CF₃ | H | H | H | CF₃ | 0 |
| CF₂CF₃ | CH₂CF₃ | H | H | H | CF₃ | 1 |
| CF₂CF₃ | CH₂CF₃ | H | H | H | CF₃ | 2 |
| CF₂CF₃ | CH₂CF₃ | H | H | H | CF₂CF₃ | 0 |
| CF₂CF₃ | CH₂CF₃ | H | H | H | CF₂CF₃ | 1 |
| CF₂CF₃ | CH₂CF₃ | H | H | H | CF₂CF₃ | 2 |
| CF₂CF₃ | CH₂CF₃ | H | H | H | CF(CF₃)₂ | 0 |
| CF₂CF₃ | CH₂CF₃ | H | H | H | CF(CF₃)₂ | 1 |
| CF₂CF₃ | CH₂CF₃ | H | H | H | CF(CF₃)₂ | 2 |
| CF₂CF₃ | CH₂CF₃ | H | H | H | SMe | 0 |
| CF₂CF₃ | CH₂CF₃ | H | H | H | SMe | 1 |
| CF₂CF₃ | CH₂CF₃ | H | H | H | SMe | 2 |
| CF₂CF₃ | CH₂CF₃ | H | H | H | SOMe | 0 |
| CF₂CF₃ | CH₂CF₃ | H | H | H | SOMe | 1 |
| CF₂CF₃ | CH₂CF₃ | H | H | H | SOMe | 2 |
| CF₂CF₃ | CH₂CF₃ | H | H | H | SO₂Me | 0 |
| CF₂CF₃ | CH₂CF₃ | H | H | H | SO₂Me | 1 |
| CF₂CF₃ | CH₂CF₃ | H | H | H | SO₂Me | 2 |
| CF₂CF₃ | CH₂CF₃ | H | H | H | OMe | 0 |
| CF₂CF₃ | CH₂CF₃ | H | H | H | OMe | 1 |
| CF₂CF₃ | CH₂CF₃ | H | H | H | OMe | 2 |
| CF₂CF₃ | CH₂CF₃ | H | H | H | OCF₃ | 0 |
| CF₂CF₃ | CH₂CF₃ | H | H | H | OCF₃ | 1 |
| CF₂CF₃ | CH₂CF₃ | H | H | H | OCF₃ | 2 |
| CF₂CF₃ | CH₂CF₃ | H | H | H | NO₂ | 0 |
| CF₂CF₃ | CH₂CF₃ | H | H | H | NO₂ | 1 |
| CF₂CF₃ | CH₂CF₃ | H | H | H | NO₂ | 2 |
| CF₂CF₃ | CH₂CF₃ | H | H | H | CN | 0 |
| CF₂CF₃ | CH₂CF₃ | H | H | H | CN | 1 |
| CF₂CF₃ | CH₂CF₃ | H | H | H | CN | 2 |
| CF₂CF₃ | CH₂CF₃ | H | F | H | F | 0 |
| CF₂CF₃ | CH₂CF₃ | H | F | H | F | 1 |
| CF₂CF₃ | CH₂CF₃ | H | F | H | F | 2 |
| CF₂CF₃ | CH₂CF₃ | H | Cl | H | Cl | 0 |
| CF₂CF₃ | CH₂CF₃ | H | Cl | H | Cl | 1 |
| CF₂CF₃ | CH₂CF₃ | H | Cl | H | Cl | 2 |
| CF₂CF₃ | CH₂CF₃ | H | Br | H | Br | 0 |
| CF₂CF₃ | CH₂CF₃ | H | Br | H | Br | 1 |
| CF₂CF₃ | CH₂CF₃ | H | Br | H | Br | 2 |
| CF₂CF₃ | CH₂CF₃ | H | I | H | I | 0 |
| CF₂CF₃ | CH₂CF₃ | H | I | H | I | 1 |
| CF₂CF₃ | CH₂CF₃ | H | I | H | I | 2 |
| CF₂CF₃ | CH₂CF₃ | H | F | H | Cl | 0 |
| CF₂CF₃ | CH₂CF₃ | H | F | H | Cl | 1 |
| CF₂CF₃ | CH₂CF₃ | H | F | H | Cl | 2 |
| CF₂CF₃ | CH₂CF₃ | H | F | H | Br | 0 |
| CF₂CF₃ | CH₂CF₃ | H | F | H | Br | 1 |
| CF₂CF₃ | CH₂CF₃ | H | F | H | Br | 2 |
| CF₂CF₃ | CH₂CF₃ | H | F | H | I | 0 |
| CF₂CF₃ | CH₂CF₃ | H | F | H | I | 1 |
| CF₂CF₃ | CH₂CF₃ | H | F | H | I | 2 |
| CF₂CF₃ | CH₂CF₃ | H | Cl | H | F | 0 |
| CF₂CF₃ | CH₂CF₃ | H | Cl | H | F | 1 |
| CF₂CF₃ | CH₂CF₃ | H | Cl | H | F | 2 |
| CF₂CF₃ | CH₂CF₃ | H | Cl | H | Br | 0 |
| CF₂CF₃ | CH₂CF₃ | H | Cl | H | Br | 1 |
| CF₂CF₃ | CH₂CF₃ | H | Cl | H | Br | 2 |
| CF₂CF₃ | CH₂CF₃ | H | Cl | H | I | 0 |
| CF₂CF₃ | CH₂CF₃ | H | Cl | H | I | 1 |
| CF₂CF₃ | CH₂CF₃ | H | Cl | H | I | 2 |
| CF₂CF₃ | CH₂CF₃ | H | Br | H | F | 0 |
| CF₂CF₃ | CH₂CF₃ | H | Br | H | F | 1 |
| CF₂CF₃ | CH₂CF₃ | H | Br | H | F | 2 |
| CF₂CF₃ | CH₂CF₃ | H | Br | H | Cl | 0 |
| CF₂CF₃ | CH₂CF₃ | H | Br | H | Cl | 1 |
| CF₂CF₃ | CH₂CF₃ | H | Br | H | Cl | 2 |
| CF₂CF₃ | CH₂CF₃ | H | Br | H | I | 0 |
| CF₂CF₃ | CH₂CF₃ | H | Br | H | I | 1 |
| CF₂CF₃ | CH₂CF₃ | H | Br | H | I | 2 |
| CF₂CF₃ | CH₂CF₃ | H | I | H | F | 0 |
| CF₂CF₃ | CH₂CF₃ | H | I | H | F | 1 |
| CF₂CF₃ | CH₂CF₃ | H | I | H | F | 2 |
| CF₂CF₃ | CH₂CF₃ | H | I | H | Cl | 0 |
| CF₂CF₃ | CH₂CF₃ | H | I | H | Cl | 1 |
| CF₂CF₃ | CH₂CF₃ | H | I | H | Cl | 2 |
| CF₂CF₃ | CH₂CF₃ | H | I | H | Br | 0 |
| CF₂CF₃ | CH₂CF₃ | H | I | H | Br | 1 |
| CF₂CF₃ | CH₂CF₃ | H | I | H | Br | 2 |
| CF₂CF₃ | CH₂CF₃ | H | F | H | CN | 0 |
| CF₂CF₃ | CH₂CF₃ | H | F | H | CN | 1 |
| CF₂CF₃ | CH₂CF₃ | H | F | H | CN | 2 |
| CF₂CF₃ | CH₂CF₃ | H | Cl | H | CN | 0 |
| CF₂CF₃ | CH₂CF₃ | H | Cl | H | CN | 1 |
| CF₂CF₃ | CH₂CF₃ | H | Cl | H | CN | 2 |
| CF₂CF₃ | CH₂CF₃ | H | Br | H | CN | 0 |
| CF₂CF₃ | CH₂CF₃ | H | Br | H | CN | 1 |
| CF₂CF₃ | CH₂CF₃ | H | Br | H | CN | 2 |
| CF₂CF₃ | CH₂CF₃ | H | I | H | CN | 0 |
| CF₂CF₃ | CH₂CF₃ | H | I | H | CN | 1 |
| CF₂CF₃ | CH₂CF₃ | H | I | H | CN | 2 |
| CF₂CF₃ | CH₂CF₃ | H | CF₃ | H | F | 0 |
| CF₂CF₃ | CH₂CF₃ | H | CF₃ | H | F | 1 |
| CF₂CF₃ | CH₂CF₃ | H | CF₃ | H | F | 2 |
| CF₂CF₃ | CH₂CF₃ | H | CF₃ | H | Cl | 0 |
| CF₂CF₃ | CH₂CF₃ | H | CF₃ | H | Cl | 1 |
| CF₂CF₃ | CH₂CF₃ | H | CF₃ | H | Cl | 2 |
| CF₂CF₃ | CH₂CF₃ | H | CF₃ | H | Br | 0 |
| CF₂CF₃ | CH₂CF₃ | H | CF₃ | H | Br | 1 |
| CF₂CF₃ | CH₂CF₃ | H | CF₃ | H | Br | 2 |
| CF₂CF₃ | CH₂CF₃ | H | CF₃ | H | I | 0 |
| CF₂CF₃ | CH₂CF₃ | H | CF₃ | H | I | 1 |
| CF₂CF₃ | CH₂CF₃ | H | CF₃ | H | I | 2 |
| CF₂CF₃ | CH₂CF₃ | H | CF₃ | H | CN | 0 |
| CF₂CF₃ | CH₂CF₃ | H | CF₃ | H | CN | 1 |
| CF₂CF₃ | CH₂CF₃ | H | CF₃ | H | CN | 2 |
| CF₂CF₃ | CH₂CF₃ | H | F | F | H | 0 |
| CF₂CF₃ | CH₂CF₃ | H | F | F | H | 1 |
| CF₂CF₃ | CH₂CF₃ | H | F | F | H | 2 |
| CF₂CF₃ | CH₂CF₃ | H | Cl | Cl | H | 0 |
| CF₂CF₃ | CH₂CF₃ | H | Cl | Cl | H | 1 |
| CF₂CF₃ | CH₂CF₃ | H | Cl | Cl | H | 2 |
| CF₂CF₃ | CH₂CF₃ | H | Br | Br | H | 0 |
| CF₂CF₃ | CH₂CF₃ | H | Br | Br | H | 1 |
| CF₂CF₃ | CH₂CF₃ | H | Br | Br | H | 2 |
| CF₂CF₃ | CH₂CF₃ | H | I | I | H | 0 |
| CF₂CF₃ | CH₂CF₃ | H | I | I | H | 1 |
| CF₂CF₃ | CH₂CF₃ | H | I | I | H | 2 |
| CF₂CF₃ | CH₂CF₃ | H | F | Cl | H | 0 |
| CF₂CF₃ | CH₂CF₃ | H | F | Cl | H | 1 |
| CF₂CF₃ | CH₂CF₃ | H | F | Cl | H | 2 |
| CF₂CF₃ | CH₂CF₃ | H | F | Br | H | 0 |
| CF₂CF₃ | CH₂CF₃ | H | F | Br | H | 1 |
| CF₂CF₃ | CH₂CF₃ | H | F | Br | H | 2 |
| CF₂CF₃ | CH₂CF₃ | H | F | I | H | 0 |

TABLE 1-continued

| | | | | | | |
|---|---|---|---|---|---|---|
| CF$_2$CF$_3$ | CH$_2$CF$_3$ | H | F | I | H | 1 |
| CF$_2$CF$_3$ | CH$_2$CF$_3$ | H | F | I | H | 2 |
| CF$_2$CF$_3$ | CH$_2$CF$_3$ | H | Cl | F | H | 0 |
| CF$_2$CF$_3$ | CH$_2$CF$_3$ | H | Cl | F | H | 1 |
| CF$_2$CF$_3$ | CH$_2$CF$_3$ | H | Cl | F | H | 2 |
| CF$_2$CF$_3$ | CH$_2$CF$_3$ | H | Cl | Br | H | 0 |
| CF$_2$CF$_3$ | CH$_2$CF$_3$ | H | Cl | Br | H | 1 |
| CF$_2$CF$_3$ | CH$_2$CF$_3$ | H | Cl | Br | H | 2 |
| CF$_2$CF$_3$ | CH$_2$CF$_3$ | H | Cl | I | H | 0 |
| CF$_2$CF$_3$ | CH$_2$CF$_3$ | H | Cl | I | H | 1 |
| CF$_2$CF$_3$ | CH$_2$CF$_3$ | H | Cl | I | H | 2 |
| CF$_2$CF$_3$ | CH$_2$CF$_3$ | H | Br | F | H | 0 |
| CF$_2$CF$_3$ | CH$_2$CF$_3$ | H | Br | F | H | 1 |
| CF$_2$CF$_3$ | CH$_2$CF$_3$ | H | Br | F | H | 2 |
| CF$_2$CF$_3$ | CH$_2$CF$_3$ | H | Br | Cl | H | 0 |
| CF$_2$CF$_3$ | CH$_2$CF$_3$ | H | Br | Cl | H | 1 |
| CF$_2$CF$_3$ | CH$_2$CF$_3$ | H | Br | Cl | H | 2 |
| CF$_2$CF$_3$ | CH$_2$CF$_3$ | H | Br | I | H | 0 |
| CF$_2$CF$_3$ | CH$_2$CF$_3$ | H | Br | I | H | 1 |
| CF$_2$CF$_3$ | CH$_2$CF$_3$ | H | Br | I | H | 2 |
| CF$_2$CF$_3$ | CH$_2$CF$_3$ | H | I | F | H | 0 |
| CF$_2$CF$_3$ | CH$_2$CF$_3$ | H | I | F | H | 1 |
| CF$_2$CF$_3$ | CH$_2$CF$_3$ | H | I | F | H | 2 |
| CF$_2$CF$_3$ | CH$_2$CF$_3$ | H | I | Cl | H | 0 |
| CF$_2$CF$_3$ | CH$_2$CF$_3$ | H | I | Cl | H | 1 |
| CF$_2$CF$_3$ | CH$_2$CF$_3$ | H | I | Cl | H | 2 |
| CF$_2$CF$_3$ | CH$_2$CF$_3$ | H | I | Br | H | 0 |
| CF$_2$CF$_3$ | CH$_2$CF$_3$ | H | I | Br | H | 1 |
| CF$_2$CF$_3$ | CH$_2$CF$_3$ | H | I | Br | H | 2 |
| CF$_2$CF$_3$ | CH$_2$CF$_3$ | H | F | CN | H | 0 |
| CF$_2$CF$_3$ | CH$_2$CF$_3$ | H | F | CN | H | 1 |
| CF$_2$CF$_3$ | CH$_2$CF$_3$ | H | F | CN | H | 2 |
| CF$_2$CF$_3$ | CH$_2$CF$_3$ | H | Cl | CN | H | 0 |
| CF$_2$CF$_3$ | CH$_2$CF$_3$ | H | Cl | CN | H | 1 |
| CF$_2$CF$_3$ | CH$_2$CF$_3$ | H | Cl | CN | H | 2 |
| CF$_2$CF$_3$ | CH$_2$CF$_3$ | H | Br | CN | H | 0 |
| CF$_2$CF$_3$ | CH$_2$CF$_3$ | H | Br | CN | H | 1 |
| CF$_2$CF$_3$ | CH$_2$CF$_3$ | H | Br | CN | H | 2 |
| CF$_2$CF$_3$ | CH$_2$CF$_3$ | H | I | CN | H | 0 |
| CF$_2$CF$_3$ | CH$_2$CF$_3$ | H | I | CN | H | 1 |
| CF$_2$CF$_3$ | CH$_2$CF$_3$ | H | I | CN | H | 2 |
| CF$_2$CF$_3$ | CH$_2$CF$_3$ | H | CF$_3$ | F | H | 0 |
| CF$_2$CF$_3$ | CH$_2$CF$_3$ | H | CF$_3$ | F | H | 1 |
| CF$_2$CF$_3$ | CH$_2$CF$_3$ | H | CF$_3$ | F | H | 2 |
| CF$_2$CF$_3$ | CH$_2$CF$_3$ | H | CF$_3$ | Cl | H | 0 |
| CF$_2$CF$_3$ | CH$_2$CF$_3$ | H | CF$_3$ | Cl | H | 1 |
| CF$_2$CF$_3$ | CH$_2$CF$_3$ | H | CF$_3$ | Cl | H | 2 |
| CF$_2$CF$_3$ | CH$_2$CF$_3$ | H | CF$_3$ | Br | H | 0 |
| CF$_2$CF$_3$ | CH$_2$CF$_3$ | H | CF$_3$ | Br | H | 1 |
| CF$_2$CF$_3$ | CH$_2$CF$_3$ | H | CF$_3$ | Br | H | 2 |
| CF$_2$CF$_3$ | CH$_2$CF$_3$ | H | CF$_3$ | I | H | 0 |
| CF$_2$CF$_3$ | CH$_2$CF$_3$ | H | CF$_3$ | I | H | 1 |
| CF$_2$CF$_3$ | CH$_2$CF$_3$ | H | CF$_3$ | I | H | 2 |
| CF$_2$CF$_3$ | CH$_2$CF$_3$ | H | CF$_3$ | CN | H | 0 |
| CF$_2$CF$_3$ | CH$_2$CF$_3$ | H | CF$_3$ | CN | H | 1 |
| CF$_2$CF$_3$ | CH$_2$CF$_3$ | H | CF$_3$ | CN | H | 2 |
| SCF$_3$ | Me | H | H | H | H | 0 |
| SCF$_3$ | Me | H | H | H | H | 1 |
| SCF$_3$ | Me | H | H | H | H | 2 |
| SCF$_3$ | Me | F | H | H | H | 0 |
| SCF$_3$ | Me | F | H | H | H | 1 |
| SCF$_3$ | Me | F | H | H | H | 2 |
| SCF$_3$ | Me | Cl | H | H | H | 0 |
| SCF$_3$ | Me | Cl | H | H | H | 1 |
| SCF$_3$ | Me | Cl | H | H | H | 2 |
| SCF$_3$ | Me | Br | H | H | H | 0 |
| SCF$_3$ | Me | Br | H | H | H | 1 |
| SCF$_3$ | Me | Br | H | H | H | 2 |
| SCF$_3$ | Me | I | H | H | H | 0 |
| SCF$_3$ | Me | I | H | H | H | 1 |
| SCF$_3$ | Me | I | H | H | H | 2 |
| SCF$_3$ | Me | Me | H | H | H | 0 |
| SCF$_3$ | Me | Me | H | H | H | 1 |
| SCF$_3$ | Me | Me | H | H | H | 2 |
| SCF$_3$ | Me | CF$_3$ | H | H | H | 0 |
| SCF$_3$ | Me | CF$_3$ | H | H | H | 1 |
| SCF$_3$ | Me | CF$_3$ | H | H | H | 2 |
| SCF$_3$ | Me | H | F | H | H | 0 |
| SCF$_3$ | Me | H | F | H | H | 1 |
| SCF$_3$ | Me | H | F | H | H | 2 |
| SCF$_3$ | Me | H | Cl | H | H | 0 |
| SCF$_3$ | Me | H | Cl | H | H | 1 |
| SCF$_3$ | Me | H | Cl | H | H | 2 |
| SCF$_3$ | Me | H | Br | H | H | 0 |
| SCF$_3$ | Me | H | Br | H | H | 1 |
| SCF$_3$ | Me | H | Br | H | H | 2 |
| SCF$_3$ | Me | H | I | H | H | 0 |
| SCF$_3$ | Me | H | I | H | H | 1 |
| SCF$_3$ | Me | H | I | H | H | 2 |
| SCF$_3$ | Me | H | Me | H | H | 0 |
| SCF$_3$ | Me | H | Me | H | H | 1 |
| SCF$_3$ | Me | H | Me | H | H | 2 |
| SCF$_3$ | Me | H | CF$_3$ | H | H | 0 |
| SCF$_3$ | Me | H | CF$_3$ | H | H | 1 |
| SCF$_3$ | Me | H | CF$_3$ | H | H | 2 |
| SCF$_3$ | Me | H | CF$_2$CF$_3$ | H | H | 0 |
| SCF$_3$ | Me | H | CF$_2$CF$_3$ | H | H | 1 |
| SCF$_3$ | Me | H | CF$_2$CF$_3$ | H | H | 2 |
| SCF$_3$ | Me | H | CF(CF$_3$)$_2$ | H | H | 0 |
| SCF$_3$ | Me | H | CF(CF$_3$)$_2$ | H | H | 1 |
| SCF$_3$ | Me | H | CF(CF$_3$)$_2$ | H | H | 2 |
| SCF$_3$ | Me | H | SMe | H | H | 0 |
| SCF$_3$ | Me | H | SMe | H | H | 1 |
| SCF$_3$ | Me | H | SMe | H | H | 2 |
| SCF$_3$ | Me | H | SOMe | H | H | 0 |
| SCF$_3$ | Me | H | SOMe | H | H | 1 |
| SCF$_3$ | Me | H | SOMe | H | H | 2 |
| SCF$_3$ | Me | H | SO$_2$Me | H | H | 0 |
| SCF$_3$ | Me | H | SO$_2$Me | H | H | 1 |
| SCF$_3$ | Me | H | SO$_2$Me | H | H | 2 |
| SCF$_3$ | Me | H | OMe | H | H | 0 |
| SCF$_3$ | Me | H | OMe | H | H | 1 |
| SCF$_3$ | Me | H | OMe | H | H | 2 |
| SCF$_3$ | Me | H | OCF$_3$ | H | H | 0 |
| SCF$_3$ | Me | H | OCF$_3$ | H | H | 1 |
| SCF$_3$ | Me | H | OCF$_3$ | H | H | 2 |
| SCF$_3$ | Me | H | NO$_2$ | H | H | 0 |
| SCF$_3$ | Me | H | NO$_2$ | H | H | 1 |
| SCF$_3$ | Me | H | NO$_2$ | H | H | 2 |
| SCF$_3$ | Me | H | CN | H | H | 0 |
| SCF$_3$ | Me | H | CN | H | H | 1 |
| SCF$_3$ | Me | H | CN | H | H | 2 |
| SCF$_3$ | Me | H | H | F | H | 0 |
| SCF$_3$ | Me | H | H | F | H | 1 |
| SCF$_3$ | Me | H | H | F | H | 2 |
| SCF$_3$ | Me | H | H | Cl | H | 0 |
| SCF$_3$ | Me | H | H | Cl | H | 1 |
| SCF$_3$ | Me | H | H | Cl | H | 2 |
| SCF$_3$ | Me | H | H | Br | H | 0 |
| SCF$_3$ | Me | H | H | Br | H | 1 |
| SCF$_3$ | Me | H | H | Br | H | 2 |
| SCF$_3$ | Me | H | H | I | H | 0 |
| SCF$_3$ | Me | H | H | I | H | 1 |
| SCF$_3$ | Me | H | H | I | H | 2 |
| SCF$_3$ | Me | H | H | Me | H | 0 |
| SCF$_3$ | Me | H | H | Me | H | 1 |
| SCF$_3$ | Me | H | H | Me | H | 2 |
| SCF$_3$ | Me | H | H | CF$_3$ | H | 0 |
| SCF$_3$ | Me | H | H | CF$_3$ | H | 1 |
| SCF$_3$ | Me | H | H | CF$_3$ | H | 2 |
| SCF$_3$ | Me | H | H | CF$_2$CF$_3$ | H | 0 |
| SCF$_3$ | Me | H | H | CF$_2$CF$_3$ | H | 1 |
| SCF$_3$ | Me | H | H | CF$_2$CF$_3$ | H | 2 |
| SCF$_3$ | Me | H | H | CF(CF$_3$)$_2$ | H | 0 |
| SCF$_3$ | Me | H | H | CF(CF$_3$)$_2$ | H | 1 |
| SCF$_3$ | Me | H | H | CF(CF$_3$)$_2$ | H | 2 |
| SCF$_3$ | Me | H | H | SMe | H | 0 |
| SCF$_3$ | Me | H | H | SMe | H | 1 |
| SCF$_3$ | Me | H | H | SMe | H | 2 |
| SCF$_3$ | Me | H | H | SOMe | H | 0 |
| SCF$_3$ | Me | H | H | SOMe | H | 1 |
| SCF$_3$ | Me | H | H | SOMe | H | 2 |
| SCF$_3$ | Me | H | H | SO$_2$Me | H | 0 |
| SCF$_3$ | Me | H | H | SO$_2$Me | H | 1 |
| SCF$_3$ | Me | H | H | SO$_2$Me | H | 2 |
| SCF$_3$ | Me | H | H | OMe | H | 0 |
| SCF$_3$ | Me | H | H | OMe | H | 1 |
| SCF$_3$ | Me | H | H | OMe | H | 2 |
| SCF$_3$ | Me | H | H | OCF$_3$ | H | 0 |
| SCF$_3$ | Me | H | H | OCF$_3$ | H | 1 |

TABLE 1-continued

| | | | | | | |
|---|---|---|---|---|---|---|
| SCF$_3$ | Me | H | H | OCF$_3$ | H | 2 |
| SCF$_3$ | Me | H | H | NO$_2$ | H | 0 |
| SCF$_3$ | Me | H | H | NO$_2$ | H | 1 |
| SCF$_3$ | Me | H | H | NO$_2$ | H | 2 |
| SCF$_3$ | Me | H | H | CN | H | 0 |
| SCF$_3$ | Me | H | H | CN | H | 1 |
| SCF$_3$ | Me | H | H | CN | H | 2 |
| SCF$_3$ | Me | H | H | H | F | 0 |
| SCF$_3$ | Me | H | H | H | F | 1 |
| SCF$_3$ | Me | H | H | H | F | 2 |
| SCF$_3$ | Me | H | H | H | Cl | 0 |
| SCF$_3$ | Me | H | H | H | Cl | 1 |
| SCF$_3$ | Me | H | H | H | Cl | 2 |
| SCF$_3$ | Me | H | H | H | Br | 0 |
| SCF$_3$ | Me | H | H | H | Br | 1 |
| SCF$_3$ | Me | H | H | H | Br | 2 |
| SCF$_3$ | Me | H | H | H | I | 0 |
| SCF$_3$ | Me | H | H | H | I | 1 |
| SCF$_3$ | Me | H | H | H | I | 2 |
| SCF$_3$ | Me | H | H | H | Me | 0 |
| SCF$_3$ | Me | H | H | H | Me | 1 |
| SCF$_3$ | Me | H | H | H | Me | 2 |
| SCF$_3$ | Me | H | H | H | CF$_3$ | 0 |
| SCF$_3$ | Me | H | H | H | CF$_3$ | 1 |
| SCF$_3$ | Me | H | H | H | CF$_3$ | 2 |
| SCF$_3$ | Me | H | H | H | CF$_2$CF$_3$ | 0 |
| SCF$_3$ | Me | H | H | H | CF$_2$CF$_3$ | 1 |
| SCF$_3$ | Me | H | H | H | CF$_2$CF$_3$ | 2 |
| SCF$_3$ | Me | H | H | H | CF(CF$_3$)$_2$ | 0 |
| SCF$_3$ | Me | H | H | H | CF(CF$_3$)$_2$ | 1 |
| SCF$_3$ | Me | H | H | H | CF(CF$_3$)$_2$ | 2 |
| SCF$_3$ | Me | H | H | H | SMe | 0 |
| SCF$_3$ | Me | H | H | H | SMe | 1 |
| SCF$_3$ | Me | H | H | H | SMe | 2 |
| SCF$_3$ | Me | H | H | H | SOMe | 0 |
| SCF$_3$ | Me | H | H | H | SOMe | 1 |
| SCF$_3$ | Me | H | H | H | SOMe | 2 |
| SCF$_3$ | Me | H | H | H | SO$_2$Me | 0 |
| SCF$_3$ | Me | H | H | H | SO$_2$Me | 1 |
| SCF$_3$ | Me | H | H | H | SO$_2$Me | 2 |
| SCF$_3$ | Me | H | H | H | OMe | 0 |
| SCF$_3$ | Me | H | H | H | OMe | 1 |
| SCF$_3$ | Me | H | H | H | OMe | 2 |
| SCF$_3$ | Me | H | H | H | OCF$_3$ | 0 |
| SCF$_3$ | Me | H | H | H | OCF$_3$ | 1 |
| SCF$_3$ | Me | H | H | H | OCF$_3$ | 2 |
| SCF$_3$ | Me | H | H | H | NO$_2$ | 0 |
| SCF$_3$ | Me | H | H | H | NO$_2$ | 1 |
| SCF$_3$ | Me | H | H | H | NO$_2$ | 2 |
| SCF$_3$ | Me | H | H | H | CN | 0 |
| SCF$_3$ | Me | H | H | H | CN | 1 |
| SCF$_3$ | Me | H | H | H | CN | 2 |
| SCF$_3$ | Me | H | F | H | F | 0 |
| SCF$_3$ | Me | H | F | H | F | 1 |
| SCF$_3$ | Me | H | F | H | F | 2 |
| SCF$_3$ | Me | H | Cl | H | Cl | 0 |
| SCF$_3$ | Me | H | Cl | H | Cl | 1 |
| SCF$_3$ | Me | H | Cl | H | Cl | 2 |
| SCF$_3$ | Me | H | Br | H | Br | 0 |
| SCF$_3$ | Me | H | Br | H | Br | 1 |
| SCF$_3$ | Me | H | Br | H | Br | 2 |
| SCF$_3$ | Me | H | I | H | I | 0 |
| SCF$_3$ | Me | H | I | H | I | 1 |
| SCF$_3$ | Me | H | I | H | I | 2 |
| SCF$_3$ | Me | H | F | H | Cl | 0 |
| SCF$_3$ | Me | H | F | H | Cl | 1 |
| SCF$_3$ | Me | H | F | H | Cl | 2 |
| SCF$_3$ | Me | H | F | H | Br | 0 |
| SCF$_3$ | Me | H | F | H | Br | 1 |
| SCF$_3$ | Me | H | F | H | Br | 2 |
| SCF$_3$ | Me | H | F | H | I | 0 |
| SCF$_3$ | Me | H | F | H | I | 1 |
| SCF$_3$ | Me | H | F | H | I | 2 |
| SCF$_3$ | Me | H | Cl | H | F | 0 |
| SCF$_3$ | Me | H | Cl | H | F | 1 |
| SCF$_3$ | Me | H | Cl | H | F | 2 |
| SCF$_3$ | Me | H | Cl | H | Br | 0 |
| SCF$_3$ | Me | H | Cl | H | Br | 1 |
| SCF$_3$ | Me | H | Cl | H | Br | 2 |
| SCF$_3$ | Me | H | Cl | H | I | 0 |
| SCF$_3$ | Me | H | Cl | H | I | 1 |
| SCF$_3$ | Me | H | Cl | H | I | 2 |
| SCF$_3$ | Me | H | Br | H | F | 0 |
| SCF$_3$ | Me | H | Br | H | F | 1 |
| SCF$_3$ | Me | H | Br | H | F | 2 |
| SCF$_3$ | Me | H | Br | H | Cl | 0 |
| SCF$_3$ | Me | H | Br | H | Cl | 1 |
| SCF$_3$ | Me | H | Br | H | Cl | 2 |
| SCF$_3$ | Me | H | Br | H | I | 0 |
| SCF$_3$ | Me | H | Br | H | I | 1 |
| SCF$_3$ | Me | H | Br | H | I | 2 |
| SCF$_3$ | Me | H | I | H | F | 0 |
| SCF$_3$ | Me | H | I | H | F | 1 |
| SCF$_3$ | Me | H | I | H | F | 2 |
| SCF$_3$ | Me | H | I | H | Cl | 0 |
| SCF$_3$ | Me | H | I | H | Cl | 1 |
| SCF$_3$ | Me | H | I | H | Cl | 2 |
| SCF$_3$ | Me | H | I | H | Br | 0 |
| SCF$_3$ | Me | H | I | H | Br | 1 |
| SCF$_3$ | Me | H | I | H | Br | 2 |
| SCF$_3$ | Me | H | F | H | CN | 0 |
| SCF$_3$ | Me | H | F | H | CN | 1 |
| SCF$_3$ | Me | H | F | H | CN | 2 |
| SCF$_3$ | Me | H | Cl | H | CN | 0 |
| SCF$_3$ | Me | H | Cl | H | CN | 1 |
| SCF$_3$ | Me | H | Cl | H | CN | 2 |
| SCF$_3$ | Me | H | Br | H | CN | 0 |
| SCF$_3$ | Me | H | Br | H | CN | 1 |
| SCF$_3$ | Me | H | Br | H | CN | 2 |
| SCF$_3$ | Me | H | I | H | CN | 0 |
| SCF$_3$ | Me | H | I | H | CN | 1 |
| SCF$_3$ | Me | H | I | H | CN | 2 |
| SCF$_3$ | Me | H | CF$_3$ | H | F | 0 |
| SCF$_3$ | Me | H | CF$_3$ | H | F | 1 |
| SCF$_3$ | Me | H | CF$_3$ | H | F | 2 |
| SCF$_3$ | Me | H | CF$_3$ | H | Cl | 0 |
| SCF$_3$ | Me | H | CF$_3$ | H | Cl | 1 |
| SCF$_3$ | Me | H | CF$_3$ | H | Cl | 2 |
| SCF$_3$ | Me | H | CF$_3$ | H | Br | 0 |
| SCF$_3$ | Me | H | CF$_3$ | H | Br | 1 |
| SCF$_3$ | Me | H | CF$_3$ | H | Br | 2 |
| SCF$_3$ | Me | H | CF$_3$ | H | I | 0 |
| SCF$_3$ | Me | H | CF$_3$ | H | I | 1 |
| SCF$_3$ | Me | H | CF$_3$ | H | I | 2 |
| SCF$_3$ | Me | H | CF$_3$ | H | CN | 0 |
| SCF$_3$ | Me | H | CF$_3$ | H | CN | 1 |
| SCF$_3$ | Me | H | CF$_3$ | H | CN | 2 |
| SCF$_3$ | Me | H | F | F | H | 0 |
| SCF$_3$ | Me | H | F | F | H | 1 |
| SCF$_3$ | Me | H | F | F | H | 2 |
| SCF$_3$ | Me | H | Cl | Cl | H | 0 |
| SCF$_3$ | Me | H | Cl | Cl | H | 1 |
| SCF$_3$ | Me | H | Cl | Cl | H | 2 |
| SCF$_3$ | Me | H | Br | Br | H | 0 |
| SCF$_3$ | Me | H | Br | Br | H | 1 |
| SCF$_3$ | Me | H | Br | Br | H | 2 |
| SCF$_3$ | Me | H | I | I | H | 0 |
| SCF$_3$ | Me | H | I | I | H | 1 |
| SCF$_3$ | Me | H | I | I | H | 2 |
| SCF$_3$ | Me | H | F | Cl | H | 0 |
| SCF$_3$ | Me | H | F | Cl | H | 1 |
| SCF$_3$ | Me | H | F | Cl | H | 2 |
| SCF$_3$ | Me | H | F | Br | H | 0 |
| SCF$_3$ | Me | H | F | Br | H | 1 |
| SCF$_3$ | Me | H | F | Br | H | 2 |
| SCF$_3$ | Me | H | F | I | H | 0 |
| SCF$_3$ | Me | H | F | I | H | 1 |
| SCF$_3$ | Me | H | F | I | H | 2 |
| SCF$_3$ | Me | H | Cl | F | H | 0 |
| SCF$_3$ | Me | H | Cl | F | H | 1 |
| SCF$_3$ | Me | H | Cl | F | H | 2 |
| SCF$_3$ | Me | H | Cl | Br | H | 0 |
| SCF$_3$ | Me | H | Cl | Br | H | 1 |
| SCF$_3$ | Me | H | Cl | Br | H | 2 |
| SCF$_3$ | Me | H | Cl | I | H | 0 |
| SCF$_3$ | Me | H | Cl | I | H | 1 |
| SCF$_3$ | Me | H | Cl | I | H | 2 |
| SCF$_3$ | Me | H | Br | F | H | 0 |
| SCF$_3$ | Me | H | Br | F | H | 1 |
| SCF$_3$ | Me | H | Br | F | H | 2 |

TABLE 1-continued

| | | | | | | |
|---|---|---|---|---|---|---|
| SCF$_3$ | Me | H | Br | Cl | H | 0 |
| SCF$_3$ | Me | H | Br | Cl | H | 1 |
| SCF$_3$ | Me | H | Br | Cl | H | 2 |
| SCF$_3$ | Me | H | Br | I | H | 0 |
| SCF$_3$ | Me | H | Br | I | H | 1 |
| SCF$_3$ | Me | H | Br | I | H | 2 |
| SCF$_3$ | Me | H | I | F | H | 0 |
| SCF$_3$ | Me | H | I | F | H | 1 |
| SCF$_3$ | Me | H | I | F | H | 2 |
| SCF$_3$ | Me | H | I | Cl | H | 0 |
| SCF$_3$ | Me | H | I | Cl | H | 1 |
| SCF$_3$ | Me | H | I | Cl | H | 2 |
| SCF$_3$ | Me | H | I | Br | H | 0 |
| SCF$_3$ | Me | H | I | Br | H | 1 |
| SCF$_3$ | Me | H | I | Br | H | 2 |
| SCF$_3$ | Me | H | F | CN | H | 0 |
| SCF$_3$ | Me | H | F | CN | H | 1 |
| SCF$_3$ | Me | H | F | CN | H | 2 |
| SCF$_3$ | Me | H | Cl | CN | H | 0 |
| SCF$_3$ | Me | H | Cl | CN | H | 1 |
| SCF$_3$ | Me | H | Cl | CN | H | 2 |
| SCF$_3$ | Me | H | Br | CN | H | 0 |
| SCF$_3$ | Me | H | Br | CN | H | 1 |
| SCF$_3$ | Me | H | Br | CN | H | 2 |
| SCF$_3$ | Me | H | I | CN | H | 0 |
| SCF$_3$ | Me | H | I | CN | H | 1 |
| SCF$_3$ | Me | H | I | CN | H | 2 |
| SCF$_3$ | Me | H | CF$_3$ | F | H | 0 |
| SCF$_3$ | Me | H | CF$_3$ | F | H | 1 |
| SCF$_3$ | Me | H | CF$_3$ | F | H | 2 |
| SCF$_3$ | Me | H | CF$_3$ | Cl | H | 0 |
| SCF$_3$ | Me | H | CF$_3$ | Cl | H | 1 |
| SCF$_3$ | Me | H | CF$_3$ | Cl | H | 2 |
| SCF$_3$ | Me | H | CF$_3$ | Br | H | 0 |
| SCF$_3$ | Me | H | CF$_3$ | Br | H | 1 |
| SCF$_3$ | Me | H | CF$_3$ | Br | H | 2 |
| SCF$_3$ | Me | H | CF$_3$ | I | H | 0 |
| SCF$_3$ | Me | H | CF$_3$ | I | H | 1 |
| SCF$_3$ | Me | H | CF$_3$ | I | H | 2 |
| SCF$_3$ | Me | H | CF$_3$ | CN | H | 0 |
| SCF$_3$ | Me | H | CF$_3$ | CN | H | 1 |
| SCF$_3$ | Me | H | CF$_3$ | CN | H | 2 |
| SCF$_3$ | Et | H | H | H | H | 0 |
| SCF$_3$ | Et | H | H | H | H | 1 |
| SCF$_3$ | Et | H | H | H | H | 2 |
| SCF$_3$ | Et | F | H | H | H | 0 |
| SCF$_3$ | Et | F | H | H | H | 1 |
| SCF$_3$ | Et | F | H | H | H | 2 |
| SCF$_3$ | Et | Cl | H | H | H | 0 |
| SCF$_3$ | Et | Cl | H | H | H | 1 |
| SCF$_3$ | Et | Cl | H | H | H | 2 |
| SCF$_3$ | Et | Br | H | H | H | 0 |
| SCF$_3$ | Et | Br | H | H | H | 1 |
| SCF$_3$ | Et | Br | H | H | H | 2 |
| SCF$_3$ | Et | I | H | H | H | 0 |
| SCF$_3$ | Et | I | H | H | H | 1 |
| SCF$_3$ | Et | I | H | H | H | 2 |
| SCF$_3$ | Et | Me | H | H | H | 0 |
| SCF$_3$ | Et | Me | H | H | H | 1 |
| SCF$_3$ | Et | Me | H | H | H | 2 |
| SCF$_3$ | Et | CF$_3$ | H | H | H | 0 |
| SCF$_3$ | Et | CF$_3$ | H | H | H | 1 |
| SCF$_3$ | Et | CF$_3$ | H | H | H | 2 |
| SCF$_3$ | Et | H | F | H | H | 0 |
| SCF$_3$ | Et | H | F | H | H | 1 |
| SCF$_3$ | Et | H | F | H | H | 2 |
| SCF$_3$ | Et | H | Cl | H | H | 0 |
| SCF$_3$ | Et | H | Cl | H | H | 1 |
| SCF$_3$ | Et | H | Cl | H | H | 2 |
| SCF$_3$ | Et | H | Br | H | H | 0 |
| SCF$_3$ | Et | H | Br | H | H | 1 |
| SCF$_3$ | Et | H | Br | H | H | 2 |
| SCF$_3$ | Et | H | I | H | H | 0 |
| SCF$_3$ | Et | H | I | H | H | 1 |
| SCF$_3$ | Et | H | I | H | H | 2 |
| SCF$_3$ | Et | H | Me | H | H | 0 |
| SCF$_3$ | Et | H | Me | H | H | 1 |
| SCF$_3$ | Et | H | Me | H | H | 2 |
| SCF$_3$ | Et | H | CF$_3$ | H | H | 0 |
| SCF$_3$ | Et | H | CF$_3$ | H | H | 1 |
| SCF$_3$ | Et | H | CF$_3$ | H | H | 2 |
| SCF$_3$ | Et | H | CF$_2$CF$_3$ | H | H | 0 |
| SCF$_3$ | Et | H | CF$_2$CF$_3$ | H | H | 1 |
| SCF$_3$ | Et | H | CF$_2$CF$_3$ | H | H | 2 |
| SCF$_3$ | Et | H | CF(CF$_3$)$_2$ | H | H | 0 |
| SCF$_3$ | Et | H | CF(CF$_3$)$_2$ | H | H | 1 |
| SCF$_3$ | Et | H | CF(CF$_3$)$_2$ | H | H | 2 |
| SCF$_3$ | Et | H | SMe | H | H | 0 |
| SCF$_3$ | Et | H | SMe | H | H | 1 |
| SCF$_3$ | Et | H | SMe | H | H | 2 |
| SCF$_3$ | Et | H | SOMe | H | H | 0 |
| SCF$_3$ | Et | H | SOMe | H | H | 1 |
| SCF$_3$ | Et | H | SOMe | H | H | 2 |
| SCF$_3$ | Et | H | SO$_2$Me | H | H | 0 |
| SCF$_3$ | Et | H | SO$_2$Me | H | H | 1 |
| SCF$_3$ | Et | H | SO$_2$Me | H | H | 2 |
| SCF$_3$ | Et | H | OMe | H | H | 0 |
| SCF$_3$ | Et | H | OMe | H | H | 1 |
| SCF$_3$ | Et | H | OMe | H | H | 2 |
| SCF$_3$ | Et | H | OCF$_3$ | H | H | 0 |
| SCF$_3$ | Et | H | OCF$_3$ | H | H | 1 |
| SCF$_3$ | Et | H | OCF$_3$ | H | H | 2 |
| SCF$_3$ | Et | H | NO$_2$ | H | H | 0 |
| SCF$_3$ | Et | H | NO$_2$ | H | H | 1 |
| SCF$_3$ | Et | H | NO$_2$ | H | H | 2 |
| SCF$_3$ | Et | H | CN | H | H | 0 |
| SCF$_3$ | Et | H | CN | H | H | 1 |
| SCF$_3$ | Et | H | CN | H | H | 2 |
| SCF$_3$ | Et | H | H | F | H | 0 |
| SCF$_3$ | Et | H | H | F | H | 1 |
| SCF$_3$ | Et | H | H | F | H | 2 |
| SCF$_3$ | Et | H | H | Cl | H | 0 |
| SCF$_3$ | Et | H | H | Cl | H | 1 |
| SCF$_3$ | Et | H | H | Cl | H | 2 |
| SCF$_3$ | Et | H | H | Br | H | 0 |
| SCF$_3$ | Et | H | H | Br | H | 1 |
| SCF$_3$ | Et | H | H | Br | H | 2 |
| SCF$_3$ | Et | H | H | I | H | 0 |
| SCF$_3$ | Et | H | H | I | H | 1 |
| SCF$_3$ | Et | H | H | I | H | 2 |
| SCF$_3$ | Et | H | H | Me | H | 0 |
| SCF$_3$ | Et | H | H | Me | H | 1 |
| SCF$_3$ | Et | H | H | Me | H | 2 |
| SCF$_3$ | Et | H | H | CF$_3$ | H | 0 |
| SCF$_3$ | Et | H | H | CF$_3$ | H | 1 |
| SCF$_3$ | Et | H | H | CF$_3$ | H | 2 |
| SCF$_3$ | Et | H | H | CF$_2$CF$_3$ | H | 0 |
| SCF$_3$ | Et | H | H | CF$_2$CF$_3$ | H | 1 |
| SCF$_3$ | Et | H | H | CF$_2$CF$_3$ | H | 2 |
| SCF$_3$ | Et | H | H | CF(CF$_3$)$_2$ | H | 0 |
| SCF$_3$ | Et | H | H | CF(CF$_3$)$_2$ | H | 1 |
| SCF$_3$ | Et | H | H | CF(CF$_3$)$_2$ | H | 2 |
| SCF$_3$ | Et | H | H | SMe | H | 0 |
| SCF$_3$ | Et | H | H | SMe | H | 1 |
| SCF$_3$ | Et | H | H | SMe | H | 2 |
| SCF$_3$ | Et | H | H | SOMe | H | 0 |
| SCF$_3$ | Et | H | H | SOMe | H | 1 |
| SCF$_3$ | Et | H | H | SOMe | H | 2 |
| SCF$_3$ | Et | H | H | SO$_2$Me | H | 0 |
| SCF$_3$ | Et | H | H | SO$_2$Me | H | 1 |
| SCF$_3$ | Et | H | H | SO$_2$Me | H | 2 |
| SCF$_3$ | Et | H | H | OMe | H | 0 |
| SCF$_3$ | Et | H | H | OMe | H | 1 |
| SCF$_3$ | Et | H | H | OMe | H | 2 |
| SCF$_3$ | Et | H | H | OCF$_3$ | H | 0 |
| SCF$_3$ | Et | H | H | OCF$_3$ | H | 1 |
| SCF$_3$ | Et | H | H | OCF$_3$ | H | 2 |
| SCF$_3$ | Et | H | H | NO$_2$ | H | 0 |
| SCF$_3$ | Et | H | H | NO$_2$ | H | 1 |
| SCF$_3$ | Et | H | H | NO$_2$ | H | 2 |
| SCF$_3$ | Et | H | H | CN | H | 0 |
| SCF$_3$ | Et | H | H | CN | H | 1 |
| SCF$_3$ | Et | H | H | CN | H | 2 |
| SCF$_3$ | Et | H | H | H | F | 0 |
| SCF$_3$ | Et | H | H | H | F | 1 |
| SCF$_3$ | Et | H | H | H | F | 2 |
| SCF$_3$ | Et | H | H | H | Cl | 0 |
| SCF$_3$ | Et | H | H | H | Cl | 1 |
| SCF$_3$ | Et | H | H | H | Cl | 2 |
| SCF$_3$ | Et | H | H | H | Br | 0 |

TABLE 1-continued

| | | | | | | |
|---|---|---|---|---|---|---|
| SCF$_3$ | Et | H | H | H | Br | 1 |
| SCF$_3$ | Et | H | H | H | Br | 2 |
| SCF$_3$ | Et | H | H | H | I | 0 |
| SCF$_3$ | Et | H | H | H | I | 1 |
| SCF$_3$ | Et | H | H | H | I | 2 |
| SCF$_3$ | Et | H | H | H | Me | 0 |
| SCF$_3$ | Et | H | H | H | Me | 1 |
| SCF$_3$ | Et | H | H | H | Me | 2 |
| SCF$_3$ | Et | H | H | H | CF$_3$ | 0 |
| SCF$_3$ | Et | H | H | H | CF$_3$ | 1 |
| SCF$_3$ | Et | H | H | H | CF$_3$ | 2 |
| SCF$_3$ | Et | H | H | H | CF$_2$CF$_3$ | 0 |
| SCF$_3$ | Et | H | H | H | CF$_2$CF$_3$ | 1 |
| SCF$_3$ | Et | H | H | H | CF$_2$CF$_3$ | 2 |
| SCF$_3$ | Et | H | H | H | CF(CF$_3$)$_2$ | 0 |
| SCF$_3$ | Et | H | H | H | CF(CF$_3$)$_2$ | 1 |
| SCF$_3$ | Et | H | H | H | CF(CF$_3$)$_2$ | 2 |
| SCF$_3$ | Et | H | H | H | SMe | 0 |
| SCF$_3$ | Et | H | H | H | SMe | 1 |
| SCF$_3$ | Et | H | H | H | SMe | 2 |
| SCF$_3$ | Et | H | H | H | SOMe | 0 |
| SCF$_3$ | Et | H | H | H | SOMe | 1 |
| SCF$_3$ | Et | H | H | H | SOMe | 2 |
| SCF$_3$ | Et | H | H | H | SO$_2$Me | 0 |
| SCF$_3$ | Et | H | H | H | SO$_2$Me | 1 |
| SCF$_3$ | Et | H | H | H | SO$_2$Me | 2 |
| SCF$_3$ | Et | H | H | H | OMe | 0 |
| SCF$_3$ | Et | H | H | H | OMe | 1 |
| SCF$_3$ | Et | H | H | H | OMe | 2 |
| SCF$_3$ | Et | H | H | H | OCF$_3$ | 0 |
| SCF$_3$ | Et | H | H | H | OCF$_3$ | 1 |
| SCF$_3$ | Et | H | H | H | OCF$_3$ | 2 |
| SCF$_3$ | Et | H | H | H | NO$_2$ | 0 |
| SCF$_3$ | Et | H | H | H | NO$_2$ | 1 |
| SCF$_3$ | Et | H | H | H | NO$_2$ | 2 |
| SCF$_3$ | Et | H | H | H | CN | 0 |
| SCF$_3$ | Et | H | H | H | CN | 1 |
| SCF$_3$ | Et | H | H | H | CN | 2 |
| SCF$_3$ | Et | H | F | H | F | 0 |
| SCF$_3$ | Et | H | F | H | F | 1 |
| SCF$_3$ | Et | H | F | H | F | 2 |
| SCF$_3$ | Et | H | Cl | H | Cl | 0 |
| SCF$_3$ | Et | H | Cl | H | Cl | 1 |
| SCF$_3$ | Et | H | Cl | H | Cl | 2 |
| SCF$_3$ | Et | H | Br | H | Br | 0 |
| SCF$_3$ | Et | H | Br | H | Br | 1 |
| SCF$_3$ | Et | H | Br | H | Br | 2 |
| SCF$_3$ | Et | H | I | H | I | 0 |
| SCF$_3$ | Et | H | I | H | I | 1 |
| SCF$_3$ | Et | H | I | H | I | 2 |
| SCF$_3$ | Et | H | F | H | Cl | 0 |
| SCF$_3$ | Et | H | F | H | Cl | 1 |
| SCF$_3$ | Et | H | F | H | Cl | 2 |
| SCF$_3$ | Et | H | F | H | Br | 0 |
| SCF$_3$ | Et | H | F | H | Br | 1 |
| SCF$_3$ | Et | H | F | H | Br | 2 |
| SCF$_3$ | Et | H | F | H | I | 0 |
| SCF$_3$ | Et | H | F | H | I | 1 |
| SCF$_3$ | Et | H | F | H | I | 2 |
| SCF$_3$ | Et | H | Cl | H | F | 0 |
| SCF$_3$ | Et | H | Cl | H | F | 1 |
| SCF$_3$ | Et | H | Cl | H | F | 2 |
| SCF$_3$ | Et | H | Cl | H | Br | 0 |
| SCF$_3$ | Et | H | Cl | H | Br | 1 |
| SCF$_3$ | Et | H | Cl | H | Br | 2 |
| SCF$_3$ | Et | H | Cl | H | I | 0 |
| SCF$_3$ | Et | H | Cl | H | I | 1 |
| SCF$_3$ | Et | H | Cl | H | I | 2 |
| SCF$_3$ | Et | H | Br | H | F | 0 |
| SCF$_3$ | Et | H | Br | H | F | 1 |
| SCF$_3$ | Et | H | Br | H | F | 2 |
| SCF$_3$ | Et | H | Br | H | Cl | 0 |
| SCF$_3$ | Et | H | Br | H | Cl | 1 |
| SCF$_3$ | Et | H | Br | H | Cl | 2 |
| SCF$_3$ | Et | H | Br | H | I | 0 |
| SCF$_3$ | Et | H | Br | H | I | 1 |
| SCF$_3$ | Et | H | Br | H | I | 2 |
| SCF$_3$ | Et | H | I | H | F | 0 |
| SCF$_3$ | Et | H | I | H | F | 1 |
| SCF$_3$ | Et | H | I | H | F | 2 |
| SCF$_3$ | Et | H | I | H | Cl | 0 |
| SCF$_3$ | Et | H | I | H | Cl | 1 |
| SCF$_3$ | Et | H | I | H | Cl | 2 |
| SCF$_3$ | Et | H | I | H | Br | 0 |
| SCF$_3$ | Et | H | I | H | Br | 1 |
| SCF$_3$ | Et | H | I | H | Br | 2 |
| SCF$_3$ | Et | H | F | H | CN | 0 |
| SCF$_3$ | Et | H | F | H | CN | 1 |
| SCF$_3$ | Et | H | F | H | CN | 2 |
| SCF$_3$ | Et | H | Cl | H | CN | 0 |
| SCF$_3$ | Et | H | Cl | H | CN | 1 |
| SCF$_3$ | Et | H | Cl | H | CN | 2 |
| SCF$_3$ | Et | H | Br | H | CN | 0 |
| SCF$_3$ | Et | H | Br | H | CN | 1 |
| SCF$_3$ | Et | H | Br | H | CN | 2 |
| SCF$_3$ | Et | H | I | H | CN | 0 |
| SCF$_3$ | Et | H | I | H | CN | 1 |
| SCF$_3$ | Et | H | I | H | CN | 2 |
| SCF$_3$ | Et | H | CF$_3$ | H | F | 0 |
| SCF$_3$ | Et | H | CF$_3$ | H | F | 1 |
| SCF$_3$ | Et | H | CF$_3$ | H | F | 2 |
| SCF$_3$ | Et | H | CF$_3$ | H | Cl | 0 |
| SCF$_3$ | Et | H | CF$_3$ | H | Cl | 1 |
| SCF$_3$ | Et | H | CF$_3$ | H | Cl | 2 |
| SCF$_3$ | Et | H | CF$_3$ | H | Br | 0 |
| SCF$_3$ | Et | H | CF$_3$ | H | Br | 1 |
| SCF$_3$ | Et | H | CF$_3$ | H | Br | 2 |
| SCF$_3$ | Et | H | CF$_3$ | H | I | 0 |
| SCF$_3$ | Et | H | CF$_3$ | H | I | 1 |
| SCF$_3$ | Et | H | CF$_3$ | H | I | 2 |
| SCF$_3$ | Et | H | CF$_3$ | H | CN | 0 |
| SCF$_3$ | Et | H | CF$_3$ | H | CN | 1 |
| SCF$_3$ | Et | H | CF$_3$ | H | CN | 2 |
| SCF$_3$ | Et | H | F | F | H | 0 |
| SCF$_3$ | Et | H | F | F | H | 1 |
| SCF$_3$ | Et | H | F | F | H | 2 |
| SCF$_3$ | Et | H | Cl | Cl | H | 0 |
| SCF$_3$ | Et | H | Cl | Cl | H | 1 |
| SCF$_3$ | Et | H | Cl | Cl | H | 2 |
| SCF$_3$ | Et | H | Br | Br | H | 0 |
| SCF$_3$ | Et | H | Br | Br | H | 1 |
| SCF$_3$ | Et | H | Br | Br | H | 2 |
| SCF$_3$ | Et | H | I | I | H | 0 |
| SCF$_3$ | Et | H | I | I | H | 1 |
| SCF$_3$ | Et | H | I | I | H | 2 |
| SCF$_3$ | Et | H | F | Cl | H | 0 |
| SCF$_3$ | Et | H | F | Cl | H | 1 |
| SCF$_3$ | Et | H | F | Cl | H | 2 |
| SCF$_3$ | Et | H | F | Br | H | 0 |
| SCF$_3$ | Et | H | F | Br | H | 1 |
| SCF$_3$ | Et | H | F | Br | H | 2 |
| SCF$_3$ | Et | H | F | I | H | 0 |
| SCF$_3$ | Et | H | F | I | H | 1 |
| SCF$_3$ | Et | H | F | I | H | 2 |
| SCF$_3$ | Et | H | Cl | F | H | 0 |
| SCF$_3$ | Et | H | Cl | F | H | 1 |
| SCF$_3$ | Et | H | Cl | F | H | 2 |
| SCF$_3$ | Et | H | Cl | Br | H | 0 |
| SCF$_3$ | Et | H | Cl | Br | H | 1 |
| SCF$_3$ | Et | H | Cl | Br | H | 2 |
| SCF$_3$ | Et | H | Cl | I | H | 0 |
| SCF$_3$ | Et | H | Cl | I | H | 1 |
| SCF$_3$ | Et | H | Cl | I | H | 2 |
| SCF$_3$ | Et | H | Br | F | H | 0 |
| SCF$_3$ | Et | H | Br | F | H | 1 |
| SCF$_3$ | Et | H | Br | F | H | 2 |
| SCF$_3$ | Et | H | Br | Cl | H | 0 |
| SCF$_3$ | Et | H | Br | Cl | H | 1 |
| SCF$_3$ | Et | H | Br | Cl | H | 2 |
| SCF$_3$ | Et | H | Br | I | H | 0 |
| SCF$_3$ | Et | H | Br | I | H | 1 |
| SCF$_3$ | Et | H | Br | I | H | 2 |
| SCF$_3$ | Et | H | I | F | H | 0 |
| SCF$_3$ | Et | H | I | F | H | 1 |
| SCF$_3$ | Et | H | I | F | H | 2 |
| SCF$_3$ | Et | H | I | Cl | H | 0 |
| SCF$_3$ | Et | H | I | Cl | H | 1 |
| SCF$_3$ | Et | H | I | Cl | H | 2 |
| SCF$_3$ | Et | H | I | Br | H | 0 |
| SCF$_3$ | Et | H | I | Br | H | 1 |

TABLE 1-continued

| | | | | | | |
|---|---|---|---|---|---|---|
| SCF₃ | Et | H | I | Br | H | 2 |
| SCF₃ | Et | H | F | CN | H | 0 |
| SCF₃ | Et | H | F | CN | H | 1 |
| SCF₃ | Et | H | F | CN | H | 2 |
| SCF₃ | Et | H | Cl | CN | H | 0 |
| SCF₃ | Et | H | Cl | CN | H | 1 |
| SCF₃ | Et | H | Cl | CN | H | 2 |
| SCF₃ | Et | H | Br | CN | H | 0 |
| SCF₃ | Et | H | Br | CN | H | 1 |
| SCF₃ | Et | H | Br | CN | H | 2 |
| SCF₃ | Et | H | I | CN | H | 0 |
| SCF₃ | Et | H | I | CN | H | 1 |
| SCF₃ | Et | H | I | CN | H | 2 |
| SCF₃ | Et | H | CF₃ | F | H | 0 |
| SCF₃ | Et | H | CF₃ | F | H | 1 |
| SCF₃ | Et | H | CF₃ | F | H | 2 |
| SCF₃ | Et | H | CF₃ | Cl | H | 0 |
| SCF₃ | Et | H | CF₃ | Cl | H | 1 |
| SCF₃ | Et | H | CF₃ | Cl | H | 2 |
| SCF₃ | Et | H | CF₃ | Br | H | 0 |
| SCF₃ | Et | H | CF₃ | Br | H | 1 |
| SCF₃ | Et | H | CF₃ | Br | H | 2 |
| SCF₃ | Et | H | CF₃ | I | H | 0 |
| SCF₃ | Et | H | CF₃ | I | H | 1 |
| SCF₃ | Et | H | CF₃ | I | H | 2 |
| SCF₃ | Et | H | CF₃ | CN | H | 0 |
| SCF₃ | Et | H | CF₃ | CN | H | 1 |
| SCF₃ | Et | H | CF₃ | CN | H | 2 |
| SCF₃ | ⁿPr | H | H | H | H | 0 |
| SCF₃ | ⁿPr | H | H | H | H | 1 |
| SCF₃ | ⁿPr | H | H | H | H | 2 |
| SCF₃ | ⁿPr | F | H | H | H | 0 |
| SCF₃ | ⁿPr | F | H | H | H | 1 |
| SCF₃ | ⁿPr | F | H | H | H | 2 |
| SCF₃ | ⁿPr | Cl | H | H | H | 0 |
| SCF₃ | ⁿPr | Cl | H | H | H | 1 |
| SCF₃ | ⁿPr | Cl | H | H | H | 2 |
| SCF₃ | ⁿPr | Br | H | H | H | 0 |
| SCF₃ | ⁿPr | Br | H | H | H | 1 |
| SCF₃ | ⁿPr | Br | H | H | H | 2 |
| SCF₃ | ⁿPr | I | H | H | H | 0 |
| SCF₃ | ⁿPr | I | H | H | H | 1 |
| SCF₃ | ⁿPr | I | H | H | H | 2 |
| SCF₃ | ⁿPr | Me | H | H | H | 0 |
| SCF₃ | ⁿPr | Me | H | H | H | 1 |
| SCF₃ | ⁿPr | Me | H | H | H | 2 |
| SCF₃ | ⁿPr | CF₃ | H | H | H | 0 |
| SCF₃ | ⁿPr | CF₃ | H | H | H | 1 |
| SCF₃ | ⁿPr | CF₃ | H | H | H | 2 |
| SCF₃ | ⁿPr | H | F | H | H | 0 |
| SCF₃ | ⁿPr | H | F | H | H | 1 |
| SCF₃ | ⁿPr | H | F | H | H | 2 |
| SCF₃ | ⁿPr | H | Cl | H | H | 0 |
| SCF₃ | ⁿPr | H | Cl | H | H | 1 |
| SCF₃ | ⁿPr | H | Cl | H | H | 2 |
| SCF₃ | ⁿPr | H | Br | H | H | 0 |
| SCF₃ | ⁿPr | H | Br | H | H | 1 |
| SCF₃ | ⁿPr | H | Br | H | H | 2 |
| SCF₃ | ⁿPr | H | I | H | H | 0 |
| SCF₃ | ⁿPr | H | I | H | H | 1 |
| SCF₃ | ⁿPr | H | I | H | H | 2 |
| SCF₃ | ⁿPr | H | Me | H | H | 0 |
| SCF₃ | ⁿPr | H | Me | H | H | 1 |
| SCF₃ | ⁿPr | H | Me | H | H | 2 |
| SCF₃ | ⁿPr | H | CF₃ | H | H | 0 |
| SCF₃ | ⁿPr | H | CF₃ | H | H | 1 |
| SCF₃ | ⁿPr | H | CF₃ | H | H | 2 |
| SCF₃ | ⁿPr | H | CF₂CF₃ | H | H | 0 |
| SCF₃ | ⁿPr | H | CF₂CF₃ | H | H | 1 |
| SCF₃ | ⁿPr | H | CF₂CF₃ | H | H | 2 |
| SCF₃ | ⁿPr | H | CF(CF₃)₂ | H | H | 0 |
| SCF₃ | ⁿPr | H | CF(CF₃)₂ | H | H | 1 |
| SCF₃ | ⁿPr | H | CF(CF₃)₂ | H | H | 2 |
| SCF₃ | ⁿPr | H | SMe | H | H | 0 |
| SCF₃ | ⁿPr | H | SMe | H | H | 1 |
| SCF₃ | ⁿPr | H | SMe | H | H | 2 |
| SCF₃ | ⁿPr | H | SOMe | H | H | 0 |
| SCF₃ | ⁿPr | H | SOMe | H | H | 1 |
| SCF₃ | ⁿPr | H | SOMe | H | H | 2 |
| SCF₃ | ⁿPr | H | SO₂Me | H | H | 0 |
| SCF₃ | ⁿPr | H | SO₂Me | H | H | 1 |
| SCF₃ | ⁿPr | H | SO₂Me | H | H | 2 |
| SCF₃ | ⁿPr | H | OMe | H | H | 0 |
| SCF₃ | ⁿPr | H | OMe | H | H | 1 |
| SCF₃ | ⁿPr | H | OMe | H | H | 2 |
| SCF₃ | ⁿPr | H | OCF₃ | H | H | 0 |
| SCF₃ | ⁿPr | H | OCF₃ | H | H | 1 |
| SCF₃ | ⁿPr | H | OCF₃ | H | H | 2 |
| SCF₃ | ⁿPr | H | NO₂ | H | H | 0 |
| SCF₃ | ⁿPr | H | NO₂ | H | H | 1 |
| SCF₃ | ⁿPr | H | NO₂ | H | H | 2 |
| SCF₃ | ⁿPr | H | CN | H | H | 0 |
| SCF₃ | ⁿPr | H | CN | H | H | 1 |
| SCF₃ | ⁿPr | H | CN | H | H | 2 |
| SCF₃ | ⁿPr | H | H | F | H | 0 |
| SCF₃ | ⁿPr | H | H | F | H | 1 |
| SCF₃ | ⁿPr | H | H | F | H | 2 |
| SCF₃ | ⁿPr | H | H | Cl | H | 0 |
| SCF₃ | ⁿPr | H | H | Cl | H | 1 |
| SCF₃ | ⁿPr | H | H | Cl | H | 2 |
| SCF₃ | ⁿPr | H | H | Br | H | 0 |
| SCF₃ | ⁿPr | H | H | Br | H | 1 |
| SCF₃ | ⁿPr | H | H | Br | H | 2 |
| SCF₃ | ⁿPr | H | H | I | H | 0 |
| SCF₃ | ⁿPr | H | H | I | H | 1 |
| SCF₃ | ⁿPr | H | H | I | H | 2 |
| SCF₃ | ⁿPr | H | H | Me | H | 0 |
| SCF₃ | ⁿPr | H | H | Me | H | 1 |
| SCF₃ | ⁿPr | H | H | Me | H | 2 |
| SCF₃ | ⁿPr | H | H | CF₃ | H | 0 |
| SCF₃ | ⁿPr | H | H | CF₃ | H | 1 |
| SCF₃ | ⁿPr | H | H | CF₃ | H | 2 |
| SCF₃ | ⁿPr | H | H | CF₂CF₃ | H | 0 |
| SCF₃ | ⁿPr | H | H | CF₂CF₃ | H | 1 |
| SCF₃ | ⁿPr | H | H | CF₂CF₃ | H | 2 |
| SCF₃ | ⁿPr | H | H | CF(CF₃)₂ | H | 0 |
| SCF₃ | ⁿPr | H | H | CF(CF₃)₂ | H | 1 |
| SCF₃ | ⁿPr | H | H | CF(CF₃)₂ | H | 2 |
| SCF₃ | ⁿPr | H | H | SMe | H | 0 |
| SCF₃ | ⁿPr | H | H | SMe | H | 1 |
| SCF₃ | ⁿPr | H | H | SMe | H | 2 |
| SCF₃ | ⁿPr | H | H | SOMe | H | 0 |
| SCF₃ | ⁿPr | H | H | SOMe | H | 1 |
| SCF₃ | ⁿPr | H | H | SOMe | H | 2 |
| SCF₃ | ⁿPr | H | H | SO₂Me | H | 0 |
| SCF₃ | ⁿPr | H | H | SO₂Me | H | 1 |
| SCF₃ | ⁿPr | H | H | SO₂Me | H | 2 |
| SCF₃ | ⁿPr | H | H | OMe | H | 0 |
| SCF₃ | ⁿPr | H | H | OMe | H | 1 |
| SCF₃ | ⁿPr | H | H | OMe | H | 2 |
| SCF₃ | ⁿPr | H | H | OCF₃ | H | 0 |
| SCF₃ | ⁿPr | H | H | OCF₃ | H | 1 |
| SCF₃ | ⁿPr | H | H | OCF₃ | H | 2 |
| SCF₃ | ⁿPr | H | H | NO₂ | H | 0 |
| SCF₃ | ⁿPr | H | H | NO₂ | H | 1 |
| SCF₃ | ⁿPr | H | H | NO₂ | H | 2 |
| SCF₃ | ⁿPr | H | H | CN | H | 0 |
| SCF₃ | ⁿPr | H | H | CN | H | 1 |
| SCF₃ | ⁿPr | H | H | CN | H | 2 |
| SCF₃ | ⁿPr | H | H | H | F | 0 |
| SCF₃ | ⁿPr | H | H | H | F | 1 |
| SCF₃ | ⁿPr | H | H | H | F | 2 |
| SCF₃ | ⁿPr | H | H | H | Cl | 0 |
| SCF₃ | ⁿPr | H | H | H | Cl | 1 |
| SCF₃ | ⁿPr | H | H | H | Cl | 2 |
| SCF₃ | ⁿPr | H | H | H | Br | 0 |
| SCF₃ | ⁿPr | H | H | H | Br | 1 |
| SCF₃ | ⁿPr | H | H | H | Br | 2 |
| SCF₃ | ⁿPr | H | H | H | I | 0 |
| SCF₃ | ⁿPr | H | H | H | I | 1 |
| SCF₃ | ⁿPr | H | H | H | I | 2 |
| SCF₃ | ⁿPr | H | H | H | Me | 0 |
| SCF₃ | ⁿPr | H | H | H | Me | 1 |
| SCF₃ | ⁿPr | H | H | H | Me | 2 |
| SCF₃ | ⁿPr | H | H | H | CF₃ | 0 |
| SCF₃ | ⁿPr | H | H | H | CF₃ | 1 |
| SCF₃ | ⁿPr | H | H | H | CF₃ | 2 |
| SCF₃ | ⁿPr | H | H | H | CF₂CF₃ | 0 |
| SCF₃ | ⁿPr | H | H | H | CF₂CF₃ | 1 |
| SCF₃ | ⁿPr | H | H | H | CF₂CF₃ | 2 |

TABLE 1-continued

| | | | | | | |
|---|---|---|---|---|---|---|
| SCF₃ | ⁿPr | H | H | H | CF(CF₃)₂ | 0 |
| SCF₃ | ⁿPr | H | H | H | CF(CF₃)₂ | 1 |
| SCF₃ | ⁿPr | H | H | H | CF(CF₃)₂ | 2 |
| SCF₃ | ⁿPr | H | H | H | SMe | 0 |
| SCF₃ | ⁿPr | H | H | H | SMe | 1 |
| SCF₃ | ⁿPr | H | H | H | SMe | 2 |
| SCF₃ | ⁿPr | H | H | H | SOMe | 0 |
| SCF₃ | ⁿPr | H | H | H | SOMe | 1 |
| SCF₃ | ⁿPr | H | H | H | SOMe | 2 |
| SCF₃ | ⁿPr | H | H | H | SO₂Me | 0 |
| SCF₃ | ⁿPr | H | H | H | SO₂Me | 1 |
| SCF₃ | ⁿPr | H | H | H | SO₂Me | 2 |
| SCF₃ | ⁿPr | H | H | H | OMe | 0 |
| SCF₃ | ⁿPr | H | H | H | OMe | 1 |
| SCF₃ | ⁿPr | H | H | H | OMe | 2 |
| SCF₃ | ⁿPr | H | H | H | OCF₃ | 0 |
| SCF₃ | ⁿPr | H | H | H | OCF₃ | 1 |
| SCF₃ | ⁿPr | H | H | H | OCF₃ | 2 |
| SCF₃ | ⁿPr | H | H | H | NO₂ | 0 |
| SCF₃ | ⁿPr | H | H | H | NO₂ | 1 |
| SCF₃ | ⁿPr | H | H | H | NO₂ | 2 |
| SCF₃ | ⁿPr | H | H | H | CN | 0 |
| SCF₃ | ⁿPr | H | H | H | CN | 1 |
| SCF₃ | ⁿPr | H | H | H | CN | 2 |
| SCF₃ | ⁿPr | H | F | H | F | 0 |
| SCF₃ | ⁿPr | H | F | H | F | 1 |
| SCF₃ | ⁿPr | H | F | H | F | 2 |
| SCF₃ | ⁿPr | H | Cl | H | Cl | 0 |
| SCF₃ | ⁿPr | H | Cl | H | Cl | 1 |
| SCF₃ | ⁿPr | H | Cl | H | Cl | 2 |
| SCF₃ | ⁿPr | H | Br | H | Br | 0 |
| SCF₃ | ⁿPr | H | Br | H | Br | 1 |
| SCF₃ | ⁿPr | H | Br | H | Br | 2 |
| SCF₃ | ⁿPr | H | I | H | I | 0 |
| SCF₃ | ⁿPr | H | I | H | I | 1 |
| SCF₃ | ⁿPr | H | I | H | I | 2 |
| SCF₃ | ⁿPr | H | F | H | Cl | 0 |
| SCF₃ | ⁿPr | H | F | H | Cl | 1 |
| SCF₃ | ⁿPr | H | F | H | Cl | 2 |
| SCF₃ | ⁿPr | H | F | H | Br | 0 |
| SCF₃ | ⁿPr | H | F | H | Br | 1 |
| SCF₃ | ⁿPr | H | F | H | Br | 2 |
| SCF₃ | ⁿPr | H | F | H | I | 0 |
| SCF₃ | ⁿPr | H | F | H | I | 1 |
| SCF₃ | ⁿPr | H | F | H | I | 2 |
| SCF₃ | ⁿPr | H | Cl | H | F | 0 |
| SCF₃ | ⁿPr | H | Cl | H | F | 1 |
| SCF₃ | ⁿPr | H | Cl | H | F | 2 |
| SCF₃ | ⁿPr | H | Cl | H | Br | 0 |
| SCF₃ | ⁿPr | H | Cl | H | Br | 1 |
| SCF₃ | ⁿPr | H | Cl | H | Br | 2 |
| SCF₃ | ⁿPr | H | Cl | H | I | 0 |
| SCF₃ | ⁿPr | H | Cl | H | I | 1 |
| SCF₃ | ⁿPr | H | Cl | H | I | 2 |
| SCF₃ | ⁿPr | H | Br | H | F | 0 |
| SCF₃ | ⁿPr | H | Br | H | F | 1 |
| SCF₃ | ⁿPr | H | Br | H | F | 2 |
| SCF₃ | ⁿPr | H | Br | H | Cl | 0 |
| SCF₃ | ⁿPr | H | Br | H | Cl | 1 |
| SCF₃ | ⁿPr | H | Br | H | Cl | 2 |
| SCF₃ | ⁿPr | H | Br | H | I | 0 |
| SCF₃ | ⁿPr | H | Br | H | I | 1 |
| SCF₃ | ⁿPr | H | Br | H | I | 2 |
| SCF₃ | ⁿPr | H | I | H | F | 0 |
| SCF₃ | ⁿPr | H | I | H | F | 1 |
| SCF₃ | ⁿPr | H | I | H | F | 2 |
| SCF₃ | ⁿPr | H | I | H | Cl | 0 |
| SCF₃ | ⁿPr | H | I | H | Cl | 1 |
| SCF₃ | ⁿPr | H | I | H | Cl | 2 |
| SCF₃ | ⁿPr | H | I | H | Br | 0 |
| SCF₃ | ⁿPr | H | I | H | Br | 1 |
| SCF₃ | ⁿPr | H | I | H | Br | 2 |
| SCF₃ | ⁿPr | H | F | H | CN | 0 |
| SCF₃ | ⁿPr | H | F | H | CN | 1 |
| SCF₃ | ⁿPr | H | F | H | CN | 2 |
| SCF₃ | ⁿPr | H | Cl | H | CN | 0 |
| SCF₃ | ⁿPr | H | Cl | H | CN | 1 |
| SCF₃ | ⁿPr | H | Cl | H | CN | 2 |
| SCF₃ | ⁿPr | H | Br | H | CN | 0 |
| SCF₃ | ⁿPr | H | Br | H | CN | 1 |
| SCF₃ | ⁿPr | H | Br | H | CN | 2 |
| SCF₃ | ⁿPr | H | I | H | CN | 0 |
| SCF₃ | ⁿPr | H | I | H | CN | 1 |
| SCF₃ | ⁿPr | H | I | H | CN | 2 |
| SCF₃ | ⁿPr | H | CF₃ | H | F | 0 |
| SCF₃ | ⁿPr | H | CF₃ | H | F | 1 |
| SCF₃ | ⁿPr | H | CF₃ | H | F | 2 |
| SCF₃ | ⁿPr | H | CF₃ | H | Cl | 0 |
| SCF₃ | ⁿPr | H | CF₃ | H | Cl | 1 |
| SCF₃ | ⁿPr | H | CF₃ | H | Cl | 2 |
| SCF₃ | ⁿPr | H | CF₃ | H | Br | 0 |
| SCF₃ | ⁿPr | H | CF₃ | H | Br | 1 |
| SCF₃ | ⁿPr | H | CF₃ | H | Br | 2 |
| SCF₃ | ⁿPr | H | CF₃ | H | I | 0 |
| SCF₃ | ⁿPr | H | CF₃ | H | I | 1 |
| SCF₃ | ⁿPr | H | CF₃ | H | I | 2 |
| SCF₃ | ⁿPr | H | CF₃ | H | CN | 0 |
| SCF₃ | ⁿPr | H | CF₃ | H | CN | 1 |
| SCF₃ | ⁿPr | H | CF₃ | H | CN | 2 |
| SCF₃ | ⁿPr | H | F | F | H | 0 |
| SCF₃ | ⁿPr | H | F | F | H | 1 |
| SCF₃ | ⁿPr | H | F | F | H | 2 |
| SCF₃ | ⁿPr | H | Cl | Cl | H | 0 |
| SCF₃ | ⁿPr | H | Cl | Cl | H | 1 |
| SCF₃ | ⁿPr | H | Cl | Cl | H | 2 |
| SCF₃ | ⁿPr | H | Br | Br | H | 0 |
| SCF₃ | ⁿPr | H | Br | Br | H | 1 |
| SCF₃ | ⁿPr | H | Br | Br | H | 2 |
| SCF₃ | ⁿPr | H | I | I | H | 0 |
| SCF₃ | ⁿPr | H | I | I | H | 1 |
| SCF₃ | ⁿPr | H | I | I | H | 2 |
| SCF₃ | ⁿPr | H | F | Cl | H | 0 |
| SCF₃ | ⁿPr | H | F | Cl | H | 1 |
| SCF₃ | ⁿPr | H | F | Cl | H | 2 |
| SCF₃ | ⁿPr | H | F | Br | H | 0 |
| SCF₃ | ⁿPr | H | F | Br | H | 1 |
| SCF₃ | ⁿPr | H | F | Br | H | 2 |
| SCF₃ | ⁿPr | H | F | I | H | 0 |
| SCF₃ | ⁿPr | H | F | I | H | 1 |
| SCF₃ | ⁿPr | H | F | I | H | 2 |
| SCF₃ | ⁿPr | H | Cl | F | H | 0 |
| SCF₃ | ⁿPr | H | Cl | F | H | 1 |
| SCF₃ | ⁿPr | H | Cl | F | H | 2 |
| SCF₃ | ⁿPr | H | Cl | Br | H | 0 |
| SCF₃ | ⁿPr | H | Cl | Br | H | 1 |
| SCF₃ | ⁿPr | H | Cl | Br | H | 2 |
| SCF₃ | ⁿPr | H | Cl | I | H | 0 |
| SCF₃ | ⁿPr | H | Cl | I | H | 1 |
| SCF₃ | ⁿPr | H | Cl | I | H | 2 |
| SCF₃ | ⁿPr | H | Br | F | H | 0 |
| SCF₃ | ⁿPr | H | Br | F | H | 1 |
| SCF₃ | ⁿPr | H | Br | F | H | 2 |
| SCF₃ | ⁿPr | H | Br | Cl | H | 0 |
| SCF₃ | ⁿPr | H | Br | Cl | H | 1 |
| SCF₃ | ⁿPr | H | Br | Cl | H | 2 |
| SCF₃ | ⁿPr | H | Br | I | H | 0 |
| SCF₃ | ⁿPr | H | Br | I | H | 1 |
| SCF₃ | ⁿPr | H | Br | I | H | 2 |
| SCF₃ | ⁿPr | H | I | F | H | 0 |
| SCF₃ | ⁿPr | H | I | F | H | 1 |
| SCF₃ | ⁿPr | H | I | F | H | 2 |
| SCF₃ | ⁿPr | H | I | Cl | H | 0 |
| SCF₃ | ⁿPr | H | I | Cl | H | 1 |
| SCF₃ | ⁿPr | H | I | Cl | H | 2 |
| SCF₃ | ⁿPr | H | I | Br | H | 0 |
| SCF₃ | ⁿPr | H | I | Br | H | 1 |
| SCF₃ | ⁿPr | H | I | Br | H | 2 |
| SCF₃ | ⁿPr | H | F | CN | H | 0 |
| SCF₃ | ⁿPr | H | F | CN | H | 1 |
| SCF₃ | ⁿPr | H | F | CN | H | 2 |
| SCF₃ | ⁿPr | H | Cl | CN | H | 0 |
| SCF₃ | ⁿPr | H | Cl | CN | H | 1 |
| SCF₃ | ⁿPr | H | Cl | CN | H | 2 |
| SCF₃ | ⁿPr | H | Br | CN | H | 0 |
| SCF₃ | ⁿPr | H | Br | CN | H | 1 |
| SCF₃ | ⁿPr | H | Br | CN | H | 2 |
| SCF₃ | ⁿPr | H | I | CN | H | 0 |
| SCF₃ | ⁿPr | H | I | CN | H | 1 |
| SCF₃ | ⁿPr | H | I | CN | H | 2 |
| SCF₃ | ⁿPr | H | CF₃ | F | H | 0 |

TABLE 1-continued

| | | | | | | |
|---|---|---|---|---|---|---|
| SCF₃ | ⁿPr | H | CF₃ | F | H | 1 |
| SCF₃ | ⁿPr | H | CF₃ | F | H | 2 |
| SCF₃ | ⁿPr | H | CF₃ | Cl | H | 0 |
| SCF₃ | ⁿPr | H | CF₃ | Cl | H | 1 |
| SCF₃ | ⁿPr | H | CF₃ | Cl | H | 2 |
| SCF₃ | ⁿPr | H | CF₃ | Br | H | 0 |
| SCF₃ | ⁿPr | H | CF₃ | Br | H | 1 |
| SCF₃ | ⁿPr | H | CF₃ | Br | H | 2 |
| SCF₃ | ⁿPr | H | CF₃ | I | H | 0 |
| SCF₃ | ⁿPr | H | CF₃ | I | H | 1 |
| SCF₃ | ⁿPr | H | CF₃ | I | H | 2 |
| SCF₃ | ⁿPr | H | CF₃ | CN | H | 0 |
| SCF₃ | ⁿPr | H | CF₃ | CN | H | 1 |
| SCF₃ | ⁿPr | H | CF₃ | CN | H | 2 |
| SCF₃ | ⁱPr | H | H | H | H | 0 |
| SCF₃ | ⁱPr | H | H | H | H | 1 |
| SCF₃ | ⁱPr | H | H | H | H | 2 |
| SCF₃ | ⁱPr | F | H | H | H | 0 |
| SCF₃ | ⁱPr | F | H | H | H | 1 |
| SCF₃ | ⁱPr | F | H | H | H | 2 |
| SCF₃ | ⁱPr | Cl | H | H | H | 0 |
| SCF₃ | ⁱPr | Cl | H | H | H | 1 |
| SCF₃ | ⁱPr | Cl | H | H | H | 2 |
| SCF₃ | ⁱPr | Br | H | H | H | 0 |
| SCF₃ | ⁱPr | Br | H | H | H | 1 |
| SCF₃ | ⁱPr | Br | H | H | H | 2 |
| SCF₃ | ⁱPr | I | H | H | H | 0 |
| SCF₃ | ⁱPr | I | H | H | H | 1 |
| SCF₃ | ⁱPr | I | H | H | H | 2 |
| SCF₃ | ⁱPr | Me | H | H | H | 0 |
| SCF₃ | ⁱPr | Me | H | H | H | 1 |
| SCF₃ | ⁱPr | Me | H | H | H | 2 |
| SCF₃ | ⁱPr | CF₃ | H | H | H | 0 |
| SCF₃ | ⁱPr | CF₃ | H | H | H | 1 |
| SCF₃ | ⁱPr | CF₃ | H | H | H | 2 |
| SCF₃ | ⁱPr | H | F | H | H | 0 |
| SCF₃ | ⁱPr | H | F | H | H | 1 |
| SCF₃ | ⁱPr | H | F | H | H | 2 |
| SCF₃ | ⁱPr | H | Cl | H | H | 0 |
| SCF₃ | ⁱPr | H | Cl | H | H | 1 |
| SCF₃ | ⁱPr | H | Cl | H | H | 2 |
| SCF₃ | ⁱPr | H | Br | H | H | 0 |
| SCF₃ | ⁱPr | H | Br | H | H | 1 |
| SCF₃ | ⁱPr | H | Br | H | H | 2 |
| SCF₃ | ⁱPr | H | I | H | H | 0 |
| SCF₃ | ⁱPr | H | I | H | H | 1 |
| SCF₃ | ⁱPr | H | I | H | H | 2 |
| SCF₃ | ⁱPr | H | Me | H | H | 0 |
| SCF₃ | ⁱPr | H | Me | H | H | 1 |
| SCF₃ | ⁱPr | H | Me | H | H | 2 |
| SCF₃ | ⁱPr | H | CF₃ | H | H | 0 |
| SCF₃ | ⁱPr | H | CF₃ | H | H | 1 |
| SCF₃ | ⁱPr | H | CF₃ | H | H | 2 |
| SCF₃ | ⁱPr | H | CF₂CF₃ | H | H | 0 |
| SCF₃ | ⁱPr | H | CF₂CF₃ | H | H | 1 |
| SCF₃ | ⁱPr | H | CF₂CF₃ | H | H | 2 |
| SCF₃ | ⁱPr | H | CF(CF₃)₂ | H | H | 0 |
| SCF₃ | ⁱPr | H | CF(CF₃)₂ | H | H | 1 |
| SCF₃ | ⁱPr | H | CF(CF₃)₂ | H | H | 2 |
| SCF₃ | ⁱPr | H | SMe | H | H | 0 |
| SCF₃ | ⁱPr | H | SMe | H | H | 1 |
| SCF₃ | ⁱPr | H | SMe | H | H | 2 |
| SCF₃ | ⁱPr | H | SOMe | H | H | 0 |
| SCF₃ | ⁱPr | H | SOMe | H | H | 1 |
| SCF₃ | ⁱPr | H | SOMe | H | H | 2 |
| SCF₃ | ⁱPr | H | SO₂Me | H | H | 0 |
| SCF₃ | ⁱPr | H | SO₂Me | H | H | 1 |
| SCF₃ | ⁱPr | H | SO₂Me | H | H | 2 |
| SCF₃ | ⁱPr | H | OMe | H | H | 0 |
| SCF₃ | ⁱPr | H | OMe | H | H | 1 |
| SCF₃ | ⁱPr | H | OMe | H | H | 2 |
| SCF₃ | ⁱPr | H | OCF₃ | H | H | 0 |
| SCF₃ | ⁱPr | H | OCF₃ | H | H | 1 |
| SCF₃ | ⁱPr | H | OCF₃ | H | H | 2 |
| SCF₃ | ⁱPr | H | NO₂ | H | H | 0 |
| SCF₃ | ⁱPr | H | NO₂ | H | H | 1 |
| SCF₃ | ⁱPr | H | NO₂ | H | H | 2 |
| SCF₃ | ⁱPr | H | CN | H | H | 0 |
| SCF₃ | ⁱPr | H | CN | H | H | 1 |
| SCF₃ | ⁱPr | H | CN | H | H | 2 |
| SCF₃ | ⁱPr | H | H | F | H | 0 |
| SCF₃ | ⁱPr | H | H | F | H | 1 |
| SCF₃ | ⁱPr | H | H | F | H | 2 |
| SCF₃ | ⁱPr | H | H | Cl | H | 0 |
| SCF₃ | ⁱPr | H | H | Cl | H | 1 |
| SCF₃ | ⁱPr | H | H | Cl | H | 2 |
| SCF₃ | ⁱPr | H | H | Br | H | 0 |
| SCF₃ | ⁱPr | H | H | Br | H | 1 |
| SCF₃ | ⁱPr | H | H | Br | H | 2 |
| SCF₃ | ⁱPr | H | H | I | H | 0 |
| SCF₃ | ⁱPr | H | H | I | H | 1 |
| SCF₃ | ⁱPr | H | H | I | H | 2 |
| SCF₃ | ⁱPr | H | H | Me | H | 0 |
| SCF₃ | ⁱPr | H | H | Me | H | 1 |
| SCF₃ | ⁱPr | H | H | Me | H | 2 |
| SCF₃ | ⁱPr | H | H | CF₃ | H | 0 |
| SCF₃ | ⁱPr | H | H | CF₃ | H | 1 |
| SCF₃ | ⁱPr | H | H | CF₃ | H | 2 |
| SCF₃ | ⁱPr | H | H | CF₂CF₃ | H | 0 |
| SCF₃ | ⁱPr | H | H | CF₂CF₃ | H | 1 |
| SCF₃ | ⁱPr | H | H | CF₂CF₃ | H | 2 |
| SCF₃ | ⁱPr | H | H | CF(CF₃)₂ | H | 0 |
| SCF₃ | ⁱPr | H | H | CF(CF₃)₂ | H | 1 |
| SCF₃ | ⁱPr | H | H | CF(CF₃)₂ | H | 2 |
| SCF₃ | ⁱPr | H | H | SMe | H | 0 |
| SCF₃ | ⁱPr | H | H | SMe | H | 1 |
| SCF₃ | ⁱPr | H | H | SMe | H | 2 |
| SCF₃ | ⁱPr | H | H | SOMe | H | 0 |
| SCF₃ | ⁱPr | H | H | SOMe | H | 1 |
| SCF₃ | ⁱPr | H | H | SOMe | H | 2 |
| SCF₃ | ⁱPr | H | H | SO₂Me | H | 0 |
| SCF₃ | ⁱPr | H | H | SO₂Me | H | 1 |
| SCF₃ | ⁱPr | H | H | SO₂Me | H | 2 |
| SCF₃ | ⁱPr | H | H | OMe | H | 0 |
| SCF₃ | ⁱPr | H | H | OMe | H | 1 |
| SCF₃ | ⁱPr | H | H | OMe | H | 2 |
| SCF₃ | ⁱPr | H | H | OCF₃ | H | 0 |
| SCF₃ | ⁱPr | H | H | OCF₃ | H | 1 |
| SCF₃ | ⁱPr | H | H | OCF₃ | H | 2 |
| SCF₃ | ⁱPr | H | H | NO₂ | H | 0 |
| SCF₃ | ⁱPr | H | H | NO₂ | H | 1 |
| SCF₃ | ⁱPr | H | H | NO₂ | H | 2 |
| SCF₃ | ⁱPr | H | H | CN | H | 0 |
| SCF₃ | ⁱPr | H | H | CN | H | 1 |
| SCF₃ | ⁱPr | H | H | CN | H | 2 |
| SCF₃ | ⁱPr | H | H | H | F | 0 |
| SCF₃ | ⁱPr | H | H | H | F | 1 |
| SCF₃ | ⁱPr | H | H | H | F | 2 |
| SCF₃ | ⁱPr | H | H | H | Cl | 0 |
| SCF₃ | ⁱPr | H | H | H | Cl | 1 |
| SCF₃ | ⁱPr | H | H | H | Cl | 2 |
| SCF₃ | ⁱPr | H | H | H | Br | 0 |
| SCF₃ | ⁱPr | H | H | H | Br | 1 |
| SCF₃ | ⁱPr | H | H | H | Br | 2 |
| SCF₃ | ⁱPr | H | H | H | I | 0 |
| SCF₃ | ⁱPr | H | H | H | I | 1 |
| SCF₃ | ⁱPr | H | H | H | I | 2 |
| SCF₃ | ⁱPr | H | H | H | Me | 0 |
| SCF₃ | ⁱPr | H | H | H | Me | 1 |
| SCF₃ | ⁱPr | H | H | H | Me | 2 |
| SCF₃ | ⁱPr | H | H | H | CF₃ | 0 |
| SCF₃ | ⁱPr | H | H | H | CF₃ | 1 |
| SCF₃ | ⁱPr | H | H | H | CF₃ | 2 |
| SCF₃ | ⁱPr | H | H | H | CF₂CF₃ | 0 |
| SCF₃ | ⁱPr | H | H | H | CF₂CF₃ | 1 |
| SCF₃ | ⁱPr | H | H | H | CF₂CF₃ | 2 |
| SCF₃ | ⁱPr | H | H | H | CF(CF₃)₂ | 0 |
| SCF₃ | ⁱPr | H | H | H | CF(CF₃)₂ | 1 |
| SCF₃ | ⁱPr | H | H | H | CF(CF₃)₂ | 2 |
| SCF₃ | ⁱPr | H | H | H | SMe | 0 |
| SCF₃ | ⁱPr | H | H | H | SMe | 1 |
| SCF₃ | ⁱPr | H | H | H | SMe | 2 |
| SCF₃ | ⁱPr | H | H | H | SOMe | 0 |
| SCF₃ | ⁱPr | H | H | H | SOMe | 1 |
| SCF₃ | ⁱPr | H | H | H | SOMe | 2 |
| SCF₃ | ⁱPr | H | H | H | SO₂Me | 0 |
| SCF₃ | ⁱPr | H | H | H | SO₂Me | 1 |

TABLE 1-continued

| | | | | | | |
|---|---|---|---|---|---|---|
| SCF$_3$ | $^i$Pr | H | H | H | SO$_2$Me | 2 |
| SCF$_3$ | $^i$Pr | H | H | H | OMe | 0 |
| SCF$_3$ | $^i$Pr | H | H | H | OMe | 1 |
| SCF$_3$ | $^i$Pr | H | H | H | OMe | 2 |
| SCF$_3$ | $^i$Pr | H | H | H | OCF$_3$ | 0 |
| SCF$_3$ | $^i$Pr | H | H | H | OCF$_3$ | 1 |
| SCF$_3$ | $^i$Pr | H | H | H | OCF$_3$ | 2 |
| SCF$_3$ | $^i$Pr | H | H | H | NO$_2$ | 0 |
| SCF$_3$ | $^i$Pr | H | H | H | NO$_2$ | 1 |
| SCF$_3$ | $^i$Pr | H | H | H | NO$_2$ | 2 |
| SCF$_3$ | $^i$Pr | H | H | H | CN | 0 |
| SCF$_3$ | $^i$Pr | H | H | H | CN | 1 |
| SCF$_3$ | $^i$Pr | H | H | H | CN | 2 |
| SCF$_3$ | $^i$Pr | H | F | H | F | 0 |
| SCF$_3$ | $^i$Pr | H | F | H | F | 1 |
| SCF$_3$ | $^i$Pr | H | F | H | F | 2 |
| SCF$_3$ | $^i$Pr | H | Cl | H | Cl | 0 |
| SCF$_3$ | $^i$Pr | H | Cl | H | Cl | 1 |
| SCF$_3$ | $^i$Pr | H | Cl | H | Cl | 2 |
| SCF$_3$ | $^i$Pr | H | Br | H | Br | 0 |
| SCF$_3$ | $^i$Pr | H | Br | H | Br | 1 |
| SCF$_3$ | $^i$Pr | H | Br | H | Br | 2 |
| SCF$_3$ | $^i$Pr | H | I | H | I | 0 |
| SCF$_3$ | $^i$Pr | H | I | H | I | 1 |
| SCF$_3$ | $^i$Pr | H | I | H | I | 2 |
| SCF$_3$ | $^i$Pr | H | F | H | Cl | 0 |
| SCF$_3$ | $^i$Pr | H | F | H | Cl | 1 |
| SCF$_3$ | $^i$Pr | H | F | H | Cl | 2 |
| SCF$_3$ | $^i$Pr | H | F | H | Br | 0 |
| SCF$_3$ | $^i$Pr | H | F | H | Br | 1 |
| SCF$_3$ | $^i$Pr | H | F | H | Br | 2 |
| SCF$_3$ | $^i$Pr | H | F | H | I | 0 |
| SCF$_3$ | $^i$Pr | H | F | H | I | 1 |
| SCF$_3$ | $^i$Pr | H | F | H | I | 2 |
| SCF$_3$ | $^i$Pr | H | Cl | H | F | 0 |
| SCF$_3$ | $^i$Pr | H | Cl | H | F | 1 |
| SCF$_3$ | $^i$Pr | H | Cl | H | F | 2 |
| SCF$_3$ | $^i$Pr | H | Cl | H | Br | 0 |
| SCF$_3$ | $^i$Pr | H | Cl | H | Br | 1 |
| SCF$_3$ | $^i$Pr | H | Cl | H | Br | 2 |
| SCF$_3$ | $^i$Pr | H | Cl | H | I | 0 |
| SCF$_3$ | $^i$Pr | H | Cl | H | I | 1 |
| SCF$_3$ | $^i$Pr | H | Cl | H | I | 2 |
| SCF$_3$ | $^i$Pr | H | Br | H | F | 0 |
| SCF$_3$ | $^i$Pr | H | Br | H | F | 1 |
| SCF$_3$ | $^i$Pr | H | Br | H | F | 2 |
| SCF$_3$ | $^i$Pr | H | Br | H | Cl | 0 |
| SCF$_3$ | $^i$Pr | H | Br | H | Cl | 1 |
| SCF$_3$ | $^i$Pr | H | Br | H | Cl | 2 |
| SCF$_3$ | $^i$Pr | H | Br | H | I | 0 |
| SCF$_3$ | $^i$Pr | H | Br | H | I | 1 |
| SCF$_3$ | $^i$Pr | H | Br | H | I | 2 |
| SCF$_3$ | $^i$Pr | H | I | H | F | 0 |
| SCF$_3$ | $^i$Pr | H | I | H | F | 1 |
| SCF$_3$ | $^i$Pr | H | I | H | F | 2 |
| SCF$_3$ | $^i$Pr | H | I | H | Cl | 0 |
| SCF$_3$ | $^i$Pr | H | I | H | Cl | 1 |
| SCF$_3$ | $^i$Pr | H | I | H | Cl | 2 |
| SCF$_3$ | $^i$Pr | H | I | H | Br | 0 |
| SCF$_3$ | $^i$Pr | H | I | H | Br | 1 |
| SCF$_3$ | $^i$Pr | H | I | H | Br | 2 |
| SCF$_3$ | $^i$Pr | H | F | H | CN | 0 |
| SCF$_3$ | $^i$Pr | H | F | H | CN | 1 |
| SCF$_3$ | $^i$Pr | H | F | H | CN | 2 |
| SCF$_3$ | $^i$Pr | H | Cl | H | CN | 0 |
| SCF$_3$ | $^i$Pr | H | Cl | H | CN | 1 |
| SCF$_3$ | $^i$Pr | H | Cl | H | CN | 2 |
| SCF$_3$ | $^i$Pr | H | Br | H | CN | 0 |
| SCF$_3$ | $^i$Pr | H | Br | H | CN | 1 |
| SCF$_3$ | $^i$Pr | H | Br | H | CN | 2 |
| SCF$_3$ | $^i$Pr | H | I | H | CN | 0 |
| SCF$_3$ | $^i$Pr | H | I | H | CN | 1 |
| SCF$_3$ | $^i$Pr | H | I | H | CN | 2 |
| SCF$_3$ | $^i$Pr | H | CF$_3$ | H | F | 0 |
| SCF$_3$ | $^i$Pr | H | CF$_3$ | H | F | 1 |
| SCF$_3$ | $^i$Pr | H | CF$_3$ | H | F | 2 |
| SCF$_3$ | $^i$Pr | H | CF$_3$ | H | Cl | 0 |
| SCF$_3$ | $^i$Pr | H | CF$_3$ | H | Cl | 1 |
| SCF$_3$ | $^i$Pr | H | CF$_3$ | H | Cl | 2 |
| SCF$_3$ | $^i$Pr | H | CF$_3$ | H | Br | 0 |
| SCF$_3$ | $^i$Pr | H | CF$_3$ | H | Br | 1 |
| SCF$_3$ | $^i$Pr | H | CF$_3$ | H | Br | 2 |
| SCF$_3$ | $^i$Pr | H | CF$_3$ | H | I | 0 |
| SCF$_3$ | $^i$Pr | H | CF$_3$ | H | I | 1 |
| SCF$_3$ | $^i$Pr | H | CF$_3$ | H | I | 2 |
| SCF$_3$ | $^i$Pr | H | CF$_3$ | H | CN | 0 |
| SCF$_3$ | $^i$Pr | H | CF$_3$ | H | CN | 1 |
| SCF$_3$ | $^i$Pr | H | CF$_3$ | H | CN | 2 |
| SCF$_3$ | $^i$Pr | H | F | F | H | 0 |
| SCF$_3$ | $^i$Pr | H | F | F | H | 1 |
| SCF$_3$ | $^i$Pr | H | F | F | H | 2 |
| SCF$_3$ | $^i$Pr | H | Cl | Cl | H | 0 |
| SCF$_3$ | $^i$Pr | H | Cl | Cl | H | 1 |
| SCF$_3$ | $^i$Pr | H | Cl | Cl | H | 2 |
| SCF$_3$ | $^i$Pr | H | Br | Br | H | 0 |
| SCF$_3$ | $^i$Pr | H | Br | Br | H | 1 |
| SCF$_3$ | $^i$Pr | H | Br | Br | H | 2 |
| SCF$_3$ | $^i$Pr | H | I | I | H | 0 |
| SCF$_3$ | $^i$Pr | H | I | I | H | 1 |
| SCF$_3$ | $^i$Pr | H | I | I | H | 2 |
| SCF$_3$ | $^i$Pr | H | F | Cl | H | 0 |
| SCF$_3$ | $^i$Pr | H | F | Cl | H | 1 |
| SCF$_3$ | $^i$Pr | H | F | Cl | H | 2 |
| SCF$_3$ | $^i$Pr | H | F | Br | H | 0 |
| SCF$_3$ | $^i$Pr | H | F | Br | H | 1 |
| SCF$_3$ | $^i$Pr | H | F | Br | H | 2 |
| SCF$_3$ | $^i$Pr | H | F | I | H | 0 |
| SCF$_3$ | $^i$Pr | H | F | I | H | 1 |
| SCF$_3$ | $^i$Pr | H | F | I | H | 2 |
| SCF$_3$ | $^i$Pr | H | Cl | F | H | 0 |
| SCF$_3$ | $^i$Pr | H | Cl | F | H | 1 |
| SCF$_3$ | $^i$Pr | H | Cl | F | H | 2 |
| SCF$_3$ | $^i$Pr | H | Cl | Br | H | 0 |
| SCF$_3$ | $^i$Pr | H | Cl | Br | H | 1 |
| SCF$_3$ | $^i$Pr | H | Cl | Br | H | 2 |
| SCF$_3$ | $^i$Pr | H | Cl | I | H | 0 |
| SCF$_3$ | $^i$Pr | H | Cl | I | H | 1 |
| SCF$_3$ | $^i$Pr | H | Cl | I | H | 2 |
| SCF$_3$ | $^i$Pr | H | Br | F | H | 0 |
| SCF$_3$ | $^i$Pr | H | Br | F | H | 1 |
| SCF$_3$ | $^i$Pr | H | Br | F | H | 2 |
| SCF$_3$ | $^i$Pr | H | Br | Cl | H | 0 |
| SCF$_3$ | $^i$Pr | H | Br | Cl | H | 1 |
| SCF$_3$ | $^i$Pr | H | Br | Cl | H | 2 |
| SCF$_3$ | $^i$Pr | H | Br | I | H | 0 |
| SCF$_3$ | $^i$Pr | H | Br | I | H | 1 |
| SCF$_3$ | $^i$Pr | H | Br | I | H | 2 |
| SCF$_3$ | $^i$Pr | H | I | F | H | 0 |
| SCF$_3$ | $^i$Pr | H | I | F | H | 1 |
| SCF$_3$ | $^i$Pr | H | I | F | H | 2 |
| SCF$_3$ | $^i$Pr | H | I | Cl | H | 0 |
| SCF$_3$ | $^i$Pr | H | I | Cl | H | 1 |
| SCF$_3$ | $^i$Pr | H | I | Cl | H | 2 |
| SCF$_3$ | $^i$Pr | H | I | Br | H | 0 |
| SCF$_3$ | $^i$Pr | H | I | Br | H | 1 |
| SCF$_3$ | $^i$Pr | H | I | Br | H | 2 |
| SCF$_3$ | $^i$Pr | H | F | CN | H | 0 |
| SCF$_3$ | $^i$Pr | H | F | CN | H | 1 |
| SCF$_3$ | $^i$Pr | H | F | CN | H | 2 |
| SCF$_3$ | $^i$Pr | H | Cl | CN | H | 0 |
| SCF$_3$ | $^i$Pr | H | Cl | CN | H | 1 |
| SCF$_3$ | $^i$Pr | H | Cl | CN | H | 2 |
| SCF$_3$ | $^i$Pr | H | Br | CN | H | 0 |
| SCF$_3$ | $^i$Pr | H | Br | CN | H | 1 |
| SCF$_3$ | $^i$Pr | H | Br | CN | H | 2 |
| SCF$_3$ | $^i$Pr | H | I | CN | H | 0 |
| SCF$_3$ | $^i$Pr | H | I | CN | H | 1 |
| SCF$_3$ | $^i$Pr | H | I | CN | H | 2 |
| SCF$_3$ | $^i$Pr | H | CF$_3$ | F | H | 0 |
| SCF$_3$ | $^i$Pr | H | CF$_3$ | F | H | 1 |
| SCF$_3$ | $^i$Pr | H | CF$_3$ | F | H | 2 |
| SCF$_3$ | $^i$Pr | H | CF$_3$ | Cl | H | 0 |
| SCF$_3$ | $^i$Pr | H | CF$_3$ | Cl | H | 1 |
| SCF$_3$ | $^i$Pr | H | CF$_3$ | Cl | H | 2 |
| SCF$_3$ | $^i$Pr | H | CF$_3$ | Br | H | 0 |
| SCF$_3$ | $^i$Pr | H | CF$_3$ | Br | H | 1 |
| SCF$_3$ | $^i$Pr | H | CF$_3$ | Br | H | 2 |
| SCF$_3$ | $^i$Pr | H | CF$_3$ | I | H | 0 |
| SCF$_3$ | $^i$Pr | H | CF$_3$ | I | H | 1 |
| SCF$_3$ | $^i$Pr | H | CF$_3$ | I | H | 2 |

TABLE 1-continued

| | | | | | | |
|---|---|---|---|---|---|---|
| SCF$_3$ | $^i$Pr | H | CF$_3$ | CN | H | 0 |
| SCF$_3$ | $^i$Pr | H | CF$_3$ | CN | H | 1 |
| SCF$_3$ | $^i$Pr | H | CF$_3$ | CN | H | 2 |
| SCF$_3$ | CH$_2$CF$_3$ | H | H | H | H | 0 |
| SCF$_3$ | CH$_2$CF$_3$ | H | H | H | H | 1 |
| SCF$_3$ | CH$_2$CF$_3$ | H | H | H | H | 2 |
| SCF$_3$ | CH$_2$CF$_3$ | F | H | H | H | 0 |
| SCF$_3$ | CH$_2$CF$_3$ | F | H | H | H | 1 |
| SCF$_3$ | CH$_2$CF$_3$ | F | H | H | H | 2 |
| SCF$_3$ | CH$_2$CF$_3$ | Cl | H | H | H | 0 |
| SCF$_3$ | CH$_2$CF$_3$ | Cl | H | H | H | 1 |
| SCF$_3$ | CH$_2$CF$_3$ | Cl | H | H | H | 2 |
| SCF$_3$ | CH$_2$CF$_3$ | Br | H | H | H | 0 |
| SCF$_3$ | CH$_2$CF$_3$ | Br | H | H | H | 1 |
| SCF$_3$ | CH$_2$CF$_3$ | Br | H | H | H | 2 |
| SCF$_3$ | CH$_2$CF$_3$ | I | H | H | H | 0 |
| SCF$_3$ | CH$_2$CF$_3$ | I | H | H | H | 1 |
| SCF$_3$ | CH$_2$CF$_3$ | I | H | H | H | 2 |
| SCF$_3$ | CH$_2$CF$_3$ | Me | H | H | H | 0 |
| SCF$_3$ | CH$_2$CF$_3$ | Me | H | H | H | 1 |
| SCF$_3$ | CH$_2$CF$_3$ | Me | H | H | H | 2 |
| SCF$_3$ | CH$_2$CF$_3$ | CF$_3$ | H | H | H | 0 |
| SCF$_3$ | CH$_2$CF$_3$ | CF$_3$ | H | H | H | 1 |
| SCF$_3$ | CH$_2$CF$_3$ | CF$_3$ | H | H | H | 2 |
| SCF$_3$ | CH$_2$CF$_3$ | H | F | H | H | 0 |
| SCF$_3$ | CH$_2$CF$_3$ | H | F | H | H | 1 |
| SCF$_3$ | CH$_2$CF$_3$ | H | F | H | H | 2 |
| SCF$_3$ | CH$_2$CF$_3$ | H | Cl | H | H | 0 |
| SCF$_3$ | CH$_2$CF$_3$ | H | Cl | H | H | 1 |
| SCF$_3$ | CH$_2$CF$_3$ | H | Cl | H | H | 2 |
| SCF$_3$ | CH$_2$CF$_3$ | H | Br | H | H | 0 |
| SCF$_3$ | CH$_2$CF$_3$ | H | Br | H | H | 1 |
| SCF$_3$ | CH$_2$CF$_3$ | H | Br | H | H | 2 |
| SCF$_3$ | CH$_2$CF$_3$ | H | I | H | H | 0 |
| SCF$_3$ | CH$_2$CF$_3$ | H | I | H | H | 1 |
| SCF$_3$ | CH$_2$CF$_3$ | H | I | H | H | 2 |
| SCF$_3$ | CH$_2$CF$_3$ | H | Me | H | H | 0 |
| SCF$_3$ | CH$_2$CF$_3$ | H | Me | H | H | 1 |
| SCF$_3$ | CH$_2$CF$_3$ | H | Me | H | H | 2 |
| SCF$_3$ | CH$_2$CF$_3$ | H | CF$_3$ | H | H | 0 |
| SCF$_3$ | CH$_2$CF$_3$ | H | CF$_3$ | H | H | 1 |
| SCF$_3$ | CH$_2$CF$_3$ | H | CF$_3$ | H | H | 2 |
| SCF$_3$ | CH$_2$CF$_3$ | H | CF$_2$CF$_3$ | H | H | 0 |
| SCF$_3$ | CH$_2$CF$_3$ | H | CF$_2$CF$_3$ | H | H | 1 |
| SCF$_3$ | CH$_2$CF$_3$ | H | CF$_2$CF$_3$ | H | H | 2 |
| SCF$_3$ | CH$_2$CF$_3$ | H | CF(CF$_3$)$_2$ | H | H | 0 |
| SCF$_3$ | CH$_2$CF$_3$ | H | CF(CF$_3$)$_2$ | H | H | 1 |
| SCF$_3$ | CH$_2$CF$_3$ | H | CF(CF$_3$)$_2$ | H | H | 2 |
| SCF$_3$ | CH$_2$CF$_3$ | H | SMe | H | H | 0 |
| SCF$_3$ | CH$_2$CF$_3$ | H | SMe | H | H | 1 |
| SCF$_3$ | CH$_2$CF$_3$ | H | SMe | H | H | 2 |
| SCF$_3$ | CH$_2$CF$_3$ | H | SOMe | H | H | 0 |
| SCF$_3$ | CH$_2$CF$_3$ | H | SOMe | H | H | 1 |
| SCF$_3$ | CH$_2$CF$_3$ | H | SOMe | H | H | 2 |
| SCF$_3$ | CH$_2$CF$_3$ | H | SO$_2$Me | H | H | 0 |
| SCF$_3$ | CH$_2$CF$_3$ | H | SO$_2$Me | H | H | 1 |
| SCF$_3$ | CH$_2$CF$_3$ | H | SO$_2$Me | H | H | 2 |
| SCF$_3$ | CH$_2$CF$_3$ | H | OMe | H | H | 0 |
| SCF$_3$ | CH$_2$CF$_3$ | H | OMe | H | H | 1 |
| SCF$_3$ | CH$_2$CF$_3$ | H | OMe | H | H | 2 |
| SCF$_3$ | CH$_2$CF$_3$ | H | OCF$_3$ | H | H | 0 |
| SCF$_3$ | CH$_2$CF$_3$ | H | OCF$_3$ | H | H | 1 |
| SCF$_3$ | CH$_2$CF$_3$ | H | OCF$_3$ | H | H | 2 |
| SCF$_3$ | CH$_2$CF$_3$ | H | NO$_2$ | H | H | 0 |
| SCF$_3$ | CH$_2$CF$_3$ | H | NO$_2$ | H | H | 1 |
| SCF$_3$ | CH$_2$CF$_3$ | H | NO$_2$ | H | H | 2 |
| SCF$_3$ | CH$_2$CF$_3$ | H | CN | H | H | 0 |
| SCF$_3$ | CH$_2$CF$_3$ | H | CN | H | H | 1 |
| SCF$_3$ | CH$_2$CF$_3$ | H | CN | H | H | 2 |
| SCF$_3$ | CH$_2$CF$_3$ | H | H | F | H | 0 |
| SCF$_3$ | CH$_2$CF$_3$ | H | H | F | H | 1 |
| SCF$_3$ | CH$_2$CF$_3$ | H | H | F | H | 2 |
| SCF$_3$ | CH$_2$CF$_3$ | H | H | Cl | H | 0 |
| SCF$_3$ | CH$_2$CF$_3$ | H | H | Cl | H | 1 |
| SCF$_3$ | CH$_2$CF$_3$ | H | H | Cl | H | 2 |
| SCF$_3$ | CH$_2$CF$_3$ | H | H | Br | H | 0 |
| SCF$_3$ | CH$_2$CF$_3$ | H | H | Br | H | 1 |
| SCF$_3$ | CH$_2$CF$_3$ | H | H | Br | H | 2 |
| SCF$_3$ | CH$_2$CF$_3$ | H | H | I | H | 0 |
| SCF$_3$ | CH$_2$CF$_3$ | H | H | I | H | 1 |
| SCF$_3$ | CH$_2$CF$_3$ | H | H | I | H | 2 |
| SCF$_3$ | CH$_2$CF$_3$ | H | H | Me | H | 0 |
| SCF$_3$ | CH$_2$CF$_3$ | H | H | Me | H | 1 |
| SCF$_3$ | CH$_2$CF$_3$ | H | H | Me | H | 2 |
| SCF$_3$ | CH$_2$CF$_3$ | H | H | CF$_3$ | H | 0 |
| SCF$_3$ | CH$_2$CF$_3$ | H | H | CF$_3$ | H | 1 |
| SCF$_3$ | CH$_2$CF$_3$ | H | H | CF$_3$ | H | 2 |
| SCF$_3$ | CH$_2$CF$_3$ | H | H | CF$_2$CF$_3$ | H | 0 |
| SCF$_3$ | CH$_2$CF$_3$ | H | H | CF$_2$CF$_3$ | H | 1 |
| SCF$_3$ | CH$_2$CF$_3$ | H | H | CF$_2$CF$_3$ | H | 2 |
| SCF$_3$ | CH$_2$CF$_3$ | H | H | CF(CF$_3$)$_2$ | H | 0 |
| SCF$_3$ | CH$_2$CF$_3$ | H | H | CF(CF$_3$)$_2$ | H | 1 |
| SCF$_3$ | CH$_2$CF$_3$ | H | H | CF(CF$_3$)$_2$ | H | 2 |
| SCF$_3$ | CH$_2$CF$_3$ | H | H | SMe | H | 0 |
| SCF$_3$ | CH$_2$CF$_3$ | H | H | SMe | H | 1 |
| SCF$_3$ | CH$_2$CF$_3$ | H | H | SMe | H | 2 |
| SCF$_3$ | CH$_2$CF$_3$ | H | H | SOMe | H | 0 |
| SCF$_3$ | CH$_2$CF$_3$ | H | H | SOMe | H | 1 |
| SCF$_3$ | CH$_2$CF$_3$ | H | H | SOMe | H | 2 |
| SCF$_3$ | CH$_2$CF$_3$ | H | H | SO$_2$Me | H | 0 |
| SCF$_3$ | CH$_2$CF$_3$ | H | H | SO$_2$Me | H | 1 |
| SCF$_3$ | CH$_2$CF$_3$ | H | H | SO$_2$Me | H | 2 |
| SCF$_3$ | CH$_2$CF$_3$ | H | H | OMe | H | 0 |
| SCF$_3$ | CH$_2$CF$_3$ | H | H | OMe | H | 1 |
| SCF$_3$ | CH$_2$CF$_3$ | H | H | OMe | H | 2 |
| SCF$_3$ | CH$_2$CF$_3$ | H | H | OCF$_3$ | H | 0 |
| SCF$_3$ | CH$_2$CF$_3$ | H | H | OCF$_3$ | H | 1 |
| SCF$_3$ | CH$_2$CF$_3$ | H | H | OCF$_3$ | H | 2 |
| SCF$_3$ | CH$_2$CF$_3$ | H | H | NO$_2$ | H | 0 |
| SCF$_3$ | CH$_2$CF$_3$ | H | H | NO$_2$ | H | 1 |
| SCF$_3$ | CH$_2$CF$_3$ | H | H | NO$_2$ | H | 2 |
| SCF$_3$ | CH$_2$CF$_3$ | H | H | CN | H | 0 |
| SCF$_3$ | CH$_2$CF$_3$ | H | H | CN | H | 1 |
| SCF$_3$ | CH$_2$CF$_3$ | H | H | CN | H | 2 |
| SCF$_3$ | CH$_2$CF$_3$ | H | H | H | F | 0 |
| SCF$_3$ | CH$_2$CF$_3$ | H | H | H | F | 1 |
| SCF$_3$ | CH$_2$CF$_3$ | H | H | H | F | 2 |
| SCF$_3$ | CH$_2$CF$_3$ | H | H | H | Cl | 0 |
| SCF$_3$ | CH$_2$CF$_3$ | H | H | H | Cl | 1 |
| SCF$_3$ | CH$_2$CF$_3$ | H | H | H | Cl | 2 |
| SCF$_3$ | CH$_2$CF$_3$ | H | H | H | Br | 0 |
| SCF$_3$ | CH$_2$CF$_3$ | H | H | H | Br | 1 |
| SCF$_3$ | CH$_2$CF$_3$ | H | H | H | Br | 2 |
| SCF$_3$ | CH$_2$CF$_3$ | H | H | H | I | 0 |
| SCF$_3$ | CH$_2$CF$_3$ | H | H | H | I | 1 |
| SCF$_3$ | CH$_2$CF$_3$ | H | H | H | I | 2 |
| SCF$_3$ | CH$_2$CF$_3$ | H | H | H | Me | 0 |
| SCF$_3$ | CH$_2$CF$_3$ | H | H | H | Me | 1 |
| SCF$_3$ | CH$_2$CF$_3$ | H | H | H | Me | 2 |
| SCF$_3$ | CH$_2$CF$_3$ | H | H | H | CF$_3$ | 0 |
| SCF$_3$ | CH$_2$CF$_3$ | H | H | H | CF$_3$ | 1 |
| SCF$_3$ | CH$_2$CF$_3$ | H | H | H | CF$_3$ | 2 |
| SCF$_3$ | CH$_2$CF$_3$ | H | H | H | CF$_2$CF$_3$ | 0 |
| SCF$_3$ | CH$_2$CF$_3$ | H | H | H | CF$_2$CF$_3$ | 1 |
| SCF$_3$ | CH$_2$CF$_3$ | H | H | H | CF$_2$CF$_3$ | 2 |
| SCF$_3$ | CH$_2$CF$_3$ | H | H | H | CF(CF$_3$)$_2$ | 0 |
| SCF$_3$ | CH$_2$CF$_3$ | H | H | H | CF(CF$_3$)$_2$ | 1 |
| SCF$_3$ | CH$_2$CF$_3$ | H | H | H | CF(CF$_3$)$_2$ | 2 |
| SCF$_3$ | CH$_2$CF$_3$ | H | H | H | SMe | 0 |
| SCF$_3$ | CH$_2$CF$_3$ | H | H | H | SMe | 1 |
| SCF$_3$ | CH$_2$CF$_3$ | H | H | H | SMe | 2 |
| SCF$_3$ | CH$_2$CF$_3$ | H | H | H | SOMe | 0 |
| SCF$_3$ | CH$_2$CF$_3$ | H | H | H | SOMe | 1 |
| SCF$_3$ | CH$_2$CF$_3$ | H | H | H | SOMe | 2 |
| SCF$_3$ | CH$_2$CF$_3$ | H | H | H | SO$_2$Me | 0 |
| SCF$_3$ | CH$_2$CF$_3$ | H | H | H | SO$_2$Me | 1 |
| SCF$_3$ | CH$_2$CF$_3$ | H | H | H | SO$_2$Me | 2 |
| SCF$_3$ | CH$_2$CF$_3$ | H | H | H | OMe | 0 |
| SCF$_3$ | CH$_2$CF$_3$ | H | H | H | OMe | 1 |
| SCF$_3$ | CH$_2$CF$_3$ | H | H | H | OMe | 2 |
| SCF$_3$ | CH$_2$CF$_3$ | H | H | H | OCF$_3$ | 0 |
| SCF$_3$ | CH$_2$CF$_3$ | H | H | H | OCF$_3$ | 1 |
| SCF$_3$ | CH$_2$CF$_3$ | H | H | H | OCF$_3$ | 2 |
| SCF$_3$ | CH$_2$CF$_3$ | H | H | H | NO$_2$ | 0 |
| SCF$_3$ | CH$_2$CF$_3$ | H | H | H | NO$_2$ | 1 |
| SCF$_3$ | CH$_2$CF$_3$ | H | H | H | NO$_2$ | 2 |
| SCF$_3$ | CH$_2$CF$_3$ | H | H | H | CN | 0 |
| SCF$_3$ | CH$_2$CF$_3$ | H | H | H | CN | 1 |
| SCF$_3$ | CH$_2$CF$_3$ | H | H | H | CN | 2 |
| SCF$_3$ | CH$_2$CF$_3$ | H | F | H | F | 0 |

TABLE 1-continued

| | | | | | | |
|---|---|---|---|---|---|---|
| SCF$_3$ | CH$_2$CF$_3$ | H | F | H | F | 1 |
| SCF$_3$ | CH$_2$CF$_3$ | H | F | H | F | 2 |
| SCF$_3$ | CH$_2$CF$_3$ | H | Cl | H | Cl | 0 |
| SCF$_3$ | CH$_2$CF$_3$ | H | Cl | H | Cl | 1 |
| SCF$_3$ | CH$_2$CF$_3$ | H | Cl | H | Cl | 2 |
| SCF$_3$ | CH$_2$CF$_3$ | H | Br | H | Br | 0 |
| SCF$_3$ | CH$_2$CF$_3$ | H | Br | H | Br | 1 |
| SCF$_3$ | CH$_2$CF$_3$ | H | Br | H | Br | 2 |
| SCF$_3$ | CH$_2$CF$_3$ | H | I | H | I | 0 |
| SCF$_3$ | CH$_2$CF$_3$ | H | I | H | I | 1 |
| SCF$_3$ | CH$_2$CF$_3$ | H | I | H | I | 2 |
| SCF$_3$ | CH$_2$CF$_3$ | H | F | H | Cl | 0 |
| SCF$_3$ | CH$_2$CF$_3$ | H | F | H | Cl | 1 |
| SCF$_3$ | CH$_2$CF$_3$ | H | F | H | Cl | 2 |
| SCF$_3$ | CH$_2$CF$_3$ | H | F | H | Br | 0 |
| SCF$_3$ | CH$_2$CF$_3$ | H | F | H | Br | 1 |
| SCF$_3$ | CH$_2$CF$_3$ | H | F | H | Br | 2 |
| SCF$_3$ | CH$_2$CF$_3$ | H | F | H | I | 0 |
| SCF$_3$ | CH$_2$CF$_3$ | H | F | H | I | 1 |
| SCF$_3$ | CH$_2$CF$_3$ | H | F | H | I | 2 |
| SCF$_3$ | CH$_2$CF$_3$ | H | Cl | H | F | 0 |
| SCF$_3$ | CH$_2$CF$_3$ | H | Cl | H | F | 1 |
| SCF$_3$ | CH$_2$CF$_3$ | H | Cl | H | F | 2 |
| SCF$_3$ | CH$_2$CF$_3$ | H | Cl | H | Br | 0 |
| SCF$_3$ | CH$_2$CF$_3$ | H | Cl | H | Br | 1 |
| SCF$_3$ | CH$_2$CF$_3$ | H | Cl | H | Br | 2 |
| SCF$_3$ | CH$_2$CF$_3$ | H | Cl | H | I | 0 |
| SCF$_3$ | CH$_2$CF$_3$ | H | Cl | H | I | 1 |
| SCF$_3$ | CH$_2$CF$_3$ | H | Cl | H | I | 2 |
| SCF$_3$ | CH$_2$CF$_3$ | H | Br | H | F | 0 |
| SCF$_3$ | CH$_2$CF$_3$ | H | Br | H | F | 1 |
| SCF$_3$ | CH$_2$CF$_3$ | H | Br | H | F | 2 |
| SCF$_3$ | CH$_2$CF$_3$ | H | Br | H | Cl | 0 |
| SCF$_3$ | CH$_2$CF$_3$ | H | Br | H | Cl | 1 |
| SCF$_3$ | CH$_2$CF$_3$ | H | Br | H | Cl | 2 |
| SCF$_3$ | CH$_2$CF$_3$ | H | Br | H | I | 0 |
| SCF$_3$ | CH$_2$CF$_3$ | H | Br | H | I | 1 |
| SCF$_3$ | CH$_2$CF$_3$ | H | Br | H | I | 2 |
| SCF$_3$ | CH$_2$CF$_3$ | H | I | H | F | 0 |
| SCF$_3$ | CH$_2$CF$_3$ | H | I | H | F | 1 |
| SCF$_3$ | CH$_2$CF$_3$ | H | I | H | F | 2 |
| SCF$_3$ | CH$_2$CF$_3$ | H | I | H | Cl | 0 |
| SCF$_3$ | CH$_2$CF$_3$ | H | I | H | Cl | 1 |
| SCF$_3$ | CH$_2$CF$_3$ | H | I | H | Cl | 2 |
| SCF$_3$ | CH$_2$CF$_3$ | H | I | H | Br | 0 |
| SCF$_3$ | CH$_2$CF$_3$ | H | I | H | Br | 1 |
| SCF$_3$ | CH$_2$CF$_3$ | H | I | H | Br | 2 |
| SCF$_3$ | CH$_2$CF$_3$ | H | F | H | CN | 0 |
| SCF$_3$ | CH$_2$CF$_3$ | H | F | H | CN | 1 |
| SCF$_3$ | CH$_2$CF$_3$ | H | F | H | CN | 2 |
| SCF$_3$ | CH$_2$CF$_3$ | H | Cl | H | CN | 0 |
| SCF$_3$ | CH$_2$CF$_3$ | H | Cl | H | CN | 1 |
| SCF$_3$ | CH$_2$CF$_3$ | H | Cl | H | CN | 2 |
| SCF$_3$ | CH$_2$CF$_3$ | H | Br | H | CN | 0 |
| SCF$_3$ | CH$_2$CF$_3$ | H | Br | H | CN | 1 |
| SCF$_3$ | CH$_2$CF$_3$ | H | Br | H | CN | 2 |
| SCF$_3$ | CH$_2$CF$_3$ | H | I | H | CN | 0 |
| SCF$_3$ | CH$_2$CF$_3$ | H | I | H | CN | 1 |
| SCF$_3$ | CH$_2$CF$_3$ | H | I | H | CN | 2 |
| SCF$_3$ | CH$_2$CF$_3$ | H | CF$_3$ | H | F | 0 |
| SCF$_3$ | CH$_2$CF$_3$ | H | CF$_3$ | H | F | 1 |
| SCF$_3$ | CH$_2$CF$_3$ | H | CF$_3$ | H | F | 2 |
| SCF$_3$ | CH$_2$CF$_3$ | H | CF$_3$ | H | Cl | 0 |
| SCF$_3$ | CH$_2$CF$_3$ | H | CF$_3$ | H | Cl | 1 |
| SCF$_3$ | CH$_2$CF$_3$ | H | CF$_3$ | H | Cl | 2 |
| SCF$_3$ | CH$_2$CF$_3$ | H | CF$_3$ | H | Br | 0 |
| SCF$_3$ | CH$_2$CF$_3$ | H | CF$_3$ | H | Br | 1 |
| SCF$_3$ | CH$_2$CF$_3$ | H | CF$_3$ | H | Br | 2 |
| SCF$_3$ | CH$_2$CF$_3$ | H | CF$_3$ | H | I | 0 |
| SCF$_3$ | CH$_2$CF$_3$ | H | CF$_3$ | H | I | 1 |
| SCF$_3$ | CH$_2$CF$_3$ | H | CF$_3$ | H | I | 2 |
| SCF$_3$ | CH$_2$CF$_3$ | H | CF$_3$ | H | CN | 0 |
| SCF$_3$ | CH$_2$CF$_3$ | H | CF$_3$ | H | CN | 1 |
| SCF$_3$ | CH$_2$CF$_3$ | H | CF$_3$ | H | CN | 2 |
| SCF$_3$ | CH$_2$CF$_3$ | H | F | F | H | 0 |
| SCF$_3$ | CH$_2$CF$_3$ | H | F | F | H | 1 |
| SCF$_3$ | CH$_2$CF$_3$ | H | F | F | H | 2 |
| SCF$_3$ | CH$_2$CF$_3$ | H | Cl | Cl | H | 0 |
| SCF$_3$ | CH$_2$CF$_3$ | H | Cl | Cl | H | 1 |
| SCF$_3$ | CH$_2$CF$_3$ | H | Cl | Cl | H | 2 |
| SCF$_3$ | CH$_2$CF$_3$ | H | Br | Br | H | 0 |
| SCF$_3$ | CH$_2$CF$_3$ | H | Br | Br | H | 1 |
| SCF$_3$ | CH$_2$CF$_3$ | H | Br | Br | H | 2 |
| SCF$_3$ | CH$_2$CF$_3$ | H | I | I | H | 0 |
| SCF$_3$ | CH$_2$CF$_3$ | H | I | I | H | 1 |
| SCF$_3$ | CH$_2$CF$_3$ | H | I | I | H | 2 |
| SCF$_3$ | CH$_2$CF$_3$ | H | F | Cl | H | 0 |
| SCF$_3$ | CH$_2$CF$_3$ | H | F | Cl | H | 1 |
| SCF$_3$ | CH$_2$CF$_3$ | H | F | Cl | H | 2 |
| SCF$_3$ | CH$_2$CF$_3$ | H | F | Br | H | 0 |
| SCF$_3$ | CH$_2$CF$_3$ | H | F | Br | H | 1 |
| SCF$_3$ | CH$_2$CF$_3$ | H | F | Br | H | 2 |
| SCF$_3$ | CH$_2$CF$_3$ | H | F | I | H | 0 |
| SCF$_3$ | CH$_2$CF$_3$ | H | F | I | H | 1 |
| SCF$_3$ | CH$_2$CF$_3$ | H | F | I | H | 2 |
| SCF$_3$ | CH$_2$CF$_3$ | H | Cl | F | H | 0 |
| SCF$_3$ | CH$_2$CF$_3$ | H | Cl | F | H | 1 |
| SCF$_3$ | CH$_2$CF$_3$ | H | Cl | F | H | 2 |
| SCF$_3$ | CH$_2$CF$_3$ | H | Cl | Br | H | 0 |
| SCF$_3$ | CH$_2$CF$_3$ | H | Cl | Br | H | 1 |
| SCF$_3$ | CH$_2$CF$_3$ | H | Cl | Br | H | 2 |
| SCF$_3$ | CH$_2$CF$_3$ | H | Cl | I | H | 0 |
| SCF$_3$ | CH$_2$CF$_3$ | H | Cl | I | H | 1 |
| SCF$_3$ | CH$_2$CF$_3$ | H | Cl | I | H | 2 |
| SCF$_3$ | CH$_2$CF$_3$ | H | Br | F | H | 0 |
| SCF$_3$ | CH$_2$CF$_3$ | H | Br | F | H | 1 |
| SCF$_3$ | CH$_2$CF$_3$ | H | Br | F | H | 2 |
| SCF$_3$ | CH$_2$CF$_3$ | H | Br | Cl | H | 0 |
| SCF$_3$ | CH$_2$CF$_3$ | H | Br | Cl | H | 1 |
| SCF$_3$ | CH$_2$CF$_3$ | H | Br | Cl | H | 2 |
| SCF$_3$ | CH$_2$CF$_3$ | H | Br | I | H | 0 |
| SCF$_3$ | CH$_2$CF$_3$ | H | Br | I | H | 1 |
| SCF$_3$ | CH$_2$CF$_3$ | H | Br | I | H | 2 |
| SCF$_3$ | CH$_2$CF$_3$ | H | I | F | H | 0 |
| SCF$_3$ | CH$_2$CF$_3$ | H | I | F | H | 1 |
| SCF$_3$ | CH$_2$CF$_3$ | H | I | F | H | 2 |
| SCF$_3$ | CH$_2$CF$_3$ | H | I | Cl | H | 0 |
| SCF$_3$ | CH$_2$CF$_3$ | H | I | Cl | H | 1 |
| SCF$_3$ | CH$_2$CF$_3$ | H | I | Cl | H | 2 |
| SCF$_3$ | CH$_2$CF$_3$ | H | I | Br | H | 0 |
| SCF$_3$ | CH$_2$CF$_3$ | H | I | Br | H | 1 |
| SCF$_3$ | CH$_2$CF$_3$ | H | I | Br | H | 2 |
| SCF$_3$ | CH$_2$CF$_3$ | H | F | CN | H | 0 |
| SCF$_3$ | CH$_2$CF$_3$ | H | F | CN | H | 1 |
| SCF$_3$ | CH$_2$CF$_3$ | H | F | CN | H | 2 |
| SCF$_3$ | CH$_2$CF$_3$ | H | Cl | CN | H | 0 |
| SCF$_3$ | CH$_2$CF$_3$ | H | Cl | CN | H | 1 |
| SCF$_3$ | CH$_2$CF$_3$ | H | Cl | CN | H | 2 |
| SCF$_3$ | CH$_2$CF$_3$ | H | Br | CN | H | 0 |
| SCF$_3$ | CH$_2$CF$_3$ | H | Br | CN | H | 1 |
| SCF$_3$ | CH$_2$CF$_3$ | H | Br | CN | H | 2 |
| SCF$_3$ | CH$_2$CF$_3$ | H | I | CN | H | 0 |
| SCF$_3$ | CH$_2$CF$_3$ | H | I | CN | H | 1 |
| SCF$_3$ | CH$_2$CF$_3$ | H | I | CN | H | 2 |
| SCF$_3$ | CH$_2$CF$_3$ | H | CF$_3$ | F | H | 0 |
| SCF$_3$ | CH$_2$CF$_3$ | H | CF$_3$ | F | H | 1 |
| SCF$_3$ | CH$_2$CF$_3$ | H | CF$_3$ | F | H | 2 |
| SCF$_3$ | CH$_2$CF$_3$ | H | CF$_3$ | Cl | H | 0 |
| SCF$_3$ | CH$_2$CF$_3$ | H | CF$_3$ | Cl | H | 1 |
| SCF$_3$ | CH$_2$CF$_3$ | H | CF$_3$ | Cl | H | 2 |
| SCF$_3$ | CH$_2$CF$_3$ | H | CF$_3$ | Br | H | 0 |
| SCF$_3$ | CH$_2$CF$_3$ | H | CF$_3$ | Br | H | 1 |
| SCF$_3$ | CH$_2$CF$_3$ | H | CF$_3$ | Br | H | 2 |
| SCF$_3$ | CH$_2$CF$_3$ | H | CF$_3$ | I | H | 0 |
| SCF$_3$ | CH$_2$CF$_3$ | H | CF$_3$ | I | H | 1 |
| SCF$_3$ | CH$_2$CF$_3$ | H | CF$_3$ | I | H | 2 |
| SCF$_3$ | CH$_2$CF$_3$ | H | CF$_3$ | CN | H | 0 |
| SCF$_3$ | CH$_2$CF$_3$ | H | CF$_3$ | CN | H | 1 |
| SCF$_3$ | CH$_2$CF$_3$ | H | CF$_3$ | CN | H | 2 |
| SOCF$_3$ | Me | H | H | H | H | 0 |
| SOCF$_3$ | Me | H | H | H | H | 1 |
| SOCF$_3$ | Me | H | H | H | H | 2 |
| SOCF$_3$ | Me | F | H | H | H | 0 |
| SOCF$_3$ | Me | F | H | H | H | 1 |
| SOCF$_3$ | Me | F | H | H | H | 2 |
| SOCF$_3$ | Me | Cl | H | H | H | 0 |
| SOCF$_3$ | Me | Cl | H | H | H | 1 |
| SOCF$_3$ | Me | Cl | H | H | H | 2 |
| SOCF$_3$ | Me | Br | H | H | H | 0 |
| SOCF$_3$ | Me | Br | H | H | H | 1 |

TABLE 1-continued

| | | | | | | |
|---|---|---|---|---|---|---|
| SOCF₃ | Me | Br | H | H | H | 2 |
| SOCF₃ | Me | I | H | H | H | 0 |
| SOCF₃ | Me | I | H | H | H | 1 |
| SOCF₃ | Me | I | H | H | H | 2 |
| SOCF₃ | Me | Me | H | H | H | 0 |
| SOCF₃ | Me | Me | H | H | H | 1 |
| SOCF₃ | Me | Me | H | H | H | 2 |
| SOCF₃ | Me | CF₃ | H | H | H | 0 |
| SOCF₃ | Me | CF₃ | H | H | H | 1 |
| SOCF₃ | Me | CF₃ | H | H | H | 2 |
| SOCF₃ | Me | H | F | H | H | 0 |
| SOCF₃ | Me | H | F | H | H | 1 |
| SOCF₃ | Me | H | F | H | H | 2 |
| SOCF₃ | Me | H | Cl | H | H | 0 |
| SOCF₃ | Me | H | Cl | H | H | 1 |
| SOCF₃ | Me | H | Cl | H | H | 2 |
| SOCF₃ | Me | H | Br | H | H | 0 |
| SOCF₃ | Me | H | Br | H | H | 1 |
| SOCF₃ | Me | H | Br | H | H | 2 |
| SOCF₃ | Me | H | I | H | H | 0 |
| SOCF₃ | Me | H | I | H | H | 1 |
| SOCF₃ | Me | H | I | H | H | 2 |
| SOCF₃ | Me | H | Me | H | H | 0 |
| SOCF₃ | Me | H | Me | H | H | 1 |
| SOCF₃ | Me | H | Me | H | H | 2 |
| SOCF₃ | Me | H | CF₃ | H | H | 0 |
| SOCF₃ | Me | H | CF₃ | H | H | 1 |
| SOCF₃ | Me | H | CF₃ | H | H | 2 |
| SOCF₃ | Me | H | CF₂CF₃ | H | H | 0 |
| SOCF₃ | Me | H | CF₂CF₃ | H | H | 1 |
| SOCF₃ | Me | H | CF₂CF₃ | H | H | 2 |
| SOCF₃ | Me | H | CF(CF₃)₂ | H | H | 0 |
| SOCF₃ | Me | H | CF(CF₃)₂ | H | H | 1 |
| SOCF₃ | Me | H | CF(CF₃)₂ | H | H | 2 |
| SOCF₃ | Me | H | SMe | H | H | 0 |
| SOCF₃ | Me | H | SMe | H | H | 1 |
| SOCF₃ | Me | H | SMe | H | H | 2 |
| SOCF₃ | Me | H | SOMe | H | H | 0 |
| SOCF₃ | Me | H | SOMe | H | H | 1 |
| SOCF₃ | Me | H | SOMe | H | H | 2 |
| SOCF₃ | Me | H | SO₂Me | H | H | 0 |
| SOCF₃ | Me | H | SO₂Me | H | H | 1 |
| SOCF₃ | Me | H | SO₂Me | H | H | 2 |
| SOCF₃ | Me | H | OMe | H | H | 0 |
| SOCF₃ | Me | H | OMe | H | H | 1 |
| SOCF₃ | Me | H | OMe | H | H | 2 |
| SOCF₃ | Me | H | OCF₃ | H | H | 0 |
| SOCF₃ | Me | H | OCF₃ | H | H | 1 |
| SOCF₃ | Me | H | OCF₃ | H | H | 2 |
| SOCF₃ | Me | H | NO₂ | H | H | 0 |
| SOCF₃ | Me | H | NO₂ | H | H | 1 |
| SOCF₃ | Me | H | NO₂ | H | H | 2 |
| SOCF₃ | Me | H | CN | H | H | 0 |
| SOCF₃ | Me | H | CN | H | H | 1 |
| SOCF₃ | Me | H | CN | H | H | 2 |
| SOCF₃ | Me | H | H | F | H | 0 |
| SOCF₃ | Me | H | H | F | H | 1 |
| SOCF₃ | Me | H | H | F | H | 2 |
| SOCF₃ | Me | H | H | Cl | H | 0 |
| SOCF₃ | Me | H | H | Cl | H | 1 |
| SOCF₃ | Me | H | H | Cl | H | 2 |
| SOCF₃ | Me | H | H | Br | H | 0 |
| SOCF₃ | Me | H | H | Br | H | 1 |
| SOCF₃ | Me | H | H | Br | H | 2 |
| SOCF₃ | Me | H | H | I | H | 0 |
| SOCF₃ | Me | H | H | I | H | 1 |
| SOCF₃ | Me | H | H | I | H | 2 |
| SOCF₃ | Me | H | H | Me | H | 0 |
| SOCF₃ | Me | H | H | Me | H | 1 |
| SOCF₃ | Me | H | H | Me | H | 2 |
| SOCF₃ | Me | H | H | CF₃ | H | 0 |
| SOCF₃ | Me | H | H | CF₃ | H | 1 |
| SOCF₃ | Me | H | H | CF₃ | H | 2 |
| SOCF₃ | Me | H | H | CF₂CF₃ | H | 0 |
| SOCF₃ | Me | H | H | CF₂CF₃ | H | 1 |
| SOCF₃ | Me | H | H | CF₂CF₃ | H | 2 |
| SOCF₃ | Me | H | H | CF(CF₃)₂ | H | 0 |
| SOCF₃ | Me | H | H | CF(CF₃)₂ | H | 1 |
| SOCF₃ | Me | H | H | CF(CF₃)₂ | H | 2 |
| SOCF₃ | Me | H | H | SMe | H | 0 |
| SOCF₃ | Me | H | H | SMe | H | 1 |
| SOCF₃ | Me | H | H | SMe | H | 2 |
| SOCF₃ | Me | H | H | SOMe | H | 0 |
| SOCF₃ | Me | H | H | SOMe | H | 1 |
| SOCF₃ | Me | H | H | SOMe | H | 2 |
| SOCF₃ | Me | H | H | SO₂Me | H | 0 |
| SOCF₃ | Me | H | H | SO₂Me | H | 1 |
| SOCF₃ | Me | H | H | SO₂Me | H | 2 |
| SOCF₃ | Me | H | H | OMe | H | 0 |
| SOCF₃ | Me | H | H | OMe | H | 1 |
| SOCF₃ | Me | H | H | OMe | H | 2 |
| SOCF₃ | Me | H | H | OCF₃ | H | 0 |
| SOCF₃ | Me | H | H | OCF₃ | H | 1 |
| SOCF₃ | Me | H | H | OCF₃ | H | 2 |
| SOCF₃ | Me | H | H | NO₂ | H | 0 |
| SOCF₃ | Me | H | H | NO₂ | H | 1 |
| SOCF₃ | Me | H | H | NO₂ | H | 2 |
| SOCF₃ | Me | H | H | CN | H | 0 |
| SOCF₃ | Me | H | H | CN | H | 1 |
| SOCF₃ | Me | H | H | CN | H | 2 |
| SOCF₃ | Me | H | H | H | F | 0 |
| SOCF₃ | Me | H | H | H | F | 1 |
| SOCF₃ | Me | H | H | H | F | 2 |
| SOCF₃ | Me | H | H | H | Cl | 0 |
| SOCF₃ | Me | H | H | H | Cl | 1 |
| SOCF₃ | Me | H | H | H | Cl | 2 |
| SOCF₃ | Me | H | H | H | Br | 0 |
| SOCF₃ | Me | H | H | H | Br | 1 |
| SOCF₃ | Me | H | H | H | Br | 2 |
| SOCF₃ | Me | H | H | H | I | 0 |
| SOCF₃ | Me | H | H | H | I | 1 |
| SOCF₃ | Me | H | H | H | I | 2 |
| SOCF₃ | Me | H | H | H | Me | 0 |
| SOCF₃ | Me | H | H | H | Me | 1 |
| SOCF₃ | Me | H | H | H | Me | 2 |
| SOCF₃ | Me | H | H | H | CF₃ | 0 |
| SOCF₃ | Me | H | H | H | CF₃ | 1 |
| SOCF₃ | Me | H | H | H | CF₃ | 2 |
| SOCF₃ | Me | H | H | H | CF₂CF₃ | 0 |
| SOCF₃ | Me | H | H | H | CF₂CF₃ | 1 |
| SOCF₃ | Me | H | H | H | CF₂CF₃ | 2 |
| SOCF₃ | Me | H | H | H | CF(CF₃)₂ | 0 |
| SOCF₃ | Me | H | H | H | CF(CF₃)₂ | 1 |
| SOCF₃ | Me | H | H | H | CF(CF₃)₂ | 2 |
| SOCF₃ | Me | H | H | H | SMe | 0 |
| SOCF₃ | Me | H | H | H | SMe | 1 |
| SOCF₃ | Me | H | H | H | SMe | 2 |
| SOCF₃ | Me | H | H | H | SOMe | 0 |
| SOCF₃ | Me | H | H | H | SOMe | 1 |
| SOCF₃ | Me | H | H | H | SOMe | 2 |
| SOCF₃ | Me | H | H | H | SO₂Me | 0 |
| SOCF₃ | Me | H | H | H | SO₂Me | 1 |
| SOCF₃ | Me | H | H | H | SO₂Me | 2 |
| SOCF₃ | Me | H | H | H | OMe | 0 |
| SOCF₃ | Me | H | H | H | OMe | 1 |
| SOCF₃ | Me | H | H | H | OMe | 2 |
| SOCF₃ | Me | H | H | H | OCF₃ | 0 |
| SOCF₃ | Me | H | H | H | OCF₃ | 1 |
| SOCF₃ | Me | H | H | H | OCF₃ | 2 |
| SOCF₃ | Me | H | H | H | NO₂ | 0 |
| SOCF₃ | Me | H | H | H | NO₂ | 1 |
| SOCF₃ | Me | H | H | H | NO₂ | 2 |
| SOCF₃ | Me | H | H | H | CN | 0 |
| SOCF₃ | Me | H | H | H | CN | 1 |
| SOCF₃ | Me | H | H | H | CN | 2 |
| SOCF₃ | Me | H | F | H | F | 0 |
| SOCF₃ | Me | H | F | H | F | 1 |
| SOCF₃ | Me | H | F | H | F | 2 |
| SOCF₃ | Me | H | Cl | H | Cl | 0 |
| SOCF₃ | Me | H | Cl | H | Cl | 1 |
| SOCF₃ | Me | H | Cl | H | Cl | 2 |
| SOCF₃ | Me | H | Br | H | Br | 0 |
| SOCF₃ | Me | H | Br | H | Br | 1 |
| SOCF₃ | Me | H | Br | H | Br | 2 |
| SOCF₃ | Me | H | I | H | I | 0 |
| SOCF₃ | Me | H | I | H | I | 1 |
| SOCF₃ | Me | H | I | H | I | 2 |
| SOCF₃ | Me | H | F | H | Cl | 0 |
| SOCF₃ | Me | H | F | H | Cl | 1 |
| SOCF₃ | Me | H | F | H | Cl | 2 |

TABLE 1-continued

| | | | | | | |
|---|---|---|---|---|---|---|
| SOCF$_3$ | Me | H | F | H | Br | 0 |
| SOCF$_3$ | Me | H | F | H | Br | 1 |
| SOCF$_3$ | Me | H | F | H | Br | 2 |
| SOCF$_3$ | Me | H | F | H | I | 0 |
| SOCF$_3$ | Me | H | F | H | I | 1 |
| SOCF$_3$ | Me | H | F | H | I | 2 |
| SOCF$_3$ | Me | H | Cl | H | F | 0 |
| SOCF$_3$ | Me | H | Cl | H | F | 1 |
| SOCF$_3$ | Me | H | Cl | H | F | 2 |
| SOCF$_3$ | Me | H | Cl | H | Br | 0 |
| SOCF$_3$ | Me | H | Cl | H | Br | 1 |
| SOCF$_3$ | Me | H | Cl | H | Br | 2 |
| SOCF$_3$ | Me | H | Cl | H | I | 0 |
| SOCF$_3$ | Me | H | Cl | H | I | 1 |
| SOCF$_3$ | Me | H | Cl | H | I | 2 |
| SOCF$_3$ | Me | H | Br | H | F | 0 |
| SOCF$_3$ | Me | H | Br | H | F | 1 |
| SOCF$_3$ | Me | H | Br | H | F | 2 |
| SOCF$_3$ | Me | H | Br | H | Cl | 0 |
| SOCF$_3$ | Me | H | Br | H | Cl | 1 |
| SOCF$_3$ | Me | H | Br | H | Cl | 2 |
| SOCF$_3$ | Me | H | Br | H | I | 0 |
| SOCF$_3$ | Me | H | Br | H | I | 1 |
| SOCF$_3$ | Me | H | Br | H | I | 2 |
| SOCF$_3$ | Me | H | I | H | F | 0 |
| SOCF$_3$ | Me | H | I | H | F | 1 |
| SOCF$_3$ | Me | H | I | H | F | 2 |
| SOCF$_3$ | Me | H | I | H | Cl | 0 |
| SOCF$_3$ | Me | H | I | H | Cl | 1 |
| SOCF$_3$ | Me | H | I | H | Cl | 2 |
| SOCF$_3$ | Me | H | I | H | Br | 0 |
| SOCF$_3$ | Me | H | I | H | Br | 1 |
| SOCF$_3$ | Me | H | I | H | Br | 2 |
| SOCF$_3$ | Me | H | F | H | CN | 0 |
| SOCF$_3$ | Me | H | F | H | CN | 1 |
| SOCF$_3$ | Me | H | F | H | CN | 2 |
| SOCF$_3$ | Me | H | Cl | H | CN | 0 |
| SOCF$_3$ | Me | H | Cl | H | CN | 1 |
| SOCF$_3$ | Me | H | Cl | H | CN | 2 |
| SOCF$_3$ | Me | H | Br | H | CN | 0 |
| SOCF$_3$ | Me | H | Br | H | CN | 1 |
| SOCF$_3$ | Me | H | Br | H | CN | 2 |
| SOCF$_3$ | Me | H | I | H | CN | 0 |
| SOCF$_3$ | Me | H | I | H | CN | 1 |
| SOCF$_3$ | Me | H | I | H | CN | 2 |
| SOCF$_3$ | Me | H | CF$_3$ | H | F | 0 |
| SOCF$_3$ | Me | H | CF$_3$ | H | F | 1 |
| SOCF$_3$ | Me | H | CF$_3$ | H | F | 2 |
| SOCF$_3$ | Me | H | CF$_3$ | H | Cl | 0 |
| SOCF$_3$ | Me | H | CF$_3$ | H | Cl | 1 |
| SOCF$_3$ | Me | H | CF$_3$ | H | Cl | 2 |
| SOCF$_3$ | Me | H | CF$_3$ | H | Br | 0 |
| SOCF$_3$ | Me | H | CF$_3$ | H | Br | 1 |
| SOCF$_3$ | Me | H | CF$_3$ | H | Br | 2 |
| SOCF$_3$ | Me | H | CF$_3$ | H | I | 0 |
| SOCF$_3$ | Me | H | CF$_3$ | H | I | 1 |
| SOCF$_3$ | Me | H | CF$_3$ | H | I | 2 |
| SOCF$_3$ | Me | H | CF$_3$ | H | CN | 0 |
| SOCF$_3$ | Me | H | CF$_3$ | H | CN | 1 |
| SOCF$_3$ | Me | H | CF$_3$ | H | CN | 2 |
| SOCF$_3$ | Me | H | F | F | H | 0 |
| SOCF$_3$ | Me | H | F | F | H | 1 |
| SOCF$_3$ | Me | H | F | F | H | 2 |
| SOCF$_3$ | Me | H | Cl | Cl | H | 0 |
| SOCF$_3$ | Me | H | Cl | Cl | H | 1 |
| SOCF$_3$ | Me | H | Cl | Cl | H | 2 |
| SOCF$_3$ | Me | H | Br | Br | H | 0 |
| SOCF$_3$ | Me | H | Br | Br | H | 1 |
| SOCF$_3$ | Me | H | Br | Br | H | 2 |
| SOCF$_3$ | Me | H | I | I | H | 0 |
| SOCF$_3$ | Me | H | I | I | H | 1 |
| SOCF$_3$ | Me | H | I | I | H | 2 |
| SOCF$_3$ | Me | H | F | Cl | H | 0 |
| SOCF$_3$ | Me | H | F | Cl | H | 1 |
| SOCF$_3$ | Me | H | F | Cl | H | 2 |
| SOCF$_3$ | Me | H | F | Br | H | 0 |
| SOCF$_3$ | Me | H | F | Br | H | 1 |
| SOCF$_3$ | Me | H | F | Br | H | 2 |
| SOCF$_3$ | Me | H | F | I | H | 0 |
| SOCF$_3$ | Me | H | F | I | H | 1 |
| SOCF$_3$ | Me | H | F | I | H | 2 |
| SOCF$_3$ | Me | H | Cl | F | H | 0 |
| SOCF$_3$ | Me | H | Cl | F | H | 1 |
| SOCF$_3$ | Me | H | Cl | F | H | 2 |
| SOCF$_3$ | Me | H | Cl | Br | H | 0 |
| SOCF$_3$ | Me | H | Cl | Br | H | 1 |
| SOCF$_3$ | Me | H | Cl | Br | H | 2 |
| SOCF$_3$ | Me | H | Cl | I | H | 0 |
| SOCF$_3$ | Me | H | Cl | I | H | 1 |
| SOCF$_3$ | Me | H | Cl | I | H | 2 |
| SOCF$_3$ | Me | H | Br | F | H | 0 |
| SOCF$_3$ | Me | H | Br | F | H | 1 |
| SOCF$_3$ | Me | H | Br | F | H | 2 |
| SOCF$_3$ | Me | H | Br | Cl | H | 0 |
| SOCF$_3$ | Me | H | Br | Cl | H | 1 |
| SOCF$_3$ | Me | H | Br | Cl | H | 2 |
| SOCF$_3$ | Me | H | Br | I | H | 0 |
| SOCF$_3$ | Me | H | Br | I | H | 1 |
| SOCF$_3$ | Me | H | Br | I | H | 2 |
| SOCF$_3$ | Me | H | I | F | H | 0 |
| SOCF$_3$ | Me | H | I | F | H | 1 |
| SOCF$_3$ | Me | H | I | F | H | 2 |
| SOCF$_3$ | Me | H | I | Cl | H | 0 |
| SOCF$_3$ | Me | H | I | Cl | H | 1 |
| SOCF$_3$ | Me | H | I | Cl | H | 2 |
| SOCF$_3$ | Me | H | I | Br | H | 0 |
| SOCF$_3$ | Me | H | I | Br | H | 1 |
| SOCF$_3$ | Me | H | I | Br | H | 2 |
| SOCF$_3$ | Me | H | F | CN | H | 0 |
| SOCF$_3$ | Me | H | F | CN | H | 1 |
| SOCF$_3$ | Me | H | F | CN | H | 2 |
| SOCF$_3$ | Me | H | Cl | CN | H | 0 |
| SOCF$_3$ | Me | H | Cl | CN | H | 1 |
| SOCF$_3$ | Me | H | Cl | CN | H | 2 |
| SOCF$_3$ | Me | H | Br | CN | H | 0 |
| SOCF$_3$ | Me | H | Br | CN | H | 1 |
| SOCF$_3$ | Me | H | Br | CN | H | 2 |
| SOCF$_3$ | Me | H | I | CN | H | 0 |
| SOCF$_3$ | Me | H | I | CN | H | 1 |
| SOCF$_3$ | Me | H | I | CN | H | 2 |
| SOCF$_3$ | Me | H | CF$_3$ | F | H | 0 |
| SOCF$_3$ | Me | H | CF$_3$ | F | H | 1 |
| SOCF$_3$ | Me | H | CF$_3$ | F | H | 2 |
| SOCF$_3$ | Me | H | CF$_3$ | Cl | H | 0 |
| SOCF$_3$ | Me | H | CF$_3$ | Cl | H | 1 |
| SOCF$_3$ | Me | H | CF$_3$ | Cl | H | 2 |
| SOCF$_3$ | Me | H | CF$_3$ | Br | H | 0 |
| SOCF$_3$ | Me | H | CF$_3$ | Br | H | 1 |
| SOCF$_3$ | Me | H | CF$_3$ | Br | H | 2 |
| SOCF$_3$ | Me | H | CF$_3$ | I | H | 0 |
| SOCF$_3$ | Me | H | CF$_3$ | I | H | 1 |
| SOCF$_3$ | Me | H | CF$_3$ | I | H | 2 |
| SOCF$_3$ | Me | H | CF$_3$ | CN | H | 0 |
| SOCF$_3$ | Me | H | CF$_3$ | CN | H | 1 |
| SOCF$_3$ | Me | H | CF$_3$ | CN | H | 2 |
| SOCF$_3$ | Et | H | H | H | H | 0 |
| SOCF$_3$ | Et | H | H | H | H | 1 |
| SOCF$_3$ | Et | H | H | H | H | 2 |
| SOCF$_3$ | Et | F | H | H | H | 0 |
| SOCF$_3$ | Et | F | H | H | H | 1 |
| SOCF$_3$ | Et | F | H | H | H | 2 |
| SOCF$_3$ | Et | Cl | H | H | H | 0 |
| SOCF$_3$ | Et | Cl | H | H | H | 1 |
| SOCF$_3$ | Et | Cl | H | H | H | 2 |
| SOCF$_3$ | Et | Br | H | H | H | 0 |
| SOCF$_3$ | Et | Br | H | H | H | 1 |
| SOCF$_3$ | Et | Br | H | H | H | 2 |
| SOCF$_3$ | Et | I | H | H | H | 0 |
| SOCF$_3$ | Et | I | H | H | H | 1 |
| SOCF$_3$ | Et | I | H | H | H | 2 |
| SOCF$_3$ | Et | Me | H | H | H | 0 |
| SOCF$_3$ | Et | Me | H | H | H | 1 |
| SOCF$_3$ | Et | Me | H | H | H | 2 |
| SOCF$_3$ | Et | CF$_3$ | H | H | H | 0 |
| SOCF$_3$ | Et | CF$_3$ | H | H | H | 1 |
| SOCF$_3$ | Et | CF$_3$ | H | H | H | 2 |
| SOCF$_3$ | Et | H | F | H | H | 0 |
| SOCF$_3$ | Et | H | F | H | H | 1 |
| SOCF$_3$ | Et | H | F | H | H | 2 |
| SOCF$_3$ | Et | H | Cl | H | H | 0 |

TABLE 1-continued

| | | | | | | |
|---|---|---|---|---|---|---|
| SOCF₃ | Et | H | Cl | H | H | 1 |
| SOCF₃ | Et | H | Cl | H | H | 2 |
| SOCF₃ | Et | H | Br | H | H | 0 |
| SOCF₃ | Et | H | Br | H | H | 1 |
| SOCF₃ | Et | H | Br | H | H | 2 |
| SOCF₃ | Et | H | I | H | H | 0 |
| SOCF₃ | Et | H | I | H | H | 1 |
| SOCF₃ | Et | H | I | H | H | 2 |
| SOCF₃ | Et | H | Me | H | H | 0 |
| SOCF₃ | Et | H | Me | H | H | 1 |
| SOCF₃ | Et | H | Me | H | H | 2 |
| SOCF₃ | Et | H | CF₃ | H | H | 0 |
| SOCF₃ | Et | H | CF₃ | H | H | 1 |
| SOCF₃ | Et | H | CF₃ | H | H | 2 |
| SOCF₃ | Et | H | CF₂CF₃ | H | H | 0 |
| SOCF₃ | Et | H | CF₂CF₃ | H | H | 1 |
| SOCF₃ | Et | H | CF₂CF₃ | H | H | 2 |
| SOCF₃ | Et | H | CF(CF₃)₂ | H | H | 0 |
| SOCF₃ | Et | H | CF(CF₃)₂ | H | H | 1 |
| SOCF₃ | Et | H | CF(CF₃)₂ | H | H | 2 |
| SOCF₃ | Et | H | SMe | H | H | 0 |
| SOCF₃ | Et | H | SMe | H | H | 1 |
| SOCF₃ | Et | H | SMe | H | H | 2 |
| SOCF₃ | Et | H | SOMe | H | H | 0 |
| SOCF₃ | Et | H | SOMe | H | H | 1 |
| SOCF₃ | Et | H | SOMe | H | H | 2 |
| SOCF₃ | Et | H | SO₂Me | H | H | 0 |
| SOCF₃ | Et | H | SO₂Me | H | H | 1 |
| SOCF₃ | Et | H | SO₂Me | H | H | 2 |
| SOCF₃ | Et | H | OMe | H | H | 0 |
| SOCF₃ | Et | H | OMe | H | H | 1 |
| SOCF₃ | Et | H | OMe | H | H | 2 |
| SOCF₃ | Et | H | OCF₃ | H | H | 0 |
| SOCF₃ | Et | H | OCF₃ | H | H | 1 |
| SOCF₃ | Et | H | OCF₃ | H | H | 2 |
| SOCF₃ | Et | H | NO₂ | H | H | 0 |
| SOCF₃ | Et | H | NO₂ | H | H | 1 |
| SOCF₃ | Et | H | NO₂ | H | H | 2 |
| SOCF₃ | Et | H | CN | H | H | 0 |
| SOCF₃ | Et | H | CN | H | H | 1 |
| SOCF₃ | Et | H | CN | H | H | 2 |
| SOCF₃ | Et | H | H | F | H | 0 |
| SOCF₃ | Et | H | H | F | H | 1 |
| SOCF₃ | Et | H | H | F | H | 2 |
| SOCF₃ | Et | H | H | Cl | H | 0 |
| SOCF₃ | Et | H | H | Cl | H | 1 |
| SOCF₃ | Et | H | H | Cl | H | 2 |
| SOCF₃ | Et | H | H | Br | H | 0 |
| SOCF₃ | Et | H | H | Br | H | 1 |
| SOCF₃ | Et | H | H | Br | H | 2 |
| SOCF₃ | Et | H | H | I | H | 0 |
| SOCF₃ | Et | H | H | I | H | 1 |
| SOCF₃ | Et | H | H | I | H | 2 |
| SOCF₃ | Et | H | H | Me | H | 0 |
| SOCF₃ | Et | H | H | Me | H | 1 |
| SOCF₃ | Et | H | H | Me | H | 2 |
| SOCF₃ | Et | H | H | CF₃ | H | 0 |
| SOCF₃ | Et | H | H | CF₃ | H | 1 |
| SOCF₃ | Et | H | H | CF₃ | H | 2 |
| SOCF₃ | Et | H | H | CF₂CF₃ | H | 0 |
| SOCF₃ | Et | H | H | CF₂CF₃ | H | 1 |
| SOCF₃ | Et | H | H | CF₂CF₃ | H | 2 |
| SOCF₃ | Et | H | H | CF(CF₃)₂ | H | 0 |
| SOCF₃ | Et | H | H | CF(CF₃)₂ | H | 1 |
| SOCF₃ | Et | H | H | CF(CF₃)₂ | H | 2 |
| SOCF₃ | Et | H | H | SMe | H | 0 |
| SOCF₃ | Et | H | H | SMe | H | 1 |
| SOCF₃ | Et | H | H | SMe | H | 2 |
| SOCF₃ | Et | H | H | SOMe | H | 0 |
| SOCF₃ | Et | H | H | SOMe | H | 1 |
| SOCF₃ | Et | H | H | SOMe | H | 2 |
| SOCF₃ | Et | H | H | SO₂Me | H | 0 |
| SOCF₃ | Et | H | H | SO₂Me | H | 1 |
| SOCF₃ | Et | H | H | SO₂Me | H | 2 |
| SOCF₃ | Et | H | H | OMe | H | 0 |
| SOCF₃ | Et | H | H | OMe | H | 1 |
| SOCF₃ | Et | H | H | OMe | H | 2 |
| SOCF₃ | Et | H | H | OCF₃ | H | 0 |
| SOCF₃ | Et | H | H | OCF₃ | H | 1 |
| SOCF₃ | Et | H | H | OCF₃ | H | 2 |
| SOCF₃ | Et | H | H | NO₂ | H | 0 |
| SOCF₃ | Et | H | H | NO₂ | H | 1 |
| SOCF₃ | Et | H | H | NO₂ | H | 2 |
| SOCF₃ | Et | H | H | CN | H | 0 |
| SOCF₃ | Et | H | H | CN | H | 1 |
| SOCF₃ | Et | H | H | CN | H | 2 |
| SOCF₃ | Et | H | H | H | F | 0 |
| SOCF₃ | Et | H | H | H | F | 1 |
| SOCF₃ | Et | H | H | H | F | 2 |
| SOCF₃ | Et | H | H | H | Cl | 0 |
| SOCF₃ | Et | H | H | H | Cl | 1 |
| SOCF₃ | Et | H | H | H | Cl | 2 |
| SOCF₃ | Et | H | H | H | Br | 0 |
| SOCF₃ | Et | H | H | H | Br | 1 |
| SOCF₃ | Et | H | H | H | Br | 2 |
| SOCF₃ | Et | H | H | H | I | 0 |
| SOCF₃ | Et | H | H | H | I | 1 |
| SOCF₃ | Et | H | H | H | I | 2 |
| SOCF₃ | Et | H | H | H | Me | 0 |
| SOCF₃ | Et | H | H | H | Me | 1 |
| SOCF₃ | Et | H | H | H | Me | 2 |
| SOCF₃ | Et | H | H | H | CF₃ | 0 |
| SOCF₃ | Et | H | H | H | CF₃ | 1 |
| SOCF₃ | Et | H | H | H | CF₃ | 2 |
| SOCF₃ | Et | H | H | H | CF₂CF₃ | 0 |
| SOCF₃ | Et | H | H | H | CF₂CF₃ | 1 |
| SOCF₃ | Et | H | H | H | CF₂CF₃ | 2 |
| SOCF₃ | Et | H | H | H | CF(CF₃)₂ | 0 |
| SOCF₃ | Et | H | H | H | CF(CF₃)₂ | 1 |
| SOCF₃ | Et | H | H | H | CF(CF₃)₂ | 2 |
| SOCF₃ | Et | H | H | H | SMe | 0 |
| SOCF₃ | Et | H | H | H | SMe | 1 |
| SOCF₃ | Et | H | H | H | SMe | 2 |
| SOCF₃ | Et | H | H | H | SOMe | 0 |
| SOCF₃ | Et | H | H | H | SOMe | 1 |
| SOCF₃ | Et | H | H | H | SOMe | 2 |
| SOCF₃ | Et | H | H | H | SO₂Me | 0 |
| SOCF₃ | Et | H | H | H | SO₂Me | 1 |
| SOCF₃ | Et | H | H | H | SO₂Me | 2 |
| SOCF₃ | Et | H | H | H | OMe | 0 |
| SOCF₃ | Et | H | H | H | OMe | 1 |
| SOCF₃ | Et | H | H | H | OMe | 2 |
| SOCF₃ | Et | H | H | H | OCF₃ | 0 |
| SOCF₃ | Et | H | H | H | OCF₃ | 1 |
| SOCF₃ | Et | H | H | H | OCF₃ | 2 |
| SOCF₃ | Et | H | H | H | NO₂ | 0 |
| SOCF₃ | Et | H | H | H | NO₂ | 1 |
| SOCF₃ | Et | H | H | H | NO₂ | 2 |
| SOCF₃ | Et | H | H | H | CN | 0 |
| SOCF₃ | Et | H | H | H | CN | 1 |
| SOCF₃ | Et | H | H | H | CN | 2 |
| SOCF₃ | Et | H | F | H | F | 0 |
| SOCF₃ | Et | H | F | H | F | 1 |
| SOCF₃ | Et | H | F | H | F | 2 |
| SOCF₃ | Et | H | Cl | H | Cl | 0 |
| SOCF₃ | Et | H | Cl | H | Cl | 1 |
| SOCF₃ | Et | H | Cl | H | Cl | 2 |
| SOCF₃ | Et | H | Br | H | Br | 0 |
| SOCF₃ | Et | H | Br | H | Br | 1 |
| SOCF₃ | Et | H | Br | H | Br | 2 |
| SOCF₃ | Et | H | I | H | I | 0 |
| SOCF₃ | Et | H | I | H | I | 1 |
| SOCF₃ | Et | H | I | H | I | 2 |
| SOCF₃ | Et | H | F | H | Cl | 0 |
| SOCF₃ | Et | H | F | H | Cl | 1 |
| SOCF₃ | Et | H | F | H | Cl | 2 |
| SOCF₃ | Et | H | F | H | Br | 0 |
| SOCF₃ | Et | H | F | H | Br | 1 |
| SOCF₃ | Et | H | F | H | Br | 2 |
| SOCF₃ | Et | H | F | H | I | 0 |
| SOCF₃ | Et | H | F | H | I | 1 |
| SOCF₃ | Et | H | F | H | I | 2 |
| SOCF₃ | Et | H | Cl | H | F | 0 |
| SOCF₃ | Et | H | Cl | H | F | 1 |
| SOCF₃ | Et | H | Cl | H | F | 2 |
| SOCF₃ | Et | H | Cl | H | Br | 0 |
| SOCF₃ | Et | H | Cl | H | Br | 1 |
| SOCF₃ | Et | H | Cl | H | Br | 2 |
| SOCF₃ | Et | H | Cl | H | I | 0 |
| SOCF₃ | Et | H | Cl | H | I | 1 |

TABLE 1-continued

| | | | | | | |
|---|---|---|---|---|---|---|
| SOCF$_3$ | Et | H | Cl | H | I | 2 |
| SOCF$_3$ | Et | H | Br | H | F | 0 |
| SOCF$_3$ | Et | H | Br | H | F | 1 |
| SOCF$_3$ | Et | H | Br | H | F | 2 |
| SOCF$_3$ | Et | H | Br | H | Cl | 0 |
| SOCF$_3$ | Et | H | Br | H | Cl | 1 |
| SOCF$_3$ | Et | H | Br | H | Cl | 2 |
| SOCF$_3$ | Et | H | Br | H | I | 0 |
| SOCF$_3$ | Et | H | Br | H | I | 1 |
| SOCF$_3$ | Et | H | Br | H | I | 2 |
| SOCF$_3$ | Et | H | I | H | F | 0 |
| SOCF$_3$ | Et | H | I | H | F | 1 |
| SOCF$_3$ | Et | H | I | H | F | 2 |
| SOCF$_3$ | Et | H | I | H | Cl | 0 |
| SOCF$_3$ | Et | H | I | H | Cl | 1 |
| SOCF$_3$ | Et | H | I | H | Cl | 2 |
| SOCF$_3$ | Et | H | I | H | Br | 0 |
| SOCF$_3$ | Et | H | I | H | Br | 1 |
| SOCF$_3$ | Et | H | I | H | Br | 2 |
| SOCF$_3$ | Et | H | F | H | CN | 0 |
| SOCF$_3$ | Et | H | F | H | CN | 1 |
| SOCF$_3$ | Et | H | F | H | CN | 2 |
| SOCF$_3$ | Et | H | Cl | H | CN | 0 |
| SOCF$_3$ | Et | H | Cl | H | CN | 1 |
| SOCF$_3$ | Et | H | Cl | H | CN | 2 |
| SOCF$_3$ | Et | H | Br | H | CN | 0 |
| SOCF$_3$ | Et | H | Br | H | CN | 1 |
| SOCF$_3$ | Et | H | Br | H | CN | 2 |
| SOCF$_3$ | Et | H | I | H | CN | 0 |
| SOCF$_3$ | Et | H | I | H | CN | 1 |
| SOCF$_3$ | Et | H | I | H | CN | 2 |
| SOCF$_3$ | Et | H | CF$_3$ | H | F | 0 |
| SOCF$_3$ | Et | H | CF$_3$ | H | F | 1 |
| SOCF$_3$ | Et | H | CF$_3$ | H | F | 2 |
| SOCF$_3$ | Et | H | CF$_3$ | H | Cl | 0 |
| SOCF$_3$ | Et | H | CF$_3$ | H | Cl | 1 |
| SOCF$_3$ | Et | H | CF$_3$ | H | Cl | 2 |
| SOCF$_3$ | Et | H | CF$_3$ | H | Br | 0 |
| SOCF$_3$ | Et | H | CF$_3$ | H | Br | 1 |
| SOCF$_3$ | Et | H | CF$_3$ | H | Br | 2 |
| SOCF$_3$ | Et | H | CF$_3$ | H | I | 0 |
| SOCF$_3$ | Et | H | CF$_3$ | H | I | 1 |
| SOCF$_3$ | Et | H | CF$_3$ | H | I | 2 |
| SOCF$_3$ | Et | H | CF$_3$ | H | CN | 0 |
| SOCF$_3$ | Et | H | CF$_3$ | H | CN | 1 |
| SOCF$_3$ | Et | H | CF$_3$ | H | CN | 2 |
| SOCF$_3$ | Et | H | F | F | H | 0 |
| SOCF$_3$ | Et | H | F | F | H | 1 |
| SOCF$_3$ | Et | H | F | F | H | 2 |
| SOCF$_3$ | Et | H | Cl | Cl | H | 0 |
| SOCF$_3$ | Et | H | Cl | Cl | H | 1 |
| SOCF$_3$ | Et | H | Cl | Cl | H | 2 |
| SOCF$_3$ | Et | H | Br | Br | H | 0 |
| SOCF$_3$ | Et | H | Br | Br | H | 1 |
| SOCF$_3$ | Et | H | Br | Br | H | 2 |
| SOCF$_3$ | Et | H | I | I | H | 0 |
| SOCF$_3$ | Et | H | I | I | H | 1 |
| SOCF$_3$ | Et | H | I | I | H | 2 |
| SOCF$_3$ | Et | H | F | Cl | H | 0 |
| SOCF$_3$ | Et | H | F | Cl | H | 1 |
| SOCF$_3$ | Et | H | F | Cl | H | 2 |
| SOCF$_3$ | Et | H | F | Br | H | 0 |
| SOCF$_3$ | Et | H | F | Br | H | 1 |
| SOCF$_3$ | Et | H | F | Br | H | 2 |
| SOCF$_3$ | Et | H | F | I | H | 0 |
| SOCF$_3$ | Et | H | F | I | H | 1 |
| SOCF$_3$ | Et | H | F | I | H | 2 |
| SOCF$_3$ | Et | H | Cl | F | H | 0 |
| SOCF$_3$ | Et | H | Cl | F | H | 1 |
| SOCF$_3$ | Et | H | Cl | F | H | 2 |
| SOCF$_3$ | Et | H | Cl | Br | H | 0 |
| SOCF$_3$ | Et | H | Cl | Br | H | 1 |
| SOCF$_3$ | Et | H | Cl | Br | H | 2 |
| SOCF$_3$ | Et | H | Cl | I | H | 0 |
| SOCF$_3$ | Et | H | Cl | I | H | 1 |
| SOCF$_3$ | Et | H | Cl | I | H | 2 |
| SOCF$_3$ | Et | H | Br | F | H | 0 |
| SOCF$_3$ | Et | H | Br | F | H | 1 |
| SOCF$_3$ | Et | H | Br | F | H | 2 |
| SOCF$_3$ | Et | H | Br | Cl | H | 0 |
| SOCF$_3$ | Et | H | Br | Cl | H | 1 |
| SOCF$_3$ | Et | H | Br | Cl | H | 2 |
| SOCF$_3$ | Et | H | Br | I | H | 0 |
| SOCF$_3$ | Et | H | Br | I | H | 1 |
| SOCF$_3$ | Et | H | Br | I | H | 2 |
| SOCF$_3$ | Et | H | I | F | H | 0 |
| SOCF$_3$ | Et | H | I | F | H | 1 |
| SOCF$_3$ | Et | H | I | F | H | 2 |
| SOCF$_3$ | Et | H | I | Cl | H | 0 |
| SOCF$_3$ | Et | H | I | Cl | H | 1 |
| SOCF$_3$ | Et | H | I | Cl | H | 2 |
| SOCF$_3$ | Et | H | I | Br | H | 0 |
| SOCF$_3$ | Et | H | I | Br | H | 1 |
| SOCF$_3$ | Et | H | I | Br | H | 2 |
| SOCF$_3$ | Et | H | F | CN | H | 0 |
| SOCF$_3$ | Et | H | F | CN | H | 1 |
| SOCF$_3$ | Et | H | F | CN | H | 2 |
| SOCF$_3$ | Et | H | Cl | CN | H | 0 |
| SOCF$_3$ | Et | H | Cl | CN | H | 1 |
| SOCF$_3$ | Et | H | Cl | CN | H | 2 |
| SOCF$_3$ | Et | H | Br | CN | H | 0 |
| SOCF$_3$ | Et | H | Br | CN | H | 1 |
| SOCF$_3$ | Et | H | Br | CN | H | 2 |
| SOCF$_3$ | Et | H | I | CN | H | 0 |
| SOCF$_3$ | Et | H | I | CN | H | 1 |
| SOCF$_3$ | Et | H | I | CN | H | 2 |
| SOCF$_3$ | Et | H | CF$_3$ | F | H | 0 |
| SOCF$_3$ | Et | H | CF$_3$ | F | H | 1 |
| SOCF$_3$ | Et | H | CF$_3$ | F | H | 2 |
| SOCF$_3$ | Et | H | CF$_3$ | Cl | H | 0 |
| SOCF$_3$ | Et | H | CF$_3$ | Cl | H | 1 |
| SOCF$_3$ | Et | H | CF$_3$ | Cl | H | 2 |
| SOCF$_3$ | Et | H | CF$_3$ | Br | H | 0 |
| SOCF$_3$ | Et | H | CF$_3$ | Br | H | 1 |
| SOCF$_3$ | Et | H | CF$_3$ | Br | H | 2 |
| SOCF$_3$ | Et | H | CF$_3$ | I | H | 0 |
| SOCF$_3$ | Et | H | CF$_3$ | I | H | 1 |
| SOCF$_3$ | Et | H | CF$_3$ | I | H | 2 |
| SOCF$_3$ | Et | H | CF$_3$ | CN | H | 0 |
| SOCF$_3$ | Et | H | CF$_3$ | CN | H | 1 |
| SOCF$_3$ | Et | H | CF$_3$ | CN | H | 2 |
| SOCF$_3$ | $^n$Pr | H | H | H | H | 0 |
| SOCF$_3$ | $^n$Pr | H | H | H | H | 1 |
| SOCF$_3$ | $^n$Pr | H | H | H | H | 2 |
| SOCF$_3$ | $^n$Pr | F | H | H | H | 0 |
| SOCF$_3$ | $^n$Pr | F | H | H | H | 1 |
| SOCF$_3$ | $^n$Pr | F | H | H | H | 2 |
| SOCF$_3$ | $^n$Pr | Cl | H | H | H | 0 |
| SOCF$_3$ | $^n$Pr | Cl | H | H | H | 1 |
| SOCF$_3$ | $^n$Pr | Cl | H | H | H | 2 |
| SOCF$_3$ | $^n$Pr | Br | H | H | H | 0 |
| SOCF$_3$ | $^n$Pr | Br | H | H | H | 1 |
| SOCF$_3$ | $^n$Pr | Br | H | H | H | 2 |
| SOCF$_3$ | $^n$Pr | I | H | H | H | 0 |
| SOCF$_3$ | $^n$Pr | I | H | H | H | 1 |
| SOCF$_3$ | $^n$Pr | I | H | H | H | 2 |
| SOCF$_3$ | $^n$Pr | Me | H | H | H | 0 |
| SOCF$_3$ | $^n$Pr | Me | H | H | H | 1 |
| SOCF$_3$ | $^n$Pr | Me | H | H | H | 2 |
| SOCF$_3$ | $^n$Pr | CF$_3$ | H | H | H | 0 |
| SOCF$_3$ | $^n$Pr | CF$_3$ | H | H | H | 1 |
| SOCF$_3$ | $^n$Pr | CF$_3$ | H | H | H | 2 |
| SOCF$_3$ | $^n$Pr | H | F | H | H | 0 |
| SOCF$_3$ | $^n$Pr | H | F | H | H | 1 |
| SOCF$_3$ | $^n$Pr | H | F | H | H | 2 |
| SOCF$_3$ | $^n$Pr | H | Cl | H | H | 0 |
| SOCF$_3$ | $^n$Pr | H | Cl | H | H | 1 |
| SOCF$_3$ | $^n$Pr | H | Cl | H | H | 2 |
| SOCF$_3$ | $^n$Pr | H | Br | H | H | 0 |
| SOCF$_3$ | $^n$Pr | H | Br | H | H | 1 |
| SOCF$_3$ | $^n$Pr | H | Br | H | H | 2 |
| SOCF$_3$ | $^n$Pr | H | I | H | H | 0 |
| SOCF$_3$ | $^n$Pr | H | I | H | H | 1 |
| SOCF$_3$ | $^n$Pr | H | I | H | H | 2 |
| SOCF$_3$ | $^n$Pr | H | Me | H | H | 0 |
| SOCF$_3$ | $^n$Pr | H | Me | H | H | 1 |
| SOCF$_3$ | $^n$Pr | H | Me | H | H | 2 |
| SOCF$_3$ | $^n$Pr | H | CF$_3$ | H | H | 0 |
| SOCF$_3$ | $^n$Pr | H | CF$_3$ | H | H | 1 |
| SOCF$_3$ | $^n$Pr | H | CF$_3$ | H | H | 2 |

TABLE 1-continued

| | | | | | | |
|---|---|---|---|---|---|---|
| SOCF$_3$ | $^n$Pr | H | CF$_2$CF$_3$ | H | H | 0 |
| SOCF$_3$ | $^n$Pr | H | CF$_2$CF$_3$ | H | H | 1 |
| SOCF$_3$ | $^n$Pr | H | CF$_2$CF$_3$ | H | H | 2 |
| SOCF$_3$ | $^n$Pr | H | CF(CF$_3$)$_2$ | H | H | 0 |
| SOCF$_3$ | $^n$Pr | H | CF(CF$_3$)$_2$ | H | H | 1 |
| SOCF$_3$ | $^n$Pr | H | CF(CF$_3$)$_2$ | H | H | 2 |
| SOCF$_3$ | $^n$Pr | H | SMe | H | H | 0 |
| SOCF$_3$ | $^n$Pr | H | SMe | H | H | 1 |
| SOCF$_3$ | $^n$Pr | H | SMe | H | H | 2 |
| SOCF$_3$ | $^n$Pr | H | SOMe | H | H | 0 |
| SOCF$_3$ | $^n$Pr | H | SOMe | H | H | 1 |
| SOCF$_3$ | $^n$Pr | H | SOMe | H | H | 2 |
| SOCF$_3$ | $^n$Pr | H | SO$_2$Me | H | H | 0 |
| SOCF$_3$ | $^n$Pr | H | SO$_2$Me | H | H | 1 |
| SOCF$_3$ | $^n$Pr | H | SO$_2$Me | H | H | 2 |
| SOCF$_3$ | $^n$Pr | H | OMe | H | H | 0 |
| SOCF$_3$ | $^n$Pr | H | OMe | H | H | 1 |
| SOCF$_3$ | $^n$Pr | H | OMe | H | H | 2 |
| SOCF$_3$ | $^n$Pr | H | OCF$_3$ | H | H | 0 |
| SOCF$_3$ | $^n$Pr | H | OCF$_3$ | H | H | 1 |
| SOCF$_3$ | $^n$Pr | H | OCF$_3$ | H | H | 2 |
| SOCF$_3$ | $^n$Pr | H | NO$_2$ | H | H | 0 |
| SOCF$_3$ | $^n$Pr | H | NO$_2$ | H | H | 1 |
| SOCF$_3$ | $^n$Pr | H | NO$_2$ | H | H | 2 |
| SOCF$_3$ | $^n$Pr | H | CN | H | H | 0 |
| SOCF$_3$ | $^n$Pr | H | CN | H | H | 1 |
| SOCF$_3$ | $^n$Pr | H | CN | H | H | 2 |
| SOCF$_3$ | $^n$Pr | H | H | F | H | 0 |
| SOCF$_3$ | $^n$Pr | H | H | F | H | 1 |
| SOCF$_3$ | $^n$Pr | H | H | F | H | 2 |
| SOCF$_3$ | $^n$Pr | H | H | Cl | H | 0 |
| SOCF$_3$ | $^n$Pr | H | H | Cl | H | 1 |
| SOCF$_3$ | $^n$Pr | H | H | Cl | H | 2 |
| SOCF$_3$ | $^n$Pr | H | H | Br | H | 0 |
| SOCF$_3$ | $^n$Pr | H | H | Br | H | 1 |
| SOCF$_3$ | $^n$Pr | H | H | Br | H | 2 |
| SOCF$_3$ | $^n$Pr | H | H | I | H | 0 |
| SOCF$_3$ | $^n$Pr | H | H | I | H | 1 |
| SOCF$_3$ | $^n$Pr | H | H | I | H | 2 |
| SOCF$_3$ | $^n$Pr | H | H | Me | H | 0 |
| SOCF$_3$ | $^n$Pr | H | H | Me | H | 1 |
| SOCF$_3$ | $^n$Pr | H | H | Me | H | 2 |
| SOCF$_3$ | $^n$Pr | H | H | CF$_3$ | H | 0 |
| SOCF$_3$ | $^n$Pr | H | H | CF$_3$ | H | 1 |
| SOCF$_3$ | $^n$Pr | H | H | CF$_3$ | H | 2 |
| SOCF$_3$ | $^n$Pr | H | H | CF$_2$CF$_3$ | H | 0 |
| SOCF$_3$ | $^n$Pr | H | H | CF$_2$CF$_3$ | H | 1 |
| SOCF$_3$ | $^n$Pr | H | H | CF$_2$CF$_3$ | H | 2 |
| SOCF$_3$ | $^n$Pr | H | H | CF(CF$_3$)$_2$ | H | 0 |
| SOCF$_3$ | $^n$Pr | H | H | CF(CF$_3$)$_2$ | H | 1 |
| SOCF$_3$ | $^n$Pr | H | H | CF(CF$_3$)$_2$ | H | 2 |
| SOCF$_3$ | $^n$Pr | H | H | SMe | H | 0 |
| SOCF$_3$ | $^n$Pr | H | H | SMe | H | 1 |
| SOCF$_3$ | $^n$Pr | H | H | SMe | H | 2 |
| SOCF$_3$ | $^n$Pr | H | H | SOMe | H | 0 |
| SOCF$_3$ | $^n$Pr | H | H | SOMe | H | 1 |
| SOCF$_3$ | $^n$Pr | H | H | SOMe | H | 2 |
| SOCF$_3$ | $^n$Pr | H | H | SO$_2$Me | H | 0 |
| SOCF$_3$ | $^n$Pr | H | H | SO$_2$Me | H | 1 |
| SOCF$_3$ | $^n$Pr | H | H | SO$_2$Me | H | 2 |
| SOCF$_3$ | $^n$Pr | H | H | OMe | H | 0 |
| SOCF$_3$ | $^n$Pr | H | H | OMe | H | 1 |
| SOCF$_3$ | $^n$Pr | H | H | OMe | H | 2 |
| SOCF$_3$ | $^n$Pr | H | H | OCF$_3$ | H | 0 |
| SOCF$_3$ | $^n$Pr | H | H | OCF$_3$ | H | 1 |
| SOCF$_3$ | $^n$Pr | H | H | OCF$_3$ | H | 2 |
| SOCF$_3$ | $^n$Pr | H | H | NO$_2$ | H | 0 |
| SOCF$_3$ | $^n$Pr | H | H | NO$_2$ | H | 1 |
| SOCF$_3$ | $^n$Pr | H | H | NO$_2$ | H | 2 |
| SOCF$_3$ | $^n$Pr | H | H | CN | H | 0 |
| SOCF$_3$ | $^n$Pr | H | H | CN | H | 1 |
| SOCF$_3$ | $^n$Pr | H | H | CN | H | 2 |
| SOCF$_3$ | $^n$Pr | H | H | H | F | 0 |
| SOCF$_3$ | $^n$Pr | H | H | H | F | 1 |
| SOCF$_3$ | $^n$Pr | H | H | H | F | 2 |
| SOCF$_3$ | $^n$Pr | H | H | H | Cl | 0 |
| SOCF$_3$ | $^n$Pr | H | H | H | Cl | 1 |
| SOCF$_3$ | $^n$Pr | H | H | H | Cl | 2 |
| SOCF$_3$ | $^n$Pr | H | H | H | Br | 0 |
| SOCF$_3$ | $^n$Pr | H | H | H | Br | 1 |
| SOCF$_3$ | $^n$Pr | H | H | H | Br | 2 |
| SOCF$_3$ | $^n$Pr | H | H | H | I | 0 |
| SOCF$_3$ | $^n$Pr | H | H | H | I | 1 |
| SOCF$_3$ | $^n$Pr | H | H | H | I | 2 |
| SOCF$_3$ | $^n$Pr | H | H | H | Me | 0 |
| SOCF$_3$ | $^n$Pr | H | H | H | Me | 1 |
| SOCF$_3$ | $^n$Pr | H | H | H | Me | 2 |
| SOCF$_3$ | $^n$Pr | H | H | H | CF$_3$ | 0 |
| SOCF$_3$ | $^n$Pr | H | H | H | CF$_3$ | 1 |
| SOCF$_3$ | $^n$Pr | H | H | H | CF$_3$ | 2 |
| SOCF$_3$ | $^n$Pr | H | H | H | CF$_2$CF$_3$ | 0 |
| SOCF$_3$ | $^n$Pr | H | H | H | CF$_2$CF$_3$ | 1 |
| SOCF$_3$ | $^n$Pr | H | H | H | CF$_2$CF$_3$ | 2 |
| SOCF$_3$ | $^n$Pr | H | H | H | CF(CF$_3$)$_2$ | 0 |
| SOCF$_3$ | $^n$Pr | H | H | H | CF(CF$_3$)$_2$ | 1 |
| SOCF$_3$ | $^n$Pr | H | H | H | CF(CF$_3$)$_2$ | 2 |
| SOCF$_3$ | $^n$Pr | H | H | H | SMe | 0 |
| SOCF$_3$ | $^n$Pr | H | H | H | SMe | 1 |
| SOCF$_3$ | $^n$Pr | H | H | H | SMe | 2 |
| SOCF$_3$ | $^n$Pr | H | H | H | SOMe | 0 |
| SOCF$_3$ | $^n$Pr | H | H | H | SOMe | 1 |
| SOCF$_3$ | $^n$Pr | H | H | H | SOMe | 2 |
| SOCF$_3$ | $^n$Pr | H | H | H | SO$_2$Me | 0 |
| SOCF$_3$ | $^n$Pr | H | H | H | SO$_2$Me | 1 |
| SOCF$_3$ | $^n$Pr | H | H | H | SO$_2$Me | 2 |
| SOCF$_3$ | $^n$Pr | H | H | H | OMe | 0 |
| SOCF$_3$ | $^n$Pr | H | H | H | OMe | 1 |
| SOCF$_3$ | $^n$Pr | H | H | H | OMe | 2 |
| SOCF$_3$ | $^n$Pr | H | H | H | OCF$_3$ | 0 |
| SOCF$_3$ | $^n$Pr | H | H | H | OCF$_3$ | 1 |
| SOCF$_3$ | $^n$Pr | H | H | H | OCF$_3$ | 2 |
| SOCF$_3$ | $^n$Pr | H | H | H | NO$_2$ | 0 |
| SOCF$_3$ | $^n$Pr | H | H | H | NO$_2$ | 1 |
| SOCF$_3$ | $^n$Pr | H | H | H | NO$_2$ | 2 |
| SOCF$_3$ | $^n$Pr | H | H | H | CN | 0 |
| SOCF$_3$ | $^n$Pr | H | H | H | CN | 1 |
| SOCF$_3$ | $^n$Pr | H | H | H | CN | 2 |
| SOCF$_3$ | $^n$Pr | H | F | H | F | 0 |
| SOCF$_3$ | $^n$Pr | H | F | H | F | 1 |
| SOCF$_3$ | $^n$Pr | H | F | H | F | 2 |
| SOCF$_3$ | $^n$Pr | H | Cl | H | Cl | 0 |
| SOCF$_3$ | $^n$Pr | H | Cl | H | Cl | 1 |
| SOCF$_3$ | $^n$Pr | H | Cl | H | Cl | 2 |
| SOCF$_3$ | $^n$Pr | H | Br | H | Br | 0 |
| SOCF$_3$ | $^n$Pr | H | Br | H | Br | 1 |
| SOCF$_3$ | $^n$Pr | H | Br | H | Br | 2 |
| SOCF$_3$ | $^n$Pr | H | I | H | I | 0 |
| SOCF$_3$ | $^n$Pr | H | I | H | I | 1 |
| SOCF$_3$ | $^n$Pr | H | I | H | I | 2 |
| SOCF$_3$ | $^n$Pr | H | F | H | Cl | 0 |
| SOCF$_3$ | $^n$Pr | H | F | H | Cl | 1 |
| SOCF$_3$ | $^n$Pr | H | F | H | Cl | 2 |
| SOCF$_3$ | $^n$Pr | H | F | H | Br | 0 |
| SOCF$_3$ | $^n$Pr | H | F | H | Br | 1 |
| SOCF$_3$ | $^n$Pr | H | F | H | Br | 2 |
| SOCF$_3$ | $^n$Pr | H | F | H | I | 0 |
| SOCF$_3$ | $^n$Pr | H | F | H | I | 1 |
| SOCF$_3$ | $^n$Pr | H | F | H | I | 2 |
| SOCF$_3$ | $^n$Pr | H | Cl | H | F | 0 |
| SOCF$_3$ | $^n$Pr | H | Cl | H | F | 1 |
| SOCF$_3$ | $^n$Pr | H | Cl | H | F | 2 |
| SOCF$_3$ | $^n$Pr | H | Cl | H | Br | 0 |
| SOCF$_3$ | $^n$Pr | H | Cl | H | Br | 1 |
| SOCF$_3$ | $^n$Pr | H | Cl | H | Br | 2 |
| SOCF$_3$ | $^n$Pr | H | Cl | H | I | 0 |
| SOCF$_3$ | $^n$Pr | H | Cl | H | I | 1 |
| SOCF$_3$ | $^n$Pr | H | Cl | H | I | 2 |
| SOCF$_3$ | $^n$Pr | H | Br | H | F | 0 |
| SOCF$_3$ | $^n$Pr | H | Br | H | F | 1 |
| SOCF$_3$ | $^n$Pr | H | Br | H | F | 2 |
| SOCF$_3$ | $^n$Pr | H | Br | H | Cl | 0 |
| SOCF$_3$ | $^n$Pr | H | Br | H | Cl | 1 |
| SOCF$_3$ | $^n$Pr | H | Br | H | Cl | 2 |
| SOCF$_3$ | $^n$Pr | H | Br | H | I | 0 |
| SOCF$_3$ | $^n$Pr | H | Br | H | I | 1 |
| SOCF$_3$ | $^n$Pr | H | Br | H | I | 2 |
| SOCF$_3$ | $^n$Pr | H | I | H | F | 0 |
| SOCF$_3$ | $^n$Pr | H | I | H | F | 1 |
| SOCF$_3$ | $^n$Pr | H | I | H | F | 2 |
| SOCF$_3$ | $^n$Pr | H | I | H | Cl | 0 |

TABLE 1-continued

| | | | | | | |
|---|---|---|---|---|---|---|
| SOCF$_3$ | $^n$Pr | H | I | H | Cl | 1 |
| SOCF$_3$ | $^n$Pr | H | I | H | Cl | 2 |
| SOCF$_3$ | $^n$Pr | H | I | H | Br | 0 |
| SOCF$_3$ | $^n$Pr | H | I | H | Br | 1 |
| SOCF$_3$ | $^n$Pr | H | I | H | Br | 2 |
| SOCF$_3$ | $^n$Pr | H | F | H | CN | 0 |
| SOCF$_3$ | $^n$Pr | H | F | H | CN | 1 |
| SOCF$_3$ | $^n$Pr | H | F | H | CN | 2 |
| SOCF$_3$ | $^n$Pr | H | Cl | H | CN | 0 |
| SOCF$_3$ | $^n$Pr | H | Cl | H | CN | 1 |
| SOCF$_3$ | $^n$Pr | H | Cl | H | CN | 2 |
| SOCF$_3$ | $^n$Pr | H | Br | H | CN | 0 |
| SOCF$_3$ | $^n$Pr | H | Br | H | CN | 1 |
| SOCF$_3$ | $^n$Pr | H | Br | H | CN | 2 |
| SOCF$_3$ | $^n$Pr | H | I | H | CN | 0 |
| SOCF$_3$ | $^n$Pr | H | I | H | CN | 1 |
| SOCF$_3$ | $^n$Pr | H | I | H | CN | 2 |
| SOCF$_3$ | $^n$Pr | H | CF$_3$ | H | F | 0 |
| SOCF$_3$ | $^n$Pr | H | CF$_3$ | H | F | 1 |
| SOCF$_3$ | $^n$Pr | H | CF$_3$ | H | F | 2 |
| SOCF$_3$ | $^n$Pr | H | CF$_3$ | H | Cl | 0 |
| SOCF$_3$ | $^n$Pr | H | CF$_3$ | H | Cl | 1 |
| SOCF$_3$ | $^n$Pr | H | CF$_3$ | H | Cl | 2 |
| SOCF$_3$ | $^n$Pr | H | CF$_3$ | H | Br | 0 |
| SOCF$_3$ | $^n$Pr | H | CF$_3$ | H | Br | 1 |
| SOCF$_3$ | $^n$Pr | H | CF$_3$ | H | Br | 2 |
| SOCF$_3$ | $^n$Pr | H | CF$_3$ | H | I | 0 |
| SOCF$_3$ | $^n$Pr | H | CF$_3$ | H | I | 1 |
| SOCF$_3$ | $^n$Pr | H | CF$_3$ | H | I | 2 |
| SOCF$_3$ | $^n$Pr | H | CF$_3$ | H | CN | 0 |
| SOCF$_3$ | $^n$Pr | H | CF$_3$ | H | CN | 1 |
| SOCF$_3$ | $^n$Pr | H | CF$_3$ | H | CN | 2 |
| SOCF$_3$ | $^n$Pr | H | F | F | H | 0 |
| SOCF$_3$ | $^n$Pr | H | F | F | H | 1 |
| SOCF$_3$ | $^n$Pr | H | F | F | H | 2 |
| SOCF$_3$ | $^n$Pr | H | Cl | Cl | H | 0 |
| SOCF$_3$ | $^n$Pr | H | Cl | Cl | H | 1 |
| SOCF$_3$ | $^n$Pr | H | Cl | Cl | H | 2 |
| SOCF$_3$ | $^n$Pr | H | Br | Br | H | 0 |
| SOCF$_3$ | $^n$Pr | H | Br | Br | H | 1 |
| SOCF$_3$ | $^n$Pr | H | Br | Br | H | 2 |
| SOCF$_3$ | $^n$Pr | H | I | I | H | 0 |
| SOCF$_3$ | $^n$Pr | H | I | I | H | 1 |
| SOCF$_3$ | $^n$Pr | H | I | I | H | 2 |
| SOCF$_3$ | $^n$Pr | H | F | Cl | H | 0 |
| SOCF$_3$ | $^n$Pr | H | F | Cl | H | 1 |
| SOCF$_3$ | $^n$Pr | H | F | Cl | H | 2 |
| SOCF$_3$ | $^n$Pr | H | F | Br | H | 0 |
| SOCF$_3$ | $^n$Pr | H | F | Br | H | 1 |
| SOCF$_3$ | $^n$Pr | H | F | Br | H | 2 |
| SOCF$_3$ | $^n$Pr | H | F | I | H | 0 |
| SOCF$_3$ | $^n$Pr | H | F | I | H | 1 |
| SOCF$_3$ | $^n$Pr | H | F | I | H | 2 |
| SOCF$_3$ | $^n$Pr | H | Cl | F | H | 0 |
| SOCF$_3$ | $^n$Pr | H | Cl | F | H | 1 |
| SOCF$_3$ | $^n$Pr | H | Cl | F | H | 2 |
| SOCF$_3$ | $^n$Pr | H | Cl | Br | H | 0 |
| SOCF$_3$ | $^n$Pr | H | Cl | Br | H | 1 |
| SOCF$_3$ | $^n$Pr | H | Cl | Br | H | 2 |
| SOCF$_3$ | $^n$Pr | H | Cl | I | H | 0 |
| SOCF$_3$ | $^n$Pr | H | Cl | I | H | 1 |
| SOCF$_3$ | $^n$Pr | H | Cl | I | H | 2 |
| SOCF$_3$ | $^n$Pr | H | Br | F | H | 0 |
| SOCF$_3$ | $^n$Pr | H | Br | F | H | 1 |
| SOCF$_3$ | $^n$Pr | H | Br | F | H | 2 |
| SOCF$_3$ | $^n$Pr | H | Br | Cl | H | 0 |
| SOCF$_3$ | $^n$Pr | H | Br | Cl | H | 1 |
| SOCF$_3$ | $^n$Pr | H | Br | Cl | H | 2 |
| SOCF$_3$ | $^n$Pr | H | Br | I | H | 0 |
| SOCF$_3$ | $^n$Pr | H | Br | I | H | 1 |
| SOCF$_3$ | $^n$Pr | H | Br | I | H | 2 |
| SOCF$_3$ | $^n$Pr | H | I | F | H | 0 |
| SOCF$_3$ | $^n$Pr | H | I | F | H | 1 |
| SOCF$_3$ | $^n$Pr | H | I | F | H | 2 |
| SOCF$_3$ | $^n$Pr | H | I | Cl | H | 0 |
| SOCF$_3$ | $^n$Pr | H | I | Cl | H | 1 |
| SOCF$_3$ | $^n$Pr | H | I | Cl | H | 2 |
| SOCF$_3$ | $^n$Pr | H | I | Br | H | 0 |
| SOCF$_3$ | $^n$Pr | H | I | Br | H | 1 |
| SOCF$_3$ | $^n$Pr | H | I | Br | H | 2 |
| SOCF$_3$ | $^n$Pr | H | F | CN | H | 0 |
| SOCF$_3$ | $^n$Pr | H | F | CN | H | 1 |
| SOCF$_3$ | $^n$Pr | H | F | CN | H | 2 |
| SOCF$_3$ | $^n$Pr | H | Cl | CN | H | 0 |
| SOCF$_3$ | $^n$Pr | H | Cl | CN | H | 1 |
| SOCF$_3$ | $^n$Pr | H | Cl | CN | H | 2 |
| SOCF$_3$ | $^n$Pr | H | Br | CN | H | 0 |
| SOCF$_3$ | $^n$Pr | H | Br | CN | H | 1 |
| SOCF$_3$ | $^n$Pr | H | Br | CN | H | 2 |
| SOCF$_3$ | $^n$Pr | H | I | CN | H | 0 |
| SOCF$_3$ | $^n$Pr | H | I | CN | H | 1 |
| SOCF$_3$ | $^n$Pr | H | I | CN | H | 2 |
| SOCF$_3$ | $^n$Pr | H | CF$_3$ | F | H | 0 |
| SOCF$_3$ | $^n$Pr | H | CF$_3$ | F | H | 1 |
| SOCF$_3$ | $^n$Pr | H | CF$_3$ | F | H | 2 |
| SOCF$_3$ | $^n$Pr | H | CF$_3$ | Cl | H | 0 |
| SOCF$_3$ | $^n$Pr | H | CF$_3$ | Cl | H | 1 |
| SOCF$_3$ | $^n$Pr | H | CF$_3$ | Cl | H | 2 |
| SOCF$_3$ | $^n$Pr | H | CF$_3$ | Br | H | 0 |
| SOCF$_3$ | $^n$Pr | H | CF$_3$ | Br | H | 1 |
| SOCF$_3$ | $^n$Pr | H | CF$_3$ | Br | H | 2 |
| SOCF$_3$ | $^n$Pr | H | CF$_3$ | I | H | 0 |
| SOCF$_3$ | $^n$Pr | H | CF$_3$ | I | H | 1 |
| SOCF$_3$ | $^n$Pr | H | CF$_3$ | I | H | 2 |
| SOCF$_3$ | $^n$Pr | H | CF$_3$ | CN | H | 0 |
| SOCF$_3$ | $^n$Pr | H | CF$_3$ | CN | H | 1 |
| SOCF$_3$ | $^n$Pr | H | CF$_3$ | CN | H | 2 |
| SOCF$_3$ | $^i$Pr | H | H | H | H | 0 |
| SOCF$_3$ | $^i$Pr | H | H | H | H | 1 |
| SOCF$_3$ | $^i$Pr | H | H | H | H | 2 |
| SOCF$_3$ | $^i$Pr | F | H | H | H | 0 |
| SOCF$_3$ | $^i$Pr | F | H | H | H | 1 |
| SOCF$_3$ | $^i$Pr | F | H | H | H | 2 |
| SOCF$_3$ | $^i$Pr | Cl | H | H | H | 0 |
| SOCF$_3$ | $^i$Pr | Cl | H | H | H | 1 |
| SOCF$_3$ | $^i$Pr | Cl | H | H | H | 2 |
| SOCF$_3$ | $^i$Pr | Br | H | H | H | 0 |
| SOCF$_3$ | $^i$Pr | Br | H | H | H | 1 |
| SOCF$_3$ | $^i$Pr | Br | H | H | H | 2 |
| SOCF$_3$ | $^i$Pr | I | H | H | H | 0 |
| SOCF$_3$ | $^i$Pr | I | H | H | H | 1 |
| SOCF$_3$ | $^i$Pr | I | H | H | H | 2 |
| SOCF$_3$ | $^i$Pr | Me | H | H | H | 0 |
| SOCF$_3$ | $^i$Pr | Me | H | H | H | 1 |
| SOCF$_3$ | $^i$Pr | Me | H | H | H | 2 |
| SOCF$_3$ | $^i$Pr | CF$_3$ | H | H | H | 0 |
| SOCF$_3$ | $^i$Pr | CF$_3$ | H | H | H | 1 |
| SOCF$_3$ | $^i$Pr | CF$_3$ | H | H | H | 2 |
| SOCF$_3$ | $^i$Pr | H | F | H | H | 0 |
| SOCF$_3$ | $^i$Pr | H | F | H | H | 1 |
| SOCF$_3$ | $^i$Pr | H | F | H | H | 2 |
| SOCF$_3$ | $^i$Pr | H | Cl | H | H | 0 |
| SOCF$_3$ | $^i$Pr | H | Cl | H | H | 1 |
| SOCF$_3$ | $^i$Pr | H | Cl | H | H | 2 |
| SOCF$_3$ | $^i$Pr | H | Br | H | H | 0 |
| SOCF$_3$ | $^i$Pr | H | Br | H | H | 1 |
| SOCF$_3$ | $^i$Pr | H | Br | H | H | 2 |
| SOCF$_3$ | $^i$Pr | H | I | H | H | 0 |
| SOCF$_3$ | $^i$Pr | H | I | H | H | 1 |
| SOCF$_3$ | $^i$Pr | H | I | H | H | 2 |
| SOCF$_3$ | $^i$Pr | H | Me | H | H | 0 |
| SOCF$_3$ | $^i$Pr | H | Me | H | H | 1 |
| SOCF$_3$ | $^i$Pr | H | Me | H | H | 2 |
| SOCF$_3$ | $^i$Pr | H | CF$_3$ | H | H | 0 |
| SOCF$_3$ | $^i$Pr | H | CF$_3$ | H | H | 1 |
| SOCF$_3$ | $^i$Pr | H | CF$_3$ | H | H | 2 |
| SOCF$_3$ | $^i$Pr | H | CF$_2$CF$_3$ | H | H | 0 |
| SOCF$_3$ | $^i$Pr | H | CF$_2$CF$_3$ | H | H | 1 |
| SOCF$_3$ | $^i$Pr | H | CF$_2$CF$_3$ | H | H | 2 |
| SOCF$_3$ | $^i$Pr | H | CF(CF$_3$)$_2$ | H | H | 0 |
| SOCF$_3$ | $^i$Pr | H | CF(CF$_3$)$_2$ | H | H | 1 |
| SOCF$_3$ | $^i$Pr | H | CF(CF$_3$)$_2$ | H | H | 2 |
| SOCF$_3$ | $^i$Pr | H | SMe | H | H | 0 |
| SOCF$_3$ | $^i$Pr | H | SMe | H | H | 1 |
| SOCF$_3$ | $^i$Pr | H | SMe | H | H | 2 |
| SOCF$_3$ | $^i$Pr | H | SOMe | H | H | 0 |
| SOCF$_3$ | $^i$Pr | H | SOMe | H | H | 1 |
| SOCF$_3$ | $^i$Pr | H | SOMe | H | H | 2 |
| SOCF$_3$ | $^i$Pr | H | SO$_2$Me | H | H | 0 |
| SOCF$_3$ | $^i$Pr | H | SO$_2$Me | H | H | 1 |

TABLE 1-continued

| | | | | | | |
|---|---|---|---|---|---|---|
| SOCF$_3$ | $^i$Pr | H | SO$_2$Me | H | H | 2 |
| SOCF$_3$ | $^i$Pr | H | OMe | H | H | 0 |
| SOCF$_3$ | $^i$Pr | H | OMe | H | H | 1 |
| SOCF$_3$ | $^i$Pr | H | OMe | H | H | 2 |
| SOCF$_3$ | $^i$Pr | H | OCF$_3$ | H | H | 0 |
| SOCF$_3$ | $^i$Pr | H | OCF$_3$ | H | H | 1 |
| SOCF$_3$ | $^i$Pr | H | OCF$_3$ | H | H | 2 |
| SOCF$_3$ | $^i$Pr | H | NO$_2$ | H | H | 0 |
| SOCF$_3$ | $^i$Pr | H | NO$_2$ | H | H | 1 |
| SOCF$_3$ | $^i$Pr | H | NO$_2$ | H | H | 2 |
| SOCF$_3$ | $^i$Pr | H | CN | H | H | 0 |
| SOCF$_3$ | $^i$Pr | H | CN | H | H | 1 |
| SOCF$_3$ | $^i$Pr | H | CN | H | H | 2 |
| SOCF$_3$ | $^i$Pr | H | H | F | H | 0 |
| SOCF$_3$ | $^i$Pr | H | H | F | H | 1 |
| SOCF$_3$ | $^i$Pr | H | H | F | H | 2 |
| SOCF$_3$ | $^i$Pr | H | H | Cl | H | 0 |
| SOCF$_3$ | $^i$Pr | H | H | Cl | H | 1 |
| SOCF$_3$ | $^i$Pr | H | H | Cl | H | 2 |
| SOCF$_3$ | $^i$Pr | H | H | Br | H | 0 |
| SOCF$_3$ | $^i$Pr | H | H | Br | H | 1 |
| SOCF$_3$ | $^i$Pr | H | H | Br | H | 2 |
| SOCF$_3$ | $^i$Pr | H | H | I | H | 0 |
| SOCF$_3$ | $^i$Pr | H | H | I | H | 1 |
| SOCF$_3$ | $^i$Pr | H | H | I | H | 2 |
| SOCF$_3$ | $^i$Pr | H | H | Me | H | 0 |
| SOCF$_3$ | $^i$Pr | H | H | Me | H | 1 |
| SOCF$_3$ | $^i$Pr | H | H | Me | H | 2 |
| SOCF$_3$ | $^i$Pr | H | H | CF$_3$ | H | 0 |
| SOCF$_3$ | $^i$Pr | H | H | CF$_3$ | H | 1 |
| SOCF$_3$ | $^i$Pr | H | H | CF$_3$ | H | 2 |
| SOCF$_3$ | $^i$Pr | H | H | CF$_2$CF$_3$ | H | 0 |
| SOCF$_3$ | $^i$Pr | H | H | CF$_2$CF$_3$ | H | 1 |
| SOCF$_3$ | $^i$Pr | H | H | CF$_2$CF$_3$ | H | 2 |
| SOCF$_3$ | $^i$Pr | H | H | CF(CF$_3$)$_2$ | H | 0 |
| SOCF$_3$ | $^i$Pr | H | H | CF(CF$_3$)$_2$ | H | 1 |
| SOCF$_3$ | $^i$Pr | H | H | CF(CF$_3$)$_2$ | H | 2 |
| SOCF$_3$ | $^i$Pr | H | H | SMe | H | 0 |
| SOCF$_3$ | $^i$Pr | H | H | SMe | H | 1 |
| SOCF$_3$ | $^i$Pr | H | H | SMe | H | 2 |
| SOCF$_3$ | $^i$Pr | H | H | SOMe | H | 0 |
| SOCF$_3$ | $^i$Pr | H | H | SOMe | H | 1 |
| SOCF$_3$ | $^i$Pr | H | H | SOMe | H | 2 |
| SOCF$_3$ | $^i$Pr | H | H | SO$_2$Me | H | 0 |
| SOCF$_3$ | $^i$Pr | H | H | SO$_2$Me | H | 1 |
| SOCF$_3$ | $^i$Pr | H | H | SO$_2$Me | H | 2 |
| SOCF$_3$ | $^i$Pr | H | H | OMe | H | 0 |
| SOCF$_3$ | $^i$Pr | H | H | OMe | H | 1 |
| SOCF$_3$ | $^i$Pr | H | H | OMe | H | 2 |
| SOCF$_3$ | $^i$Pr | H | H | OCF$_3$ | H | 0 |
| SOCF$_3$ | $^i$Pr | H | H | OCF$_3$ | H | 1 |
| SOCF$_3$ | $^i$Pr | H | H | OCF$_3$ | H | 2 |
| SOCF$_3$ | $^i$Pr | H | H | NO$_2$ | H | 0 |
| SOCF$_3$ | $^i$Pr | H | H | NO$_2$ | H | 1 |
| SOCF$_3$ | $^i$Pr | H | H | NO$_2$ | H | 2 |
| SOCF$_3$ | $^i$Pr | H | H | CN | H | 0 |
| SOCF$_3$ | $^i$Pr | H | H | CN | H | 1 |
| SOCF$_3$ | $^i$Pr | H | H | CN | H | 2 |
| SOCF$_3$ | $^i$Pr | H | H | H | F | 0 |
| SOCF$_3$ | $^i$Pr | H | H | H | F | 1 |
| SOCF$_3$ | $^i$Pr | H | H | H | F | 2 |
| SOCF$_3$ | $^i$Pr | H | H | H | Cl | 0 |
| SOCF$_3$ | $^i$Pr | H | H | H | Cl | 1 |
| SOCF$_3$ | $^i$Pr | H | H | H | Cl | 2 |
| SOCF$_3$ | $^i$Pr | H | H | H | Br | 0 |
| SOCF$_3$ | $^i$Pr | H | H | H | Br | 1 |
| SOCF$_3$ | $^i$Pr | H | H | H | Br | 2 |
| SOCF$_3$ | $^i$Pr | H | H | H | I | 0 |
| SOCF$_3$ | $^i$Pr | H | H | H | I | 1 |
| SOCF$_3$ | $^i$Pr | H | H | H | I | 2 |
| SOCF$_3$ | $^i$Pr | H | H | H | Me | 0 |
| SOCF$_3$ | $^i$Pr | H | H | H | Me | 1 |
| SOCF$_3$ | $^i$Pr | H | H | H | Me | 2 |
| SOCF$_3$ | $^i$Pr | H | H | H | CF$_3$ | 0 |
| SOCF$_3$ | $^i$Pr | H | H | H | CF$_3$ | 1 |
| SOCF$_3$ | $^i$Pr | H | H | H | CF$_3$ | 2 |
| SOCF$_3$ | $^i$Pr | H | H | H | CF$_2$CF$_3$ | 0 |
| SOCF$_3$ | $^i$Pr | H | H | H | CF$_2$CF$_3$ | 1 |
| SOCF$_3$ | $^i$Pr | H | H | H | CF$_2$CF$_3$ | 2 |
| SOCF$_3$ | $^i$Pr | H | H | H | CF(CF$_3$)$_2$ | 0 |
| SOCF$_3$ | $^i$Pr | H | H | H | CF(CF$_3$)$_2$ | 1 |
| SOCF$_3$ | $^i$Pr | H | H | H | CF(CF$_3$)$_2$ | 2 |
| SOCF$_3$ | $^i$Pr | H | H | H | SMe | 0 |
| SOCF$_3$ | $^i$Pr | H | H | H | SMe | 1 |
| SOCF$_3$ | $^i$Pr | H | H | H | SMe | 2 |
| SOCF$_3$ | $^i$Pr | H | H | H | SOMe | 0 |
| SOCF$_3$ | $^i$Pr | H | H | H | SOMe | 1 |
| SOCF$_3$ | $^i$Pr | H | H | H | SOMe | 2 |
| SOCF$_3$ | $^i$Pr | H | H | H | SO$_2$Me | 0 |
| SOCF$_3$ | $^i$Pr | H | H | H | SO$_2$Me | 1 |
| SOCF$_3$ | $^i$Pr | H | H | H | SO$_2$Me | 2 |
| SOCF$_3$ | $^i$Pr | H | H | H | OMe | 0 |
| SOCF$_3$ | $^i$Pr | H | H | H | OMe | 1 |
| SOCF$_3$ | $^i$Pr | H | H | H | OMe | 2 |
| SOCF$_3$ | $^i$Pr | H | H | H | OCF$_3$ | 0 |
| SOCF$_3$ | $^i$Pr | H | H | H | OCF$_3$ | 1 |
| SOCF$_3$ | $^i$Pr | H | H | H | OCF$_3$ | 2 |
| SOCF$_3$ | $^i$Pr | H | H | H | NO$_2$ | 0 |
| SOCF$_3$ | $^i$Pr | H | H | H | NO$_2$ | 1 |
| SOCF$_3$ | $^i$Pr | H | H | H | NO$_2$ | 2 |
| SOCF$_3$ | $^i$Pr | H | H | H | CN | 0 |
| SOCF$_3$ | $^i$Pr | H | H | H | CN | 1 |
| SOCF$_3$ | $^i$Pr | H | H | H | CN | 2 |
| SOCF$_3$ | $^i$Pr | H | F | H | F | 0 |
| SOCF$_3$ | $^i$Pr | H | F | H | F | 1 |
| SOCF$_3$ | $^i$Pr | H | F | H | F | 2 |
| SOCF$_3$ | $^i$Pr | H | Cl | H | Cl | 0 |
| SOCF$_3$ | $^i$Pr | H | Cl | H | Cl | 1 |
| SOCF$_3$ | $^i$Pr | H | Cl | H | Cl | 2 |
| SOCF$_3$ | $^i$Pr | H | Br | H | Br | 0 |
| SOCF$_3$ | $^i$Pr | H | Br | H | Br | 1 |
| SOCF$_3$ | $^i$Pr | H | Br | H | Br | 2 |
| SOCF$_3$ | $^i$Pr | H | I | H | I | 0 |
| SOCF$_3$ | $^i$Pr | H | I | H | I | 1 |
| SOCF$_3$ | $^i$Pr | H | I | H | I | 2 |
| SOCF$_3$ | $^i$Pr | H | F | H | Cl | 0 |
| SOCF$_3$ | $^i$Pr | H | F | H | Cl | 1 |
| SOCF$_3$ | $^i$Pr | H | F | H | Cl | 2 |
| SOCF$_3$ | $^i$Pr | H | F | H | Br | 0 |
| SOCF$_3$ | $^i$Pr | H | F | H | Br | 1 |
| SOCF$_3$ | $^i$Pr | H | F | H | Br | 2 |
| SOCF$_3$ | $^i$Pr | H | F | H | I | 0 |
| SOCF$_3$ | $^i$Pr | H | F | H | I | 1 |
| SOCF$_3$ | $^i$Pr | H | F | H | I | 2 |
| SOCF$_3$ | $^i$Pr | H | Cl | H | F | 0 |
| SOCF$_3$ | $^i$Pr | H | Cl | H | F | 1 |
| SOCF$_3$ | $^i$Pr | H | Cl | H | F | 2 |
| SOCF$_3$ | $^i$Pr | H | Cl | H | Br | 0 |
| SOCF$_3$ | $^i$Pr | H | Cl | H | Br | 1 |
| SOCF$_3$ | $^i$Pr | H | Cl | H | Br | 2 |
| SOCF$_3$ | $^i$Pr | H | Cl | H | I | 0 |
| SOCF$_3$ | $^i$Pr | H | Cl | H | I | 1 |
| SOCF$_3$ | $^i$Pr | H | Cl | H | I | 2 |
| SOCF$_3$ | $^i$Pr | H | Br | H | F | 0 |
| SOCF$_3$ | $^i$Pr | H | Br | H | F | 1 |
| SOCF$_3$ | $^i$Pr | H | Br | H | F | 2 |
| SOCF$_3$ | $^i$Pr | H | Br | H | Cl | 0 |
| SOCF$_3$ | $^i$Pr | H | Br | H | Cl | 1 |
| SOCF$_3$ | $^i$Pr | H | Br | H | Cl | 2 |
| SOCF$_3$ | $^i$Pr | H | Br | H | I | 0 |
| SOCF$_3$ | $^i$Pr | H | Br | H | I | 1 |
| SOCF$_3$ | $^i$Pr | H | Br | H | I | 2 |
| SOCF$_3$ | $^i$Pr | H | I | H | F | 0 |
| SOCF$_3$ | $^i$Pr | H | I | H | F | 1 |
| SOCF$_3$ | $^i$Pr | H | I | H | F | 2 |
| SOCF$_3$ | $^i$Pr | H | I | H | Cl | 0 |
| SOCF$_3$ | $^i$Pr | H | I | H | Cl | 1 |
| SOCF$_3$ | $^i$Pr | H | I | H | Cl | 2 |
| SOCF$_3$ | $^i$Pr | H | I | H | Br | 0 |
| SOCF$_3$ | $^i$Pr | H | I | H | Br | 1 |
| SOCF$_3$ | $^i$Pr | H | I | H | Br | 2 |
| SOCF$_3$ | $^i$Pr | H | F | H | CN | 0 |
| SOCF$_3$ | $^i$Pr | H | F | H | CN | 1 |
| SOCF$_3$ | $^i$Pr | H | F | H | CN | 2 |
| SOCF$_3$ | $^i$Pr | H | Cl | H | CN | 0 |
| SOCF$_3$ | $^i$Pr | H | Cl | H | CN | 1 |
| SOCF$_3$ | $^i$Pr | H | Cl | H | CN | 2 |
| SOCF$_3$ | $^i$Pr | H | Br | H | CN | 0 |
| SOCF$_3$ | $^i$Pr | H | Br | H | CN | 1 |
| SOCF$_3$ | $^i$Pr | H | Br | H | CN | 2 |

TABLE 1-continued

| | | | | | | |
|---|---|---|---|---|---|---|
| SOCF$_3$ | $^i$Pr | H | I | H | CN | 0 |
| SOCF$_3$ | $^i$Pr | H | I | H | CN | 1 |
| SOCF$_3$ | $^i$Pr | H | I | H | CN | 2 |
| SOCF$_3$ | $^i$Pr | H | CF$_3$ | H | F | 0 |
| SOCF$_3$ | $^i$Pr | H | CF$_3$ | H | F | 1 |
| SOCF$_3$ | $^i$Pr | H | CF$_3$ | H | F | 2 |
| SOCF$_3$ | $^i$Pr | H | CF$_3$ | H | Cl | 0 |
| SOCF$_3$ | $^i$Pr | H | CF$_3$ | H | Cl | 1 |
| SOCF$_3$ | $^i$Pr | H | CF$_3$ | H | Cl | 2 |
| SOCF$_3$ | $^i$Pr | H | CF$_3$ | H | Br | 0 |
| SOCF$_3$ | $^i$Pr | H | CF$_3$ | H | Br | 1 |
| SOCF$_3$ | $^i$Pr | H | CF$_3$ | H | Br | 2 |
| SOCF$_3$ | $^i$Pr | H | CF$_3$ | H | I | 0 |
| SOCF$_3$ | $^i$Pr | H | CF$_3$ | H | I | 1 |
| SOCF$_3$ | $^i$Pr | H | CF$_3$ | H | I | 2 |
| SOCF$_3$ | $^i$Pr | H | CF$_3$ | H | CN | 0 |
| SOCF$_3$ | $^i$Pr | H | CF$_3$ | H | CN | 1 |
| SOCF$_3$ | $^i$Pr | H | CF$_3$ | H | CN | 2 |
| SOCF$_3$ | $^i$Pr | H | F | F | H | 0 |
| SOCF$_3$ | $^i$Pr | H | F | F | H | 1 |
| SOCF$_3$ | $^i$Pr | H | F | F | H | 2 |
| SOCF$_3$ | $^i$Pr | H | Cl | Cl | H | 0 |
| SOCF$_3$ | $^i$Pr | H | Cl | Cl | H | 1 |
| SOCF$_3$ | $^i$Pr | H | Cl | Cl | H | 2 |
| SOCF$_3$ | $^i$Pr | H | Br | Br | H | 0 |
| SOCF$_3$ | $^i$Pr | H | Br | Br | H | 1 |
| SOCF$_3$ | $^i$Pr | H | Br | Br | H | 2 |
| SOCF$_3$ | $^i$Pr | H | I | I | H | 0 |
| SOCF$_3$ | $^i$Pr | H | I | I | H | 1 |
| SOCF$_3$ | $^i$Pr | H | I | I | H | 2 |
| SOCF$_3$ | $^i$Pr | H | F | Cl | H | 0 |
| SOCF$_3$ | $^i$Pr | H | F | Cl | H | 1 |
| SOCF$_3$ | $^i$Pr | H | F | Cl | H | 2 |
| SOCF$_3$ | $^i$Pr | H | F | Br | H | 0 |
| SOCF$_3$ | $^i$Pr | H | F | Br | H | 1 |
| SOCF$_3$ | $^i$Pr | H | F | Br | H | 2 |
| SOCF$_3$ | $^i$Pr | H | F | I | H | 0 |
| SOCF$_3$ | $^i$Pr | H | F | I | H | 1 |
| SOCF$_3$ | $^i$Pr | H | F | I | H | 2 |
| SOCF$_3$ | $^i$Pr | H | Cl | F | H | 0 |
| SOCF$_3$ | $^i$Pr | H | Cl | F | H | 1 |
| SOCF$_3$ | $^i$Pr | H | Cl | F | H | 2 |
| SOCF$_3$ | $^i$Pr | H | Cl | Br | H | 0 |
| SOCF$_3$ | $^i$Pr | H | Cl | Br | H | 1 |
| SOCF$_3$ | $^i$Pr | H | Cl | Br | H | 2 |
| SOCF$_3$ | $^i$Pr | H | Cl | I | H | 0 |
| SOCF$_3$ | $^i$Pr | H | Cl | I | H | 1 |
| SOCF$_3$ | $^i$Pr | H | Cl | I | H | 2 |
| SOCF$_3$ | $^i$Pr | H | Br | F | H | 0 |
| SOCF$_3$ | $^i$Pr | H | Br | F | H | 1 |
| SOCF$_3$ | $^i$Pr | H | Br | F | H | 2 |
| SOCF$_3$ | $^i$Pr | H | Br | Cl | H | 0 |
| SOCF$_3$ | $^i$Pr | H | Br | Cl | H | 1 |
| SOCF$_3$ | $^i$Pr | H | Br | Cl | H | 2 |
| SOCF$_3$ | $^i$Pr | H | Br | I | H | 0 |
| SOCF$_3$ | $^i$Pr | H | Br | I | H | 1 |
| SOCF$_3$ | $^i$Pr | H | Br | I | H | 2 |
| SOCF$_3$ | $^i$Pr | H | I | F | H | 0 |
| SOCF$_3$ | $^i$Pr | H | I | F | H | 1 |
| SOCF$_3$ | $^i$Pr | H | I | F | H | 2 |
| SOCF$_3$ | $^i$Pr | H | I | Cl | H | 0 |
| SOCF$_3$ | $^i$Pr | H | I | Cl | H | 1 |
| SOCF$_3$ | $^i$Pr | H | I | Cl | H | 2 |
| SOCF$_3$ | $^i$Pr | H | I | Br | H | 0 |
| SOCF$_3$ | $^i$Pr | H | I | Br | H | 1 |
| SOCF$_3$ | $^i$Pr | H | I | Br | H | 2 |
| SOCF$_3$ | $^i$Pr | H | F | CN | H | 0 |
| SOCF$_3$ | $^i$Pr | H | F | CN | H | 1 |
| SOCF$_3$ | $^i$Pr | H | F | CN | H | 2 |
| SOCF$_3$ | $^i$Pr | H | Cl | CN | H | 0 |
| SOCF$_3$ | $^i$Pr | H | Cl | CN | H | 1 |
| SOCF$_3$ | $^i$Pr | H | Cl | CN | H | 2 |
| SOCF$_3$ | $^i$Pr | H | Br | CN | H | 0 |
| SOCF$_3$ | $^i$Pr | H | Br | CN | H | 1 |
| SOCF$_3$ | $^i$Pr | H | Br | CN | H | 2 |
| SOCF$_3$ | $^i$Pr | H | I | CN | H | 0 |
| SOCF$_3$ | $^i$Pr | H | I | CN | H | 1 |
| SOCF$_3$ | $^i$Pr | H | I | CN | H | 2 |
| SOCF$_3$ | $^i$Pr | H | CF$_3$ | F | H | 0 |
| SOCF$_3$ | $^i$Pr | H | CF$_3$ | F | H | 1 |
| SOCF$_3$ | $^i$Pr | H | CF$_3$ | F | H | 2 |
| SOCF$_3$ | $^i$Pr | H | CF$_3$ | Cl | H | 0 |
| SOCF$_3$ | $^i$Pr | H | CF$_3$ | Cl | H | 1 |
| SOCF$_3$ | $^i$Pr | H | CF$_3$ | Cl | H | 2 |
| SOCF$_3$ | $^i$Pr | H | CF$_3$ | Br | H | 0 |
| SOCF$_3$ | $^i$Pr | H | CF$_3$ | Br | H | 1 |
| SOCF$_3$ | $^i$Pr | H | CF$_3$ | Br | H | 2 |
| SOCF$_3$ | $^i$Pr | H | CF$_3$ | I | H | 0 |
| SOCF$_3$ | $^i$Pr | H | CF$_3$ | I | H | 1 |
| SOCF$_3$ | $^i$Pr | H | CF$_3$ | I | H | 2 |
| SOCF$_3$ | $^i$Pr | H | CF$_3$ | CN | H | 0 |
| SOCF$_3$ | $^i$Pr | H | CF$_3$ | CN | H | 1 |
| SOCF$_3$ | $^i$Pr | H | CF$_3$ | CN | H | 2 |
| SOCF$_3$ | CH$_2$CF$_3$ | H | H | H | H | 0 |
| SOCF$_3$ | CH$_2$CF$_3$ | H | H | H | H | 1 |
| SOCF$_3$ | CH$_2$CF$_3$ | H | H | H | H | 2 |
| SOCF$_3$ | CH$_2$CF$_3$ | F | H | H | H | 0 |
| SOCF$_3$ | CH$_2$CF$_3$ | F | H | H | H | 1 |
| SOCF$_3$ | CH$_2$CF$_3$ | F | H | H | H | 2 |
| SOCF$_3$ | CH$_2$CF$_3$ | Cl | H | H | H | 0 |
| SOCF$_3$ | CH$_2$CF$_3$ | Cl | H | H | H | 1 |
| SOCF$_3$ | CH$_2$CF$_3$ | Cl | H | H | H | 2 |
| SOCF$_3$ | CH$_2$CF$_3$ | Br | H | H | H | 0 |
| SOCF$_3$ | CH$_2$CF$_3$ | Br | H | H | H | 1 |
| SOCF$_3$ | CH$_2$CF$_3$ | Br | H | H | H | 2 |
| SOCF$_3$ | CH$_2$CF$_3$ | I | H | H | H | 0 |
| SOCF$_3$ | CH$_2$CF$_3$ | I | H | H | H | 1 |
| SOCF$_3$ | CH$_2$CF$_3$ | I | H | H | H | 2 |
| SOCF$_3$ | CH$_2$CF$_3$ | Me | H | H | H | 0 |
| SOCF$_3$ | CH$_2$CF$_3$ | Me | H | H | H | 1 |
| SOCF$_3$ | CH$_2$CF$_3$ | Me | H | H | H | 2 |
| SOCF$_3$ | CH$_2$CF$_3$ | CF$_3$ | H | H | H | 0 |
| SOCF$_3$ | CH$_2$CF$_3$ | CF$_3$ | H | H | H | 1 |
| SOCF$_3$ | CH$_2$CF$_3$ | CF$_3$ | H | H | H | 2 |
| SOCF$_3$ | CH$_2$CF$_3$ | H | F | H | H | 0 |
| SOCF$_3$ | CH$_2$CF$_3$ | H | F | H | H | 1 |
| SOCF$_3$ | CH$_2$CF$_3$ | H | F | H | H | 2 |
| SOCF$_3$ | CH$_2$CF$_3$ | H | Cl | H | H | 0 |
| SOCF$_3$ | CH$_2$CF$_3$ | H | Cl | H | H | 1 |
| SOCF$_3$ | CH$_2$CF$_3$ | H | Cl | H | H | 2 |
| SOCF$_3$ | CH$_2$CF$_3$ | H | Br | H | H | 0 |
| SOCF$_3$ | CH$_2$CF$_3$ | H | Br | H | H | 1 |
| SOCF$_3$ | CH$_2$CF$_3$ | H | Br | H | H | 2 |
| SOCF$_3$ | CH$_2$CF$_3$ | H | I | H | H | 0 |
| SOCF$_3$ | CH$_2$CF$_3$ | H | I | H | H | 1 |
| SOCF$_3$ | CH$_2$CF$_3$ | H | I | H | H | 2 |
| SOCF$_3$ | CH$_2$CF$_3$ | H | Me | H | H | 0 |
| SOCF$_3$ | CH$_2$CF$_3$ | H | Me | H | H | 1 |
| SOCF$_3$ | CH$_2$CF$_3$ | H | Me | H | H | 2 |
| SOCF$_3$ | CH$_2$CF$_3$ | H | CF$_3$ | H | H | 0 |
| SOCF$_3$ | CH$_2$CF$_3$ | H | CF$_3$ | H | H | 1 |
| SOCF$_3$ | CH$_2$CF$_3$ | H | CF$_3$ | H | H | 2 |
| SOCF$_3$ | CH$_2$CF$_3$ | H | CF$_2$CF$_3$ | H | H | 0 |
| SOCF$_3$ | CH$_2$CF$_3$ | H | CF$_2$CF$_3$ | H | H | 1 |
| SOCF$_3$ | CH$_2$CF$_3$ | H | CF$_2$CF$_3$ | H | H | 2 |
| SOCF$_3$ | CH$_2$CF$_3$ | H | CF(CF$_3$)$_2$ | H | H | 0 |
| SOCF$_3$ | CH$_2$CF$_3$ | H | CF(CF$_3$)$_2$ | H | H | 1 |
| SOCF$_3$ | CH$_2$CF$_3$ | H | CF(CF$_3$)$_2$ | H | H | 2 |
| SOCF$_3$ | CH$_2$CF$_3$ | H | SMe | H | H | 0 |
| SOCF$_3$ | CH$_2$CF$_3$ | H | SMe | H | H | 1 |
| SOCF$_3$ | CH$_2$CF$_3$ | H | SMe | H | H | 2 |
| SOCF$_3$ | CH$_2$CF$_3$ | H | SOMe | H | H | 0 |
| SOCF$_3$ | CH$_2$CF$_3$ | H | SOMe | H | H | 1 |
| SOCF$_3$ | CH$_2$CF$_3$ | H | SOMe | H | H | 2 |
| SOCF$_3$ | CH$_2$CF$_3$ | H | SO$_2$Me | H | H | 0 |
| SOCF$_3$ | CH$_2$CF$_3$ | H | SO$_2$Me | H | H | 1 |
| SOCF$_3$ | CH$_2$CF$_3$ | H | SO$_2$Me | H | H | 2 |
| SOCF$_3$ | CH$_2$CF$_3$ | H | OMe | H | H | 0 |
| SOCF$_3$ | CH$_2$CF$_3$ | H | OMe | H | H | 1 |
| SOCF$_3$ | CH$_2$CF$_3$ | H | OMe | H | H | 2 |
| SOCF$_3$ | CH$_2$CF$_3$ | H | OCF$_3$ | H | H | 0 |
| SOCF$_3$ | CH$_2$CF$_3$ | H | OCF$_3$ | H | H | 1 |
| SOCF$_3$ | CH$_2$CF$_3$ | H | OCF$_3$ | H | H | 2 |
| SOCF$_3$ | CH$_2$CF$_3$ | H | NO$_2$ | H | H | 0 |
| SOCF$_3$ | CH$_2$CF$_3$ | H | NO$_2$ | H | H | 1 |
| SOCF$_3$ | CH$_2$CF$_3$ | H | NO$_2$ | H | H | 2 |
| SOCF$_3$ | CH$_2$CF$_3$ | H | CN | H | H | 0 |
| SOCF$_3$ | CH$_2$CF$_3$ | H | CN | H | H | 1 |
| SOCF$_3$ | CH$_2$CF$_3$ | H | CN | H | H | 2 |
| SOCF$_3$ | CH$_2$CF$_3$ | H | H | F | H | 0 |

TABLE 1-continued

| | | | | | | |
|---|---|---|---|---|---|---|
| SOCF$_3$ | CH$_2$CF$_3$ | H | H | F | H | 1 |
| SOCF$_3$ | CH$_2$CF$_3$ | H | H | F | H | 2 |
| SOCF$_3$ | CH$_2$CF$_3$ | H | H | Cl | H | 0 |
| SOCF$_3$ | CH$_2$CF$_3$ | H | H | Cl | H | 1 |
| SOCF$_3$ | CH$_2$CF$_3$ | H | H | Cl | H | 2 |
| SOCF$_3$ | CH$_2$CF$_3$ | H | H | Br | H | 0 |
| SOCF$_3$ | CH$_2$CF$_3$ | H | H | Br | H | 1 |
| SOCF$_3$ | CH$_2$CF$_3$ | H | H | Br | H | 2 |
| SOCF$_3$ | CH$_2$CF$_3$ | H | H | I | H | 0 |
| SOCF$_3$ | CH$_2$CF$_3$ | H | H | I | H | 1 |
| SOCF$_3$ | CH$_2$CF$_3$ | H | H | I | H | 2 |
| SOCF$_3$ | CH$_2$CF$_3$ | H | H | Me | H | 0 |
| SOCF$_3$ | CH$_2$CF$_3$ | H | H | Me | H | 1 |
| SOCF$_3$ | CH$_2$CF$_3$ | H | H | Me | H | 2 |
| SOCF$_3$ | CH$_2$CF$_3$ | H | H | CF$_3$ | H | 0 |
| SOCF$_3$ | CH$_2$CF$_3$ | H | H | CF$_3$ | H | 1 |
| SOCF$_3$ | CH$_2$CF$_3$ | H | H | CF$_3$ | H | 2 |
| SOCF$_3$ | CH$_2$CF$_3$ | H | H | CF$_2$CF$_3$ | H | 0 |
| SOCF$_3$ | CH$_2$CF$_3$ | H | H | CF$_2$CF$_3$ | H | 1 |
| SOCF$_3$ | CH$_2$CF$_3$ | H | H | CF$_2$CF$_3$ | H | 2 |
| SOCF$_3$ | CH$_2$CF$_3$ | H | H | CF(CF$_3$)$_2$ | H | 0 |
| SOCF$_3$ | CH$_2$CF$_3$ | H | H | CF(CF$_3$)$_2$ | H | 1 |
| SOCF$_3$ | CH$_2$CF$_3$ | H | H | CF(CF$_3$)$_2$ | H | 2 |
| SOCF$_3$ | CH$_2$CF$_3$ | H | H | SMe | H | 0 |
| SOCF$_3$ | CH$_2$CF$_3$ | H | H | SMe | H | 1 |
| SOCF$_3$ | CH$_2$CF$_3$ | H | H | SMe | H | 2 |
| SOCF$_3$ | CH$_2$CF$_3$ | H | H | SOMe | H | 0 |
| SOCF$_3$ | CH$_2$CF$_3$ | H | H | SOMe | H | 1 |
| SOCF$_3$ | CH$_2$CF$_3$ | H | H | SOMe | H | 2 |
| SOCF$_3$ | CH$_2$CF$_3$ | H | H | SO$_2$Me | H | 0 |
| SOCF$_3$ | CH$_2$CF$_3$ | H | H | SO$_2$Me | H | 1 |
| SOCF$_3$ | CH$_2$CF$_3$ | H | H | SO$_2$Me | H | 2 |
| SOCF$_3$ | CH$_2$CF$_3$ | H | H | OMe | H | 0 |
| SOCF$_3$ | CH$_2$CF$_3$ | H | H | OMe | H | 1 |
| SOCF$_3$ | CH$_2$CF$_3$ | H | H | OMe | H | 2 |
| SOCF$_3$ | CH$_2$CF$_3$ | H | H | OCF$_3$ | H | 0 |
| SOCF$_3$ | CH$_2$CF$_3$ | H | H | OCF$_3$ | H | 1 |
| SOCF$_3$ | CH$_2$CF$_3$ | H | H | OCF$_3$ | H | 2 |
| SOCF$_3$ | CH$_2$CF$_3$ | H | H | NO$_2$ | H | 0 |
| SOCF$_3$ | CH$_2$CF$_3$ | H | H | NO$_2$ | H | 1 |
| SOCF$_3$ | CH$_2$CF$_3$ | H | H | NO$_2$ | H | 2 |
| SOCF$_3$ | CH$_2$CF$_3$ | H | H | CN | H | 0 |
| SOCF$_3$ | CH$_2$CF$_3$ | H | H | CN | H | 1 |
| SOCF$_3$ | CH$_2$CF$_3$ | H | H | CN | H | 2 |
| SOCF$_3$ | CH$_2$CF$_3$ | H | H | H | F | 0 |
| SOCF$_3$ | CH$_2$CF$_3$ | H | H | H | F | 1 |
| SOCF$_3$ | CH$_2$CF$_3$ | H | H | H | F | 2 |
| SOCF$_3$ | CH$_2$CF$_3$ | H | H | H | Cl | 0 |
| SOCF$_3$ | CH$_2$CF$_3$ | H | H | H | Cl | 1 |
| SOCF$_3$ | CH$_2$CF$_3$ | H | H | H | Cl | 2 |
| SOCF$_3$ | CH$_2$CF$_3$ | H | H | H | Br | 0 |
| SOCF$_3$ | CH$_2$CF$_3$ | H | H | H | Br | 1 |
| SOCF$_3$ | CH$_2$CF$_3$ | H | H | H | Br | 2 |
| SOCF$_3$ | CH$_2$CF$_3$ | H | H | H | I | 0 |
| SOCF$_3$ | CH$_2$CF$_3$ | H | H | H | I | 1 |
| SOCF$_3$ | CH$_2$CF$_3$ | H | H | H | I | 2 |
| SOCF$_3$ | CH$_2$CF$_3$ | H | H | H | Me | 0 |
| SOCF$_3$ | CH$_2$CF$_3$ | H | H | H | Me | 1 |
| SOCF$_3$ | CH$_2$CF$_3$ | H | H | H | Me | 2 |
| SOCF$_3$ | CH$_2$CF$_3$ | H | H | H | CF$_3$ | 0 |
| SOCF$_3$ | CH$_2$CF$_3$ | H | H | H | CF$_3$ | 1 |
| SOCF$_3$ | CH$_2$CF$_3$ | H | H | H | CF$_3$ | 2 |
| SOCF$_3$ | CH$_2$CF$_3$ | H | H | H | CF$_2$CF$_3$ | 0 |
| SOCF$_3$ | CH$_2$CF$_3$ | H | H | H | CF$_2$CF$_3$ | 1 |
| SOCF$_3$ | CH$_2$CF$_3$ | H | H | H | CF$_2$CF$_3$ | 2 |
| SOCF$_3$ | CH$_2$CF$_3$ | H | H | H | CF(CF$_3$)$_2$ | 0 |
| SOCF$_3$ | CH$_2$CF$_3$ | H | H | H | CF(CF$_3$)$_2$ | 1 |
| SOCF$_3$ | CH$_2$CF$_3$ | H | H | H | CF(CF$_3$)$_2$ | 2 |
| SOCF$_3$ | CH$_2$CF$_3$ | H | H | H | SMe | 0 |
| SOCF$_3$ | CH$_2$CF$_3$ | H | H | H | SMe | 1 |
| SOCF$_3$ | CH$_2$CF$_3$ | H | H | H | SMe | 2 |
| SOCF$_3$ | CH$_2$CF$_3$ | H | H | H | SOMe | 0 |
| SOCF$_3$ | CH$_2$CF$_3$ | H | H | H | SOMe | 1 |
| SOCF$_3$ | CH$_2$CF$_3$ | H | H | H | SOMe | 2 |
| SOCF$_3$ | CH$_2$CF$_3$ | H | H | H | SO$_2$Me | 0 |
| SOCF$_3$ | CH$_2$CF$_3$ | H | H | H | SO$_2$Me | 1 |
| SOCF$_3$ | CH$_2$CF$_3$ | H | H | H | SO$_2$Me | 2 |
| SOCF$_3$ | CH$_2$CF$_3$ | H | H | H | OMe | 0 |
| SOCF$_3$ | CH$_2$CF$_3$ | H | H | H | OMe | 1 |
| SOCF$_3$ | CH$_2$CF$_3$ | H | H | H | OMe | 2 |
| SOCF$_3$ | CH$_2$CF$_3$ | H | H | H | OCF$_3$ | 0 |
| SOCF$_3$ | CH$_2$CF$_3$ | H | H | H | OCF$_3$ | 1 |
| SOCF$_3$ | CH$_2$CF$_3$ | H | H | H | OCF$_3$ | 2 |
| SOCF$_3$ | CH$_2$CF$_3$ | H | H | H | NO$_2$ | 0 |
| SOCF$_3$ | CH$_2$CF$_3$ | H | H | H | NO$_2$ | 1 |
| SOCF$_3$ | CH$_2$CF$_3$ | H | H | H | NO$_2$ | 2 |
| SOCF$_3$ | CH$_2$CF$_3$ | H | H | H | CN | 0 |
| SOCF$_3$ | CH$_2$CF$_3$ | H | H | H | CN | 1 |
| SOCF$_3$ | CH$_2$CF$_3$ | H | H | H | CN | 2 |
| SOCF$_3$ | CH$_2$CF$_3$ | H | F | H | F | 0 |
| SOCF$_3$ | CH$_2$CF$_3$ | H | F | H | F | 1 |
| SOCF$_3$ | CH$_2$CF$_3$ | H | F | H | F | 2 |
| SOCF$_3$ | CH$_2$CF$_3$ | H | Cl | H | Cl | 0 |
| SOCF$_3$ | CH$_2$CF$_3$ | H | Cl | H | Cl | 1 |
| SOCF$_3$ | CH$_2$CF$_3$ | H | Cl | H | Cl | 2 |
| SOCF$_3$ | CH$_2$CF$_3$ | H | Br | H | Br | 0 |
| SOCF$_3$ | CH$_2$CF$_3$ | H | Br | H | Br | 1 |
| SOCF$_3$ | CH$_2$CF$_3$ | H | Br | H | Br | 2 |
| SOCF$_3$ | CH$_2$CF$_3$ | H | I | H | I | 0 |
| SOCF$_3$ | CH$_2$CF$_3$ | H | I | H | I | 1 |
| SOCF$_3$ | CH$_2$CF$_3$ | H | I | H | I | 2 |
| SOCF$_3$ | CH$_2$CF$_3$ | H | F | H | Cl | 0 |
| SOCF$_3$ | CH$_2$CF$_3$ | H | F | H | Cl | 1 |
| SOCF$_3$ | CH$_2$CF$_3$ | H | F | H | Cl | 2 |
| SOCF$_3$ | CH$_2$CF$_3$ | H | Cl | H | Br | 0 |
| SOCF$_3$ | CH$_2$CF$_3$ | H | Cl | H | Br | 1 |
| SOCF$_3$ | CH$_2$CF$_3$ | H | Cl | H | Br | 2 |
| SOCF$_3$ | CH$_2$CF$_3$ | H | F | H | I | 0 |
| SOCF$_3$ | CH$_2$CF$_3$ | H | F | H | I | 1 |
| SOCF$_3$ | CH$_2$CF$_3$ | H | F | H | I | 2 |
| SOCF$_3$ | CH$_2$CF$_3$ | H | Cl | H | F | 0 |
| SOCF$_3$ | CH$_2$CF$_3$ | H | Cl | H | F | 1 |
| SOCF$_3$ | CH$_2$CF$_3$ | H | Cl | H | F | 2 |
| SOCF$_3$ | CH$_2$CF$_3$ | H | Cl | H | Br | 0 |
| SOCF$_3$ | CH$_2$CF$_3$ | H | Cl | H | Br | 1 |
| SOCF$_3$ | CH$_2$CF$_3$ | H | Cl | H | Br | 2 |
| SOCF$_3$ | CH$_2$CF$_3$ | H | Cl | H | I | 0 |
| SOCF$_3$ | CH$_2$CF$_3$ | H | Cl | H | I | 1 |
| SOCF$_3$ | CH$_2$CF$_3$ | H | Cl | H | I | 2 |
| SOCF$_3$ | CH$_2$CF$_3$ | H | Br | H | F | 0 |
| SOCF$_3$ | CH$_2$CF$_3$ | H | Br | H | F | 1 |
| SOCF$_3$ | CH$_2$CF$_3$ | H | Br | H | F | 2 |
| SOCF$_3$ | CH$_2$CF$_3$ | H | Br | H | Cl | 0 |
| SOCF$_3$ | CH$_2$CF$_3$ | H | Br | H | Cl | 1 |
| SOCF$_3$ | CH$_2$CF$_3$ | H | Br | H | Cl | 2 |
| SOCF$_3$ | CH$_2$CF$_3$ | H | Br | H | I | 0 |
| SOCF$_3$ | CH$_2$CF$_3$ | H | Br | H | I | 1 |
| SOCF$_3$ | CH$_2$CF$_3$ | H | Br | H | I | 2 |
| SOCF$_3$ | CH$_2$CF$_3$ | H | I | H | F | 0 |
| SOCF$_3$ | CH$_2$CF$_3$ | H | I | H | F | 1 |
| SOCF$_3$ | CH$_2$CF$_3$ | H | I | H | F | 2 |
| SOCF$_3$ | CH$_2$CF$_3$ | H | I | H | Cl | 0 |
| SOCF$_3$ | CH$_2$CF$_3$ | H | I | H | Cl | 1 |
| SOCF$_3$ | CH$_2$CF$_3$ | H | I | H | Cl | 2 |
| SOCF$_3$ | CH$_2$CF$_3$ | H | I | H | Br | 0 |
| SOCF$_3$ | CH$_2$CF$_3$ | H | I | H | Br | 1 |
| SOCF$_3$ | CH$_2$CF$_3$ | H | I | H | Br | 2 |
| SOCF$_3$ | CH$_2$CF$_3$ | H | F | H | CN | 0 |
| SOCF$_3$ | CH$_2$CF$_3$ | H | F | H | CN | 1 |
| SOCF$_3$ | CH$_2$CF$_3$ | H | F | H | CN | 2 |
| SOCF$_3$ | CH$_2$CF$_3$ | H | Cl | H | CN | 0 |
| SOCF$_3$ | CH$_2$CF$_3$ | H | Cl | H | CN | 1 |
| SOCF$_3$ | CH$_2$CF$_3$ | H | Cl | H | CN | 2 |
| SOCF$_3$ | CH$_2$CF$_3$ | H | Br | H | CN | 0 |
| SOCF$_3$ | CH$_2$CF$_3$ | H | Br | H | CN | 1 |
| SOCF$_3$ | CH$_2$CF$_3$ | H | Br | H | CN | 2 |
| SOCF$_3$ | CH$_2$CF$_3$ | H | I | H | CN | 0 |
| SOCF$_3$ | CH$_2$CF$_3$ | H | I | H | CN | 1 |
| SOCF$_3$ | CH$_2$CF$_3$ | H | I | H | CN | 2 |
| SOCF$_3$ | CH$_2$CF$_3$ | H | CF$_3$ | H | F | 0 |
| SOCF$_3$ | CH$_2$CF$_3$ | H | CF$_3$ | H | F | 1 |
| SOCF$_3$ | CH$_2$CF$_3$ | H | CF$_3$ | H | F | 2 |
| SOCF$_3$ | CH$_2$CF$_3$ | H | CF$_3$ | H | Cl | 0 |
| SOCF$_3$ | CH$_2$CF$_3$ | H | CF$_3$ | H | Cl | 1 |
| SOCF$_3$ | CH$_2$CF$_3$ | H | CF$_3$ | H | Cl | 2 |
| SOCF$_3$ | CH$_2$CF$_3$ | H | CF$_3$ | H | Br | 0 |
| SOCF$_3$ | CH$_2$CF$_3$ | H | CF$_3$ | H | Br | 1 |
| SOCF$_3$ | CH$_2$CF$_3$ | H | CF$_3$ | H | Br | 2 |
| SOCF$_3$ | CH$_2$CF$_3$ | H | CF$_3$ | H | I | 0 |
| SOCF$_3$ | CH$_2$CF$_3$ | H | CF$_3$ | H | I | 1 |

TABLE 1-continued

| | | | | | | |
|---|---|---|---|---|---|---|
| SOCF$_3$ | CH$_2$CF$_3$ | H | CF$_3$ | H | I | 2 |
| SOCF$_3$ | CH$_2$CF$_3$ | H | CF$_3$ | H | CN | 0 |
| SOCF$_3$ | CH$_2$CF$_3$ | H | CF$_3$ | H | CN | 1 |
| SOCF$_3$ | CH$_2$CF$_3$ | H | CF$_3$ | H | CN | 2 |
| SOCF$_3$ | CH$_2$CF$_3$ | H | F | F | H | 0 |
| SOCF$_3$ | CH$_2$CF$_3$ | H | F | F | H | 1 |
| SOCF$_3$ | CH$_2$CF$_3$ | H | F | F | H | 2 |
| SOCF$_3$ | CH$_2$CF$_3$ | H | Cl | Cl | H | 0 |
| SOCF$_3$ | CH$_2$CF$_3$ | H | Cl | Cl | H | 1 |
| SOCF$_3$ | CH$_2$CF$_3$ | H | Cl | Cl | H | 2 |
| SOCF$_3$ | CH$_2$CF$_3$ | H | Br | Br | H | 0 |
| SOCF$_3$ | CH$_2$CF$_3$ | H | Br | Br | H | 1 |
| SOCF$_3$ | CH$_2$CF$_3$ | H | Br | Br | H | 2 |
| SOCF$_3$ | CH$_2$CF$_3$ | H | I | I | H | 0 |
| SOCF$_3$ | CH$_2$CF$_3$ | H | I | I | H | 1 |
| SOCF$_3$ | CH$_2$CF$_3$ | H | I | I | H | 2 |
| SOCF$_3$ | CH$_2$CF$_3$ | H | F | Cl | H | 0 |
| SOCF$_3$ | CH$_2$CF$_3$ | H | F | Cl | H | 1 |
| SOCF$_3$ | CH$_2$CF$_3$ | H | F | Cl | H | 2 |
| SOCF$_3$ | CH$_2$CF$_3$ | H | F | Br | H | 0 |
| SOCF$_3$ | CH$_2$CF$_3$ | H | F | Br | H | 1 |
| SOCF$_3$ | CH$_2$CF$_3$ | H | F | Br | H | 2 |
| SOCF$_3$ | CH$_2$CF$_3$ | H | F | I | H | 0 |
| SOCF$_3$ | CH$_2$CF$_3$ | H | F | I | H | 1 |
| SOCF$_3$ | CH$_2$CF$_3$ | H | F | I | H | 2 |
| SOCF$_3$ | CH$_2$CF$_3$ | H | Cl | F | H | 0 |
| SOCF$_3$ | CH$_2$CF$_3$ | H | Cl | F | H | 1 |
| SOCF$_3$ | CH$_2$CF$_3$ | H | Cl | F | H | 2 |
| SOCF$_3$ | CH$_2$CF$_3$ | H | Cl | Br | H | 0 |
| SOCF$_3$ | CH$_2$CF$_3$ | H | Cl | Br | H | 1 |
| SOCF$_3$ | CH$_2$CF$_3$ | H | Cl | Br | H | 2 |
| SOCF$_3$ | CH$_2$CF$_3$ | H | Cl | I | H | 0 |
| SOCF$_3$ | CH$_2$CF$_3$ | H | Cl | I | H | 1 |
| SOCF$_3$ | CH$_2$CF$_3$ | H | Cl | I | H | 2 |
| SOCF$_3$ | CH$_2$CF$_3$ | H | Br | F | H | 0 |
| SOCF$_3$ | CH$_2$CF$_3$ | H | Br | F | H | 1 |
| SOCF$_3$ | CH$_2$CF$_3$ | H | Br | F | H | 2 |
| SOCF$_3$ | CH$_2$CF$_3$ | H | Br | Cl | H | 0 |
| SOCF$_3$ | CH$_2$CF$_3$ | H | Br | Cl | H | 1 |
| SOCF$_3$ | CH$_2$CF$_3$ | H | Br | Cl | H | 2 |
| SOCF$_3$ | CH$_2$CF$_3$ | H | Br | I | H | 0 |
| SOCF$_3$ | CH$_2$CF$_3$ | H | Br | I | H | 1 |
| SOCF$_3$ | CH$_2$CF$_3$ | H | Br | I | H | 2 |
| SOCF$_3$ | CH$_2$CF$_3$ | H | I | F | H | 0 |
| SOCF$_3$ | CH$_2$CF$_3$ | H | I | F | H | 1 |
| SOCF$_3$ | CH$_2$CF$_3$ | H | I | F | H | 2 |
| SOCF$_3$ | CH$_2$CF$_3$ | H | I | Cl | H | 0 |
| SOCF$_3$ | CH$_2$CF$_3$ | H | I | Cl | H | 1 |
| SOCF$_3$ | CH$_2$CF$_3$ | H | I | Cl | H | 2 |
| SOCF$_3$ | CH$_2$CF$_3$ | H | I | Br | H | 0 |
| SOCF$_3$ | CH$_2$CF$_3$ | H | I | Br | H | 1 |
| SOCF$_3$ | CH$_2$CF$_3$ | H | I | Br | H | 2 |
| SOCF$_3$ | CH$_2$CF$_3$ | H | F | CN | H | 0 |
| SOCF$_3$ | CH$_2$CF$_3$ | H | F | CN | H | 1 |
| SOCF$_3$ | CH$_2$CF$_3$ | H | F | CN | H | 2 |
| SOCF$_3$ | CH$_2$CF$_3$ | H | Cl | CN | H | 0 |
| SOCF$_3$ | CH$_2$CF$_3$ | H | Cl | CN | H | 1 |
| SOCF$_3$ | CH$_2$CF$_3$ | H | Cl | CN | H | 2 |
| SOCF$_3$ | CH$_2$CF$_3$ | H | Br | CN | H | 0 |
| SOCF$_3$ | CH$_2$CF$_3$ | H | Br | CN | H | 1 |
| SOCF$_3$ | CH$_2$CF$_3$ | H | Br | CN | H | 2 |
| SOCF$_3$ | CH$_2$CF$_3$ | H | I | CN | H | 0 |
| SOCF$_3$ | CH$_2$CF$_3$ | H | I | CN | H | 1 |
| SOCF$_3$ | CH$_2$CF$_3$ | H | I | CN | H | 2 |
| SOCF$_3$ | CH$_2$CF$_3$ | H | CF$_3$ | F | H | 0 |
| SOCF$_3$ | CH$_2$CF$_3$ | H | CF$_3$ | F | H | 1 |
| SOCF$_3$ | CH$_2$CF$_3$ | H | CF$_3$ | F | H | 2 |
| SOCF$_3$ | CH$_2$CF$_3$ | H | CF$_3$ | Cl | H | 0 |
| SOCF$_3$ | CH$_2$CF$_3$ | H | CF$_3$ | Cl | H | 1 |
| SOCF$_3$ | CH$_2$CF$_3$ | H | CF$_3$ | Cl | H | 2 |
| SOCF$_3$ | CH$_2$CF$_3$ | H | CF$_3$ | Br | H | 0 |
| SOCF$_3$ | CH$_2$CF$_3$ | H | CF$_3$ | Br | H | 1 |
| SOCF$_3$ | CH$_2$CF$_3$ | H | CF$_3$ | Br | H | 2 |
| SOCF$_3$ | CH$_2$CF$_3$ | H | CF$_3$ | I | H | 0 |
| SOCF$_3$ | CH$_2$CF$_3$ | H | CF$_3$ | I | H | 1 |
| SOCF$_3$ | CH$_2$CF$_3$ | H | CF$_3$ | I | H | 2 |
| SOCF$_3$ | CH$_2$CF$_3$ | H | CF$_3$ | CN | H | 0 |
| SOCF$_3$ | CH$_2$CF$_3$ | H | CF$_3$ | CN | H | 1 |
| SOCF$_3$ | CH$_2$CF$_3$ | H | CF$_3$ | CN | H | 2 |
| SO$_2$CF$_3$ | Me | H | H | H | H | 0 |
| SO$_2$CF$_3$ | Me | H | H | H | H | 1 |
| SO$_2$CF$_3$ | Me | H | H | H | H | 2 |
| SO$_2$CF$_3$ | Me | F | H | H | H | 0 |
| SO$_2$CF$_3$ | Me | F | H | H | H | 1 |
| SO$_2$CF$_3$ | Me | F | H | H | H | 2 |
| SO$_2$CF$_3$ | Me | Cl | H | H | H | 0 |
| SO$_2$CF$_3$ | Me | Cl | H | H | H | 1 |
| SO$_2$CF$_3$ | Me | Cl | H | H | H | 2 |
| SO$_2$CF$_3$ | Me | Br | H | H | H | 0 |
| SO$_2$CF$_3$ | Me | Br | H | H | H | 1 |
| SO$_2$CF$_3$ | Me | Br | H | H | H | 2 |
| SO$_2$CF$_3$ | Me | I | H | H | H | 0 |
| SO$_2$CF$_3$ | Me | I | H | H | H | 1 |
| SO$_2$CF$_3$ | Me | I | H | H | H | 2 |
| SO$_2$CF$_3$ | Me | Me | H | H | H | 0 |
| SO$_2$CF$_3$ | Me | Me | H | H | H | 1 |
| SO$_2$CF$_3$ | Me | Me | H | H | H | 2 |
| SO$_2$CF$_3$ | Me | CF$_3$ | H | H | H | 0 |
| SO$_2$CF$_3$ | Me | CF$_3$ | H | H | H | 1 |
| SO$_2$CF$_3$ | Me | CF$_3$ | H | H | H | 2 |
| SO$_2$CF$_3$ | Me | H | F | H | H | 0 |
| SO$_2$CF$_3$ | Me | H | F | H | H | 1 |
| SO$_2$CF$_3$ | Me | H | F | H | H | 2 |
| SO$_2$CF$_3$ | Me | H | Cl | H | H | 0 |
| SO$_2$CF$_3$ | Me | H | Cl | H | H | 1 |
| SO$_2$CF$_3$ | Me | H | Cl | H | H | 2 |
| SO$_2$CF$_3$ | Me | H | Br | H | H | 0 |
| SO$_2$CF$_3$ | Me | H | Br | H | H | 1 |
| SO$_2$CF$_3$ | Me | H | Br | H | H | 2 |
| SO$_2$CF$_3$ | Me | H | I | H | H | 0 |
| SO$_2$CF$_3$ | Me | H | I | H | H | 1 |
| SO$_2$CF$_3$ | Me | H | I | H | H | 2 |
| SO$_2$CF$_3$ | Me | H | Me | H | H | 0 |
| SO$_2$CF$_3$ | Me | H | Me | H | H | 1 |
| SO$_2$CF$_3$ | Me | H | Me | H | H | 2 |
| SO$_2$CF$_3$ | Me | H | CF$_3$ | H | H | 0 |
| SO$_2$CF$_3$ | Me | H | CF$_3$ | H | H | 1 |
| SO$_2$CF$_3$ | Me | H | CF$_3$ | H | H | 2 |
| SO$_2$CF$_3$ | Me | H | CF$_2$CF$_3$ | H | H | 0 |
| SO$_2$CF$_3$ | Me | H | CF$_2$CF$_3$ | H | H | 1 |
| SO$_2$CF$_3$ | Me | H | CF$_2$CF$_3$ | H | H | 2 |
| SO$_2$CF$_3$ | Me | H | CF(CF$_3$)$_2$ | H | H | 0 |
| SO$_2$CF$_3$ | Me | H | CF(CF$_3$)$_2$ | H | H | 1 |
| SO$_2$CF$_3$ | Me | H | CF(CF$_3$)$_2$ | H | H | 2 |
| SO$_2$CF$_3$ | Me | H | SMe | H | H | 0 |
| SO$_2$CF$_3$ | Me | H | SMe | H | H | 1 |
| SO$_2$CF$_3$ | Me | H | SMe | H | H | 2 |
| SO$_2$CF$_3$ | Me | H | SOMe | H | H | 0 |
| SO$_2$CF$_3$ | Me | H | SOMe | H | H | 1 |
| SO$_2$CF$_3$ | Me | H | SOMe | H | H | 2 |
| SO$_2$CF$_3$ | Me | H | SO$_2$Me | H | H | 0 |
| SO$_2$CF$_3$ | Me | H | SO$_2$Me | H | H | 1 |
| SO$_2$CF$_3$ | Me | H | SO$_2$Me | H | H | 2 |
| SO$_2$CF$_3$ | Me | H | OMe | H | H | 0 |
| SO$_2$CF$_3$ | Me | H | OMe | H | H | 1 |
| SO$_2$CF$_3$ | Me | H | OMe | H | H | 2 |
| SO$_2$CF$_3$ | Me | H | OCF$_3$ | H | H | 0 |
| SO$_2$CF$_3$ | Me | H | OCF$_3$ | H | H | 1 |
| SO$_2$CF$_3$ | Me | H | OCF$_3$ | H | H | 2 |
| SO$_2$CF$_3$ | Me | H | NO$_2$ | H | H | 0 |
| SO$_2$CF$_3$ | Me | H | NO$_2$ | H | H | 1 |
| SO$_2$CF$_3$ | Me | H | NO$_2$ | H | H | 2 |
| SO$_2$CF$_3$ | Me | H | CN | H | H | 0 |
| SO$_2$CF$_3$ | Me | H | CN | H | H | 1 |
| SO$_2$CF$_3$ | Me | H | CN | H | H | 2 |
| SO$_2$CF$_3$ | Me | H | H | F | H | 0 |
| SO$_2$CF$_3$ | Me | H | H | F | H | 1 |
| SO$_2$CF$_3$ | Me | H | H | F | H | 2 |
| SO$_2$CF$_3$ | Me | H | H | Cl | H | 0 |
| SO$_2$CF$_3$ | Me | H | H | Cl | H | 1 |
| SO$_2$CF$_3$ | Me | H | H | Cl | H | 2 |
| SO$_2$CF$_3$ | Me | H | H | Br | H | 0 |
| SO$_2$CF$_3$ | Me | H | H | Br | H | 1 |
| SO$_2$CF$_3$ | Me | H | H | Br | H | 2 |
| SO$_2$CF$_3$ | Me | H | H | I | H | 0 |
| SO$_2$CF$_3$ | Me | H | H | I | H | 1 |
| SO$_2$CF$_3$ | Me | H | H | I | H | 2 |
| SO$_2$CF$_3$ | Me | H | H | Me | H | 0 |
| SO$_2$CF$_3$ | Me | H | H | Me | H | 1 |
| SO$_2$CF$_3$ | Me | H | H | Me | H | 2 |

TABLE 1-continued

| | | | | | | |
|---|---|---|---|---|---|---|
| $SO_2CF_3$ | Me | H | H | $CF_3$ | H | 0 |
| $SO_2CF_3$ | Me | H | H | $CF_3$ | H | 1 |
| $SO_2CF_3$ | Me | H | H | $CF_3$ | H | 2 |
| $SO_2CF_3$ | Me | H | H | $CF_2CF_3$ | H | 0 |
| $SO_2CF_3$ | Me | H | H | $CF_2CF_3$ | H | 1 |
| $SO_2CF_3$ | Me | H | H | $CF_2CF_3$ | H | 2 |
| $SO_2CF_3$ | Me | H | H | $CF(CF_3)_2$ | H | 0 |
| $SO_2CF_3$ | Me | H | H | $CF(CF_3)_2$ | H | 1 |
| $SO_2CF_3$ | Me | H | H | $CF(CF_3)_2$ | H | 2 |
| $SO_2CF_3$ | Me | H | H | SMe | H | 0 |
| $SO_2CF_3$ | Me | H | H | SMe | H | 1 |
| $SO_2CF_3$ | Me | H | H | SMe | H | 2 |
| $SO_2CF_3$ | Me | H | H | SOMe | H | 0 |
| $SO_2CF_3$ | Me | H | H | SOMe | H | 1 |
| $SO_2CF_3$ | Me | H | H | SOMe | H | 2 |
| $SO_2CF_3$ | Me | H | H | $SO_2Me$ | H | 0 |
| $SO_2CF_3$ | Me | H | H | $SO_2Me$ | H | 1 |
| $SO_2CF_3$ | Me | H | H | $SO_2Me$ | H | 2 |
| $SO_2CF_3$ | Me | H | H | OMe | H | 0 |
| $SO_2CF_3$ | Me | H | H | OMe | H | 1 |
| $SO_2CF_3$ | Me | H | H | OMe | H | 2 |
| $SO_2CF_3$ | Me | H | H | $OCF_3$ | H | 0 |
| $SO_2CF_3$ | Me | H | H | $OCF_3$ | H | 1 |
| $SO_2CF_3$ | Me | H | H | $OCF_3$ | H | 2 |
| $SO_2CF_3$ | Me | H | H | $NO_2$ | H | 0 |
| $SO_2CF_3$ | Me | H | H | $NO_2$ | H | 1 |
| $SO_2CF_3$ | Me | H | H | $NO_2$ | H | 2 |
| $SO_2CF_3$ | Me | H | H | CN | H | 0 |
| $SO_2CF_3$ | Me | H | H | CN | H | 1 |
| $SO_2CF_3$ | Me | H | H | CN | H | 2 |
| $SO_2CF_3$ | Me | H | H | H | F | 0 |
| $SO_2CF_3$ | Me | H | H | H | F | 1 |
| $SO_2CF_3$ | Me | H | H | H | F | 2 |
| $SO_2CF_3$ | Me | H | H | H | Cl | 0 |
| $SO_2CF_3$ | Me | H | H | H | Cl | 1 |
| $SO_2CF_3$ | Me | H | H | H | Cl | 2 |
| $SO_2CF_3$ | Me | H | H | H | Br | 0 |
| $SO_2CF_3$ | Me | H | H | H | Br | 1 |
| $SO_2CF_3$ | Me | H | H | H | Br | 2 |
| $SO_2CF_3$ | Me | H | H | H | I | 0 |
| $SO_2CF_3$ | Me | H | H | H | I | 1 |
| $SO_2CF_3$ | Me | H | H | H | I | 2 |
| $SO_2CF_3$ | Me | H | H | H | Me | 0 |
| $SO_2CF_3$ | Me | H | H | H | Me | 1 |
| $SO_2CF_3$ | Me | H | H | H | Me | 2 |
| $SO_2CF_3$ | Me | H | H | H | $CF_3$ | 0 |
| $SO_2CF_3$ | Me | H | H | H | $CF_3$ | 1 |
| $SO_2CF_3$ | Me | H | H | H | $CF_3$ | 2 |
| $SO_2CF_3$ | Me | H | H | H | $CF_2CF_3$ | 0 |
| $SO_2CF_3$ | Me | H | H | H | $CF_2CF_3$ | 1 |
| $SO_2CF_3$ | Me | H | H | H | $CF_2CF_3$ | 2 |
| $SO_2CF_3$ | Me | H | H | H | $CF(CF_3)_2$ | 0 |
| $SO_2CF_3$ | Me | H | H | H | $CF(CF_3)_2$ | 1 |
| $SO_2CF_3$ | Me | H | H | H | $CF(CF_3)_2$ | 2 |
| $SO_2CF_3$ | Me | H | H | H | SMe | 0 |
| $SO_2CF_3$ | Me | H | H | H | SMe | 1 |
| $SO_2CF_3$ | Me | H | H | H | SMe | 2 |
| $SO_2CF_3$ | Me | H | H | H | SOMe | 0 |
| $SO_2CF_3$ | Me | H | H | H | SOMe | 1 |
| $SO_2CF_3$ | Me | H | H | H | SOMe | 2 |
| $SO_2CF_3$ | Me | H | H | H | $SO_2Me$ | 0 |
| $SO_2CF_3$ | Me | H | H | H | $SO_2Me$ | 1 |
| $SO_2CF_3$ | Me | H | H | H | $SO_2Me$ | 2 |
| $SO_2CF_3$ | Me | H | H | H | OMe | 0 |
| $SO_2CF_3$ | Me | H | H | H | OMe | 1 |
| $SO_2CF_3$ | Me | H | H | H | OMe | 2 |
| $SO_2CF_3$ | Me | H | H | H | $OCF_3$ | 0 |
| $SO_2CF_3$ | Me | H | H | H | $OCF_3$ | 1 |
| $SO_2CF_3$ | Me | H | H | H | $OCF_3$ | 2 |
| $SO_2CF_3$ | Me | H | H | H | $NO_2$ | 0 |
| $SO_2CF_3$ | Me | H | H | H | $NO_2$ | 1 |
| $SO_2CF_3$ | Me | H | H | H | $NO_2$ | 2 |
| $SO_2CF_3$ | Me | H | H | H | CN | 0 |
| $SO_2CF_3$ | Me | H | H | H | CN | 1 |
| $SO_2CF_3$ | Me | H | H | H | CN | 2 |
| $SO_2CF_3$ | Me | H | F | H | F | 0 |
| $SO_2CF_3$ | Me | H | F | H | F | 1 |
| $SO_2CF_3$ | Me | H | F | H | F | 2 |
| $SO_2CF_3$ | Me | H | Cl | H | Cl | 0 |
| $SO_2CF_3$ | Me | H | Cl | H | Cl | 1 |
| $SO_2CF_3$ | Me | H | Cl | H | Cl | 2 |
| $SO_2CF_3$ | Me | H | Br | H | Br | 0 |
| $SO_2CF_3$ | Me | H | Br | H | Br | 1 |
| $SO_2CF_3$ | Me | H | Br | H | Br | 2 |
| $SO_2CF_3$ | Me | H | I | H | I | 0 |
| $SO_2CF_3$ | Me | H | I | H | I | 1 |
| $SO_2CF_3$ | Me | H | I | H | I | 2 |
| $SO_2CF_3$ | Me | H | F | H | Cl | 0 |
| $SO_2CF_3$ | Me | H | F | H | Cl | 1 |
| $SO_2CF_3$ | Me | H | F | H | Cl | 2 |
| $SO_2CF_3$ | Me | H | F | H | Br | 0 |
| $SO_2CF_3$ | Me | H | F | H | Br | 1 |
| $SO_2CF_3$ | Me | H | F | H | Br | 2 |
| $SO_2CF_3$ | Me | H | F | H | I | 0 |
| $SO_2CF_3$ | Me | H | F | H | I | 1 |
| $SO_2CF_3$ | Me | H | F | H | I | 2 |
| $SO_2CF_3$ | Me | H | Cl | H | F | 0 |
| $SO_2CF_3$ | Me | H | Cl | H | F | 1 |
| $SO_2CF_3$ | Me | H | Cl | H | F | 2 |
| $SO_2CF_3$ | Me | H | Cl | H | Br | 0 |
| $SO_2CF_3$ | Me | H | Cl | H | Br | 1 |
| $SO_2CF_3$ | Me | H | Cl | H | Br | 2 |
| $SO_2CF_3$ | Me | H | Cl | H | I | 0 |
| $SO_2CF_3$ | Me | H | Cl | H | I | 1 |
| $SO_2CF_3$ | Me | H | Cl | H | I | 2 |
| $SO_2CF_3$ | Me | H | Br | H | F | 0 |
| $SO_2CF_3$ | Me | H | Br | H | F | 1 |
| $SO_2CF_3$ | Me | H | Br | H | F | 2 |
| $SO_2CF_3$ | Me | H | Br | H | Cl | 0 |
| $SO_2CF_3$ | Me | H | Br | H | Cl | 1 |
| $SO_2CF_3$ | Me | H | Br | H | Cl | 2 |
| $SO_2CF_3$ | Me | H | Br | H | I | 0 |
| $SO_2CF_3$ | Me | H | Br | H | I | 1 |
| $SO_2CF_3$ | Me | H | Br | H | I | 2 |
| $SO_2CF_3$ | Me | H | I | H | F | 0 |
| $SO_2CF_3$ | Me | H | I | H | F | 1 |
| $SO_2CF_3$ | Me | H | I | H | F | 2 |
| $SO_2CF_3$ | Me | H | I | H | Cl | 0 |
| $SO_2CF_3$ | Me | H | I | H | Cl | 1 |
| $SO_2CF_3$ | Me | H | I | H | Cl | 2 |
| $SO_2CF_3$ | Me | H | I | H | Br | 0 |
| $SO_2CF_3$ | Me | H | I | H | Br | 1 |
| $SO_2CF_3$ | Me | H | I | H | Br | 2 |
| $SO_2CF_3$ | Me | H | F | H | CN | 0 |
| $SO_2CF_3$ | Me | H | F | H | CN | 1 |
| $SO_2CF_3$ | Me | H | F | H | CN | 2 |
| $SO_2CF_3$ | Me | H | Cl | H | CN | 0 |
| $SO_2CF_3$ | Me | H | Cl | H | CN | 1 |
| $SO_2CF_3$ | Me | H | Cl | H | CN | 2 |
| $SO_2CF_3$ | Me | H | Br | H | CN | 0 |
| $SO_2CF_3$ | Me | H | Br | H | CN | 1 |
| $SO_2CF_3$ | Me | H | Br | H | CN | 2 |
| $SO_2CF_3$ | Me | H | I | H | CN | 0 |
| $SO_2CF_3$ | Me | H | I | H | CN | 1 |
| $SO_2CF_3$ | Me | H | I | H | CN | 2 |
| $SO_2CF_3$ | Me | H | $CF_3$ | H | F | 0 |
| $SO_2CF_3$ | Me | H | $CF_3$ | H | F | 1 |
| $SO_2CF_3$ | Me | H | $CF_3$ | H | F | 2 |
| $SO_2CF_3$ | Me | H | $CF_3$ | H | Cl | 0 |
| $SO_2CF_3$ | Me | H | $CF_3$ | H | Cl | 1 |
| $SO_2CF_3$ | Me | H | $CF_3$ | H | Cl | 2 |
| $SO_2CF_3$ | Me | H | $CF_3$ | H | Br | 0 |
| $SO_2CF_3$ | Me | H | $CF_3$ | H | Br | 1 |
| $SO_2CF_3$ | Me | H | $CF_3$ | H | Br | 2 |
| $SO_2CF_3$ | Me | H | $CF_3$ | H | I | 0 |
| $SO_2CF_3$ | Me | H | $CF_3$ | H | I | 1 |
| $SO_2CF_3$ | Me | H | $CF_3$ | H | I | 2 |
| $SO_2CF_3$ | Me | H | $CF_3$ | H | CN | 0 |
| $SO_2CF_3$ | Me | H | $CF_3$ | H | CN | 1 |
| $SO_2CF_3$ | Me | H | $CF_3$ | H | CN | 2 |
| $SO_2CF_3$ | Me | H | F | F | H | 0 |
| $SO_2CF_3$ | Me | H | F | F | H | 1 |
| $SO_2CF_3$ | Me | H | F | F | H | 2 |
| $SO_2CF_3$ | Me | H | Cl | Cl | H | 0 |
| $SO_2CF_3$ | Me | H | Cl | Cl | H | 1 |
| $SO_2CF_3$ | Me | H | Cl | Cl | H | 2 |
| $SO_2CF_3$ | Me | H | Br | Br | H | 0 |
| $SO_2CF_3$ | Me | H | Br | Br | H | 1 |
| $SO_2CF_3$ | Me | H | Br | Br | H | 2 |
| $SO_2CF_3$ | Me | H | I | I | H | 0 |

TABLE 1-continued

| | | | | | | |
|---|---|---|---|---|---|---|
| SO$_2$CF$_3$ | Me | H | I | I | H | 1 |
| SO$_2$CF$_3$ | Me | H | I | I | H | 2 |
| SO$_2$CF$_3$ | Me | H | F | Cl | H | 0 |
| SO$_2$CF$_3$ | Me | H | F | Cl | H | 1 |
| SO$_2$CF$_3$ | Me | H | F | Cl | H | 2 |
| SO$_2$CF$_3$ | Me | H | F | Br | H | 0 |
| SO$_2$CF$_3$ | Me | H | F | Br | H | 1 |
| SO$_2$CF$_3$ | Me | H | F | Br | H | 2 |
| SO$_2$CF$_3$ | Me | H | F | I | H | 0 |
| SO$_2$CF$_3$ | Me | H | F | I | H | 1 |
| SO$_2$CF$_3$ | Me | H | F | I | H | 2 |
| SO$_2$CF$_3$ | Me | H | Cl | F | H | 0 |
| SO$_2$CF$_3$ | Me | H | Cl | F | H | 1 |
| SO$_2$CF$_3$ | Me | H | Cl | F | H | 2 |
| SO$_2$CF$_3$ | Me | H | Cl | Br | H | 0 |
| SO$_2$CF$_3$ | Me | H | Cl | Br | H | 1 |
| SO$_2$CF$_3$ | Me | H | Cl | Br | H | 2 |
| SO$_2$CF$_3$ | Me | H | Cl | I | H | 0 |
| SO$_2$CF$_3$ | Me | H | Cl | I | H | 1 |
| SO$_2$CF$_3$ | Me | H | Cl | I | H | 2 |
| SO$_2$CF$_3$ | Me | H | Br | F | H | 0 |
| SO$_2$CF$_3$ | Me | H | Br | F | H | 1 |
| SO$_2$CF$_3$ | Me | H | Br | F | H | 2 |
| SO$_2$CF$_3$ | Me | H | Br | Cl | H | 0 |
| SO$_2$CF$_3$ | Me | H | Br | Cl | H | 1 |
| SO$_2$CF$_3$ | Me | H | Br | Cl | H | 2 |
| SO$_2$CF$_3$ | Me | H | Br | I | H | 0 |
| SO$_2$CF$_3$ | Me | H | Br | I | H | 1 |
| SO$_2$CF$_3$ | Me | H | Br | I | H | 2 |
| SO$_2$CF$_3$ | Me | H | I | F | H | 0 |
| SO$_2$CF$_3$ | Me | H | I | F | H | 1 |
| SO$_2$CF$_3$ | Me | H | I | F | H | 2 |
| SO$_2$CF$_3$ | Me | H | I | Cl | H | 0 |
| SO$_2$CF$_3$ | Me | H | I | Cl | H | 1 |
| SO$_2$CF$_3$ | Me | H | I | Cl | H | 2 |
| SO$_2$CF$_3$ | Me | H | I | Br | H | 0 |
| SO$_2$CF$_3$ | Me | H | I | Br | H | 1 |
| SO$_2$CF$_3$ | Me | H | I | Br | H | 2 |
| SO$_2$CF$_3$ | Me | H | F | CN | H | 0 |
| SO$_2$CF$_3$ | Me | H | F | CN | H | 1 |
| SO$_2$CF$_3$ | Me | H | F | CN | H | 2 |
| SO$_2$CF$_3$ | Me | H | Cl | CN | H | 0 |
| SO$_2$CF$_3$ | Me | H | Cl | CN | H | 1 |
| SO$_2$CF$_3$ | Me | H | Cl | CN | H | 2 |
| SO$_2$CF$_3$ | Me | H | Br | CN | H | 0 |
| SO$_2$CF$_3$ | Me | H | Br | CN | H | 1 |
| SO$_2$CF$_3$ | Me | H | Br | CN | H | 2 |
| SO$_2$CF$_3$ | Me | H | I | CN | H | 0 |
| SO$_2$CF$_3$ | Me | H | I | CN | H | 1 |
| SO$_2$CF$_3$ | Me | H | I | CN | H | 2 |
| SO$_2$CF$_3$ | Me | H | CF$_3$ | F | H | 0 |
| SO$_2$CF$_3$ | Me | H | CF$_3$ | F | H | 1 |
| SO$_2$CF$_3$ | Me | H | CF$_3$ | F | H | 2 |
| SO$_2$CF$_3$ | Me | H | CF$_3$ | Cl | H | 0 |
| SO$_2$CF$_3$ | Me | H | CF$_3$ | Cl | H | 1 |
| SO$_2$CF$_3$ | Me | H | CF$_3$ | Cl | H | 2 |
| SO$_2$CF$_3$ | Me | H | CF$_3$ | Br | H | 0 |
| SO$_2$CF$_3$ | Me | H | CF$_3$ | Br | H | 1 |
| SO$_2$CF$_3$ | Me | H | CF$_3$ | Br | H | 2 |
| SO$_2$CF$_3$ | Me | H | CF$_3$ | I | H | 0 |
| SO$_2$CF$_3$ | Me | H | CF$_3$ | I | H | 1 |
| SO$_2$CF$_3$ | Me | H | CF$_3$ | I | H | 2 |
| SO$_2$CF$_3$ | Me | H | CF$_3$ | CN | H | 0 |
| SO$_2$CF$_3$ | Me | H | CF$_3$ | CN | H | 1 |
| SO$_2$CF$_3$ | Me | H | CF$_3$ | CN | H | 2 |
| SO$_2$CF$_3$ | Et | H | H | H | H | 0 |
| SO$_2$CF$_3$ | Et | H | H | H | H | 1 |
| SO$_2$CF$_3$ | Et | H | H | H | H | 2 |
| SO$_2$CF$_3$ | Et | F | H | H | H | 0 |
| SO$_2$CF$_3$ | Et | F | H | H | H | 1 |
| SO$_2$CF$_3$ | Et | F | H | H | H | 2 |
| SO$_2$CF$_3$ | Et | Cl | H | H | H | 0 |
| SO$_2$CF$_3$ | Et | Cl | H | H | H | 1 |
| SO$_2$CF$_3$ | Et | Cl | H | H | H | 2 |
| SO$_2$CF$_3$ | Et | Br | H | H | H | 0 |
| SO$_2$CF$_3$ | Et | Br | H | H | H | 1 |
| SO$_2$CF$_3$ | Et | Br | H | H | H | 2 |
| SO$_2$CF$_3$ | Et | I | H | H | H | 0 |
| SO$_2$CF$_3$ | Et | I | H | H | H | 1 |
| SO$_2$CF$_3$ | Et | I | H | H | H | 2 |
| SO$_2$CF$_3$ | Et | Me | H | H | H | 0 |
| SO$_2$CF$_3$ | Et | Me | H | H | H | 1 |
| SO$_2$CF$_3$ | Et | Me | H | H | H | 2 |
| SO$_2$CF$_3$ | Et | CF$_3$ | H | H | H | 0 |
| SO$_2$CF$_3$ | Et | CF$_3$ | H | H | H | 1 |
| SO$_2$CF$_3$ | Et | CF$_3$ | H | H | H | 2 |
| SO$_2$CF$_3$ | Et | H | F | H | H | 0 |
| SO$_2$CF$_3$ | Et | H | F | H | H | 1 |
| SO$_2$CF$_3$ | Et | H | F | H | H | 2 |
| SO$_2$CF$_3$ | Et | H | Cl | H | H | 0 |
| SO$_2$CF$_3$ | Et | H | Cl | H | H | 1 |
| SO$_2$CF$_3$ | Et | H | Cl | H | H | 2 |
| SO$_2$CF$_3$ | Et | H | Br | H | H | 0 |
| SO$_2$CF$_3$ | Et | H | Br | H | H | 1 |
| SO$_2$CF$_3$ | Et | H | Br | H | H | 2 |
| SO$_2$CF$_3$ | Et | H | I | H | H | 0 |
| SO$_2$CF$_3$ | Et | H | I | H | H | 1 |
| SO$_2$CF$_3$ | Et | H | I | H | H | 2 |
| SO$_2$CF$_3$ | Et | H | Me | H | H | 0 |
| SO$_2$CF$_3$ | Et | H | Me | H | H | 1 |
| SO$_2$CF$_3$ | Et | H | Me | H | H | 2 |
| SO$_2$CF$_3$ | Et | H | CF$_3$ | H | H | 0 |
| SO$_2$CF$_3$ | Et | H | CF$_3$ | H | H | 1 |
| SO$_2$CF$_3$ | Et | H | CF$_3$ | H | H | 2 |
| SO$_2$CF$_3$ | Et | H | CF$_2$CF$_3$ | H | H | 0 |
| SO$_2$CF$_3$ | Et | H | CF$_2$CF$_3$ | H | H | 1 |
| SO$_2$CF$_3$ | Et | H | CF$_2$CF$_3$ | H | H | 2 |
| SO$_2$CF$_3$ | Et | H | CF(CF$_3$)$_2$ | H | H | 0 |
| SO$_2$CF$_3$ | Et | H | CF(CF$_3$)$_2$ | H | H | 1 |
| SO$_2$CF$_3$ | Et | H | CF(CF$_3$)$_2$ | H | H | 2 |
| SO$_2$CF$_3$ | Et | H | SMe | H | H | 0 |
| SO$_2$CF$_3$ | Et | H | SMe | H | H | 1 |
| SO$_2$CF$_3$ | Et | H | SMe | H | H | 2 |
| SO$_2$CF$_3$ | Et | H | SOMe | H | H | 0 |
| SO$_2$CF$_3$ | Et | H | SOMe | H | H | 1 |
| SO$_2$CF$_3$ | Et | H | SOMe | H | H | 2 |
| SO$_2$CF$_3$ | Et | H | SO$_2$Me | H | H | 0 |
| SO$_2$CF$_3$ | Et | H | SO$_2$Me | H | H | 1 |
| SO$_2$CF$_3$ | Et | H | SO$_2$Me | H | H | 2 |
| SO$_2$CF$_3$ | Et | H | OMe | H | H | 0 |
| SO$_2$CF$_3$ | Et | H | OMe | H | H | 1 |
| SO$_2$CF$_3$ | Et | H | OMe | H | H | 2 |
| SO$_2$CF$_3$ | Et | H | OCF$_3$ | H | H | 0 |
| SO$_2$CF$_3$ | Et | H | OCF$_3$ | H | H | 1 |
| SO$_2$CF$_3$ | Et | H | OCF$_3$ | H | H | 2 |
| SO$_2$CF$_3$ | Et | H | NO$_2$ | H | H | 0 |
| SO$_2$CF$_3$ | Et | H | NO$_2$ | H | H | 1 |
| SO$_2$CF$_3$ | Et | H | NO$_2$ | H | H | 2 |
| SO$_2$CF$_3$ | Et | H | CN | H | H | 0 |
| SO$_2$CF$_3$ | Et | H | CN | H | H | 1 |
| SO$_2$CF$_3$ | Et | H | CN | H | H | 2 |
| SO$_2$CF$_3$ | Et | H | H | F | H | 0 |
| SO$_2$CF$_3$ | Et | H | H | F | H | 1 |
| SO$_2$CF$_3$ | Et | H | H | F | H | 2 |
| SO$_2$CF$_3$ | Et | H | H | Cl | H | 0 |
| SO$_2$CF$_3$ | Et | H | H | Cl | H | 1 |
| SO$_2$CF$_3$ | Et | H | H | Cl | H | 2 |
| SO$_2$CF$_3$ | Et | H | H | Br | H | 0 |
| SO$_2$CF$_3$ | Et | H | H | Br | H | 1 |
| SO$_2$CF$_3$ | Et | H | H | Br | H | 2 |
| SO$_2$CF$_3$ | Et | H | H | I | H | 0 |
| SO$_2$CF$_3$ | Et | H | H | I | H | 1 |
| SO$_2$CF$_3$ | Et | H | H | I | H | 2 |
| SO$_2$CF$_3$ | Et | H | H | Me | H | 0 |
| SO$_2$CF$_3$ | Et | H | H | Me | H | 1 |
| SO$_2$CF$_3$ | Et | H | H | Me | H | 2 |
| SO$_2$CF$_3$ | Et | H | H | CF$_3$ | H | 0 |
| SO$_2$CF$_3$ | Et | H | H | CF$_3$ | H | 1 |
| SO$_2$CF$_3$ | Et | H | H | CF$_3$ | H | 2 |
| SO$_2$CF$_3$ | Et | H | H | CF$_2$CF$_3$ | H | 0 |
| SO$_2$CF$_3$ | Et | H | H | CF$_2$CF$_3$ | H | 1 |
| SO$_2$CF$_3$ | Et | H | H | CF$_2$CF$_3$ | H | 2 |
| SO$_2$CF$_3$ | Et | H | H | CF(CF$_3$)$_2$ | H | 0 |
| SO$_2$CF$_3$ | Et | H | H | CF(CF$_3$)$_2$ | H | 1 |
| SO$_2$CF$_3$ | Et | H | H | CF(CF$_3$)$_2$ | H | 2 |
| SO$_2$CF$_3$ | Et | H | H | SMe | H | 0 |
| SO$_2$CF$_3$ | Et | H | H | SMe | H | 1 |
| SO$_2$CF$_3$ | Et | H | H | SMe | H | 2 |
| SO$_2$CF$_3$ | Et | H | H | SOMe | H | 0 |
| SO$_2$CF$_3$ | Et | H | H | SOMe | H | 1 |

TABLE 1-continued

| | | | | | | |
|---|---|---|---|---|---|---|
| SO₂CF₃ | Et | H | H | SOMe | H | 2 |
| SO₂CF₃ | Et | H | H | SO₂Me | H | 0 |
| SO₂CF₃ | Et | H | H | SO₂Me | H | 1 |
| SO₂CF₃ | Et | H | H | SO₂Me | H | 2 |
| SO₂CF₃ | Et | H | H | OMe | H | 0 |
| SO₂CF₃ | Et | H | H | OMe | H | 1 |
| SO₂CF₃ | Et | H | H | OMe | H | 2 |
| SO₂CF₃ | Et | H | H | OCF₃ | H | 0 |
| SO₂CF₃ | Et | H | H | OCF₃ | H | 1 |
| SO₂CF₃ | Et | H | H | OCF₃ | H | 2 |
| SO₂CF₃ | Et | H | H | NO₂ | H | 0 |
| SO₂CF₃ | Et | H | H | NO₂ | H | 1 |
| SO₂CF₃ | Et | H | H | NO₂ | H | 2 |
| SO₂CF₃ | Et | H | H | CN | H | 0 |
| SO₂CF₃ | Et | H | H | CN | H | 1 |
| SO₂CF₃ | Et | H | H | CN | H | 2 |
| SO₂CF₃ | Et | H | H | H | F | 0 |
| SO₂CF₃ | Et | H | H | H | F | 1 |
| SO₂CF₃ | Et | H | H | H | F | 2 |
| SO₂CF₃ | Et | H | H | H | Cl | 0 |
| SO₂CF₃ | Et | H | H | H | Cl | 1 |
| SO₂CF₃ | Et | H | H | H | Cl | 2 |
| SO₂CF₃ | Et | H | H | H | Br | 0 |
| SO₂CF₃ | Et | H | H | H | Br | 1 |
| SO₂CF₃ | Et | H | H | H | Br | 2 |
| SO₂CF₃ | Et | H | H | H | I | 0 |
| SO₂CF₃ | Et | H | H | H | I | 1 |
| SO₂CF₃ | Et | H | H | H | I | 2 |
| SO₂CF₃ | Et | H | H | H | Me | 0 |
| SO₂CF₃ | Et | H | H | H | Me | 1 |
| SO₂CF₃ | Et | H | H | H | Me | 2 |
| SO₂CF₃ | Et | H | H | H | CF₃ | 0 |
| SO₂CF₃ | Et | H | H | H | CF₃ | 1 |
| SO₂CF₃ | Et | H | H | H | CF₃ | 2 |
| SO₂CF₃ | Et | H | H | H | CF₂CF₃ | 0 |
| SO₂CF₃ | Et | H | H | H | CF₂CF₃ | 1 |
| SO₂CF₃ | Et | H | H | H | CF₂CF₃ | 2 |
| SO₂CF₃ | Et | H | H | H | CF(CF₃)₂ | 0 |
| SO₂CF₃ | Et | H | H | H | CF(CF₃)₂ | 1 |
| SO₂CF₃ | Et | H | H | H | CF(CF₃)₂ | 2 |
| SO₂CF₃ | Et | H | H | H | SMe | 0 |
| SO₂CF₃ | Et | H | H | H | SMe | 1 |
| SO₂CF₃ | Et | H | H | H | SMe | 2 |
| SO₂CF₃ | Et | H | H | H | SOMe | 0 |
| SO₂CF₃ | Et | H | H | H | SOMe | 1 |
| SO₂CF₃ | Et | H | H | H | SOMe | 2 |
| SO₂CF₃ | Et | H | H | H | SO₂Me | 0 |
| SO₂CF₃ | Et | H | H | H | SO₂Me | 1 |
| SO₂CF₃ | Et | H | H | H | SO₂Me | 2 |
| SO₂CF₃ | Et | H | H | H | OMe | 0 |
| SO₂CF₃ | Et | H | H | H | OMe | 1 |
| SO₂CF₃ | Et | H | H | H | OMe | 2 |
| SO₂CF₃ | Et | H | H | H | OCF₃ | 0 |
| SO₂CF₃ | Et | H | H | H | OCF₃ | 1 |
| SO₂CF₃ | Et | H | H | H | OCF₃ | 2 |
| SO₂CF₃ | Et | H | H | H | NO₂ | 0 |
| SO₂CF₃ | Et | H | H | H | NO₂ | 1 |
| SO₂CF₃ | Et | H | H | H | NO₂ | 2 |
| SO₂CF₃ | Et | H | H | H | CN | 0 |
| SO₂CF₃ | Et | H | H | H | CN | 1 |
| SO₂CF₃ | Et | H | H | H | CN | 2 |
| SO₂CF₃ | Et | H | F | H | F | 0 |
| SO₂CF₃ | Et | H | F | H | F | 1 |
| SO₂CF₃ | Et | H | F | H | F | 2 |
| SO₂CF₃ | Et | H | Cl | H | Cl | 0 |
| SO₂CF₃ | Et | H | Cl | H | Cl | 1 |
| SO₂CF₃ | Et | H | Cl | H | Cl | 2 |
| SO₂CF₃ | Et | H | Br | H | Br | 0 |
| SO₂CF₃ | Et | H | Br | H | Br | 1 |
| SO₂CF₃ | Et | H | Br | H | Br | 2 |
| SO₂CF₃ | Et | H | I | H | I | 0 |
| SO₂CF₃ | Et | H | I | H | I | 1 |
| SO₂CF₃ | Et | H | I | H | I | 2 |
| SO₂CF₃ | Et | H | F | H | Cl | 0 |
| SO₂CF₃ | Et | H | F | H | Cl | 1 |
| SO₂CF₃ | Et | H | F | H | Cl | 2 |
| SO₂CF₃ | Et | H | F | H | Br | 0 |
| SO₂CF₃ | Et | H | F | H | Br | 1 |
| SO₂CF₃ | Et | H | F | H | Br | 2 |
| SO₂CF₃ | Et | H | F | H | I | 0 |
| SO₂CF₃ | Et | H | F | H | I | 1 |
| SO₂CF₃ | Et | H | F | H | I | 2 |
| SO₂CF₃ | Et | H | Cl | H | F | 0 |
| SO₂CF₃ | Et | H | Cl | H | F | 1 |
| SO₂CF₃ | Et | H | Cl | H | F | 2 |
| SO₂CF₃ | Et | H | Cl | H | Br | 0 |
| SO₂CF₃ | Et | H | Cl | H | Br | 1 |
| SO₂CF₃ | Et | H | Cl | H | Br | 2 |
| SO₂CF₃ | Et | H | Cl | H | I | 0 |
| SO₂CF₃ | Et | H | Cl | H | I | 1 |
| SO₂CF₃ | Et | H | Cl | H | I | 2 |
| SO₂CF₃ | Et | H | Br | H | F | 0 |
| SO₂CF₃ | Et | H | Br | H | F | 1 |
| SO₂CF₃ | Et | H | Br | H | F | 2 |
| SO₂CF₃ | Et | H | Br | H | Cl | 0 |
| SO₂CF₃ | Et | H | Br | H | Cl | 1 |
| SO₂CF₃ | Et | H | Br | H | Cl | 2 |
| SO₂CF₃ | Et | H | Br | H | I | 0 |
| SO₂CF₃ | Et | H | Br | H | I | 1 |
| SO₂CF₃ | Et | H | Br | H | I | 2 |
| SO₂CF₃ | Et | H | I | H | F | 0 |
| SO₂CF₃ | Et | H | I | H | F | 1 |
| SO₂CF₃ | Et | H | I | H | F | 2 |
| SO₂CF₃ | Et | H | I | H | Cl | 0 |
| SO₂CF₃ | Et | H | I | H | Cl | 1 |
| SO₂CF₃ | Et | H | I | H | Cl | 2 |
| SO₂CF₃ | Et | H | I | H | Br | 0 |
| SO₂CF₃ | Et | H | I | H | Br | 1 |
| SO₂CF₃ | Et | H | I | H | Br | 2 |
| SO₂CF₃ | Et | H | F | H | CN | 0 |
| SO₂CF₃ | Et | H | F | H | CN | 1 |
| SO₂CF₃ | Et | H | F | H | CN | 2 |
| SO₂CF₃ | Et | H | Cl | H | CN | 0 |
| SO₂CF₃ | Et | H | Cl | H | CN | 1 |
| SO₂CF₃ | Et | H | Cl | H | CN | 2 |
| SO₂CF₃ | Et | H | Br | H | CN | 0 |
| SO₂CF₃ | Et | H | Br | H | CN | 1 |
| SO₂CF₃ | Et | H | Br | H | CN | 2 |
| SO₂CF₃ | Et | H | I | H | CN | 0 |
| SO₂CF₃ | Et | H | I | H | CN | 1 |
| SO₂CF₃ | Et | H | I | H | CN | 2 |
| SO₂CF₃ | Et | H | CF₃ | H | F | 0 |
| SO₂CF₃ | Et | H | CF₃ | H | F | 1 |
| SO₂CF₃ | Et | H | CF₃ | H | F | 2 |
| SO₂CF₃ | Et | H | CF₃ | H | Cl | 0 |
| SO₂CF₃ | Et | H | CF₃ | H | Cl | 1 |
| SO₂CF₃ | Et | H | CF₃ | H | Cl | 2 |
| SO₂CF₃ | Et | H | CF₃ | H | Br | 0 |
| SO₂CF₃ | Et | H | CF₃ | H | Br | 1 |
| SO₂CF₃ | Et | H | CF₃ | H | Br | 2 |
| SO₂CF₃ | Et | H | CF₃ | H | I | 0 |
| SO₂CF₃ | Et | H | CF₃ | H | I | 1 |
| SO₂CF₃ | Et | H | CF₃ | H | I | 2 |
| SO₂CF₃ | Et | H | CF₃ | H | CN | 0 |
| SO₂CF₃ | Et | H | CF₃ | H | CN | 1 |
| SO₂CF₃ | Et | H | CF₃ | H | CN | 2 |
| SO₂CF₃ | Et | H | F | F | H | 0 |
| SO₂CF₃ | Et | H | F | F | H | 1 |
| SO₂CF₃ | Et | H | F | F | H | 2 |
| SO₂CF₃ | Et | H | Cl | Cl | H | 0 |
| SO₂CF₃ | Et | H | Cl | Cl | H | 1 |
| SO₂CF₃ | Et | H | Cl | Cl | H | 2 |
| SO₂CF₃ | Et | H | Br | Br | H | 0 |
| SO₂CF₃ | Et | H | Br | Br | H | 1 |
| SO₂CF₃ | Et | H | Br | Br | H | 2 |
| SO₂CF₃ | Et | H | I | I | H | 0 |
| SO₂CF₃ | Et | H | I | I | H | 1 |
| SO₂CF₃ | Et | H | I | I | H | 2 |
| SO₂CF₃ | Et | H | F | Cl | H | 0 |
| SO₂CF₃ | Et | H | F | Cl | H | 1 |
| SO₂CF₃ | Et | H | F | Cl | H | 2 |
| SO₂CF₃ | Et | H | F | Br | H | 0 |
| SO₂CF₃ | Et | H | F | Br | H | 1 |
| SO₂CF₃ | Et | H | F | Br | H | 2 |
| SO₂CF₃ | Et | H | F | I | H | 0 |
| SO₂CF₃ | Et | H | F | I | H | 1 |
| SO₂CF₃ | Et | H | F | I | H | 2 |
| SO₂CF₃ | Et | H | Cl | F | H | 0 |
| SO₂CF₃ | Et | H | Cl | F | H | 1 |
| SO₂CF₃ | Et | H | Cl | F | H | 2 |

TABLE 1-continued

| | | | | | | |
|---|---|---|---|---|---|---|
| SO₂CF₃ | Et | H | Cl | Br | H | 0 |
| SO₂CF₃ | Et | H | Cl | Br | H | 1 |
| SO₂CF₃ | Et | H | Cl | Br | H | 2 |
| SO₂CF₃ | Et | H | Cl | I | H | 0 |
| SO₂CF₃ | Et | H | Cl | I | H | 1 |
| SO₂CF₃ | Et | H | Cl | I | H | 2 |
| SO₂CF₃ | Et | H | Br | F | H | 0 |
| SO₂CF₃ | Et | H | Br | F | H | 1 |
| SO₂CF₃ | Et | H | Br | F | H | 2 |
| SO₂CF₃ | Et | H | Br | Cl | H | 0 |
| SO₂CF₃ | Et | H | Br | Cl | H | 1 |
| SO₂CF₃ | Et | H | Br | Cl | H | 2 |
| SO₂CF₃ | Et | H | Br | I | H | 0 |
| SO₂CF₃ | Et | H | Br | I | H | 1 |
| SO₂CF₃ | Et | H | Br | I | H | 2 |
| SO₂CF₃ | Et | H | I | F | H | 0 |
| SO₂CF₃ | Et | H | I | F | H | 1 |
| SO₂CF₃ | Et | H | I | F | H | 2 |
| SO₂CF₃ | Et | H | I | Cl | H | 0 |
| SO₂CF₃ | Et | H | I | Cl | H | 1 |
| SO₂CF₃ | Et | H | I | Cl | H | 2 |
| SO₂CF₃ | Et | H | I | Br | H | 0 |
| SO₂CF₃ | Et | H | I | Br | H | 1 |
| SO₂CF₃ | Et | H | I | Br | H | 2 |
| SO₂CF₃ | Et | H | F | CN | H | 0 |
| SO₂CF₃ | Et | H | F | CN | H | 1 |
| SO₂CF₃ | Et | H | F | CN | H | 2 |
| SO₂CF₃ | Et | H | Cl | CN | H | 0 |
| SO₂CF₃ | Et | H | Cl | CN | H | 1 |
| SO₂CF₃ | Et | H | Cl | CN | H | 2 |
| SO₂CF₃ | Et | H | Br | CN | H | 0 |
| SO₂CF₃ | Et | H | Br | CN | H | 1 |
| SO₂CF₃ | Et | H | Br | CN | H | 2 |
| SO₂CF₃ | Et | H | I | CN | H | 0 |
| SO₂CF₃ | Et | H | I | CN | H | 1 |
| SO₂CF₃ | Et | H | I | CN | H | 2 |
| SO₂CF₃ | Et | H | CF₃ | F | H | 0 |
| SO₂CF₃ | Et | H | CF₃ | F | H | 1 |
| SO₂CF₃ | Et | H | CF₃ | F | H | 2 |
| SO₂CF₃ | Et | H | CF₃ | Cl | H | 0 |
| SO₂CF₃ | Et | H | CF₃ | Cl | H | 1 |
| SO₂CF₃ | Et | H | CF₃ | Cl | H | 2 |
| SO₂CF₃ | Et | H | CF₃ | Br | H | 0 |
| SO₂CF₃ | Et | H | CF₃ | Br | H | 1 |
| SO₂CF₃ | Et | H | CF₃ | Br | H | 2 |
| SO₂CF₃ | Et | H | CF₃ | I | H | 0 |
| SO₂CF₃ | Et | H | CF₃ | I | H | 1 |
| SO₂CF₃ | Et | H | CF₃ | I | H | 2 |
| SO₂CF₃ | Et | H | CF₃ | CN | H | 0 |
| SO₂CF₃ | Et | H | CF₃ | CN | H | 1 |
| SO₂CF₃ | Et | H | CF₃ | CN | H | 2 |
| SO₂CF₃ | ⁿPr | H | H | H | H | 0 |
| SO₂CF₃ | ⁿPr | H | H | H | H | 1 |
| SO₂CF₃ | ⁿPr | H | H | H | H | 2 |
| SO₂CF₃ | ⁿPr | F | H | H | H | 0 |
| SO₂CF₃ | ⁿPr | F | H | H | H | 1 |
| SO₂CF₃ | ⁿPr | F | H | H | H | 2 |
| SO₂CF₃ | ⁿPr | Cl | H | H | H | 0 |
| SO₂CF₃ | ⁿPr | Cl | H | H | H | 1 |
| SO₂CF₃ | ⁿPr | Cl | H | H | H | 2 |
| SO₂CF₃ | ⁿPr | Br | H | H | H | 0 |
| SO₂CF₃ | ⁿPr | Br | H | H | H | 1 |
| SO₂CF₃ | ⁿPr | Br | H | H | H | 2 |
| SO₂CF₃ | ⁿPr | I | H | H | H | 0 |
| SO₂CF₃ | ⁿPr | I | H | H | H | 1 |
| SO₂CF₃ | ⁿPr | I | H | H | H | 2 |
| SO₂CF₃ | ⁿPr | Me | H | H | H | 0 |
| SO₂CF₃ | ⁿPr | Me | H | H | H | 1 |
| SO₂CF₃ | ⁿPr | Me | H | H | H | 2 |
| SO₂CF₃ | ⁿPr | CF₃ | H | H | H | 0 |
| SO₂CF₃ | ⁿPr | CF₃ | H | H | H | 1 |
| SO₂CF₃ | ⁿPr | CF₃ | H | H | H | 2 |
| SO₂CF₃ | ⁿPr | H | F | H | H | 0 |
| SO₂CF₃ | ⁿPr | H | F | H | H | 1 |
| SO₂CF₃ | ⁿPr | H | F | H | H | 2 |
| SO₂CF₃ | ⁿPr | H | Cl | H | H | 0 |
| SO₂CF₃ | ⁿPr | H | Cl | H | H | 1 |
| SO₂CF₃ | ⁿPr | H | Cl | H | H | 2 |
| SO₂CF₃ | ⁿPr | H | Br | H | H | 0 |
| SO₂CF₃ | ⁿPr | H | Br | H | H | 1 |
| SO₂CF₃ | ⁿPr | H | Br | H | H | 2 |
| SO₂CF₃ | ⁿPr | H | I | H | H | 0 |
| SO₂CF₃ | ⁿPr | H | I | H | H | 1 |
| SO₂CF₃ | ⁿPr | H | I | H | H | 2 |
| SO₂CF₃ | ⁿPr | H | Me | H | H | 0 |
| SO₂CF₃ | ⁿPr | H | Me | H | H | 1 |
| SO₂CF₃ | ⁿPr | H | Me | H | H | 2 |
| SO₂CF₃ | ⁿPr | H | CF₃ | H | H | 0 |
| SO₂CF₃ | ⁿPr | H | CF₃ | H | H | 1 |
| SO₂CF₃ | ⁿPr | H | CF₃ | H | H | 2 |
| SO₂CF₃ | ⁿPr | H | CF₂CF₃ | H | H | 0 |
| SO₂CF₃ | ⁿPr | H | CF₂CF₃ | H | H | 1 |
| SO₂CF₃ | ⁿPr | H | CF₂CF₃ | H | H | 2 |
| SO₂CF₃ | ⁿPr | H | CF(CF₃)₂ | H | H | 0 |
| SO₂CF₃ | ⁿPr | H | CF(CF₃)₂ | H | H | 1 |
| SO₂CF₃ | ⁿPr | H | CF(CF₃)₂ | H | H | 2 |
| SO₂CF₃ | ⁿPr | H | SMe | H | H | 0 |
| SO₂CF₃ | ⁿPr | H | SMe | H | H | 1 |
| SO₂CF₃ | ⁿPr | H | SMe | H | H | 2 |
| SO₂CF₃ | ⁿPr | H | SOMe | H | H | 0 |
| SO₂CF₃ | ⁿPr | H | SOMe | H | H | 1 |
| SO₂CF₃ | ⁿPr | H | SOMe | H | H | 2 |
| SO₂CF₃ | ⁿPr | H | SO₂Me | H | H | 0 |
| SO₂CF₃ | ⁿPr | H | SO₂Me | H | H | 1 |
| SO₂CF₃ | ⁿPr | H | SO₂Me | H | H | 2 |
| SO₂CF₃ | ⁿPr | H | OMe | H | H | 0 |
| SO₂CF₃ | ⁿPr | H | OMe | H | H | 1 |
| SO₂CF₃ | ⁿPr | H | OMe | H | H | 2 |
| SO₂CF₃ | ⁿPr | H | OCF₃ | H | H | 0 |
| SO₂CF₃ | ⁿPr | H | OCF₃ | H | H | 1 |
| SO₂CF₃ | ⁿPr | H | OCF₃ | H | H | 2 |
| SO₂CF₃ | ⁿPr | H | NO₂ | H | H | 0 |
| SO₂CF₃ | ⁿPr | H | NO₂ | H | H | 1 |
| SO₂CF₃ | ⁿPr | H | NO₂ | H | H | 2 |
| SO₂CF₃ | ⁿPr | H | CN | H | H | 0 |
| SO₂CF₃ | ⁿPr | H | CN | H | H | 1 |
| SO₂CF₃ | ⁿPr | H | CN | H | H | 2 |
| SO₂CF₃ | ⁿPr | H | H | F | H | 0 |
| SO₂CF₃ | ⁿPr | H | H | F | H | 1 |
| SO₂CF₃ | ⁿPr | H | H | F | H | 2 |
| SO₂CF₃ | ⁿPr | H | H | Cl | H | 0 |
| SO₂CF₃ | ⁿPr | H | H | Cl | H | 1 |
| SO₂CF₃ | ⁿPr | H | H | Cl | H | 2 |
| SO₂CF₃ | ⁿPr | H | H | Br | H | 0 |
| SO₂CF₃ | ⁿPr | H | H | Br | H | 1 |
| SO₂CF₃ | ⁿPr | H | H | Br | H | 2 |
| SO₂CF₃ | ⁿPr | H | H | I | H | 0 |
| SO₂CF₃ | ⁿPr | H | H | I | H | 1 |
| SO₂CF₃ | ⁿPr | H | H | I | H | 2 |
| SO₂CF₃ | ⁿPr | H | H | Me | H | 0 |
| SO₂CF₃ | ⁿPr | H | H | Me | H | 1 |
| SO₂CF₃ | ⁿPr | H | H | Me | H | 2 |
| SO₂CF₃ | ⁿPr | H | H | CF₃ | H | 0 |
| SO₂CF₃ | ⁿPr | H | H | CF₃ | H | 1 |
| SO₂CF₃ | ⁿPr | H | H | CF₃ | H | 2 |
| SO₂CF₃ | ⁿPr | H | H | CF₂CF₃ | H | 0 |
| SO₂CF₃ | ⁿPr | H | H | CF₂CF₃ | H | 1 |
| SO₂CF₃ | ⁿPr | H | H | CF₂CF₃ | H | 2 |
| SO₂CF₃ | ⁿPr | H | H | CF(CF₃)₂ | H | 0 |
| SO₂CF₃ | ⁿPr | H | H | CF(CF₃)₂ | H | 1 |
| SO₂CF₃ | ⁿPr | H | H | CF(CF₃)₂ | H | 2 |
| SO₂CF₃ | ⁿPr | H | H | SMe | H | 0 |
| SO₂CF₃ | ⁿPr | H | H | SMe | H | 1 |
| SO₂CF₃ | ⁿPr | H | H | SMe | H | 2 |
| SO₂CF₃ | ⁿPr | H | H | SOMe | H | 0 |
| SO₂CF₃ | ⁿPr | H | H | SOMe | H | 1 |
| SO₂CF₃ | ⁿPr | H | H | SOMe | H | 2 |
| SO₂CF₃ | ⁿPr | H | H | SO₂Me | H | 0 |
| SO₂CF₃ | ⁿPr | H | H | SO₂Me | H | 1 |
| SO₂CF₃ | ⁿPr | H | H | SO₂Me | H | 2 |
| SO₂CF₃ | ⁿPr | H | H | OMe | H | 0 |
| SO₂CF₃ | ⁿPr | H | H | OMe | H | 1 |
| SO₂CF₃ | ⁿPr | H | H | OMe | H | 2 |
| SO₂CF₃ | ⁿPr | H | H | OCF₃ | H | 0 |
| SO₂CF₃ | ⁿPr | H | H | OCF₃ | H | 1 |
| SO₂CF₃ | ⁿPr | H | H | OCF₃ | H | 2 |
| SO₂CF₃ | ⁿPr | H | H | NO₂ | H | 0 |
| SO₂CF₃ | ⁿPr | H | H | NO₂ | H | 1 |
| SO₂CF₃ | ⁿPr | H | H | NO₂ | H | 2 |
| SO₂CF₃ | ⁿPr | H | H | CN | H | 0 |

TABLE 1-continued

| | | | | | | |
|---|---|---|---|---|---|---|
| SO$_2$CF$_3$ | $^n$Pr | H | H | CN | H | 1 |
| SO$_2$CF$_3$ | $^n$Pr | H | H | CN | H | 2 |
| SO$_2$CF$_3$ | $^n$Pr | H | H | H | F | 0 |
| SO$_2$CF$_3$ | $^n$Pr | H | H | H | F | 1 |
| SO$_2$CF$_3$ | $^n$Pr | H | H | H | F | 2 |
| SO$_2$CF$_3$ | $^n$Pr | H | H | H | Cl | 0 |
| SO$_2$CF$_3$ | $^n$Pr | H | H | H | Cl | 1 |
| SO$_2$CF$_3$ | $^n$Pr | H | H | H | Cl | 2 |
| SO$_2$CF$_3$ | $^n$Pr | H | H | H | Br | 0 |
| SO$_2$CF$_3$ | $^n$Pr | H | H | H | Br | 1 |
| SO$_2$CF$_3$ | $^n$Pr | H | H | H | Br | 2 |
| SO$_2$CF$_3$ | $^n$Pr | H | H | H | I | 0 |
| SO$_2$CF$_3$ | $^n$Pr | H | H | H | I | 1 |
| SO$_2$CF$_3$ | $^n$Pr | H | H | H | I | 2 |
| SO$_2$CF$_3$ | $^n$Pr | H | H | H | Me | 0 |
| SO$_2$CF$_3$ | $^n$Pr | H | H | H | Me | 1 |
| SO$_2$CF$_3$ | $^n$Pr | H | H | H | Me | 2 |
| SO$_2$CF$_3$ | $^n$Pr | H | H | H | CF$_3$ | 0 |
| SO$_2$CF$_3$ | $^n$Pr | H | H | H | CF$_3$ | 1 |
| SO$_2$CF$_3$ | $^n$Pr | H | H | H | CF$_3$ | 2 |
| SO$_2$CF$_3$ | $^n$Pr | H | H | H | CF$_2$CF$_3$ | 0 |
| SO$_2$CF$_3$ | $^n$Pr | H | H | H | CF$_2$CF$_3$ | 1 |
| SO$_2$CF$_3$ | $^n$Pr | H | H | H | CF$_2$CF$_3$ | 2 |
| SO$_2$CF$_3$ | $^n$Pr | H | H | H | CF(CF$_3$)$_2$ | 0 |
| SO$_2$CF$_3$ | $^n$Pr | H | H | H | CF(CF$_3$)$_2$ | 1 |
| SO$_2$CF$_3$ | $^n$Pr | H | H | H | CF(CF$_3$)$_2$ | 2 |
| SO$_2$CF$_3$ | $^n$Pr | H | H | H | SMe | 0 |
| SO$_2$CF$_3$ | $^n$Pr | H | H | H | SMe | 1 |
| SO$_2$CF$_3$ | $^n$Pr | H | H | H | SMe | 2 |
| SO$_2$CF$_3$ | $^n$Pr | H | H | H | SOMe | 0 |
| SO$_2$CF$_3$ | $^n$Pr | H | H | H | SOMe | 1 |
| SO$_2$CF$_3$ | $^n$Pr | H | H | H | SOMe | 2 |
| SO$_2$CF$_3$ | $^n$Pr | H | H | H | SO$_2$Me | 0 |
| SO$_2$CF$_3$ | $^n$Pr | H | H | H | SO$_2$Me | 1 |
| SO$_2$CF$_3$ | $^n$Pr | H | H | H | SO$_2$Me | 2 |
| SO$_2$CF$_3$ | $^n$Pr | H | H | H | OMe | 0 |
| SO$_2$CF$_3$ | $^n$Pr | H | H | H | OMe | 1 |
| SO$_2$CF$_3$ | $^n$Pr | H | H | H | OMe | 2 |
| SO$_2$CF$_3$ | $^n$Pr | H | H | H | OCF$_3$ | 0 |
| SO$_2$CF$_3$ | $^n$Pr | H | H | H | OCF$_3$ | 1 |
| SO$_2$CF$_3$ | $^n$Pr | H | H | H | OCF$_3$ | 2 |
| SO$_2$CF$_3$ | $^n$Pr | H | H | H | NO$_2$ | 0 |
| SO$_2$CF$_3$ | $^n$Pr | H | H | H | NO$_2$ | 1 |
| SO$_2$CF$_3$ | $^n$Pr | H | H | H | NO$_2$ | 2 |
| SO$_2$CF$_3$ | $^n$Pr | H | H | H | CN | 0 |
| SO$_2$CF$_3$ | $^n$Pr | H | H | H | CN | 1 |
| SO$_2$CF$_3$ | $^n$Pr | H | H | H | CN | 2 |
| SO$_2$CF$_3$ | $^n$Pr | H | F | H | F | 0 |
| SO$_2$CF$_3$ | $^n$Pr | H | F | H | F | 1 |
| SO$_2$CF$_3$ | $^n$Pr | H | F | H | F | 2 |
| SO$_2$CF$_3$ | $^n$Pr | H | Cl | H | Cl | 0 |
| SO$_2$CF$_3$ | $^n$Pr | H | Cl | H | Cl | 1 |
| SO$_2$CF$_3$ | $^n$Pr | H | Cl | H | Cl | 2 |
| SO$_2$CF$_3$ | $^n$Pr | H | Br | H | Br | 0 |
| SO$_2$CF$_3$ | $^n$Pr | H | Br | H | Br | 1 |
| SO$_2$CF$_3$ | $^n$Pr | H | Br | H | Br | 2 |
| SO$_2$CF$_3$ | $^n$Pr | H | I | H | I | 0 |
| SO$_2$CF$_3$ | $^n$Pr | H | I | H | I | 1 |
| SO$_2$CF$_3$ | $^n$Pr | H | I | H | I | 2 |
| SO$_2$CF$_3$ | $^n$Pr | H | F | H | Cl | 0 |
| SO$_2$CF$_3$ | $^n$Pr | H | F | H | Cl | 1 |
| SO$_2$CF$_3$ | $^n$Pr | H | F | H | Cl | 2 |
| SO$_2$CF$_3$ | $^n$Pr | H | F | H | Br | 0 |
| SO$_2$CF$_3$ | $^n$Pr | H | F | H | Br | 1 |
| SO$_2$CF$_3$ | $^n$Pr | H | F | H | Br | 2 |
| SO$_2$CF$_3$ | $^n$Pr | H | F | H | I | 0 |
| SO$_2$CF$_3$ | $^n$Pr | H | F | H | I | 1 |
| SO$_2$CF$_3$ | $^n$Pr | H | F | H | I | 2 |
| SO$_2$CF$_3$ | $^n$Pr | H | Cl | H | F | 0 |
| SO$_2$CF$_3$ | $^n$Pr | H | Cl | H | F | 1 |
| SO$_2$CF$_3$ | $^n$Pr | H | Cl | H | F | 2 |
| SO$_2$CF$_3$ | $^n$Pr | H | Cl | H | Br | 0 |
| SO$_2$CF$_3$ | $^n$Pr | H | Cl | H | Br | 1 |
| SO$_2$CF$_3$ | $^n$Pr | H | Cl | H | Br | 2 |
| SO$_2$CF$_3$ | $^n$Pr | H | Cl | H | I | 0 |
| SO$_2$CF$_3$ | $^n$Pr | H | Cl | H | I | 1 |
| SO$_2$CF$_3$ | $^n$Pr | H | Cl | H | I | 2 |
| SO$_2$CF$_3$ | $^n$Pr | H | Br | H | F | 0 |
| SO$_2$CF$_3$ | $^n$Pr | H | Br | H | F | 1 |
| SO$_2$CF$_3$ | $^n$Pr | H | Br | H | F | 2 |
| SO$_2$CF$_3$ | $^n$Pr | H | Br | H | Cl | 0 |
| SO$_2$CF$_3$ | $^n$Pr | H | Br | H | Cl | 1 |
| SO$_2$CF$_3$ | $^n$Pr | H | Br | H | Cl | 2 |
| SO$_2$CF$_3$ | $^n$Pr | H | Br | H | I | 0 |
| SO$_2$CF$_3$ | $^n$Pr | H | Br | H | I | 1 |
| SO$_2$CF$_3$ | $^n$Pr | H | Br | H | I | 2 |
| SO$_2$CF$_3$ | $^n$Pr | H | I | H | F | 0 |
| SO$_2$CF$_3$ | $^n$Pr | H | I | H | F | 1 |
| SO$_2$CF$_3$ | $^n$Pr | H | I | H | F | 2 |
| SO$_2$CF$_3$ | $^n$Pr | H | I | H | Cl | 0 |
| SO$_2$CF$_3$ | $^n$Pr | H | I | H | Cl | 1 |
| SO$_2$CF$_3$ | $^n$Pr | H | I | H | Cl | 2 |
| SO$_2$CF$_3$ | $^n$Pr | H | I | H | Br | 0 |
| SO$_2$CF$_3$ | $^n$Pr | H | I | H | Br | 1 |
| SO$_2$CF$_3$ | $^n$Pr | H | I | H | Br | 2 |
| SO$_2$CF$_3$ | $^n$Pr | H | F | H | CN | 0 |
| SO$_2$CF$_3$ | $^n$Pr | H | F | H | CN | 1 |
| SO$_2$CF$_3$ | $^n$Pr | H | F | H | CN | 2 |
| SO$_2$CF$_3$ | $^n$Pr | H | Cl | H | CN | 0 |
| SO$_2$CF$_3$ | $^n$Pr | H | Cl | H | CN | 1 |
| SO$_2$CF$_3$ | $^n$Pr | H | Cl | H | CN | 2 |
| SO$_2$CF$_3$ | $^n$Pr | H | Br | H | CN | 0 |
| SO$_2$CF$_3$ | $^n$Pr | H | Br | H | CN | 1 |
| SO$_2$CF$_3$ | $^n$Pr | H | Br | H | CN | 2 |
| SO$_2$CF$_3$ | $^n$Pr | H | I | H | CN | 0 |
| SO$_2$CF$_3$ | $^n$Pr | H | I | H | CN | 1 |
| SO$_2$CF$_3$ | $^n$Pr | H | I | H | CN | 2 |
| SO$_2$CF$_3$ | $^n$Pr | H | CF$_3$ | H | F | 0 |
| SO$_2$CF$_3$ | $^n$Pr | H | CF$_3$ | H | F | 1 |
| SO$_2$CF$_3$ | $^n$Pr | H | CF$_3$ | H | F | 2 |
| SO$_2$CF$_3$ | $^n$Pr | H | CF$_3$ | H | Cl | 0 |
| SO$_2$CF$_3$ | $^n$Pr | H | CF$_3$ | H | Cl | 1 |
| SO$_2$CF$_3$ | $^n$Pr | H | CF$_3$ | H | Cl | 2 |
| SO$_2$CF$_3$ | $^n$Pr | H | CF$_3$ | H | Br | 0 |
| SO$_2$CF$_3$ | $^n$Pr | H | CF$_3$ | H | Br | 1 |
| SO$_2$CF$_3$ | $^n$Pr | H | CF$_3$ | H | Br | 2 |
| SO$_2$CF$_3$ | $^n$Pr | H | CF$_3$ | H | I | 0 |
| SO$_2$CF$_3$ | $^n$Pr | H | CF$_3$ | H | I | 1 |
| SO$_2$CF$_3$ | $^n$Pr | H | CF$_3$ | H | I | 2 |
| SO$_2$CF$_3$ | $^n$Pr | H | CF$_3$ | H | CN | 0 |
| SO$_2$CF$_3$ | $^n$Pr | H | CF$_3$ | H | CN | 1 |
| SO$_2$CF$_3$ | $^n$Pr | H | CF$_3$ | H | CN | 2 |
| SO$_2$CF$_3$ | $^n$Pr | H | F | F | H | 0 |
| SO$_2$CF$_3$ | $^n$Pr | H | F | F | H | 1 |
| SO$_2$CF$_3$ | $^n$Pr | H | F | F | H | 2 |
| SO$_2$CF$_3$ | $^n$Pr | H | Cl | Cl | H | 0 |
| SO$_2$CF$_3$ | $^n$Pr | H | Cl | Cl | H | 1 |
| SO$_2$CF$_3$ | $^n$Pr | H | Cl | Cl | H | 2 |
| SO$_2$CF$_3$ | $^n$Pr | H | Br | Br | H | 0 |
| SO$_2$CF$_3$ | $^n$Pr | H | Br | Br | H | 1 |
| SO$_2$CF$_3$ | $^n$Pr | H | Br | Br | H | 2 |
| SO$_2$CF$_3$ | $^n$Pr | H | I | I | H | 0 |
| SO$_2$CF$_3$ | $^n$Pr | H | I | I | H | 1 |
| SO$_2$CF$_3$ | $^n$Pr | H | I | I | H | 2 |
| SO$_2$CF$_3$ | $^n$Pr | H | F | Cl | H | 0 |
| SO$_2$CF$_3$ | $^n$Pr | H | F | Cl | H | 1 |
| SO$_2$CF$_3$ | $^n$Pr | H | F | Cl | H | 2 |
| SO$_2$CF$_3$ | $^n$Pr | H | F | Br | H | 0 |
| SO$_2$CF$_3$ | $^n$Pr | H | F | Br | H | 1 |
| SO$_2$CF$_3$ | $^n$Pr | H | F | Br | H | 2 |
| SO$_2$CF$_3$ | $^n$Pr | H | F | I | H | 0 |
| SO$_2$CF$_3$ | $^n$Pr | H | F | I | H | 1 |
| SO$_2$CF$_3$ | $^n$Pr | H | F | I | H | 2 |
| SO$_2$CF$_3$ | $^n$Pr | H | Cl | F | H | 0 |
| SO$_2$CF$_3$ | $^n$Pr | H | Cl | F | H | 1 |
| SO$_2$CF$_3$ | $^n$Pr | H | Cl | F | H | 2 |
| SO$_2$CF$_3$ | $^n$Pr | H | Cl | Br | H | 0 |
| SO$_2$CF$_3$ | $^n$Pr | H | Cl | Br | H | 1 |
| SO$_2$CF$_3$ | $^n$Pr | H | Cl | Br | H | 2 |
| SO$_2$CF$_3$ | $^n$Pr | H | Cl | I | H | 0 |
| SO$_2$CF$_3$ | $^n$Pr | H | Cl | I | H | 1 |
| SO$_2$CF$_3$ | $^n$Pr | H | Cl | I | H | 2 |
| SO$_2$CF$_3$ | $^n$Pr | H | Br | F | H | 0 |
| SO$_2$CF$_3$ | $^n$Pr | H | Br | F | H | 1 |
| SO$_2$CF$_3$ | $^n$Pr | H | Br | F | H | 2 |
| SO$_2$CF$_3$ | $^n$Pr | H | Br | Cl | H | 0 |
| SO$_2$CF$_3$ | $^n$Pr | H | Br | Cl | H | 1 |
| SO$_2$CF$_3$ | $^n$Pr | H | Br | Cl | H | 2 |
| SO$_2$CF$_3$ | $^n$Pr | H | Br | I | H | 0 |
| SO$_2$CF$_3$ | $^n$Pr | H | Br | I | H | 1 |

TABLE 1-continued

| | | | | | | |
|---|---|---|---|---|---|---|
| SO$_2$CF$_3$ | $^n$Pr | H | Br | I | H | 2 |
| SO$_2$CF$_3$ | $^n$Pr | H | I | F | H | 0 |
| SO$_2$CF$_3$ | $^n$Pr | H | I | F | H | 1 |
| SO$_2$CF$_3$ | $^n$Pr | H | I | F | H | 2 |
| SO$_2$CF$_3$ | $^n$Pr | H | I | Cl | H | 0 |
| SO$_2$CF$_3$ | $^n$Pr | H | I | Cl | H | 1 |
| SO$_2$CF$_3$ | $^n$Pr | H | I | Cl | H | 2 |
| SO$_2$CF$_3$ | $^n$Pr | H | I | Br | H | 0 |
| SO$_2$CF$_3$ | $^n$Pr | H | I | Br | H | 1 |
| SO$_2$CF$_3$ | $^n$Pr | H | I | Br | H | 2 |
| SO$_2$CF$_3$ | $^n$Pr | H | F | CN | H | 0 |
| SO$_2$CF$_3$ | $^n$Pr | H | F | CN | H | 1 |
| SO$_2$CF$_3$ | $^n$Pr | H | F | CN | H | 2 |
| SO$_2$CF$_3$ | $^n$Pr | H | Cl | CN | H | 0 |
| SO$_2$CF$_3$ | $^n$Pr | H | Cl | CN | H | 1 |
| SO$_2$CF$_3$ | $^n$Pr | H | Cl | CN | H | 2 |
| SO$_2$CF$_3$ | $^n$Pr | H | Br | CN | H | 0 |
| SO$_2$CF$_3$ | $^n$Pr | H | Br | CN | H | 1 |
| SO$_2$CF$_3$ | $^n$Pr | H | Br | CN | H | 2 |
| SO$_2$CF$_3$ | $^n$Pr | H | I | CN | H | 0 |
| SO$_2$CF$_3$ | $^n$Pr | H | I | CN | H | 1 |
| SO$_2$CF$_3$ | $^n$Pr | H | I | CN | H | 2 |
| SO$_2$CF$_3$ | $^n$Pr | H | CF$_3$ | F | H | 0 |
| SO$_2$CF$_3$ | $^n$Pr | H | CF$_3$ | F | H | 1 |
| SO$_2$CF$_3$ | $^n$Pr | H | CF$_3$ | F | H | 2 |
| SO$_2$CF$_3$ | $^n$Pr | H | CF$_3$ | Cl | H | 0 |
| SO$_2$CF$_3$ | $^n$Pr | H | CF$_3$ | Cl | H | 1 |
| SO$_2$CF$_3$ | $^n$Pr | H | CF$_3$ | Cl | H | 2 |
| SO$_2$CF$_3$ | $^n$Pr | H | CF$_3$ | Br | H | 0 |
| SO$_2$CF$_3$ | $^n$Pr | H | CF$_3$ | Br | H | 1 |
| SO$_2$CF$_3$ | $^n$Pr | H | CF$_3$ | Br | H | 2 |
| SO$_2$CF$_3$ | $^n$Pr | H | CF$_3$ | I | H | 0 |
| SO$_2$CF$_3$ | $^n$Pr | H | CF$_3$ | I | H | 1 |
| SO$_2$CF$_3$ | $^n$Pr | H | CF$_3$ | I | H | 2 |
| SO$_2$CF$_3$ | $^n$Pr | H | CF$_3$ | CN | H | 0 |
| SO$_2$CF$_3$ | $^n$Pr | H | CF$_3$ | CN | H | 1 |
| SO$_2$CF$_3$ | $^n$Pr | H | CF$_3$ | CN | H | 2 |
| SO$_2$CF$_3$ | $^i$Pr | H | H | H | H | 0 |
| SO$_2$CF$_3$ | $^i$Pr | H | H | H | H | 1 |
| SO$_2$CF$_3$ | $^i$Pr | H | H | H | H | 2 |
| SO$_2$CF$_3$ | $^i$Pr | F | H | H | H | 0 |
| SO$_2$CF$_3$ | $^i$Pr | F | H | H | H | 1 |
| SO$_2$CF$_3$ | $^i$Pr | F | H | H | H | 2 |
| SO$_2$CF$_3$ | $^i$Pr | Cl | H | H | H | 0 |
| SO$_2$CF$_3$ | $^i$Pr | Cl | H | H | H | 1 |
| SO$_2$CF$_3$ | $^i$Pr | Cl | H | H | H | 2 |
| SO$_2$CF$_3$ | $^i$Pr | Br | H | H | H | 0 |
| SO$_2$CF$_3$ | $^i$Pr | Br | H | H | H | 1 |
| SO$_2$CF$_3$ | $^i$Pr | Br | H | H | H | 2 |
| SO$_2$CF$_3$ | $^i$Pr | I | H | H | H | 0 |
| SO$_2$CF$_3$ | $^i$Pr | I | H | H | H | 1 |
| SO$_2$CF$_3$ | $^i$Pr | I | H | H | H | 2 |
| SO$_2$CF$_3$ | $^i$Pr | Me | H | H | H | 0 |
| SO$_2$CF$_3$ | $^i$Pr | Me | H | H | H | 1 |
| SO$_2$CF$_3$ | $^i$Pr | Me | H | H | H | 2 |
| SO$_2$CF$_3$ | $^i$Pr | CF$_3$ | H | H | H | 0 |
| SO$_2$CF$_3$ | $^i$Pr | CF$_3$ | H | H | H | 1 |
| SO$_2$CF$_3$ | $^i$Pr | CF$_3$ | H | H | H | 2 |
| SO$_2$CF$_3$ | $^i$Pr | H | F | H | H | 0 |
| SO$_2$CF$_3$ | $^i$Pr | H | F | H | H | 1 |
| SO$_2$CF$_3$ | $^i$Pr | H | F | H | H | 2 |
| SO$_2$CF$_3$ | $^i$Pr | H | Cl | H | H | 0 |
| SO$_2$CF$_3$ | $^i$Pr | H | Cl | H | H | 1 |
| SO$_2$CF$_3$ | $^i$Pr | H | Cl | H | H | 2 |
| SO$_2$CF$_3$ | $^i$Pr | H | Br | H | H | 0 |
| SO$_2$CF$_3$ | $^i$Pr | H | Br | H | H | 1 |
| SO$_2$CF$_3$ | $^i$Pr | H | Br | H | H | 2 |
| SO$_2$CF$_3$ | $^i$Pr | H | I | H | H | 0 |
| SO$_2$CF$_3$ | $^i$Pr | H | I | H | H | 1 |
| SO$_2$CF$_3$ | $^i$Pr | H | I | H | H | 2 |
| SO$_2$CF$_3$ | $^i$Pr | H | Me | H | H | 0 |
| SO$_2$CF$_3$ | $^i$Pr | H | Me | H | H | 1 |
| SO$_2$CF$_3$ | $^i$Pr | H | Me | H | H | 2 |
| SO$_2$CF$_3$ | $^i$Pr | H | CF$_3$ | H | H | 0 |
| SO$_2$CF$_3$ | $^i$Pr | H | CF$_3$ | H | H | 1 |
| SO$_2$CF$_3$ | $^i$Pr | H | CF$_3$ | H | H | 2 |
| SO$_2$CF$_3$ | $^i$Pr | H | CF$_2$CF$_3$ | H | H | 0 |
| SO$_2$CF$_3$ | $^i$Pr | H | CF$_2$CF$_3$ | H | H | 1 |
| SO$_2$CF$_3$ | $^i$Pr | H | CF$_2$CF$_3$ | H | H | 2 |
| SO$_2$CF$_3$ | $^i$Pr | H | CF(CF$_3$)$_2$ | H | H | 0 |
| SO$_2$CF$_3$ | $^i$Pr | H | CF(CF$_3$)$_2$ | H | H | 1 |
| SO$_2$CF$_3$ | $^i$Pr | H | CF(CF$_3$)$_2$ | H | H | 2 |
| SO$_2$CF$_3$ | $^i$Pr | H | SMe | H | H | 0 |
| SO$_2$CF$_3$ | $^i$Pr | H | SMe | H | H | 1 |
| SO$_2$CF$_3$ | $^i$Pr | H | SMe | H | H | 2 |
| SO$_2$CF$_3$ | $^i$Pr | H | SOMe | H | H | 0 |
| SO$_2$CF$_3$ | $^i$Pr | H | SOMe | H | H | 1 |
| SO$_2$CF$_3$ | $^i$Pr | H | SOMe | H | H | 2 |
| SO$_2$CF$_3$ | $^i$Pr | H | SO$_2$Me | H | H | 0 |
| SO$_2$CF$_3$ | $^i$Pr | H | SO$_2$Me | H | H | 1 |
| SO$_2$CF$_3$ | $^i$Pr | H | SO$_2$Me | H | H | 2 |
| SO$_2$CF$_3$ | $^i$Pr | H | OMe | H | H | 0 |
| SO$_2$CF$_3$ | $^i$Pr | H | OMe | H | H | 1 |
| SO$_2$CF$_3$ | $^i$Pr | H | OMe | H | H | 2 |
| SO$_2$CF$_3$ | $^i$Pr | H | OCF$_3$ | H | H | 0 |
| SO$_2$CF$_3$ | $^i$Pr | H | OCF$_3$ | H | H | 1 |
| SO$_2$CF$_3$ | $^i$Pr | H | OCF$_3$ | H | H | 2 |
| SO$_2$CF$_3$ | $^i$Pr | H | NO$_2$ | H | H | 0 |
| SO$_2$CF$_3$ | $^i$Pr | H | NO$_2$ | H | H | 1 |
| SO$_2$CF$_3$ | $^i$Pr | H | NO$_2$ | H | H | 2 |
| SO$_2$CF$_3$ | $^i$Pr | H | CN | H | H | 0 |
| SO$_2$CF$_3$ | $^i$Pr | H | CN | H | H | 1 |
| SO$_2$CF$_3$ | $^i$Pr | H | CN | H | H | 2 |
| SO$_2$CF$_3$ | $^i$Pr | H | H | F | H | 0 |
| SO$_2$CF$_3$ | $^i$Pr | H | H | F | H | 1 |
| SO$_2$CF$_3$ | $^i$Pr | H | H | F | H | 2 |
| SO$_2$CF$_3$ | $^i$Pr | H | H | Cl | H | 0 |
| SO$_2$CF$_3$ | $^i$Pr | H | H | Cl | H | 1 |
| SO$_2$CF$_3$ | $^i$Pr | H | H | Cl | H | 2 |
| SO$_2$CF$_3$ | $^i$Pr | H | H | Br | H | 0 |
| SO$_2$CF$_3$ | $^i$Pr | H | H | Br | H | 1 |
| SO$_2$CF$_3$ | $^i$Pr | H | H | Br | H | 2 |
| SO$_2$CF$_3$ | $^i$Pr | H | H | I | H | 0 |
| SO$_2$CF$_3$ | $^i$Pr | H | H | I | H | 1 |
| SO$_2$CF$_3$ | $^i$Pr | H | H | I | H | 2 |
| SO$_2$CF$_3$ | $^i$Pr | H | H | Me | H | 0 |
| SO$_2$CF$_3$ | $^i$Pr | H | H | Me | H | 1 |
| SO$_2$CF$_3$ | $^i$Pr | H | H | Me | H | 2 |
| SO$_2$CF$_3$ | $^i$Pr | H | H | CF$_3$ | H | 0 |
| SO$_2$CF$_3$ | $^i$Pr | H | H | CF$_3$ | H | 1 |
| SO$_2$CF$_3$ | $^i$Pr | H | H | CF$_3$ | H | 2 |
| SO$_2$CF$_3$ | $^i$Pr | H | H | CF$_2$CF$_3$ | H | 0 |
| SO$_2$CF$_3$ | $^i$Pr | H | H | CF$_2$CF$_3$ | H | 1 |
| SO$_2$CF$_3$ | $^i$Pr | H | H | CF$_2$CF$_3$ | H | 2 |
| SO$_2$CF$_3$ | $^i$Pr | H | H | CF(CF$_3$)$_2$ | H | 0 |
| SO$_2$CF$_3$ | $^i$Pr | H | H | CF(CF$_3$)$_2$ | H | 1 |
| SO$_2$CF$_3$ | $^i$Pr | H | H | CF(CF$_3$)$_2$ | H | 2 |
| SO$_2$CF$_3$ | $^i$Pr | H | H | SMe | H | 0 |
| SO$_2$CF$_3$ | $^i$Pr | H | H | SMe | H | 1 |
| SO$_2$CF$_3$ | $^i$Pr | H | H | SMe | H | 2 |
| SO$_2$CF$_3$ | $^i$Pr | H | H | SOMe | H | 0 |
| SO$_2$CF$_3$ | $^i$Pr | H | H | SOMe | H | 1 |
| SO$_2$CF$_3$ | $^i$Pr | H | H | SOMe | H | 2 |
| SO$_2$CF$_3$ | $^i$Pr | H | H | SO$_2$Me | H | 0 |
| SO$_2$CF$_3$ | $^i$Pr | H | H | SO$_2$Me | H | 1 |
| SO$_2$CF$_3$ | $^i$Pr | H | H | SO$_2$Me | H | 2 |
| SO$_2$CF$_3$ | $^i$Pr | H | H | OMe | H | 0 |
| SO$_2$CF$_3$ | $^i$Pr | H | H | OMe | H | 1 |
| SO$_2$CF$_3$ | $^i$Pr | H | H | OMe | H | 2 |
| SO$_2$CF$_3$ | $^i$Pr | H | H | OCF$_3$ | H | 0 |
| SO$_2$CF$_3$ | $^i$Pr | H | H | OCF$_3$ | H | 1 |
| SO$_2$CF$_3$ | $^i$Pr | H | H | OCF$_3$ | H | 2 |
| SO$_2$CF$_3$ | $^i$Pr | H | H | NO$_2$ | H | 0 |
| SO$_2$CF$_3$ | $^i$Pr | H | H | NO$_2$ | H | 1 |
| SO$_2$CF$_3$ | $^i$Pr | H | H | NO$_2$ | H | 2 |
| SO$_2$CF$_3$ | $^i$Pr | H | H | CN | H | 0 |
| SO$_2$CF$_3$ | $^i$Pr | H | H | CN | H | 1 |
| SO$_2$CF$_3$ | $^i$Pr | H | H | CN | H | 2 |
| SO$_2$CF$_3$ | $^i$Pr | H | H | H | F | 0 |
| SO$_2$CF$_3$ | $^i$Pr | H | H | H | F | 1 |
| SO$_2$CF$_3$ | $^i$Pr | H | H | H | F | 2 |
| SO$_2$CF$_3$ | $^i$Pr | H | H | H | Cl | 0 |
| SO$_2$CF$_3$ | $^i$Pr | H | H | H | Cl | 1 |
| SO$_2$CF$_3$ | $^i$Pr | H | H | H | Cl | 2 |
| SO$_2$CF$_3$ | $^i$Pr | H | H | H | Br | 0 |
| SO$_2$CF$_3$ | $^i$Pr | H | H | H | Br | 1 |
| SO$_2$CF$_3$ | $^i$Pr | H | H | H | Br | 2 |
| SO$_2$CF$_3$ | $^i$Pr | H | H | H | I | 0 |
| SO$_2$CF$_3$ | $^i$Pr | H | H | H | I | 1 |
| SO$_2$CF$_3$ | $^i$Pr | H | H | H | I | 2 |

TABLE 1-continued

| | | | | | | |
|---|---|---|---|---|---|---|
| SO$_2$CF$_3$ | $^i$Pr | H | H | H | Me | 0 |
| SO$_2$CF$_3$ | $^i$Pr | H | H | H | Me | 1 |
| SO$_2$CF$_3$ | $^i$Pr | H | H | H | Me | 2 |
| SO$_2$CF$_3$ | $^i$Pr | H | H | H | CF$_3$ | 0 |
| SO$_2$CF$_3$ | $^i$Pr | H | H | H | CF$_3$ | 1 |
| SO$_2$CF$_3$ | $^i$Pr | H | H | H | CF$_3$ | 2 |
| SO$_2$CF$_3$ | $^i$Pr | H | H | H | CF$_2$CF$_3$ | 0 |
| SO$_2$CF$_3$ | $^i$Pr | H | H | H | CF$_2$CF$_3$ | 1 |
| SO$_2$CF$_3$ | $^i$Pr | H | H | H | CF$_2$CF$_3$ | 2 |
| SO$_2$CF$_3$ | $^i$Pr | H | H | H | CF(CF$_3$)$_2$ | 0 |
| SO$_2$CF$_3$ | $^i$Pr | H | H | H | CF(CF$_3$)$_2$ | 1 |
| SO$_2$CF$_3$ | $^i$Pr | H | H | H | CF(CF$_3$)$_2$ | 2 |
| SO$_2$CF$_3$ | $^i$Pr | H | H | H | SMe | 0 |
| SO$_2$CF$_3$ | $^i$Pr | H | H | H | SMe | 1 |
| SO$_2$CF$_3$ | $^i$Pr | H | H | H | SMe | 2 |
| SO$_2$CF$_3$ | $^i$Pr | H | H | H | SOMe | 0 |
| SO$_2$CF$_3$ | $^i$Pr | H | H | H | SOMe | 1 |
| SO$_2$CF$_3$ | $^i$Pr | H | H | H | SOMe | 2 |
| SO$_2$CF$_3$ | $^i$Pr | H | H | H | SO$_2$Me | 0 |
| SO$_2$CF$_3$ | $^i$Pr | H | H | H | SO$_2$Me | 1 |
| SO$_2$CF$_3$ | $^i$Pr | H | H | H | SO$_2$Me | 2 |
| SO$_2$CF$_3$ | $^i$Pr | H | H | H | OMe | 0 |
| SO$_2$CF$_3$ | $^i$Pr | H | H | H | OMe | 1 |
| SO$_2$CF$_3$ | $^i$Pr | H | H | H | OMe | 2 |
| SO$_2$CF$_3$ | $^i$Pr | H | H | H | OCF$_3$ | 0 |
| SO$_2$CF$_3$ | $^i$Pr | H | H | H | OCF$_3$ | 1 |
| SO$_2$CF$_3$ | $^i$Pr | H | H | H | OCF$_3$ | 2 |
| SO$_2$CF$_3$ | $^i$Pr | H | H | H | NO$_2$ | 0 |
| SO$_2$CF$_3$ | $^i$Pr | H | H | H | NO$_2$ | 1 |
| SO$_2$CF$_3$ | $^i$Pr | H | H | H | NO$_2$ | 2 |
| SO$_2$CF$_3$ | $^i$Pr | H | H | H | CN | 0 |
| SO$_2$CF$_3$ | $^i$Pr | H | H | H | CN | 1 |
| SO$_2$CF$_3$ | $^i$Pr | H | H | H | CN | 2 |
| SO$_2$CF$_3$ | $^i$Pr | H | F | H | F | 0 |
| SO$_2$CF$_3$ | $^i$Pr | H | F | H | F | 1 |
| SO$_2$CF$_3$ | $^i$Pr | H | F | H | F | 2 |
| SO$_2$CF$_3$ | $^i$Pr | H | Cl | H | Cl | 0 |
| SO$_2$CF$_3$ | $^i$Pr | H | Cl | H | Cl | 1 |
| SO$_2$CF$_3$ | $^i$Pr | H | Cl | H | Cl | 2 |
| SO$_2$CF$_3$ | $^i$Pr | H | Br | H | Br | 0 |
| SO$_2$CF$_3$ | $^i$Pr | H | Br | H | Br | 1 |
| SO$_2$CF$_3$ | $^i$Pr | H | Br | H | Br | 2 |
| SO$_2$CF$_3$ | $^i$Pr | H | I | H | I | 0 |
| SO$_2$CF$_3$ | $^i$Pr | H | I | H | I | 1 |
| SO$_2$CF$_3$ | $^i$Pr | H | I | H | I | 2 |
| SO$_2$CF$_3$ | $^i$Pr | H | F | H | Cl | 0 |
| SO$_2$CF$_3$ | $^i$Pr | H | F | H | Cl | 1 |
| SO$_2$CF$_3$ | $^i$Pr | H | F | H | Cl | 2 |
| SO$_2$CF$_3$ | $^i$Pr | H | F | H | Br | 0 |
| SO$_2$CF$_3$ | $^i$Pr | H | F | H | Br | 1 |
| SO$_2$CF$_3$ | $^i$Pr | H | F | H | Br | 2 |
| SO$_2$CF$_3$ | $^i$Pr | H | F | H | I | 0 |
| SO$_2$CF$_3$ | $^i$Pr | H | F | H | I | 1 |
| SO$_2$CF$_3$ | $^i$Pr | H | F | H | I | 2 |
| SO$_2$CF$_3$ | $^i$Pr | H | Cl | H | F | 0 |
| SO$_2$CF$_3$ | $^i$Pr | H | Cl | H | F | 1 |
| SO$_2$CF$_3$ | $^i$Pr | H | Cl | H | F | 2 |
| SO$_2$CF$_3$ | $^i$Pr | H | Cl | H | Br | 0 |
| SO$_2$CF$_3$ | $^i$Pr | H | Cl | H | Br | 1 |
| SO$_2$CF$_3$ | $^i$Pr | H | Cl | H | Br | 2 |
| SO$_2$CF$_3$ | $^i$Pr | H | Cl | H | I | 0 |
| SO$_2$CF$_3$ | $^i$Pr | H | Cl | H | I | 1 |
| SO$_2$CF$_3$ | $^i$Pr | H | Cl | H | I | 2 |
| SO$_2$CF$_3$ | $^i$Pr | H | Br | H | F | 0 |
| SO$_2$CF$_3$ | $^i$Pr | H | Br | H | F | 1 |
| SO$_2$CF$_3$ | $^i$Pr | H | Br | H | F | 2 |
| SO$_2$CF$_3$ | $^i$Pr | H | Br | H | Cl | 0 |
| SO$_2$CF$_3$ | $^i$Pr | H | Br | H | Cl | 1 |
| SO$_2$CF$_3$ | $^i$Pr | H | Br | H | Cl | 2 |
| SO$_2$CF$_3$ | $^i$Pr | H | Br | H | I | 0 |
| SO$_2$CF$_3$ | $^i$Pr | H | Br | H | I | 1 |
| SO$_2$CF$_3$ | $^i$Pr | H | Br | H | I | 2 |
| SO$_2$CF$_3$ | $^i$Pr | H | I | H | F | 0 |
| SO$_2$CF$_3$ | $^i$Pr | H | I | H | F | 1 |
| SO$_2$CF$_3$ | $^i$Pr | H | I | H | F | 2 |
| SO$_2$CF$_3$ | $^i$Pr | H | I | H | Cl | 0 |
| SO$_2$CF$_3$ | $^i$Pr | H | I | H | Cl | 1 |
| SO$_2$CF$_3$ | $^i$Pr | H | I | H | Cl | 2 |
| SO$_2$CF$_3$ | $^i$Pr | H | I | H | Br | 0 |
| SO$_2$CF$_3$ | $^i$Pr | H | I | H | Br | 1 |
| SO$_2$CF$_3$ | $^i$Pr | H | I | H | Br | 2 |
| SO$_2$CF$_3$ | $^i$Pr | H | F | H | CN | 0 |
| SO$_2$CF$_3$ | $^i$Pr | H | F | H | CN | 1 |
| SO$_2$CF$_3$ | $^i$Pr | H | F | H | CN | 2 |
| SO$_2$CF$_3$ | $^i$Pr | H | Cl | H | CN | 0 |
| SO$_2$CF$_3$ | $^i$Pr | H | Cl | H | CN | 1 |
| SO$_2$CF$_3$ | $^i$Pr | H | Cl | H | CN | 2 |
| SO$_2$CF$_3$ | $^i$Pr | H | Br | H | CN | 0 |
| SO$_2$CF$_3$ | $^i$Pr | H | Br | H | CN | 1 |
| SO$_2$CF$_3$ | $^i$Pr | H | Br | H | CN | 2 |
| SO$_2$CF$_3$ | $^i$Pr | H | I | H | CN | 0 |
| SO$_2$CF$_3$ | $^i$Pr | H | I | H | CN | 1 |
| SO$_2$CF$_3$ | $^i$Pr | H | I | H | CN | 2 |
| SO$_2$CF$_3$ | $^i$Pr | H | CF$_3$ | H | F | 0 |
| SO$_2$CF$_3$ | $^i$Pr | H | CF$_3$ | H | F | 1 |
| SO$_2$CF$_3$ | $^i$Pr | H | CF$_3$ | H | F | 2 |
| SO$_2$CF$_3$ | $^i$Pr | H | CF$_3$ | H | Cl | 0 |
| SO$_2$CF$_3$ | $^i$Pr | H | CF$_3$ | H | Cl | 1 |
| SO$_2$CF$_3$ | $^i$Pr | H | CF$_3$ | H | Cl | 2 |
| SO$_2$CF$_3$ | $^i$Pr | H | CF$_3$ | H | Br | 0 |
| SO$_2$CF$_3$ | $^i$Pr | H | CF$_3$ | H | Br | 2 |
| SO$_2$CF$_3$ | $^i$Pr | H | CF$_3$ | H | I | 0 |
| SO$_2$CF$_3$ | $^i$Pr | H | CF$_3$ | H | I | 1 |
| SO$_2$CF$_3$ | $^i$Pr | H | CF$_3$ | H | CN | 0 |
| SO$_2$CF$_3$ | $^i$Pr | H | CF$_3$ | H | CN | 1 |
| SO$_2$CF$_3$ | $^i$Pr | H | CF$_3$ | H | CN | 2 |
| SO$_2$CF$_3$ | $^i$Pr | H | F | F | H | 0 |
| SO$_2$CF$_3$ | $^i$Pr | H | F | F | H | 1 |
| SO$_2$CF$_3$ | $^i$Pr | H | F | F | H | 2 |
| SO$_2$CF$_3$ | $^i$Pr | H | Cl | Cl | H | 0 |
| SO$_2$CF$_3$ | $^i$Pr | H | Cl | Cl | H | 1 |
| SO$_2$CF$_3$ | $^i$Pr | H | Cl | Cl | H | 2 |
| SO$_2$CF$_3$ | $^i$Pr | H | Br | Br | H | 0 |
| SO$_2$CF$_3$ | $^i$Pr | H | Br | Br | H | 1 |
| SO$_2$CF$_3$ | $^i$Pr | H | Br | Br | H | 2 |
| SO$_2$CF$_3$ | $^i$Pr | H | I | I | H | 0 |
| SO$_2$CF$_3$ | $^i$Pr | H | I | I | H | 1 |
| SO$_2$CF$_3$ | $^i$Pr | H | I | I | H | 2 |
| SO$_2$CF$_3$ | $^i$Pr | H | F | Cl | H | 0 |
| SO$_2$CF$_3$ | $^i$Pr | H | F | Cl | H | 1 |
| SO$_2$CF$_3$ | $^i$Pr | H | F | Cl | H | 2 |
| SO$_2$CF$_3$ | $^i$Pr | H | F | Br | H | 0 |
| SO$_2$CF$_3$ | $^i$Pr | H | F | Br | H | 1 |
| SO$_2$CF$_3$ | $^i$Pr | H | F | Br | H | 2 |
| SO$_2$CF$_3$ | $^i$Pr | H | F | I | H | 0 |
| SO$_2$CF$_3$ | $^i$Pr | H | F | I | H | 1 |
| SO$_2$CF$_3$ | $^i$Pr | H | F | I | H | 2 |
| SO$_2$CF$_3$ | $^i$Pr | H | Cl | F | H | 0 |
| SO$_2$CF$_3$ | $^i$Pr | H | Cl | F | H | 1 |
| SO$_2$CF$_3$ | $^i$Pr | H | Cl | F | H | 2 |
| SO$_2$CF$_3$ | $^i$Pr | H | Cl | Br | H | 0 |
| SO$_2$CF$_3$ | $^i$Pr | H | Cl | Br | H | 1 |
| SO$_2$CF$_3$ | $^i$Pr | H | Cl | Br | H | 2 |
| SO$_2$CF$_3$ | $^i$Pr | H | Cl | I | H | 0 |
| SO$_2$CF$_3$ | $^i$Pr | H | Cl | I | H | 1 |
| SO$_2$CF$_3$ | $^i$Pr | H | Cl | I | H | 2 |
| SO$_2$CF$_3$ | $^i$Pr | H | Br | F | H | 0 |
| SO$_2$CF$_3$ | $^i$Pr | H | Br | F | H | 1 |
| SO$_2$CF$_3$ | $^i$Pr | H | Br | F | H | 2 |
| SO$_2$CF$_3$ | $^i$Pr | H | Br | Cl | H | 0 |
| SO$_2$CF$_3$ | $^i$Pr | H | Br | Cl | H | 1 |
| SO$_2$CF$_3$ | $^i$Pr | H | Br | Cl | H | 2 |
| SO$_2$CF$_3$ | $^i$Pr | H | Br | I | H | 0 |
| SO$_2$CF$_3$ | $^i$Pr | H | Br | I | H | 1 |
| SO$_2$CF$_3$ | $^i$Pr | H | Br | I | H | 2 |
| SO$_2$CF$_3$ | $^i$Pr | H | I | F | H | 0 |
| SO$_2$CF$_3$ | $^i$Pr | H | I | F | H | 1 |
| SO$_2$CF$_3$ | $^i$Pr | H | I | F | H | 2 |
| SO$_2$CF$_3$ | $^i$Pr | H | I | Cl | H | 0 |
| SO$_2$CF$_3$ | $^i$Pr | H | I | Cl | H | 1 |
| SO$_2$CF$_3$ | $^i$Pr | H | I | Cl | H | 2 |
| SO$_2$CF$_3$ | $^i$Pr | H | I | Br | H | 0 |
| SO$_2$CF$_3$ | $^i$Pr | H | I | Br | H | 1 |
| SO$_2$CF$_3$ | $^i$Pr | H | I | Br | H | 2 |
| SO$_2$CF$_3$ | $^i$Pr | H | F | CN | H | 0 |
| SO$_2$CF$_3$ | $^i$Pr | H | F | CN | H | 1 |
| SO$_2$CF$_3$ | $^i$Pr | H | F | CN | H | 2 |
| SO$_2$CF$_3$ | $^i$Pr | H | Cl | CN | H | 0 |

TABLE 1-continued

| | | | | | | |
|---|---|---|---|---|---|---|
| SO$_2$CF$_3$ | $^i$Pr | H | Cl | CN | H | 1 |
| SO$_2$CF$_3$ | $^i$Pr | H | Cl | CN | H | 2 |
| SO$_2$CF$_3$ | $^i$Pr | H | Br | CN | H | 0 |
| SO$_2$CF$_3$ | $^i$Pr | H | Br | CN | H | 1 |
| SO$_2$CF$_3$ | $^i$Pr | H | Br | CN | H | 2 |
| SO$_2$CF$_3$ | $^i$Pr | H | I | CN | H | 0 |
| SO$_2$CF$_3$ | $^i$Pr | H | I | CN | H | 1 |
| SO$_2$CF$_3$ | $^i$Pr | H | I | CN | H | 2 |
| SO$_2$CF$_3$ | $^i$Pr | H | CF$_3$ | F | H | 0 |
| SO$_2$CF$_3$ | $^i$Pr | H | CF$_3$ | F | H | 1 |
| SO$_2$CF$_3$ | $^i$Pr | H | CF$_3$ | F | H | 2 |
| SO$_2$CF$_3$ | $^i$Pr | H | CF$_3$ | Cl | H | 0 |
| SO$_2$CF$_3$ | $^i$Pr | H | CF$_3$ | Cl | H | 1 |
| SO$_2$CF$_3$ | $^i$Pr | H | CF$_3$ | Cl | H | 2 |
| SO$_2$CF$_3$ | $^i$Pr | H | CF$_3$ | Br | H | 0 |
| SO$_2$CF$_3$ | $^i$Pr | H | CF$_3$ | Br | H | 1 |
| SO$_2$CF$_3$ | $^i$Pr | H | CF$_3$ | Br | H | 2 |
| SO$_2$CF$_3$ | $^i$Pr | H | CF$_3$ | I | H | 0 |
| SO$_2$CF$_3$ | $^i$Pr | H | CF$_3$ | I | H | 1 |
| SO$_2$CF$_3$ | $^i$Pr | H | CF$_3$ | I | H | 2 |
| SO$_2$CF$_3$ | $^i$Pr | H | CF$_3$ | CN | H | 0 |
| SO$_2$CF$_3$ | $^i$Pr | H | CF$_3$ | CN | H | 1 |
| SO$_2$CF$_3$ | $^i$Pr | H | CF$_3$ | CN | H | 2 |
| SO$_2$CF$_3$ | CH$_2$CF$_3$ | H | H | H | H | 0 |
| SO$_2$CF$_3$ | CH$_2$CF$_3$ | H | H | H | H | 1 |
| SO$_2$CF$_3$ | CH$_2$CF$_3$ | H | H | H | H | 2 |
| SO$_2$CF$_3$ | CH$_2$CF$_3$ | F | H | H | H | 0 |
| SO$_2$CF$_3$ | CH$_2$CF$_3$ | F | H | H | H | 1 |
| SO$_2$CF$_3$ | CH$_2$CF$_3$ | F | H | H | H | 2 |
| SO$_2$CF$_3$ | CH$_2$CF$_3$ | Cl | H | H | H | 0 |
| SO$_2$CF$_3$ | CH$_2$CF$_3$ | Cl | H | H | H | 1 |
| SO$_2$CF$_3$ | CH$_2$CF$_3$ | Cl | H | H | H | 2 |
| SO$_2$CF$_3$ | CH$_2$CF$_3$ | Br | H | H | H | 0 |
| SO$_2$CF$_3$ | CH$_2$CF$_3$ | Br | H | H | H | 1 |
| SO$_2$CF$_3$ | CH$_2$CF$_3$ | Br | H | H | H | 2 |
| SO$_2$CF$_3$ | CH$_2$CF$_3$ | I | H | H | H | 0 |
| SO$_2$CF$_3$ | CH$_2$CF$_3$ | I | H | H | H | 1 |
| SO$_2$CF$_3$ | CH$_2$CF$_3$ | I | H | H | H | 2 |
| SO$_2$CF$_3$ | CH$_2$CF$_3$ | Me | H | H | H | 0 |
| SO$_2$CF$_3$ | CH$_2$CF$_3$ | Me | H | H | H | 1 |
| SO$_2$CF$_3$ | CH$_2$CF$_3$ | Me | H | H | H | 2 |
| SO$_2$CF$_3$ | CH$_2$CF$_3$ | CF$_3$ | H | H | H | 0 |
| SO$_2$CF$_3$ | CH$_2$CF$_3$ | CF$_3$ | H | H | H | 1 |
| SO$_2$CF$_3$ | CH$_2$CF$_3$ | CF$_3$ | H | H | H | 2 |
| SO$_2$CF$_3$ | CH$_2$CF$_3$ | H | F | H | H | 0 |
| SO$_2$CF$_3$ | CH$_2$CF$_3$ | H | F | H | H | 1 |
| SO$_2$CF$_3$ | CH$_2$CF$_3$ | H | F | H | H | 2 |
| SO$_2$CF$_3$ | CH$_2$CF$_3$ | H | Cl | H | H | 0 |
| SO$_2$CF$_3$ | CH$_2$CF$_3$ | H | Cl | H | H | 1 |
| SO$_2$CF$_3$ | CH$_2$CF$_3$ | H | Cl | H | H | 2 |
| SO$_2$CF$_3$ | CH$_2$CF$_3$ | H | Br | H | H | 0 |
| SO$_2$CF$_3$ | CH$_2$CF$_3$ | H | Br | H | H | 1 |
| SO$_2$CF$_3$ | CH$_2$CF$_3$ | H | Br | H | H | 2 |
| SO$_2$CF$_3$ | CH$_2$CF$_3$ | H | I | H | H | 0 |
| SO$_2$CF$_3$ | CH$_2$CF$_3$ | H | I | H | H | 1 |
| SO$_2$CF$_3$ | CH$_2$CF$_3$ | H | I | H | H | 2 |
| SO$_2$CF$_3$ | CH$_2$CF$_3$ | H | Me | H | H | 0 |
| SO$_2$CF$_3$ | CH$_2$CF$_3$ | H | Me | H | H | 1 |
| SO$_2$CF$_3$ | CH$_2$CF$_3$ | H | Me | H | H | 2 |
| SO$_2$CF$_3$ | CH$_2$CF$_3$ | H | CF$_3$ | H | H | 0 |
| SO$_2$CF$_3$ | CH$_2$CF$_3$ | H | CF$_3$ | H | H | 1 |
| SO$_2$CF$_3$ | CH$_2$CF$_3$ | H | CF$_3$ | H | H | 2 |
| SO$_2$CF$_3$ | CH$_2$CF$_3$ | H | CF$_2$CF$_3$ | H | H | 0 |
| SO$_2$CF$_3$ | CH$_2$CF$_3$ | H | CF$_2$CF$_3$ | H | H | 1 |
| SO$_2$CF$_3$ | CH$_2$CF$_3$ | H | CF$_2$CF$_3$ | H | H | 2 |
| SO$_2$CF$_3$ | CH$_2$CF$_3$ | H | CF(CF$_3$)$_2$ | H | H | 0 |
| SO$_2$CF$_3$ | CH$_2$CF$_3$ | H | CF(CF$_3$)$_2$ | H | H | 1 |
| SO$_2$CF$_3$ | CH$_2$CF$_3$ | H | CF(CF$_3$)$_2$ | H | H | 2 |
| SO$_2$CF$_3$ | CH$_2$CF$_3$ | H | SMe | H | H | 0 |
| SO$_2$CF$_3$ | CH$_2$CF$_3$ | H | SMe | H | H | 1 |
| SO$_2$CF$_3$ | CH$_2$CF$_3$ | H | SMe | H | H | 2 |
| SO$_2$CF$_3$ | CH$_2$CF$_3$ | H | SOMe | H | H | 0 |
| SO$_2$CF$_3$ | CH$_2$CF$_3$ | H | SOMe | H | H | 1 |
| SO$_2$CF$_3$ | CH$_2$CF$_3$ | H | SOMe | H | H | 2 |
| SO$_2$CF$_3$ | CH$_2$CF$_3$ | H | SO$_2$Me | H | H | 0 |
| SO$_2$CF$_3$ | CH$_2$CF$_3$ | H | SO$_2$Me | H | H | 1 |
| SO$_2$CF$_3$ | CH$_2$CF$_3$ | H | SO$_2$Me | H | H | 2 |
| SO$_2$CF$_3$ | CH$_2$CF$_3$ | H | OMe | H | H | 0 |
| SO$_2$CF$_3$ | CH$_2$CF$_3$ | H | OMe | H | H | 1 |
| SO$_2$CF$_3$ | CH$_2$CF$_3$ | H | OMe | H | H | 2 |
| SO$_2$CF$_3$ | CH$_2$CF$_3$ | H | OCF$_3$ | H | H | 0 |
| SO$_2$CF$_3$ | CH$_2$CF$_3$ | H | OCF$_3$ | H | H | 1 |
| SO$_2$CF$_3$ | CH$_2$CF$_3$ | H | OCF$_3$ | H | H | 2 |
| SO$_2$CF$_3$ | CH$_2$CF$_3$ | H | NO$_2$ | H | H | 0 |
| SO$_2$CF$_3$ | CH$_2$CF$_3$ | H | NO$_2$ | H | H | 1 |
| SO$_2$CF$_3$ | CH$_2$CF$_3$ | H | NO$_2$ | H | H | 2 |
| SO$_2$CF$_3$ | CH$_2$CF$_3$ | H | CN | H | H | 0 |
| SO$_2$CF$_3$ | CH$_2$CF$_3$ | H | CN | H | H | 1 |
| SO$_2$CF$_3$ | CH$_2$CF$_3$ | H | CN | H | H | 2 |
| SO$_2$CF$_3$ | CH$_2$CF$_3$ | H | H | F | H | 0 |
| SO$_2$CF$_3$ | CH$_2$CF$_3$ | H | H | F | H | 1 |
| SO$_2$CF$_3$ | CH$_2$CF$_3$ | H | H | F | H | 2 |
| SO$_2$CF$_3$ | CH$_2$CF$_3$ | H | H | Cl | H | 0 |
| SO$_2$CF$_3$ | CH$_2$CF$_3$ | H | H | Cl | H | 1 |
| SO$_2$CF$_3$ | CH$_2$CF$_3$ | H | H | Cl | H | 2 |
| SO$_2$CF$_3$ | CH$_2$CF$_3$ | H | H | Br | H | 0 |
| SO$_2$CF$_3$ | CH$_2$CF$_3$ | H | H | Br | H | 1 |
| SO$_2$CF$_3$ | CH$_2$CF$_3$ | H | H | Br | H | 2 |
| SO$_2$CF$_3$ | CH$_2$CF$_3$ | H | H | I | H | 0 |
| SO$_2$CF$_3$ | CH$_2$CF$_3$ | H | H | I | H | 1 |
| SO$_2$CF$_3$ | CH$_2$CF$_3$ | H | H | I | H | 2 |
| SO$_2$CF$_3$ | CH$_2$CF$_3$ | H | H | Me | H | 0 |
| SO$_2$CF$_3$ | CH$_2$CF$_3$ | H | H | Me | H | 1 |
| SO$_2$CF$_3$ | CH$_2$CF$_3$ | H | H | Me | H | 2 |
| SO$_2$CF$_3$ | CH$_2$CF$_3$ | H | H | CF$_3$ | H | 0 |
| SO$_2$CF$_3$ | CH$_2$CF$_3$ | H | H | CF$_3$ | H | 1 |
| SO$_2$CF$_3$ | CH$_2$CF$_3$ | H | H | CF$_3$ | H | 2 |
| SO$_2$CF$_3$ | CH$_2$CF$_3$ | H | H | CF$_2$CF$_3$ | H | 0 |
| SO$_2$CF$_3$ | CH$_2$CF$_3$ | H | H | CF$_2$CF$_3$ | H | 1 |
| SO$_2$CF$_3$ | CH$_2$CF$_3$ | H | H | CF$_2$CF$_3$ | H | 2 |
| SO$_2$CF$_3$ | CH$_2$CF$_3$ | H | H | CF(CF$_3$)$_2$ | H | 0 |
| SO$_2$CF$_3$ | CH$_2$CF$_3$ | H | H | CF(CF$_3$)$_2$ | H | 1 |
| SO$_2$CF$_3$ | CH$_2$CF$_3$ | H | H | CF(CF$_3$)$_2$ | H | 2 |
| SO$_2$CF$_3$ | CH$_2$CF$_3$ | H | H | SMe | H | 0 |
| SO$_2$CF$_3$ | CH$_2$CF$_3$ | H | H | SMe | H | 1 |
| SO$_2$CF$_3$ | CH$_2$CF$_3$ | H | H | SMe | H | 2 |
| SO$_2$CF$_3$ | CH$_2$CF$_3$ | H | H | SOMe | H | 0 |
| SO$_2$CF$_3$ | CH$_2$CF$_3$ | H | H | SOMe | H | 1 |
| SO$_2$CF$_3$ | CH$_2$CF$_3$ | H | H | SOMe | H | 2 |
| SO$_2$CF$_3$ | CH$_2$CF$_3$ | H | H | SO$_2$Me | H | 0 |
| SO$_2$CF$_3$ | CH$_2$CF$_3$ | H | H | SO$_2$Me | H | 1 |
| SO$_2$CF$_3$ | CH$_2$CF$_3$ | H | H | SO$_2$Me | H | 2 |
| SO$_2$CF$_3$ | CH$_2$CF$_3$ | H | H | OMe | H | 0 |
| SO$_2$CF$_3$ | CH$_2$CF$_3$ | H | H | OMe | H | 1 |
| SO$_2$CF$_3$ | CH$_2$CF$_3$ | H | H | OMe | H | 2 |
| SO$_2$CF$_3$ | CH$_2$CF$_3$ | H | H | OCF$_3$ | H | 0 |
| SO$_2$CF$_3$ | CH$_2$CF$_3$ | H | H | OCF$_3$ | H | 1 |
| SO$_2$CF$_3$ | CH$_2$CF$_3$ | H | H | OCF$_3$ | H | 2 |
| SO$_2$CF$_3$ | CH$_2$CF$_3$ | H | H | NO$_2$ | H | 0 |
| SO$_2$CF$_3$ | CH$_2$CF$_3$ | H | H | NO$_2$ | H | 1 |
| SO$_2$CF$_3$ | CH$_2$CF$_3$ | H | H | NO$_2$ | H | 2 |
| SO$_2$CF$_3$ | CH$_2$CF$_3$ | H | H | CN | H | 0 |
| SO$_2$CF$_3$ | CH$_2$CF$_3$ | H | H | CN | H | 1 |
| SO$_2$CF$_3$ | CH$_2$CF$_3$ | H | H | CN | H | 2 |
| SO$_2$CF$_3$ | CH$_2$CF$_3$ | H | H | H | F | 0 |
| SO$_2$CF$_3$ | CH$_2$CF$_3$ | H | H | H | F | 1 |
| SO$_2$CF$_3$ | CH$_2$CF$_3$ | H | H | H | F | 2 |
| SO$_2$CF$_3$ | CH$_2$CF$_3$ | H | H | H | Cl | 0 |
| SO$_2$CF$_3$ | CH$_2$CF$_3$ | H | H | H | Cl | 1 |
| SO$_2$CF$_3$ | CH$_2$CF$_3$ | H | H | H | Cl | 2 |
| SO$_2$CF$_3$ | CH$_2$CF$_3$ | H | H | H | Br | 0 |
| SO$_2$CF$_3$ | CH$_2$CF$_3$ | H | H | H | Br | 1 |
| SO$_2$CF$_3$ | CH$_2$CF$_3$ | H | H | H | Br | 2 |
| SO$_2$CF$_3$ | CH$_2$CF$_3$ | H | H | H | I | 0 |
| SO$_2$CF$_3$ | CH$_2$CF$_3$ | H | H | H | I | 1 |
| SO$_2$CF$_3$ | CH$_2$CF$_3$ | H | H | H | I | 2 |
| SO$_2$CF$_3$ | CH$_2$CF$_3$ | H | H | H | Me | 0 |
| SO$_2$CF$_3$ | CH$_2$CF$_3$ | H | H | H | Me | 1 |
| SO$_2$CF$_3$ | CH$_2$CF$_3$ | H | H | H | Me | 2 |
| SO$_2$CF$_3$ | CH$_2$CF$_3$ | H | H | H | CF$_3$ | 0 |
| SO$_2$CF$_3$ | CH$_2$CF$_3$ | H | H | H | CF$_3$ | 1 |
| SO$_2$CF$_3$ | CH$_2$CF$_3$ | H | H | H | CF$_3$ | 2 |
| SO$_2$CF$_3$ | CH$_2$CF$_3$ | H | H | H | CF$_2$CF$_3$ | 0 |
| SO$_2$CF$_3$ | CH$_2$CF$_3$ | H | H | H | CF$_2$CF$_3$ | 1 |
| SO$_2$CF$_3$ | CH$_2$CF$_3$ | H | H | H | CF$_2$CF$_3$ | 2 |
| SO$_2$CF$_3$ | CH$_2$CF$_3$ | H | H | H | CF(CF$_3$)$_2$ | 0 |
| SO$_2$CF$_3$ | CH$_2$CF$_3$ | H | H | H | CF(CF$_3$)$_2$ | 1 |
| SO$_2$CF$_3$ | CH$_2$CF$_3$ | H | H | H | CF(CF$_3$)$_2$ | 2 |
| SO$_2$CF$_3$ | CH$_2$CF$_3$ | H | H | H | SMe | 0 |
| SO$_2$CF$_3$ | CH$_2$CF$_3$ | H | H | H | SMe | 1 |

TABLE 1-continued

| | | | | | | |
|---|---|---|---|---|---|---|
| SO₂CF₃ | CH₂CF₃ | H | H | H | SMe | 2 |
| SO₂CF₃ | CH₂CF₃ | H | H | H | SOMe | 0 |
| SO₂CF₃ | CH₂CF₃ | H | H | H | SOMe | 1 |
| SO₂CF₃ | CH₂CF₃ | H | H | H | SOMe | 2 |
| SO₂CF₃ | CH₂CF₃ | H | H | H | SO₂Me | 0 |
| SO₂CF₃ | CH₂CF₃ | H | H | H | SO₂Me | 1 |
| SO₂CF₃ | CH₂CF₃ | H | H | H | SO₂Me | 2 |
| SO₂CF₃ | CH₂CF₃ | H | H | H | OMe | 0 |
| SO₂CF₃ | CH₂CF₃ | H | H | H | OMe | 1 |
| SO₂CF₃ | CH₂CF₃ | H | H | H | OMe | 2 |
| SO₂CF₃ | CH₂CF₃ | H | H | H | OCF₃ | 0 |
| SO₂CF₃ | CH₂CF₃ | H | H | H | OCF₃ | 1 |
| SO₂CF₃ | CH₂CF₃ | H | H | H | OCF₃ | 2 |
| SO₂CF₃ | CH₂CF₃ | H | H | H | NO₂ | 0 |
| SO₂CF₃ | CH₂CF₃ | H | H | H | NO₂ | 1 |
| SO₂CF₃ | CH₂CF₃ | H | H | H | NO₂ | 2 |
| SO₂CF₃ | CH₂CF₃ | H | H | H | CN | 0 |
| SO₂CF₃ | CH₂CF₃ | H | H | H | CN | 1 |
| SO₂CF₃ | CH₂CF₃ | H | H | H | CN | 2 |
| SO₂CF₃ | CH₂CF₃ | H | F | H | F | 0 |
| SO₂CF₃ | CH₂CF₃ | H | F | H | F | 1 |
| SO₂CF₃ | CH₂CF₃ | H | F | H | F | 2 |
| SO₂CF₃ | CH₂CF₃ | H | Cl | H | Cl | 0 |
| SO₂CF₃ | CH₂CF₃ | H | Cl | H | Cl | 1 |
| SO₂CF₃ | CH₂CF₃ | H | Cl | H | Cl | 2 |
| SO₂CF₃ | CH₂CF₃ | H | Br | H | Br | 0 |
| SO₂CF₃ | CH₂CF₃ | H | Br | H | Br | 1 |
| SO₂CF₃ | CH₂CF₃ | H | Br | H | Br | 2 |
| SO₂CF₃ | CH₂CF₃ | H | I | H | I | 0 |
| SO₂CF₃ | CH₂CF₃ | H | I | H | I | 1 |
| SO₂CF₃ | CH₂CF₃ | H | I | H | I | 2 |
| SO₂CF₃ | CH₂CF₃ | H | F | H | Cl | 0 |
| SO₂CF₃ | CH₂CF₃ | H | F | H | Cl | 1 |
| SO₂CF₃ | CH₂CF₃ | H | F | H | Cl | 2 |
| SO₂CF₃ | CH₂CF₃ | H | F | H | Br | 0 |
| SO₂CF₃ | CH₂CF₃ | H | F | H | Br | 1 |
| SO₂CF₃ | CH₂CF₃ | H | F | H | Br | 2 |
| SO₂CF₃ | CH₂CF₃ | H | F | H | I | 0 |
| SO₂CF₃ | CH₂CF₃ | H | F | H | I | 1 |
| SO₂CF₃ | CH₂CF₃ | H | F | H | I | 2 |
| SO₂CF₃ | CH₂CF₃ | H | Cl | H | F | 0 |
| SO₂CF₃ | CH₂CF₃ | H | Cl | H | F | 1 |
| SO₂CF₃ | CH₂CF₃ | H | Cl | H | F | 2 |
| SO₂CF₃ | CH₂CF₃ | H | Cl | H | Br | 0 |
| SO₂CF₃ | CH₂CF₃ | H | Cl | H | Br | 1 |
| SO₂CF₃ | CH₂CF₃ | H | Cl | H | Br | 2 |
| SO₂CF₃ | CH₂CF₃ | H | Cl | H | I | 0 |
| SO₂CF₃ | CH₂CF₃ | H | Cl | H | I | 1 |
| SO₂CF₃ | CH₂CF₃ | H | Cl | H | I | 2 |
| SO₂CF₃ | CH₂CF₃ | H | Br | H | F | 0 |
| SO₂CF₃ | CH₂CF₃ | H | Br | H | F | 1 |
| SO₂CF₃ | CH₂CF₃ | H | Br | H | F | 2 |
| SO₂CF₃ | CH₂CF₃ | H | Br | H | Cl | 0 |
| SO₂CF₃ | CH₂CF₃ | H | Br | H | Cl | 1 |
| SO₂CF₃ | CH₂CF₃ | H | Br | H | Cl | 2 |
| SO₂CF₃ | CH₂CF₃ | H | Br | H | I | 0 |
| SO₂CF₃ | CH₂CF₃ | H | Br | H | I | 1 |
| SO₂CF₃ | CH₂CF₃ | H | Br | H | I | 2 |
| SO₂CF₃ | CH₂CF₃ | H | I | H | F | 0 |
| SO₂CF₃ | CH₂CF₃ | H | I | H | F | 1 |
| SO₂CF₃ | CH₂CF₃ | H | I | H | F | 2 |
| SO₂CF₃ | CH₂CF₃ | H | I | H | Cl | 0 |
| SO₂CF₃ | CH₂CF₃ | H | I | H | Cl | 1 |
| SO₂CF₃ | CH₂CF₃ | H | I | H | Cl | 2 |
| SO₂CF₃ | CH₂CF₃ | H | I | H | Br | 0 |
| SO₂CF₃ | CH₂CF₃ | H | I | H | Br | 1 |
| SO₂CF₃ | CH₂CF₃ | H | I | H | Br | 2 |
| SO₂CF₃ | CH₂CF₃ | H | F | H | CN | 0 |
| SO₂CF₃ | CH₂CF₃ | H | F | H | CN | 1 |
| SO₂CF₃ | CH₂CF₃ | H | F | H | CN | 2 |
| SO₂CF₃ | CH₂CF₃ | H | Cl | H | CN | 0 |
| SO₂CF₃ | CH₂CF₃ | H | Cl | H | CN | 1 |
| SO₂CF₃ | CH₂CF₃ | H | Cl | H | CN | 2 |
| SO₂CF₃ | CH₂CF₃ | H | Br | H | CN | 0 |
| SO₂CF₃ | CH₂CF₃ | H | Br | H | CN | 1 |
| SO₂CF₃ | CH₂CF₃ | H | Br | H | CN | 2 |
| SO₂CF₃ | CH₂CF₃ | H | I | H | CN | 0 |
| SO₂CF₃ | CH₂CF₃ | H | I | H | CN | 1 |
| SO₂CF₃ | CH₂CF₃ | H | I | H | CN | 2 |
| SO₂CF₃ | CH₂CF₃ | H | CF₃ | H | F | 0 |
| SO₂CF₃ | CH₂CF₃ | H | CF₃ | H | F | 1 |
| SO₂CF₃ | CH₂CF₃ | H | CF₃ | H | F | 2 |
| SO₂CF₃ | CH₂CF₃ | H | CF₃ | H | Cl | 0 |
| SO₂CF₃ | CH₂CF₃ | H | CF₃ | H | Cl | 1 |
| SO₂CF₃ | CH₂CF₃ | H | CF₃ | H | Cl | 2 |
| SO₂CF₃ | CH₂CF₃ | H | CF₃ | H | Br | 0 |
| SO₂CF₃ | CH₂CF₃ | H | CF₃ | H | Br | 1 |
| SO₂CF₃ | CH₂CF₃ | H | CF₃ | H | Br | 2 |
| SO₂CF₃ | CH₂CF₃ | H | CF₃ | H | I | 0 |
| SO₂CF₃ | CH₂CF₃ | H | CF₃ | H | I | 1 |
| SO₂CF₃ | CH₂CF₃ | H | CF₃ | H | I | 2 |
| SO₂CF₃ | CH₂CF₃ | H | CF₃ | H | CN | 0 |
| SO₂CF₃ | CH₂CF₃ | H | CF₃ | H | CN | 1 |
| SO₂CF₃ | CH₂CF₃ | H | CF₃ | H | CN | 2 |
| SO₂CF₃ | CH₂CF₃ | H | F | F | H | 0 |
| SO₂CF₃ | CH₂CF₃ | H | F | F | H | 1 |
| SO₂CF₃ | CH₂CF₃ | H | F | F | H | 2 |
| SO₂CF₃ | CH₂CF₃ | H | Cl | Cl | H | 0 |
| SO₂CF₃ | CH₂CF₃ | H | Cl | Cl | H | 1 |
| SO₂CF₃ | CH₂CF₃ | H | Cl | Cl | H | 2 |
| SO₂CF₃ | CH₂CF₃ | H | Br | Br | H | 0 |
| SO₂CF₃ | CH₂CF₃ | H | Br | Br | H | 1 |
| SO₂CF₃ | CH₂CF₃ | H | Br | Br | H | 2 |
| SO₂CF₃ | CH₂CF₃ | H | I | I | H | 0 |
| SO₂CF₃ | CH₂CF₃ | H | I | I | H | 1 |
| SO₂CF₃ | CH₂CF₃ | H | I | I | H | 2 |
| SO₂CF₃ | CH₂CF₃ | H | F | Cl | H | 0 |
| SO₂CF₃ | CH₂CF₃ | H | F | Cl | H | 1 |
| SO₂CF₃ | CH₂CF₃ | H | F | Cl | H | 2 |
| SO₂CF₃ | CH₂CF₃ | H | F | Br | H | 0 |
| SO₂CF₃ | CH₂CF₃ | H | F | Br | H | 1 |
| SO₂CF₃ | CH₂CF₃ | H | F | Br | H | 2 |
| SO₂CF₃ | CH₂CF₃ | H | F | I | H | 0 |
| SO₂CF₃ | CH₂CF₃ | H | F | I | H | 1 |
| SO₂CF₃ | CH₂CF₃ | H | F | I | H | 2 |
| SO₂CF₃ | CH₂CF₃ | H | Cl | F | H | 0 |
| SO₂CF₃ | CH₂CF₃ | H | Cl | F | H | 1 |
| SO₂CF₃ | CH₂CF₃ | H | Cl | F | H | 2 |
| SO₂CF₃ | CH₂CF₃ | H | Cl | Br | H | 0 |
| SO₂CF₃ | CH₂CF₃ | H | Cl | Br | H | 1 |
| SO₂CF₃ | CH₂CF₃ | H | Cl | Br | H | 2 |
| SO₂CF₃ | CH₂CF₃ | H | Cl | I | H | 0 |
| SO₂CF₃ | CH₂CF₃ | H | Cl | I | H | 1 |
| SO₂CF₃ | CH₂CF₃ | H | Cl | I | H | 2 |
| SO₂CF₃ | CH₂CF₃ | H | Br | F | H | 0 |
| SO₂CF₃ | CH₂CF₃ | H | Br | F | H | 1 |
| SO₂CF₃ | CH₂CF₃ | H | Br | F | H | 2 |
| SO₂CF₃ | CH₂CF₃ | H | Br | Cl | H | 0 |
| SO₂CF₃ | CH₂CF₃ | H | Br | Cl | H | 1 |
| SO₂CF₃ | CH₂CF₃ | H | Br | Cl | H | 2 |
| SO₂CF₃ | CH₂CF₃ | H | Br | I | H | 0 |
| SO₂CF₃ | CH₂CF₃ | H | Br | I | H | 1 |
| SO₂CF₃ | CH₂CF₃ | H | Br | I | H | 2 |
| SO₂CF₃ | CH₂CF₃ | H | I | F | H | 0 |
| SO₂CF₃ | CH₂CF₃ | H | I | F | H | 1 |
| SO₂CF₃ | CH₂CF₃ | H | I | F | H | 2 |
| SO₂CF₃ | CH₂CF₃ | H | I | Cl | H | 0 |
| SO₂CF₃ | CH₂CF₃ | H | I | Cl | H | 1 |
| SO₂CF₃ | CH₂CF₃ | H | I | Cl | H | 2 |
| SO₂CF₃ | CH₂CF₃ | H | I | Br | H | 0 |
| SO₂CF₃ | CH₂CF₃ | H | I | Br | H | 1 |
| SO₂CF₃ | CH₂CF₃ | H | I | Br | H | 2 |
| SO₂CF₃ | CH₂CF₃ | H | F | CN | H | 0 |
| SO₂CF₃ | CH₂CF₃ | H | F | CN | H | 1 |
| SO₂CF₃ | CH₂CF₃ | H | F | CN | H | 2 |
| SO₂CF₃ | CH₂CF₃ | H | Cl | CN | H | 0 |
| SO₂CF₃ | CH₂CF₃ | H | Cl | CN | H | 1 |
| SO₂CF₃ | CH₂CF₃ | H | Cl | CN | H | 2 |
| SO₂CF₃ | CH₂CF₃ | H | Br | CN | H | 0 |
| SO₂CF₃ | CH₂CF₃ | H | Br | CN | H | 1 |
| SO₂CF₃ | CH₂CF₃ | H | Br | CN | H | 2 |
| SO₂CF₃ | CH₂CF₃ | H | I | CN | H | 0 |
| SO₂CF₃ | CH₂CF₃ | H | I | CN | H | 1 |
| SO₂CF₃ | CH₂CF₃ | H | I | CN | H | 2 |
| SO₂CF₃ | CH₂CF₃ | H | CF₃ | F | H | 0 |
| SO₂CF₃ | CH₂CF₃ | H | CF₃ | F | H | 1 |
| SO₂CF₃ | CH₂CF₃ | H | CF₃ | F | H | 2 |
| SO₂CF₃ | CH₂CF₃ | H | CF₃ | Cl | H | 0 |
| SO₂CF₃ | CH₂CF₃ | H | CF₃ | Cl | H | 1 |
| SO₂CF₃ | CH₂CF₃ | H | CF₃ | Cl | H | 2 |

TABLE 1-continued
| | | | | | | |
|---|---|---|---|---|---|---|
| SO$_2$CF$_3$ | CH$_2$CF$_3$ | H | CF$_3$ | Br | H | 0 |
| SO$_2$CF$_3$ | CH$_2$CF$_3$ | H | CF$_3$ | Br | H | 1 |
| SO$_2$CF$_3$ | CH$_2$CF$_3$ | H | CF$_3$ | Br | H | 2 |
| SO$_2$CF$_3$ | CH$_2$CF$_3$ | H | CF$_3$ | I | H | 0 |
| SO$_2$CF$_3$ | CH$_2$CF$_3$ | H | CF$_3$ | I | H | 1 |
| SO$_2$CF$_3$ | CH$_2$CF$_3$ | H | CF$_3$ | I | H | 2 |
| SO$_2$CF$_3$ | CH$_2$CF$_3$ | H | CF$_3$ | CN | H | 0 |
| SO$_2$CF$_3$ | CH$_2$CF$_3$ | H | CF$_3$ | CN | H | 1 |
| SO$_2$CF$_3$ | CH$_2$CF$_3$ | H | CF$_3$ | CN | H | 2 |
TABLE 2
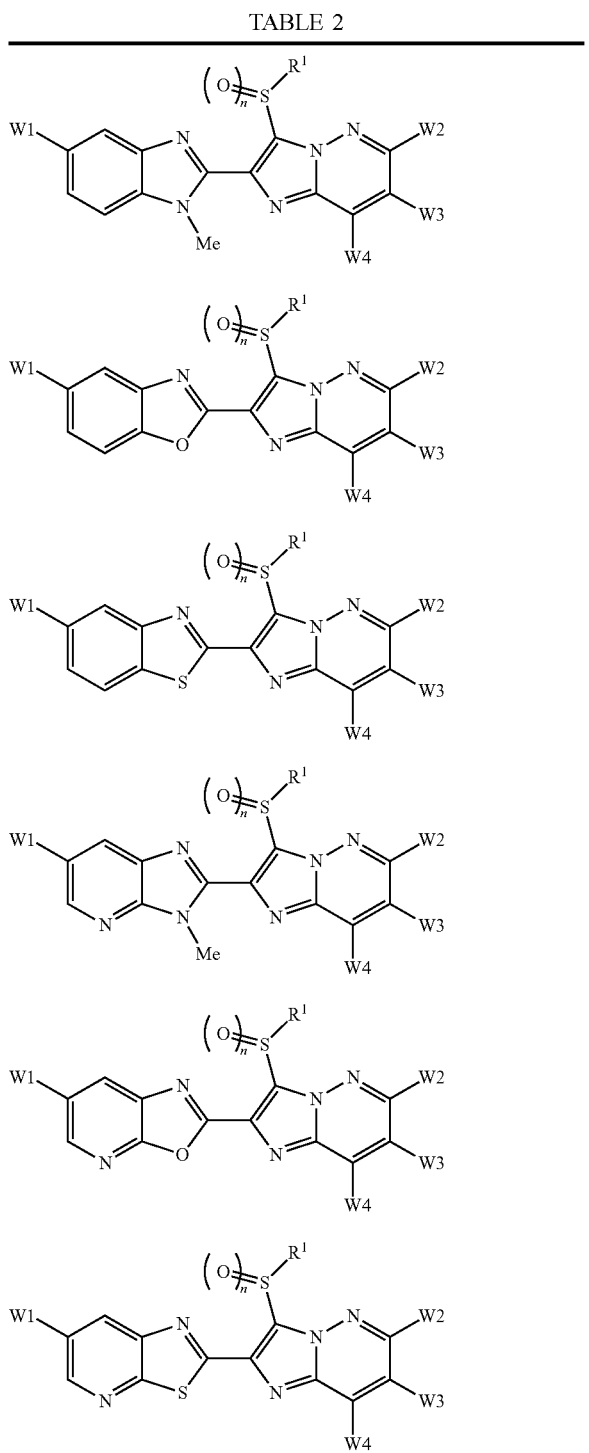
TABLE 2-continued
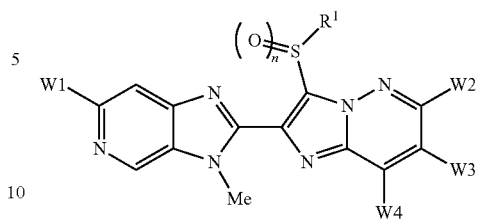
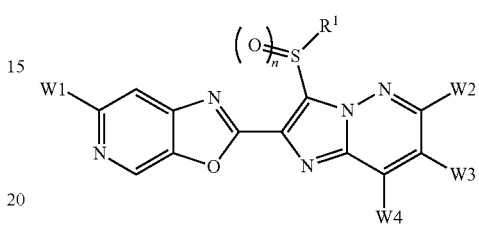
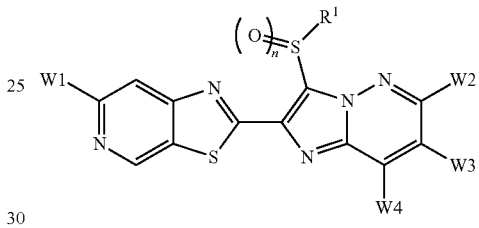
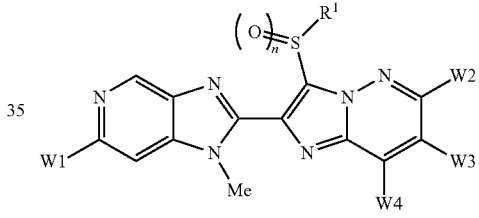
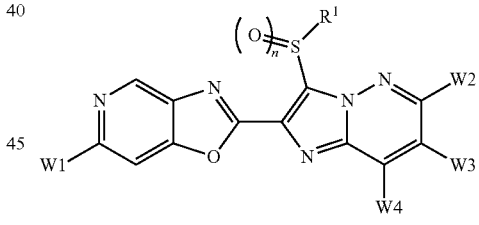
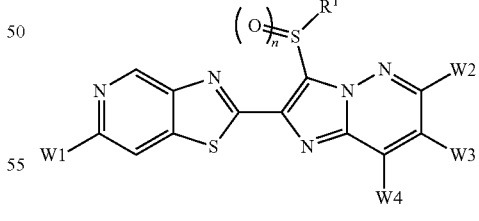
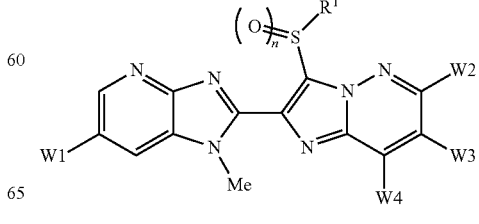

TABLE 2-continued
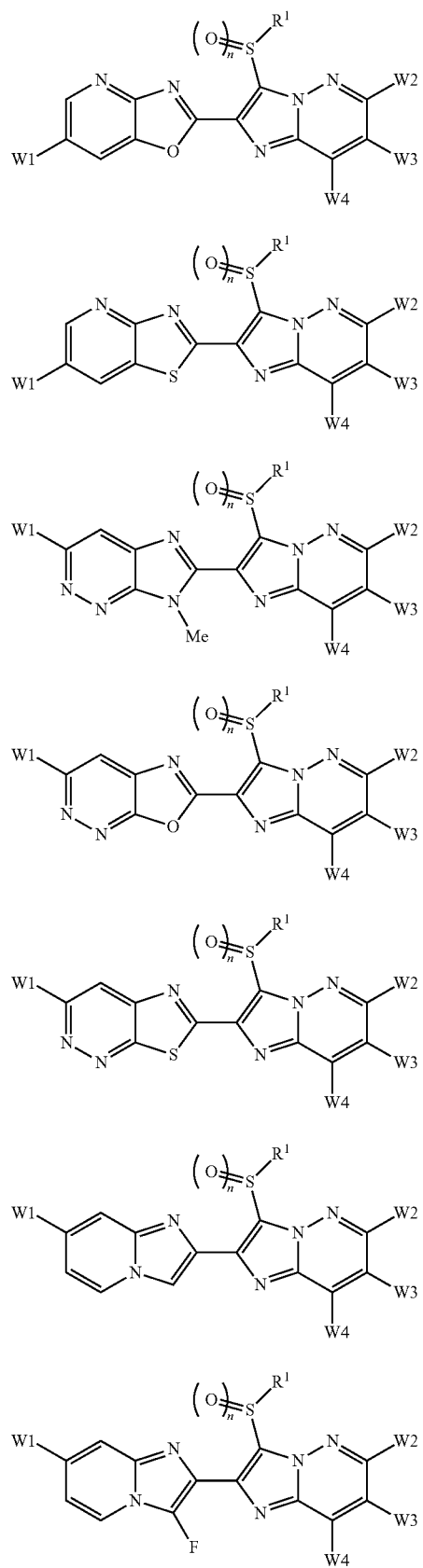
TABLE 2-continued
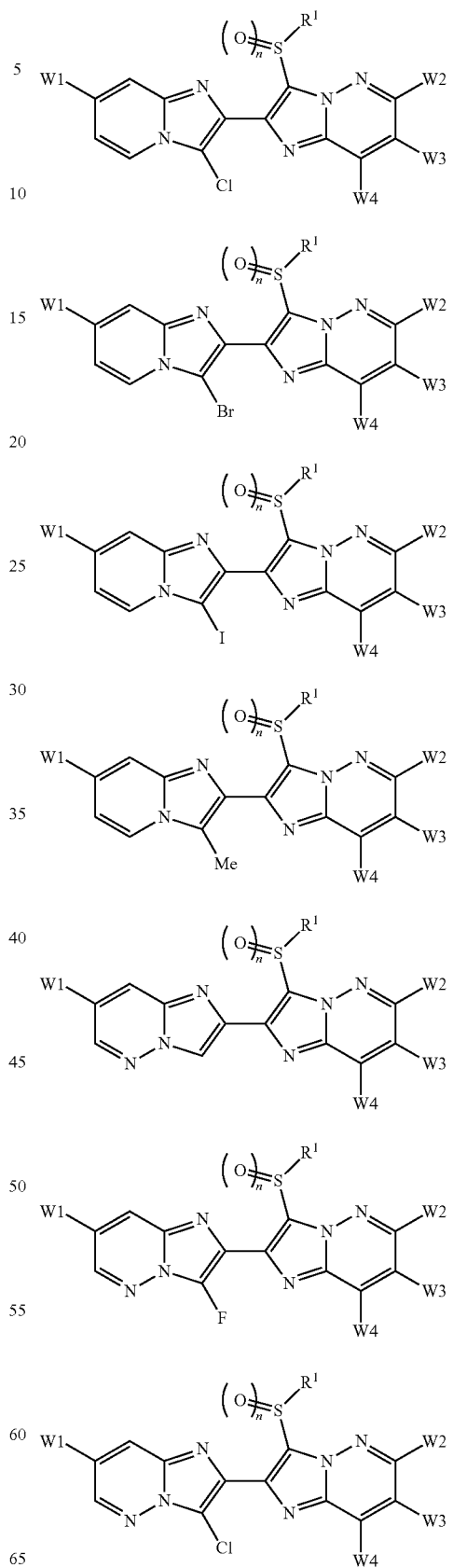

TABLE 2-continued
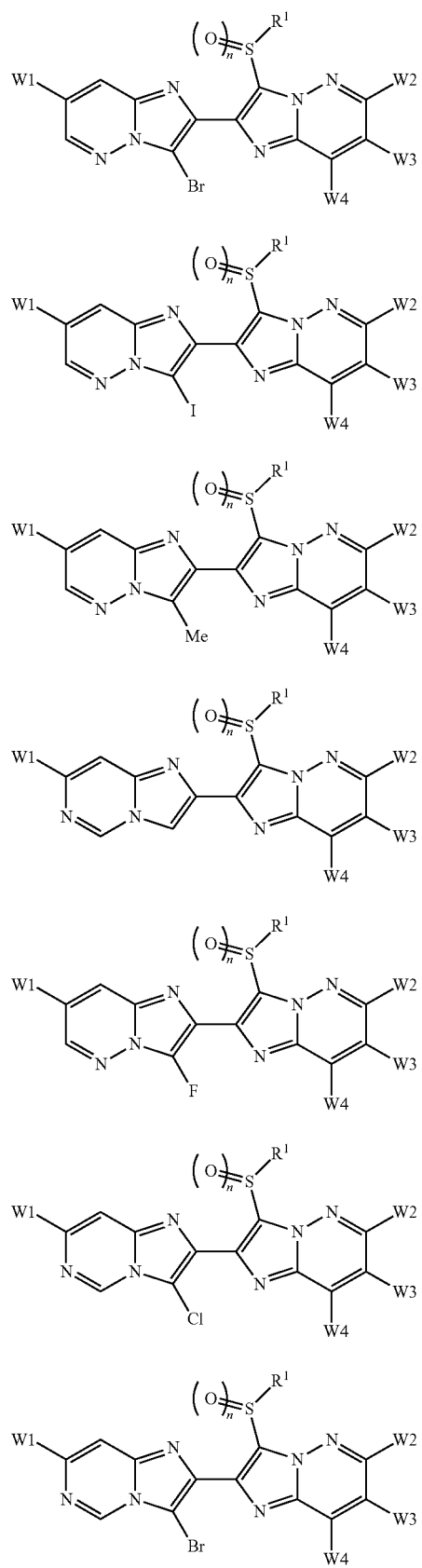
TABLE 2-continued
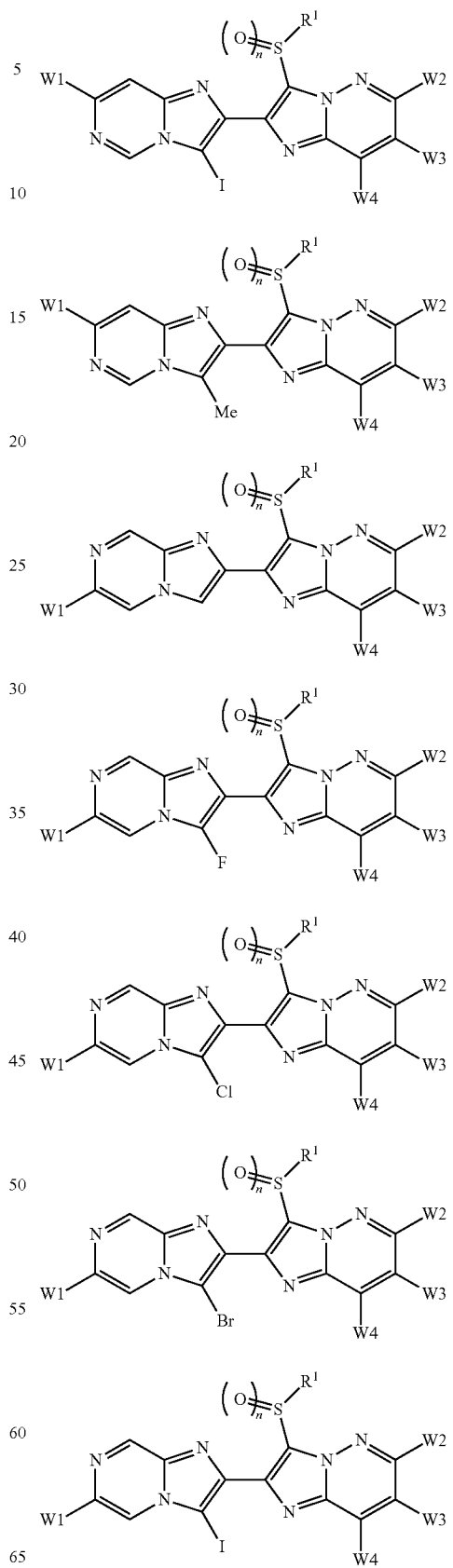

TABLE 2-continued
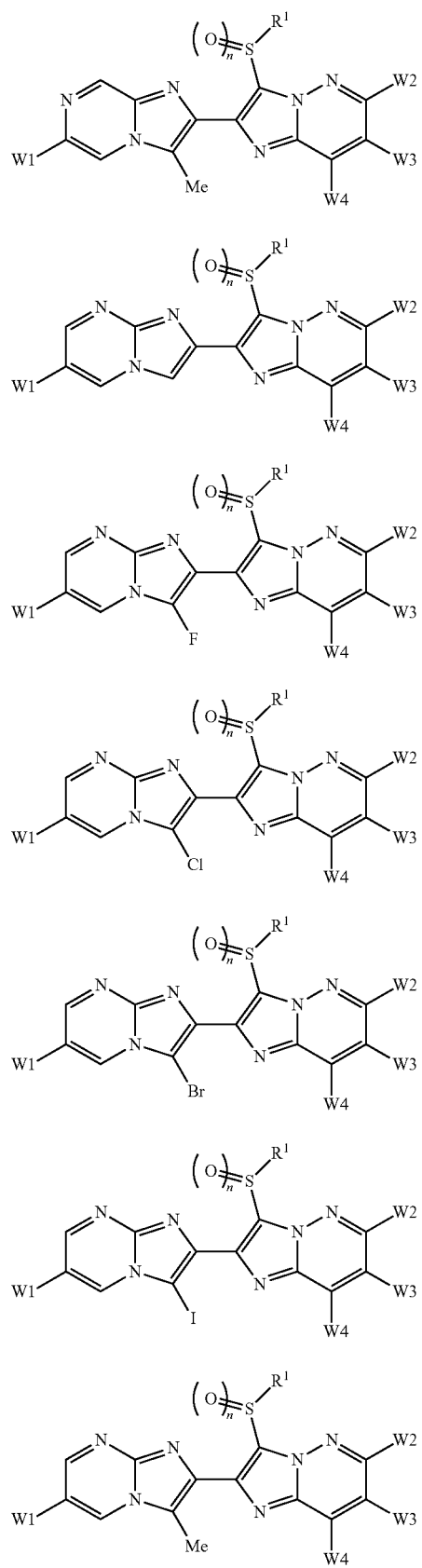
TABLE 2-continued
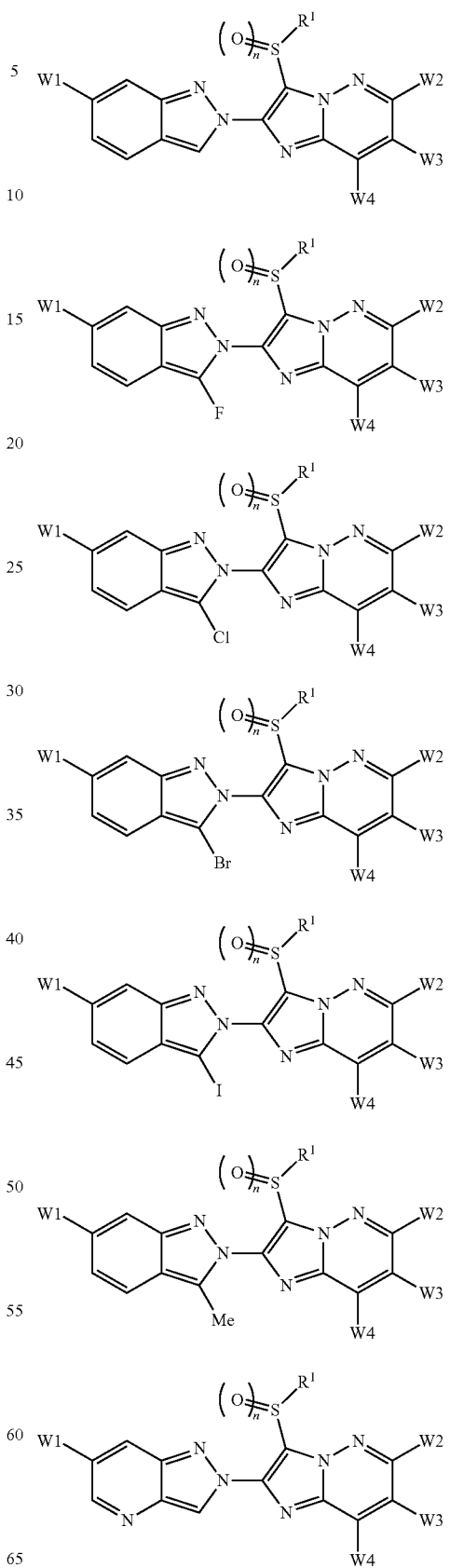

TABLE 2-continued
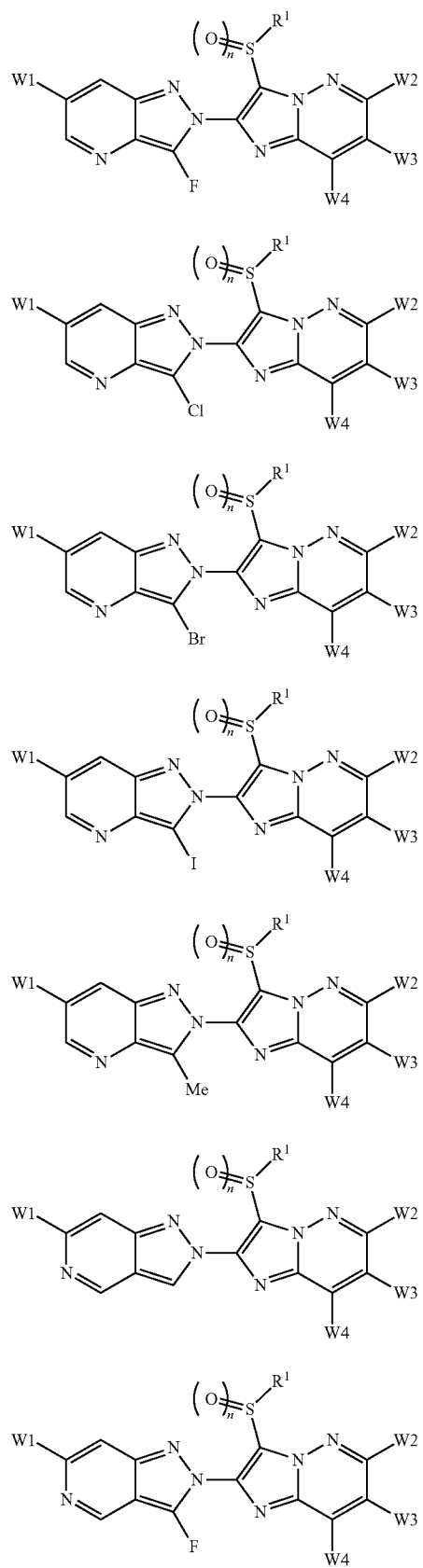
TABLE 2-continued
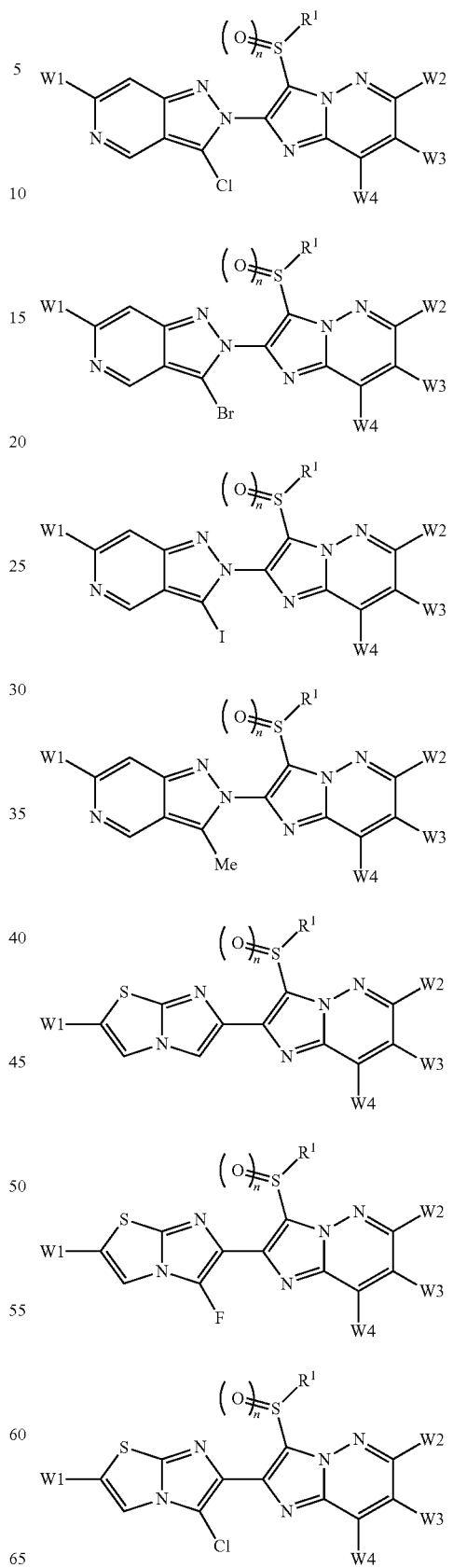

TABLE 2-continued
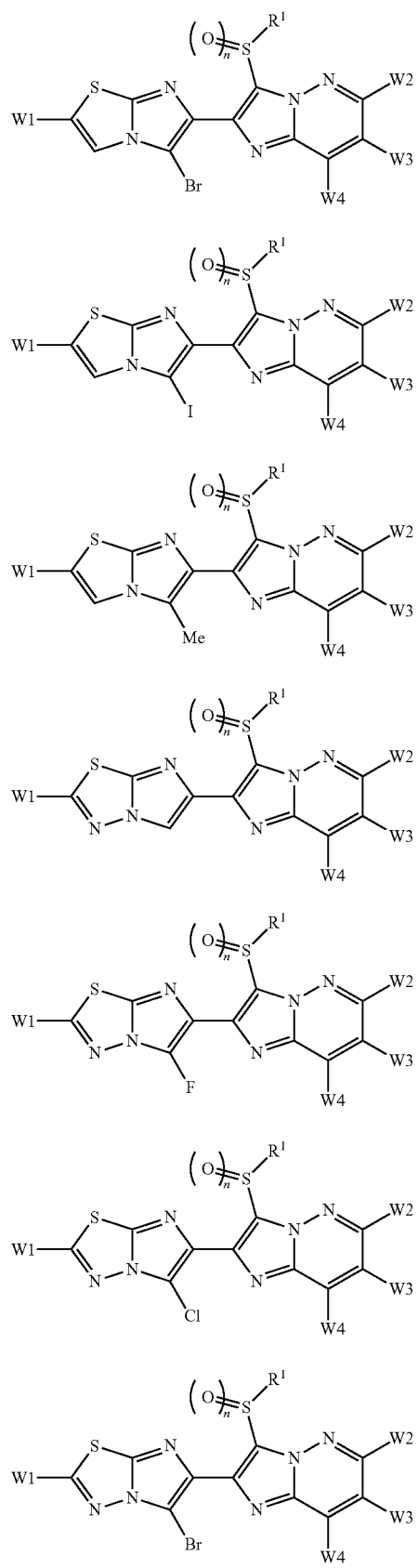
TABLE 2-continued
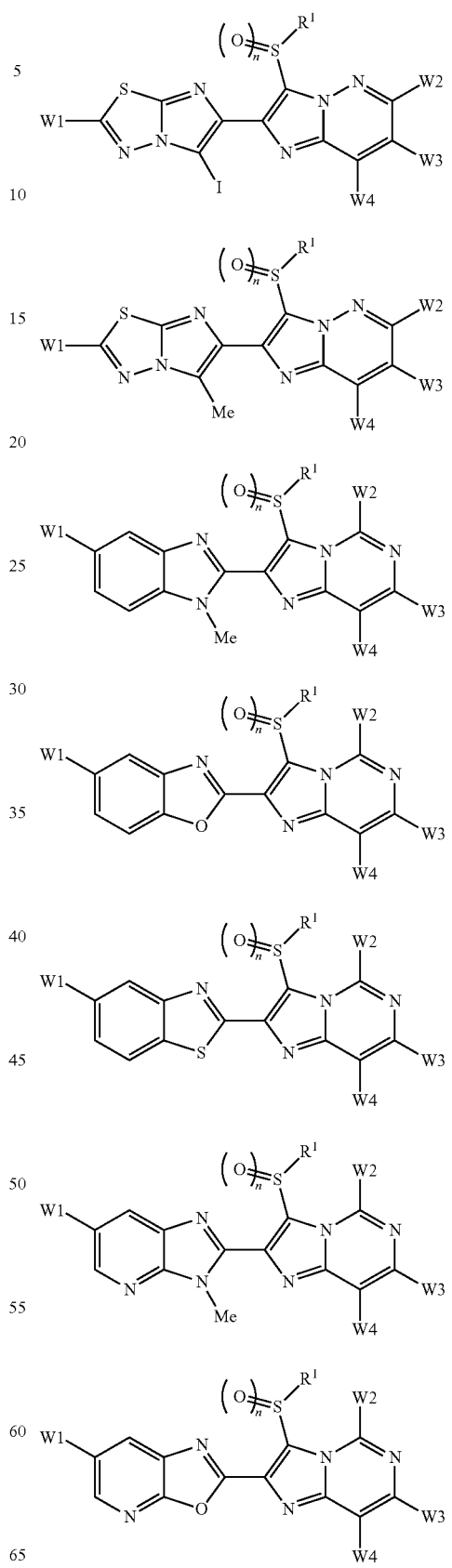

TABLE 2-continued
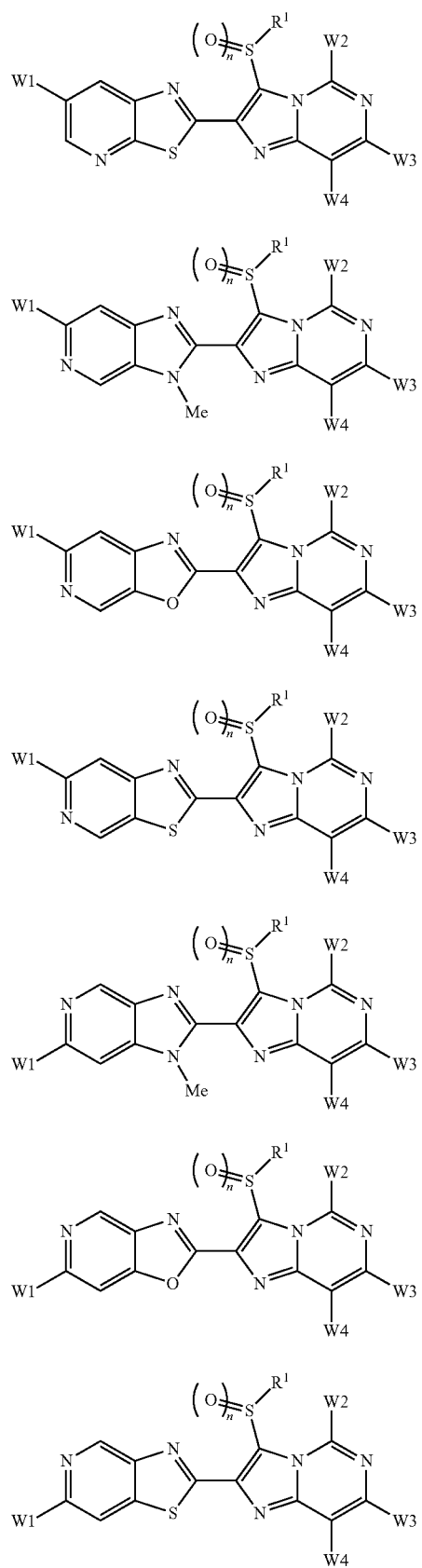
TABLE 2-continued
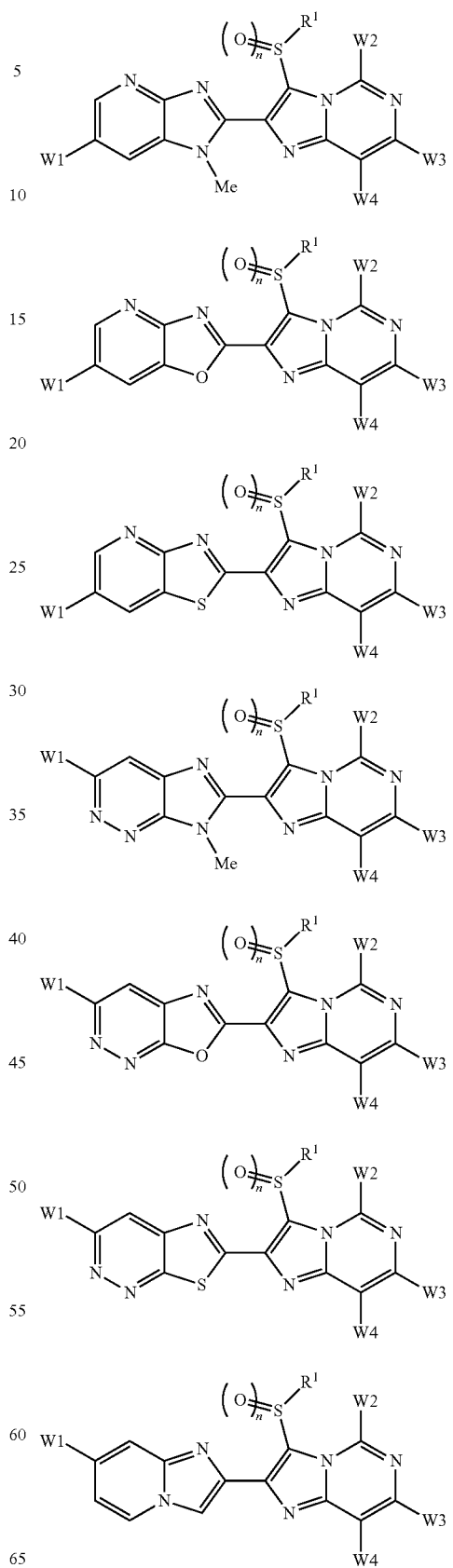

TABLE 2-continued
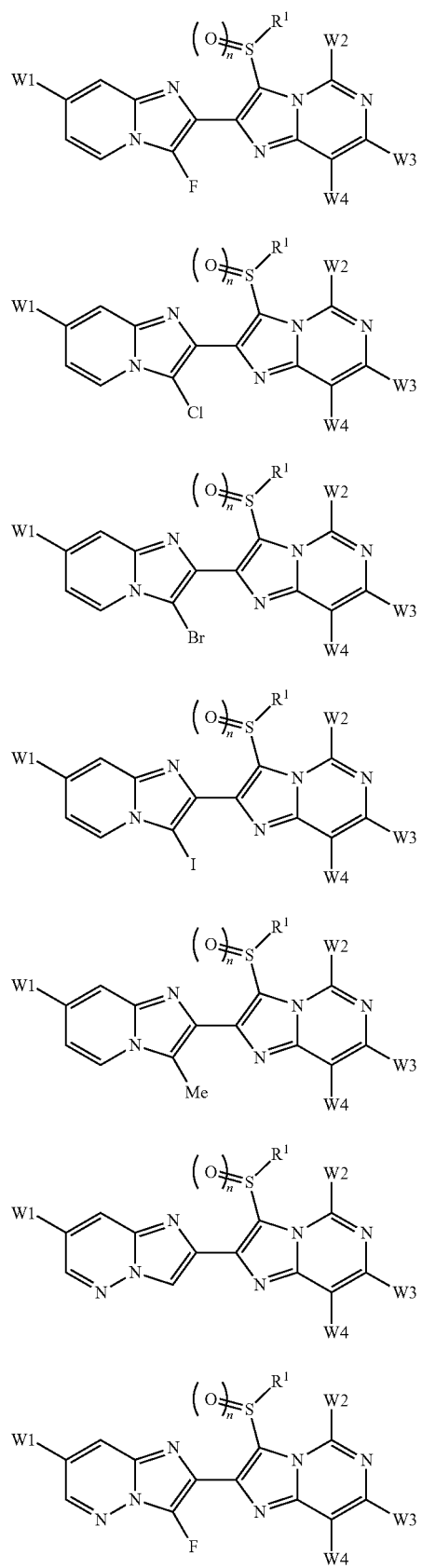
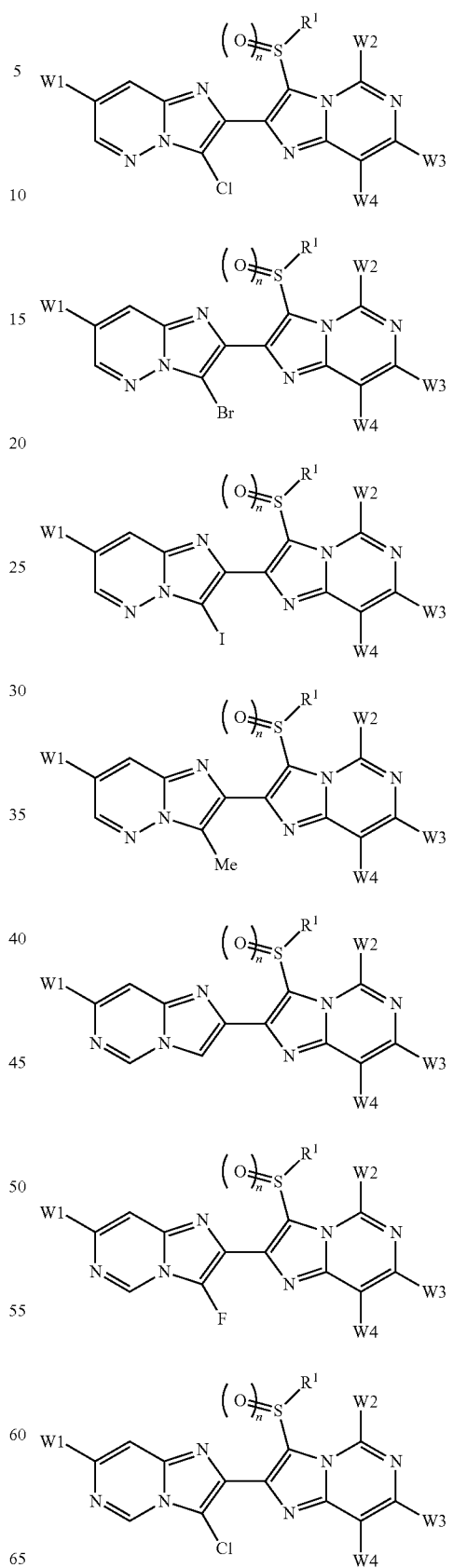

TABLE 2-continued
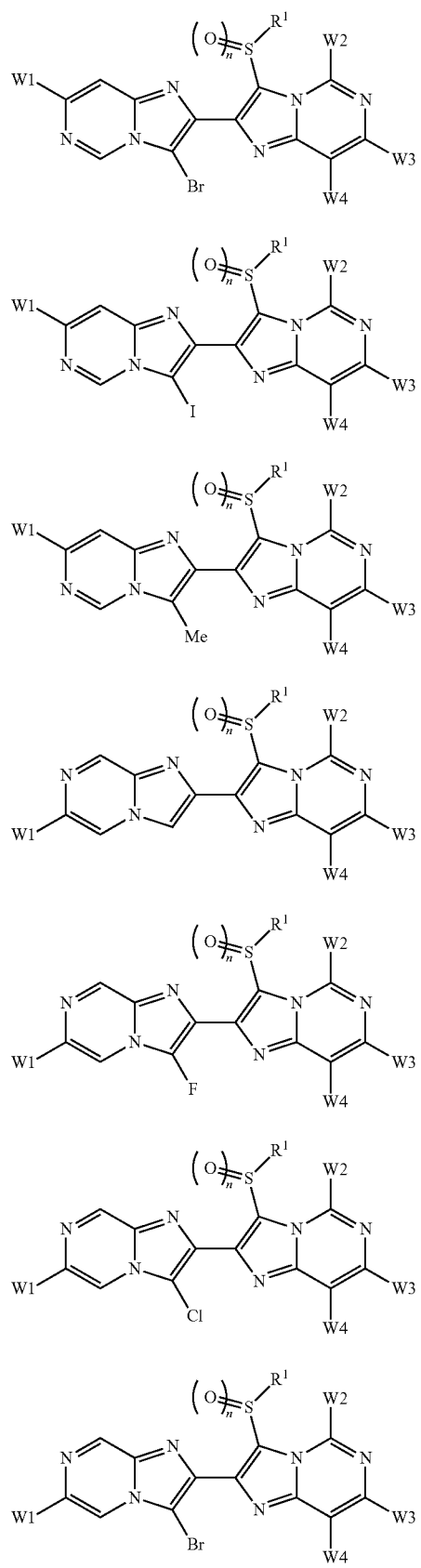
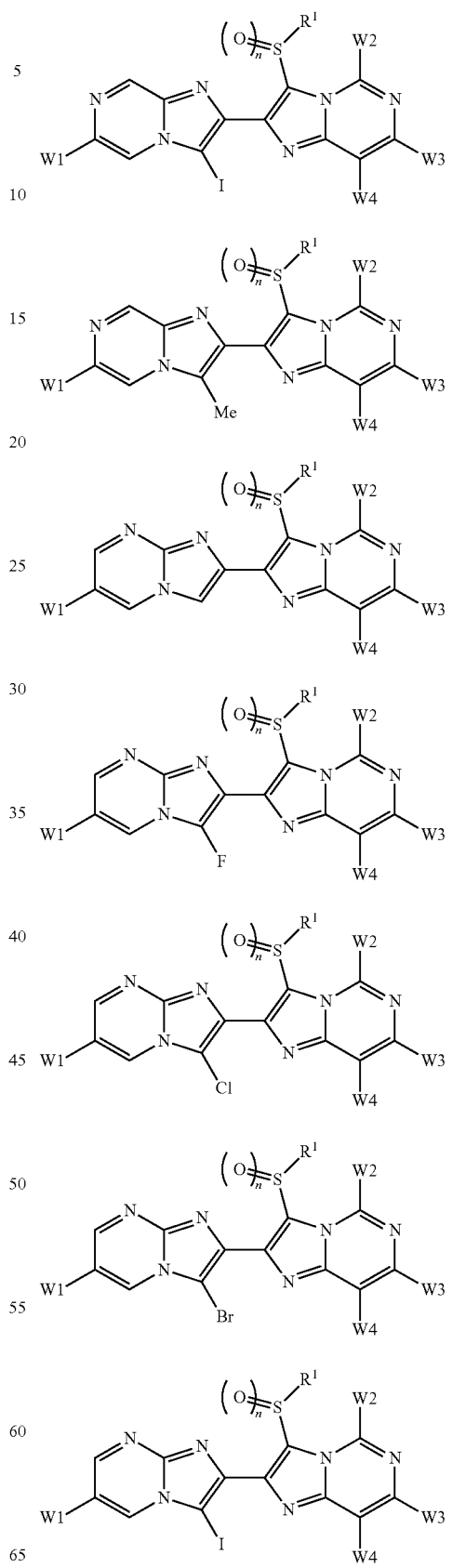

TABLE 2-continued
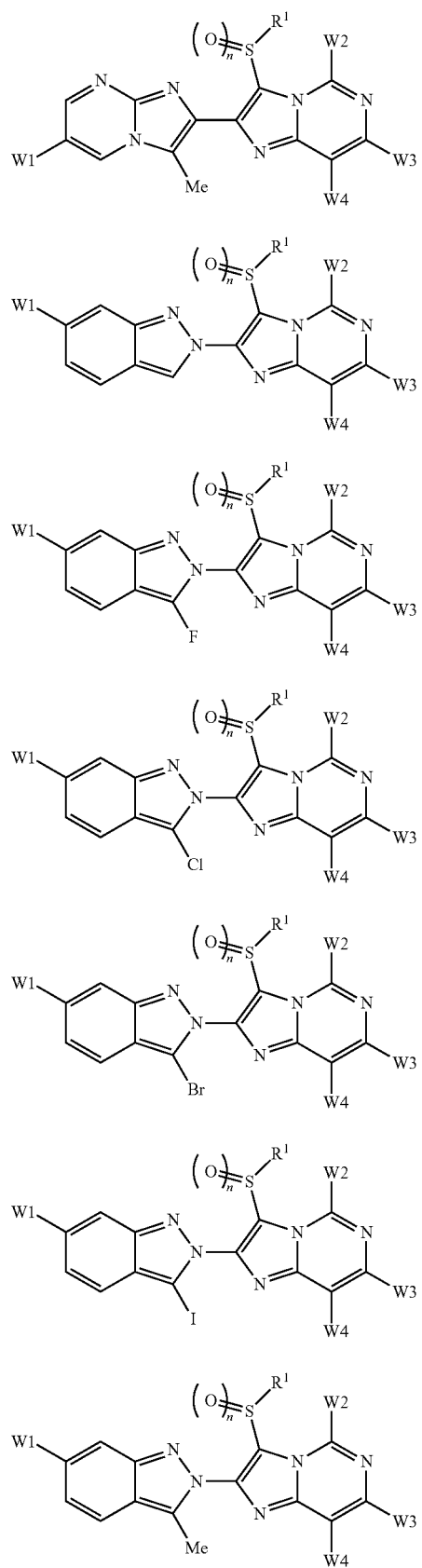
TABLE 2-continued
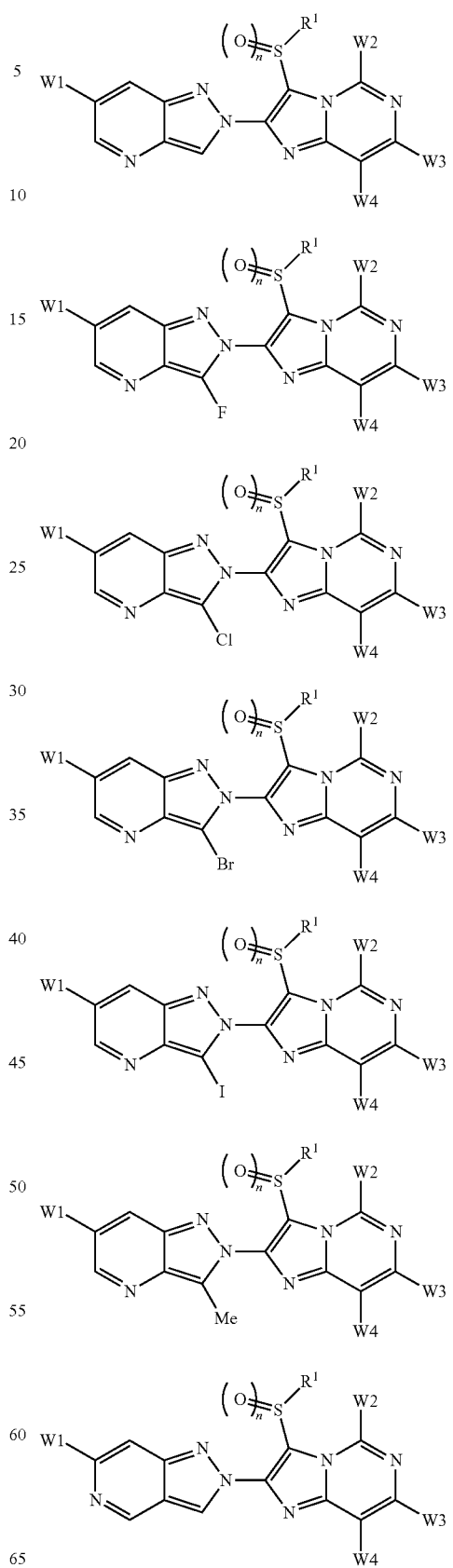

TABLE 2-continued
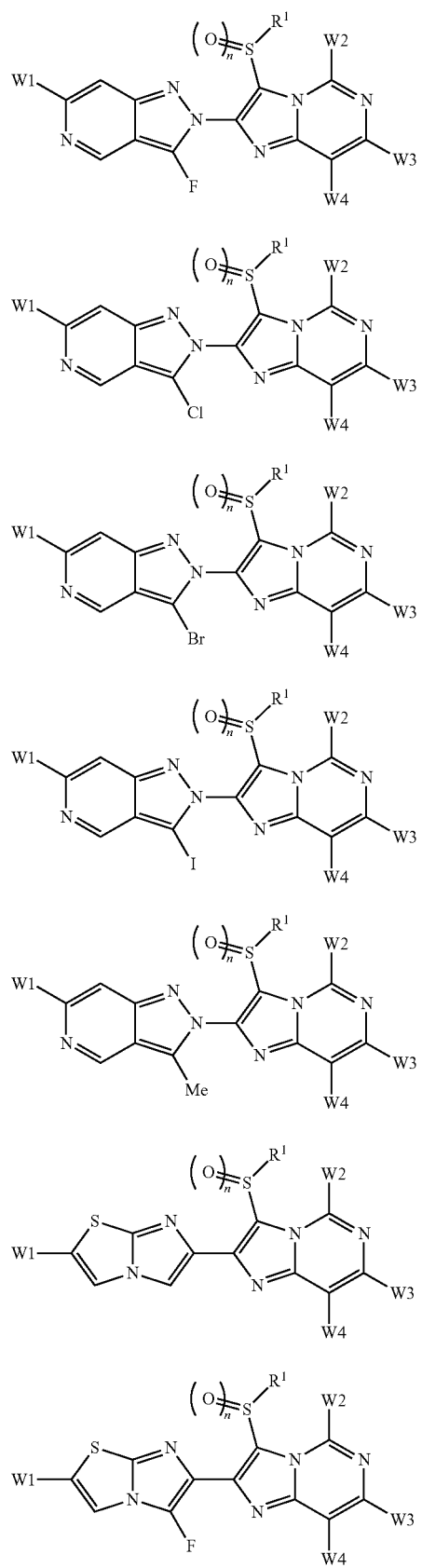
TABLE 2-continued
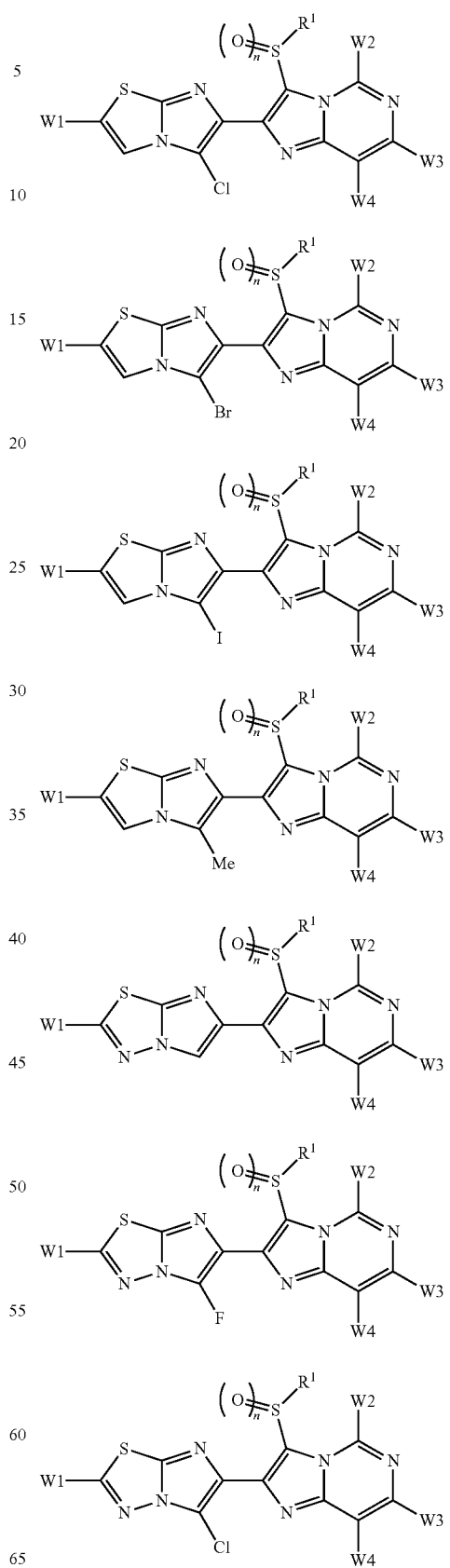

TABLE 2-continued
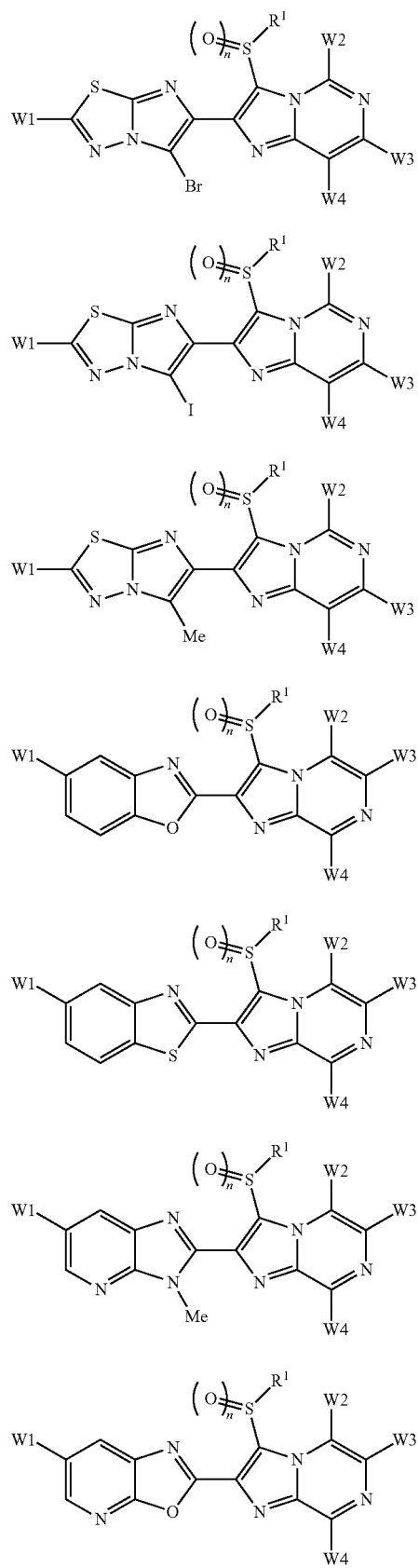
TABLE 2-continued
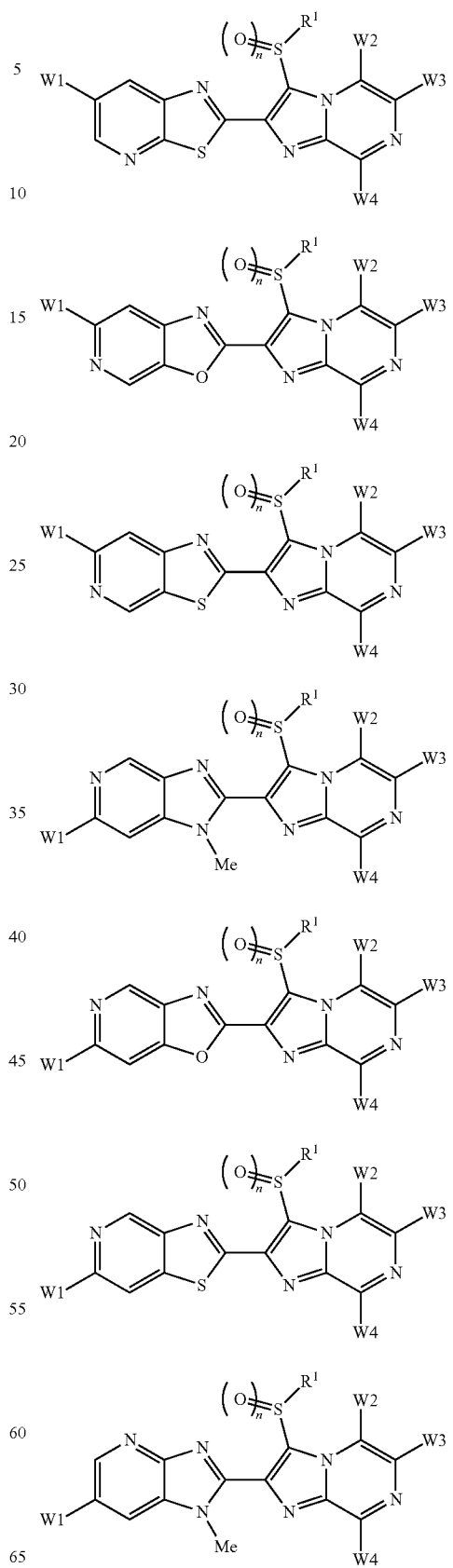

TABLE 2-continued
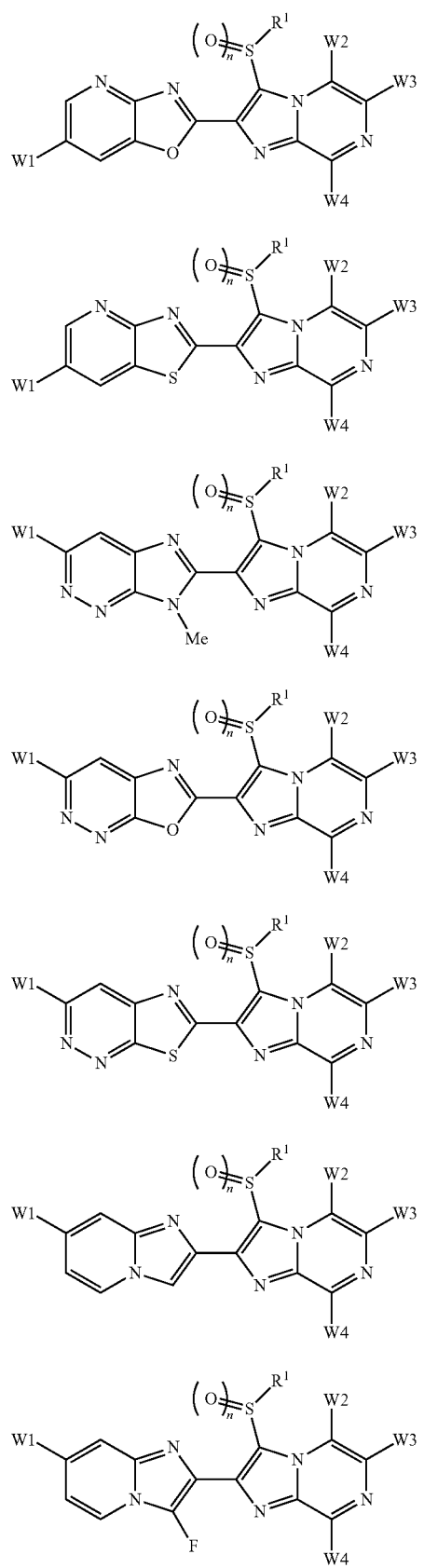
TABLE 2-continued
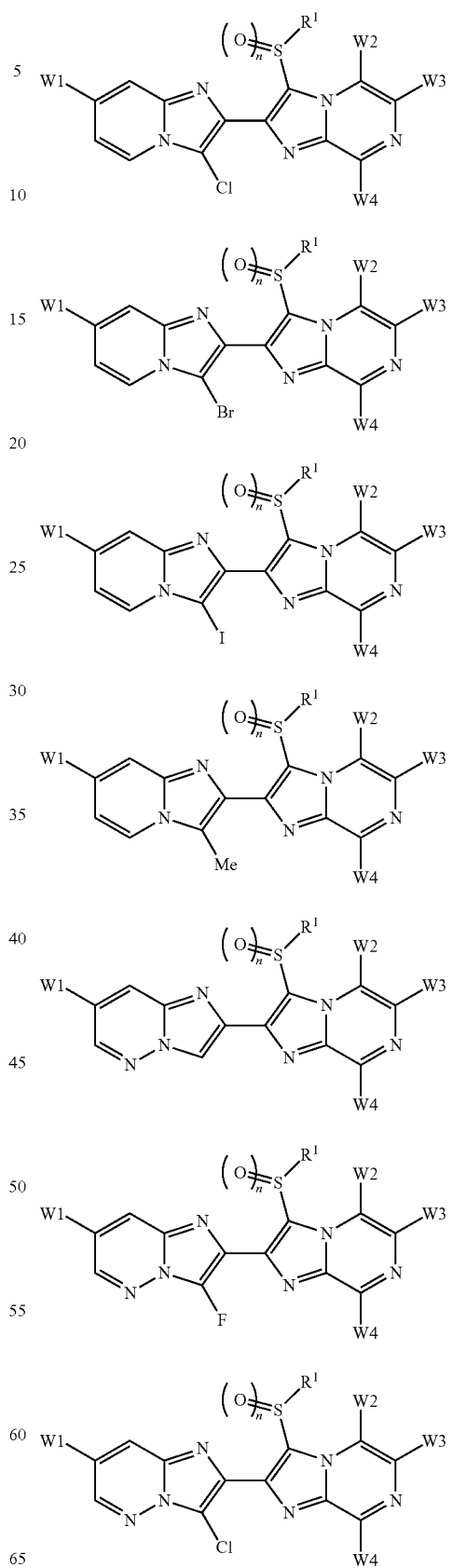

TABLE 2-continued
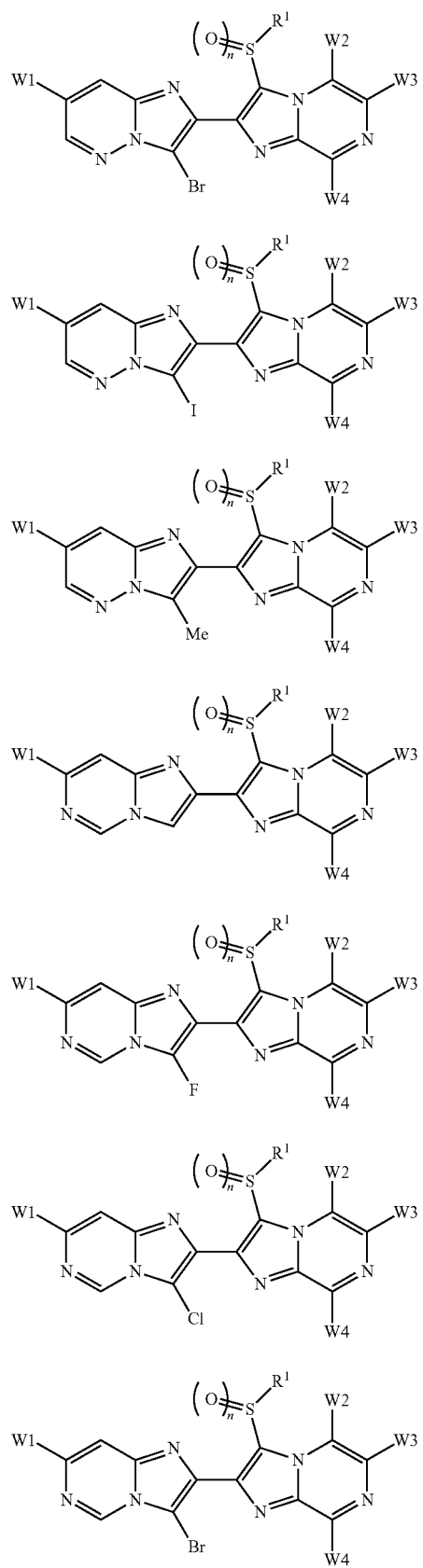
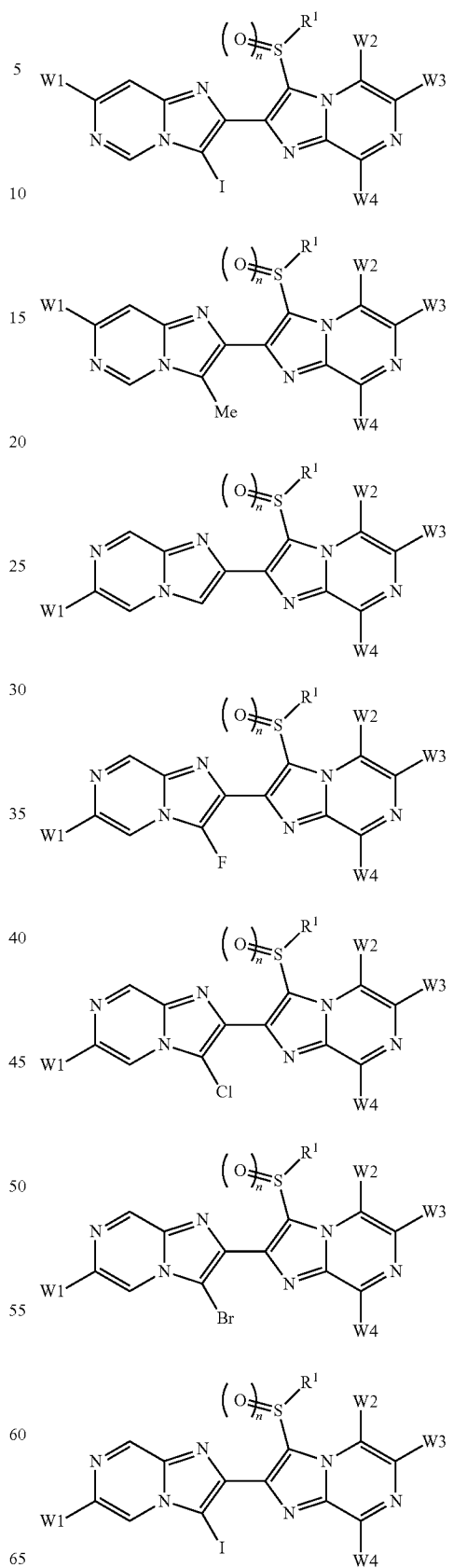

TABLE 2-continued
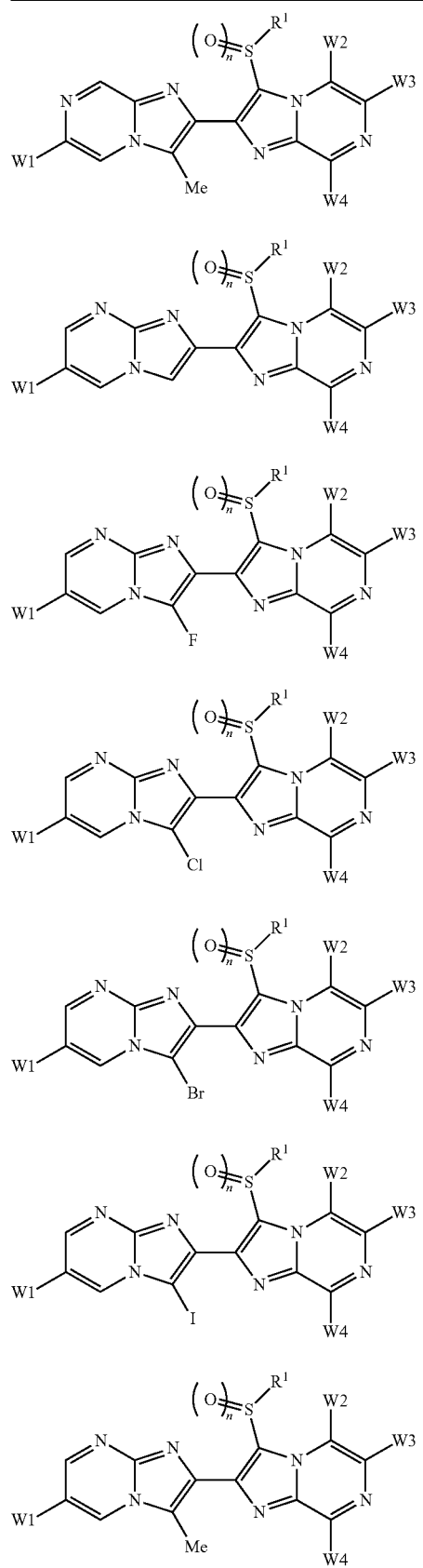
TABLE 2-continued
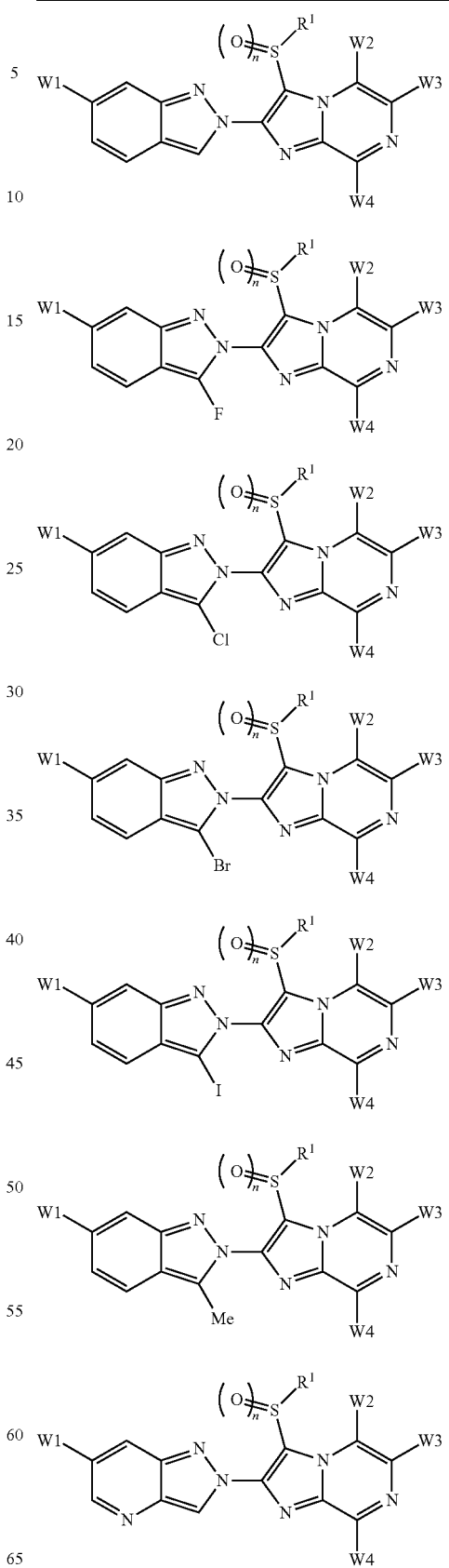

TABLE 2-continued
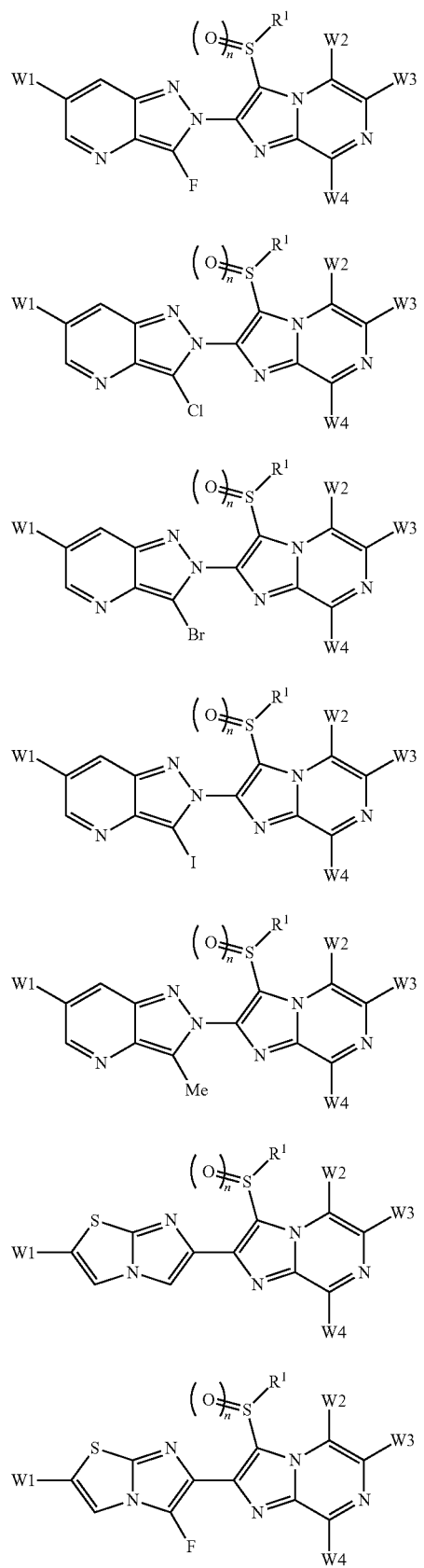
TABLE 2-continued
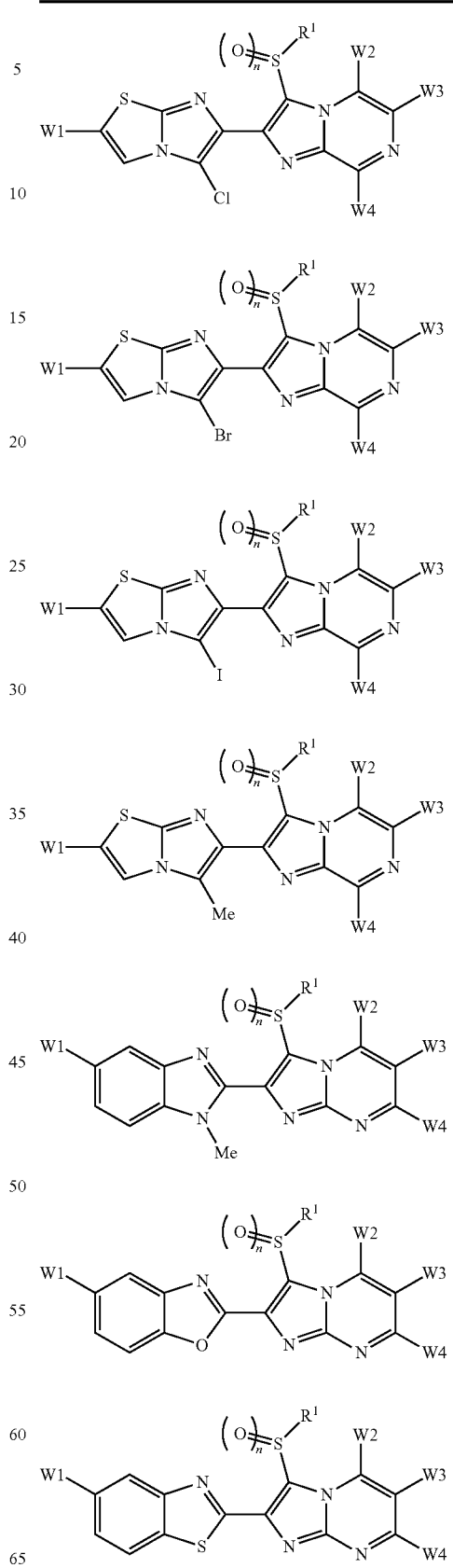

TABLE 2-continued
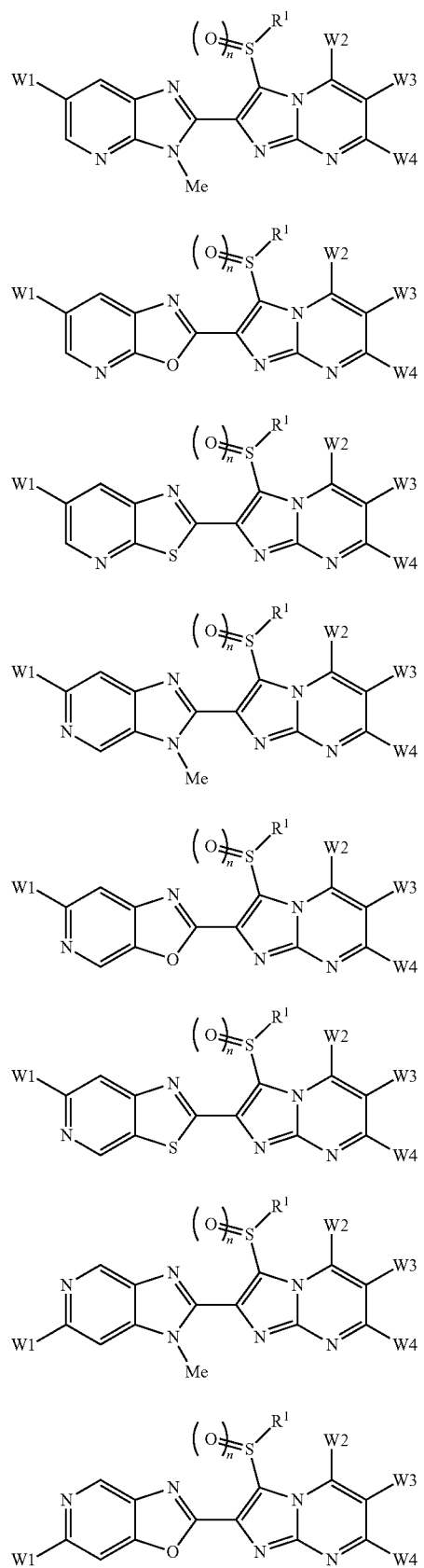
TABLE 2-continued
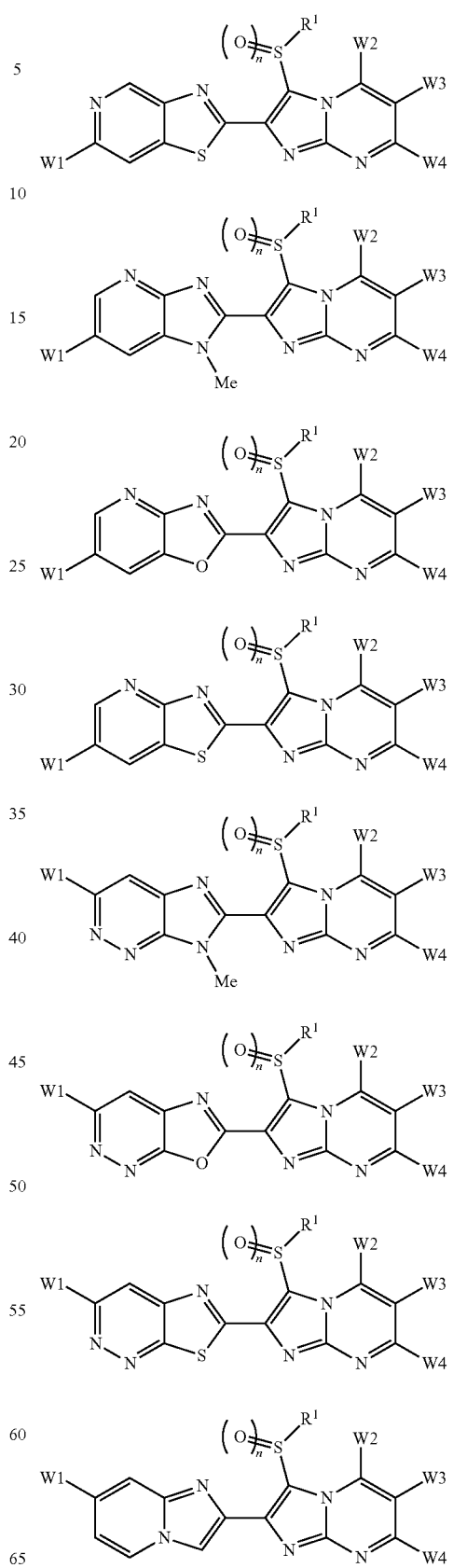

TABLE 2-continued
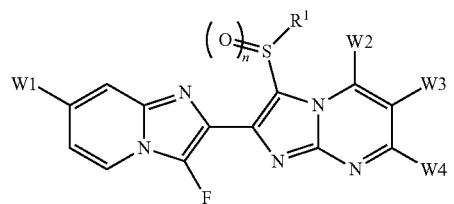
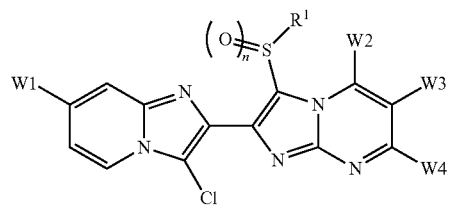
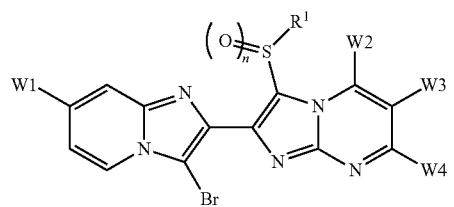
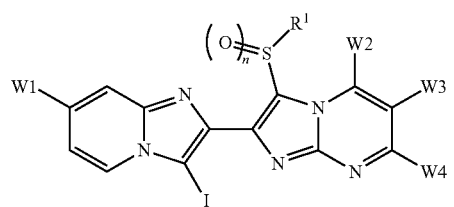
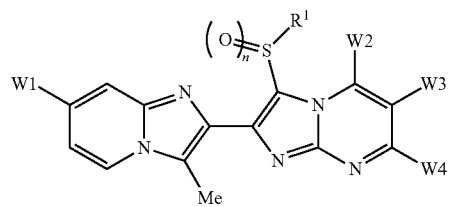
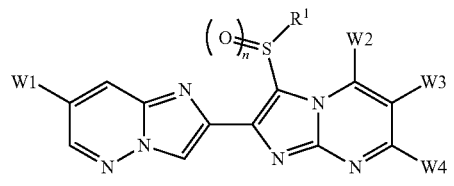
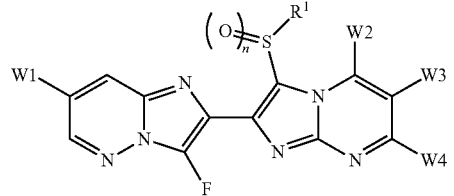
TABLE 2-continued
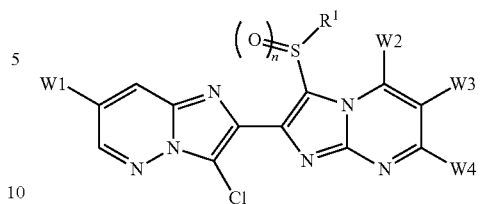
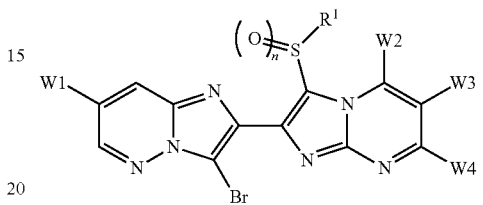
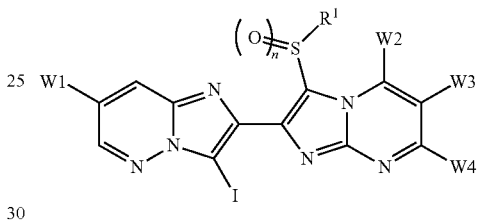
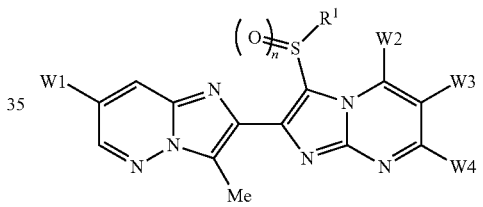
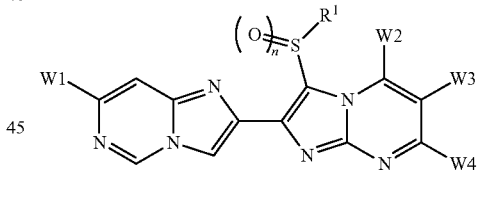
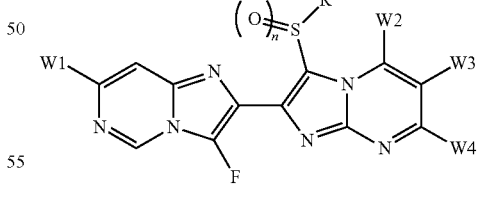
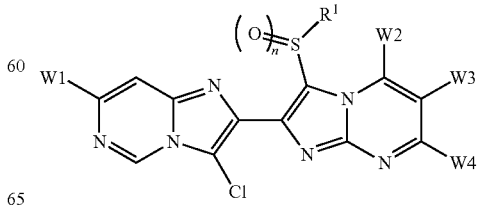

TABLE 2-continued
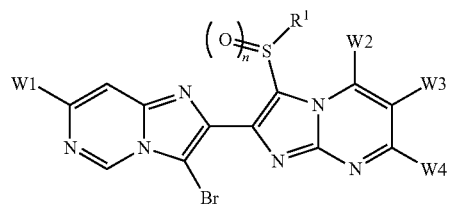
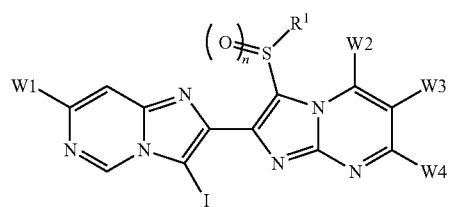
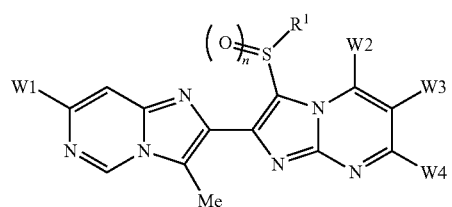
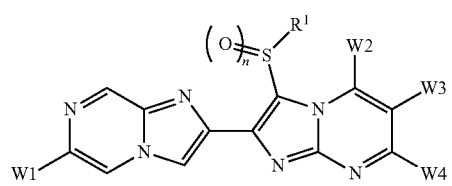
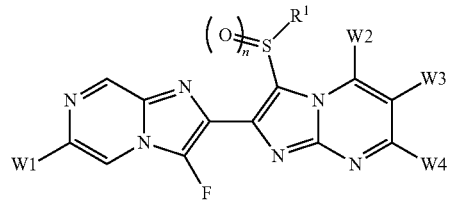
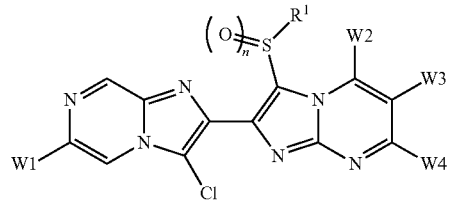
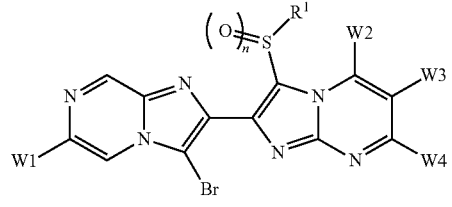
TABLE 2-continued
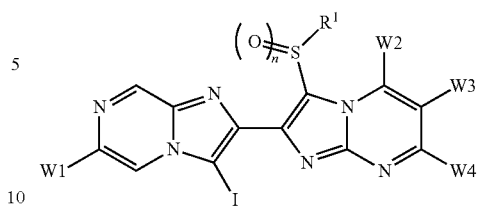
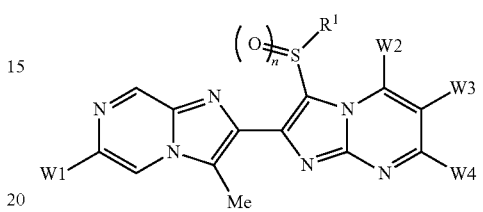
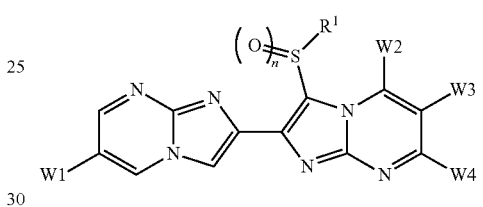
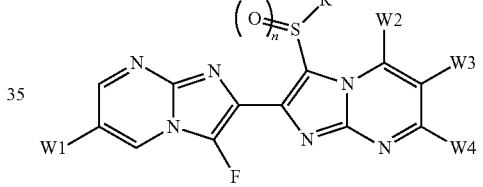
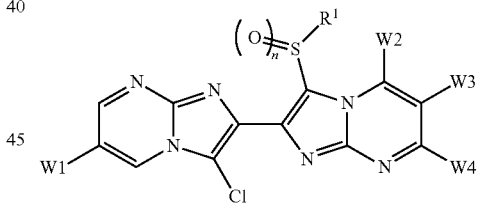
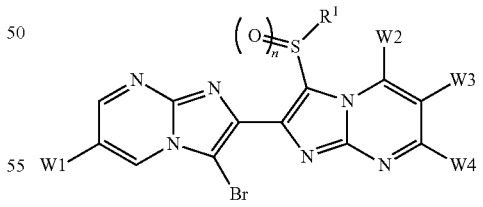
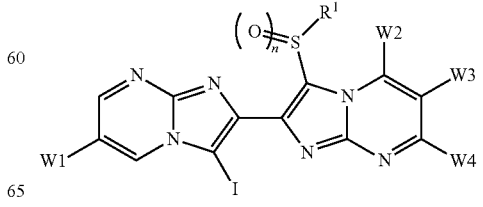

TABLE 2-continued
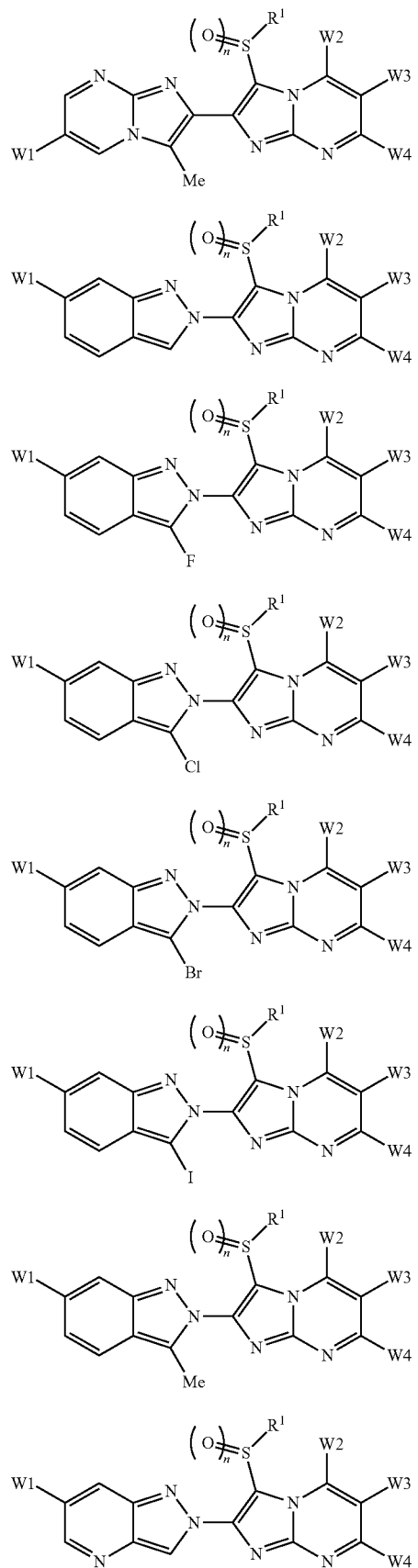
TABLE 2-continued
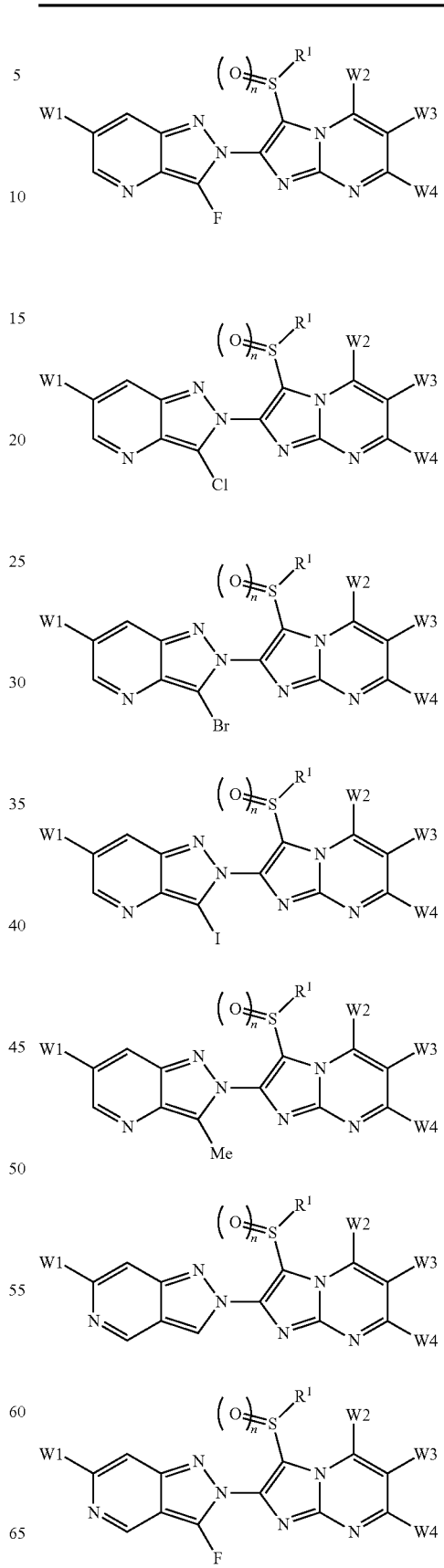

TABLE 2-continued
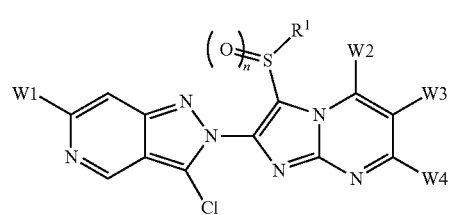
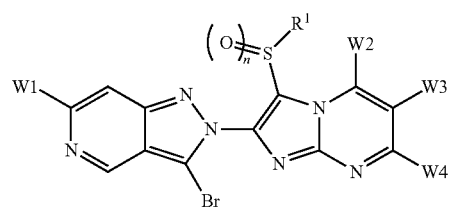
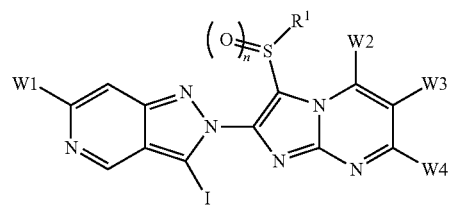
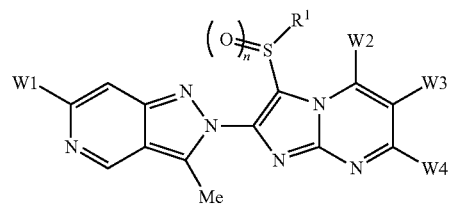
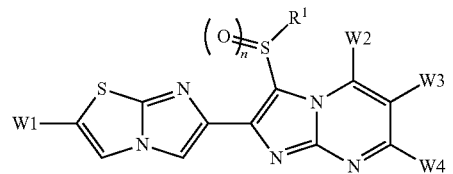
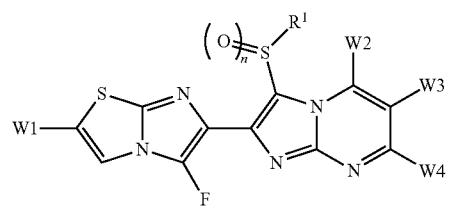
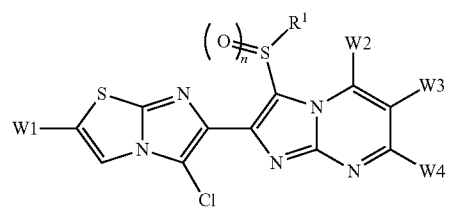
TABLE 2-continued
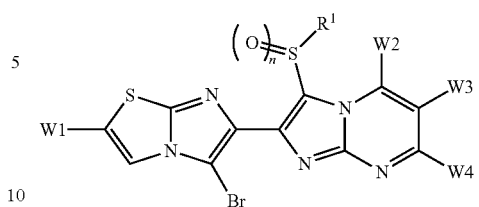
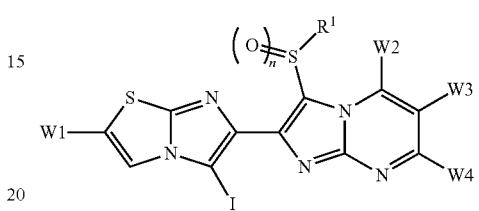
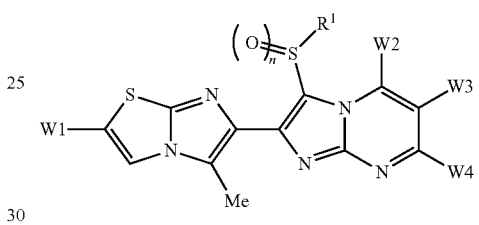
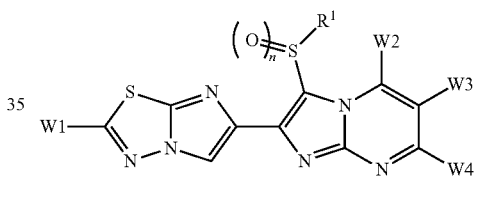
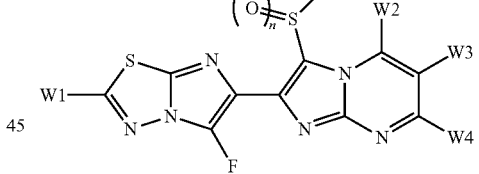
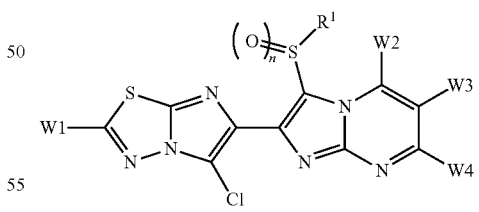
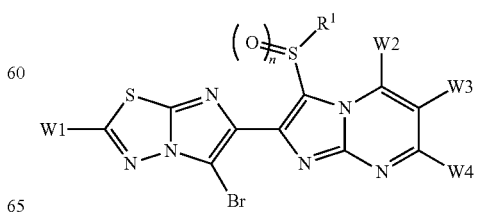

TABLE 2-continued

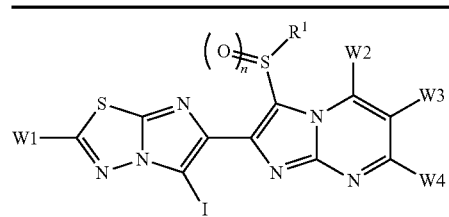

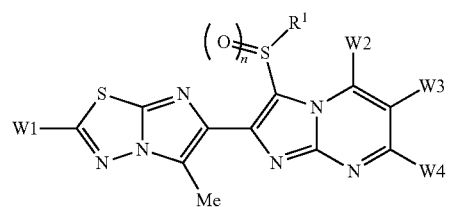

| W1 | R¹ | W2 | W3 | W4 | n |
|---|---|---|---|---|---|
| $CF_3$ | Et | H | H | H | 0 |
| $CF_3$ | Et | H | H | H | 1 |
| $CF_3$ | Et | H | H | H | 2 |
| $CF_3$ | Et | F | H | H | 0 |
| $CF_3$ | Et | F | H | H | 1 |
| $CF_3$ | Et | F | H | H | 2 |
| $CF_3$ | Et | Cl | H | H | 0 |
| $CF_3$ | Et | Cl | H | H | 1 |
| $CF_3$ | Et | Cl | H | H | 2 |
| $CF_3$ | Et | Br | H | H | 0 |
| $CF_3$ | Et | Br | H | H | 1 |
| $CF_3$ | Et | Br | H | H | 2 |
| $CF_3$ | Et | I | H | H | 0 |
| $CF_3$ | Et | I | H | H | 1 |
| $CF_3$ | Et | I | H | H | 2 |
| $CF_3$ | Et | Me | H | H | 0 |
| $CF_3$ | Et | Me | H | H | 1 |
| $CF_3$ | Et | Me | H | H | 2 |
| $CF_3$ | Et | $CF_3$ | H | H | 0 |
| $CF_3$ | Et | $CF_3$ | H | H | 1 |
| $CF_3$ | Et | $CF_3$ | H | H | 2 |
| $CF_3$ | Et | $CF_2CF_3$ | H | H | 0 |
| $CF_3$ | Et | $CF_2CF_3$ | H | H | 1 |
| $CF_3$ | Et | $CF_2CF_3$ | H | H | 2 |
| $CF_3$ | Et | $CF(CF_3)_2$ | H | H | 0 |
| $CF_3$ | Et | $CF(CF_3)_2$ | H | H | 1 |
| $CF_3$ | Et | $CF(CF_3)_2$ | H | H | 2 |
| $CF_3$ | Et | SMe | H | H | 0 |
| $CF_3$ | Et | SMe | H | H | 1 |
| $CF_3$ | Et | SMe | H | H | 2 |
| $CF_3$ | Et | SOMe | H | H | 0 |
| $CF_3$ | Et | SOMe | H | H | 1 |
| $CF_3$ | Et | SOMe | H | H | 2 |
| $CF_3$ | Et | $SO_2Me$ | H | H | 0 |
| $CF_3$ | Et | $SO_2Me$ | H | H | 1 |
| $CF_3$ | Et | $SO_2Me$ | H | H | 2 |
| $CF_3$ | Et | OMe | H | H | 0 |
| $CF_3$ | Et | OMe | H | H | 1 |
| $CF_3$ | Et | OMe | H | H | 2 |
| $CF_3$ | Et | $OCF_3$ | H | H | 0 |
| $CF_3$ | Et | $OCF_3$ | H | H | 1 |
| $CF_3$ | Et | $OCF_3$ | H | H | 2 |
| $CF_3$ | Et | $NO_2$ | H | H | 0 |
| $CF_3$ | Et | $NO_2$ | H | H | 1 |
| $CF_3$ | Et | $NO_2$ | H | H | 2 |
| $CF_3$ | Et | CN | H | H | 0 |
| $CF_3$ | Et | CN | H | H | 1 |
| $CF_3$ | Et | CN | H | H | 2 |
| $CF_3$ | Et | H | F | H | 0 |
| $CF_3$ | Et | H | F | H | 1 |
| $CF_3$ | Et | H | F | H | 2 |
| $CF_3$ | Et | H | Cl | H | 0 |
| $CF_3$ | Et | H | Cl | H | 1 |
| $CF_3$ | Et | H | Cl | H | 2 |
| $CF_3$ | Et | H | Br | H | 0 |
| $CF_3$ | Et | H | Br | H | 1 |
| $CF_3$ | Et | H | Br | H | 2 |
| $CF_3$ | Et | H | I | H | 0 |
| $CF_3$ | Et | H | I | H | 1 |
| $CF_3$ | Et | H | I | H | 2 |
| $CF_3$ | Et | H | Me | H | 0 |
| $CF_3$ | Et | H | Me | H | 1 |
| $CF_3$ | Et | H | Me | H | 2 |
| $CF_3$ | Et | H | $CF_3$ | H | 0 |
| $CF_3$ | Et | H | $CF_3$ | H | 1 |
| $CF_3$ | Et | H | $CF_3$ | H | 2 |
| $CF_3$ | Et | H | $CF_2CF_3$ | H | 0 |
| $CF_3$ | Et | H | $CF_2CF_3$ | H | 1 |
| $CF_3$ | Et | H | $CF_2CF_3$ | H | 2 |
| $CF_3$ | Et | H | $CF(CF_3)_2$ | H | 0 |
| $CF_3$ | Et | H | $CF(CF_3)_2$ | H | 1 |
| $CF_3$ | Et | H | $CF(CF_3)_2$ | H | 2 |
| $CF_3$ | Et | H | SMe | H | 0 |
| $CF_3$ | Et | H | SMe | H | 1 |
| $CF_3$ | Et | H | SMe | H | 2 |
| $CF_3$ | Et | H | SOMe | H | 0 |
| $CF_3$ | Et | H | SOMe | H | 1 |
| $CF_3$ | Et | H | SOMe | H | 2 |
| $CF_3$ | Et | H | $SO_2Me$ | H | 0 |
| $CF_3$ | Et | H | $SO_2Me$ | H | 1 |
| $CF_3$ | Et | H | $SO_2Me$ | H | 2 |
| $CF_3$ | Et | H | OMe | H | 0 |
| $CF_3$ | Et | H | OMe | H | 1 |
| $CF_3$ | Et | H | OMe | H | 2 |
| $CF_3$ | Et | H | $OCF_3$ | H | 0 |
| $CF_3$ | Et | H | $OCF_3$ | H | 1 |
| $CF_3$ | Et | H | $OCF_3$ | H | 2 |
| $CF_3$ | Et | H | $NO_2$ | H | 0 |
| $CF_3$ | Et | H | $NO_2$ | H | 1 |
| $CF_3$ | Et | H | $NO_2$ | H | 2 |
| $CF_3$ | Et | H | CN | H | 0 |
| $CF_3$ | Et | H | CN | H | 1 |
| $CF_3$ | Et | H | CN | H | 2 |
| $CF_3$ | Et | H | H | F | 0 |
| $CF_3$ | Et | H | H | F | 1 |
| $CF_3$ | Et | H | H | F | 2 |
| $CF_3$ | Et | H | H | Cl | 0 |
| $CF_3$ | Et | H | H | Cl | 1 |
| $CF_3$ | Et | H | H | Cl | 2 |
| $CF_3$ | Et | H | H | Br | 0 |
| $CF_3$ | Et | H | H | Br | 1 |
| $CF_3$ | Et | H | H | Br | 2 |
| $CF_3$ | Et | H | H | I | 0 |
| $CF_3$ | Et | H | H | I | 1 |
| $CF_3$ | Et | H | H | I | 2 |
| $CF_3$ | Et | H | H | Me | 0 |
| $CF_3$ | Et | H | H | Me | 1 |
| $CF_3$ | Et | H | H | Me | 2 |
| $CF_3$ | Et | H | H | $CF_3$ | 0 |
| $CF_3$ | Et | H | H | $CF_3$ | 1 |
| $CF_3$ | Et | H | H | $CF_3$ | 2 |
| $CF_3$ | Et | H | H | $CF_2CF_3$ | 0 |
| $CF_3$ | Et | H | H | $CF_2CF_3$ | 1 |
| $CF_3$ | Et | H | H | $CF_2CF_3$ | 2 |
| $CF_3$ | Et | H | H | $CF(CF_3)_2$ | 0 |
| $CF_3$ | Et | H | H | $CF(CF_3)_2$ | 1 |
| $CF_3$ | Et | H | H | $CF(CF_3)_2$ | 2 |
| $CF_3$ | Et | H | H | SMe | 0 |
| $CF_3$ | Et | H | H | SMe | 1 |
| $CF_3$ | Et | H | H | SMe | 2 |
| $CF_3$ | Et | H | H | SOMe | 0 |
| $CF_3$ | Et | H | H | SOMe | 1 |
| $CF_3$ | Et | H | H | SOMe | 2 |
| $CF_3$ | Et | H | H | $SO_2Me$ | 0 |
| $CF_3$ | Et | H | H | $SO_2Me$ | 1 |
| $CF_3$ | Et | H | H | $SO_2Me$ | 2 |
| $CF_3$ | Et | H | H | OMe | 0 |
| $CF_3$ | Et | H | H | OMe | 1 |
| $CF_3$ | Et | H | H | OMe | 2 |
| $CF_3$ | Et | H | H | $OCF_3$ | 0 |
| $CF_3$ | Et | H | H | $OCF_3$ | 1 |
| $CF_3$ | Et | H | H | $OCF_3$ | 2 |
| $CF_3$ | Et | H | H | $NO_2$ | 0 |
| $CF_3$ | Et | H | H | $NO_2$ | 1 |
| $CF_3$ | Et | H | H | $NO_2$ | 2 |
| $CF_3$ | Et | H | H | CN | 0 |
| $CF_3$ | Et | H | H | CN | 1 |

TABLE 2-continued

| | | | | | |
|---|---|---|---|---|---|
| CF₃ | Et | H | H | CN | 2 |
| CF₂CF₃ | Et | H | H | H | 0 |
| CF₂CF₃ | Et | H | H | H | 1 |
| CF₂CF₃ | Et | H | H | H | 2 |
| CF₂CF₃ | Et | F | H | H | 0 |
| CF₂CF₃ | Et | F | H | H | 1 |
| CF₂CF₃ | Et | F | H | H | 2 |
| CF₂CF₃ | Et | Cl | H | H | 0 |
| CF₂CF₃ | Et | Cl | H | H | 1 |
| CF₂CF₃ | Et | Cl | H | H | 2 |
| CF₂CF₃ | Et | Br | H | H | 0 |
| CF₂CF₃ | Et | Br | H | H | 1 |
| CF₂CF₃ | Et | Br | H | H | 2 |
| CF₂CF₃ | Et | I | H | H | 0 |
| CF₂CF₃ | Et | I | H | H | 1 |
| CF₂CF₃ | Et | I | H | H | 2 |
| CF₂CF₃ | Et | Me | H | H | 0 |
| CF₂CF₃ | Et | Me | H | H | 1 |
| CF₂CF₃ | Et | Me | H | H | 2 |
| CF₂CF₃ | Et | CF₃ | H | H | 0 |
| CF₂CF₃ | Et | CF₃ | H | H | 1 |
| CF₂CF₃ | Et | CF₃ | H | H | 2 |
| CF₂CF₃ | Et | CF₂CF₃ | H | H | 0 |
| CF₂CF₃ | Et | CF₂CF₃ | H | H | 1 |
| CF₂CF₃ | Et | CF₂CF₃ | H | H | 2 |
| CF₂CF₃ | Et | CF(CF₃)₂ | H | H | 0 |
| CF₂CF₃ | Et | CF(CF₃)₂ | H | H | 1 |
| CF₂CF₃ | Et | CF(CF₃)₂ | H | H | 2 |
| CF₂CF₃ | Et | SMe | H | H | 0 |
| CF₂CF₃ | Et | SMe | H | H | 1 |
| CF₂CF₃ | Et | SMe | H | H | 2 |
| CF₂CF₃ | Et | SOMe | H | H | 0 |
| CF₂CF₃ | Et | SOMe | H | H | 1 |
| CF₂CF₃ | Et | SOMe | H | H | 2 |
| CF₂CF₃ | Et | SO₂Me | H | H | 0 |
| CF₂CF₃ | Et | SO₂Me | H | H | 1 |
| CF₂CF₃ | Et | SO₂Me | H | H | 2 |
| CF₂CF₃ | Et | OMe | H | H | 0 |
| CF₂CF₃ | Et | OMe | H | H | 1 |
| CF₂CF₃ | Et | OMe | H | H | 2 |
| CF₂CF₃ | Et | OCF₃ | H | H | 0 |
| CF₂CF₃ | Et | OCF₃ | H | H | 1 |
| CF₂CF₃ | Et | OCF₃ | H | H | 2 |
| CF₂CF₃ | Et | NO₂ | H | H | 0 |
| CF₂CF₃ | Et | NO₂ | H | H | 1 |
| CF₂CF₃ | Et | NO₂ | H | H | 2 |
| CF₂CF₃ | Et | CN | H | H | 0 |
| CF₂CF₃ | Et | CN | H | H | 1 |
| CF₂CF₃ | Et | CN | H | H | 2 |
| CF₂CF₃ | Et | H | F | H | 0 |
| CF₂CF₃ | Et | H | F | H | 1 |
| CF₂CF₃ | Et | H | F | H | 2 |
| CF₂CF₃ | Et | H | Cl | H | 0 |
| CF₂CF₃ | Et | H | Cl | H | 1 |
| CF₂CF₃ | Et | H | Cl | H | 2 |
| CF₂CF₃ | Et | H | Br | H | 0 |
| CF₂CF₃ | Et | H | Br | H | 1 |
| CF₂CF₃ | Et | H | Br | H | 2 |
| CF₂CF₃ | Et | H | I | H | 0 |
| CF₂CF₃ | Et | H | I | H | 1 |
| CF₂CF₃ | Et | H | I | H | 2 |
| CF₂CF₃ | Et | H | Me | H | 0 |
| CF₂CF₃ | Et | H | Me | H | 1 |
| CF₂CF₃ | Et | H | Me | H | 2 |
| CF₂CF₃ | Et | H | CF₃ | H | 0 |
| CF₂CF₃ | Et | H | CF₃ | H | 1 |
| CF₂CF₃ | Et | H | CF₃ | H | 2 |
| CF₂CF₃ | Et | H | CF₂CF₃ | H | 0 |
| CF₂CF₃ | Et | H | CF₂CF₃ | H | 1 |
| CF₂CF₃ | Et | H | CF₂CF₃ | H | 2 |
| CF₂CF₃ | Et | H | CF(CF₃)₂ | H | 0 |
| CF₂CF₃ | Et | H | CF(CF₃)₂ | H | 1 |
| CF₂CF₃ | Et | H | CF(CF₃)₂ | H | 2 |
| CF₂CF₃ | Et | H | SMe | H | 0 |
| CF₂CF₃ | Et | H | SMe | H | 1 |
| CF₂CF₃ | Et | H | SMe | H | 2 |
| CF₂CF₃ | Et | H | SOMe | H | 0 |
| CF₂CF₃ | Et | H | SOMe | H | 1 |
| CF₂CF₃ | Et | H | SOMe | H | 2 |
| CF₂CF₃ | Et | H | SO₂Me | H | 0 |

TABLE 2-continued

| | | | | | |
|---|---|---|---|---|---|
| CF₂CF₃ | Et | H | SO₂Me | H | 1 |
| CF₂CF₃ | Et | H | SO₂Me | H | 2 |
| CF₂CF₃ | Et | H | OMe | H | 0 |
| CF₂CF₃ | Et | H | OMe | H | 1 |
| CF₂CF₃ | Et | H | OMe | H | 2 |
| CF₂CF₃ | Et | H | OCF₃ | H | 0 |
| CF₂CF₃ | Et | H | OCF₃ | H | 1 |
| CF₂CF₃ | Et | H | OCF₃ | H | 2 |
| CF₂CF₃ | Et | H | NO₂ | H | 0 |
| CF₂CF₃ | Et | H | NO₂ | H | 1 |
| CF₂CF₃ | Et | H | NO₂ | H | 2 |
| CF₂CF₃ | Et | H | CN | H | 0 |
| CF₂CF₃ | Et | H | CN | H | 1 |
| CF₂CF₃ | Et | H | CN | H | 2 |
| CF₂CF₃ | Et | H | H | F | 0 |
| CF₂CF₃ | Et | H | H | F | 1 |
| CF₂CF₃ | Et | H | H | F | 2 |
| CF₂CF₃ | Et | H | H | Cl | 0 |
| CF₂CF₃ | Et | H | H | Cl | 1 |
| CF₂CF₃ | Et | H | H | Cl | 2 |
| CF₂CF₃ | Et | H | H | Br | 0 |
| CF₂CF₃ | Et | H | H | Br | 1 |
| CF₂CF₃ | Et | H | H | Br | 2 |
| CF₂CF₃ | Et | H | H | I | 0 |
| CF₂CF₃ | Et | H | H | I | 1 |
| CF₂CF₃ | Et | H | H | I | 2 |
| CF₂CF₃ | Et | H | H | Me | 0 |
| CF₂CF₃ | Et | H | H | Me | 1 |
| CF₂CF₃ | Et | H | H | Me | 2 |
| CF₂CF₃ | Et | H | H | CF₃ | 0 |
| CF₂CF₃ | Et | H | H | CF₃ | 1 |
| CF₂CF₃ | Et | H | H | CF₃ | 2 |
| CF₂CF₃ | Et | H | H | CF₂CF₃ | 0 |
| CF₂CF₃ | Et | H | H | CF₂CF₃ | 1 |
| CF₂CF₃ | Et | H | H | CF₂CF₃ | 2 |
| CF₂CF₃ | Et | H | H | CF(CF₃)₂ | 0 |
| CF₂CF₃ | Et | H | H | CF(CF₃)₂ | 1 |
| CF₂CF₃ | Et | H | H | CF(CF₃)₂ | 2 |
| CF₂CF₃ | Et | H | H | SMe | 0 |
| CF₂CF₃ | Et | H | H | SMe | 1 |
| CF₂CF₃ | Et | H | H | SMe | 2 |
| CF₂CF₃ | Et | H | H | SOMe | 0 |
| CF₂CF₃ | Et | H | H | SOMe | 1 |
| CF₂CF₃ | Et | H | H | SOMe | 2 |
| CF₂CF₃ | Et | H | H | SO₂Me | 0 |
| CF₂CF₃ | Et | H | H | SO₂Me | 1 |
| CF₂CF₃ | Et | H | H | SO₂Me | 2 |
| CF₂CF₃ | Et | H | H | OMe | 0 |
| CF₂CF₃ | Et | H | H | OMe | 1 |
| CF₂CF₃ | Et | H | H | OMe | 2 |
| CF₂CF₃ | Et | H | H | OCF₃ | 0 |
| CF₂CF₃ | Et | H | H | OCF₃ | 1 |
| CF₂CF₃ | Et | H | H | OCF₃ | 2 |
| CF₂CF₃ | Et | H | H | NO₂ | 0 |
| CF₂CF₃ | Et | H | H | NO₂ | 1 |
| CF₂CF₃ | Et | H | H | NO₂ | 2 |
| CF₂CF₃ | Et | H | H | CN | 0 |
| CF₂CF₃ | Et | H | H | CN | 1 |
| CF₂CF₃ | Et | H | H | CN | 2 |

TABLE 3

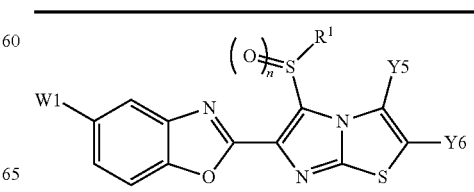

TABLE 3-continued
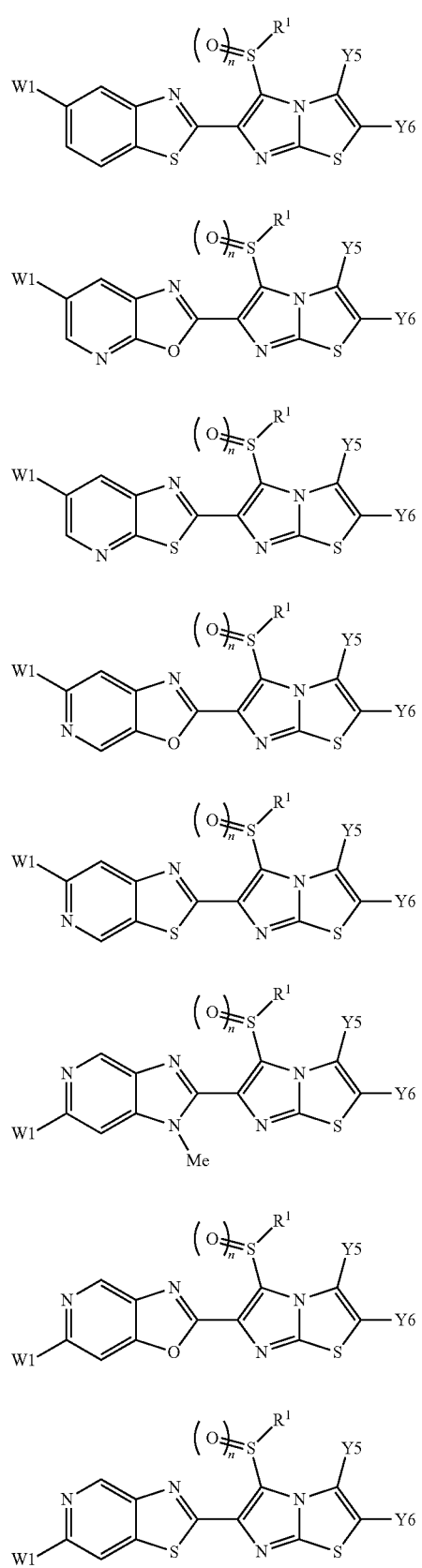

TABLE 3-continued
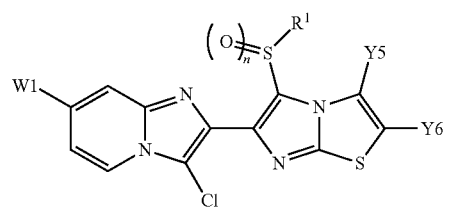
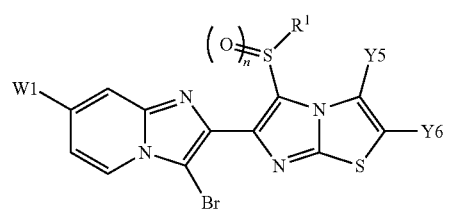
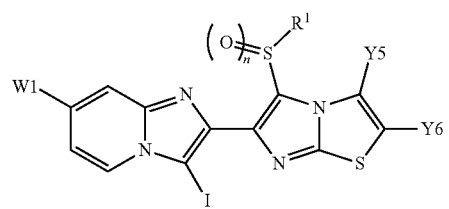
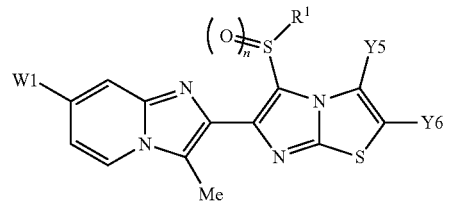
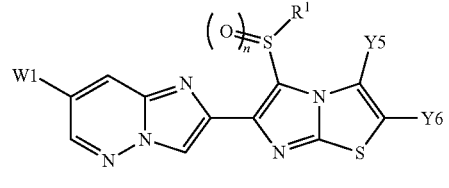
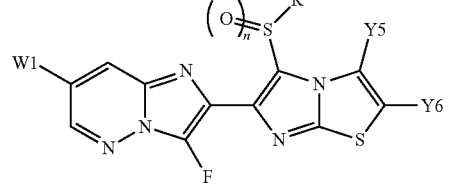
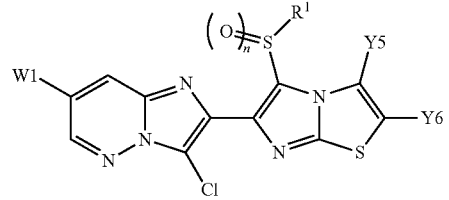
TABLE 3-continued
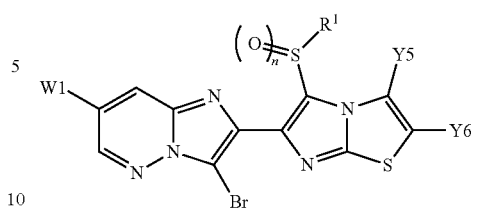
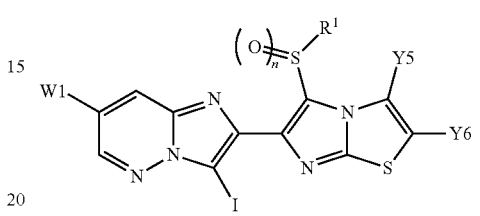
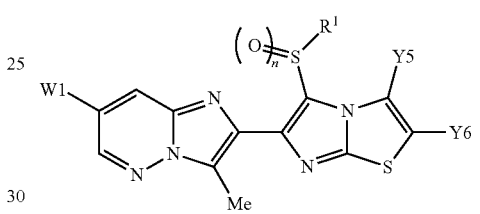
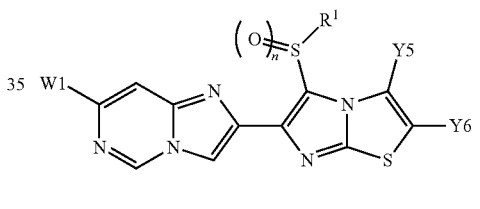
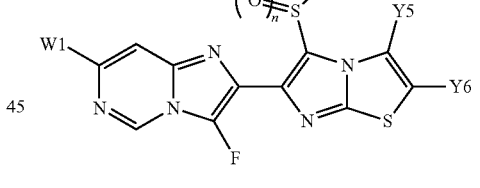
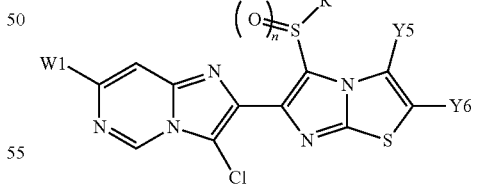
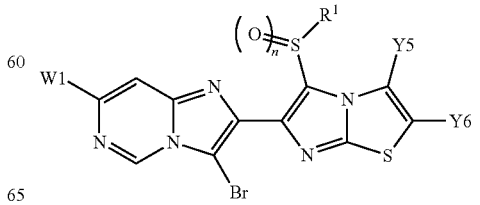

TABLE 3-continued
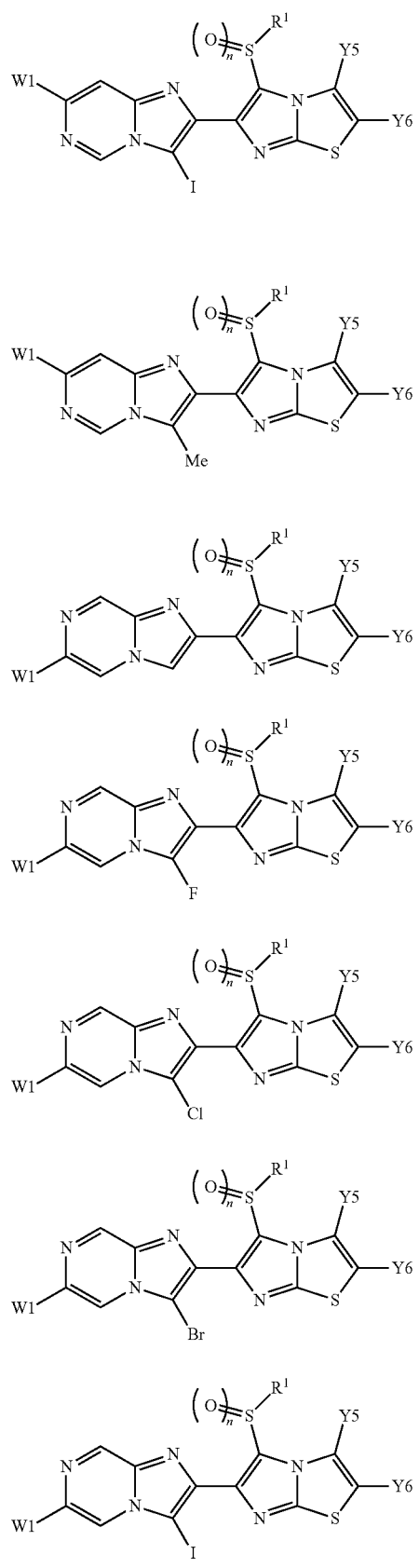
TABLE 3-continued
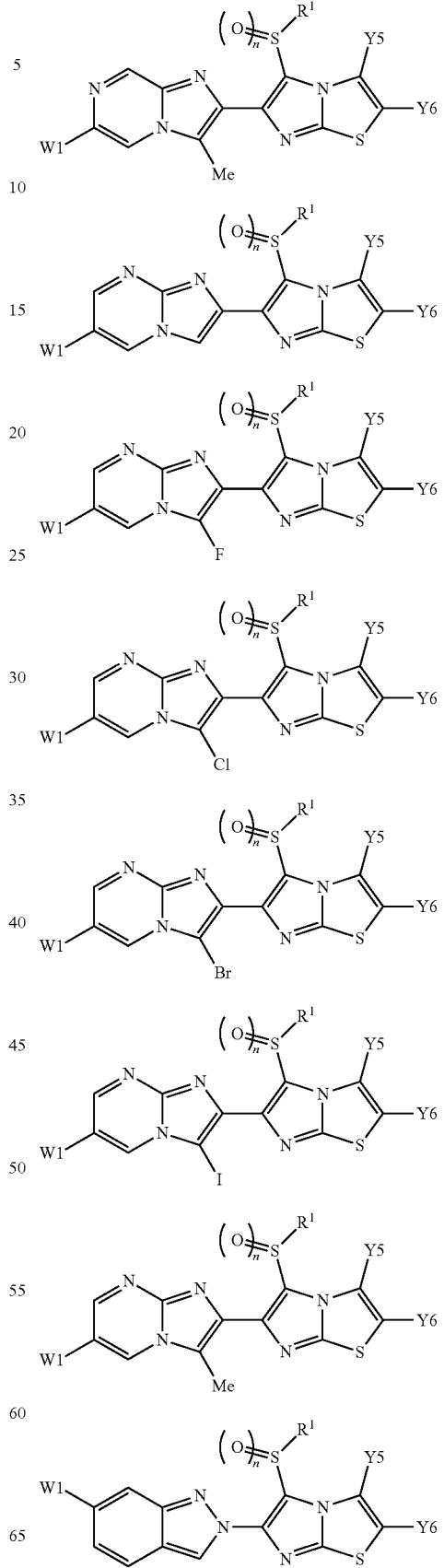

TABLE 3-continued
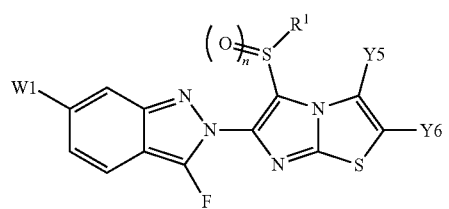
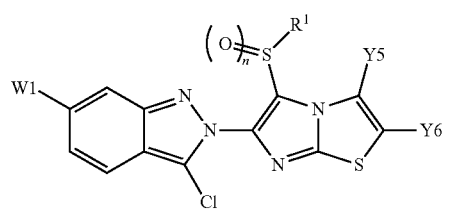
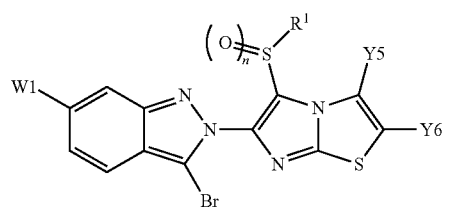
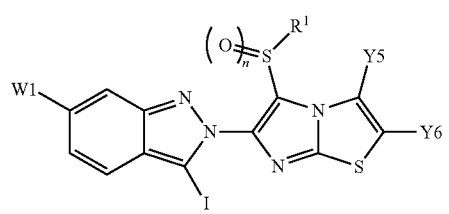
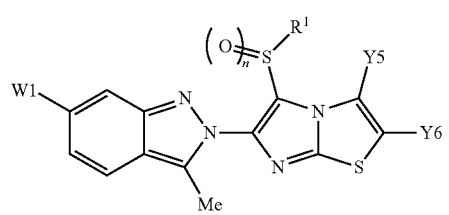
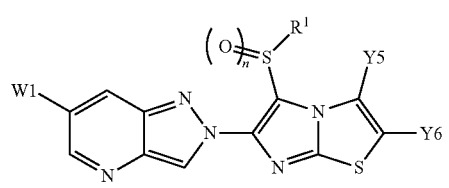
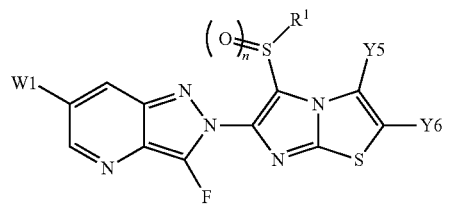
TABLE 3-continued
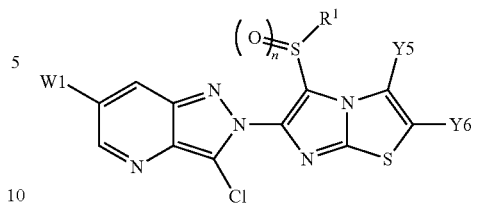
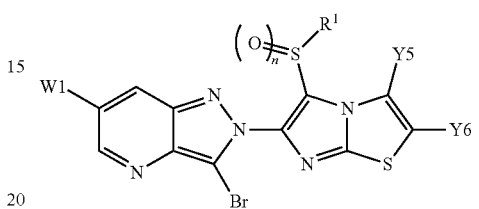
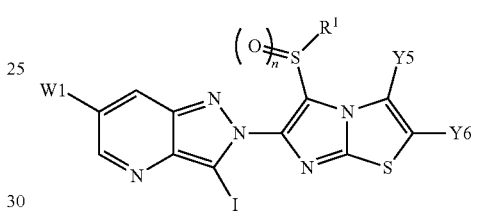
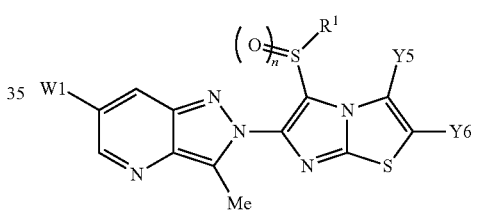
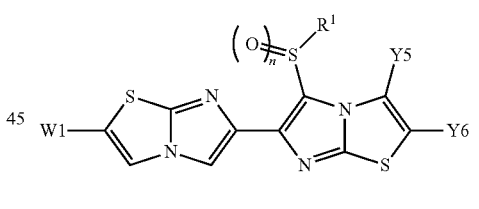
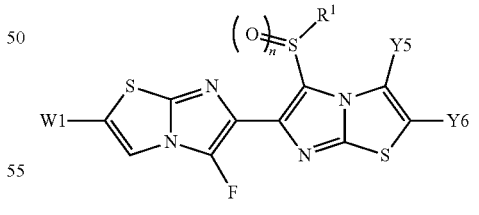
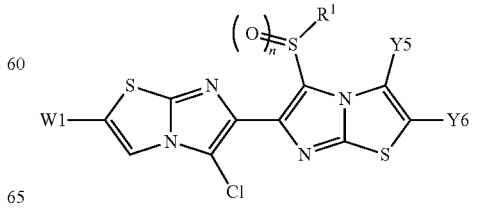

TABLE 3-continued

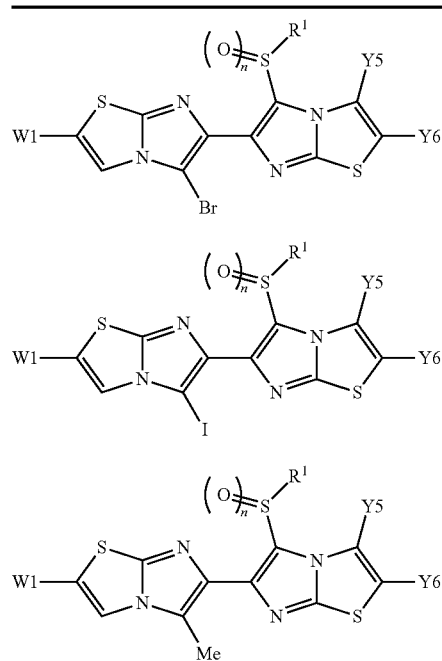

| W1 | R¹ | Y5 | Y6 | n |
|---|---|---|---|---|
| CF₃ | Et | H | H | 0 |
| CF₃ | Et | H | H | 1 |
| CF₃ | Et | H | H | 2 |
| CF₃ | Et | H | F | 0 |
| CF₃ | Et | H | F | 1 |
| CF₃ | Et | H | F | 2 |
| CF₃ | Et | H | Cl | 0 |
| CF₃ | Et | H | Cl | 1 |
| CF₃ | Et | H | Cl | 2 |
| CF₃ | Et | H | Br | 0 |
| CF₃ | Et | H | Br | 1 |
| CF₃ | Et | H | Br | 2 |
| CF₃ | Et | H | I | 0 |
| CF₃ | Et | H | I | 1 |
| CF₃ | Et | H | I | 2 |
| CF₃ | Et | H | Me | 0 |
| CF₃ | Et | H | Me | 1 |
| CF₃ | Et | H | Me | 2 |
| CF₃ | Et | H | CF₃ | 0 |
| CF₃ | Et | H | CF₃ | 1 |
| CF₃ | Et | H | CF₃ | 2 |
| CF₃ | Et | H | CF₂CF₃ | 0 |
| CF₃ | Et | H | CF₂CF₃ | 1 |
| CF₃ | Et | H | CF₂CF₃ | 2 |
| CF₃ | Et | H | CF(CF₃)₂ | 0 |
| CF₃ | Et | H | CF(CF₃)₂ | 1 |
| CF₃ | Et | H | CF(CF₃)₂ | 2 |
| CF₃ | Et | H | SMe | 0 |
| CF₃ | Et | H | SMe | 1 |
| CF₃ | Et | H | SMe | 2 |
| CF₃ | Et | H | SOMe | 0 |
| CF₃ | Et | H | SOMe | 1 |
| CF₃ | Et | H | SOMe | 2 |
| CF₃ | Et | H | SO₂Me | 0 |
| CF₃ | Et | H | SO₂Me | 1 |
| CF₃ | Et | H | SO₂Me | 2 |
| CF₃ | Et | H | OMe | 0 |
| CF₃ | Et | H | OMe | 1 |
| CF₃ | Et | H | OMe | 2 |
| CF₃ | Et | H | OCF₃ | 0 |
| CF₃ | Et | H | OCF₃ | 1 |
| CF₃ | Et | H | OCF₃ | 2 |
| CF₃ | Et | H | NO₂ | 0 |
| CF₃ | Et | H | NO₂ | 1 |
| CF₃ | Et | H | NO₂ | 2 |
| CF₃ | Et | H | CN | 0 |
| CF₃ | Et | H | CN | 1 |
| CF₃ | Et | H | CN | 2 |
| CF₂CF₃ | Et | H | H | 0 |
| CF₂CF₃ | Et | H | H | 1 |
| CF₂CF₃ | Et | H | H | 2 |
| CF₂CF₃ | Et | H | F | 0 |
| CF₂CF₃ | Et | H | F | 1 |
| CF₂CF₃ | Et | H | F | 2 |
| CF₂CF₃ | Et | H | Cl | 0 |
| CF₂CF₃ | Et | H | Cl | 1 |
| CF₂CF₃ | Et | H | Cl | 2 |
| CF₂CF₃ | Et | H | Br | 0 |
| CF₂CF₃ | Et | H | Br | 1 |
| CF₂CF₃ | Et | H | Br | 2 |
| CF₂CF₃ | Et | H | I | 0 |
| CF₂CF₃ | Et | H | I | 1 |
| CF₂CF₃ | Et | H | I | 2 |
| CF₂CF₃ | Et | H | Me | 0 |
| CF₂CF₃ | Et | H | Me | 1 |
| CF₂CF₃ | Et | H | Me | 2 |
| CF₂CF₃ | Et | H | CF₃ | 0 |
| CF₂CF₃ | Et | H | CF₃ | 1 |
| CF₂CF₃ | Et | H | CF₃ | 2 |
| CF₂CF₃ | Et | H | CF₂CF₃ | 0 |
| CF₂CF₃ | Et | H | CF₂CF₃ | 1 |
| CF₂CF₃ | Et | H | CF₂CF₃ | 2 |
| CF₂CF₃ | Et | H | CF(CF₃)₂ | 0 |
| CF₂CF₃ | Et | H | CF(CF₃)₂ | 1 |
| CF₂CF₃ | Et | H | CF(CF₃)₂ | 2 |
| CF₂CF₃ | Et | H | SMe | 0 |
| CF₂CF₃ | Et | H | SMe | 1 |
| CF₂CF₃ | Et | H | SMe | 2 |
| CF₂CF₃ | Et | H | SOMe | 0 |
| CF₂CF₃ | Et | H | SOMe | 1 |
| CF₂CF₃ | Et | H | SOMe | 2 |
| CF₂CF₃ | Et | H | SO₂Me | 0 |
| CF₂CF₃ | Et | H | SO₂Me | 1 |
| CF₂CF₃ | Et | H | SO₂Me | 2 |
| CF₂CF₃ | Et | H | OMe | 0 |
| CF₂CF₃ | Et | H | OMe | 1 |
| CF₂CF₃ | Et | H | OMe | 2 |
| CF₂CF₃ | Et | H | OCF₃ | 0 |
| CF₂CF₃ | Et | H | OCF₃ | 1 |
| CF₂CF₃ | Et | H | OCF₃ | 2 |
| CF₂CF₃ | Et | H | NO₂ | 0 |
| CF₂CF₃ | Et | H | NO₂ | 1 |
| CF₂CF₃ | Et | H | NO₂ | 2 |
| CF₂CF₃ | Et | H | CN | 0 |
| CF₂CF₃ | Et | H | CN | 1 |
| CF₂CF₃ | Et | H | CN | 2 |

TABLE 4

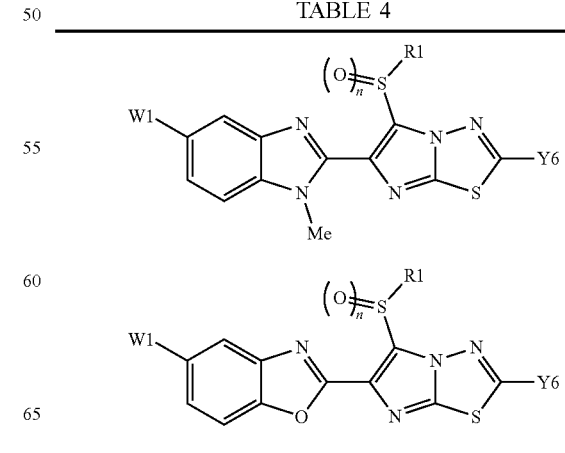

TABLE 4-continued
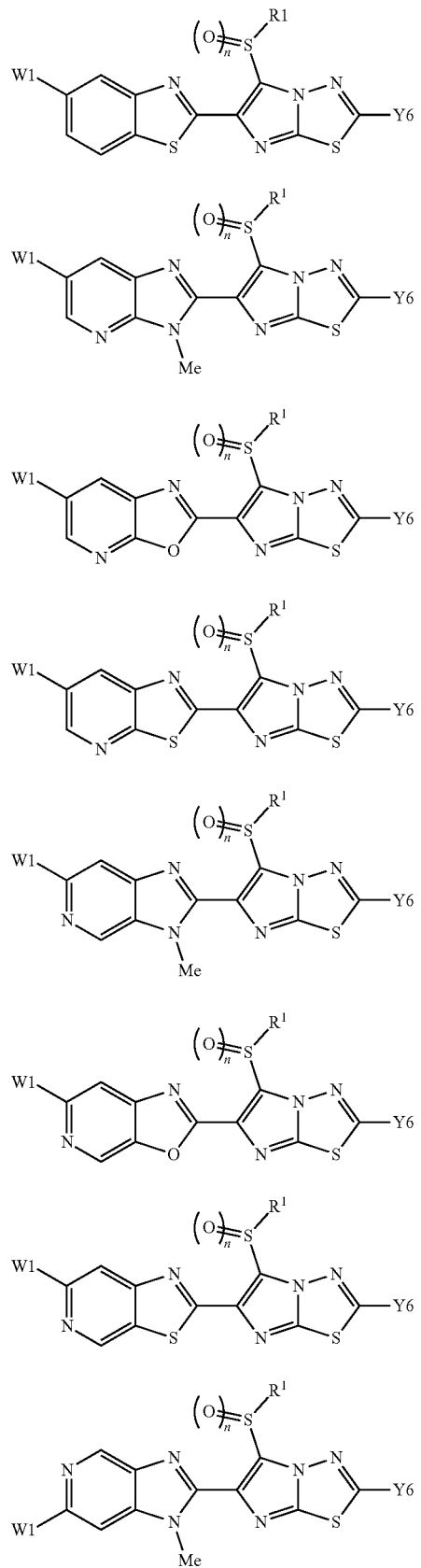
TABLE 4-continued
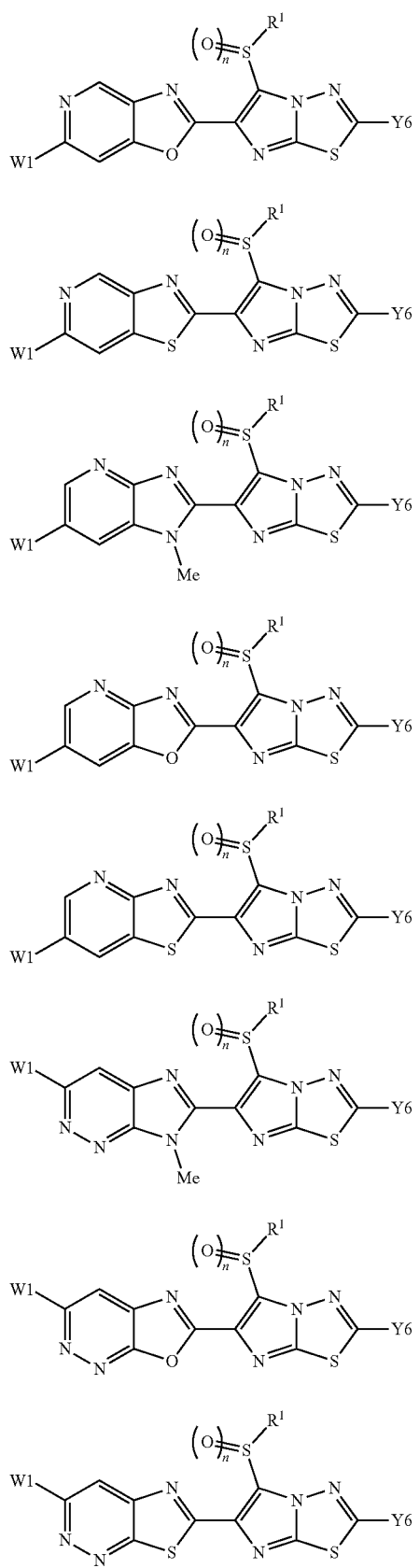

TABLE 4-continued
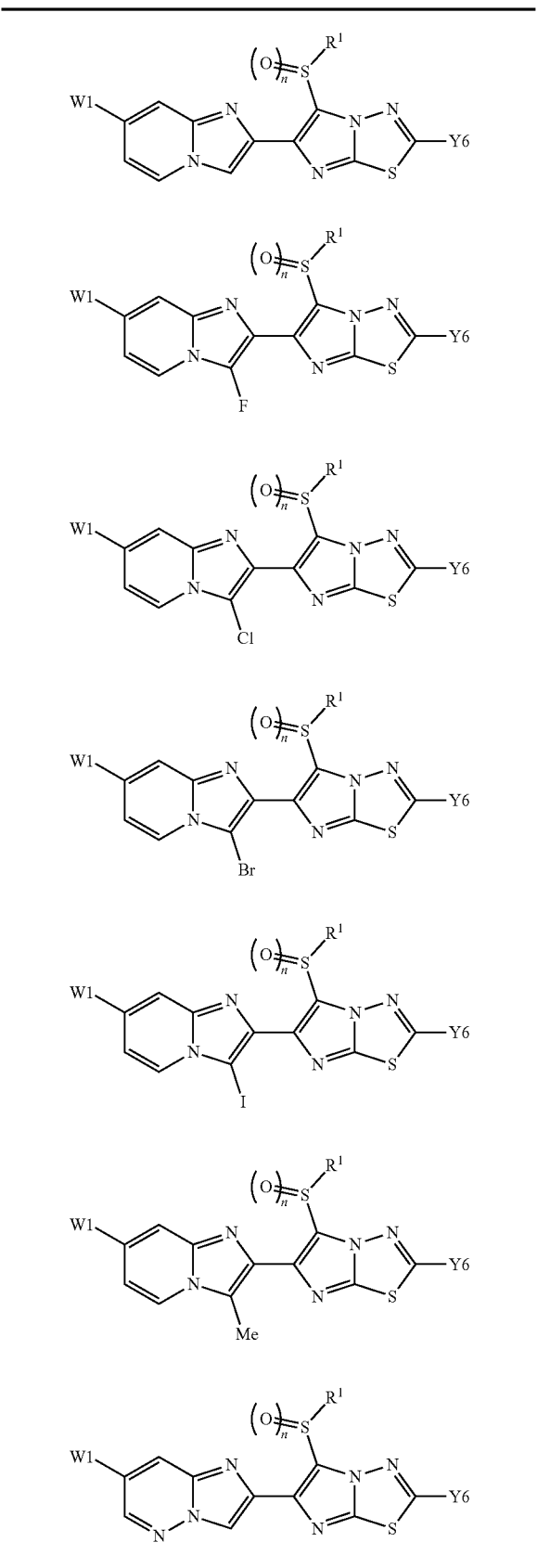
TABLE 4-continued
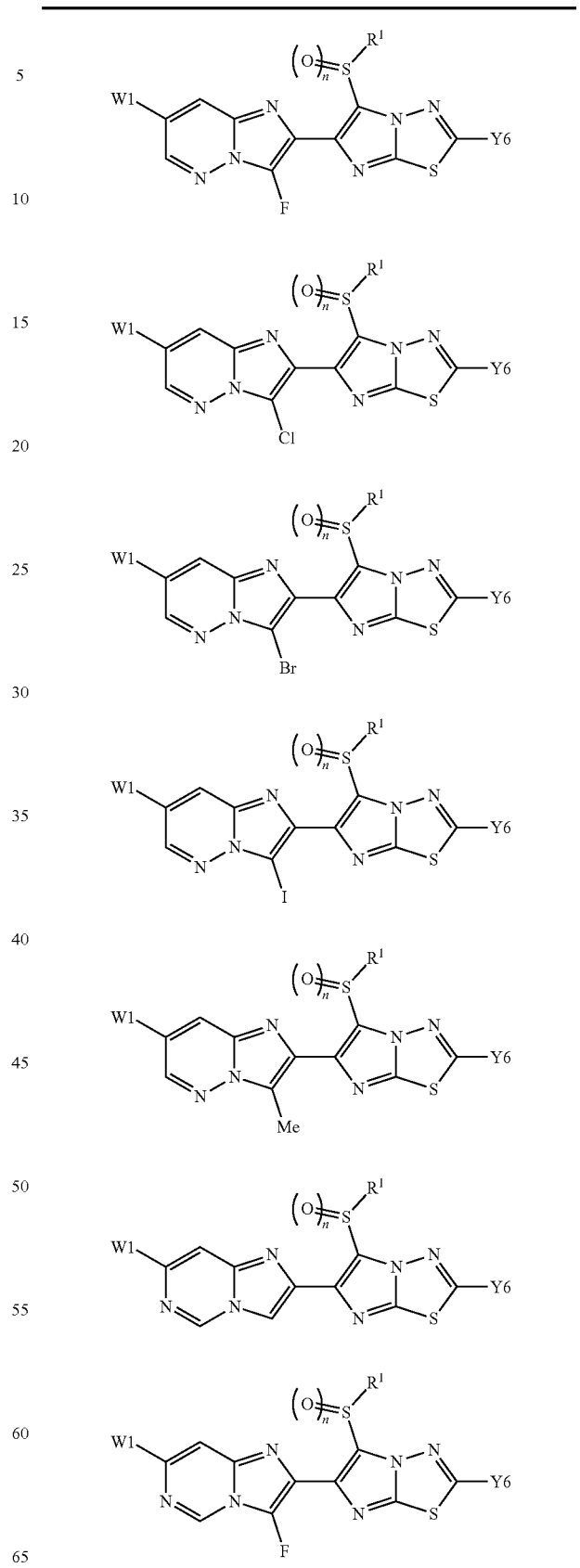

TABLE 4-continued
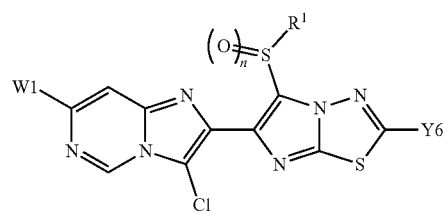
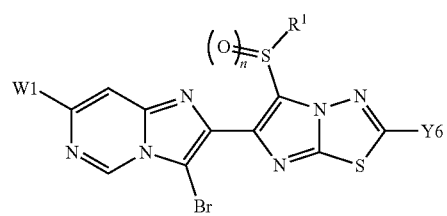
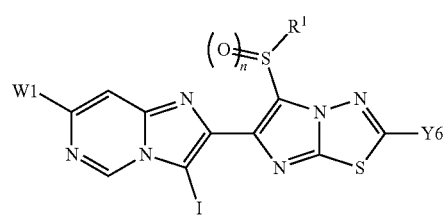
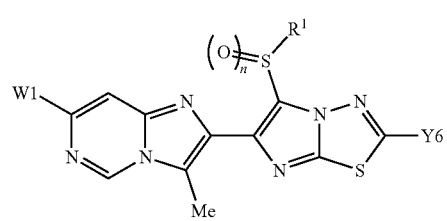
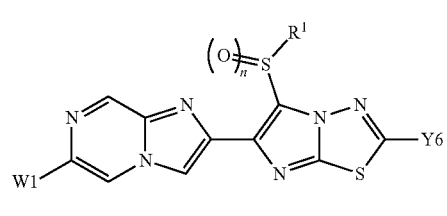
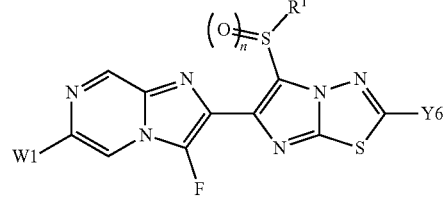
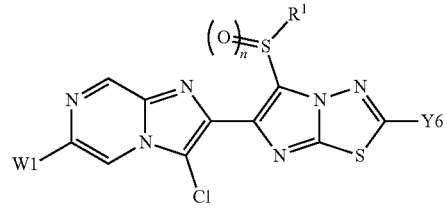
TABLE 4-continued
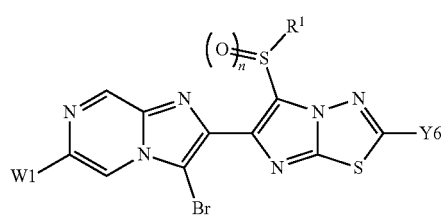
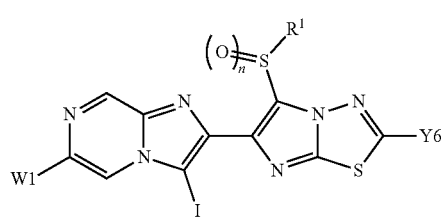
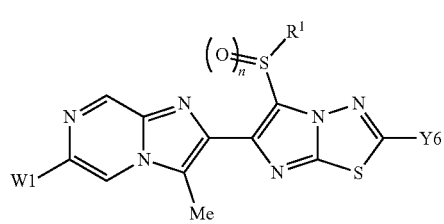
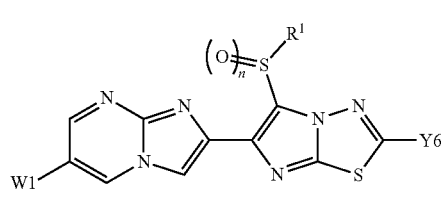
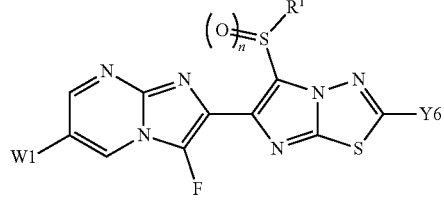
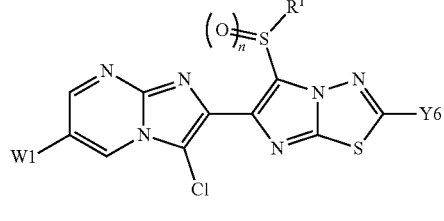
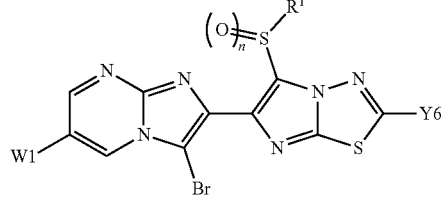

TABLE 4-continued
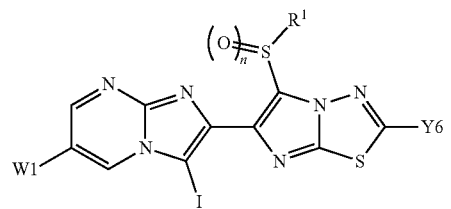
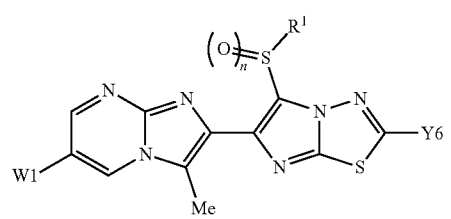
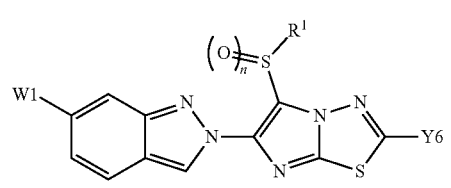
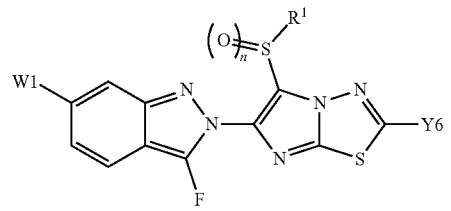
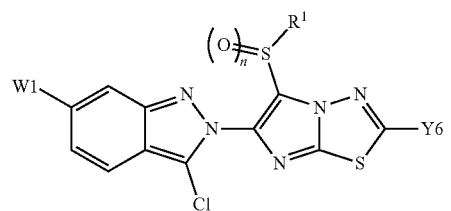
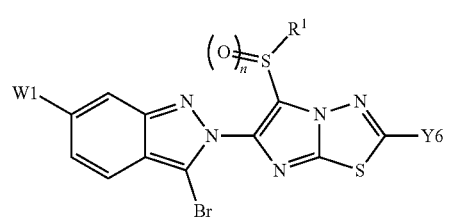
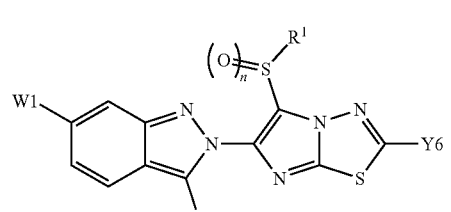
TABLE 4-continued
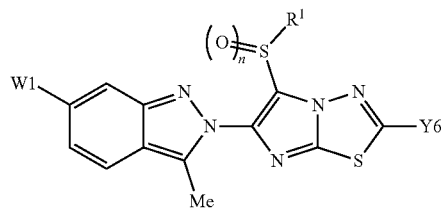
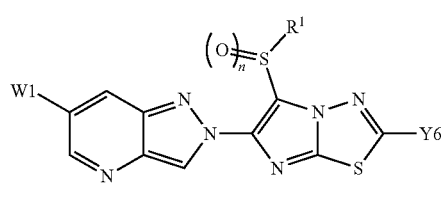
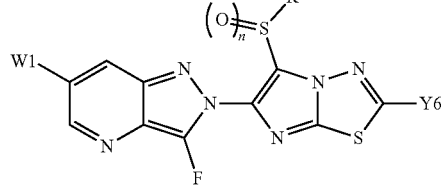
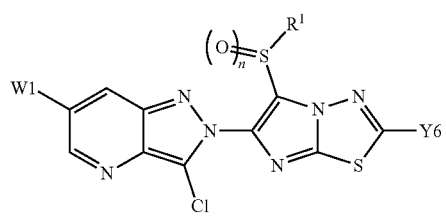
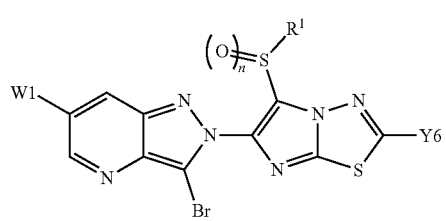
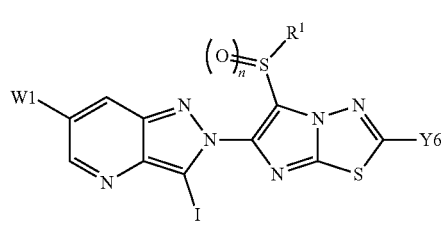
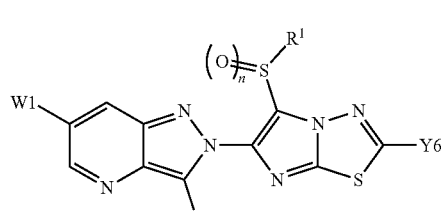

TABLE 4-continued
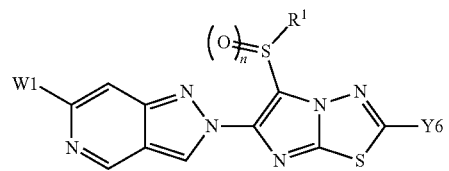
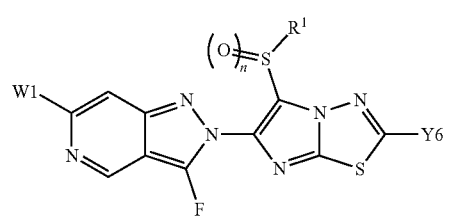
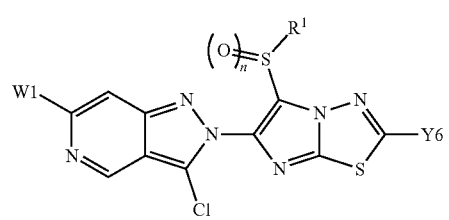
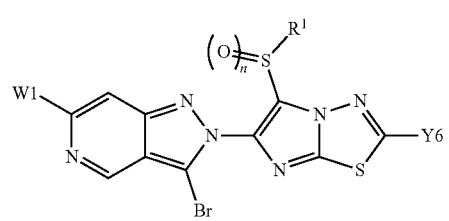
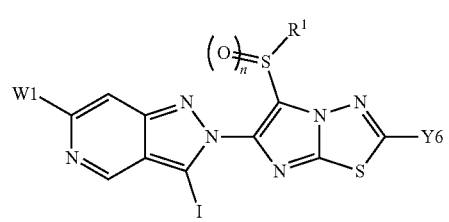
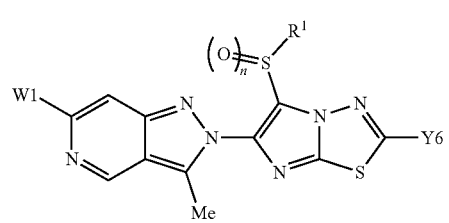
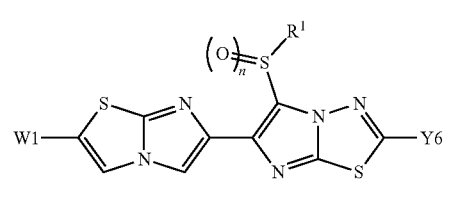
TABLE 4-continued
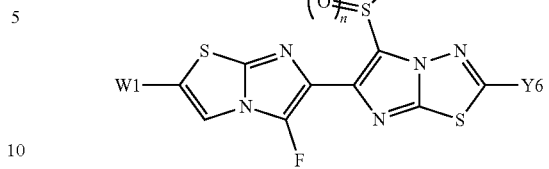
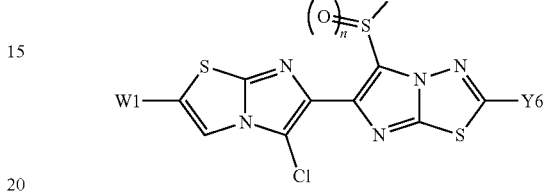
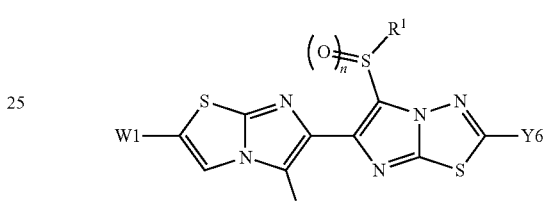
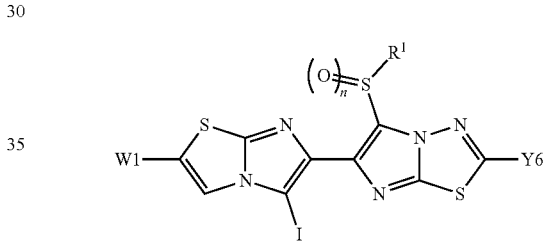
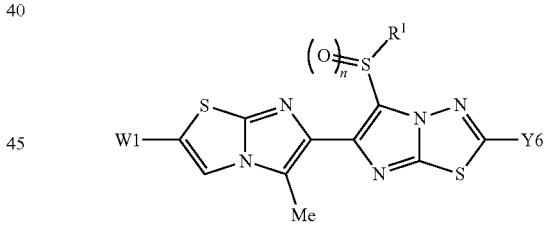
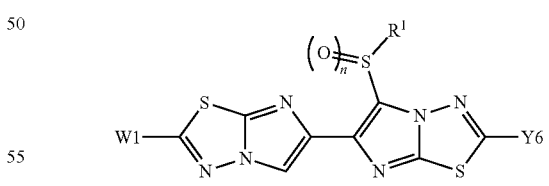
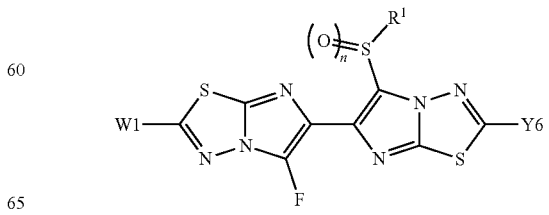

TABLE 4-continued

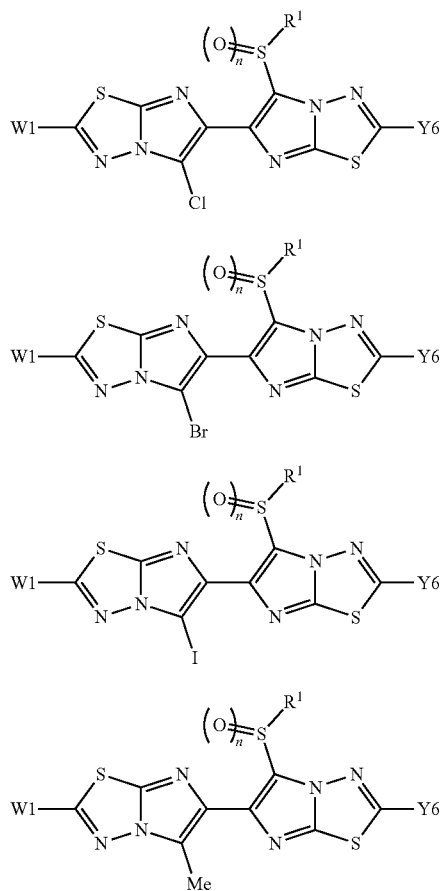

| W1 | R¹ | Y6 | n |
|---|---|---|---|
| CF₃ | Et | H | 0 |
| CF₃ | Et | H | 1 |
| CF₃ | Et | H | 2 |
| CF₃ | Et | F | 0 |
| CF₃ | Et | F | 1 |
| CF₃ | Et | F | 2 |
| CF₃ | Et | Cl | 0 |
| CF₃ | Et | Cl | 1 |
| CF₃ | Et | Cl | 2 |
| CF₃ | Et | Br | 0 |
| CF₃ | Et | Br | 1 |
| CF₃ | Et | Br | 2 |
| CF₃ | Et | I | 0 |
| CF₃ | Et | I | 1 |
| CF₃ | Et | I | 2 |
| CF₃ | Et | Me | 0 |
| CF₃ | Et | Me | 1 |
| CF₃ | Et | Me | 2 |
| CF₃ | Et | CF₃ | 0 |
| CF₃ | Et | CF₃ | 1 |
| CF₃ | Et | CF₃ | 2 |
| CF₃ | Et | CF₂CF₃ | 0 |
| CF₃ | Et | CF₂CF₃ | 1 |
| CF₃ | Et | CF₂CF₃ | 2 |
| CF₃ | Et | CF(CF₃)₂ | 0 |
| CF₃ | Et | CF(CF₃)₂ | 1 |
| CF₃ | Et | CF(CF₃)₃ | 2 |
| CF₃ | Et | SMe | 0 |
| CF₃ | Et | SMe | 1 |
| CF₃ | Et | SMe | 2 |
| CF₃ | Et | SOMe | 0 |
| CF₃ | Et | SOMe | 1 |
| CF₃ | Et | SOMe | 2 |
| CF₃ | Et | SO₂Me | 0 |
| CF₃ | Et | SO₂Me | 1 |
| CF₃ | Et | SO₂Me | 2 |
| CF₃ | Et | OMe | 0 |
| CF₃ | Et | OMe | 1 |
| CF₃ | Et | OMe | 2 |
| CF₃ | Et | OCF₃ | 0 |
| CF₃ | Et | OCF₃ | 1 |
| CF₃ | Et | OCF₃ | 2 |
| CF₃ | Et | NO₂ | 0 |
| CF₃ | Et | NO₂ | 1 |
| CF₃ | Et | NO₂ | 2 |
| CF₃ | Et | CN | 0 |
| CF₃ | Et | CN | 1 |
| CF₃ | Et | CN | 2 |
| CF₂CF₃ | Et | H | 0 |
| CF₂CF₃ | Et | H | 1 |
| CF₂CF₃ | Et | H | 2 |
| CF₂CF₃ | Et | F | 0 |
| CF₂CF₃ | Et | F | 1 |
| CF₂CF₃ | Et | F | 2 |
| CF₂CF₃ | Et | Cl | 0 |
| CF₂CF₃ | Et | Cl | 1 |
| CF₂CF₃ | Et | Cl | 2 |
| CF₂CF₃ | Et | Br | 0 |
| CF₂CF₃ | Et | Br | 1 |
| CF₂CF₃ | Et | Br | 2 |
| CF₂CF₃ | Et | I | 0 |
| CF₂CF₃ | Et | I | 1 |
| CF₂CF₃ | Et | I | 2 |
| CF₂CF₃ | Et | Me | 0 |
| CF₂CF₃ | Et | Me | 1 |
| CF₂CF₃ | Et | Me | 2 |
| CF₂CF₃ | Et | CF₃ | 0 |
| CF₂CF₃ | Et | CF₃ | 1 |
| CF₂CF₃ | Et | CF₃ | 2 |
| CF₂CF₃ | Et | CF₂CF₃ | 0 |
| CF₂CF₃ | Et | CF₂CF₃ | 1 |
| CF₂CF₃ | Et | CF₂CF₃ | 2 |
| CF₂CF₃ | Et | CF(CF₃)₂ | 0 |
| CF₂CF₃ | Et | CF(CF₃)₂ | 1 |
| CF₂CF₃ | Et | CF(CF₃)₃ | 2 |
| CF₂CF₃ | Et | SMe | 0 |
| CF₂CF₃ | Et | SMe | 1 |
| CF₂CF₃ | Et | SMe | 2 |
| CF₂CF₃ | Et | SOMe | 0 |
| CF₂CF₃ | Et | SOMe | 1 |
| CF₂CF₃ | Et | SOMe | 2 |
| CF₂CF₃ | Et | SO₂Me | 0 |
| CF₂CF₃ | Et | SO₂Me | 1 |
| CF₂CF₃ | Et | SO₂Me | 2 |
| CF₂CF₃ | Et | OMe | 0 |
| CF₂CF₃ | Et | OMe | 1 |
| CF₂CF₃ | Et | OMe | 2 |
| CF₂CF₃ | Et | OCF₃ | 0 |
| CF₂CF₃ | Et | OCF₃ | 1 |
| CF₂CF₃ | Et | OCF₃ | 2 |
| CF₂CF₃ | Et | NO₂ | 0 |
| CF₂CF₃ | Et | NO₂ | 1 |
| CF₂CF₃ | Et | NO₂ | 2 |
| CF₂CF₃ | Et | CN | 0 |
| CF₂CF₃ | Et | CN | 1 |
| CF₂CF₃ | Et | CN | 2 |

| W1 | R¹ | Y1 | Y2 | Y3 | Y4 | n |
|---|---|---|---|---|---|---|
| CF₃ | Et | H | H | H | H | 0 |
| CF₃ | Et | H | H | H | H | 1 |
| CF₃ | Et | H | H | H | H | 2 |
| CF₃ | Et | F | H | H | H | 0 |
| CF₃ | Et | F | H | H | H | 1 |
| CF₃ | Et | F | H | H | H | 2 |
| CF₃ | Et | Cl | H | H | H | 0 |
| CF₃ | Et | Cl | H | H | H | 1 |
| CF₃ | Et | Cl | H | H | H | 2 |
| CF₃ | Et | Br | H | H | H | 0 |
| CF₃ | Et | Br | H | H | H | 1 |
| CF₃ | Et | Br | H | H | H | 2 |
| CF₃ | Et | I | H | H | H | 0 |
| CF₃ | Et | I | H | H | H | 1 |
| CF₃ | Et | I | H | H | H | 2 |
| CF₃ | Et | Me | H | H | H | 0 |

TABLE 4-continued

| | | | | | | |
|---|---|---|---|---|---|---|
| CF$_3$ | Et | Me | H | H | H | 1 |
| CF$_3$ | Et | Me | H | H | H | 2 |
| CF$_3$ | Et | CF$_3$ | H | H | H | 0 |
| CF$_3$ | Et | CF$_3$ | H | H | H | 1 |
| CF$_3$ | Et | CF$_3$ | H | H | H | 2 |
| CF$_3$ | Et | H | F | H | H | 0 |
| CF$_3$ | Et | H | F | H | H | 1 |
| CF$_3$ | Et | H | F | H | H | 2 |
| CF$_3$ | Et | H | Cl | H | H | 0 |
| CF$_3$ | Et | H | Cl | H | H | 1 |
| CF$_3$ | Et | H | Cl | H | H | 2 |
| CF$_3$ | Et | H | Br | H | H | 0 |
| CF$_3$ | Et | H | Br | H | H | 1 |
| CF$_3$ | Et | H | Br | H | H | 2 |
| CF$_3$ | Et | H | I | H | H | 0 |
| CF$_3$ | Et | H | I | H | H | 1 |
| CF$_3$ | Et | H | I | H | H | 2 |
| CF$_3$ | Et | H | Me | H | H | 0 |
| CF$_3$ | Et | H | Me | H | H | 1 |
| CF$_3$ | Et | H | Me | H | H | 2 |
| CF$_3$ | Et | H | CF$_3$ | H | H | 0 |
| CF$_3$ | Et | H | CF$_3$ | H | H | 1 |
| CF$_3$ | Et | H | CF$_3$ | H | H | 2 |
| CF$_3$ | Et | H | CF$_2$CF$_3$ | H | H | 0 |
| CF$_3$ | Et | H | CF$_2$CF$_3$ | H | H | 1 |
| CF$_3$ | Et | H | CF$_2$CF$_3$ | H | H | 2 |
| CF$_3$ | Et | H | CF(CF$_3$)$_2$ | H | H | 0 |
| CF$_3$ | Et | H | CF(CF$_3$)$_2$ | H | H | 1 |
| CF$_3$ | Et | H | CF(CF$_3$)$_2$ | H | H | 2 |
| CF$_3$ | Et | H | SMe | H | H | 0 |
| CF$_3$ | Et | H | SMe | H | H | 1 |
| CF$_3$ | Et | H | SMe | H | H | 2 |
| CF$_3$ | Et | H | SOMe | H | H | 0 |
| CF$_3$ | Et | H | SOMe | H | H | 1 |
| CF$_3$ | Et | H | SOMe | H | H | 2 |
| CF$_3$ | Et | H | SO$_2$Me | H | H | 0 |
| CF$_3$ | Et | H | SO$_2$Me | H | H | 1 |
| CF$_3$ | Et | H | SO$_2$Me | H | H | 2 |
| CF$_3$ | Et | H | OMe | H | H | 0 |
| CF$_3$ | Et | H | OMe | H | H | 1 |
| CF$_3$ | Et | H | OMe | H | H | 2 |
| CF$_3$ | Et | H | OCF$_3$ | H | H | 0 |
| CF$_3$ | Et | H | OCF$_3$ | H | H | 1 |
| CF$_3$ | Et | H | OCF$_3$ | H | H | 2 |
| CF$_3$ | Et | H | NO$_2$ | H | H | 0 |
| CF$_3$ | Et | H | NO$_2$ | H | H | 1 |
| CF$_3$ | Et | H | NO$_2$ | H | H | 2 |
| CF$_3$ | Et | H | CN | H | H | 0 |
| CF$_3$ | Et | H | CN | H | H | 1 |
| CF$_3$ | Et | H | CN | H | H | 2 |
| CF$_3$ | Et | H | H | F | H | 0 |
| CF$_3$ | Et | H | H | F | H | 1 |
| CF$_3$ | Et | H | H | F | H | 2 |
| CF$_3$ | Et | H | H | Cl | H | 0 |
| CF$_3$ | Et | H | H | Cl | H | 1 |
| CF$_3$ | Et | H | H | Cl | H | 2 |
| CF$_3$ | Et | H | H | Br | H | 0 |
| CF$_3$ | Et | H | H | Br | H | 1 |
| CF$_3$ | Et | H | H | Br | H | 2 |
| CF$_3$ | Et | H | H | I | H | 0 |
| CF$_3$ | Et | H | H | I | H | 1 |
| CF$_3$ | Et | H | H | I | H | 2 |
| CF$_3$ | Et | H | H | Me | H | 0 |
| CF$_3$ | Et | H | H | Me | H | 1 |
| CF$_3$ | Et | H | H | Me | H | 2 |
| CF$_3$ | Et | H | H | CF$_3$ | H | 0 |
| CF$_3$ | Et | H | H | CF$_3$ | H | 1 |
| CF$_3$ | Et | H | H | CF$_3$ | H | 2 |
| CF$_3$ | Et | H | H | CF$_2$CF$_3$ | H | 0 |
| CF$_3$ | Et | H | H | CF$_2$CF$_3$ | H | 1 |
| CF$_3$ | Et | H | H | CF$_2$CF$_3$ | H | 2 |
| CF$_3$ | Et | H | H | CF(CF$_3$)$_2$ | H | 0 |
| CF$_3$ | Et | H | H | CF(CF$_3$)$_2$ | H | 1 |
| CF$_3$ | Et | H | H | CF(CF$_3$)$_2$ | H | 2 |
| CF$_3$ | Et | H | H | SMe | H | 0 |
| CF$_3$ | Et | H | H | SMe | H | 1 |
| CF$_3$ | Et | H | H | SMe | H | 2 |
| CF$_3$ | Et | H | H | SOMe | H | 0 |
| CF$_3$ | Et | H | H | SOMe | H | 1 |
| CF$_3$ | Et | H | H | SOMe | H | 2 |

TABLE 4-continued

| | | | | | | |
|---|---|---|---|---|---|---|
| CF$_3$ | Et | H | H | SO$_2$Me | H | 0 |
| CF$_3$ | Et | H | H | SO$_2$Me | H | 1 |
| CF$_3$ | Et | H | H | SO$_2$Me | H | 2 |
| CF$_3$ | Et | H | H | OMe | H | 0 |
| CF$_3$ | Et | H | H | OMe | H | 1 |
| CF$_3$ | Et | H | H | OMe | H | 2 |
| CF$_3$ | Et | H | H | OCF$_3$ | H | 0 |
| CF$_3$ | Et | H | H | OCF$_3$ | H | 1 |
| CF$_3$ | Et | H | H | OCF$_3$ | H | 2 |
| CF$_3$ | Et | H | H | NO$_2$ | H | 0 |
| CF$_3$ | Et | H | H | NO$_2$ | H | 1 |
| CF$_3$ | Et | H | H | NO$_2$ | H | 2 |
| CF$_3$ | Et | H | H | CN | H | 0 |
| CF$_3$ | Et | H | H | CN | H | 1 |
| CF$_3$ | Et | H | H | CN | H | 2 |
| CF$_3$ | Et | H | H | H | F | 0 |
| CF$_3$ | Et | H | H | H | F | 1 |
| CF$_3$ | Et | H | H | H | F | 2 |
| CF$_3$ | Et | H | H | H | Cl | 0 |
| CF$_3$ | Et | H | H | H | Cl | 1 |
| CF$_3$ | Et | H | H | H | Cl | 2 |
| CF$_3$ | Et | H | H | H | Br | 0 |
| CF$_3$ | Et | H | H | H | Br | 1 |
| CF$_3$ | Et | H | H | H | Br | 2 |
| CF$_3$ | Et | H | H | H | I | 0 |
| CF$_3$ | Et | H | H | H | I | 1 |

TABLE 5

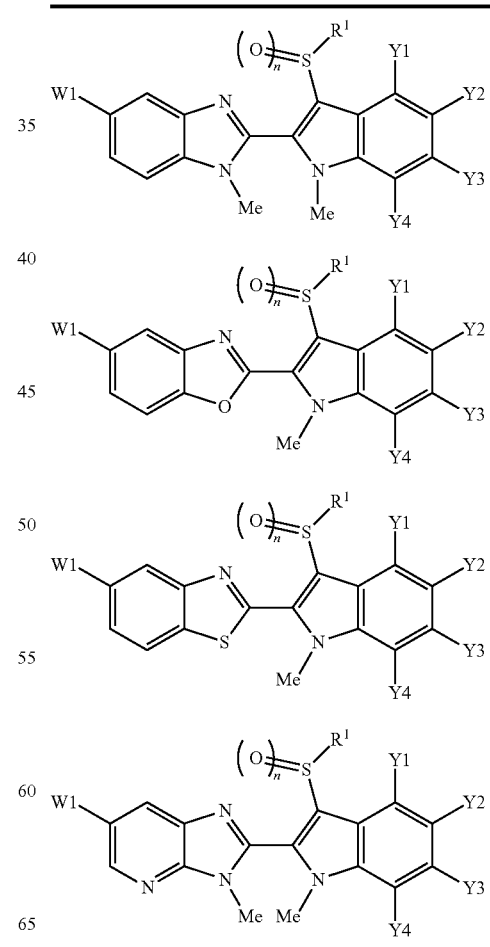

TABLE 5-continued
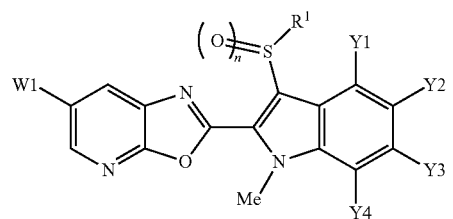
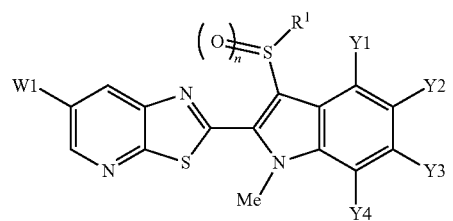
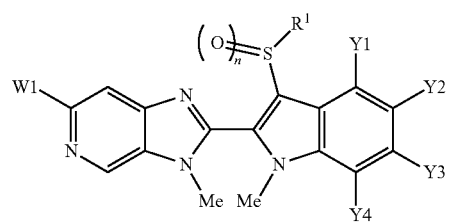
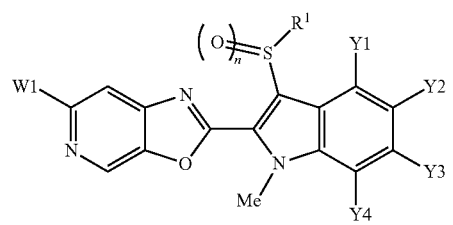
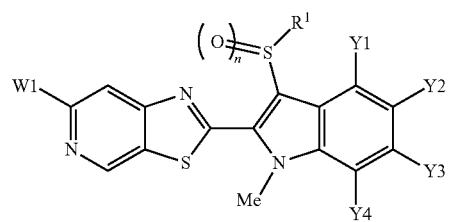
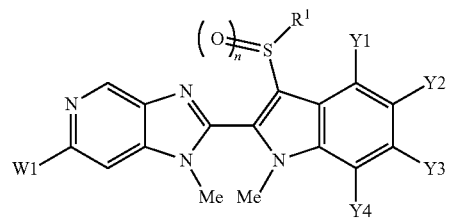
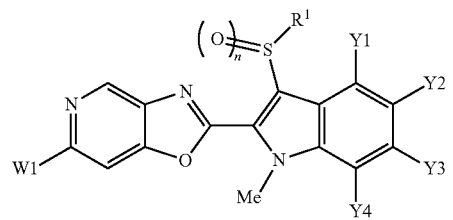
TABLE 5-continued
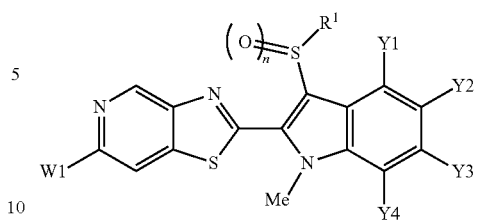
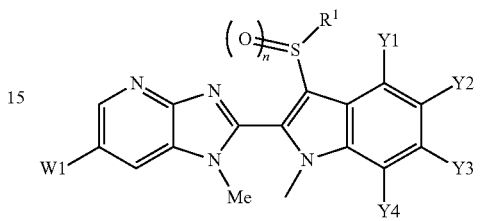
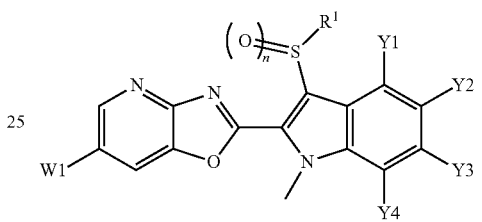
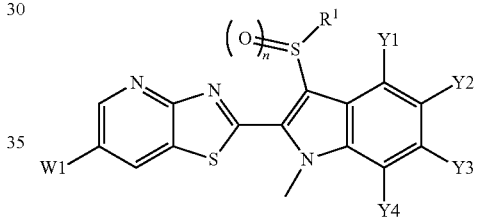
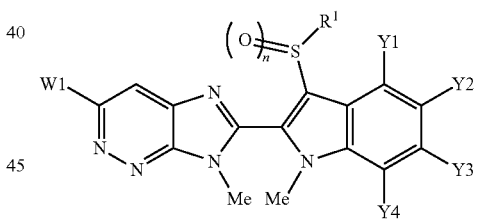
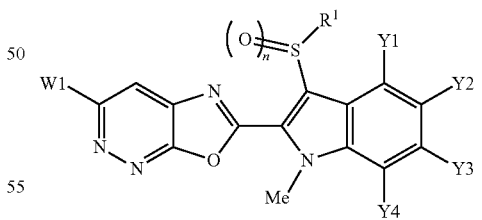
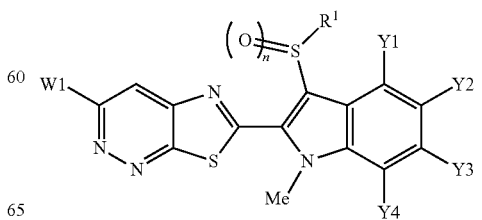

TABLE 5-continued
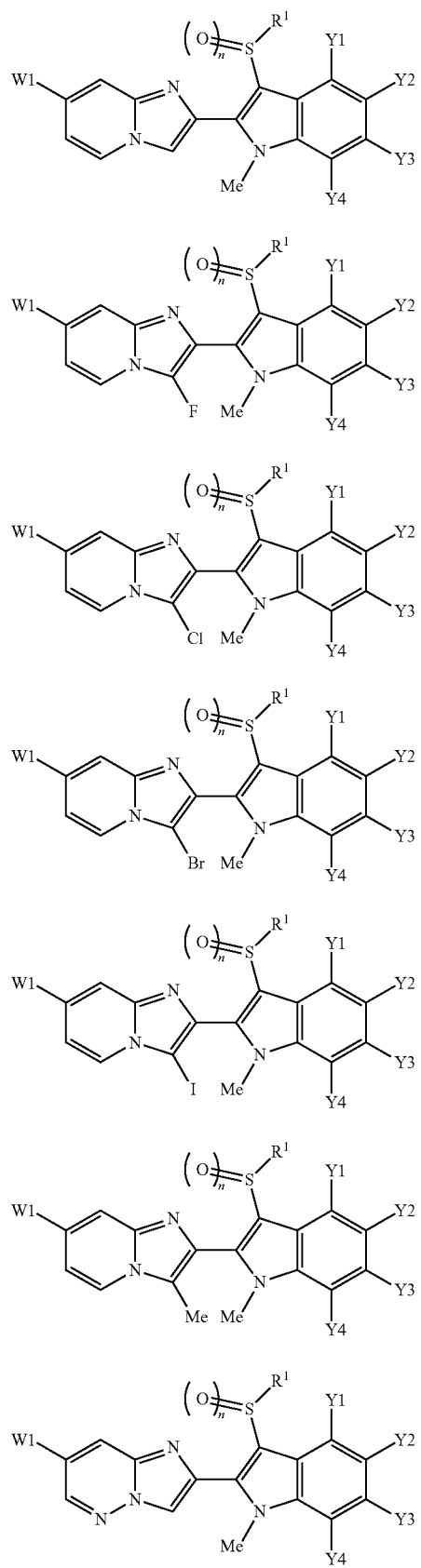
TABLE 5-continued
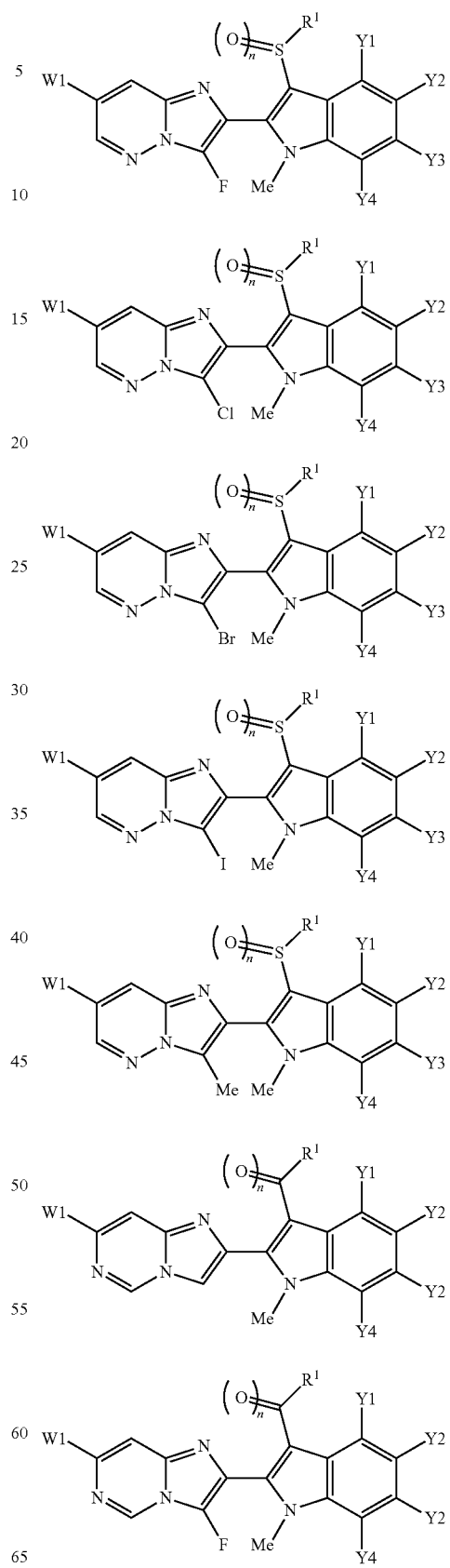

TABLE 5-continued
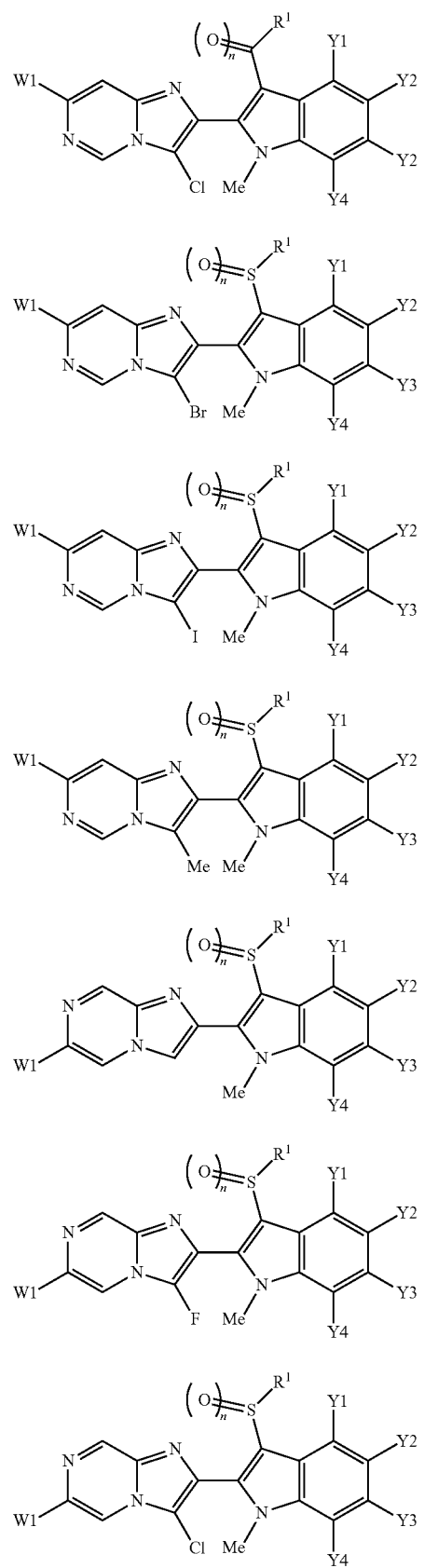
TABLE 5-continued
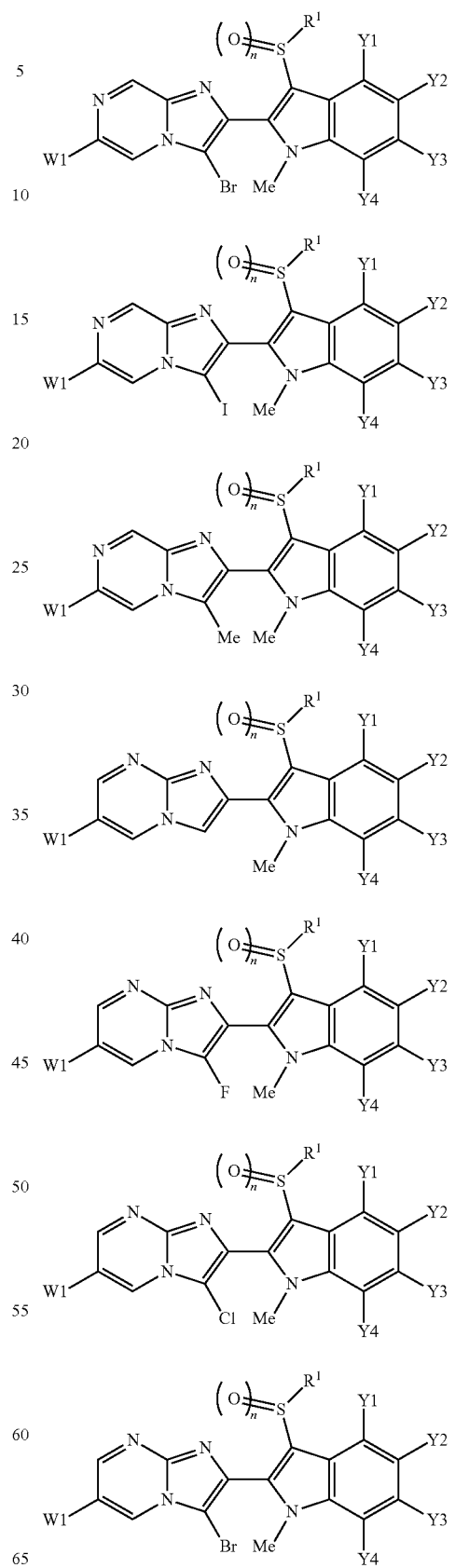

TABLE 5-continued
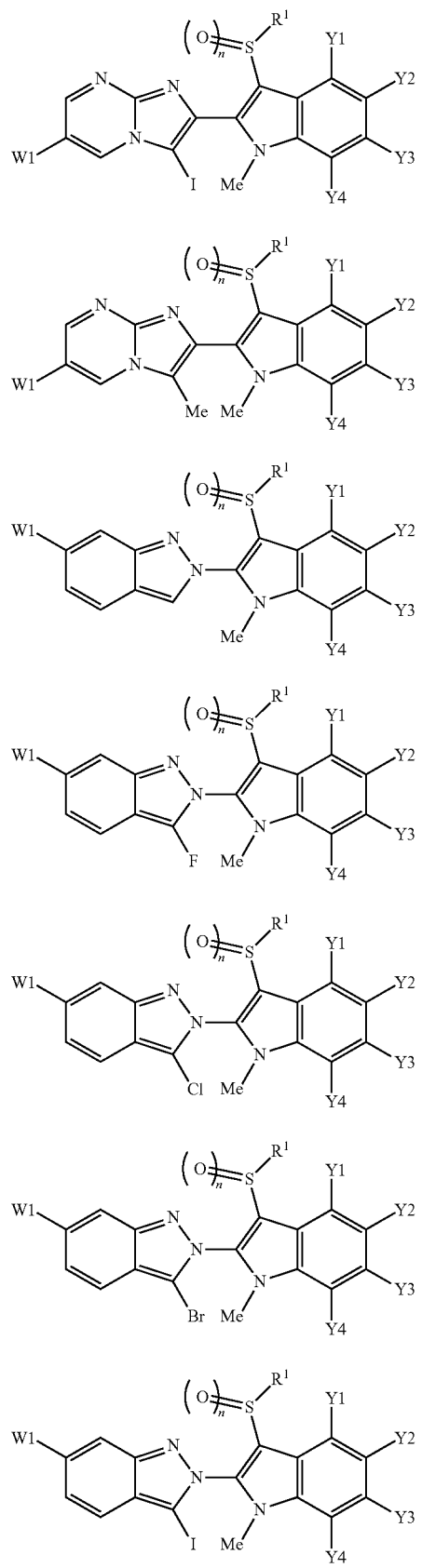
TABLE 5-continued
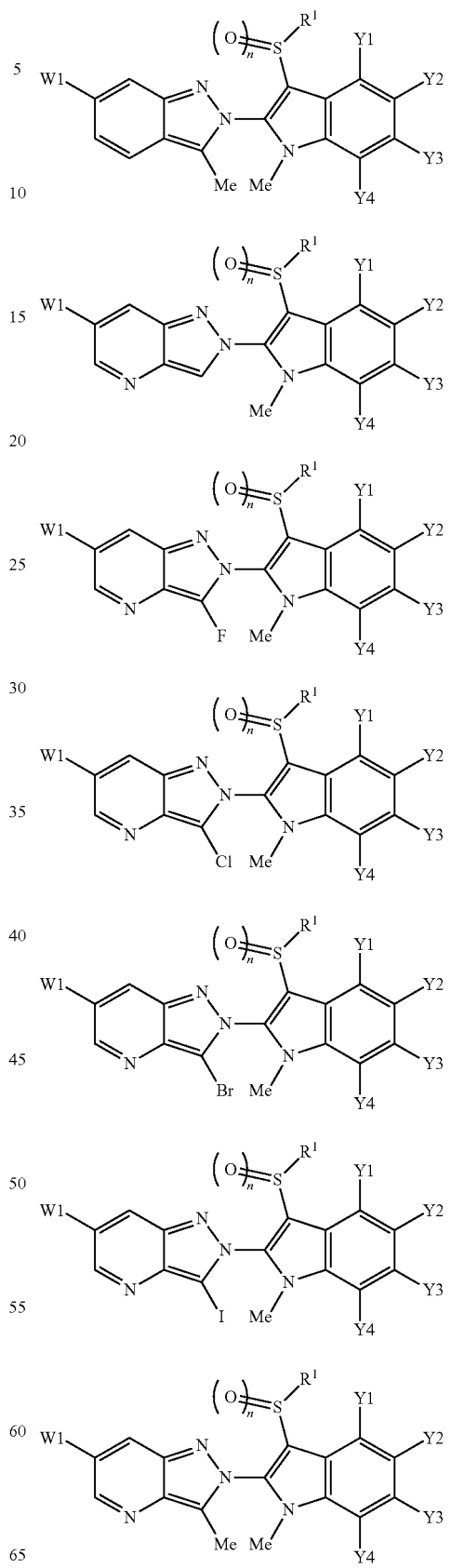

TABLE 5-continued
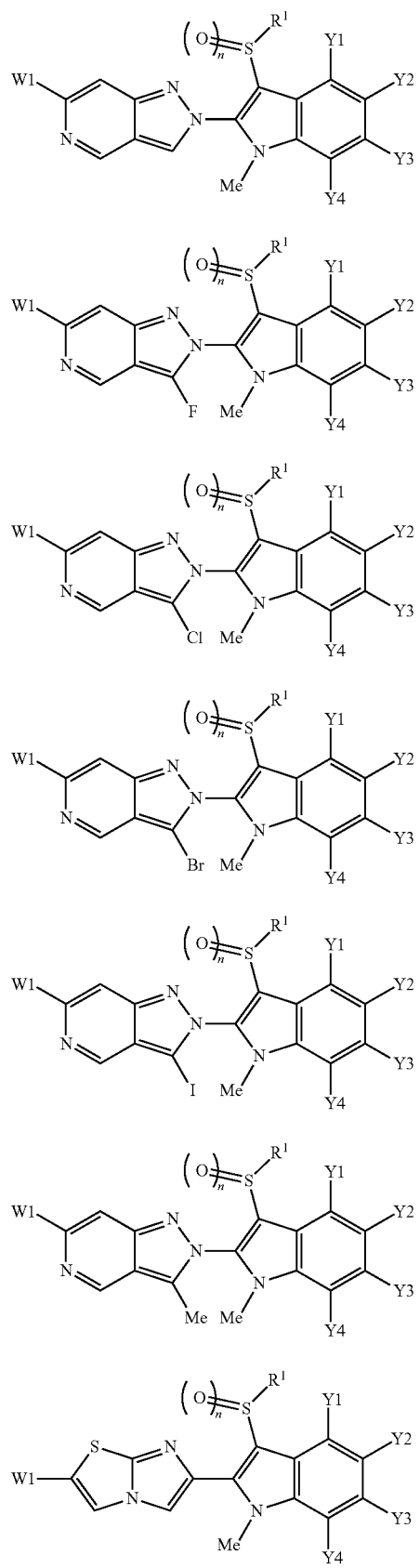
TABLE 5-continued
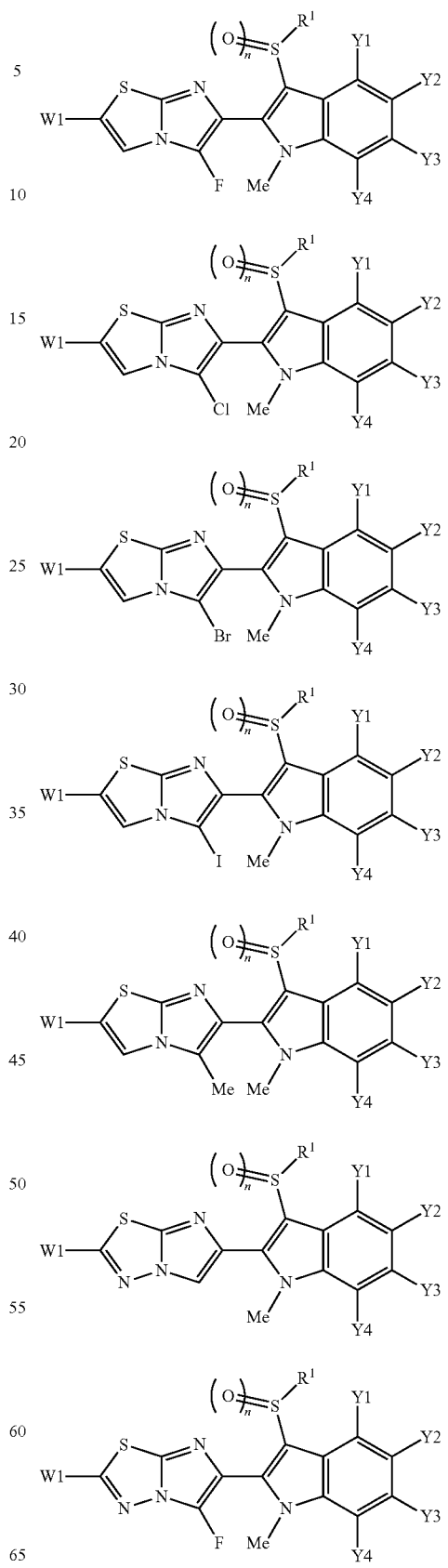

TABLE 5-continued
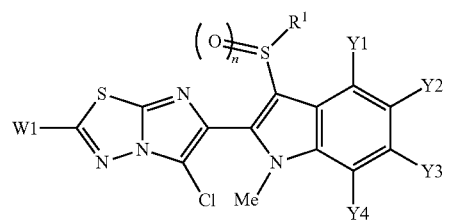
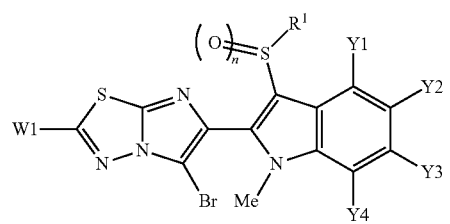
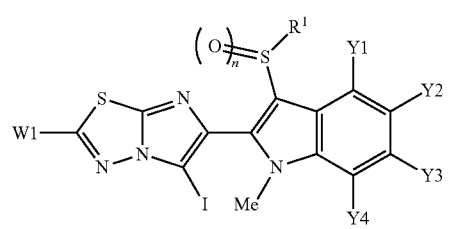
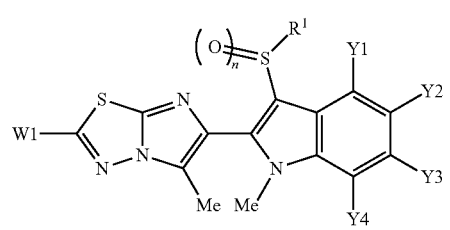
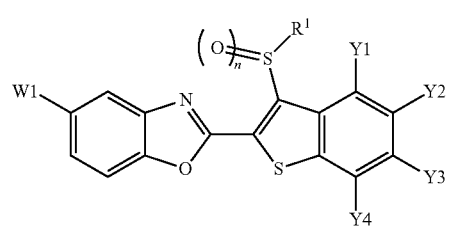
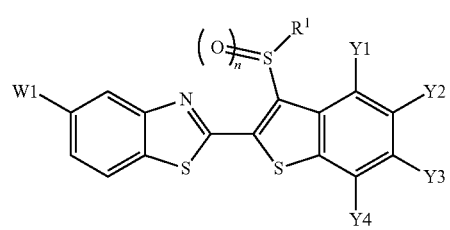
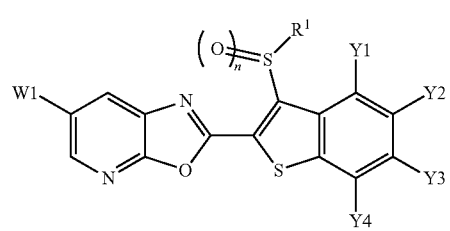
TABLE 5-continued
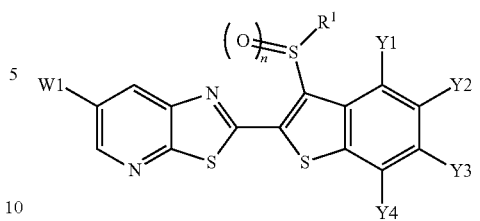
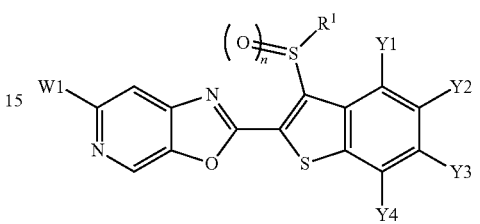
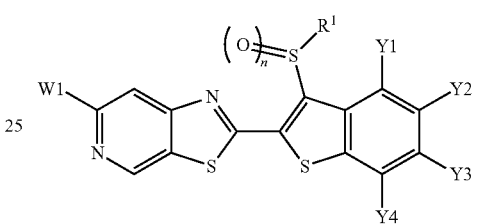
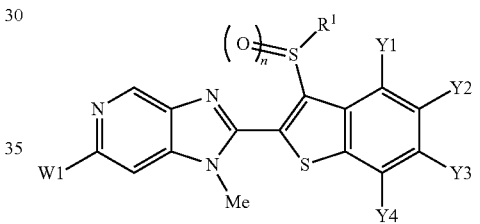
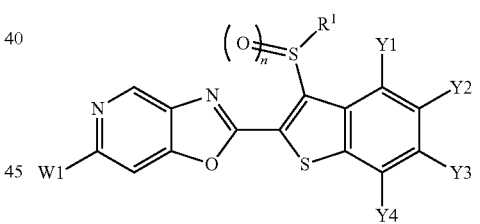
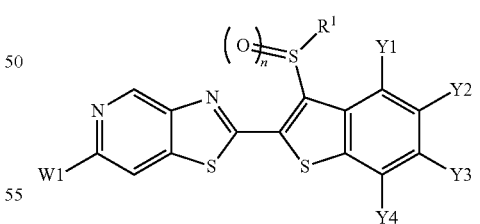
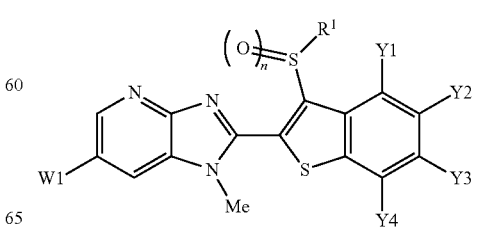

TABLE 5-continued
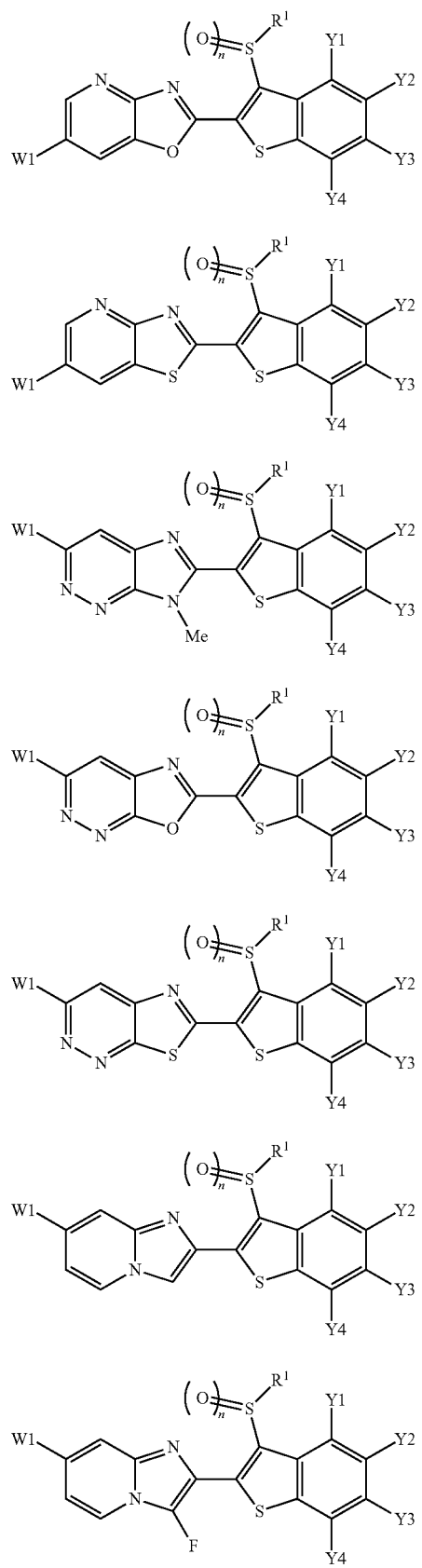
TABLE 5-continued
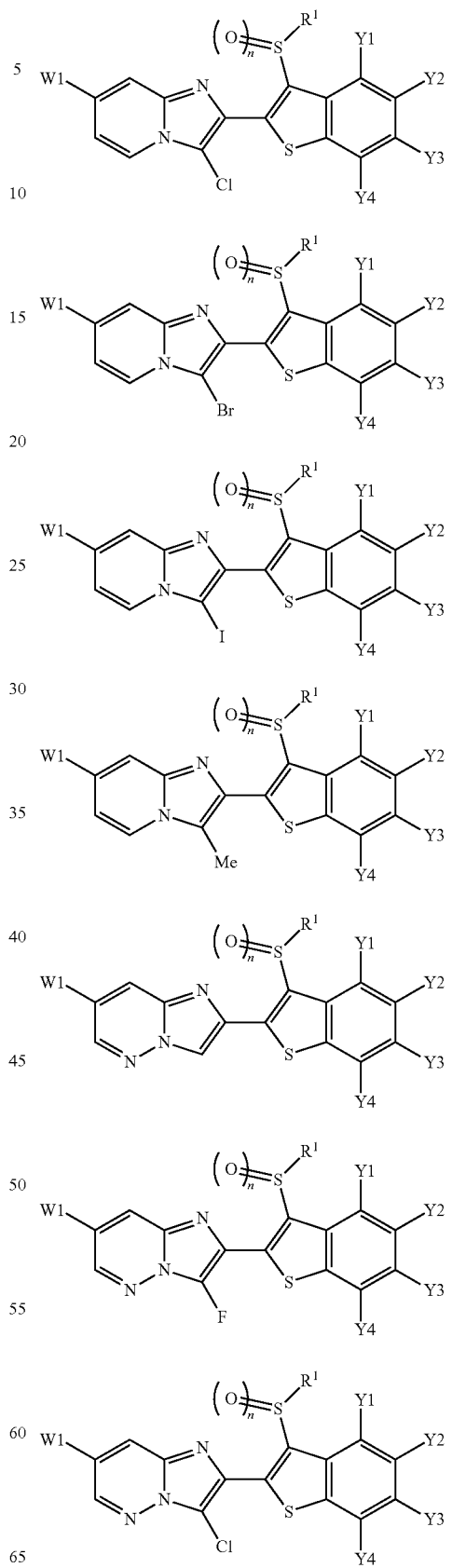

TABLE 5-continued
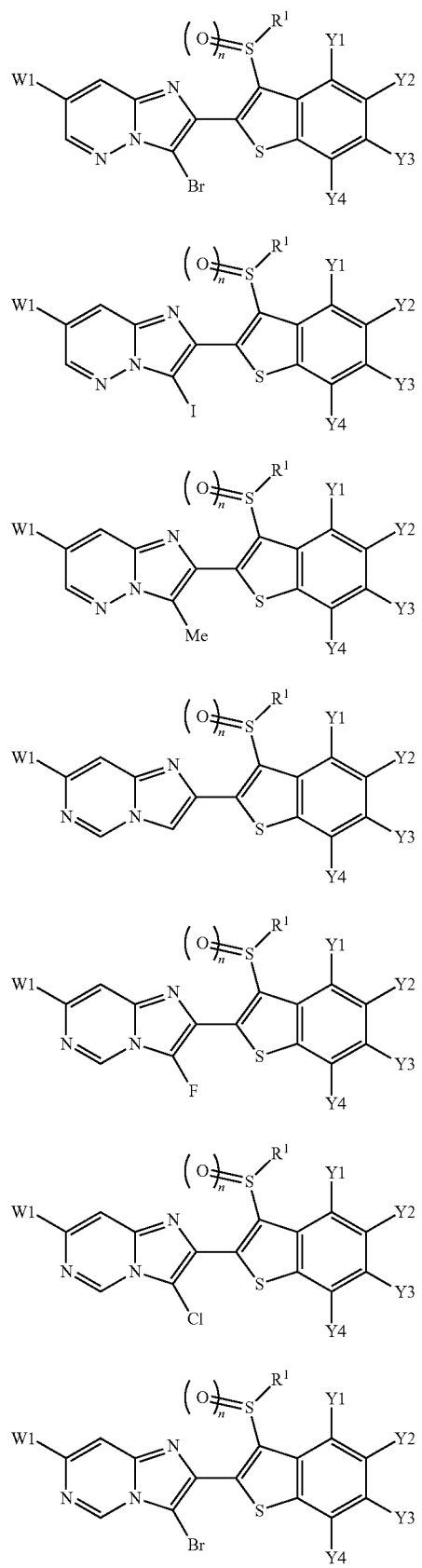
TABLE 5-continued
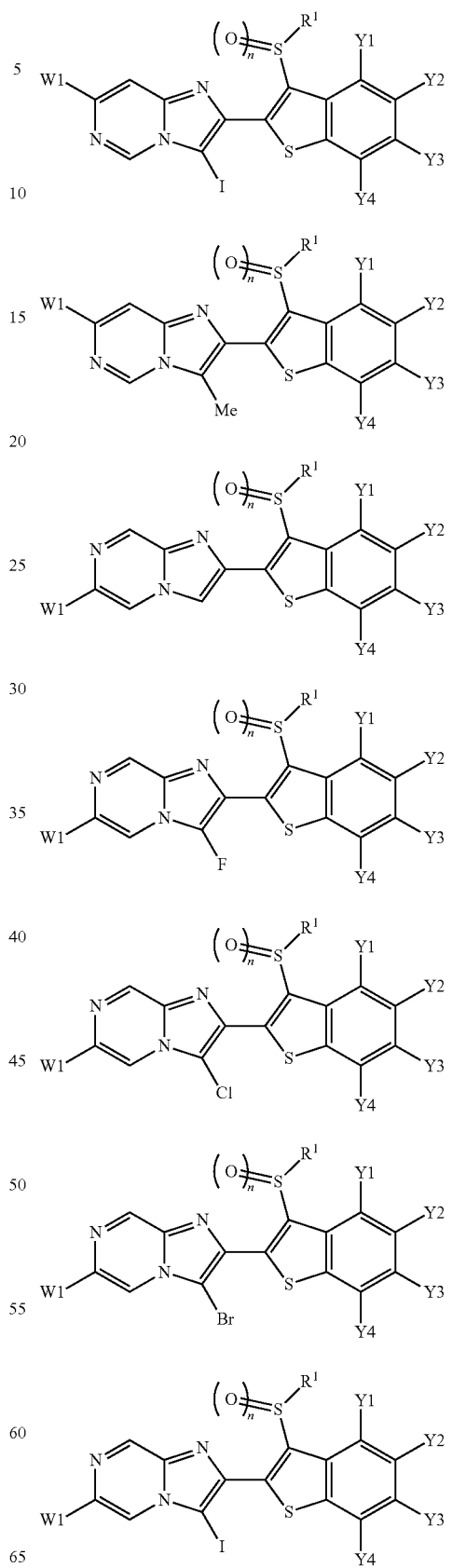

TABLE 5-continued
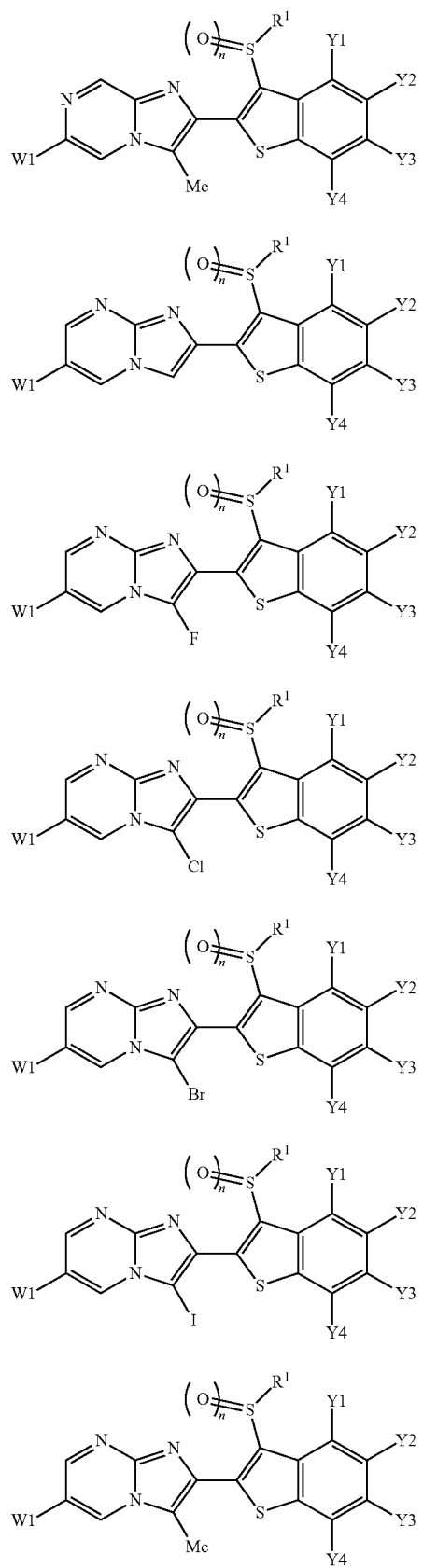
TABLE 5-continued
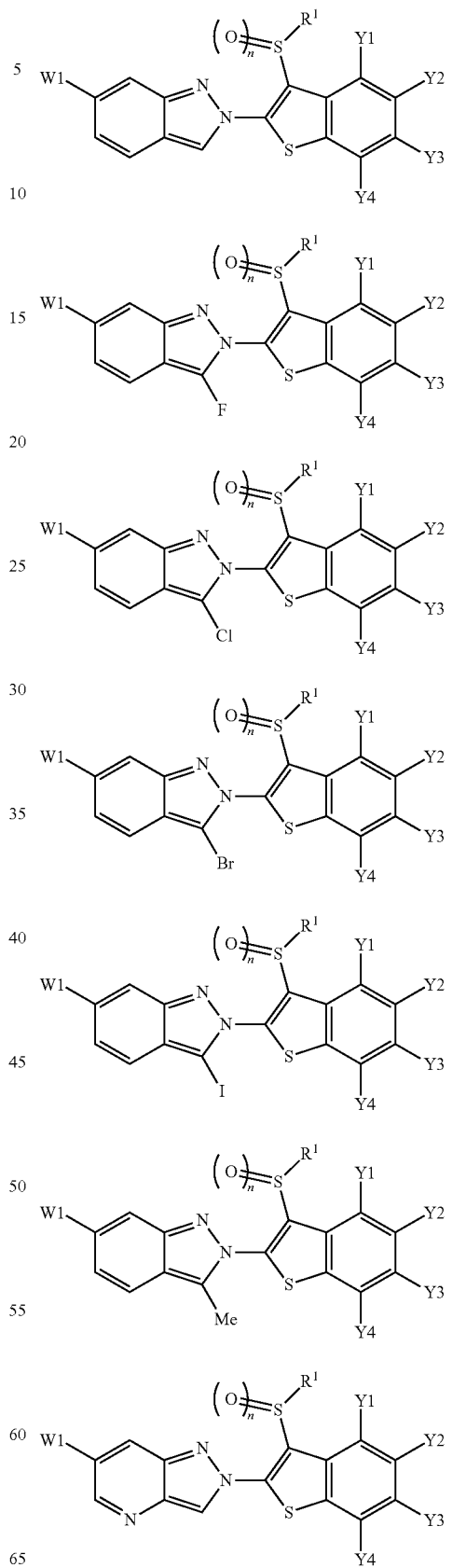

TABLE 5-continued

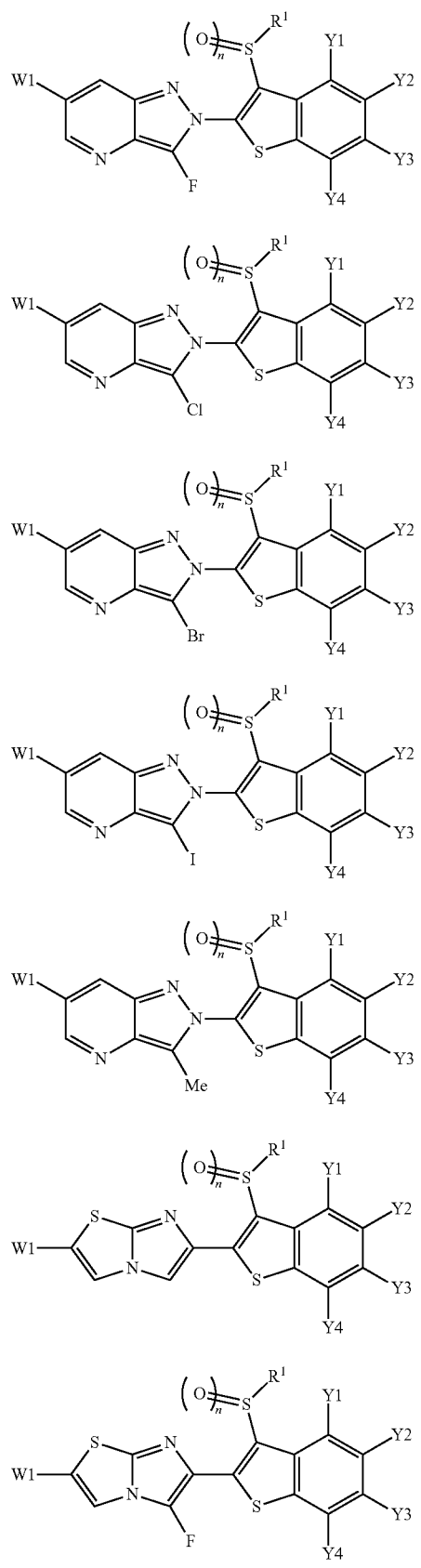

TABLE 5-continued

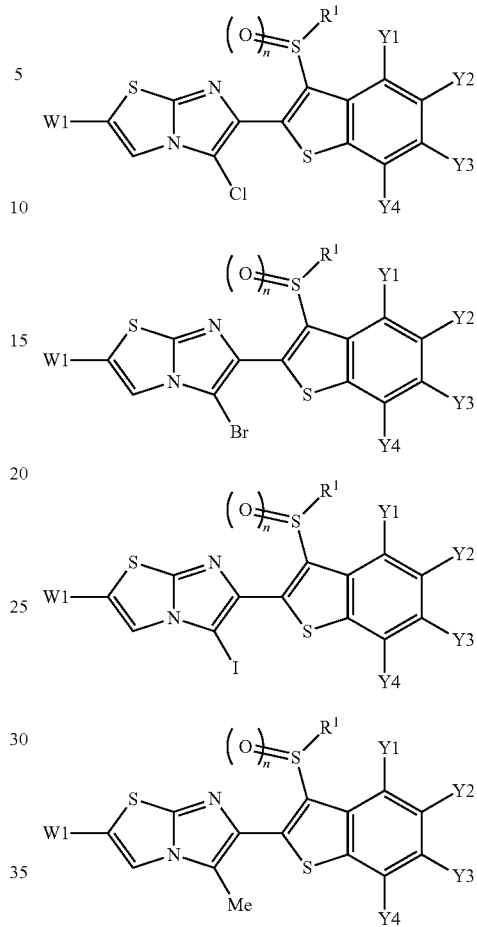

| W1 | R¹ | Y1 | Y2 | Y3 | Y4 | n |
|---|---|---|---|---|---|---|
| CF₃ | Et | H | H | H | I | 2 |
| CF₃ | Et | H | H | H | Me | 0 |
| CF₃ | Et | H | H | H | Me | 1 |
| CF₃ | Et | H | H | H | Me | 2 |
| CF₃ | Et | H | H | H | CF₃ | 0 |
| CF₃ | Et | H | H | H | CF₃ | 1 |
| CF₃ | Et | H | H | H | CF₃ | 2 |
| CF₃ | Et | H | H | H | CF₂CF₃ | 0 |
| CF₃ | Et | H | H | H | CF₂CF₃ | 1 |
| CF₃ | Et | H | H | H | CF₂CF₃ | 2 |
| CF₃ | Et | H | H | H | CF(CF₃)₂ | 0 |
| CF₃ | Et | H | H | H | CF(CF₃)₂ | 1 |
| CF₃ | Et | H | H | H | CF(CF₃)₂ | 2 |
| CF₃ | Et | H | H | H | SMe | 0 |
| CF₃ | Et | H | H | H | SMe | 1 |
| CF₃ | Et | H | H | H | SMe | 2 |
| CF₃ | Et | H | H | H | SOMe | 0 |
| CF₃ | Et | H | H | H | SOMe | 1 |
| CF₃ | Et | H | H | H | SOMe | 2 |
| CF₃ | Et | H | H | H | SO₂Me | 0 |
| CF₃ | Et | H | H | H | SO₂Me | 1 |
| CF₃ | Et | H | H | H | SO₂Me | 2 |
| CF₃ | Et | H | H | H | OMe | 0 |
| CF₃ | Et | H | H | H | OMe | 1 |
| CF₃ | Et | H | H | H | OMe | 2 |
| CF₃ | Et | H | H | H | OCF₃ | 0 |
| CF₃ | Et | H | H | H | OCF₃ | 1 |
| CF₃ | Et | H | H | H | OCF₃ | 2 |
| CF₃ | Et | H | H | H | NO₂ | 0 |
| CF₃ | Et | H | H | H | NO₂ | 1 |
| CF₃ | Et | H | H | H | NO₂ | 2 |
| CF₃ | Et | H | H | H | CN | 0 |
| CF₃ | Et | H | H | H | CN | 1 |

TABLE 5-continued

| | | | | | | |
|---|---|---|---|---|---|---|
| CF3 | Et | H | H | H | CN | 2 |
| CF2CF3 | Et | H | H | H | H | 0 |
| CF2CF3 | Et | H | H | H | H | 1 |
| CF2CF3 | Et | H | H | H | H | 2 |
| CF2CF3 | Et | F | H | H | H | 0 |
| CF2CF3 | Et | F | H | H | H | 1 |
| CF2CF3 | Et | F | H | H | H | 2 |
| CF2CF3 | Et | Cl | H | H | H | 0 |
| CF2CF3 | Et | Cl | H | H | H | 1 |
| CF2CF3 | Et | Cl | H | H | H | 2 |
| CF2CF3 | Et | Br | H | H | H | 0 |
| CF2CF3 | Et | Br | H | H | H | 1 |
| CF2CF3 | Et | Br | H | H | H | 2 |
| CF2CF3 | Et | I | H | H | H | 0 |
| CF2CF3 | Et | I | H | H | H | 1 |
| CF2CF3 | Et | I | H | H | H | 2 |
| CF2CF3 | Et | Me | H | H | H | 0 |
| CF2CF3 | Et | Me | H | H | H | 1 |
| CF2CF3 | Et | Me | H | H | H | 2 |
| CF2CF3 | Et | CF3 | H | H | H | 0 |
| CF2CF3 | Et | CF3 | H | H | H | 1 |
| CF2CF3 | Et | CF3 | H | H | H | 2 |
| CF2CF3 | Et | H | F | H | H | 0 |
| CF2CF3 | Et | H | F | H | H | 1 |
| CF2CF3 | Et | H | F | H | H | 2 |
| CF2CF3 | Et | H | Cl | H | H | 0 |
| CF2CF3 | Et | H | Cl | H | H | 1 |
| CF2CF3 | Et | H | Cl | H | H | 2 |
| CF2CF3 | Et | H | Br | H | H | 0 |
| CF2CF3 | Et | H | Br | H | H | 1 |
| CF2CF3 | Et | H | Br | H | H | 2 |
| CF2CF3 | Et | H | I | H | H | 0 |
| CF2CF3 | Et | H | I | H | H | 1 |
| CF2CF3 | Et | H | I | H | H | 2 |
| CF2CF3 | Et | H | Me | H | H | 0 |
| CF2CF3 | Et | H | Me | H | H | 1 |
| CF2CF3 | Et | H | Me | H | H | 2 |
| CF2CF3 | Et | H | CF3 | H | H | 0 |
| CF2CF3 | Et | H | CF3 | H | H | 1 |
| CF2CF3 | Et | H | CF3 | H | H | 2 |
| CF2CF3 | Et | H | CF2CF3 | H | H | 0 |
| CF2CF3 | Et | H | CF2CF3 | H | H | 1 |
| CF2CF3 | Et | H | CF2CF3 | H | H | 2 |
| CF2CF3 | Et | H | CF(CF3)2 | H | H | 0 |
| CF2CF3 | Et | H | CF(CF3)2 | H | H | 1 |
| CF2CF3 | Et | H | CF(CF3)2 | H | H | 2 |
| CF2CF3 | Et | H | SMe | H | H | 0 |
| CF2CF3 | Et | H | SMe | H | H | 1 |
| CF2CF3 | Et | H | SMe | H | H | 2 |
| CF2CF3 | Et | H | SOMe | H | H | 0 |
| CF2CF3 | Et | H | SOMe | H | H | 1 |
| CF2CF3 | Et | H | SOMe | H | H | 2 |
| CF2CF3 | Et | H | SO2Me | H | H | 0 |
| CF2CF3 | Et | H | SO2Me | H | H | 1 |
| CF2CF3 | Et | H | SO2Me | H | H | 2 |
| CF2CF3 | Et | H | OMe | H | H | 0 |
| CF2CF3 | Et | H | OMe | H | H | 1 |
| CF2CF3 | Et | H | OMe | H | H | 2 |
| CF2CF3 | Et | H | OCF3 | H | H | 0 |
| CF2CF3 | Et | H | OCF3 | H | H | 1 |
| CF2CF3 | Et | H | OCF3 | H | H | 2 |
| CF2CF3 | Et | H | NO2 | H | H | 0 |
| CF2CF3 | Et | H | NO2 | H | H | 1 |
| CF3+LCF2 | Et | H | NO2 | H | H | 2 |
| CF2CF3 | Et | H | CN | H | H | 0 |
| CF2CF3 | Et | H | CN | H | H | 1 |
| CF2CF3 | Et | H | CN | H | H | 2 |
| CF2CF3 | Et | H | H | F | H | 0 |
| CF2CF3 | Et | H | H | F | H | 1 |
| CF2CF3 | Et | H | H | F | H | 2 |
| CF2CF3 | Et | H | H | Cl | H | 0 |
| CF2CF3 | Et | H | H | Cl | H | 1 |
| CF2CF3 | Et | H | H | Cl | H | 2 |
| CF2CF3 | Et | H | H | Br | H | 0 |
| CF2CF3 | Et | H | H | Br | H | 1 |
| CF2CF3 | Et | H | H | Br | H | 2 |
| CF2CF3 | Et | H | H | I | H | 0 |
| CF2CF3 | Et | H | H | I | H | 1 |
| CF2CF3 | Et | H | H | I | H | 2 |
| CF2CF3 | Et | H | H | Me | H | 0 |
| CF2CF3 | Et | H | H | Me | H | 1 |
| CF2CF3 | Et | H | H | Me | H | 2 |
| CF2CF3 | Et | H | H | CF3 | H | 0 |
| CF2CF3 | Et | H | H | CF3 | H | 1 |
| CF2CF3 | Et | H | H | CF3 | H | 2 |
| CF2CF3 | Et | H | H | CF2CF3 | H | 0 |
| CF2CF3 | Et | H | H | CF2CF3 | H | 1 |
| CF2CF3 | Et | H | H | CF2CF3 | H | 2 |
| CF2CF3 | Et | H | H | CF(CF3)2 | H | 0 |
| CF2CF3 | Et | H | H | CF(CF3)2 | H | 1 |
| CF2CF3 | Et | H | H | CF(CF3)2 | H | 2 |
| CF2CF3 | Et | H | H | SMe | H | 0 |
| CF2CF3 | Et | H | H | SMe | H | 1 |
| CF2CF3 | Et | H | H | SMe | H | 2 |
| CF2CF3 | Et | H | H | SOMe | H | 0 |
| CF2CF3 | Et | H | H | SOMe | H | 1 |
| CF2CF3 | Et | H | H | SOMe | H | 2 |
| CF2CF3 | Et | H | H | SO2Me | H | 0 |
| CF2CF3 | Et | H | H | SO2Me | H | 1 |
| CF2CF3 | Et | H | H | SO2Me | H | 2 |
| CF2CF3 | Et | H | H | OMe | H | 0 |
| CF2CF3 | Et | H | H | OMe | H | 1 |
| CF2CF3 | Et | H | H | OMe | H | 2 |
| CF2CF3 | Et | H | H | OCF3 | H | 0 |
| CF2CF3 | Et | H | H | OCF3 | H | 1 |
| CF2CF3 | Et | H | H | OCF3 | H | 2 |
| CF2CF3 | Et | H | H | NO2 | H | 0 |
| CF2CF3 | Et | H | H | NO2 | H | 1 |
| CF2CF3 | Et | H | H | NO2 | H | 2 |
| CF2CF3 | Et | H | H | CN | H | 0 |
| CF2CF3 | Et | H | H | CN | H | 1 |
| CF2CF3 | Et | H | H | CN | H | 2 |
| CF2CF3 | Et | H | H | H | F | 0 |
| CF2CF3 | Et | H | H | H | F | 1 |
| CF2CF3 | Et | H | H | H | F | 2 |
| CF2CF3 | Et | H | H | H | Cl | 0 |
| CF2CF3 | Et | H | H | H | Cl | 1 |
| CF2CF3 | Et | H | H | H | Cl | 2 |
| CF2CF3 | Et | H | H | H | Br | 0 |
| CF2CF3 | Et | H | H | H | Br | 1 |
| CF2CF3 | Et | H | H | H | Br | 2 |
| CF2CF3 | Et | H | H | H | I | 0 |
| CF2CF3 | Et | H | H | H | I | 1 |
| CF2CF3 | Et | H | H | H | I | 2 |
| CF2CF3 | Et | H | H | H | Me | 0 |
| CF2CF3 | Et | H | H | H | Me | 1 |
| CF2CF3 | Et | H | H | H | Me | 2 |
| CF2CF3 | Et | H | H | H | CF3 | 0 |
| CF2CF3 | Et | H | H | H | CF3 | 1 |
| CF2CF3 | Et | H | H | H | CF3 | 2 |
| CF2CF3 | Et | H | H | H | CF2CF3 | 0 |
| CF2CF3 | Et | H | H | H | CF2CF3 | 1 |
| CF2CF3 | Et | H | H | H | CF2CF3 | 2 |
| CF2CF3 | Et | H | H | H | CF(CF3)2 | 0 |
| CF2CF3 | Et | H | H | H | CF(CF3)2 | 1 |
| CF2CF3 | Et | H | H | H | CF(CF3)2 | 2 |
| CF2CF3 | Et | H | H | H | SMe | 0 |
| CF2CF3 | Et | H | H | H | SMe | 1 |
| CF2CF3 | Et | H | H | H | SMe | 2 |
| CF2CF3 | Et | H | H | H | SOMe | 0 |
| CF2CF3 | Et | H | H | H | SOMe | 1 |
| CF2CF3 | Et | H | H | H | SOMe | 2 |
| CF2CF3 | Et | H | H | H | SO2Me | 0 |
| CF2CF3 | Et | H | H | H | SO2Me | 1 |
| CF2CF3 | Et | H | H | H | SO2Me | 2 |
| CF2CF3 | Et | H | H | H | OMe | 0 |
| CF2CF3 | Et | H | H | H | OMe | 1 |
| CF2CF3 | Et | H | H | H | OMe | 2 |
| CF2CF3 | Et | H | H | H | OCF3 | 0 |
| CF2CF3 | Et | H | H | H | OCF3 | 1 |
| CF2CF3 | Et | H | H | H | OCF3 | 2 |
| CF2CF3 | Et | H | H | H | NO2 | 0 |
| CF2CF3 | Et | H | H | H | NO2 | 1 |
| CF2CF3 | Et | H | H | H | NO2 | 2 |
| CF2CF3 | Et | H | H | H | CN | 0 |
| CF2CF3 | Et | H | H | H | CN | 1 |
| CF2CF3 | Et | H | H | H | CN | 2 |

The pesticides herein mean pesticides for controlling harmful arthropods in agricultural fields or in zootechnical/ hygienic fields (internal/external parasites in or on mammals and birds as livestock and pets, and domestic or industrial hygienic insects/nuisance insects). Further, the agricultural chemicals herein mean insecticides/acaricides, nematicides, herbicides and fungicides in agricultural fields.

The insects, mites, crustaceans, mollusks and nematodes that the compounds of the present invention can control specifically include the following organisms, but the present invention is not restricted thereto.

Insects of the order Lepidoptera such as *Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconsoersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodotera exigua, Spodoptera frugiperda, Spodoptera littoralis, Spodoptera litura, Spodoptera depravata, Trichoplusia ni, Endopiza viteana, Manduca guinguemaculata* and *Manduca sexta*.

Insects of the order Thysanoptera such as *Frankliniella intonsa, Frankliniella occidentalis, Heliothrips haemorrhoidalis, Scirtothrips dorsalis, Thrips palmi, Thrips tabaci* and *Ponticulothrips diospyrosi*.

Insects of the order Hemiptera such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scoiophora lurida, Cleltus punctiger, Leptcorisa chinensis, Riptortus clavatus, Rhopalus msculatus, Cavelerius saccharivorus, Togo hemipterus, Dysdercus sibiricum, Stenotus rubrovittatus, Trigonotylus caelestialium, Arboridia apicalis, Balclutha saltuella, Epicanthus stramineus, Empoasca fabae, Empoasca nipponica, Empoasca onukii, Empoasca sakaii, Macrosteles striifrons, Nephotettix cinctinceps, Psuedatomnoscelis seriatus, Laodelphax striatella, Nilaparvata lugens, Sogatella furcifera, Diaphorina citri, Psylla pyrisuga, Alerocanthus spiniferus, Bemnisia argentifolii, Bemisia tabaci, Dialeurodes citri, Trialeurodes vaporariorum, Viteus vitifoii, Aphis gossypii, Apis spiraecola, Myzus persicae, Toxoptera aurantii, Drosicha corpulenta, Icerya purchasi, Penacoccus solani, Planococcus citri, Planococcus kuraunhhiae, Pseudococcus comstocki, Ceroplastes ceriferus, Ceroplastes rubens, Aonidiella auratii, Comstockaspis perniciosa, Fiorinia theae, Pseudaonidia paeoniae, Pseudaulacaspis petagona, Pseudaulacaspis prunicola, Unaspis euonymi, Unaspis yanonensis* and *Cimex lectularius*.

Insects of the order Coleoptera such as *Anomala cuprea, Anomala rufocuprea, Gametis jucunda, Heptophylla picea Popillia japonica, Lepinotarsa decemlineata, Melanotus fortumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiortiynchus sulcatus, Sitophilus granarius, Sitophilus zeamais, Sphenophorus venatus vestitus* and *Paederus fuscipes*.

Insects of the order Diptera such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis, Glossina morsitans, Prosimulium yezoensis, Tabanus trigonus, Telmatoscopus albipunctatus, Leptoconops nipponensis, Culex pipiens pallens, Aedes aegypti, Aedes albopicutus* and *Anopheles hyracanus sinesis*.

Insects of the order Hymenoptera such as *Apethymus kuri, Athalia rosae, Arge pagana, Neodiprion sertifer, Dryocosmus kuriphilus, Eciton burchelli, Eciton schmitti, Camponotus japonicus, Vespa mandarina, Myrmecia* spp., *Solenopsis* spp. and *Monomorium pharaonis*.

Insects of the order Orthoptera such as *Teleogryllus emma, Gryllotalpa orientalis, Locusta migratoria, Oxya yezoensis* and *Schistocerca gregaria*.

Insects of the order Collembola such as *Onychiurus folsomi, Onychiurus sibiricus* and *Bourletiella hortensis*.

Insects of the order Dictyoptera such as *Periplaneta fuliginosa, Periplaneta japonica* and *Blattella germanica*.

Insects of the order Isoptera such as *Coptotermes formosanus, Reticulitermes speratus* and *Odontotermes formosanus*.

Insects of the order Siphonaptera such as *Ctenocephalidae fells, Ctenocephalides canis, Echidnophaga gallinacea, Pulex irritans* and *Xenopsylla cheopis*.

Insects of the order Mallophaga such as *Menacanthus stramineus* and *Bovicola bovis*.

Insects of the order Anoplura such as *Haematopinus eurysternus, Haematopinus suis, Linognathus vituli* and *Solenopotes capillatus*.

Tarsonemidae mites such as *Phytonemus pallidus, Polyphagotarsonemus latus* and *Tarsonemus bilobatus*.

Eupodidae mites such as *Penthaleus erythrocephalus* and *Penthaleus major*.

Tetranychidae mites such as *Oligonychus shinkajii, Panonychus citri, Panonychus mori, Panonychus ulmi, Tetranychus kanzawai* and *Tetranychus urticae*.

Eriophyidae mites such as *Acaphylla theavagrans, Aceria tulipae, Aculops lycopersici, Aculops pelekassi, Aculus schlechtendali, Eriophyes chibaensis* and *Phyllocoptruta oleivora*.

Acaridae mites such as *Rhizoglyphus robini, Tyrophaqus putrescentiae* and *Tyrophagus similis*.

Bee mites such as *Varroa jacobsoni*.

Ticks such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp. and *Dermacentor* spp.

Mites of the suborder Mesostigmata such as red mite (*Dermanyssus gallinae*), tropical rat mite (*Ornithonyssus bacoti*) and northern fowl mite (*Ornithonyssus sylviarum*).

Cheyletidae mites such as *Chevletiella yasguri* and *Cheyletiella blakei*.

Demodicidae mites such as *Demodex canis* and *Demodex cati*.

Psoroptidae mites such as *Psoroptes ovis*.

Sarcoptidae mites such as *Sarcoptes scabiei*, *Notoedres cati* and *Knemidocoptes* spp.

Crustaceans such as *Armadillidium vulgare*.

Gastropods such as *Pomacea canaliculata*, *Achatina fulica*, *Meghimatium bilineatum*, *Limax Valentiana*, *Acusta despecta sieboldiana* and *Euhadra peliomphala*.

Nematodes such as *Prathylenchus coffeae*, *Prathylenchus penetrans*, *Prathylenchus vulnus*, *Globodera rostochiensis*, *Heterodera glycines*, *Meloidogyne hapla*, *Meloidogyne incognita*, *Aphelenchoides besseyi* and *Bursaphelenchus xylophilus*.

Adult flies such as horn fly (*Haematobia irritans*), horse fly (*Tabanus* spp.), *Stomoxys calcitrans*, blackfly (*Simulium* spp.), deer fly (*Chrysops* spp.), louse fly (*Melophagus ovinus*) and tsetse fly (*Glossina* spp.).

Parasitic worms such as sheep bot fly (*Oestrus ovis*, *Cuterebra* spp.), blowfly (*Phaenicia* spp.), screwworm (*Cochliomyia hominivorax*), warble fly (*Hypoderma* spp.), fleeceworm and *Gastrophilus*.

Mosquitos such as *Culex* spp., *Anopheles* spp. and *Aedes* spp.

The internal, livestock, poultry or pet parasites that the compounds of the present invention can control specifically include the following internal pests, but the present invention is not restricted thereto.

Nematodes of the genera *Haemonchus*, *Trichostronqylus*, *Ostertagia*, *Nematodirus*, *Cooperia*, *Ascaris*, *Bunostomum*, *Oesophagostomum*, *Chabertia*, *Trichuris*, *Storongylus*, *Trichonema*, *Dictyocaulus*, *Capillaria*, *Heterakis*, *Toxocara*, *Ascaridia*, *Oxyuris*, *Ancylostoma*, *Uncinaria*, *Toxascaris*, *Parascaris*, and the like.

Nematodes of the family Filariidae such as the genera *Wuchereria*, *Brugia*, *Onchoceca*, *Dirofilaria*, *Loa*, and the like.

Nematodes of the family Dracunculidae such as the genus *Dracunculus*.

Cestodes such as *Dipylidium caninum*, *Taenia taeniaeformis*, *Taenia solium*, *Taenia saginata*, *Hymenolepis diminuta*, *Moniezia benedeni*, *Diphyllobothrium latum*, *Diphyllobothrium erinacei*, *Echinococcus granulosus* and *Echinococcus multilocularis*.

Trematodes such as *Fasciola hepatica*, *F. gigantica*, *Paragonimus westermanii*, *Fasciolopsic bruski*, *Eurytrema pancreaticum*, *E. coelomaticum*, *Clonorchis sinensis*, *Schistosoma japonicum*, *Schistosoma haematobium* and *Schistosoma mansoni*.

*Eimeria* spp. such as *Eimeria tenella*, *Eimeria acervulina*, *Eimeria brunetti*, *Eimeria maxima*, *Eimeria necatrix*, *Eimeria bovis* and *Eimeria ovinoidalis*.

*Trypanosomsa cruzi*, *Leishmania* spp., *Plasmodium* spp., *Babesis* spp., *Trichomonadidae* spp., *Histomanas* spp., *Giardia* spp., *Toxoplasma* spp., *Entamoeba histolytica* and *Theileria* spp.

The compounds of the present invention are effective against pests that have acquired resistance to conventional insecticides such as organic phosphorus compounds, carbamate compounds or pyrethroid compounds.

That is, the compounds of the present invention can effectively control pests such as insects of the order Collembola, the order Dictyoptera, the order Orthoptera, the order Isoptera, the order Thysanoptera, the order Hemiptera, the order Lepidoptera, the order Coleoptera, the order Hymenoptera, the order Diptera, the order Aphaniptera, the order Anoplura, Acari, gastropods and nematodes at low doses. On the other hand, the compounds of the present invention have a quite advantageous feature that they are almost harmless to mammals, fishes, crustaceans and beneficial insects (useful insects such as honey bees and bumblebees and natural enemies such as aphelinids, Aphidiinae, tachina flies, Orius spp., Phytoseiidae spp. etc.).

The compounds of the present invention may be used in any dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet or an emulsifiable gel usually after mixed with an appropriate solid carrier or liquid carrier, and if necessary, with a surfactant, a penetrant, a spreader, a thickener, an anti-freezing agent, a binder, an anti-caking agent, a disintegrant, an antifoaming agent, a preservative, a stabilizer or the like. A formulation in an arbitrary dosage form may be sealed in water-soluble packaging such as a water-soluble capsule or a water-soluble film, for labor saving or improved safety.

As solid carriers, natural minerals such as quartz, calcite, meerschaum, dolomite, chalk, kaolinite, pyrophyllite, sericite, halloysite, methahalloysite, kibushi day, gairome clay, pottery stone, zeeklite, allophane, Shirasu, mica, talc, bentonite, activated clay, acid clay, pumice, attapulgite, zeolite and diatomaceous earth; calcined natural minerals such as calcined clay, pearlite, Shirasu-balloons, vermiculite, attapulgus clay and calcined diatomaceous earth; inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride, saccharides such as glucose, fructose, sucrose and lactose; polysaccharides such as starch, cellulose powder and dextrin; organic substances such as urea, urea derivatives, benzoic acid and benzoic acid salts; plants such as wood flour, powdered cork, corncob, walnut shell and tobacco stems, fly ash, white carbon (such as hydrated synthetic silica, anhydrous synthetic silica and hydrous synthetic silicate), fertilizers and the like may be mentioned.

As liquid carriers, aromatic hydrocarbons such as xylene, alkyl ($C_9$ or $C_{10}$ etc.) benzene, phenylxylylethane and alkyl ($C_1$ or $C_3$ etc.) naphthalene; aliphatic hydrocarbons such as machine oil, normal paraffin, isoparaffin and naphthene; mixtures of aromatic hydrocarbons and aliphatic hydrocarbons such as kerosene; alcohols such as ethanol, isopropanol, cyclohexanol, phenoxyethanol and benzyl alcohol; polyhydric alcohols such as ethylene glycol, propylene glycol, diethylene glycol, hexylene glycol, polyethylene glycol and polypropylene glycol; ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether; ketones such as acetophenone, cyclohexanone and γ-butyrolactone; esters such as fatty acid methyl esters, dialkyl succinates, dialkyl glutamate, dialkyl adipates and dialkyl phthalates; acid amides such as N-alkyl ($C_1$, $C_8$ or $C_{12}$ etc.) pyrrolidone; fats and oils such as soybean oil, linseed oil, rapeseed oil, coconut oil, cottonseed oil and castor oil; dimethyl sulfoxide; water and the like may be mentioned.

These solid and liquid carriers may be used alone or in combinations of two or more.

As surfactants, nonionic surfactants such as polyoxyethylene alkyl ether, polyoxyethylene alkyl (mono or di) phenyl ether, polyoxyethylene(mono, di or tri)styrylphenyl ether, polyoxyethylenepolyoxypropylene block copolymers, polyoxyethylene fatty acid (mono or di) ester, sorbitan fatty acid ester, polyoxyethylene sorbitan fatty acid ester, ethylene oxide adducts of castor oil, acetylene glycol, acetylene alcohol, ethylene oxide adducts of acetylene glycol, ethylene oxide adducts of acetylene alcohol and alkyl glycosides; anionic surfactants such as alkyl sulfate salts, alkylbenzenesulfonic acid salts, lignin sulfonate, alkylsulfosuccinic acid salts, naphthalenesulfonic acid salts, alkylnaphthalenesulfonic acid salts, salts of naphthalenesulfonic acid-formalin condensates, salts of alkylnaphthalenesulfonic acid-formalin condensates, polyoxyethylene alkyl ether sulfate or phosphate salts, polyoxyethylene (mono or di) alkylphenyl ether sulfate or phosphate salts, polyoxyethylene (mono, di or tri) styrylphenyl ether sulfate or phosphate salts, polycarboxylic acid salts (such as polyacrylates, polymaleates and copolymers of maleic acid and an olefin) and polystyrenesulfonic acid salts; cationic surfactants such as alkylamine salts and alkyl quaternary ammonium salts; amphoteric surfactants such as amino acid types and betaine types, silicone surfactants; and fluorine surfactants may be mentioned.

The amount of these surfactants is usually preferably from 0.05 to 20 parts by weight per 100 parts by weight of the agent of the present invention, though there is no particular restrictions. These surfactants may be used alone or in combination of two or more.

The suitable application dose of the compounds of the present invention is generally about from 0.005 to 50 kg per hectare (ha) in terms of the active ingredient, though it varies depending on the application situation, the application season, the application method and the cultivated crop.

When the compounds of the present invention are used to control external or internal parasites in or on mammals and birds as farm animals/poultry and pet animals, the compounds of the present invention may be administered in an effective amount together with pharmaceutically acceptable additives orally, parenterally by injection (intramuscular, subcutaneously, intravenously or intraperitoneally); percutaneously by dipping, spraying, bathing, washing, pouring-on and spotting-on and dusting, or intranasally. The compounds of the present invention may be administered through molded articles such as chips, plates, bands, collars, ear marks, limb bands and ID tags.

The compounds of the present invention are administered in an arbitrary dosage form suitable for the administration route.

In a case where the compounds of the present invention are used to control external or internal parasites, the suitable application dose of the compound of the present invention represented by the formula (1) as an active ingredient is generally from 0.01 to 100 mg/kg body weight, preferably from 0.01 to 50 mg/kg body weight of a target animal, though it varies depending on e.g. the type of pests to be controlled, the type of the target animal, or the application method. Particularly with respect to application to a dog, the suitable application dose is generally from 1 to 5,000 mg/kg body weight, preferably from 1 to 100 mg/g body weight of a target dog, though it varies depending on the type or the age of the target dog, or the external parasites to be controlled.

In a case where the compounds of the present invention are used to control external or internal parasites, the application interval may be optionally set usually within a range of from daily to annually, though it varies depending on e.g. the type of pests to be controlled, the type of the target animal, or the application method. The application interval is preferably from once a week to every six months, more preferably daily (every 24 hours), monthly, once a month, every two months, or every three months.

In a case where the compounds of the present invention are used to control external paracites on a dog, with respect to the timing of application of the compound of the present invention to the dog, the compound of the present invention may be orally administered to the dog 30 minutes before start of feeding or 120 minutes after completion of feeding. "30 minutes before start of feeding or 120 minutes after completion of feeding" here is based on an action of the dog to take nutritious food. For example, in a case where the dog feeding time is 20 minutes, the time specified is 30 minutes before start of feeding to 120 minutes after completion of feeding, that is, 170 minutes in total. A case where feeding is suspended, the compound of the present invention is orally administered and feeding is restarted, is included. In this specification, feeding means an action of an animal to take food.

The number of feeding of a dug is usually three to four times a day in the case of a dog of less than six months old, twice to three times a day in the case of a dog of six months to less than one year old, twice a day in the case of an adult dog of about one to five years old, and twice to three times a day in the case of an old dog of 6 years old or older, though it varies depending on the type or the age of the dog or the habit. In the present invention, feeding means an action of an animal to take nutritious food, and does not include an action to give food and the like to a dog for training or breeding.

The dosage form may be a solid preparation such as dusts, granules, wettable powders, pellets, tablets, boluses, capsules and a molded article containing an active ingredient; a liquid preparation such as an injection fluid, an oral liquid, a liquid preparation applied to the skin or coelom; a solution preparation such as a pour-on preparation, a spot-on preparation, flowables and emulsions; and a semisolid preparation such as an ointment and gels.

In a case where the compounds of the present invention are orally administered, the dosage form may, for example, be a solid preparation such as tablets, chewables, capsules, pills, boluses, granules and powders; a semisolid preparation such as pastes and gels; and a liquid preparation such as drinks.

In the case of percutaneous administration, the dosage form may, for example, be a solid preparation such as powders; a semisolid preparation such as a cream, a salve and ointment, pastes and gels; and a liquid preparation such as a spary, aerosols, solutions and emulsions, suspensions, and lotions.

Further, in the case of administration by injection, the dosage form may, for example, be a liquid preparation such as solutions and emulsions, and suspensions, and in the case of intranasal administration, the dosage form may, for example, be a liquid preparation such as aerosols. In the case of spraying over an environment where animals are bred, such as a stable, the dosage form may, for example, be a solid preparation such as wettale powders, dusts or granules; and a liquid preparation such as emulsions and suspension concentrates.

The formulation to be used for parasiticides of the present invention is not limited to such dosage forms.

The solid preparation may be orally administered as it is, or may be percutaneously administered or sprayed over an environment where animals are bred, such as a stable, after dilution with water.

The solid preparation to be orally administered, may be prepared by mixing the compound represented by the formula (1) or its salt and one or more vehicles or binders suitable for oral administration, and as the case requires, physiologically acceptable additives such as a lubricant, a disintegrant, a dye and a pigment, and forming the mixture into a desired shape.

The vehicle and the binder may, for example, be a saccharide or saccharide derivative such as lactose, sucrose, mannitol or sorbitol; a starch such as corn starch, wheat startch, rice starch or potato starch; a cellulse or cellulose derivative such as methyl cellulose, carboxymethyl cellulose, hydroxyethyl cellulose, hydroxypropyl cellulose or hydroxypropylmethyl cellulose; a protein or protein derivative such as zein or gelatin; honey, gum arabic glue, or a synthetic polymer compound such as polyvinyl alcohol or polyvinyl pyrolidone.

The lubricant may, for example, be magnesium stearate, and the disintegrant may, for example, be cellulose, agar, alginic acid, crosslinked polyvinyl pyrrolidone or a carbonate.

Among solid preparations to be orally administered, in the case of a solid formulation such as chewables, additives which impart a taste, texture or flavor desired by animals to which the preparation is to be administered, may be used. The carriers and additives to be used for the solid preparation of the parasiticidal composition of the present invention are not limited thereto.

The liquid preparation may be administered percutaneously or by injection as it is, or may be administered orally by being mixed with food, percutaneously administered after being diluted with water, or sprayed to an environment where animals are bred, such as a stable.

An injection fluid may be administered intravenously, intramuscularly or subcutaneously. An injection fluid can be prepared by dissolving an active ingredient in an appropriate solvent and, if necessary, adding additives such as a solubilizer, an acid, a base, a buffering salt, an antioxidant and a protectant.

As appropriate solvents, water, ethanol, butanol, benzyl alcohol, glycerin, propylene glycol, polyethylene glycol, N-methylpyrrolidone and mixtures thereof, physiologically acceptable vegetable oils, and synthetic oils suitable for injection may be mentioned.

As solubilizers, polyvinylpyrrolidone, polyoxyethylated castor oil, polyoxyethylated sorbitan ester and the like may be mentioned.

As protectants, benzyl alcohol, trichlorobutanol, p-hydroxybenzoic acid esters, n-butanol and the like may be mentioned.

An oral liquid may be administered directly or after dilution and can be prepared in the same manner as an injection fluid.

A flowable, an emulsion or the like may be administered directly or after dilution percutaneously or by environmental application.

A liquid preparation applied to the skin is administered by dripping, spreading, rubbing, spraying, sprinkling or dipping (soaking, bathing or washing) and can be prepared in the same manner as an injection fluid.

A pour-on preparation and a spot-on preparation are dripped or sprayed to a limited area of the skin so that they permeate through the skin and act systemically. A pour-on preparation and a spot-on preparation can be prepared by dissolving, suspending or emulsifying an active ingredient in an appropriate skin-friendly solvent or solvent mixture. If necessary, additives such as a surfactant, a colorant, an absorbefacient, an antioxidant, a light stabilizer and an adhesive may be added.

As appropriate solvents, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF (N,N-dimethylformamide), liquid paraffin, light liquid paraffin, silicone, dimethylacetamide, N-methylpyrrolidone or 2,2-dimethyl-4-oxy-methylene-1,3-dioxolane may be mentioned.

As absorbefacients, DMSO (dimethyl sulfoxide), isopropyl myristate, pelargonic acid dipropylene glycol, silicone oil, fatty acid esters, triglycerides and aliphatic alcohols may be mentioned.

As antioxidants, sulfites, metabisulfites, ascorbic acid, butylhydroxytoluene, butylhydroxyanisole and tocopherol may be mentioned.

An emulsion may be administered orally, percutaneously or by injection. An emulsion can be prepared by dissolving an active ingredient in a hydrophobic phase or a hydrophilic phase and homogenizing the resulting solution with another liquid phase together with an appropriate emulsifier, and further if necessary with additives such as a colorant, an absorbefacient, a protectant, an antioxidant, a light screen and a thickner.

As hydrophobic phases (oils), paraffin oil, silicone oil, sesame oil, almond oil, castor oil, synthetic triglycerides, ethyl stearate, di-n-butyryl adipate, hexyl laurate, pelargonic acid dipropylene glycol, esters of branched short-chain fatty acids with $C_{16}$-$C_{18}$ saturated fatty acids, isopropyl myristate, isopropyl palmitate, esters of $C_{12}$-$C_{18}$ saturated alcohols with caprylic/capric acid, isopropyl stearate, oleyl oleate, decyl oleate, ethyl oleate, ethyl lactate, fatty acid ester waxes, dibutyl phthalate, diisopropyl adipate, isotridecyl alcohol, 2-octyldodecanol, cetylstearyl alcohol and oleyl alcohol may be mentioned.

As hydrophilic phases, water, propylene glycol, glycerin and sorbitol may be mentioned.

As emulsifiers, nonionic surfactants such as polyoxyethylated castor oil, polyoxyethylated sorbitan monoolefinic acid, sorbitan monostearate, glycerin monostearate, polyoxyethyl stearate and alkyl phenol polyglycol ether; amphoteric surfactants such as disodium N-lauryl-β-iminodipropionate and lecithin; anionic surfactants such as sodium lauryl sulfate, aliphatic alcohol sulfate ether and mono/dialkylpolyglycol orthophosphate monoethanolamine salt; and cationic surfactants such as cetyltrimethylammonium chloride may, for example, be mentioned.

As other additives, carboxymethylcellulose, methylcellulose, polyacrylate, alginate, gelatin, gum arabic, polyvinylpyrrolidone, polyvinyl alcohol, methyl vinyl ether, maleic anhydride copolymers, polyethylene glycol, waxes and colloidal silica may be mentioned.

A semisolid preparation is administered by applying or spreading onto the skin or introducing into the coelom. A gel can be prepared by adding a thickener to a solution prepared in the same manner as an injection fluid sufficiently to give a transparent viscous substance like an ointment.

Next, Formulation Examples of preparations using the compounds of the present invention are given below. However, formulations of the present invention are by no means restricted thereto. In the following Formulation Examples, "parts" means parts by weight.

| [Wettable powder] | |
| --- | --- |
| Compound of the present invention | 0.1 to 80 parts |
| Solid carrier | 5 to 98.9 parts |
| Surfactant | 1 to 10 parts |
| Others | 0 to 5 parts |

As the others, an anti-caking agent, a stabilizer and the like may be mentioned.

| [Emulsifiable concentrate] | |
| --- | --- |
| Compound of the present invention | 0.1 to 30 parts |
| Liquid carrier | 45 to 95 parts |
| Surfactant | 4.9 to 15 parts |
| Others | 0 to 10 parts |

As the others, a spreader, a stabilizer and the like may be mentioned.

| [Suspension concentrate] | |
| --- | --- |
| Compound of the present invention | 0.1 to 70 parts |
| Liquid carrier | 15 to 98.89 parts |
| Surfactant | 1 to 12 parts |
| Others | 0.01 to 30 parts |

As the others, an anti-freezing agent, a thickener and the like may be mentioned.

| [Water dispersible granule] | |
| --- | --- |
| Compound of the present invention | 0.1 to 90 parts |
| Solid carrier | 0 to 98.9 parts |
| Surfactant | 1 to 20 parts |
| Others | 0 to 10 parts |

As the others, a binder, a stabilizer and the like may be mentioned.

| [Soluble concentrate] | |
| --- | --- |
| Compound of the present invention | 0.01 to 70 parts |
| Liquid carrier | 20 to 99.99 parts |
| Others | 0 to 0 parts |

As the others, an anti-freezing agent, a spreader and the like may be mentioned.

| [Granule] | |
| --- | --- |
| Compound of the present invention | 0.01 to 80 parts |
| Solid carrier | 10 to 99.99 parts |
| Others | 0 to 10 parts |

As the others, a binder, a stabilizer and the like may be mentioned.

| [Dustable powder] | |
| --- | --- |
| Compound of the present invention | 0.01 to 30 parts |
| Solid carrier | 65 to 99.99 parts |
| Others | 0 to 5 parts |

As the others, an anti-drift agent, a stabilizer and the like may be mentioned.

Next, more specific Formulation Examples of preparations containing the compounds of the present invention as an active ingredient are given below. However, the present invention is by no means restricted thereto.

In the following Formulation Examples, "parts" means parts by weight.

| [Formulation Example 1] Wettable powder | |
| --- | --- |
| Compound No.1-1-001a of the present invention | 20 parts |
| Pyrophyllite | 74 parts |
| Sorpol 5039 (tradename for a mixture of a nonionic surfactant and an anionic surfactant: manufactured by TOHO Chemical Industry Co., Ltd.) | 4 parts |
| CARPLEX #80D (tradename for hydrous synthetic silicic acid: manufactured by Shionogi & Co., Ltd.) | 2 parts |

The above ingredients are mixed and pulverized homogenously to obtain a wettable powder.

| [Formulation Example 2] Emulsifiable concentrate | |
| --- | --- |
| Compound No.1-1-001a of the present invention | 5 parts |
| Xylene | 75 parts |
| N-methylpyrrolidone | 15 parts |
| Sorpol 2680 (tradename for a mixture of a nonionic surfactant and an anionic surfactant: manufactured by TOHO Chemical Industry Co., Ltd.) | 5 parts |

The above ingredients are mixed homogenously to obtain an emulsifiable concentrate.

| [Formulation Example 3] Suspension concentrate | |
| --- | --- |
| Compound No.1-1-001a | 25 parts |
| AGRISOL S-710 (tradename for a nonionic surfactant: manufactured by Kao Corporation) | 10 parts |
| Runox 1000C (tradename for an anionic surfactant: manufactured by TOHO Chemical Industry Co., Ltd.) | 0.5 part |
| Xanthan gum | 0.2 part |
| Water | 64.3 parts |

The above ingredients are mixed homogenously and wet-pulverized to obtain a suspension concentration.

[Formulation Example 4] Water dispersible granule

| | |
|---|---|
| Compound No. 1-1-001a of the present invention | 75 parts |
| HITENOL NE-15 (tradename for an anionic surfactant: manufactured by DKS Co., Ltd.) | 5 parts |
| VANILLEX N (tradename for an anionic surfactant: manufactured by Nippon Paper Industries Co., Ltd.) | 10 parts |
| CARPLEX #80D (tradename for hydrous synthetic silicic acid: manufactured by Shionogi & Co., Ltd.) | 10 parts |

The above ingredients are mixed and pulverized homogenously, then kneaded with a small amount of water, granulated through an extrusion granulator and dried to obtain a water dispersible granule.

[Formulation Example 5] Granule

| | |
|---|---|
| Compound No. 1-1-001a of the present invention | 5 parts |
| Bentonite | 50 parts |
| Talc | 45 parts |

The above ingredients are mixed and pulverized homogenously, then kneaded with a small amount of water, granulated through an extrusion granulator and dried to obtain a granule.

[Formulation Example 6] Dustable powder

| | |
|---|---|
| Compound No. 1-1-001a of the present invention | 3 parts |
| CARPLEX #80D (tradename for a hydrous synthetic silicic acid: manufactured by Shionogi & Co., Ltd.) | 0.5 part |
| Kaolinite | 95 parts |
| Diisopropyl phosphate | 1.5 parts |

The above ingredients are mixed and pulverized homogeneously to obtain a dustable powder.

It is applied after diluted with water by a factor of from 1 to 10000 or directly without dilution.

[Formulation Example 7] Wettable powder preparation

| | |
|---|---|
| Compound No. 1-1-001a of the present invention | 25 parts |
| Sodium diisobutylnaphthalenesulfonate | 1 part |
| Calcium n-dodecylbenzenesulfonate | 10 parts |
| Alkyl aryl polyglycol ether | 12 parts |
| Naphthalenesulfonic acid-formalin condensate sodium salt | 3 parts |
| Silicone emulsion | 1 part |
| Silicon dioxide | 3 parts |
| Kaolin | 45 parts |

[Formulation Example 8] Water-soluble concentrate preparation

| | |
|---|---|
| Compound No. 1-1-001a of the present invention | 20 parts |
| Polyoxyethylenelauryl ether | 3 parts |
| Sodium dioctylsulfosuccinate | 3.5 parts |
| Dimethyl sulfoxide | 37 parts |
| 2-Propanol | 36.5 parts |

[Formulation Example 9] Liquid preparation for spraying

| | |
|---|---|
| Compound No. 1-1-001a of the present invention | 2 parts |
| Dimethyl sulfoxide | 10 parts |
| 2-Propanol | 35 parts |
| Acetone | 53 parts |

[Formulation Example 10] Liquid preparation for percutaneous administration

| | |
|---|---|
| Compound No. 1-1-001a of the present invention | 5 parts |
| Hexylene glycol | 50 parts |
| Isopropanol | 45 parts |

[Formulation Example 11] Liquid preparation for percutaneous administration

| | |
|---|---|
| Compound No. 1-1-001a of the present invention | 5 parts |
| Propylene glycol monomethyl ether | 50 parts |
| Dipropylene glycol | 45 parts |

[Formulation Example 12] Liquid preparation for percutaneous administration (by dripping)

| | |
|---|---|
| Compound No. 1-1-001a of the present invention | 2 parts |
| Light liquid paraffin | 98 parts |

[Formulation Example 13] Liquid preparation for percutaneous administration (by dripping)

| | |
|---|---|
| Compound No. 1-1-001a of the present invention | 2 parts |
| Light liquid paraffin | 58 parts |
| Olive oil | 30 parts |
| ODO-H | 9 parts |
| Shin-etsu silicone | 1 part |

For use as agricultural chemicals, the compounds of the present invention may be mixed with other herbicides, insecticides, acaricides, nematocides, fungicides, plant growth regulators, synergists, fertilizers, soil conditioners and the like at the time of formulation or application.

Particularly, the combined use with other agricultural chemicals or plant hormone is expected to reduce the cost by enabling control at lower doses, to broaden the insecticidal spectrum by the synergistic effect of the other agrochemicals, and to achieve a higher pesticidal effect. In such cases, they may be combined with a plurality of known agricultural chemicals.

The agricultural chemicals to be used in combination with the compounds of the present invention include, for example, the compounds disclosed in e.g. The Pesticide Manual, 15th edition, 2009, having the generic names listed below, but are not necessarily restricted thereto.

Fungicides: acibenzolar-S-methyl, acylaminobenzamide, acypetacs, aldimorph, ametoctradin, amisulbrom, amobam, ampropyfos, anilazine, azaconazole, azithiram, azoxystrobin, barium polysulfide, benalaxyl, benalaxyl-M, benodanil, benomyl, benquinox, bentaluron, benthiavalicarb-isopropyl, benthiazole, benzamacril, benzamorf, benzovindiflupyr, bethoxazine, binapacryl, biphenyl, bitertanol, blasticidin-S, bixafen, bordeaux mixture, boscalid, bromuconazole, bupirimate, buthiobate, calcium polysulfide, calcium polysulfide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper sulfate, copper sulfate, basic, copper zinc chromate, cufraneb, coumoxystrobin, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, diclobutrazol, diclocymet, diclomedine, dicloran, etc.

Fungicides (continued): diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipymetitrone, dipyrithione, ditalimfos, dithianon, dodemorph-acetate, dodine, drazoxolon, edifenphos, enestrobin, enoxastrobin, epoxiconazole, etaconazole, ethaboxam, etem, ethirimol, ethoxyquin, etridiazole, famoxadone, fenarimol, fenbuconazole, fenamidone, fenaminosulf, fenaminstrobin, fenapanil, fendazosulam, fenfuram, fenhexamid, fenitropan, fenoxanil, fenpiclonil, fenpropidin, fenpyrazamine, fenpropimorph, fentin, ferbam, ferimzone, fluazinam, fludioxonil, flufenoxystrobin, flumetover, flumorph, fluopicolide, fluopyram, fluoroim ide, fluotrimazole, fluoxastrobin, fluquinconazole, flusilazole, flusulfamide, flutianil, flutolanil, flutriafol, fluxapyroxad, folpet, fosetyl-aluminium, fuberidazole, furalaxyl, furametpyr, furcarbanil, furconazole, furconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine-albesilate, iminoctadine-triacetate, ipconazole, iprobenfos, iprodione, iprovalicarb, isofetamid, isoprothiolane, isopyrazam, isotianil, isovaledione, etc.

Fungicides (continued): kasugamycin, kresoxim-methyl, laminarin, mancopper, mancozeb, mandestrobin, mandipropamid, maneb, mebenil, mecarbinzid, mepanipyrim, meptyldinocap, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis(dimethyldithiocarbamate), nitrostyrene, nitrothal-isopropyl, nuarimol, OCH, octhilinone, ofurace, orysastrobin, oxathiapiprolin, oxadixyl, oxine copper, oxycarboxin, oxpoconazole fumarate, pefurzoate, penconazole, penflufen, pencycuron, penthiopyrad, o-phenylphenol, phosdiphen, phthalide, picarbutrazox, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pydiflumetofen, pyracarbolid, pyraclostrobin, pyrametostrobin, pyraoxystrobin, pyraziflumid, pyrazophos, pyribencarb-methyl, pyridinitril, pyrifenox, pyrimethanil, pyriminostrobin, pyrimorph, pyriofenone, pyrisoxazole, pyroquilon, pyroxychlor, pyroxyfur, quinomethionate, quinoxyfen, quintozene, quinacetol-sulfate, quinazamid, quinconazole, rabenzazole, *Bacillus subtilis* (Strain:D747, FZB24, GBO3, HA10404, MBI600, QST713, Y1336, etc.), etc.

Fungicides (continued): sedaxane, sodium azide, sodium hydrogen carbonate, sodium hypochlorite, sulfur, spiroxamine, salycylanilide, silthiofam, simeconazole, tebuconazole, tebufloquin, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolprocarb, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triclopyricarb, triticonazole, validamycin, valifenalate, vinclozolin, zarilamide, zinc sulfate, zineb, ziram, zoxamide, shiitake mushroom mycelium extracts, shiitake mushroom fruiting body extracts, ZF-9646 (test name), NF-180 (test name), MIF-1002 (test name), S-2399 (test name), AKD-5195 (test name), NNF-0721 (test name), etc.

Bactericides: benzalkonium chloride, bithionol, bronopol, cresol, formaldehyde, nitrapyrin, oxolinic acid, oxyterracycline, streptomycin, tecloftalam, etc.

Nematicides: aldoxycarb, benclothiaz, cadusafos, DBCP, dichlofenthion, DSP, ethoprophos, fenamiphos, fensulfothion, fluazaindolizine, fluensulfone, fosthiazate, fosthietan, imicyafos, isamidofos, isazofos, oxamyl, thiaxazafen, thionazin, tioxazafen, BYI-1921 (test name), MAI-08015 (test name), etc.

Acaricides: acequinocyl, acrinathrin, amidoflumet, amitraz, azocyclotin, BCI-033 (test name), benzoximate, bifenazate, bromopropylate, chinomethionat, chlorobezilate, clofentezine, cyenopyrafen, cyflumetofen, cyhexatine, dicofol, dienochlor, diflovidazin, DNOC, etoxazole, fenazaquin, fenbutatin oxide, fenothiocarb, fenpropathrin, fenpyroximate, fluacrypyrim, halfenprox, hexythiazox, milbemectin, propargite, pyflubumide, pyridaben, pyrimidifen, S-1870 (test name), spirodiclofen, spyromesifen, CL900167 (test name), tebufenpyrad, NA-89 (test name), etc.

Insecticides: abamectin, acephate, acetamipirid, afidopyropen, afoxolaner, alanycarb, aldicarb, allethrin, azamethiphos, azinphos-ethyl, azinphos-methyl, *Bacillus thuringiensis*, bendiocarb, benfluthrin, benfuracarb, bensultap, bifenthrin, bioallethrin, bioresmethrin, bistrifluron, broflanilide, buprofezin, butocarboxim, carbaryl, carbofuran, carbosulfan, cartap, chlorantraniliprole, chlorethxyfos, chlorfenapyr, chlorfenvinphos, chlorfluazuron, chlormephos, chloroprallethrin, chlorpyrifos, chlorpyrifos-methyl, chromafenozide, clothianidin, cyanophos, cyantraniliprole, cyclaniliprole, cycloprothrin, cyflumetofen, cyfluthrin, beta-cyfluthrin, cyhalodiamide, cyhalothrin, lambda-cyhalothrin, cypermethrin, alpha-cypermethrin, beta-cypermethrin, zeta-cypermethrin, cyphenothrin, cyromazine, deltamethrin, diacloden, diafenthiuron, diazinon, dicloromezotiaz, dichlorvos, diflubenzuron, dimefluthrin, dimethylvinphos, dinotefuran, diofenolan, disulfoton, dimethoate, emamectinbenzoate, empenthrin, endosulfan, alpha-endosulfan, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, fluazuron, flubendiamide, flucycloxuron, flucythrinate, flufenerim, flufenoxuron, flufenprox, flumethrin, fluralaner, fluvalinate, tau-fluvalinate, fonophos, formetanate, formothion, furathiocarb, flufiprole, fluhexafon, flupyradifurone, flometoquin, etc.

Insecticides (continued): gamma-cyhalothrin, halofenozide, heptafluthrin, hexaflumuron, hydramethylnon, imidacloprid, imiprothrin, isofenphos, indoxacarb, indoxacarb-MNP, isoprocarb, isoxathion, kappa-bifenthrin, kappa-tefluthrin, lepimectin, lufenuron, malathion, meperfluthrin, metaflumizone, metaldehyde, methamidophos, methidathion, methacrifos, metalcarb, methomyl, methoprene, methoxychlor, methoxyfenozide, methyl bromide, epsilon-metofluthrin, metofluthrin, momfluorothrin, epsilon-momfluorothrin, monocrotophos, muscalure, nitenpyram, novaluron, noviflumuron, omethoate, oxamyl, oxydemetonmethyl, oxydeprofos, parathion, parathion-methyl, pentachlorophenol (PCP), permethrin, phenothrin, phenthoate, phoxim, phorate, phosalone, phosmet, phosphamidon, pirimicarb, pirimiphos-methyl, profenofos, profluthrin, prothiofos, propaphos, protrifenbute, pymetrozine, pyraclofos, pyrethrins, pyridalyl, pyrifluquinazon, pyriprole, pyrafluprole, pyriproxyfen, resmethrin, rotenone, SI-0405 (test name), sulprofos, silafluofen, spinetoram, spinosad, spiromesifen, spirotetramat, sulfoxaflor, sulfotep, SYJ-159 (test name), tebfenozide, teflubenzuron, tefluthorin, terbufos, tetrachlorvinphos, tetramethrin, d-tetramethrin, tetramethylfluthrin, tetraniliprole, thiacloprid, thiocyclam, thiodicarb, thiamethoxam, thiofanox, thiometon, tolfenpyrad, tralomethrin, transfluthrin, triazamate, trichlorfon, triazuron, triflumezopyrim, triflumuron, vamidothion, fluxametamide, MIE-1209 (test name), ME5382 (test name), etc.

EXAMPLES

Now, the present invention will be described in further detail with reference to Examples of synthesis of and tests on the compounds of the present invention. However, the present invention is by no means restricted thereto.

For the preparative medium pressure liquid chromatography described in Synthetic Examples and Reference Examples, a preparative medium pressure chromatograph YFLC-Wprep manufactured by Yamazen Science, Inc. (flow rate: 18 ml/min, 40-μm silica gel column) was used.

Chemical shift values of proton nuclear magnetic resonance (NMR) in Synthetic Examples and Reference Examples were measured by using Me$_4$Si (tetramethylsilane) as a standard substance at 300 MHz (ECX300 or ECP300 manufactured by JEOL Ltd.).

Reference symbols in proton nuclear magnetic resonance chemical shift values have the following meanings.

s: singlet, brs: broad singlet, d: doublet, dd: double doublet, t: triplet, q: quartet, and m: multiplet.

Solvents used for NMR measurement are represented in brackets in the chemical shift value data.

Synthetic Example 1: Synthesis of 2-[3-(ethylsulfonyl)-7-(trifluoromethyl)imidazo[1,2-a]pyridin-2-yl]-7-(trifluoromethyl)imidazo[1,2-c]pyrimidine (Compound No. 1-3-001a of the Present Invention)

82 mg of 6-(trifluoromethyl)pyrimidin-4-amine was dissolved in 5 ml of chlorobenzene, and 200 mg of 2-bromo-1-[3-(ethylsulfonyl)-7-(trifluoromethyl)imidazo[1,2-a]pyridin-2-yl]ethanone was added at room temperature. After the addition, the reaction mixture was stirred under reflux with heating for 9 hours. After the reaction, the reaction mixture was mixed with 10 ml of a 1M sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate [with a gradient of from 100:0 to 0:100 (volume ratio, the same applies hereinafter)] as the eluent to obtain 163.5 mg of the desired product as a flesh-colored solid.

Melting point: 235-237° C.
$^1$H-NMR (CDCl$_3$): δ9.38 (d, J=7.5 Hz, 1H), 9.19 (s, 1H), 8.63 (s, 1H), 8.12-8.09 (m, 1H), 8.02-8.00 (m, 1H), 7.28-7.23 (m, 1H), 3.73 (q, J=7.4 Hz, 2H), 1.34 (t, J=7.4 Hz, 3H).

Synthetic Example 2: Synthesis of 2-[3-(ethylthio)-7-(trifluoromethyl)imidazo[1,2-a]pyridin-2-yl]-3-methyl-6-trifluoromethyl)-3H-imidazo[4,5-b]pyridine (Compound No. 1-1-002b of the Present Invention) and 2-[3-(ethylsulfonyl)-7-(trifluoromethyl)imidazo[1,2-a]pyridin-2-yl]-3-methyl-6-trifluoromethyl)-3H-imidazo[4,5-b]pyridine (Compound No. 1-1-002a of the Present Invention)

Step 1: Synthesis of 3-(ethylthio)-N-[2-(methylamino)-5-(trifluoromethyl)pyridin-3-yl]-7-(trifluoromethyl)imidazo[1,2-a]pyridine-2-carboxamide 856 mg of N$^2$-methyl-5-(trifluoromethyl)pyridine-2,3-diamine was dissolved in 20 ml of pyridine, and 1.00 g of 3-(ethylthio)-7-(trifluoromethyl)imidazo[1,2-a]pyridine-2-carboxylic acid, 1.32 g of 1-ethyl-3-(3-dimethylaminopropyl)carbodiimide hydrochloride and 42 mg of 4-(dimethylamino)pyridine were added at room temperature. After the addition, the reaction mixture was stirred for 6 hours at room temperature. After the reaction, the solvent was evaporated under reduced pressure. The resulting residue was mixed with 10 ml of water and extracted with ethyl acetate (10 ml×2). The resulting organic layer was washed with a 1M hydrochloric acid aqueous solution, and dehydrated with saturated aqueous sodium chloride and dried over anhydrous sodium sulfate, and the solvent was evaporated under reduced pressure to obtain 1.40 g of the desired crude product. The crude product was used in the next step without further purification.

Step 2: Synthesis of 2-[3-(ethylthio)-7-(trifluoromethyl)imidazo[1,2-a]pyridin-2-yl]-3-methyl-6-(trifluoromethyl)-3H-imidazo[4,5-b]pyridine (Compound No. 1-1-002b of the Present Invention)

1.40 g of the crude 3-(ethylthio)-N-[2-(methylamino)-5-(trifluoromethyl)pyridin-3-yl]-7-(trifluoromethyl)imidazo[1,2-a]pyridine-2-carboxamide obtained in Step 1 was dissolved in 15 ml of acetic acid, and the solution was stirred under reflux with heating for 2 hours. After the stirring, the reaction mixture was stirred at room temperature overnight. After the stirring, the solid precipitated in the reaction mixture was collected by filtration. The obtained solid was washed with diisopropyl ether to obtain 645 mg of the desired product as a white solid.

Melting point: 199-202° C.

¹H-NMR (CDCl₃): δ8.78 (d, J=7.2 Hz, 1H), 8.73 (d, J=1.5 Hz, 1H), 8.40 (d, J=2.0 Hz, 1H), 8.06-8.04 (m, 1H), 7.21 (dd, J=7.2, 1.5 Hz, 1H), 4.33 (s, 3H), 3.15 (q, J=7.4 Hz, 2H), 1.22 (t, J=7.4 Hz, 3H).

Step 3: Synthesis of 2-[3-(ethylsulfonyl)-7-(trifluoromethyl)imidazo[1,2-a]pyridin-2-yl]-3-methyl-6-(trifluoromethyl)-3H-imidazo[4,5-b]pyridine (Compound No. 1-1-002a of the Present Invention)

To a solution of 645 mg of 2-[3-(ethylthio)-7-(trifluoromethyl)imidazo[1,2-a]pyridin-2-yl]-3-methyl-6-(trifluoromethyl)-3H-imidazo[4,5-b]pyridine in 15 ml of chloroform, 961 mg of 65 weight % m-chloroperbenzoic acid (containing about 30 weight % of water) was added under cooling with ice. After the addition, the reaction mixture was stirred at room temperature for 2.5 hours. After the reaction, the reaction mixture was mixed with a saturated sodium thiosulfate aqueous solution and extracted with chloroform (10 ml). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatograph using n-hexane/ethyl acetate (with a gradient of from 100:0 to 50:50) as the eluent to obtain 660 mg of the desired product as a white solid.

Melting point: 203-205° C.
¹H-NMR (CDCl₃): δ9.42 (d, J=7.5 Hz, 1H), 8.77 (s, 1H), 8.36 (d, J=1.7 Hz, 1H), 8.16 (s, 1H), 7.32 (dd, J=7.5, 1.7 Hz, 1H), 4.18 (s, 3H), 4.11 (q, J=7.5 Hz, 2H), 1.47 (t, J=7.5 Hz, 3H).

Synthetic Example 3: Synthesis of 2-[3-(ethylthio)-6-(trifluoromethyl)imidazo[1,2-a]pyridin-2-yl]-5-[(trifluoromethyl)thio]benz[d]oxazole (Compound No. 1-2-003b of the Present Invention), 2-[3-(ethylsulfonyl)-6-(trifluoromethyl)imidazo[1,2-a]pyridin-2-yl]-5-[(trifluoromethyl)sulfinyl]benz[d]oxazole (Compound No. 1-2-002a of the Present Invention) and 2-[3-(ethylsulfonyl)-6-(trifluoromethyl)imidazo[1,2-a]pyridin-2-yl]-5-[(trifluoromethyl)sulfonyl]benz[d]oxazole (Compound No. 1-2-001a of the Present Invention)

Step 1: Synthesis of 3-(ethylthio)-N-{2-hydroxy-5-[(trifluoromethyl)thio]phenyl}-6-(trifluoromethyl)imidazo[1,2-a]pyridine-2-carboxamide 466 mg of 2-amino-4-[(trifluoromethyl)thio]phenol was dissolved in 10 ml of pyridine, and 356 mg of 3-(ethylthio)-6-(trifluoromethyl)imidazo[1,2-a]pyridine-2-carboxylic acid, 471 mg of 1-ethyl-3-(3-dimethylaminopropyl)carbodiimide hydrochloride and 75 mg of 4-(dimethylamino)pyridine were added. After the addition, the reaction mixture was stirred at room temperature overnight. After the reaction, the solvent was evapoarated under reduced pressure. The resulting residue was purified by preparative medium pressure liquid chromatography using n-hexane/ethyl acetate (with a gradient of from 100:0 to 0:100) as the eluent to obtain 100 mg of the desired product as a reddish brown solid.

Step 2: Synthesis of 2-[3-(ethylthio)-6-(trifluoromethyl)imidazo[1,2-a]pyridin-2-yl]-5-[(trifluoromethyl)thio]benz[d]oxazole (Compound No. 1-2-003b of the Present Invention)

A solution of 89 mg of 3-(ethylthio)-N-{2-hydroxy-5-[(trifluoromethyl)thio]phenyl}-6-(trifluoromethyl)imidazo[1,2-a]pyridine-2-carboxamide in 5 ml of tetrahydrofuran was warmed to 50° C., and 65 mg of bis(2-methoxyethyl) azodicarboxylate and 73 mg of triphenylphosphine were added.

After the addition, the reaction mixture was stirred at 50° C. for 3 hours. After the stirring, the reaction mixture was stirred at room temperature overnight. After the reaction, the reaction mixture was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 85:15 to 0:100) as the eluent to obtain 21 mg of the desired product as a pale brown solid.

¹H-NMR (CDCl₃): δ8.96 (s, 1H), 8.23 (s, 1H), 8.00-7.45 (m, 4H), 3.11 (q, J=7.4 Hz, 2H), 1.26 (t, J=7.4 Hz, 3H).

Step 3: Synthesis of 2-[3-(ethylsulfonyl)-6-(trifluoromethyl)imidazo[1,2-a]pyridin-2-yl]-5-[(trifluoromethyl)sulfinyl]benz[d]oxazole (Compound No. 1-2-002a of the Present Invention) and 2-[3-(ethylsulfonyl)-6-(trifluoromethyl)imidazo[1,2-a]pyridin-2-yl]-5-[(trifluoromethyl)sulfonyl]benz[d]oxazole (Compound No. 1-2-001a of the Present Invention)

To a solution of 21 mg of 2-[3-(ethylthio)-6-(trifluoromethyl)imidazo[1,2-a]pyridin-2-yl]-5-[(trifluoromethyl)thio]benz[d]oxazole in 5 ml of chloroform, 67 mg of 65 weight % m-chloroperbenzoic acid (containing about 30 weight % of water) was added. After the addition, the reaction mixture was stirred at room temperature overnight. After the stirring, the reaction mixture was stirred under reflux with heating for another 2 hours. After the reaction, the reaction mixture was mixed with a saturated sodium thiosulfate aqueous solution and extracted with chloroform (10 ml). The resulting organic layer was washed with a satrated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 5 mg of the desired 2-[3-(ethylsulfonyl)-6-(trifluoromethyl)imidazo[1,2-a]pyridin-2-yl]-5-[(trifluoromethyl)sulfinyl]benz[d]oxazole as a desired product and 13 mg of the desired 2-[3-(ethylsulfonyl)-6-(trifluoromethyl)imidazo[1,2-a]pyridin-2-yl]-5-[(trifluoromethyl)sulfonyl]benz[d]oxazole respectively as a pale brown solid.

¹H-NMR (CDCl₃) of 2-[3-(ethylsulfonyl)-6-(trifluoromethyl)imidazo[1,2-a]pyridin-2-yl]-5-[(trifluoromethyl)sulfinyl]benz[d]oxazole: δ 9.75 (s, 1H), 8.37 (s, 1H), 8.05-7.35 (m, 4H), 4.09 (q, J=7.5 Hz, 2H), 1.48 (t, J=7.5 Hz, 3H).

¹H-NMR (CDCl₃) of 2-[3-(ethylsulfonyl)-6-(trifluoromethyl)imidazo[1,2-a]pyridin-2-yl]-5-[(trifluoromethyl)sulfonyl]benz[d]oxazole: δ 9.74 (s, 1H), 8.62 (s, 1H), 8.25-7.40 (m, 4H), 4.07 (q, J=7.5 Hz, 2H), 1.50 (t, J=7.5 Hz, 3H).

Synthetic Example 4: Synthesis of 5-(ethylthio)-6-[3-methyl-6-(trifluoromethyl)-3H-imidazo[4,5-b]pyridin-2-yl]-2-[(trifluoromethyl)imidazo[2,1-b]thiazole (Compound No. 2-1-001b of the Present Invention) and 5-(ethylsulfonyl)-6-[3-methyl-6-(trifluoromethyl)-3H-imidazo[4,5-b]pyridin-2-yl]-2-(trifluoromethyl)imidazo[2,1-b]thiazole (Compound No. 2-1-001a of the Present Invention)

Step 1: Synthesis of 5-(ethylthio)-N-[2-(methylamino)-5-(trifluoromethyl)pyridin-3-yl]-2-(trifluoromethyl)imidazo[2,1-b]thiazole-6-carboxamide 242 mg of $N^2$-methyl-5-(trifluoromethyl)pyridine-2,3-diamine was dissolved in 10 ml of pyridine, and 250 mg of 5-(ethylthio)-2-(trifluoromethyl)imidazo[2,1-b]thiazole-6-carboxylic acid, 322 mg of 1-ethyl-3-(3-dimethylaminopropyl)carbodiimide hydrochloride and 10 mg of 4-(dimethylamino)pyridine were added at room temperature. After the addition, the reaction mixture was stirred at room temperature overnight. After the reaction, the solvent was evaporated under reduced pressure. The resulting residue was mixed with 10 ml of water and extracted with ethyl acetate (10 ml×2). The resulting organic layer was washed with a 1M hydrochloric acid aqueous solution, and dehydrated with saturated aqueous sodium chloride and dried over anhydrous sodium sulfate, and the solvent was evaporated under reduced pressure to obtain crude 5-(ethylthio)-N-[2-(methylamino)-5-(trifluoromethyl)pyridin-3-yl]-2-(trifluoromethyl)imidazo[2,1-b]thiazole-6-carboxamide as the desired product. The crude product was used in the next step without further purification.

Step 2: Synthesis of 5-(ethylhio)-6-[3-methyl-6-(trifluoromethyl)-3H-imidazo[4,5-b]pyridin-2-yl]-2-(trifluoromethyl)imidazo[2,1-b]thiazole (Compound No. 2-1-001b of the Present Invention)

The crude 5-(ethylthio)-N-[2-(methylamino)-5-(trifluoromethyl)pyridin-3-yl]-2-(trifluoromethyl)imidazo[2,1-b]thiazole-6-carboxamide obtained in Step 1 was dissolved in 10 ml of acetic acid, and the solution was stirred under reflux with heating for 4.5 hours. After the reaction, the solvent was evaporated under reduced pressure. The resulting residue was mixed with 10 ml of a 1M hydrochloric acid aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The precipitated solid was collected by filtration. The obtained solid was washed with diisopropyl ether to obtain 332 mg of the desired product as a white solid.

Melting point: 200-203° C.
$^1$H-NMR (CDCl$_3$): δ8.72-8.67 (m, 1H), 8.37-8.33 (m, 1H), 8.12-8.08 (m, 1H), 4.25 (s, 3H), 3.14 (q, J=7.5 Hz, 2H), 1.25 (t, J=7.5 Hz, 3H).

Step 3: Synthesis of 5-(ethylsulfonyl)-6-[3-methyl-6-(trifluoromethyl)-3H-imidazo[4,5-b]pyridin-2-yl]-2-(trifluoromethyl)imidazo[2,1-b]thiazole (Compound No. 2-1-001a of the Present Invention)

To a solution of 132 mg of 5-(ethylthio)-6-[3-methyl-6-(trifluoromethyl)-3H-imidazo[4,5-b]pyridin-2-yl]-2-(trifluoromethyl)imidazo[2,1-b]thiazole in 3 ml of chloroform, 155 mg of 65 weight % m-chloroperbenzoic acid (containing about 30 weight % of water) was added under cooling with ice. After the addition, the reaction mixture was stirred at room temperature for 1.5 hours. After the reaction, the reaction mixture was mixed with a saturated sodium thiosulfate aqueous solution and extracted with chloroform (10 ml). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 110 mg of the desired product as a white solid.

Melting point: 249-251° C.
$^1$H-NMR (CDCl$_3$): δ8.76-8.71 (m, 1H), 8.71-8.66 (m, 1H), 8.36-8.32 (m, 1H), 4.23 (s, 3H), 4.19 (q, J=7.5 Hz, 2H), 1.45 (t, J=7.5 Hz, 3H).

Synthetic Example 5: Synthesis of 2-[3-(ethylsulfonyl)-7-(trifluoromethyl)imidazo[1,2-a]pyridin-2-yl]-7-(trifluoromethyl)imidazo[1,2-b]pyridazine (Compound No. 1-4-001a of the Present Invention)

82 mg of 5-(trifluoromethyl)pyridazin-3-amine was dissolved in 5 ml of chlorobenzene, and 200 mg of 2-bromo-1-[3-(ethylsulfonyl)-7-(trifluoromethyl)imidazo[1,2-a]pyridin-2-yl]ethanone was added at room temperature. After the addition, the reaction mixture was stirred under reflux with heating for 3 hours. After the reaction, the reaction mixture was mixed with 10 ml of a 1M sodium hydroxide aqueous solution and extracted with ethyl acetate (10 ml×2). The obtained organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 142 mg of the desired product as a brown solid.

Melting point: 214-218° C.
$^1$H-NMR (CDCl$_3$): δ9.40 (d, J=7.5 Hz, 1H), 8.94 (s, 1H), 8.58 (d, J=2.0 Hz, 1H), 8.34-8.30 (m, 1H), 8.11-8.09 (m, 1H), 7.24 (dd, J=7.5, 2.0 Hz, 1H), 3.79 (q, J=7.4 Hz, 2H), 1.36 (t, J=7.4 Hz, 3H).

Synthetic Example 6: Synthesis of 2-[3-(ethylthio)-6-(trifluoromethyl)imidazo[1,2-a]pyrazin-2-yl]-3-methyl-6-(trifluoromethyl)-3H-imidazo[4,5-b]pyridine (Compound No. 1-1-029b of the Present Invention) and 2-[3-(ethylsulfonyl)-6-(trifluoromethyl)imidazo[1,2-a]pyrazin-2-yl]-3-methyl-6-(trifluoromethyl)-3H-imidazo[4,5-b]pyridine (Compound No. 1-1-029a of the Present Invention)

Step 1: Synthesis of 3-(ethylthio)-N-[2-(methylamino)-5-(trifluoromethyl)pyridin-3-yl]-6-(trifluoromethyl)imidazo[1,2-a]pyrazine-2-carboxamide 271 mg of $N^2$-methyl-5-(trifluoromethyl)pyridine-2,3-diamine was dissolved in 10 ml of pyridine, and 270 mg of 3-(ethylthio)-6-(trifluoromethyl)imidazo[1,2-a]pyrazine-2-carboxylic acid and 357 mg of 1-ethyl-3-(3-dimethylaminopropyl)carbodiimide hydroxhloride were added. After the addition, the reaction mixture was stirred at room temperature for 2 hours. After the reaction, the solvent was evaporated under reduced pressure. The resulting residue was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduce pressure to obtain crude 3-(ethylthio)-N-[2-(methylamino)-5-(trifluoromethyl)pyridin-3-yl]-6-(trifluoromethyl)imidazo[1,2-a]pyrazine-2-carboxamide. The crude product was used in the next step without further purification.

Step 2: Synthesis of 2-[3-(ethylthio)-6-(trifluoromethyl)imidazo[1,2-a]pyrazin-2-yl]-3-methyl-6-(trifluoromethyl)-3H-imidazo[4,5-b]pyridine (Compound No. 1-1-029b of the Present Invention)

The crude 3-(ethylthio)-N-[2-(methylamino)-5-(trifluoromethyl)pyridin-3-yl]-6-(trifluoromethyl)imidazo[1,2-a]pyrazine-2-carboxamide obtained in Step 1 was dissolved in 10 ml of acetic acid, and the solution was stirred under reflux with heating for 17 hours. After the reaction, the solvent was evaporated under reduced pressure. The resulting residue was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chlromatography using n-hexane/ethyl acetate (with a gradient of from 100:0 to 80:20) as the eluent to obtain 257 mg of the desired product as a white solid.

Melting point: 220-222° C.
$^1$H-NMR (CDCl$_3$): δ 9.24 (s, 1H), 8.99 (s, 1H), 8.76 (d, J=1.5 Hz, 1H), 8.42 (d, J=1.5 Hz, 1H), 4.37 (s, 3H), 3.26 (q, J=7.5 Hz, 2H), 1.25 (t, J=7.5 Hz, 3H).

Step 3: Synthesis of 2-[3-(ethylsulfonyl)-6-(trifluoromethyl)imidazo[1,2-a]pyrazin-2-yl]-3-methyl-6-(trifluoromethyl)-3H-imidazo[4,5-b]pyridine (Compound No. 1-1-029a of the Present Invention)

To a solution of 232 mg of 2-[3-(ethylthio)-6-(trifluoromethyl)imidazo[1,2-a]pyrazin-2-yl]-3-methyl-6-(trifluoromethyl)-3H-imidazo[4,5-b]pyridine in 5 ml of chloroform, 326 mg of 65 weight % m-chloroperbenzoic acid (containing about 30 weight % of water) was added under cooling with ice. After the addition, the reaction mixture was stirred at room temperature for 2 hours. After the reaction, the reaction mixture was mixed with a saturated sodium thiosulfate aqueous solution and extracted with chloroform (10 ml). The resulting organic layer was washed with a saturated sodium hydrogen carbonate aqueous solution and dried over anhydrous sodium sulfate, and the solvent was evaporated under reduced pressure. The obtained solid was mixed with 10 ml of diisopropyl ether, followed by filtration to obtain 203 mg of the desired product as a white solid.

Melting point: 234-236° C.
$^1$H-NMR (CDCl$_3$): δ9.63 (s, 1H), 9.39 (s, 1H), 8.81-8.77 (m, 1H), 8.39-8.36 (m, 1H), 4.25 (s, 3H), 4.23 (q, J=7.5 Hz, 2H), 1.49 (t, J=7.5 Hz, 3H).

Synthetic Example 7: Synthesis of 2-[6-bromo-3-(ethylthio)-7-(trifluoromethyl)imidazo[1,2-a]pyridin-2-yl]-3-methyl-6-(trifluoromethyl)-3H-imidazo[4,5-b]pyridine (Compound No. 1-1-023b of the Present Invention) and 2-[6-bromo-3-(ethylsulfonyl)-7-(trifluoromethyl)imidazo[1,2-a]pyridin-2-yl]-3-methyl-6-(trifluoromethyl)-3H-imidazo[4,5-b]pyridine (Compound No. 1-1-023a of the Present Invention)

Step 1: Synthesis of 6-bromo-N-[2-(methylamino)-5-(trifluoromethyl)pyridin-3-yl]-7-(trifluoromethyl)imidazo[1,2-a]pyridine-2-carboxamide 1.51 g of N$^2$-methyl-5-(trifluoromethyl)pyridine-2,3-diamine was dissolved in 20 ml of pyridine, and 2.04 g of 6-bromo-7-(trifluoromethyl)imidazo[1,2-a]pyridine-2-carboxylic acid and 2.53 g of 1-ethyl-3-(3-dimethylaminopropyl)carbodiimide hydrochloride were added. After the addition, the reaction mixture was stirred at room temperature for 3 hours. After the reaction, 20 ml of water was added to the reaction mixture, and the precipitated solid was collected by filtration to obtain 2.98 g of desired product as a flesh-colored solid.

Melting point: 200-205° C.
$^1$H-NMR (CDCl$_3$): δ8.77 (brs, 1H), 8.54 (s, 1H), 8.40-8.36 (m, 1H), 8.28 (s, 1H), 8.04 (s, 1H), 7.85 (d, J=2.0 Hz, 1H), 5.20 (brs, 1H), 3.10 (d, J=4.8 Hz, 3H).

Step 2: Synthesis of 2-[6-bromo-7-(trifluoromethyl)imidazo[1,2-a]pyridin-2-yl]-3-methyl-6-(trifluoromethyl)-3H-imidazo[4,5-b]pyridine 2.93 g of 6-bromo-N-[2-(methylamino)-5-(trifluoromethyl)pyridin-3-yl]-7-(trifluoromethyl)imidazo[1,2-a]pyridine-2-carboxamide was dissolved in 15 ml of acetic acid, and the solution was stirred under reflux with heating for 2 hours. After the reaction, the solvent was evaporated under reduced pressure. The resulting residue was mixed with 10 ml of water and extracted with chloroform (10 ml×2). The resulting organic layer was dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 2.82 g of the desired product as a pale brown solid.

Melting point: 220-225° C.
$^1$H-NMR (CDCl$_3$): δ8.71 (d, J=1.4 Hz, 1H), 8.55 (s, 1H), 8.51 (s, 1H), 8.27 (d, J=1.4 Hz, 1H), 8.14 (s, 1H), 4.47 (s, 3H).

Step 3: Synthesis of 2-[6-bromo-3-(ethylthio)-7-(trifluoromethyl)imidazo[1,2-a]pyridin-2-yl]-3-methyl-6-(trifluoromethyl)-3H-imidazo[4,5-b]pyridine (Compound No. 1-1-023b of the Present Invention)

518 mg of N-chlorosuccinimide was dissolved in 5 ml of 1,2-dichloroethane, and 321 mg of ethanethiol was added at −40° C. After the addition, the reaction mixture was stirred at room temperature for 30 minutes. After the stirring, to the reaction mixture, a solution of 300 mg of 2-[6-bromo-7-(trifluoromethyl)imidazo[1,2-a]pyridin-2-yl]-3-methyl-6-(trifluoromethyl)-3H-imidazo[4,5-b]pyridine in 2 ml of 1,2-dichloroethane was added at room temperature. After the addition, the reaction mixture was stirred under reflux with heating for 3 hours. After the stirring, to the reaction mixture, a solution of 1.04 g of N-chlorosuccinimide and 642 mg of ethanethiol in 5 ml of 1,2-dichloroethane prepared in a separate container was added at room temperature. After the addition, the reaction mixture was stirred under reflux with heating for 3 hours. After the reaction, the reaction mixture was mixed with 10 ml of water and extracted with chloroform (10 ml×2). The resulting organic layer was dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 212 mg of the desired product as a white solid.

Melting point: 214-215° C.

¹H-NMR (CDCl₃): δ8.93 (s, 1H), 8.74 (d, J=1.4 Hz, 1H), 8.40 (d, J=1.4 Hz, 1H), 8.13 (s, 1H), 4.33 (s, 3H), 3.18 (q, J=7.4 Hz, 2H), 1.24 (t, J=7.4 Hz, 3H).

Step 4: Synthesis of 2-[6-bromo-3-(ethylsulfonyl)-7-(trifluoromethyl)imidazo[1,2-a]pyridin-2-yl]-3-methyl-6-(trifluoromethyl)-3H-imidazo[4,5-b]pyridine (Compound No. 1-1-023a of the Present Invention)

To a solution of 150 mg of 2-[6-bromo-3-(ethylthio)-7-(trifluoromethyl)imidazo[1,2-a]pyridin-2-yl]-3-methyl-6-(trifluoromethyl)-3H-imidazo[4,5-b]pyridine in 5 ml of chloroform, 175 mg of 65 weight % m-chloroperbenzoic acid (containing about 30 weight % of water) was added under cooling with ice. After the addition, the reaction mixture was stirred at room temperature for 2 hours. After the reaction, the reaction mixture was mixed with a saturated sodium thiosulfate aqueous solution and extracted with chloroform (10 ml). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 142 mg of the desired product as a white solid.
Melting point: 226-228° C.
¹H-NMR (CDCl₃): δ9.60 (s, 1H), 8.77 (d, J=1.4 Hz, 1H), 8.36 (d, J=1.4 Hz, 1H), 8.23 (s, 1H), 4.19 (s, 3H), 4.15 (q, J=7.5 Hz, 2H), 1.49 (t, J=7.5 Hz, 3H).

Synthetic Example 8: Synthesis of 2-[3-(ethylthio)-7-(trifluoromethyl)imidazo[1,2-a]pyridin-2-yl]-5-(trifluoromethyl)-3H-imidazo[4,5-b]pyridine (Compound No. 1-1-031b of the Present Invention), 2-[3-(ethylthio)-7-(trifluoromethyl)imidazo[1,2-a]pyridin-2-yl]-1-methyl-5-(trifluoromethyl)-1H-imidazo[4,5-b]pyridine (Compound No. 1-7-001 b of the Present Invention) and 2-[3-(ethylthio)-7-(trifluoromethyl)imidazo[1,2-a]pyridin-2-yl]-3-methyl-5-(trifluoromethyl)-3H-imidazo[4,5-b]pyridine (Compound No. 1-1-030b of the Present Invention)

Step 1: Synthesis of N-[2-amino-6-(trifluoromethyl)pyridin-3-yl]-3-ethylthio-7-(trifluoromethyl)imidazo[1,2-a]pyridine-2-carboxamide 712 mg of 6-(trifluoromethyl)pyridine-2,3-diamine was dissolved in 10 ml of pyridine, and 972 mg of 3-(ethylthio)-7-(trifluoromethyl)imidazo[1,2-a]pyridine-2-carboxylic acid and 1.32 g of 1-ethyl-3-(3-dimethylaminopropyl)carbodiimide hydrochloride were added at room temperature. After the addition, the reaction mixture was stirred at room temperature overnight. After the reaction, 20 ml of water was added to the reaction mixture, and the precipitated solid was collected by filtration to obtain 1.20 g of the desired crude product as a reddish brown solid. The crude product was used in the next step without further purification.

Step 2: Synthesis of 2-[3-(ethylthio)-7-(trifluoromethyl)imidazo[1,2-a]pyridin-2-yl]-5-(trifluoromethyl)-3H-imidazo[4,5-b]pyridine (Compound No. 1-1-031 b of the Present Invention)

1.2 g of the crude N-[2-amino-6-(trifluoromethyl)pyridin-3-yl]-3-ethylthio-7-(trifluoromethyl)imidazo[1,2-a]pyridine-2-carboxamide obtained in Step 1 was dissolved in 10 ml of propionic acid, and the solution was stirred under reflux with heating for 3 hours. After the reaction, the solvent was evaporated under reduced pressure. The resulting residue was mixed with 10 ml of water and extracted with ethyl acetate (10 ml×2). The resulting organic layer was washed with a 1M sodium hydroxide aqueous solution and dried over anhydrous sodium sulfate, and the solvent was evaporated under reduced pressure to obtain 1.0 g of the desired product as a brown solid. The product was used in the next step without further purification.
¹H-NMR (CDCl₃): δ8.59 (d, J=7.2 Hz, 1H), 8.03 (d, J=7.8 Hz, 1H), 7.83 (s, 1H), 7.36 (d, J=7.8 Hz, 1H), 7.04-6.98 (m, 1H), 3.02 (q, J=7.4 Hz, 2H), 1.05 (t, J=7.4 Hz, 3H) (no peak of proton of NH was observed).

Step 3: Synthesis of 2-[3-(ethylthio)-7-(trifluoromethyl)imidazo[1,2-a]pyridin-2-yl]-1-methyl-5-(trifluoromethyl)-1H-imidazo[4,5-b]pyridine (Compound No. 1-7-001 b of the Present Invention) and 2-[3-(ethylthio)-7-(trifluoromethyl)imidazo[1,2-a]pyridin-2-yl]-3-methyl-5-(trifluoromethyl)-3H-imidazo[4,5-b]pyridine (Compound No. 1-1-030b of the Present Invention)

To a solution of 66 mg of 63 weight % sodium hydride (dispersed in mineral oil) in 3 ml of N,N-dimethylformamide, a solution of 500 mg of 2-[3-(ethylthio)-7-(trifluoromethyl)imidazo[1,2-a]pyridin-2-yl]-5-(trifluoromethyl)-3H-imidazo[4,5-b]pyridine in 7 ml of N,N-dimethylformamide was added under cooling with ice. After the addition, the reaction mixture was stirred under cooling with ice for 30 minutes. After the stirring, to the reaction mixture, 286 mg of methyl trifluoromethanesulfonate was added under cooling with ice. After the addition, the reaction mixture was stirred at room temperature for 1.5 hours. After the reaction, the reaction mixture was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 150 mg of the desired 2-[3-(ethylthio)-7-(trifluoromethyl)imidazo[1,2-a]pyridin-2-yl]-1-methyl-5-(trifluoromethyl)-1H-imidazo[4,5-b]pyridine and 218 mg of the desired 2-[3-(ethylthio)-7-(trifluoromethyl)imidazo[1,2-a]pyridin-2-yl]-3-methyl-5-(trifluoromethyl)-3H-imidazo[4,5-b]pyridine respectively as a brown solid and as a white solid.
Melting point of 2-[3-(ethylthio)-7-(trifluoromethyl)imidazo[1,2-a]pyridin-2-yl]-1-methyl-5-(trifluoromethyl)-1H-imidazo[4,5-b]pyridine: 164-166° C.
¹H-NMR (CDCl₃): δ8.81 (d, J=7.5 Hz, 1H), 8.03 (s, 1H), 7.91 (d, J=8.2 Hz, 1H), 7.70 (d, J=8.2 Hz, 1H), 7.20 (dd, J=7.5, 1.7 Hz, 1H), 4.31 (s, 3H), 3.35 (q, J=7.4 Hz, 2H), 1.24 (t, J=7.4 Hz, 3H).
Melting point of 2-[3-(ethylthio)-7-(trifluoromethyl)imidazo[1,2-a]pyridin-2-yl]-3-methyl-5-(trifluoromethyl)-3H-imidazo[4,5-b]pyridine: 163-165° C.
¹H-NMR (CDCl₃): δ8.77 (d, J=7.2 Hz, 1H), 8.26 (d, J=8.2 Hz, 1H), 8.06 (s, 1H), 7.68 (d, J=8.2 Hz, 1H), 7.21 (dd, J=7.2, 1.5 Hz, 1H), 4.33 (s, 3H), 3.12 (q, J=7.4 Hz, 2H), 1.20 (t, J=7.4 Hz, 3H).

Synthetic Example 9: Synthesis of 2-[3-(ethylthio)-7-(trifluoromethyl)imidazo[1,2-a]pyridin-2-yl]-3-methyl-6-(trifluoromethyl)-3H-imidazo[4,5-c]pyridine (Compound No. 1-8-005b of the Present Invention) and synthesis of 2-[3-(ethylsulfonyl)-7-(trifluoromethyl)imidazo[1,2-a]pyridin-2-yl]-3-methyl-6-(trifluoromethyl)-3H-imidazo[4,5-c]pyridine (Compound No. 1-8-005a of the Present Invention)

Step 1: Synthesis of 3-(ethylthio)-N-[5-(methylamino)-2-(trifluoromethyl)pyridin-4-yl]-7-(trifluoromethyl)imidazo[1,2-a]pyridine-2-carboxamide 303 mg of $N^3$-methyl-6-(trifluoromethyl)pyridine-3,4-diamine was dissolved in 15 ml of pyridine, and 552 mg of 3-(ethylthio)-7-(trifluoromethyl)imidazo[1,2-a]pyridine-2-carboxylic acid and 732 mg of 1-ethyl-3-(3-dimethylaminopropyl)carbodiimide hydrochloride were added at room temperature. After the addition, the reaction mixture was stirred at room temperature overnight. After the reaction, the solvent was evaporated under reduced pressure. The obtained residue was mixed with 10 ml of water and extracted with chloroform (10 ml×2). The resulting organic layer was dried over anhydrous sodium sulfate, and the solvent was evaporated under reduced pressure to obtain 986 mg of the desired crude product. The crude product was used in the next step without further purification.

Step 2: Synthesis of 2-[3-(ethylthio)-7-(trifluoromethyl)imidazo[1,2-a]pyridin-2-yl]-3-methyl-6-(trifluoromethyl)-3H-imidazo[4,5-c]pyridine (Compound No. 1-8-005b of the Present Invention)

986 mg of the crude 3-(ethylthio)-N-[5-(methylamino)-2-(trifluoromethyl)pyridin-4-yl]-7-(trifluoromethyl)imidazo[1,2-a]pyridine-2-carboxamide obtained in Step 1 was dissolved in 15 ml of acetic acid, and the solution was stirred under reflux with heating for 22 hours. After the stirring, the reaction mixture was stirred at room temperature overnight. After the reaction, the solvent was evaporated under reduced pressure. The resulting residue was mixed with 10 ml of water and extracted with chloroform (10 ml×2). The resulting organic layer was dried over anhydrous sodium sulfate, and the solvent was evaporated under reduced pressure. The resulting residue was purified by preparative medium pressure liquid chromatography using n-hexane/ethyl acetate (with a gradient of from 100:0 to 70:30) as the eluent to obtain 358 mg of the desired product as a yellow solid.

Melting point: 217-219° C.
$^1$H-NMR (CDCl$_3$): δ8.97 (s, 1H), 8.78 (d, J=7.2 Hz, 1H), 8.20 (s, 1H), 8.05 (s, 1H), 7.22 (d, J=7.2 Hz, 1H), 4.37 (s, 3H), 3.15 (q, J=7.5 Hz, 2H), 1.22 (t, J=7.5 Hz, 3H).

Step 3: Synthesis of 2-[3-(ethylsulfonyl)-7-(trifluoromethyl)imidazo[1,2-a]pyridin-2-yl]-3-methyl-6-(trifluoromethyl)-3H-imidazo[4,5-c]pyridine (Compound No. 1-8-005a of the Present Invention)

To a solution of 258 mg of 2-[3-(ethylthio)-7-(trifluoromethyl)imidazo[1,2-a]pyridin-2-yl]-3-methyl-6-(trifluoromethyl)-3H-imidazo[4,5-c]pyridine in 8 ml of chloroform, 323 mg of 65 weight % m-chloroperbenzoic acid (containing about 30 weight % of water) was added under cooling with ice. After the addition, the reaction mixture was stirred at room temperature for one hour. After the reaction, the reaction mixture was mixed with a saturated sodium thiosulfate aqueous solution and extracted with chloroform (10 ml). The resulting organic layer was washed with a saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent. 10 ml of diisopropyl ether was added to the obtained solid, followed by filtration to obtain 200 mg of the desired product as a yellow solid.

Melting point: 245-247° C.
$^1$H-NMR (CDCl$_3$): δ9.39 (d, J=7.2 Hz, 1H), 9.00 (s, 1H), 8.14 (s, 2H), 7.33 (d, J=7.2 Hz, 1H), 4.20 (s, 3H), 4.07 (q, J=7.5 Hz, 2H), 1.46 (t, J=7.5 Hz, 3H).

Synthetic Example 10: Synthesis of 2-[3-(ethylthio)-6-(trifluoromethyl)imidazo[1,2-a]pyridin-2-yl]-3,4-dimethyl-6-(trifluoromethyl)-3H-imidazo[4,5-c]pyridine (Compound No. 1-8-003b of the Present Invention) and 2-[3-(ethylsulfonyl)-6-(trifluoromethyl)imidazo[1,2-a]pyridin-2-yl]-3,4-dimethyl-6-(trifluoromethyl)-3H-imidazo[4,5-c]pyridine (Compound No. 1-8-003a of the Present Invention)

Step 1: Synthesis of 3-(ethylthio)-N-[2-methyl-3-(methylamino)-6-(trifluoromethyl)pyridin-4-yl]-6-(trifluoromethyl)imidazo[1,2-a]pyridine-2-carboxamide 212 mg of $N^3$,2-dimethyl-6-(trifluoromethyl)pyridine-3,4-diamine was dissolved in 10 ml of pyridine, and 200 mg of 3-(ethylthio)-6-(trifluoromethyl)imidazo[1,2-a]pyridine-2-carboxylic acid, 264 mg of 1-ethyl-3-(3-dimethylaminopropyl)carbodiimide hydrochloride and 9 mg of 4-(dimethylamino)pyridine were added at room temperature. After the addition, the reaction mixture was stirred at room temperature overnight. After the reaction, the solvent was evaporated under reduced pressure. The resulting residue was mixed with 10 ml of water and extracted with ethyl acetate (10 ml×2). The resulting organic layer was dried over anhydrous sodium sulfate, and the solvent was evaporated under reduced pressure to obtain crude 3-(ethylthio)-N-[2-methyl-3-(methylamino)-6-(trifluoromethyl)pyridin-4-yl]-6-(trifluoromethyl)imidazo[1,2-a]pyridine-2-carboxamide. The crude product was used in the next step without further purification.

Step 2: Synthesis of 2-[3-(ethylthio)-6-(trifluoromethyl)imidazo[1,2-a]pyridin-2-yl]-3,4-dimethyl-6-(trifluoromethyl)-3H-imidazo[4,5-c]pyridine (Compound No. 1-8-003b of the Present Invention)

The crude 3-(ethylthio)-N-[2-methyl-3-(methylamino)-6-(trifluoromethyl)pyridin-4-yl]-6-(trifluoromethyl)imidazo[1,2-a]pyridine-2-carboxamide obtained in Step 1 was dissolved in 10 ml of acetic acid, and the solution was stirred under reflux with heating for 3 hours. After the reaction, the solvent was evaporated under reduced pressure. The resulting residue was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 70:30) as the eluent to obtain 85 mg of the desired product as a white solid.

Melting point: 169-171° C.

$^1$H-NMR (CDCl$_3$): δ9.01 (s, 1H), 8.03 (s, 1H), 7.83 (d, J=9.3 Hz, 1H), 7.54 (dd, J=9.3, 1.8 Hz, 1H), 4.41 (s, 3H), 3.10 (q, J=7.5 Hz, 2H), 3.08 (s, 3H), 1.22 (t, J=7.5 Hz, 3H).

Step 3: Synthesis of 2-[3-(ethylsulfonyl)-6-(trifluoromethyl)imidazo[1,2-a]pyridin-2-yl]-3,4-dimethyl-6-(trifluoromethyl)-3H-imidazo[4,5-c]pyridine (Compound No. 1-8-003a of the Present Invention)

To a solution of 49 mg of 2-[3-(ethylthio)-6-(trifluoromethyl)imidazo[1,2-a]pyridin-2-yl]-3,4-dimethyl-6-(trifluoromethyl)-3H-imidazo[4,5-c]pyridine in 3 ml of chloroform, 57 mg of 65 weight % m-chloroperbenzoic acid (containing about 30 weight % of water) was added under cooling with ice. After the addition, the reaction mixture was stirred at room temperature for 2 hours. After the reaction, the reaction mixture was mixed with a saturated sodium thiosulfate aqueous solution and extracted with chloroform (10 ml). The resulting organic layer was washed with a saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 37 mg of the desired product as a white solid.

Melting point: 200-205° C.

$^1$H-NMR (CDCl$_3$): δ9.59 (s, 1H), 7.97 (s, 1H), 7.96 (d, J=9.6 Hz, 1H), 7.74 (dd, J=9.6, 1.5 Hz, 1H), 4.25 (s, 3H), 3.96 (q, J=7.5 Hz, 2H), 3.08 (s, 3H), 1.45 (t, J=7.5 Hz, 3H).

Synthetic Example 11: Synthesis of 3-(ethylsulfonyl)-6,7'-bis(trifluoromethyl)-2,2'-biimidazo[1,2-a]pyridine (Compound No. 1-5-002a of the Present Invention)

102 mg of 4-(trifluoromethyl)pyridin-2-amine was dissolved in 4 ml of bromobenzene, and 300 mg of 2-bromo-1-[3-(ethylsulfonyl)-6-(trifluoromethyl)imidazo[1,2-a]pyridin-2-yl]ethanone was added at room temperature. After the addition, the reaction mixture was stirred under reflux with heating for 5 hours. After the reaction, the reaction mixture was mixed with 10 ml of a 1M sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 168 mg of the desired product as a white solid.

Melting point: 245-248° C.

$^1$H-NMR (CDCl$_3$): δ9.65 (s, 1H), 8.57 (s, 1H), 8.30 (d, J=7.2 Hz, 1H), 8.01 (s, 1H), 7.90 (d, J=9.6 Hz, 1H), 7.63 (dd, J=9.6, 1.8 Hz, 1H), 7.03 (dd, J=7.2, 1.8 Hz, 1H), 3.73 (q, J=7.5 Hz, 2H), 1.33 (t, J=7.5 Hz, 3H).

Synthetic Example 12: Synthesis of 2-[3-(ethylsulfonyl)-6-(trifluoromethyl)imidazo[1,2-a]pyridin-2-yl]-7-(perfluoroethyl)imidazo[1,2-c]pyridine (Compound No. 1-3-008a of the Present Invention) and 3-bromo-2-[3-(ethylsulfonyl)-6-(trifluoromethyl) imidazo[1,2-a]pyridin-2-yl]-7-(perfluoroethyl) imidazo[1,2-c]pyrimidine (Compound No. 1-3-010a of the Present Invention)

Step 1: Synthesis of 2-[3-(ethylsulfonyl)-6-(trifluoromethyl)imidazo[1,2-a]pyridin-2-yl]-7-(perfluoroethyl)imidazo[1,2-c]pyrimidine (Compound No. 1-3-008a of the Present Invention)

800 mg of 6-(perfluoroethyl)pyrimidin-4-amine was dissolved in 10 ml of chlorobenzene, and 1,780 mg of 2-bromo-1-[3-(ethylsulfonyl)-6-(trifluoromethyl)imidazo[1,2-a]pyridin-2-yl]ethanone was added at room temperature. After the addition, the reaction mixture was stirred under reflux with heating for 3 hours. After the reaction, the reaction mixture was mixed with 10 ml of a 1M sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure.

The resulting residue was purified by preparative medium pressure liquid chromatography using n-hexane/ethyl acetate (with a gradient of from 100:0 to 50:50) as the eluent to obtain 926 mg of the desired product as a pale solid.

Melting point: 233-239° C.

$^1$H-NMR (CDCl$_3$): δ9.63 (s, 1H), 9.19 (s, 1H), 8.64 (s, 1H), 8.05 (s, 1H), 7.92 (d, J=9.6 Hz, 1H), 7.66 (dd, J=9.6, 1.5 Hz, 1H), 3.72 (q, J=7.5 Hz, 2H), 1.35 (t, J=7.5 Hz, 3H).

Step 2: Synthesis of 3-bromo-2-[3-(ethylsulfonyl)-6-(trifluoromethyl)imidazo[1,2-a]pyridin-2-yl]-7-(perfluoroethyl)imidazo[1,2-c]pyrimidine (Compound No. 1-3-010a of the Present Invention)

To a solution of 150 mg of 2-[3-(ethylsulfonyl)-6-(trifluoromethyl)imidazo[1,2-a]pyridin-2-yl]-7-(perfluoroethyl) imidazo[1,2-c]pyrimidine in 2 ml of N,N-dimethylformamide, 57 mg of N-bromosuccinimide was added under cooling with ice. After the addition, the reaction mixture was stirred at room temperature for 2 hours. After the reaction, the reaction mixture was mixed with 10 ml of water and extracted with diethyl ether (10 ml×2). The resulting organic layer was washed with a saturated sodium thiosulfate aqueous solution and then with saturated sodium hydrogen carbonate, dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 127 mg of the desired product as a white solid.

Melting point: 200-205° C.

$^1$H-NMR (CDCl$_3$): δ9.61 (s, 1H), 9.20 (s, 1H), 7.99 (s, 1H), 7.96 (d, J=9.6 Hz, 1H), 7.68 (d, J=9.6 Hz, 1H), 4.00 (q, J=7.5 Hz, 2H), 1.46 (t, J=7.5 Hz, 3H).

Synthetic Example 13: Synthesis of 2-[3-(ethylsulfonyl)-6-(trifluoromethyl)imidazo[1,2-a]pyridin-2-yl]-5-methyl-7-(perfluoroethyl)imidazo[1,2-c] pyrimidine (Compound No. 1-3-007a of the Present Invention)

143 mg of 2-methyl-6-(perfluoroethyl)pyrimidin-4-amine was dissolved in 4 ml of bromobenzene, and 300 mg of 2-bromo-1-[3-(ethylsulfonyl)-6-(trifluoromethyl)imidazo[1,2-a]pyridin-2-yl]ethanone was added at room temperature. After the addition, the reaction mixture was stirred under reflux with heating for 5 hours. After the reaction, the reaction mixture was mixed with 10 ml of a 1M sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 82 mg of the desired product as a pale yellow solid.

Melting point: 224-226° C.
$^1$H-NMR (CDCl$_3$): δ9.66 (s, 1H), 8.46 (s, 1H), 7.94 (s, 1H), 7.90 (d, J=9.6 Hz, 1H), 7.66 (dd, J=9.6, 1.8 Hz, 1H), 3.85 (q, J=7.5 Hz, 2H), 2.97 (s, 3H), 1.37 (t, J=7.5 Hz, 3H).

Synthetic Example 14: Synthesis of 6-[3-(ethylsulfonyl)-6-(trifluoromethyl)imidazo[1,2-a]pyridin-2-yl]-2-(trifluoromethyl)imidazo[2,1-b]thiazole (Compound No. 1-12-001a of the Present Invention)

106 mg of 5-(trifluoromethyl)thiazol-2-amine was dissolved in 4 ml of bromobenzene, and 300 mg of 2-bromo-1-[3-(ethylsulfonyl)-6-(trifluoromethyl)imidazo[1,2-a]pyridin-2-yl]ethanone was added at room temperature. After the addition, the reaction mixture was stirred under reflux with heating for 5 hours. After the reaction, the reaction mixture was mixed with 10 ml of a 1M sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 153 mg of the desired product as a white solid.

Melting point: 219-220° C.
$^1$H-NMR (CDCl$_3$): δ9.60 (s, 1H), 8.44 (s, 1H), 7.97-7.94 (m, 1H), 7.87 (d, J=9.6 Hz, 1H), 7.62 (dd, J=9.6, 1.5 Hz, 1H), 3.59 (q, J=7.5 Hz, 2H), 1.30 (t, J=7.5 Hz, 3H).

Synthetic Example 15: Synthesis of 2-[3-(ethylthio)-1-methyl-5-(trifluoromethyl)-1H-indol-2-yl]-3-methyl-6-(trifluoromethyl)-3H-imidazo[4,5-b]pyridine (Compound No. 3-1-001 b of the Present Invention) and 2-[3-(ethylsulfonyl)-1-methyl-5-(trifluoromethyl)-1H-indol-2-yl]-3-methyl-6-(trifluoromethyl)-3H-imidazo[4,5-b]pyridine (Compound No. 3-1-001a of the Present Invention)

Step 1: Synthesis of 1-methyl-N-[2-(methylamino)-5-(trifluoromethyl)pyridin-3-yl]-5-(trifluoromethyl)-1H-indole-2-carboxamide 573 mg of N$^2$-methyl-5-(trifluoromethyl)pyridine-2,3-diamine was dissolved in 10 ml of pyridine, and 608 mg of 1-methyl-5-(trifluoromethyl)-1H-indole-2-carboxylic acid, 959 mg of 1-ethyl-3-(3-dimethylaminopropyl)carbodiimide hydrochloride and 31 mg of 4-(dimethylamino)pyridine were added at room temperature. After the addition, the reaction mixture was stirred at room temperature overnight. After the reaction, 20 ml of water was added to the reaction mixture, and the precipitated solid was collected by filtration to obtain 1.02 g of the desired crude product as a gray solid. The crude product was used in the next step without further purification.

Step 2: Synthesis of 3-methyl-2-[1-methyl-5-(trifluoromethyl)-1H-indol-2-yl]-6-(trifluoromethyl)-3H-imidazo[4,5-b]pyridine 968 mg of the crude 1-methyl-N-[2-(methylamino)-5-(trifluoromethyl)pyridin-3-yl]-5-(trifluoromethyl)-1H-indole-2-carboxamide obtained in Step 1 was dissolved in 10 ml of acetic acid, and the solution was stirred under reflux with heating for 3 hours. After the reaction, the solvent was evaporated under reduced pressure. The resulting residue was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 638 mg of the desired product as a flesh-colored solid.

Melting point: 200-202° C.
$^1$H-NMR (DMSO-d6): δ8.84 (d, J=1.4 Hz, 1H), 8.64 (d, J=1.4 Hz, 1H), 8.15 (s, 1H), 7.86 (d, J=8.9 Hz, 1H), 7.63 (dd, J=8.9, 1.4 Hz, 1H), 7.46 (s, 1H), 4.12 (s, 3H), 4.06 (s, 3H).

Step 3: Synthesis of 2-[3-iodo-1-methyl-5-(trifluoromethyl)-1H-indol-2-yl]-3-methyl-6-(trifluoromethyl)-3H-imidazo[4,5-b]pyridine To a solution of 478 mg of 3-methyl-2-[1-methyl-5-(trifluoromethyl)-1H-indol-2-yl]-6-(trifluoromethyl)-3H-imidazo[4,5-b]pyridine in 8 ml of N,N-dimethylformamide, 405 mg of N-iodosuccinimide was added at room temperature. After the addition, the reaction mixture was stirred under reflux with heating for 7 hours. After the reaction, a saturated sodium thiosulfate aqueous solution was added to the reaction mixture, and the precipitated solid was collected by filtration to obtain 675 mg of the desired product as a white solid.

Melting point: 165-167° C.
$^1$H-NMR (CDCl$_3$): δ8.82 (d, J=1.4 Hz, 1H), 8.43 (d, J=1.4 Hz, 1H), 7.90-7.87 (m, 1H), 7.66 (dd, J=8.7, 1.4 Hz, 1H), 7.52 (d, J=8.7 Hz, 1H), 3.97 (s, 3H), 3.85 (s, 3H).

Step 4: Synthesis of 2-[3-(ethylthio)-1-methyl-5-(trifluoromethyl)-1H-indol-2-yl]-3-methyl-6-(trifluoromethyl)-3H-imidazo[4,5-b]pyridine (Compound No. 3-1-001 b of the Present Invention)

To a solution of 626 mg of 2-[3-iodo-1-methyl-5-(trifluoromethyl)-1H-indol-2-yl]-3-methyl-6-(trifluoromethyl)-3H-imidazo[4,5-b]pyridine in 10 ml of 1,4-dioxane, 154 mg of diisopropylethylamine, 69 mg of 4,5'-bis(diphenylphosphino)-9,9'-dimethylxanthene, 54 mg of tris(dibenzylideneacetone)dipalladium(0) and 111 mg of ethanethiol were successively added at room temperature. After the addition, the atmosphere in the reaction vessel was replaced by nitrogen gas, and the mixture was stirred under reflux with heating for 1.5 hours. After the reaction, the reaction mixture was subjected to filtration through Celite, and the Celite was washed with chloroform. The resulting filtrate and washing solution were put together, and the solvent was evaporated under reduced pressure. The resulting residue was purified by preparative medium pressure liquid chromatography using n-hexane/ethyl acetate (with a gradient of from 100:0 to 50:50) as the eluent to obtain 545 mg of the desired product as a pale yellow solid.

Melting point: 153-155° C.

$^1$H-NMR (CDCl$_3$): δ8.80 (s, 1H), 8.40 (s, 1H), 8.19 (s, 1H), 7.65 (d, J=8.5 Hz, 1H), 7.55 (d, J=8.5 Hz, 1H), 3.95 (s, 3H), 3.85 (s, 3H), 2.59 (q, J=7.4 Hz, 2H), 1.00 (t, J=7.4 Hz, 3H).

Step 5: Synthesis of 2-[3-(ethylsulfonyl)-1-methyl-5-(trifluoromethyl)-1H-indol-2-yl]-3-methyl-6-(trifluoromethyl)-3H-imidazo[4,5-b]pyridine (Compound No. 3-1-001a of the Present Invention)

To a solution of 250 mg of 2-[3-(ethylthio)-1-methyl-5-(trifluoromethyl)-1H-indol-2-yl]-3-methyl-6-(trifluoromethyl)-3H-imidazo[4,5-b]pyridine in 5 ml of chloroform, 333 mg of 65 weight % m-chloroperbenzoic acid (containing about 30 weight % of water) was added under cooling with ice. After the addition, the reaction mixture was stirred at room temperature for 2 hours. After the reaction, the reaction mixture was mixed with a saturated sodium thiosulfate aqueous solution and extracted with chloroform (10 ml). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 245 mg of the desired product as a white solid.

Melting point: 143-146° C.

$^1$H-NMR (CDCl$_3$): δ8.83 (s, 1H), 8.50 (s, 1H), 8.40 (d, =1.7 Hz, 1H), 7.75 (dd, J=8.5, 1.7 Hz, 1H), 7.63 (d, J=8.5 Hz, 1H), 3.88 (s, 3H), 3.73 (s, 3H), 3.30-3.11 (m, 2H), 1.27 (t, J=7.2 Hz, 3H).

Synthetic Example 16: Synthesis of 2-[3-(ethylthio)-5-(trifluoromethyl)benzo[b]thiophen-2-yl]-3-methyl-6-(trifluoromethyl)-3H-imidazo[4,5-b]pyridine (Compound No. 3-1-002b of the Present Invention) and 2-[3-(ethylsulfonyl)-5-(trifluoromethyl)benzo[b]thiophen-2-yl]-3-methyl-6-(trifluoromethyl)-3H-imidazo[4,5-b]pyridine (Compound No. 3-1-002a of the Present Invention)

Step 1: Synthesis of N-[2-(methylamino)-5-(trifluoromethyl)pyridin-3-yl]-5-(trifluoromethyl)benzo[b]thiophene-2-carboxamide 573 mg of N$^2$-methyl-5-(trifluoromethyl)pyridine-2,3-diamine was dissolved in 10 ml of pyridine, and 615 mg of 5-(trifluoromethyl)benzo[b]thiophene-2-carboxylic acid, 959 mg of 1-ethyl-3-(3-dimethylaminopropyl)carbodiimide hydrochloride and 31 mg of 4-(dimethylamino)pyridine were added at room temperature. After the addition, the reaction mixture was stirred at room temperature overnight. After the reaction, 20 ml of water was added to the reaction mixture, and the precipitated solid was collected by filtration to obtain 939 mg of the desired crude product as a gray solid. The crude product was used in the next step without further purification.

Step 2: Synthesis of 3-methyl-6-(trifluoromethyl)-2-[5-(trifluoromethyl)benzo[b]thiophen-2-yl]-3H-imidazo[4,5-b]pyridine 877 mg of the crude N-[2-(methylamino)-5-(trifluoromethyl)pyridin-3-yl]-5-(trifluoromethyl)benzo[b]thiophene-2-carboxamide obtained in Step 1 was dissolved in 10 ml of acetic acid, and the solution was stirred under reflux with heating for 3 hours. After the reaction, the solvent was evaporated under reduced pressure. The resulting residue was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 683 mg of the desired product as a flesh-colored solid.

Melting point: 191-193° C.

$^1$H-NMR (DMSO-d6): δ8.83-8.79 (m, 1H), 8.62-8.59 (m, 1H), 8.53 (s, 1H), 8.44 (s, 1H), 8.36 (d, J=8.5 Hz, 1H), 7.80 (d, J=8.5 Hz, 1H), 4.24 (s, 3H).

Step 3: Synthesis of 2-[3-chloro-5-(trifluoromethyl)benzo[b]thiophen-2-yl]-3-methyl-6-(trifluoromethyl)-3H-imidazo[4,5-b]pyridine To a solution of 400 mg of 3-methyl-6-(trifluoromethyl)-2-[5-(trifluoromethyl)benzo[b]thiophen-2-yl]-3H-imidazo[4,5-b]pyridine in 5 ml of N,N-dimethylformamide, 590 mg of 1,3-dichloro-5,5-dimethylhydantoin was added at 80° C. After the addition, the reaction mixture was stirred at 80° C. for 1.5 hours. After the reaction, a saturated sodium thiosulfate aqueous solution was added to the reaction mixture, and the precipitated solid was collected by filtration to obtain 390 mg of the desired product as a white solid.

Melting point: 158-160° C.

$^1$H-NMR (CDCl$_3$): δ8.81-8.77 (m, 1H), 8.41-8.38 (m, 1H), 8.29-8.26 (m, 1H), 8.06 (d, J=8.5 Hz, 1H), 7.80 (d, J=8.5 Hz, 1H), 4.04 (s, 3H).

Step 4: Synthesis of 2-[3-(ethylthio)-5-(trifluoromethyl)benzo[b]thiophen-2-yl]-3-methyl-6-(trifluoromethyl)-3H-imidazo[4,5-b]pyridine (Compound No. 3-1-002b of the Present Invention)

To a solution of 370 mg of 2-[3-chloro-5-(trifluoromethyl)benzo[b]thiophen-2-yl]-3-methyl-6-(trifluoromethyl)-3H-imidazo[4,5-b]pyridine in 5 ml of N,N-dimethylformamide, 119 mg of sodium ethanethiolate was added at 80° C. After the addition, the reaction mixture was stirred at 80° C. for 1.5 hours. After the stirring, 159 mg of sodium ethanethiolate was added to the reaction mixture at 80° C. After the reaction, the reaction mixture was mixed with 20 ml of water and extracted with ethyl acetate (20 ml×2). The resulting organic layer was dehydrated with saturated aqueous sodium chloride and dried over anhydrous sodium sulfate, and the solvent was evaporated under reduced pressure. The resulting residue was purified by silica gel column chromatography using n-hexane/ethyl acetate (with a gradient of from 100:0 to 0:100) as the eluent to obtain 186 mg of the desired product as a yellow solid.

Melting point: 120-122° C.

$^1$H-NMR (CDCl$_3$): δ8.78 (s, 1H), 8.41 (s, 1H), 8.38 (d, J=1.8 Hz, 1H), 8.06 (d, J=8.6 Hz, 1H), 7.77-7.74 (m, 1H), 3.96 (s, 3H), 2.69 (q, J=7.4 Hz, 2H), 1.05 (t, J=7.4 Hz, 3H).

Step 5: Synthesis of 2-[3-(ethylsulfonyl)-5-(trifluoromethyl)benzo[b]thiophen-2-yl]-3-methyl-6-(trifluoromethyl)-3H-imidazo[4,5-b]pyridine (Compound No. 3-1-002a of the Present Invention)

To a solution of 147 mg of 2-[3-(ethylthio)-5-(trifluoromethyl)benzo[b]thiophen-2-yl]-3-methyl-6-(trifluoromethyl)-

3H-imidazo[4,5-b]pyridine in 3 ml of chloroform, 195 mg of 65 weight % m-chloroperbenzoic acid (containing about 30 weight % of water) was added under cooling with ice. After the addition, the reaction mixture was stirred at room temperature for 4 hours. After the reaction, the reaction mixture was mixed with a saturated sodium thiosulfate aqueous solution and extracted with chloroform (10 ml). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 104 mg of the desired product as a white solid.

Melting point: 70-75° C.

$^1$H-NMR (CDCl$_3$): δ8.85 (s, 1H), 8.79 (d, J=1.5 Hz, 1H), 8.35 (d, J=1.8 Hz, 1H), 8.13 (d, J=8.6 Hz, 1H), 7.85 (dd, J=8.6, 1.8 Hz, 1H), 3.89 (s, 3H), 3.38 (q, J=7.5 Hz, 2H), 1.32 (t, J=7.5 Hz, 3H).

Synthetic Example 17: Synthesis of 2-[3-(ethylthio)-7-(trifluoromethyl)imidazo[1,2-a]pyridin-2-yl]-6-(trifluoromethyl)-2H-pyrazolo[4,3-b]pyridine (Compound No. 1-10-002b of the Present Invention) and 2-[3-(ethylsulfonyl)-7-(trifluoromethyl)imidazo[1,2-a]pyridin-2-yl]-6-(trifluoromethyl)-2H-pyrazolo[4,3-b]pyridine (Compound No. 1-10-002a of the Present Invention)

Step 1: Synthesis of 2-[3-(ethylthio)-7-(trifluoromethyl)imidazo[1,2-a]pyridin-2-yl]-6-(trifluoromethyl)-2H-pyrazolo[4,3-b]pyridine (Compound No. 1-10-002b)

A solution of 400 mg of 3-nitro-5-(trifluoromethyl)picolinaldehyde and 522 mg of 3-(ethylthio)-7-(trifluoromethyl)imidazo[1,2-a]pyridin-2-amine in 5 ml of xylene was stirred under reflux with heating for one hour. After the stirring, 1.50 g of triethyl phosphite was added to the reaction mixture at room temperature. After the addition, the reaction mixture was stirred under reflux with heating for one hour. After the reaction, the solvent was evaporated from the reaction mixture. The resulting residue was purified by preparative medium pressure liquid chromatography using n-hexane/ethyl acetate (with a gradient of from 100:0 to 50:50) as the eluent to obtain 613 mg of the desired product as a pale yellow solid.

Melting point: 161-163° C.

$^1$H-NMR (CDCl$_3$): δ9.43-9.41 (m, 1H), 8.85 (d, J=2.1 Hz, 1H), 8.76 (d, J=7.4 Hz, 1H), 8.53-8.49 (m, 1H), 8.05-8.00 (m, 1H), 7.30-7.20 (m, 1H), 2.99 (q, J=7.5 Hz, 2H), 1.21 (t, J=7.5 Hz, 3H).

Step 2: Synthesis of 2-[3-(ethylsulfonyl)-7-(trifluoromethyl)imidazo[1,2-a]pyridin-2-yl]-6-(trifluoromethyl)-2H-pyrazolo[4,3-b]pyridine (Compound No. 1-10-002a of the Present Invention)

To a solution of 150 mg of 2-[3-(ethylthio)-7-(trifluoromethyl)imidazo[1,2-a]pyridin-2-yl]-6-(trifluoromethyl)-2H-pyrazolo[4,3-b]pyridine in 5 ml of chloroform, 204 mg of m-chloroperbenzoic acid (containing 35 weight % of water) was added under cooling with ice. After the addition, the reaction mixture was stirred at room temperature for 2 hours. After the stirring, 40 mg of m-chloroperbenzoic acid (containing 35 weight % of water) was added to the reaction mixture at room temperature. After the addition, the reaction mixture was stirred at room temperature for 2 hours. After the reaction, the reaction mixture was mixed with 3 ml of a saturated sodium thiosulfate aqueous solution and extracted with chloroform (10 ml×2). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 61 mg of the desired product as a white solid.

Melting point: 245-247° C.

$^1$H-NMR (CDCl$_3$): δ9.44 (d, J=7.2 Hz, 1H), 9.17-9.15 (m, 1H), 8.86 (d, J=1.8 Hz, 1H), 8.48-8.43 (m, 1H), 8.13-8.09 (m, 1H), 7.35-7.30 (m, 1H), 4.04 (q, J=7.5 Hz, 2H), 1.48 (t, J=7.5 Hz, 3H).

Synthetic Example 18: Synthesis of 2-[3-(ethylthio)-7-(trifluoromethyl)imidazo[1,2-a]pyridin-2-yl]-6-(trifluoromethyl)-2H-pyrazolo[4,3-c]pyridine (Compound No. 1-11-001 b of the Present Invention) and 2-[3-(ethylsulfonyl)-7-(trifluoromethyl)imidazo[1,2-a]pyridin-2-yl]-6-(trifluoromethyl)-2H-pyrazolo[4,3-c]pyridine (Compound No. 1-11-001a of the Present Invention)

Step 1: Synthesis of 4-azido-6-(trifluoromethyl)nicotinaldehyde

To a solution of 1.50 g of 4-chloro-6-(trifluoromethyl)nicotinaldehyde in 10 ml of N,N-dimethylformamide, 511 mg of sodium azide was added under cooling with ice. After the addition, the reaction mixture was stirred at room temperature for 3 hours. After the reaction, the reaction mixture was mixed with 10 ml of water and extracted with diethyl ether (20 ml×2). The resulting organic layer was dehydrated with saturated aqueous sodium chloride and dried over anhydrous sodium sulfate, and the solvent was evaporated under reduced pressure. The resulting residue was purified by silica gel column chromatography using n-hexane/ethyl acetate (with a gradient of from 100:0 to 80:20) as the eluent to obtain 2.13 g of the desired product as a white solid.

Melting point: 54-56° C.

$^1$H-NMR (CDCl$_3$): δ 10.39 (s, 1H), 9.06 (s, 1H), 7.54 (s, 1H).

Step 2: Synthesis of 2-[3-(ethylthio)-7-(trifluoromethyl)imidazo[1,2-a]pyridin-2-yl]-6-(trifluoromethyl)-2H-pyrazolo[4,3-c]pyridine (Compound No. 1-11-001b of the present invention) To a solution of 200 mg of 4-azido-6-(trifluoromethyl)nicotinaldehyde and 266 mg of 3-(ethylthio)-7-(trifluoromethyl)imidazo[1,2-a]pyridin-2-amine in 5 ml of dichloromethane, 282 mg of triethylamine and 1 ml of 0.56 ml of about 1M titanium(IV) chloride in dichloromethane were successively added. After the addition, the reaction mixture was stirred at room temperature for one hour. After the reaction, the solvent was evaporated from the reaction mixture under reduced pressure. The resulting residue was subjected to filtration through Celite, and the Celite was washed with 20 ml of xylene. The resulting washing solution was stirred under reflux with heating for 2 hours. After the reaction, the reaction mixture was mixed with 10 ml of water and extracted with ethyl acetate (20 ml×2). The resulting organic layer was washed with saturated aqueous sodium chloride and dried over anhydrous sodium sulfate, and the solvent was evaporated under reduced pressure. The resulting residue was purified by silica gel chromatography using n-hexane/ethyl acetate (with a gradient of from 100:0 to 50:50) as the eluent to obtain 250 mg of the desired product as a pale yellow solid.

Melting point: 183-185° C.

$^1$H-NMR (CDCl$_3$): δ9.40-9.37 (m, 1H), 9.29 (d, J=0.9 Hz, 1H), 8.77 (d, J=7.4 Hz, 1H), 8.14 (s, 1H), 8.04-7.99 (m, 1H), 7.30-7.25 (m, 1H), 3.02 (q, J=7.4 Hz, 2H), 1.21 (t, J=7.4 Hz, 3H).

Step 3: Synthesis of 2-[3-(ethylsulfonyl)-7-(trifluoromethyl)imidazo[1,2-a]pyridin-2-yl]-6-(trifluoromethyl)-2H-pyrazolo[4,3-c]pyridine (Compound No. 1-11-001a of the Present Invention) To a solution of 120 mg of 2-[3-(ethylthio)-7-(trifluoromethyl)imidazo[1,2-a]pyridin-2-yl]-6-(trifluoromethyl)-2H-pyrazolo[4,3-c]pyridine in 5 ml of chloroform, 164 mg of 65 weight % m-chloroperbenzoic acid (containing about 30 weight % of water) was added under cooling with ice. After the addition, the reaction mixture was stirred at room temperature overnight. After the reaction, the reaction mixture was mixed with a saturated sodium thiosulfate aqueous solution and extracted with chloroform (10 ml×2).

The resulting organic layer was washed with the saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 63 mg of the desired product as a white solid.

Melting point: 230-233° C.

$^1$H-NMR (CDCl$_3$): δ9.43 (d, J=7.4 Hz, 1H), 9.41-9.37 (m, 1H), 9.07 (s, 1H), 8.12-8.06 (m, 2H), 7.36 (dd, J=7.4, 1.8 Hz, 1H), 4.03 (q, J=7.4 Hz, 2H), 1.48 (t, J=7.4 Hz, 3H).

Synthetic Example 19: Synthesis of 2-[3-(ethylthio)-7-(trifluoromethyl)imidazo[1,2-a]pyridin-2-yl]-6-(trifluoromethyl)thiazolo[5,4-b]pyridine (Compound No. 1-13-001b of the Present Invention) and 2-[3-(ethylsulfonyl)-7-(trifluoromethyl)imidazo[1,2-a]pyridin-2-yl]-6-(trifluoromethyl)thiazolo[5,4-b]pyridine (Compound No. 1-13-001a of the Present Invention)

Step 1: Synthesis of 3-(ethylthio)-N-[2-mercapto-5-(trifluoromethyl)pyridin-3-yl]-7-(trifluoromethyl)imidazo[1,2-a]pyridine-2-carboxamide 500 mg of 3-amino-5-(trifluoromethyl)pyridine-2-thiol was dissolved in 5 ml of pyridine, and 621 mg of 3-(ethylthio)-7-(trifluoromethyl)imidazo[1,2-a]pyridine-2-carboxylic acid, 820 mg of 1-ethyl-3-(3-dimethylaminopropyl)carbodiimide hydrochloride and 10 mg of 1-hydroxybenzotriazole were added at room temperature. After the addition, the reaction mixture was stirred at room temperature overnight. After the reaction, water was added to the reaction mixture, and the precipitated solid was collected by filtration to obtain 234 mg of the desired crude product as a brown solid. The crude product was used in the next step without further purification.

Step 2: Synthesis of 2-[3-(ethylthio)-7-(trifluoromethyl)imidazo[1,2-a]pyridin-2-yl]-6-(trifluoromethyl)thiazolo[5,4-b]pyridine (Compound No. 1-13-001 b of the Present Invention)

214 mg of the crude 3-(ethylthio)-N-[2-mercapto-5-(trifluoromethyl)pyridin-3-yl]-7-(trifluoromethyl)imidazo[1,2-a]pyridine-2-carboxamide obtained in Step 1 was dissolved in 5 ml of propionic acid, and the solution was stirred under reflux with heating for 4 hours. After the stirring, the reaction mixture was stirred at room temperature overnignt. After the reaction, water was added to the reaction mixture and extracted with ethyl acetate (10 ml×2). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 20 mg of the desired product as a white solid.

Melting point: 150-160° C.

$^1$H-NMR (CDCl$_3$): δ8.91-8.87 (m, 1H), 8.71 (d, J=7.5 Hz, 1H), 8.65-8.61 (m, 1H), 8.06 (s, 1H), 7.20 (dd, J=7.5, 1.5 Hz, 1H), 3.08 (q, J=7.4 Hz, 2H), 1.27 (t, J=7.4 Hz, 3H).

Step 3: Synthesis of 2-[3-(ethylsulfonyl)-7-(trifluoromethyl)imidazo[1,2-a]pyridin-2-yl]-6-(trifluoromethyl)thiazolo[5,4-b]pyridine (Compound No. 1-13-001a of the Present Invention)

To a solution of 20 mg of 2-[3-(ethylthio)-7-(trifluoromethyl)imidazo[1,2-a]pyridin-2-yl]-6-(trifluoromethyl)thiazolo[5,4-b]pyridine in 3 ml of chloroform, 27 mg of 65 weight % m-chloroperbenzoic acid (containing about 30 weight % of water) was added under cooling with ice. After the addition, the reaction mixture was stirred at room temperature for 2 hours. After the reaction, the reaction mixture was mixed with a saturated sodium thiosulfate aqueous solution and extracted with chloroform (10 ml×2).

The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 15 mg of the desired product as a white solid.

Melting point: 243-245° C.

$^1$H-NMR (CDCl$_3$): δ9.53 (d, J=7.5 Hz, 1H), 8.95-8.93 (m, 1H), 8.63-8.61 (m, 1H), 8.17-8.14 (m, 1H), 7.30 (dd, J=7.5, 1.9 Hz, 1H), 4.10 (q, J=7.5 Hz, 2H), 1.45 (t, J=7.5 Hz, 3H).

Synthetic Example 20: Synthesis of 2-[3-(ethylthio)-7-(trifluoromethyl)imidazo[1,2-a]pyridin-2-yl]-6-iodo-3-methyl-3H-imidazo[4,5-b]pyridine (Compound No. 1-1-026b of the Present Invention), 2-ethylhexyl-3-((2-(3-(ethylthio)-7-(trifluoromethyl)imidazo[1,2-a]pyridin-2-yl)-3-methyl-3H-imidazo[4,5-b]pyridin-6-yl)thio)propanoate (Compound No. 1-1-028b of the Present Invention), 2-[3-(ethylthio)-7-(trifluoromethyl)imidazo[1,2-a]pyridin-2-yl]-3-methyl-6-((trifluoromethyl)thio)-3H-imidazo[4,5-b]pyridine (Compound No. 1-1-027b of the Present Invention) and 2-[3-(ethylsulfonyl)-7-(trifluoromethyl)imidazo[1,2-a]pyridin-2-yl]-3-methyl-6-((trifluoromethyl)thio)-3H-imidazo[4,5-b]pyridine (Compound No. 1-1-027a of the Present Invention)

Step 1: Synthesis of 3-(ethylthio)-N-[5-iodo-2-(methylamino)pyridin-3-yl]-7-(trifluoromethyl)imidazo[1,2-a]pyridine-2-carboxamide 1.59 g of 5-iodo-N$^2$-methylpyridine-2,3-diamine was dissolved in 15 ml of pyridine, and 1.54 g of 3-(ethylthio)-7-

(trifluoromethyl)imidazo[1,2-a]pyridine-2-carboxylic acid and 2.45 g of 1-ethyl-3-(3-dimethylaminopropyl)carbodiimide hydrochloride were added at room temperature. After the addition, the reaction mixture was stirred at room temperature overnight. After the reaction, water was added to the reaction mixture, and the precipitated solid was collected by filtration to obtain 2.49 g of the desired crude product as a gray solid. The crude product was used in the next step without further purification.

$^1$H-NMR (CDCl$_3$): δ8.97 (brs, 1H), 8.71 (d, J=7.2 Hz, 1H), 8.27 (d, J=2.0 Hz, 1H), 8.07 (d, J=2.0 Hz, 1H), 7.96 (s, 1H), 7.19 (dd, J=7.2, 2.0 Hz, 1H), 4.78 (brs, 1H), 3.08 (q, J=7.4 Hz, 2H), 3.03 (d, J=4.8 Hz, 3H), 1.22 (t, J=7.4 Hz, 3H).

Step 2: Synthesis of 2-[3-(ethylthio)-7-(trifluoromethyl)imidazo[1,2-a]pyridin-2-yl]-6-iodo-3-methyl-3H-imidazo[4,5-b]pyridine (Compound No. 1-1-026b of the Present Invention)

2.49 g of the crude 3-(ethylthio)-N-[5-iodo-2-(methylamino)pyridin-3-yl]-7-(trifluoromethyl)imidazo[1,2-a]pyridine-2-carboxamide obtained in Step 1 was dissolved in 15 ml of acetic acid, and the solution was stirred under reflux with heating for 3.5 hours. After the reaction, water was added to the reaction mixture, and the precipitated solid was collected by filtration. The resulting solid was washed with n-hexane to obtain 2.02 g of the desired product as a brown solid.

Melting point: 230-233° C.
$^1$H-NMR (CDCl$_3$): δ8.76 (d, J=7.2 Hz, 1H), 8.62 (d, J=1.7 Hz, 1H), 8.47 (d, J=1.7 Hz, 1H), 8.03 (s, 1H), 7.19 (dd, J=7.2, 1.7 Hz, 1H), 4.25 (s, 3H), 3.11 (q, J=7.5 Hz, 2H), 1.20 (t, J=7.5 Hz, 3H).

Step 3: Synthesis of 2-ethylhexyl 3-((2-(3-(ethylthio)-7-(trifluoromethyl)imidazo[1,2-a]pyridin-2-yl)-3-methyl-3H-imidazo[4,5-b]pyridin-6-yl)thio)propanoate (Compound No. 1-1-028b of the Present Invention)

To a solution of 503 mg of 2-[3-(ethylthio)-7-(trifluoromethyl)imidazo[1,2-a]pyridin-2-yl]-6-iodo-3-methyl-3H-imidazo[4,5-b]pyridine in 10 ml of 1,4-dioxane, 387 mg of diisopropylethylamine, 58 mg of 4,5'-bis(diphenylphosphino)-9,9'-dimethylxanthene, 92 mg of tris(dibenzylideneacetone)dipalladium(0) and 262 mg of 2-ethylhexyl 3-mercaptopropionate were successively added at room temperature. After the addition, the atmosphere in the reaction vessel was replaced by nitrogen gas, and the mixture was stirred under reflux with heating for 4 hours. After the reaction, the reaction mixture was mixed with 10 ml of water and extracted with diethyl ether (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 80:20) as the eluent to obtain 599 mg of the desired product as a yellow solid.

Melting point: 94-96° C.
$^1$H-NMR (CDCl$_3$): δ8.76 (d, J=7.2 Hz, 1H), 8.53 (d, J=2.0 Hz, 1H), 8.27 (d, J=2.0 Hz, 1H), 8.03 (s, 1H), 7.18 (dd, J=7.2, 1.9 Hz, 1H), 4.27 (s, 3H), 4.01 (dd, J=5.8, 1.7 Hz, 2H), 3.20-3.05 (m, 4H), 2.62 (t, J=7.3 Hz, 2H), 1.45-1.20 (m, 12H), 0.89 (t, J=7.5 Hz, 6H).

Step 4: Synthesis of 2-[3-(ethylthio)-7-(trifluoromethyl)imidazo[1,2-a]pyridin-2-yl]-3-methyl-6-((trifluoromethyl)thio)-3H-imidazo[4,5-b]pyridine (Compound No. 1-1-027b of the Present Invention)

Under a nitrogen atmosphere, to a solution of 560 mg of 2-ethylhexyl 3-((2-(3-(ethylthio)-7-(trifluoromethyl)imidazo[1,2-a]pyridin-2-yl)-3-methyl-3H-imidazo[4,5-b]pyridin-6-yl)thio)propanoate in 5 ml of tetrahydrofuran, 159 mg of potassium tert-butoxide was added under cooling with ice. After the addition, the reaction mixture was stirred under cooling with ice for 30 minutes. After the stirring, to the reaction mixture, 756 mg of S-(trifluoromethyl)dibenzothiophenium trifluoromethanesulfonate was added under cooling with ice. After the addition, the reaction mixture was stirred at room temperature overnight. After the reaction, the reaction mixture was mixed with water and extracted with chloroform (10 ml×2). The resulting organic layer was washed with a saturated sodium hydrogen carbonate aqueous solution and dried over anhydrous sodium sulfate, and the solvent was evaporated under reduced pressure. The resulting residue was purified by thin layer chromatography using n-hexane/ethyl acetate (with a gradient of from 100:0 to 80:20) as the eluent to obtain 69 mg of the desired product as a pale yellow solid.

Melting point: 209-210° C.
$^1$H-NMR (CDCl$_3$): δ8.77 (d, J=7.2 Hz, 1H), 8.66 (d, J=2.0 Hz, 1H), 8.46 (d, J=2.0 Hz, 1H), 8.05-8.02 (m, 1H), 7.20 (dd, J=7.2, 1.9 Hz, 1H), 4.31 (s, 3H), 3.14 (q, J=7.4 Hz, 2H), 1.21 (t, J=7.4 Hz, 3H).

Step 5: Synthesis of 2-[3-(ethylsulfonyl)-7-(trifluoromethyl)imidazo[1,2-a]pyridin-2-yl]-3-methyl-6-((trifluoromethyl)thio)-3H-imidazo[4,5-b]pyridine (Compound No. 1-1-027a of the Present Invention)

To a solution of 31 mg of 2-[3-(ethylthio)-7-(trifluoromethyl)imidazo[1,2-a]pyridin-2-yl]-3-methyl-6-((trifluoromethyl)thio)-3H-imidazo[4,5-b]pyridine in 3 ml of chloroform, 38 mg of 65 weight % m-chloroperbenzoic acid (containing about 30 weight % of water) was added under cooling with ice. After the addition, the reaction mixture was stirred at room temperature for 2 hours. After the reaction, the reaction mixture was mixed with a saturated sodium thiosulfate aqueous solution and extracted with chloroform (10 ml×2). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 34 mg of the desired product as a white solid.

Melting point: 220-223° C.
$^1$H-NMR (CDCl$_3$): δ9.41 (d, J=7.4 Hz, 1H), 8.70 (d, J=2.0 Hz, 1H), 8.41 (d, J=2.0 Hz, 1H), 8.14 (s, 1H), 7.31 (dd, J=7.4, 1.6 Hz, 1H), 4.16 (s, 3H), 4.11 (q, J=7.4 Hz, 2H), 1.45 (t, J=7.4 Hz, 3H).

Synthetic Example 21: Synthesis of 2-[3-(ethylsulfonyl)-7-(trifluoromethyl)imidazo[1,2-a]pyridin-2-yl]-3-methyl-6-(trifluoromethyl)-3H-imidazo[4,5-b]pyridine 4-oxide (Compound No. 1-14-001a of the Present Invention)

To a solution of 500 mg of 2-[3-(ethylsulfonyl)-7-(trif-luoromethyl)imidazo[1,2-a]pyridin-2-yl]-3-methyl-6-(trifluoromethyl)-3H-imidazo[4,5-b]pyridine in 15 ml of acetonitrile, 834 mg of 65 weight % m-chloroperbenzoic acid (containing about 30 weight % of water) was added under cooling with ice. After the addition, the reaction mixture was stirred at 50° C. for 20 hours. After the stirring, 279 mg of 65 weight % m-chloroperbenzoic acid (containing about 30 weight % of water) was added to the reaction mixture at room temperature. After the addition, the reaction mixture was stirred at 50° C. for 20 hours. After the stirring, 418 mg of 65 weight % m-chloroperbenzoic acid (containing about 30 weight % of water) was added to the reaction mixture at room temperature. After the addition, the reaction mixture was stirred to 50° C. for 20 hours. After the reaction, the reaction mixture was mixed with a saturated sodium thiosulfate aqueous solution and extracted with chloroform (20 ml×2). The resulting organic layer was washed with a 1M sodium hydroxide aqueous solution and dried over anhydrous sodium sulfate, and the solvent was evaporated under reduced pressure. The resulting residue was purified by preparative medium pressure liquid chromatography using n-hexane/ethyl acetate with a gradient of from 100:0 to 0:100) as the eluent to obtain 67 mg of the desired product as a white solid.

$^1$H-NMR (CDCl$_3$): δ9.35 (d, J=7.2 Hz, 1H), 8.48-8.46 (m, 1H), 8.19-8.16 (m, 1H), 7.96 (s, 1H), 7.35 (dd, J=7.2, 1.7 Hz, 1H), 4.58 (s, 3H), 3.94 (q, J=7.4 Hz, 2H), 1.46 (t, J=7.4 Hz, 3H).

Synthetic Example 22: Synthesis of 8-[3-(ethylthio)-6-(trifluoromethyl)imidazo[1,2-a]pyridin-2-yl]-9-methyl-(trifluoromethyl)-9H-imidazo[4,5-c]pyridazine (Compound No. 1-16-001 b of the Present Invention) and 8-[3-(ethylsulfonyl)-6-(trifluoromethyl)imidazo[1,2-a]pyridin-2-yl]-9-methyl-(trifluoromethyl)-9H-imidazo[4,5-c]pyridazine (Compound No. 1-16-001a of the Present Invention)

Step 1: Synthesis of 3-(ethylthio)-N-[3-(methylamino)-6-(trifluoromethyl)pyridazin-4-yl]-6-(trifluoromethyl)imidazo[1,2-a]pyridine-2-carboxamide 300 mg of 4-bromo-N-methyl-6-(trifluoromethyl)pyridazin-3-amine, 509 mg of 3-(ethylthio)-6-(trifluoromethyl)imidazo[1,2-a]pyridine-carboxamide, 497 mg of potassium phosphate and 52 mg of N,N'-dimethylethylenediamine were dissolved in 4 ml of N,N-dimethylformamide, and 56 mg of copper(I) iodide was added at room temperature. After the addition, the atmosphere in the reaction vessel was replaced by nitrogen gas, and the mixture was stirred at 90° C. for 9 hours. After the reaction, the reaction mixture was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure to obtain crude 3-(ethylthio)-N-[3-(methylamino)-6-(trifluoromethyl)pyridazin-4-yl]-6-(trifluoromethyl)imidazo[1,2-a]pyridine-2-carboxamide as the desired product. The crude product was used in the next step without further purification.

Step 2: Synthesis of 8-[3-(ethylthio)-6-(trifluoromethyl)imidazo[1,2-a]pyridin-2-yl]-9-methyl-(trifluoromethyl)-9H-imidazo[4,5-c]pyridazine (Compound No. 1-16-001 b of the Present Invention)

The crude 3-(ethylthio)-N-[3-(methylamino)-6-(trifluoromethyl)pyridazin-4-yl]-7-(trifluoromethyl)imidazo[1,2-a] pyridine-2-carboxamide obtained in Step 1 was dissolved in 10 ml of acetic acid, and the solution was stirred under reflux with heating for 7 hours. After the reaction, the solvent was evaporated under reduced pressure. The resulting residue was mixed with 10 ml of water and extracted with ethyl acetate (10 ml×2). The resulting organic layer was washed with a saturated sodium hydrogen carbonate aqueous solution and then with 28 weight % aqueous ammonia, dehydrated with saturated aqueous sodium chloride and dried over anhydrous sodium sulfate, and the solvent was evaporated under reduced pressure. The resulting residue was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 25:75) as the eluent to obtain 72 mg of the desired product as a pale yellow solid.

Melting point: 240-242° C.

$^1$H-NMR (CDCl$_3$): δ9.05-9.00 (m, 1H), 8.23 (s, 1H), 7.85 (d, J=9.8 Hz, 1H), 7.56 (dd, J=9.4, 1.6 Hz, 1H), 4.55 (s, 3H), 3.16 (q, J=7.4 Hz, 2H), 1.25 (t, J=7.4 Hz, 3H).

Step 3: Synthesis of 8-[3-(ethylsulfonyl)-6-(trifluoromethyl)imidazo[1,2-a]pyridin-2-yl]-9-methyl-(trifluoromethyl)-9H-imidazo[4,5-c]pyridazine (Compound No. 1-16-001a of the Present Invention)

To a solution of 62 mg of 8-[3-(ethylthio)-6-(trifluoromethyl)imidazo[1,2-a]pyridin-2-yl]-9-methyl-(trifluoromethyl)-9H-imidazo[4,5-c]pyridazine in 5 ml of chloroform, 81 mg of 65 weight % m-chloroperbenzoic acid (containing about 30 weight % of water) was added under cooling with ice. After the addition, the reaction mixture was stirred at room temperature for one hour. After the reaction, the reaction mixture was mixed with a saturated sodium thiosulfate aqueous solution and extracted with chloroform (10 ml). The resulting organic layer was washed with a saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 25:75) as the eluent to obtain 66 mg of the desired product as a pale yellow solid.

Melting point: 274-276° C.

$^1$H-NMR (CDCl$_3$): δ9.70-9.60 (m, 1H), 8.22 (s, 1H), 7.99 (d, J=9.4 Hz, 1H), 7.75 (dd, J=9.4, 1.6 Hz, 1H), 4.38 (s, 3H), 4.05 (q, J=7.4 Hz, 2H), 1.48 (t, J=7.4 Hz, 3H).

Synthetic Example 23: Synthesis of 2-[3-(ethylthio)-6-(trifluoromethyl)imidazo[1,2-a]pyrimidin-2-yl]-3-methyl-6-(trifluoromethyl)-3H-imidazo[4,5-b]pyridine (Compound No. 1-1-054b of the Present Invention) and 2-[3-(ethylsulfonyl)-6-(trifluoromethyl)imidazo[1,2-a]pyrimidin-2-yl]-3-methyl-6-(trifluoromethyl)-3H-imidazo[4,5-b]pyridine (Compound No. 1-1-054a of the Present Invention)

Step 1: Synthesis of 3-methyl-6-(trifluoromethyl)-2-[6-(trifluoromethyl)imidazo[1,2-a]pyrimidin-2-yl]-3H-imidazo[4,5-b]pyridine 250 mg of 5-(trifluoromethyl)pyrimidin-2-amine was dissolved in 10 ml of acetonitrile, and 550 mg of 2-bromo-1-[3-methyl-6-(trifluoromethyl)-3H-imidazo[4,5-b]pyridin-2-yl]ethanone was added at room temperature. After the addition, the reaction mixture was stirred under reflux with heating for 7.5 hours. After the reaction, 10 ml of water was added to the reaction mixture, and the precipitated solid was collected by filtration to obtain 445 mg of the desired product as a yellow solid.

Melting point: 283-285° C.

$^1$H-NMR (CDCl$_3$): δ8.92-8.89 (m, 1H), 8.84 (d, J=2.4 Hz, 1H), 8.73 (s, 1H), 8.57 (s, 1H), 8.29 (s, 1H), 4.53 (s, 3H).

Step 2: Synthesis of 2-[3-iodo-6-(trifluoromethyl) imidazo[1,2-a]pyrimidin-2-yl]-3-methyl-6-(trifluoromethyl)-3H-imidazo[4,5-b]pyridine To a solution of 415 mg of 3-methyl-6-(trifluoromethyl)-2-[6-(trifluoromethyl)imidazo[1,2-a]pyrimidin-2-yl]-3H-imidazo[4,5-b]pyridine in 4 ml of N,N-dimethylformamide, 408 mg of 1,3-diiodo-5,5-dimethylhydantoin was added at 80° C. After the addition, the reaction mixture was stirred at 80° C. for 3 hours. After the reaction, a saturated sodium thiosulfate aqueous solution was added to the reaction mixture, and the precipitated solid was collected by filtration to obtain 468 mg of the desired product as a yellow solid.

Melting point: 260-265° C.

$^1$H-NMR (CDCl$_3$): δ9.00-8.86 (m, 1H), 8.81 (d, J=2.4 Hz, 1H), 8.74 (d, J=1.5 Hz, 1H), 8.42 (d, J=1.5 Hz, 1H), 4.43 (s, 3H).

Step 3: Synthesis of 2-[3-(ethylthio)-6-(trifluoromethyl)imidazo[1,2-a]pyrimidin-2-yl]-3-methyl-6-(trifluoromethyl)-3H-imidazo[4,5-b]pyridine (Compound No. 1-1-054b of the Present Invention)

To a solution of 438 mg of 2-[3-iodo-6-(trifluoromethyl) imidazo[1,2-a]pyrimidin-2-yl]-3-methyl-6-(trifluoromethyl)-3H-imidazo[4,5-b]pyridine in 10 ml of 1,4-dioxane, 334 mg of diisopropylethylamine, 50 mg of 4,5'-bis(diphenylphosphino)-9,9'-dimethylxathene, 39 mg of tris(dibenzylideneacetone)dipalladium(0) and 106 mg of ethanethiol were successively added at room temperature. After the addition, the atmosphere in the reaction vessel was replaced by nitrogen gas, and the mixture was stirred under reflux with heating for 3 hours. After the reaction, water was added to the reaction mixture, and the precipitated solid was collected by filtration. The resulting solid was washed with diisopropyl ether to obtain 337 mg of the desired product as a yellow solid.

Melting point: 220-222° C.

$^1$H-NMR (CDCl$_3$): δ9.27-9.23 (m, 1H), 8.88 (d, J=2.1 Hz, 1H), 8.75 (s, 1H), 8.42 (s, 1H), 4.42 (s, 3H), 3.25 (q, J=7.5 Hz, 2H), 1.26 (t, J=7.5 Hz, 3H).

Step 4: Synthesis of 2-[3-(ethylsulfonyl)-6-(trifluoromethyl)imidazo[1,2-a]pyrimidin-2-yl]-3-methyl-6-(trifluoromethyl)-3H-imidazo[4,5-b]pyridine (Compound No. 1-1-054a of the Present Invention)

To a solution of 297 mg of 2-[3-(ethylthio)-6-(trifluoromethyl)imidazo[1,2-a]pyrimidin-2-yl]-3-methyl-6-(trifluoromethyl)-3H-imidazo[4,5-b]pyridine in 7 ml of chloroform, 371 mg of 65 weight % m-chloroperbenzoic acid (containing about 30 weight % of water) was added under cooling with ice. After the addition, the reaction mixture was stirred at room temperature for 3.5 hours. After the stirring, m-chloroperbenzoic acid (containing 35 weight % of water) was added to the reaction mixture at room temperature. After the addition, the reaction mixture was stirred at room temperature for one hour. After the stirring, 50 mg of m-chloroperbenzoic acid (containing 35 weight % of water) was added to the reaction mixture at room temperature. After the addition, the reaction mixture was stirred at room temperature for one hour. After the reaction, the reaction mixture was mixed with a saturated sodium thiosulfate aqueous solution and extracted with chloroform (10 ml×2). The resulting organic layer was washed with a saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 150 mg of the desired product as a white solid.

Melting point: 244-248° C.

$^1$H-NMR (CDCl$_3$): δ10.00-9.95 (m, 1H), 9.04 (d, J=2.4 Hz, 1H), 8.80 (s, 1H), 8.41-8.37 (m, 1H), 4.30 (s, 3H), 4.27 (q, J=7.5 Hz, 2H), 1.49 (t, J=7.5 Hz, 3H).

Synthetic Example 24: Synthesis of 2-[3-(ethylthio)-7-(trifluoromethyl)imidazo[1,2-c]pyrimidin-2-yl]-3-methyl-6-(trifluoromethyl)-3H-imidazo[4,5-b] pyridine (Compound No. 1-1-055b of the Present Invention) and 2-[3-(ethylsulfonyl)-7-(trifluoromethyl)imidazo[1,2-c]pyrimidin-2-yl]-3-methyl-6-(trifluoromethyl)-3H-imidazo[4,5-b]pyridine (Compound No. 1-1-055a of the Present Invention)

Step 1: Synthesis of 3-methyl-6-(trifluoromethyl)-2-[7-(trifluoromethyl)imidazo[1,2-c]pyrimidin-2-yl]-3H-imidazo[4,5-b]pyridine 251 mg of 6-(trifluoromethyl)pyrimidin-4-amine was dissolved in 10 ml of acetonitrile, and 550 mg of 2-bromo-1-[3-methyl-6-(trifluoromethyl)-3H-imidazo[4,5-b]pyridin-2-yl]ethanone was added at room temperature. After the addition, the reaction mixture was stirred under reflux with heating for 7.5 hours. After the reaction, 10 ml of water was added to the reaction mixture, and the precipitated solid was collected by filtration to obtain 335 mg of the desired product as a yellow solid.

Melting point: 257-260° C.

$^1$H-NMR (CDCl$_3$): δ9.22 (s, 1H), 8.73 (d, J=1.2 Hz, 1H), 8.64 (s, 1H), 8.29 (d, J=1.8 Hz, 1H), 8.05 (s, 1H), 4.47 (s, 3H).

Step 2: Synthesis of 2-[3-bromo-7-(trifluoromethyl) imidazo[1,2-c]pyrimidin-2-yl]-3-methyl-6-(trifluoromethyl)-3H-imidazo[4,5-b]pyridine To a solution of 300 mg of 3-methyl-6-(trifluoromethyl)-2-[7-(trifluoromethyl)imidazo[1,2-c]pyrimidin-2-yl]-3H-imidazo[4,5-b]pyridine in 5 ml of N,N-dimethylformamide, 244 mg of 1,3-dibromo-5,5-dimethylhydantoin was added at 80° C. After the addition, the reaction mixture was stirred at 80° C. for 30 minutes. After the reaction, a saturated sodium thiosulfate aqueous solution was added to the reaction mixture, and the precipitated solid was collected by filtration to obtain 468 mg of the desired crude product as a yellow solid. The crude product was used in the next step without further purification.

¹H-NMR (CDCl₃): δ9.27 (s, 1H), 8.75 (d, J=0.9 Hz, 1H), 8.43 (d, J=1.5 Hz, 1H), 8.02 (s, 1H), 4.37 (s, 3H).

Step 3: Synthesis of 2-[3-(ethylthio)-7-(trifluoromethyl)imidazo[1,2-c]pyrimidin-2-yl]-3-methyl-6-(trifluoromethyl)-3H-imidazo[4,5-b]pyridine (Compound No. 1-1-055b of the Present Invention)

To a solution of 452 mg of the crude 2-[3-bromo-7-(trifluoromethyl)imidazo[1,2-c]pyrimidin-2-yl]-3-methyl-6-(trifluoromethyl)-3H-imidazo[4,5-b]pyridine obtained in Step 2 in 10 ml of 1,4-dioxane, 377 mg of diisopropylethylamine, 56 mg of 4,5'-bis(diphenylphosphino)-9,9'-dimethylxanthene, 44 mg of tris(dibenzylideneacetone)dipalladium (0) and 121 mg of ethanethiol were successively added at room temperature. After the addition, the atmosphere in the reaction vessel was replaced by nitrogen gas, and the mixture was stirred under reflux with heating for 6.5 hours. After the stirring, to the reaction mixture, 754 mg of diisopropylethylamine, 112 mg of 4,5'-bis(diphenylphosphino)-9,9'-dimethylxanthene, 88 mg of tris(dibenzylideneacetone)dipalladium(0) and 242 mg of ethanethiol were successively added at room temperature. After the addition, the atmosphere in the reaction vessel was replaced by nitrogen gas, and the mixture was stirred under reflux with heating for 5 hours. After the reaction, water was added to the reaction mixture, and the precipitated solid was collected by filtration. The resulting solid was washed with diisopropyl ether to obtain 371 mg of the desired product as a brown solid.

Melting point: 198-200° C.

¹H-NMR (CDCl₃): δ9.54 (s, 1H), 8.77-8.73 (m, 1H), 8.41 (s, 1H), 8.01 (s, 1H), 4.32 (s, 3H), 3.24 (q, J=7.5 Hz, 2H), 1.26 (t, J=7.5 Hz, 3H).

Step 4: Synthesis of 2-[3-(ethylsulfonyl)-7-(trifluoromethyl)imidazo[1,2-c]pyrimidin-2-yl]-3-methyl-6-(trifluoromethyl)-3H-imidazo[4,5-b]pyridine (Compound No. 1-1-055a of the Present Invention)

To a solution of 315 mg of 2-[3-(ethylthio)-7-(trifluoromethyl)imidazo[1,2-c]pyrimidin-2-yl]-3-methyl-6-(trifluoromethyl)-3H-imidazo[4,5-b]pyridine obtained in Step 3 in 10 ml of chloroform, 412 mg of 65 weight % m-chloroperbenzoic acid (containing about 30 weight % of water) was added under cooling with ice. After the addition, the reaction mixture was stirred at room temperature for 3 hours. After the stirring, 206 mg of m-chloroperbenzoic acid (containing 35 weight % of water) was added to the reaction mixture at room temperature. After the addition, the reaction mixture was stirred at room temperature for 2 hours. After the reaction, the reaction mixture was mixed with a saturated sodium thiosulfate aqueous solution and extracted with chloroform (10 ml×2). The resulting organic layer was washed with a saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 139 mg of the desired product as a white solid.

Melting point: 238-240° C.

¹H-NMR (CDCl₃): δ10.15 (s, 1H), 8.80 (s, 1H), 8.39 (s, 1H), 8.15 (s, 1H), 4.22 (s, 3H), 4.22 (q, J=7.5 Hz, 2H), 1.50 (t, J=7.5 Hz, 3H).

Synthetic Example 25: Synthesis of 2-[3-(ethylsulfonyl)-6-(trifluoromethyl)imidazo[1,2-a]pyridin-2-yl]-6-(trifluoromethyl)imidazo[1,2-a]pyrazine (Compound No. 1-6-002a of the Present Invention)

103 mg of 5-(trifluoromethyl)pyrazin-2-amine was dissolved in 4 ml of bromobenzene, and 300 mg of 2-bromo-1-[3-(ethylsulfonyl)-6-(trifluoromethyl)imidazo[1,2-a]pyridin-2-yl]ethanone was added at room temperature. After the addition, the reaction mixture was stirred under reflux with heating for 5 hours. After the reaction, the reaction mixture was mixed with 10 ml of a 1M sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 38 mg of the desired product as a white solid.

Melting point: 266-270° C.

¹H-NMR (CDCl₃): δ9.63 (s, 1H), 9.24 (s, 1H), 8.68 (s, 1H), 8.62 (s, 1H), 7.93 (d, J=9.3 Hz, 1H), 7.66 (dd, J=9.3, 1.8 Hz, 1H), 3.70 (q, J=7.5 Hz, 2H), 1.35 (t, J=7.5 Hz, 3H).

Synthetic Example 26: Synthesis of 2-[7-chloro-3-(ethylthio)imidazo[1,2-a]pyridin-2-yl]-6-(trifluoromethyl)-3H-imidazo[4,5-c]pyridine (Compound No. 1-8-012b of the Present Invention), 2-[7-chloro-3-(ethylthio)imidazo[1,2-a]pyridin-2-yl]-3-methyl-6-(trifluoromethyl)-3H-imidazo[4,5-c]pyridine (Compound No. 1-8-006b of the Present Invention) and 2-[7-chloro-3-(ethylthio)imidazo[1,2-a]pyridin-2-yl]-1-methyl-6-(trifluoromethyl)-1H-imidazo[4,5-c]pyridine (Compound No. 1-9-003b of the Present Invention)

Step 1: Synthesis of N-[5-amino-2-(trifluoromethyl)pyridin-4-yl]-7-chloro-3-(ethylthio)imidazo[1,2-a]pyridine-2-carboxamide 470 mg of 6-(trifluoromethyl)pyridine-3,4-diamine was dissolved in 7 ml of pyridine, and 486 mg of 7-chloro-3-(ethylthio)imidazo[1,2-a]pyridine-2-carboxylic acid and 752 mg of 1-ethyl-3-(3-dimethylaminopropyl)carbodiimide hydrochloride were added at room temperature. After the addition, the reaction mixture was stirred at room temperature overnight. After the reaction, 20 ml of water was added to the reaction mixture, and the precipitated solid was collected by filtration to obtain 749 mg of the desired crude product as a pale solid. The crude product was used in the next step without further purification.

Step 2: Synthesis of 2-[7-chloro-3-(ethylthio)imidazo[1,2-a]pyridin-2-yl]-6-(trifluoromethyl)-3H-imidazo[4,5-c]pyridine (Compound No. 1-8-012b of the Present Invention)

749 mg of the crude N-[5-amino-2-(trifluoromethyl)pyridin-4-yl]-7-chloro-3-(ethylthio)imidazo[1,2-a]pyridine-2-carboxamide obtained in Step 1 was dissolved in 7 ml of propionic acid, and the solution was stirred under reflux with heating for 20 hours. After the stirring, the solid precipitated in the reaction mixture was collected by filtration. The resulting solid was washed with water to obtain 761 mg of the desired product as a brown solid. The product was used in the next step without further purification.

Step 3: Synthesis of 2-[7-chloro-3-(ethylthio)imidazo[1,2-a]pyridin-2-yl]-3-methyl-6-(trifluoromethyl)-3H-imidazo[4,5-c]pyridine (Compound No. 1-8-006b of the Present Invention) and 2-[7-chloro-3-(ethylthio)imidazo[1,2-a]pyridin-2-yl]-1-methyl-6-(trifluoromethyl)-1H-imidazo[4,5-c]pyridine (Compound No. 1-9-003b of the Present Invention)

To a solution of 219 mg of 63 weight % sodium hydroxide (dispersed in mineral oil) in 10 ml of N,N-dimethylformamide, a solution of 761 mg of 2-[7-chloro-3-(ethylthio)imidazo[1,2-a]pyridin-2-yl]-6-(trifluoromethyl)-3H-imidazo[4,5-c]pyridine in 10 ml of N,N-dimethylformamide was added under cooling with ice. After the addition, the reaction mixture was stirred under cooling with ice for 30 minutes. After the stirring, 940 mg of methyl trifluoromethanesulfonate was added to the reaction mixture under cooling with ice. After the addition, the reaction mixture was stirred to room temperature for one hour. After the reaction, the reaction mixture was mixed with 20 ml of water and extracted with diethyl ether (20 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 65 mg of the desired 2-[7-chloro-3-(ethylthio)imidazo[1,2-a]pyridin-2-yl]-3-methyl-6-(trifluoromethyl)-3H-imidazo[4,5-c]pyridine and 247 mg of the desired 2-[7-chloro-3-(ethylthio)imidazo[1,2-a]pyridin-2-yl]-1-methyl-6-(trifluoromethyl)-1H-imidazo[4,5-c]pyridine respectively as a white solid.

Melting point of 2-[7-chloro-3-(ethylthio)imidazo[1,2-a]pyridin-2-yl]-3-methyl-6-(trifluoromethyl)-3H-imidazo[4,5-c]pyridine: 215-217° C.

$^1$H-NMR (CDCl$_3$): δ8.95 (s, 1H), 8.59 (d, J=7.5 Hz, 1H), 8.19 (s, 1H), 7.74-7.71 (m, 1H), 7.03 (dd, J=7.5, 2.1 Hz, 1H), 4.33 (s, 3H), 3.09 (q, J=7.5 Hz, 2H), 1.19 (t, J=7.5 Hz, 3H).

Melting point of 2-[7-chloro-3-(ethylthio)imidazo[1,2-a]pyridin-2-yl]-1-methyl-6-(trifluoromethyl)-1H-imidazo[4,5-c]pyridine: 187-188° C.

$^1$H-NMR (CDCl$_3$): δ9.24 (s, 1H), 8.59 (dd, J=7.2, 0.6 Hz, 1H), 7.81 (s, 1H), 7.73-7.69 (m, 1H), 7.03 (dd, J=7.2, 1.8 Hz, 1H), 4.26 (s, 3H), 3.10 (q, J=7.5 Hz, 2H), 1.20 (t, J=7.5 Hz, 3H).

Synthetic Example 27: Synthesis of 2-[3-(ethylthio)-6-iodo-8-(trifluoromethyl)imidazo[1,2-a]pyridin-2-yl]-3-methyl-6-(trifluoromethyl)-3H-imidazo[4,5-b]pyridine (Compound No. 1-1-066b of the Present Invention)

Step 1: Synthesis of 2-(ethylthio)-1-[3-methyl-6-(trifluoromethyl)-3H-imidazo[4,5-b]pyridin-2-yl]ethanone To a solution of 20 g of 2-bromo-1-[3-methyl-6-(trifluoromethyl)-3H-imidazo[4,5-b]pyridin-2-yl]ethanone in 80 ml of N,N-dimethylformamide, 4.2 g of ethanethiol and 9.4 g of potassium carbonate were successively added under cooling with ice. After the addition, the reaction mixture was stirred under cooling with ice for 30 minutes. After the stirring, the reaction mixture was stirred at room temperature for one hour. After the reaction, the reaction mixture was mixed with 100 ml of water and extracted with ethyl acetate (100 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hecane/ethyl acetate (with a gradient of from 100:0 to 80:20) as the eluent to obtain 13.8 g of the desired product as a pale yellow solid.

Melting point: 67-69° C.

$^1$H-NMR (CDCl$_3$): δ8.85-8.80 (m, 1H), 8.45-8.40 (m, 1H), 4.24 (s, 3H), 4.07 (s, 2H), 2.66 (q, J=7.4 Hz, 2H), 1.31 (t, J=7.4 Hz, 3H).

Step 2: Synthesis of 2-bromo-2-(ethylthio)-1-[3-methyl-6-(trifluoromethyl)-3H-imidazo[4,5-b]pyridin-2-yl]ethanone To a solution of 11.4 g of 2-(ethylthio)-1-[3-methyl-6-(trifluoromethyl)-3H-imidazo[4,5-b]pyridin-2-yl]ethanone in 100 ml of dichloromethane, 4.2 g of triethylamine was added at room temperature. After the addition, the reaction mixture was cooled to −20° C., and 8.8 g of trimethylsilyl trifluoromethanesulfonate was added. After the addition, the reaction mixture was stirred under cooling with ice for 20 minutes. After the stirring, the reaction mixture was cooled to −20° C., and 14.1 g of trimethylphenylammonium tribromide was added. After the addition, the reaction mixture was stirred under cooling with ice for 30 minutes. After the reaction, the reaction mixture was added dropwise to 100 ml of water under cooling with ice, and the mixture was extracted with chloroform (100 ml×2). The resulting organic layer was dried over anhydrous sodium sulfate, and the solvent was evaporated under reduced pressure to obtain 13.4 g of the desired product as a reddish brown oil.

$^1$H-NMR (CDCl$_3$): δ8.90-8.80 (m, 1H), 8.50-8.40 (m, 1H), 7.14 (s, 1H), 4.27 (s, 3H), 3.05-2.80 (m, 2H), 1.39 (t, J=7.6 Hz, 3H).

Step 3: Synthesis of 2-[3-(ethylthio)-6-iodo-8-(trifluoromethyl) imidazo[1,2-a]pyridin-2-yl]-3-methyl-6-(trifluoromethyl)-3H-imidazo[4,5-b]pyridine (Compound No. 1-1-066b of the Present Invention)

300 mg of 5-iodo-3-(trifluoromethyl)pyridin-2-amine was dissolved in 8 ml of propionitrile, and 345 mg of 2-bromo-2-(ethylthio)-1-[3-methyl-6-(trifluoromethyl)-3H-imidazo[4,5-b]pyridin-2-yl]ethanone was added at room temperature. After the addition, the reaction mixture was stirred under reflux with heating for 1.5 hours. After the reaction, the reaction mixture was mixed with 20 ml of water and extracted with chloroform (20 ml×2). The resulting organic layer was dried over anhydrous sodium sulfate, and the solvent was evaporated under reduced pressure. 10 ml of diisopropyl ether was added to the precipitated solid, followed by filtration to obtain 294 mg of the desired product as an orange solid.

Melting point: 222-225° C.

$^1$H-NMR (CDCl$_3$): δ9.10-9.00 (m, 1H), 8.75-8.70 (m, 1H), 8.40-8.35 (m, 1H), 7.90-7.85 (m, 1H), 4.35 (s, 3H), 3.18 (q, J=7.4 Hz, 2H), 1.24 (t, J=7.4 Hz, 3H).

Synthetic Example 28: Synthesis of 2-[3-(ethylthio)-7-(trifluoromethyl)imidazo[1,2-b]pyridazin-2-yl]-3-methyl-6-(trifluoromethyl)-3H-imidazo[4,5-b]pyridine (Compound No. 1-1-057b of the Present Invention), 2-[3-(ethylsulfonyl)-7-(trifluoromethyl)imidazo[1,2-b]pyridazin-2-yl]-3-methyl-6-(trifluoromethyl)-3H-imidazo[4,5-b]pyridine (Compound No. 1-1-057a of the Present Invention) and 2-[3-(ethylsulfinyl)-7-(trifluoromethyl)imidazo[1,2-b]pyridazin-2-yl]-3-methyl-6-(trifluoromethyl)-3H-imidazo[4,5-b]pyridine (Compound No. 1-1-057c of the Present Invention)

Step 1: Synthesis of 2-[3-(ethylthio)-7-(trifluoromethyl)imidazo[1,2-b]pyridazin-2-yl]-3-methyl-6-(trifluoromethyl)-3H-imidazo[4,5-b]pyridine (Compound No. 1-1-057b of the Present Invention)

42 mg of 5-(trifluoromethyl)pyridazin-3-amine was dissolved in 3 ml of acetonitrile, and 100 mg of 2-bromo-2-

(ethylthio)-1-[3-methyl-6-(trifluoromethyl)-3H-imidazo[4,5-b]pyridin-2-yl]ethanone was added at room temperature. After the addition, the reaction mixture was stirred under reflux with heating for 2 hours. After the reaction, the reaction mixture was mixed with 10 ml of water and extracted with chloroform (10 ml×2). The resulting organic layer was dried over anhydrous sodium sulfate, and the solvent was evaporated under reduced pressure to obtain 130 mg of the desired crude product. The crude product was used in the next step without further purification.

Step 2: Synthesis of 2-[3-(ethylsulfonyl)-7-(trifluoromethyl)imidazo[1,2-b]pyridazin-2-yl]-3-methyl-6-(trifluoromethyl)-3H-imidazo[4,5-b]pyridine (Compound No. 1-1-057a of the Present Invention) and 2-[3-(ethylsulfinyl)-7-(trifluoromethyl)imidazo[1,2-b]pyridazin-2-yl]-3-methyl-6-(trifluoromethyl)-3H-imidazo[4,5-b]pyridine (Compound No. 1-1-057c of the Present Invention)

To a solution of 120 mg of the crude 2-[3-(ethylthio)-7-(trifluoromethyl)imidazo[1,2-b]pyridazin-2-yl]-3-methyl-6-(trifluoromethyl)-3H-imidazo[4,5-b]pyridine obtained in Step 1 in 10 ml of chloroform, 99 mg of 65 weight % m-chloroperbenzoic acid (containing about 30 weight % of water) was added under cooling with ice. After the addition, the reaction mixture was stirred at room temperature overnight. After the reaction, the reaction mixture was mixed with a saturated sodium thiosulfate aqueous solution and extracted with chloroform (10 ml×2). The resulting organic layer was washed with a saturated sodium hydrogen carbonate aqueous solution and dried over anhydrous sodium sulfate, and the solvent was evaporated under reduced pressure. The resulding residue was purified by preparative medium pressure liquid chromatography using n-hexane/ethyl acetate (with a gradient of from 100:0 to 50:50) as the eluent to obtain 70 mg of the desired 2-[3-(ethylsulfonyl)-7-(trifluoromethyl)imidazo[1,2-b]pyridazin-2-yl]-3-methyl-6-(trifluoromethyl)-3H-imidazo[4,5-b]pyridine and 41 mg of the desired 2-[3-(ethylsulfinyl)-7-(trifluoromethyl)imidazo[1,2-b]pyridazin-2-yl]-3-methyl-6-(trifluoromethyl)-3H-imidazo[4,5-b]pyridine respectively as a pale yellow oil.

$^1$H-NMR of 2-[3-(ethylsulfonyl)-7-(trifluoromethyl)imidazo[1,2-b]pyridazin-2-yl]-3-methyl-6-(trifluoromethyl)-3H-imidazo[4,5-b]pyridine: $\delta$8.90 (d, J=1.8 Hz, 1H), 8.79 (d, J=1.5 Hz, 1H), 8.55-8.50 (m, 1H), 8.42 (d, J=2.1 Hz, 1H), 4.02 (s, 3H), 3.75 (q, J=7.5 Hz, 2H), 1.46 (t, J=7.5 Hz, 3H).

$^1$H-NMR of 2-[3-(ethylsulfinyl)-7-(trifluoromethyl)imidazo[1,2-b]pyridazin-2-yl]-3-methyl-6-(trifluoromethyl)-3H-imidazo[4,5-b]pyridine: $\delta$8.82 (d, J=2.1 Hz, 1H), 8.78-8.74 (m, 1H), 8.49-8.45 (m, 1H), 8.42-8.38 (m, 1H), 4.36 (s, 3H), 4.18-4.00 (m, 1H), 3.85-3.70 (m, 1H), 1.55 (t, J=7.5 Hz, 3H).

Synthetic Example 29: Synthesis of 5-(ethylthio)-6-[3-methyl-6-(trifluoromethyl)-3H-imidazo[4,5-b]pyridin-2-yl]-2-(trifluoromethyl)imidazo[2,1-b][1,3,4]thiadiazole (Compound No. 2-1-002b of the Present Invention) and 5-(ethylsulfonyl)-6-[3-methyl-6-(trifluoromethyl)-3H-imidazo[4,5-b]pyridin-2-yl]-2-(trifluoromethyl)imidazo[2,1-b][1,3,4]thiadiazole (Compound No. 2-1-002a of the Present Invention)

Step 1: Synthesis of 5-(ethylthio)-6-[3-methyl-6-(trifluoromethyl)-3H-imidazo[4,5-b]pyridin-2-yl]-2-(trifluoromethyl)imidazo[2,1-b][1,3,4]thiadiazole (Compound No. 2-1-002b of the Present Invention)

195 mg of 5-(trifluoromethyl)-1,3,4-thiadiazol-2-amine was dissolved in 5 ml of propionitrile, and 400 mg of 2-bromo-2-(ethylthio)-1-[3-methyl-6-(trifluoromethyl)-3H-imidazo[4,5-b]pyridin-2-yl]ethanone was added at room temperature. After the addition, the reaction mixture was stirred under reflux with heating for 3 hours. After the reaction, the reaction mixture was mixed with 10 ml of water and extracted with chloroform (10 ml×2). The resulting organic layer was dried over anhydrous sodium sulfate, and the solvent was evaporated under reduced pressure. The resulting residue was purified by preparative medium pressure liquid chromatography using n-hexane/ethyl acetate (with a gradient of from 100:0 to 0:100) as the eluent to obtain 130 mg of the desired product as a white solid.

$^1$H-NMR (CDCl$_3$): $\delta$8.82 (d, J=1.2 Hz, 1H), 8.43 (d, J=1.2 Hz, 1H), 4.24 (s, 3H), 2.66 (q, J=7.5 Hz, 2H), 1.31 (t, J=7.5 Hz, 3H).

Step 2: Synthesis of 5-(ethylsulfonyl)-[3-methyl-6-(trifluoromethyl)-3H-imidazo[4,5-b]pyridin-2-yl]-2-(trifluoromethyl)imidazo[2,1-b][1,3,4]thiadiazole (Compound No. 2-1-002a of the Present Invention)

To a solution of 130 mg of 5-(ethylthio)-6-[3-methyl-6-(trifluoromethyl)-3H-imidazo[4,5-b]pyridin-2-yl]-2-(trifluoromethyl)imidazo[2,1-b][1,3,4]thiadiazole in 10 ml of chloroform, 191 mg of 65 weight % m-chloroperbenzoic acid (containing about 30 weight % of water) was added under cooling with ice. After the addition, the reaction mixture was stirred at room temperature overnight. After the reaction, the reaction mixture was mixed with a saturated sodium thiosulfate aqueous solution and extracted with chloroform (10 ml×2). The resulting organic layer was washed with a saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 52 mg of the desired product as a white solid.

Melting point: 231-234° C.

$^1$H-NMR (CDCl$_3$): $\delta$8.76 (s, 1H), 8.35 (s, 1H), 4.11 (s, 3H), 3.92 (q, J=7.5 Hz, 2H), 1.51 (t, J=7.5 Hz, 3H).

Synthetic Example 30: Synthesis of 2-[3-(ethylthio)-8-fluoro-6-iodoimidazo[1,2-a]pyridin-2-yl]-3-methyl-6-(trifluoromethyl)-3H-imidazo[4,5-c]pyridine (Compound No. 1-8-008b of the Present Invention)

Step 1: Synthesis of 2-(ethylthio)-1-[3-methyl-6-(trifluoromethyl)-3H-imidazo[4,5-c]pyridin-2-yl]ethanone To 2.36 g of 2-bromo-1-[3-methyl-6-(trifluoromethyl)-3H-imidazo[4,5-c]pyridin-2-yl]ethanone in 25 ml of N,N-dimethylformamide, 546 mg of ethanethiol and 1.21 g of potassium carbonate were successively added under cooling with ice. After the addition, the reaction mixture was stirred at room temperature for one hour. After the reaction, the reaction mixture was mixed with 50 ml of water and extracted with ethyl acetate (50 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 80:20) as the eluent to obtain 1.70 g of the desired product as a white solid.

Melting point: 90-93° C.

¹H-NMR (CDCl₃): 9.03 (s, 1H), 8.19 (d, J=1.0 Hz, 1H), 4.29 (s, 3H), 4.08 (s, 2H), 2.65 (q, J=7.4 Hz, 2H), 1.32 (t, J=7.4 Hz, 3H).

Step 2: Synthesis of 2-bromo-2-(ethylthio)-1-[3-methyl-6-(trifluoromethyl)-3H-imidazo[4,5-c]pyridin-2-yl]ethanone To a solution of 1.63 g of 2-(ethylthio)-1-[3-methyl-6-(trifluoromethyl)-3H-imidazo[4,5-c]pyridin-2-yl]ethanone in 15 ml of dichloromethane, 600 mg of triethylamine was added at room temperature. After the addition, 1.25 g of trimethylsilyl trifluoromethanesulfonate was added to the reaction mixture under cooling with ice. After the addition, the reaction mixture was stirred under cooling with ice for 30 minutes. After the stirring, 2.02 g of trimethylphenylammonium tribromide was added to the reaction mixture under cooling with ice. After the addition, the reaction mixture was stirred under cooling with ice for one hour. After the reaction, the reaction mixture was added dropwise to 20 ml of water under cooling with ice, and the mixture was extracted with chloroform (20 ml×2). The resulting organic layer was dried over anhydrous sodium sulfate, and the solvent was evaporated under reduced pressure to obtain 2.09 g of the desired product as a yellow oil.
¹H-NMR (CDCl₃): δ9.06 (s, 1H), 8.19 (s, 1H), 7.12 (s, 1H), 4.31 (s, 3H), 3.01-2.77 (m, 2H), 1.39 (t, J=7.5 Hz, 3H).

Step 3: Synthesis of 2-[3-(ethylthio)-8-fluoro-6-iodoimidazo[1,2-a]pyridin-2-yl]-3-methyl-6-(trifluoromethyl)-3H-imidazo[4,5-c]pyridine (Compound No. 1-8-008b of the Present Invention)

250 mg of 3-fluoro-5-iodopyridin-2-amine was dissolved in 5 ml of acetonitrile, and 400 mg of 2-bromo-2-(ethylthio)-1-[3-methyl-6-(trifluoromethyl)-3H-imidazo[4,5-c]pyridin-2-yl]ethanone was added at room temperature. After the addition, the reaction mixture was stirred unde reflux with heating for one hour. After the reaction, the reaction mixture was mixed with 10 ml of water and extracted with chloroform (10 ml×2). The resulting organic layer was dried over anhydrous sodium sulfate, and the solvent was evaporated under reduced pressure. The precipitated solid was collected by filtration to obtain 338 mg of the desired product as a brown solid.
¹H-NMR (CDCl₃): δ8.96 (s, 1H), 8.73 (d, J=1.5 Hz, 1H), 8.19 (d, J=0.9 Hz, 1H), 7.33 (dd, J=9.0, 1.5 Hz, 1H), 4.36 (s, 3H), 3.15 (q, J=7.5 Hz, 2H), 1.23 (t, J=7.5 Hz, 3H).

Reference Example 1: Synthesis of 2-bromo-1-[3-(ethylsulfonyl)-7-(trifluoromethyl)imidazo[1,2-a]pyridin-2-yl]ethanone Step 1: Synthesis of ethyl 7-(trifluoromethyl)imidazo[1,2-a]pyridine-2-carboxylate 5.0 g of 4-(trifluoromethyl)pyridin-2-amine was dissolved in 50 ml of chlorobenzene, and 6.67 g of ethyl 3-bromo-2-oxopropanoate was added at room temperature. After the addition, the reaction mixture was stirred under reflux with heating for 6.5 hours. After the reaction, the reaction mixture was mixed with 20 ml of a 1M sodium hydroxide aqueous solution and extracted with ethyl acetate (20 ml×2). The resulting organic layer was dehydrated with saturated aqueous sodium chloride and dried over anhydrous sodium sulfate, and the solvent was evaporated under reduced pressure. The resulting residue was mixed with a 3M hydrochloric acid aqueous solution and washed with 10 ml of ethyl acetate. The aqueous layer was adjusted to have a pH of from 2 to 3 with a 10M sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure to obtain 3.94 g of the desired product as a yellow solid.
Melting point: 170-175° C.
¹H-NMR (CDCl₃): δ8.29 (s, 1H), 8.27 (d, J=7.2 Hz, 1H), 8.01 (s, 1H), 7.07 (dd, J=7.2, 1.7 Hz, 1H), 4.49 (q, J=7.2 Hz, 2H), 1.46 (t, J=7.2 Hz, 3H).

Step 2: Synthesis of ethyl 3-iodo-7-(trifluoromethyl)imidazo[1,2-a]pyridine-2-carboxylate To a solution of 3.73 g of ethyl 7-(trifluoromethyl)imidazo[1,2-a]pyridine-2-carboxylate in 20 ml of N,N-dimethylformamide, 6.5 g N-iodosuccinimide was added at room temperature. After the addition, the reaction mixture was stirred at 80° C. for 5 hours. After the reaction, water was added to the reaction mixture, and the precipitated solid was collected by filtration. The resulting solid was dissolved in 20 ml of chloroform, and washed with a saturated sodium thiosulfate aqueous solution and then with saturated sodium hydrogen carbonate. The resulting organic layer was dried over anhydrous sodium sulfate, and the solvent was evaporated under reduced pressure to obtain 5.08 g of the desired product as a flesh-colored solid.
Melting point: 183-185° C.
¹H-NMR (CDCl₃): δ8.40 (d, J=7.2 Hz, 1H), 7.99 (s, 1H), 7.17 (dd, J=7.2, 1.7 Hz, 1H), 4.53 (q, J=7.2 Hz, 2H), 1.50 (t, J=7.2 Hz, 3H).

Step 3: Synthesis of ethyl 3-(ethylthio)-7-(trifluoromethyl)imidazo[1,2-a]pyridine-2-carboxylate To a solution of 5.73 g of ethyl 3-iodo-7-(trifluoromethyl)imidazo[1,2-a]pyridine-2-carboxylate in 40 ml of 1,4-dioxane, 5.79 g of diisopropylethylamine, 862 mg of 4,5-bis(diphenylphosphino)-9,9-dimethylxanthene, 682 mg of tris(dibenzylideneacetone)dipalladium(0) and 1.85 g of ethanethiol were successively added at room temperature. After the addition, the atmosphere in the reaction vessel was replaced by nitrogen gas, and the mixture was stirred under reflux with heating for 2 hours. After the reaction, the reaction mixture was subjected to filtration through Celite, and the Celite was washed with 30 ml of chloroform. The resulting filtrate and washing solution were put together, and the solvent was evaporated under reduced pressure. The resulting residue was purified by preparative medium pressure liquid chromatography using n-hexane/ethyl acetate (with a gradient of from 100:0 to 50:50) as the eluent to obtain 5.58 g of the desired product as a brown solid.
Melting point: 50-52° C.
¹H-NMR (CDCl₃): δ8.67 (d, J=7.4 Hz, 1H), 8.02-8.00 (m, 1H), 7.15 (dd, J=7.4, 1.8 Hz, 1H), 4.52 (q, J=7.0 Hz, 2H), 2.98 (q, J=7.5 Hz, 2H), 1.48 (t, J=7.0 Hz, 3H), 1.20 (t, J=7.5 Hz, 3H).

Step 4: Synthesis of 3-(ethylthio)-7-(trifluoromethyl)imidazo[1,2-a]pyridine-2-carboxylic Acid To a solution of 5.58 g of ethyl 3-(ethylthio)-7-(trifluoromethyl)imidazo[1,2-a]pyridine-2-carboxylate in 60 ml of ethanol and 30 ml of tetrahydrofuran, 10 ml of a 3M sodium hydroxide aqueous solution was added at room temperature. After the addition, the reaction mixture was stirred at room temperature for 5 hours. After the reaction, the solvent was evaporated from the reaction mixture under reduced pressure. The resulting residue was mixed with a 1M hydrochloric acid aqueous solution to adjust the aqueous layer to have a pH of 2, and extracted with ethyl acetate (20 ml×2). The resulting organic layer was dehydrated with saturated aqueous sodium chloride and dried over anhydrous sodium sulfate, and the solvent was evaporated under reduced pressure to obtain 3.40 g of the desired product as a yellow solid.

Melting point: 163-171° C.

$^1$H-NMR (CDCl$_3$): δ8.69 (d, J=7.2 Hz, 1H), 8.19 (s, 1H), 7.22 (dd, J=7.2, 1.4 Hz, 1H), 3.06 (q, J=7.4 Hz, 2H), 1.23 (t, J=7.4 Hz, 3H) (no peak of proton of CO$_2$H was observed).

Step 5: Synthesis of 3-(ethylthio)-N-methoxy-N-methyl-7-(trifluoromethyl)imidazo[1,2-a]pyridine-2-carboxamide To a solution of 2.52 g of 3-(ethylthio)-7-(trifluoromethyl)imidazo[1,2-a]pyridine-2-carboxylic acid in 30 ml of dichloromethane, 3.31 g of oxalyl chloride and 30 mg of N,N-dimethylformamide were added under cooling with ice. After the addition, the reaction mixture was stirred at room temperature for 3 hours. After the stirring, the solvent was evaporated from the reaction mixture under reduced pressure to obtain crude 3-(ethylthio)-7-(trifluoromethyl)imidazo[1,2-a]pyridine-2-carboxylic acid chloride. The obtained crude 3-(ethylthio)-7-(trifluoromethyl)imidazo[1,2-a]pyridine-2-carboxylic acid chloride was dissolved in 5 ml of dichloromethane, and the solution was added to a solution of 931 mg of N,O-dimethylhydroxylamine hydrochloride and 1.93 g of triethylamine in 15 ml of dichloromethane prepared in a separate container, under cooling with ice. After the addition, the reaction mixture was stirred at room temperature for 1.5 hours. After the reaction, the reaction mixture was mixed with 10 ml of water and extracted with chloroform (10 ml×2). The resulting organic layer was washed with dilute hydrochloric acid and then with a saturated sodium hydrogen carbonate aqueous solution and dried over anhydrous sodium sulfate, and the solvent was evaporated under reduced pressure to obtain 2.50 g of the desired product as a flesh-colored solid.

Melting point: 82-84° C.

$^1$H-NMR (CDCl$_3$): δ8.62 (d, J=7.2 Hz, 1H), 7.98-7.95 (m, 1H), 7.14 (dd, J=7.2, 1.7 Hz, 1H), 3.80 (s, 3H), 3.44 (s, 3H), 2.91 (q, J=7.4 Hz, 2H), 1.22 (t, J=7.4 Hz, 3H).

Step 6: Synthesis of 1-[3-(ethylthio)-7-(trifluoromethyl)imidazo[1,2-a]pyridin-2-yl]ethanone Under a nitrogen atmosphere, to a solution of 2.45 g of 3-(ethylthio)-N-methoxy-N-methyl-7-(trifluoromethyl)imidazo[1,2-a]pyridine-2-carboxamide in 25 ml of tetrahydrofuran, 2.7 ml of a solution of about 3M methylmagnesium bromide in diethyl ether was added under cooling with ice. After the addition, the reaction mixture was stirred under cooling with ice for one hour. After the reaction, the reaction mixture was added dropwise to 10 ml of a 4M hydrochloric acid aqueous solution under cooling with ice and extracted with ethyl acetate (20 ml×2). The resulting organic layer was washed with a saturated sodium hydrogen carbonate aqueous solution and dehydrated with saturated aqueous sodium chloride and dried over anhydrous sodium sulfate, and the solvent was evaporated under reduced pressure to obtain 2.08 g of the desired product as a brown solid.

Melting point: 60-64° C.

$^1$H-NMR (CDCl$_3$): δ8.67 (d, J=7.2 Hz, 1H), 8.03-7.99 (m, 1H), 7.15 (dd, J=7.2, 1.7 Hz, 1H), 3.01 (q, J=7.4 Hz, 2H), 2.80 (s, 3H), 1.18 (t, J=7.4 Hz, 3H).

Step 7: Synthesis of 1-[3-(ethylsulfonyl)-7-(trifluoromethyl)imidazo[1,2-a]pyridin-2-yl]ethanone To a solution of 2.08 g of 1-[3-(ethylthio)-7-(trifluoromethyl)imidazo[1,2-a]pyridin-2-yl]ethanone in 40 ml of methanol and 20 ml of water, 13.3 g of Oxone (registered trademark by DuPont) was added under cooling with ice. After the addition, the reaction mixture was stirred at room temperature overnight. After the reaction, to the reaction mixture, a solution of 2.28 g of sodium thiosulfate in 25 ml of water was added, and then a 10M sodium hydroxide aqueous solution was added to adjust the aqueous layer to be alkaline, and methanol was evaporated under reduced pressure. The resulting residue was extracted with ethyl acetate (40 ml×2). The resulting organic layer was dehydrated with saturated aqueous sodium chloride and dried over anhydrous sodium sulfate, and the solvent was evaporated under reduced pressure to obtain 2.11 g of the desired product as a yellow solid.

Melting point: 135-138° C.

$^1$H-NMR (CDCl$_3$): δ9.44 (d, J=7.5 Hz, 1H), 8.12-8.09 (m, 1H), 7.27-7.24 (m, 1H), 3.80 (q, J=7.5 Hz, 2H), 2.80 (s, 3H), 1.35 (t, J=7.5 Hz, 3H).

Step 8: Synthesis of 2-bromo-1-[3-(ethylsulfonyl)-7-(trifluoromethyl)imidazo[1,2-a]pyridin-2-yl]ethanone To a solution of 2.05 g 1-[3-(ethylsulfonyl)-7-(trifluoromethyl)imidazo[1,2-a]pyridin-2-yl]ethanone in 15 ml of toluene, 10.2 g of a solution of about 5.1M hydrogen bromide in acetic acid and 1.13 g of bromine were successively added at 10° C. After the addition, the reaction mixture was stirred at room temperature for 2 hours. After the stirring, the reaction mixture was mixed with 205 mg of bromine and stirred at room temperature overnight. After the reaction, the reaction mixture was mixed with 10 ml of water and extracted with ethyl acetate (20 ml×2). The resulting organic layer was washed with a 5 weight % sodium hydrogen sulfite aqueous solution and dried over anhydrous sodium sulfate, and the solvent was evaporated under reduced pressure to obtain 2.48 g of the desired product as a yellow solid.

Melting point: 122-123° C.

$^1$H-NMR (CDCl$_3$): δ9.45 (d, J=7.5 Hz, 1H), 8.14-8.11 (m, 1H), 7.33-7.27 (m, 1H), 4.78 (s, 2H), 3.78 (q, J=7.4 Hz, 2H), 1.37 (t, J=7.4 Hz, 3H).

Reference Example 2: Synthesis of 5-(ethylthio)-2-(trifluoromethyl)imidazo[2,1-b]thiazole-6-carboxylic Acid Step 1: Synthesis of ethyl 2-(trifluoromethyl)imidazo[2,1-b]thiazole-6-carboxylate 4.0 g of 5-(trifluoromethyl)thiazol-2-amine was dissolved in 80 ml of chlorobenzene, and 7.2 g of ethyl 3-bromo-2-oxopropanoate was added at room temperature. After the addition, the reaction mixture was stirred under reflux with heating for 3 hours. After the stirring, 3.09 g of ethyl 3-bromo-2-oxopropanoate was added to the reaction mixture. After the addition, the reaction mixture was stirred under reflux with heating for one hour. After the stirring, 2.4 g of ethyl 3-bromo-2-oxopropanoate was added to the reaction mixture. After the addition, the reaction mixture was stirred under reflux with heating for 2 hours. After the reaction, the solvent was evaporated from the reaction mixture under reduced pressure. The resulting residue was mixed with a 1M sodium hydroxide aqueous solution to adjust the aqueous layer to have a pH of 8, and extracted with ethyl acetate (20 ml×3). The resulting organic layer was dehydrated with saturated aqueous sodium chloride and dried over anhydrous sodium sulfate, and the solvent was evaporated under reduced pressure. The precipitated solid was collected by filtration. The resulting solid was washed with diisopropyl ether to obtain 2.12 g of the desired product as a white solid.

$^1$H-NMR (CDCl$_3$): δ8.14 (s, 1H), 7.92 (s, 1H), 4.42 (q, J=7.5 Hz, 2H), 1.43 (t, J=7.5 Hz, 3H).

Step 2: Synthesis of ethyl 5-iodo-2-(trifluoromethyl)imidazo[2,1-b]thiazole-6-carboxylate To a solution of 7.97 g of ethyl 2-(trifluoromethyl)imidazo[2,1-b]thiazole-6-carboxylate in 10 ml of N,N-dimethylformamide, 3.58 g of N-iodosuccinimide was added at room temperature. After the addition, the reaction mixture was stirred at 80° C. for 4 hours. After the reaction, a saturated sodium thiosulfate aqueous solution was added to the reaction mixture, and the precipitated solid was collected by filtration to obtain 3.09 g of the desired product as a white solid.

$^1$H-NMR (CDCl$_3$): δ7.90-7.86 (m, 1H), 4.44 (q, J=7.5 Hz, 2H), 1.45 (t, J=7.5 Hz, 3H).

Step 3: Synthesis of ethyl 3-(ethylthio)-2-(trifluoromethyl)imidazo[2,1-b]thiazole-6-carboxylate To a solution of 2.00 g of ethyl 5-iodo-2-(trifluoromethyl)imidazo[2,1-b]thiazole-6-carboxylate in 20 ml of 1,4-dioxane, 1.98 g of diisopropylethylamine, 296 mg of 4,5-bis(diphenylphosphino)-9,9-dimethylxanthene, 234 mg of tris(dibenzylideneacetone)dipalladium(0) and 636 mg of ethanethiol were successively added at room temperature. After the addition, the atmosphere in the reaction vessel was replaced by nitrogen gas, and the mixture was stirred under reflux with heating for 4 hours. After the reaction, the reaction mixture was subjected to filtration through Celite, and the Celite was washed with 30 ml of chloroform. The resulting filtrate and washing solution were put together, and the solvent was evaporated under reduced pressure. The resulting residue was purified by preparative medium pressure liquid chromatography using n-hexane/ethyl acetate (with a gradient of from 100:0 to 50:50) as the eluent to obtain 1.11 g of the desired product as a yellow solid.

$^1$H-NMR (CDCl$_3$): δ8.04-7.98 (m, 1H), 4.44 (q, J=7.5 Hz, 2H), 2.99 (q, J=7.5 Hz, 2H), 1.46 (t, J=7.5 Hz, 3H), 1.23 (t, J=7.5 Hz, 3H).

Step 4: Synthesis of 5-(ethylthio)-2-(trifluoromethyl)imidazo[2,1-b]thiazole-6-carboxylic Acid To a solution of 1.09 g of ethyl 3-(ethylthio)-2-(trifluoromethyl)imidazo[2,1-b]thiazole-6-carboxylate in 10 ml of ethanol and 10 ml of tetrahydrofuran, 6.8 ml of a 1M sodium hydroxide aqueous solution was added at room temperature. After the addition, the reaction mixture was stirred at room temperature overnight. After the reaction, the solvent was evaporated from the reaction mixture under reduced pressure. The resulting residue was mixed with a 1M hydrochloric acid aqueous solution to adjust the aqueous layer to have a pH of from 2 to 3, and extracted with chloroform (20 ml×2). The resulting organic layer was dried over anhydrous sodium sulfate, and the solvent was evaporated under reduced pressure to obtain 896 mg of the desired product as a yellow solid.

$^1$H-NMR (CDCl$_3$): 8.06-8.02 (m, 1H), 3.04 (q, J=7.5 Hz, 2H), 1.25 (t, J=7.5 Hz, 3H) (no peak of proton of CO$_2$H was observed).

Reference Example 3: The Following Compounds were Synthesized in the Same Manner as in Steps 1 to 4 in Reference Example 1

3-(Ethylthio)-6-(trifluoromethyl)imidazo[1,2-a]pyridine-2-carboxylic Acid

Melting point: 200-201° C.
$^1$H-NMR (CDCl$_3$): δ8.93 (s, 1H), 8.20 (d, J=9.6 Hz, 1H), 7.56 (dd, J=9.6, 1.8 Hz, 1H), 3.06 (q. J=7.4 Hz, 2H), 1.23 (t, J=7.4 Hz, 3H) (no peak of proton of CO$_2$H was observed).

3-(Ethylthio)-6-(trifluoromethyl)imidazo[1,2-a]pyrazine-2-carboxylic Acid

Melting point: 175-178° C.
$^1$H-NMR (CDCl$_3$): δ9.21 (s, 1H), 8.84 (s, 1H), 3.08 (q, J=7.2 Hz, 2H), 1.22 (t, J=7.2 Hz, 3H) (no peak of proton of CO$_2$H was observed).

Reference Example 4: Synthesis of N$^3$,2-dimethyl-6-(trifluoromethyl)pyridine-3,4-diamine Step 1: Synthesis of 4-bromo-2-methyl-6-(trifluoromethyl)pyridin-3-amine To a solution of 3.0 g of 2-methyl-6-(trifluoromethyl)pyridin-3-amine in 30 ml of acetonitrile, 3.03 g of N-bromosuccinimide was added at room temperature. After the addition, the reaction mixture was stirred at room temperature for 1.5 hours. After the reaction, the solvent was evaporated under reduced pressure. The resulting residue was purified by preparative medium pressure liquid chromatography using n-hexane/ethyl acetate (with a gradient of from 100:0 to 50:50) as the eluent to obtain 4.0 g of the desired product as a brown solid.

Melting point: 40-41° C.
$^1$H-NMR (CDCl$_3$): δ7.61 (s, 1H), 4.40 (brs, 2H), 2.52 (s, 3H).

Step 2: Synthesis of 4-bromo-N,2-dimethyl-6-(trifluoromethyl)pyridin-3-amine

To a solution of 537 mg of 63 weight % sodium hydride (dispersed in mineral oil) in 5 ml of N,N-dimethylformamide, a solution of 3.0 g of 4-bromo-2-methyl-6-(trifluoromethyl)pyridin-3-amine in 12 ml of N,N-dimethylformamide was added under cooling with ice. After the addition, the reaction mixture was stirred at room temperature for one hour. After the stirring, 2.0 g of methyl iodide was added to the reaction mixture under cooling with ice. After the addition, the reaction mixture was stirred at room temperature for 30 minutes. After the reaction, the reaction mixture was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent to obtain 2.82 g of the desired product as a yellow oil.

$^1$H-NMR (CDCl$_3$): δ7.62 (s, 1H), 3.01 (s, 3H), 2.65 (s, 3H) (no peak of proton of NH was observed).

Step 3: Synthesis of N$^3$,2-dimethyl-6-(trifluoromethyl)pyridine-3,4-diamine To a solution of 1.0 g of 4-bromo-N,2-dimethyl-6-(trifluoromethyl)pyridin-3-amine, 186 mg of acetylacetone, 243 mg of copper(II) acetylacetonate and 1.81 g of cesium carbonate in 30 ml of N-methylpyrrolidone was added to an autoclave reactor. After the addition, 20 ml of 28 weight % aqueous ammonia was added to the reaction mixture at room temperature. After the addition, the reactor was closely sealed, and the reaction mixture was heated to 140° C. and stirred for one hour. After the reaction, the reaction mixture was mixed with 20 ml of water and extracted with ethyl acetate (20 ml×2). The resulting organic layer was dehydrated with saturated aqueous sodium chloride and dried over anhydrous sodium sulfate, and the solvent was evaporated under reduced pressure. The resulting residue was purified by silica gel column chromatography using n-hexane/ethyl acetate (with a gradient of from 100:0 to 0:100) as the eluent to obtain 189 mg of the desired product as a white solid.

$^1$H-NMR (CDCl$_3$): 6.84 (s, 1H), 4.53 (brs, 2H), 2.69 (s, 3H), 2.50 (s, 3H) (no peak of proton of NH was observed).

Reference Example 5: Synthesis of 2-methyl-6-(perfluoroethyl)pyrimidin-4-amine

Step 1: Synthesis of (Z)-ethyl 3-ethoxy-4,4,5,5,5-pentafluoropent-2-enoate

To a solution of 20.7 g of ethyl 4,4,5,5,5-pentafluoro-3-oxovalerate in 150 ml of acetone, 24.4 g of potassium carbonate and 15.7 g of ethyl trifluoromethanesulfonate were successively added under cooling with ice. After the addition, the reaction mixture was stirred at room temperature for 30 minutes. After the reaction, the reaction mixture was subjected to filtration through Celite, and the Celite was washed with 50 ml of acetone. The resulting filtrate and washing solution were put together, and the solvent was evaporated under reduced pressure. The resulting residue was mixed with 30 ml of water and extracted with hexane (30 ml×2). The resulting organic layer was dehydrated with saturated aqueous sodium chloride and dried over anhydrous sodium sulfate, and the solvent was evaporated under reduced pressure to obtain 20.53 g of the desired crude product as a colorless and transparent oil.

$^1$H-NMR (CDCl$_3$): δ5.80 (s, 1H), 4.33 (q, J=7.0 Hz, 2H), 4.22 (q, J=7.0 Hz, 2H), 1.36 (t, J=7.0 Hz, 3H), 1.32 (t, J=7.0 Hz, 3H).

Step 2: Synthesis of 2-methyl-6-(perfluoroethyl)pyrimidin-4-ol

To a solution of 6.49 g of acetamidine hydrochloride in 75 ml of dimethyl sulfoxide, 23.3 g of a solution of about 20 weight % sodium ethoxide in ethanol, and 15.0 g of (Z)-ethyl 3-ethoxy-4,4,5,5,5-pentafluoropent-2-enoate were successively added at 50° C. After the addition, the reaction mixture was stirred at 50° C. for 2 hours. After the stirring, 5.84 g of a solution of about 20 weight % sodium ethoxide in ethanol was added to the reaction mixture at 50° C. After the addition, the reaction mixture was stirred at 50° C. for 2.5 hours. After the stirring, the reaction mixture was stirred at room temperature overnight. After the reaction, the reaction mixture was mixed with 50 ml of water and extracted with diethyl ether (50 ml×2). The resulting aqueous layer was mixed with concentrated hydrochloric acid to adjust the aqueous layer to have a pH of from 1 to 2, and extracted with chloroform (20 ml×2). The resulting organic layer was dried over anhydrous sodium sulfate, and the solvent was evaporated under reduced pressure to obtain 7.0 g of the desired crude product as a white solid.

Melting point: 135-138° C.

$^1$H-NMR (CDCl$_3$): δ6.77 (s, 1H), 2.57 (s, 3H) (no peak of proton of OH was observed).

Step 3: Synthesis of 4-chloro-2-methyl-6-(perfluoroethyl)pyrimidine

To a solution of 8.7 g of 2-methyl-6-(perfluoroethyl)pyrimidin-4-ol in 20 ml of thionyl chloride, 30 mg of N,N-dimethylformamide was added at room temperature. After the addition, the reaction mixture was stirred under reflux with heating for one hour. After the reaction, the reaction mixture was allowed to cool to room temperature, added dropwise to ice water and extracted with diethyl ether (20 ml×2). The resulting organic layer was dehydrated with saturated aqueous sodium chloride and dried over anhydrous sodium sulfate, and the solvent was evaporated under reduced pressure to obtain 9.33 g of the desired crude product as a reddish brown oil.

$^1$H-NMR (CDCl$_3$): δ7.54 (s, 1H), 2.82 (s, 3H).

Step 4: Synthesis of 2-methyl-6-(perfluoroethyl)pyrimidin-4-amine

To a solution of 9.33 g of the crude 4-chloro-2-methyl-6-(perfluoroethyl)pyrimidine in 20 ml of acetonitrile, 20 ml of 28 weight % aqueous ammonia was added at room temperature. After the addition, the reaction mixture was stirred at room temperature for 3 days. After the reaction, the solvent was evaporated from the reaction mixture under reduced pressure. The resulting residue was mixed with 20 ml of water and extracted with ethyl acetate (20 ml×2). The resulting organic layer was dehydrated with saturated aqueous salt solution and dried over anhydrous sodium sulfate, and the solvent was evaporated under reduced pressure to obtain 6.75 g of the desired product as a reddish brown solid.

Melting point: 95-105° C.

$^1$H-NMR (CDCl$_3$): δ6.61 (s, 1H), 5.12 (brs, 2H), 2.59 (s, 3H).

Reference Example 6: The Following Compound was Synthesized in the Same Manner as in Steps 1 to 4 in Reference Example 5

6-(Perfluoroethyl)pyrimidin-4-amine $^1$H-NMR (CDCl$_3$): δ8.70 (s, 1H), 6.79 (s, 1H), 5.22 (brs, 2H).

Reference Example 7: Synthesis of 4-chloro-6-(perfluoroethyl)nicotinaldehyde

Step 1: Synthesis of 4-chloro-6-(perfluoroethyl)nicotinic Acid

Under a nitrogen atmosphere, to a solution of 4.04 g of 2,2,6,6-tetramethylpiperidine in 20 ml of tetrahydrofuran, 17.9 ml of a solution of about 1.6M n-butyllithium in n-hexane was added at −78° C. After the addition, the temperature of the reaction mixture was raised to 0° C., and the reaction mixture was stirred for 10 minutes. After the stirring, the reaction mixture was cooled to −78° C., and a solution of 2.3 g of 6-(perfluoroethyl)nicotinic acid in 20 ml of tetrahydrofuran was added. After the addition, the temperature of the reaction mixture was raised to −40° C., and the reaction mixture was stirred for 1.5 hours. After the stirring, the reaction mixture was cooled to −78° C., and 4.5 g of hexachloroethane was added. After the addition, the reaction mixture was stirred at −78° C. for 1.5 hours. After the reaction, 25 ml of a saturated ammonium chloride aqueous solution was added at −78° C. After the addition, the reaction mixture was warmed to room temperature, mixed with an about 1.0M sodium hydroxide aqueous solution to adjust to have a pH of 9, and washed with diethyl ether (20 ml). The resulting aqueous layer was mixed with concentrated hydrochlorid acid to adjust the aqueous solution to have a pH of 2, and extracted with ethyl acetate (20 ml×2). The resulting organic layer was dehydrated with saturated aqueous sodium chloride and dried over anhydrous sodium sulfate, and the solvent was evaporated under reduced pressure to obtain 1.08 g of the desired 4-chloro-6-(perfluoroethyl)nicotinic acid as a brown oil.

$^1$H-NMR (CDCl$_3$): δ9.25 (s, 1H), 7.84 (s, 1H) (no peak of proton of CO$_2$H was observed).

Step 2: Synthesis of [4-chloro-6-(perfluoroethyl)pyridin-3-yl]methanol

To a solution of 1.0 g of 4-chloro-6-(perfluoroethyl)nicotinic acid in 10 ml of tetrahydrofuran, 8.5 ml of a solution of 0.85M borane-tetrahydrofuran complex in tetrahydrofuran was added at −50° C. After the addition, the reaction mixture was warmed to room temperature and stirred overnight. After the reaction, the reaction mixture was added dropwise to a 1M hydrochloric acid aqueous solution under cooling with ice and extracted with ethyl acetate (20 ml×2). The resulting organic layer was dehydrated with saturated aqueous sodium chloride and dried over anhydrous sodium sulfate, and the solvent was evaporated under reduced pressure to obtain 950 mg of the desired [4-chloro-6-(perfluoroethyl)pyridin-3-yl]methanol as an orange oil.

$^1$H-NMR (CDCl$_3$): δ8.87 (s, 1H), 7.71 (s, 1H), 4.92 (s, 2H) (no peak of proton of OH was observed).

Step 3: Synthesis of 4-chloro-6-(perfluoroethyl)nicotinaldehyde

To a solution of 930 mg of [4-chloro-6-(perfluoroethyl)pyridin-3-yl]methanol in 10 ml of dichloromethane, 3 g of silicon dioxide and 1.53 g of pyridinium chlorochromate were successively added at room temperature. After the addition, the reaction mixture was stirred at room temperature for one hour. After the stirring, 500 mg of pyridinium chlorochromate was added to the reaction mixture. After the addition, the reaction mixture was stirred at room temperature for 30 minutes. After the reaction, the reaction mixture was subjected to filtration through Celite, and the Celite was washed with 100 ml of n-hexane/ethyl acetate [2:1 (volume ratio)]. The resulting filtrate and washing solution were put together, and the solvent was evaporated under reduced pressure. The resulting residue was purified by preparative medium pressure liquid chromatography using n-hexane/ethyl acetate (with a gradient of from 100:0 to 30:70) as the eluent to obtain 154 mg of the desired product as a yellow oil.

$^1$H-NMR (CDCl$_3$): δ10.54 (s, 1H), 9.14 (s, 1H), 7.84 (s, 1H).

Reference Example 8: The Following Compound was Synthesized in the Same Manner as in Steps 1 to 3 in Reference Example 7

4-Chloro-6-(trifluoromethyl)nicotinaldehyde $^1$H-NMR (CDCl$_3$): δ10.54 (s, 1H), 9.12 (s, 1H), 7.81 (s, 1H).

Reference Example 9: Synthesis of 3-nitro-5-(trifluoromethyl)picolinaldehyde A solution of 930 mg of selenium dioxide and 1.46 g of 2-methyl-3-nitro-5-(trifluoromethyl)pyridine in 10 ml of 1,4-dioxane was stirred under reflux with heating for 8 hours. After the stirring, the reaction mixture was subjected to filtration through Celite, and the Celite was washed with 10 ml of 1,4-dioxane. The resulting filtrate and washing solution were put together, and the solvent was evaporated under reduced pressure, and the resulting residue was mixed with 5 ml of saturated aqueous sodium bicarbonate and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography using n-hexane/ethyl acetate (with a gradient of from 100:0 to 50:50) as the eluent. To the residue obtained by concentration, 10 ml of toluene was added, and the solvent was evaporated under reduced pressure. Then, 10 ml of toluene was added, and the solvent was evaporated under reduced pressure to obtain 1.07 g of the desired product as a brown liquid.

$^1$H-NMR (CDCl$_3$): δ10.32 (s, 1H), 9.25-9.20 (m, 1H), 8.53-8.49 (m, 1H).

Reference Example 10: Synthesis of 3-(ethylthio)-7-(trifluoromethyl)imidazo[1,2-a]pyridin-2-amine

Step 1: Synthesis of tert-butyl [3-(ethylthio)-7-(trifluoromethyl)imidazo[1,2-a]pyridin-2-yl]carbamate To a solution of 3.0 g of 3-(ethylthio)-7-(trifluoromethyl)imidazo[1,2-a]pyridine-2-carboxylic acid in 30 ml of 2-methyl-2-propanol, 3.14 g of triethylamine and 3.40 g of diphenylphosphoryl azide were added at room temperature. After the addition, the reaction mixture was stirred under reflux with heating for 2 hours. After the reaction, the solvent was evaporated from the reaction mixture. The resulting residue was mixed with 20 ml of water and extracted with ethyl acetate (20 ml×2). The resulting organic layer was washed with a saturated sodium hydrogen carbonate aqueous solution and dried over anhydrous sodium sulfate, and the solvent was evaporated under reduced pressure. The resulting residue was purified by preparative medium pressure liquid chromatography using n-hexane/ethyl acetate (50:50) as the eluent to obtain 2.12 g of the desired product as a pale yellow solid.

$^1$H-NMR (CDCl$_3$): δ8.42 (d, J=7.0 Hz, 1H), 7.93-7.88 (m, 1H), 7.13-7.01 (m, 2H), 2.68 (q, J=7.4 Hz, 2H), 1.56 (s, 9H), 1.21 (t, J=7.4 Hz, 3H).

Step 2: Synthesis of 3-(ethylthio)-7-(trifluoromethyl)imidazo[1,2-a]pyridin-2-amine To a solution of 2.0 g of tert-butyl [3-(ethylthio)-7-(trifluoromethyl)imidazo[1,2-a]pyridin-2-yl]carbamate in 10 ml of dichloromethane, 2.1 ml of trifluoroacetic acid was added under cooling with ice. After the addition, the reaction mixture was stirred at room temperature for 30 minutes. After the stirring, 10 ml of trifluoroacetic acid was added to the reaction mixture. After the addition, the reaction mixture was stirred at room temperature for 30 minutes. After the reaction, the solvent was evaporated from the reaction mixture. The resulting residue was mixed with 20 ml of water and extracted with chloroform (20 ml×2). The resulting organic layer was washed with a 1M sodium hydroxide aqueous solution and dried over anhydrous sodium sulfate, and the solvent was evaporated under reduced pressure to obtain 1.69 g of the desired product as a yellow oil.

$^1$H-NMR (CDCl$_3$): δ8.31 (d, J=7.0 Hz, 1H), 7.63-7.58 (m, 1H), 6.98 (dd, J=7.0, 1.6 Hz, 1H), 4.41 (brs, 2H), 2.63 (q, J=7.4 Hz, 2H), 1.21 (t, J=7.4 Hz, 3H).

Reference Example 11: Synthesis of 3-(ethylthio)-6-(trifluoromethyl)imidazo[1,2-a]pyridine-2-carboxamide To a solution of 1.34 g of 3-(ethylthio)-6-(trifluoromethyl)imidazo[1,2-a]pyridine-2-carboxylic acid in 20 ml of dichloromethane, 882 mg of oxalyl chloride and 10 mg N,N-dimethylformamide were added under cooling with ice. After the addition, the reaction mixture was stirred at room temperature for 2.5 hours. After the stirring, the solvent was evaporated from the reaction mixture under reduced pressure to obtain crude 3-(ethylthio)-6-(trifluoromethyl)imidazo[1,2-a]pyridine-2-carboxylic acid chloride. The obtained crude 3-(ethylthio)-6-(trifluoromethyl)imidazo[1,2-a]pyridine-2-carboxylic acid chloride was dissolved in 2 ml of tetrahydrofuran and added to 20 ml of 28 weight % aqueous ammonia prepared in a separate container, under cooling with ice. After the addition, the reaction mixture was stirred under cooling with ice for 30 minutes. After the addition, the reaction mixture was mixed with 10 ml of water and extracted with chloroform (10 ml×2). The resulting organic layer was dried over anhydrous sodium sulfate, and the solvent was evaporated under reduced pressure to obtain 1.8 g of the desired product as a pale yellow solid.

$^1$H-NMR (CDCl$_3$): δ8.90 (s, 1H), 7.71 (d, J=9.4 Hz 1H), 7.47 (dd, J=9.4, 2.0 Hz, 1H), 7.38 (brs, 1H), 5.66 (brs, 1H), 3.03 (q, J=7.4 Hz, 2H), 1.21 (t, J=7.4 Hz, 3H).

Reference Example 12: Synthesis of 2-bromo-1-[3-methyl-6-(trifluoromethyl)-3H-imidazo[4,5-b]pyridin-2-yl]ethanone

Step 1: Synthesis of (S)-1-[3-methyl-6-(trifluoromethyl)-3H-imidazo[4,5-b]pyridin-2-yl]ethanol 37.7 g of N$^2$-methyl-5-(trifluoromethyl)pyridine-2,3-diamine was dissolved in 150 ml of pyridine, and 32.8 g of (S)-(−)-2-acetoxypropionyl chloride was added at −20° C. After the addition, the reaction mixture was stirred at room temperature for 30 minutes. After the stirring, the solvent was evaporated from the reaction mixture under reduced pressure. The resulting residue was dissolved in 150 ml of ethanol, and 39.4 ml of a 10M sodium hydroxide aqueous solution was added at room temperature. After the addition, the reaction mixture was stirred under reflux with heating for 2 hours. After the stirring, 20 ml of a 10M sodium hydroxide aqueous solution was added to the reaction mixture at room temperature. After the addition, the reaction mixture was stirred under reflux with heating for 4.5 hours. After the reaction, the solvent was evaporated from the reaction mixture under reduced pressure. The resulting residue was mixed with concentrated hydrochloric acid to adjust the aqueous solution to have a pH of 4, and extracted with ethyl acetate (100 ml×2). The resulting organic layer was dehydrated with saturated aqueous sodium chloride and dried over anhydrous sodium sulfate, and the solvent was evaporated under reduced pressure to obtain 59.8 g of the desired (S)-1-[3-methyl-6-(trifluoromethyl)-3H-imidazo[4,5-b]pyridin-2-yl]ethanol as a black solid.

$^1$H-NMR (CDCl$_3$): δ8.65 (s, 1H), 8.23 (s, 1H), 5.20 (brs, 1H), 3.97 (s, 3H), 2.99 (brs, 1H), 1.75 (d, J=6.3 Hz, 3H).

Step 2: Synthesis of 1-[3-methyl-6-(trifluoromethyl)-3H-imidazo[4,5-b]pyridin-2-yl]ethanone A solution of 48.3 g of (S)-1-[3-methyl-6-(trifluoromethyl)-3H-imidazo[4,5-b]pyridin-2-yl]ethanol in 200 ml of acetic acid was heated to 90° C., and a solution of 14.8 g of chromium(VI) oxide in 50 ml of water was added. After the addition, the reaction mixture was stirred under reflux with heating for 1.5 hours. After the stirring, a solution of 5 g of chromium(VI) oxide in 10 ml of water was added to the reaction mixture at 90° C. After the addition, the reaction mixture was stirred under reflux with heating for 1.5 hours. After the reaction, the reaction mixture was added dropwise to 800 ml of water at room temperature. The precipitated solid was collected by filtration. The resulting solid was washed with water to obtain 35.6 g of the desired 1-[3-methyl-6-(trifluoromethyl)-3H-imidazo[4,5-b]pyridin-2-yl]ethanone as a brown solid.

Melting point: 106-108° C.

$^1$H-NMR (CDCl$_3$): δ8.82 (d, J=1.5 Hz, 1H), 8.43 (d, J=1.5 Hz, 1H), 4.23 (s, 3H), 2.86 (s, 3H).

Step 3: Synthesis of 2-bromo-1-[3-methyl-6-(trifluoromethyl)-3H-imidazo[4,5-b]pyridin-2-yl]ethanone 35.6 g of 1-[3-methyl-6-(trifluoromethyl)-3H-imidazo[4,5-b]pyridin-2-yl]ethanone was dissolved in 300 ml of toluene and a solution of about 5.1M hydrogen bromide in 150 ml of acetic acid, and 25.8 g of bromine was added under cooling with ice. After the addition, the reaction mixture was stirred at room temperature for 2 hours. After the stirring, 3.12 g of bromine was added to the reaction mixture at room temperature. After the addition, the reaction mixture was stirred at room temperature for one hour. After the stirring, 2.58 g of bromine was added to the reaction mixture at room temperature. After the addition, the reaction mixture was stirred at room temperature for 30 minutes. After the reaction, the reaction mixture was mixed with a 10M sodium hydroxide aqueous solution to have a pH of 3, and extracted with toluene (200 ml×2). The resulting organic layer was washed with a saturated sodium hydrogen sulfite aqueous solution, dehydrated with saturated aqueous sodium chloride and dried over anhydrous sodium sulfate, and the solvent was evaporated under reduced pressure. The precipitated solid was collected by filtration. The resulting solid was washed with diisopropyl ether to obtain 36.6 g of the desired 2-bromo-1-[3-methyl-6-(trifluoromethyl)-3H-imidazo[4,5-b]pyridin-2-yl]ethanone as a white solid.

Melting point: 90-91° C.

$^1$H-NMR (CDCl$_3$): δ8.86 (d, J=1.8 Hz, 1H), 8.47 (d, J=1.8 Hz, 1H), 4.85 (s, 2H), 4.26 (s, 3H).

Reference Example 13: Synthesis of 2-bromo-1-[3-methyl-6-(trifluoromethyl)-3H-imidazo[4,5-c]pyridin-2-yl]ethanone Step 1: Synthesis of (S)-1-[3-methyl-6-(trifluoromethyl)-3H-imidazo[4,5-c]pyridin-2-yl]ethanol 3.34 g of N$^3$-methyl-6-(trifluoromethyl)pyridine-3,4-diamine was dissolved in 20 ml of pyridine, and 2.89 g of (S)-(−)-2-acetoxypropionyl chloride was added at −20° C. After the addition, the reaction mixture was stirred at room temperature for 20 minutes. After the stirring, the solvent was evaporated from the reaction mixture under reduced pressure. The resulting residue was dissolved in 20 ml of ethanol, and 3.5 ml of a 10M sodium hydroxide aqueous solution was added at room temperature. After the addition, the reaction mixture was stirred under reflux with heating for one hour. After the stirring, 1.8 ml of a 10M sodium hydroxide aqueous solution was added to the reaction mixture at room temperature. After the addition, the reaction mixture was stirred under reflux with heating for 2 hours. After the reaction, the reaction mixture was mixed with 50 ml of water and extracted with ethyl acetate (50 ml×2). The resulting organic layer was dried over anhydrous sodium sulfate, and the solvent was evaporated under reduced pressure. The resulting residue was purified by preparative medium pressure liquid chromatography using n-hexane/ethyl acetate (with a gradient of 100:0 to 50:50) as the eluent to obtain 3.0 g of the desired product as a pale pink solid.

Melting point: 97-100° C.

$^1$H-NMR (CDCl$_3$): δ8.84 (s, 1H), 8.04 (d, J=0.7 Hz, 1H), 5.31-5.14 (m, 1H), 4.02 (s, 3H), 3.03 (d, J=7.2 Hz, 1H), 1.78 (d, J=6.5 Hz, 3H).

Step 2: Synthesis of 1-[3-methyl-6-(trifluoromethyl)-3H-imidazo[4,5-c]pyridin-2-yl]ethanone A solution of 3.0 g of (S)-1-[3-methyl-6-(trifluoromethyl)-3H-imidazo[4,5-c]pyridin-2-yl]ethanol in 30 ml of acetic acid was heated to 90° C., and a solution of 1.22 g of chromium(VI) oxide in 10 ml of water was added. After the addition, the reaction mixture was stirred under reflux with heating for one hour. After the reaction, the reaction mixture was mixed with 50 ml of water and extracted with ethyl acetate (50 ml×2). The resulting organic layer was dried over anhydrous sodium sulfate, and the solvent was evaporated under reduced pressure to obtain 2.59 g of the desired 1-[3-methyl-6-(trifluoromethyl)-3H-imidazo[4,5-c]pyridin-2-yl]ethanone as a pale yellow solid.

Melting point: 136-140° C.

$^1$H-NMR (CDCl$_3$): δ9.03 (s, 1H), 8.19 (d, J=0.9 Hz, 1H), 4.28 (s, 3H), 2.89 (s, 3H).

Step 3: Synthesis of 2-bromo-1-[3-methyl-6-(trifluoromethyl)-3H-imidazo[4,5-c]pyridin-2-yl]ethanone To a solution of 2.55 g of 1-[3-methyl-6-(trifluoromethyl)-3H-imidazo[4,5-c]pyridin-2-yl]ethanone in 30 ml of dichloromethane, 1.16 g of triethylamine was added at room temperature. After the addition, 2.44 g of trimethylsilyl trifluoromethanesulfonate was added to the reaction mixture under cooling with ice. After the addition, the reaction mixture was stirred under cooling with ice for 30 minutes. After the stirring, 3.95 g of trimethylphenylammonium tribromide was added to the reaction mixture under cooling with ice. After the addition, the reaction mixture was stirred under cooling with ice for 30 minutes. After the reaction, the reaction mixture was mixed with 50 ml of water and extracted with chloroform (30 ml×2). The resulting organic layer was dried over anhydrous sodium sulfate, and the solvent was evaporated under reduced pressure. The precipitated solid was collected by filtration. The resulting solid was washed with n-hexane to obtain 2.66 g of the desired 2-bromo-1-[3-methyl-6-(trifluoromethyl)-3H-imidazo[4,5-c]pyridin-2-yl]ethanone as a white solid.

Melting point: 127-131° C.

$^1$H-NMR (CDCl$_3$): δ9.07 (s, 1H), 8.21 (d, J=1.0 Hz, 1H), 4.87 (s, 2H), 4.31 (s, 3H).

The compounds of the present invention may be synthesized in accordance with the above Processes and Synthetic Examples. Examples of condensed heterocyclic compounds produced in the same manner as in Synthetic Examples 1 to 30 are shown in Tables 6 to 24, and examples of intermediates thereof are shown in Tables 25 to 32, however, the condensed heterocyclic compounds of the present invention and the intermediates thereof are not limited thereto.

In Tables, "Me" represents a methyl group, "Et" an ethyl group, and "Ph" a phenyl group. Substituents represented by Z1 to Z16 in Tables have the following structures. Further, in Tables, "*1" represents that the compound is a solid, "*2" represents that the compound is an oil, "*5" represents that the compound was decomposed when its melting point was measured, and "m.p." represents the melting point (unit: ° C.). Further, with respect to the description of the melting point in Tables, ">" represents that the melting point of the compound is higher than the described temperature, for example, ">250" means that the compound did not melt at 250° C.

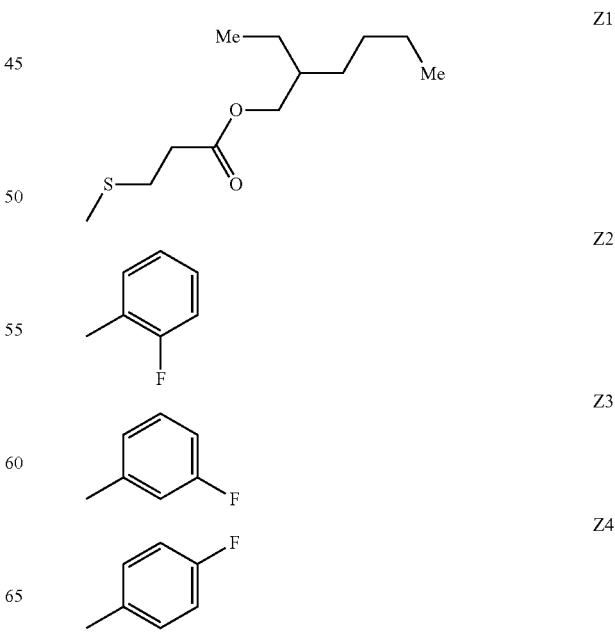

-continued

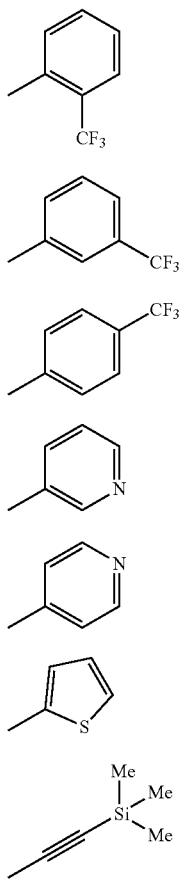

-continued

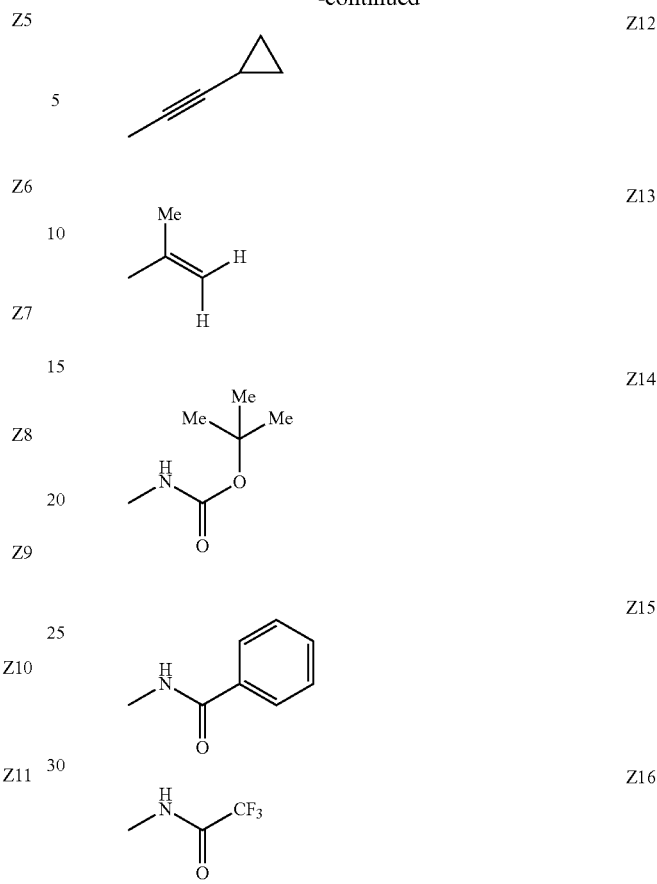

TABLE 6

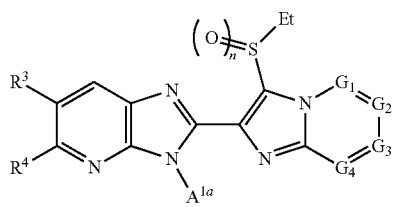

(1-A-A)

| NO. | R³ | R⁴ | A¹ᵃ | G₁ | G₂ | G₃ | G₄ | n | m. p. |
|---|---|---|---|---|---|---|---|---|---|
| 1-1-001a | CF₃ | H | Me | C—H | C—CF₃ | C—H | C—H | 2 | 212-213 |
| 1-1-001b | CF₃ | H | Me | C—H | C—CF₃ | C—H | C—H | 0 | 208-209 |
| 1-1-001c | CF₃ | H | Me | C—H | C—CF₃ | C—H | C—H | 1 | 202-203 |
| 1-1-002a | CF₃ | H | Me | C—H | C—H | C—CF₃ | C—H | 2 | 203-205 |
| 1-1-002b | CF₃ | H | Me | C—H | C—H | C—CF₃ | C—H | 0 | 199-202 |
| 1-1-003a | CF₃ | H | Me | C—H | C—Cl | C—H | C—H | 2 | 217-218 |
| 1-1-003b | CF₃ | H | Me | C—H | C—Cl | C—H | C—H | 0 | 228-230 |
| 1-1-003c | CF₃ | H | Me | C—H | C—Cl | C—H | C—H | 1 | 217-219 |
| 1-1-004a | CF₃ | H | Me | C—H | C—F | C—H | C—H | 2 | 187-189 |
| 1-1-004b | CF₃ | H | Me | C—H | C—F | C—H | C—H | 0 | 190-195 |
| 1-1-004c | CF₃ | H | Me | C—H | C—F | C—H | C—H | 1 | 195-200 |
| 1-1-005a | CF₃ | H | Me | C—H | C—I | C—H | C—H | 2 | 215-218 |
| 1-1-005b | CF₃ | H | Me | C—H | C—I | C—H | C—H | 0 | 260-263 |
| 1-1-005c | CF₃ | H | Me | C—H | C—I | C—H | C—H | 1 | 239-241 |
| 1-1-006a | CF₃ | H | Me | C—H | C—Br | C—H | C—H | 2 | 205-207 |
| 1-1-006b | CF₃ | H | Me | C—H | C—Br | C—H | C—H | 0 | 233-236 |
| 1-1-007a | CF₃ | H | Me | C—H | C—OMe | C—H | C—H | 2 | 186-188 |
| 1-1-007b | CF₃ | H | Me | C—H | C—OMe | C—H | C—H | 0 | 209-211 |
| 1-1-008a | CF₃ | H | Me | C—H | C—NO₂ | C—H | C—H | 2 | 258-262 |
| 1-1-008b | CF₃ | H | Me | C—H | C—NO₂ | C—H | C—H | 0 | 218-221 |
| 1-1-009a | CF₃ | H | Me | C—H | C—Me | C—H | C—H | 2 | 162-165 |

TABLE 6-continued (1-A-A)

| NO. | R³ | R⁴ | A¹ᵃ | G₁ | G₂ | G₃ | G₄ | n | m. p. |
|---|---|---|---|---|---|---|---|---|---|
| 1-1-010a | CF₃ | H | Me | C—H | C—Z1 | C—H | C—H | 2 | *2 |
| 1-1-011a | CF₃ | H | Me | C—H | C—SCF₃ | C—H | C—H | 2 | 208-210 |
| 1-1-012a | CF₃ | H | Me | C—H | C—H | C—H | C—H | 2 | 122-125 |
| 1-1-012b | CF₃ | H | Me | C—H | C—H | C—H | C—H | 0 | 183-184 |
| 1-1-013a | CF₃ | H | Me | C—H | C—H | C—Cl | C—H | 2 | 214-215 |
| 1-1-013b | CF₃ | H | Me | C—H | C—H | C—Cl | C—H | 0 | 198-203 |
| 1-1-013c | CF₃ | H | Me | C—H | C—H | C—Cl | C—H | 1 | *1 |
| 1-1-014a | CF₃ | H | Me | C—H | C—H | C—F | C—H | 2 | 170-171 |
| 1-1-014b | CF₃ | H | Me | C—H | C—H | C—F | C—H | 0 | 210-212 |
| 1-1-014c | CF₃ | H | Me | C—H | C—H | C—F | C—H | 1 | *5 |
| 1-1-015a | CF₃ | H | Me | C—H | C—H | C—I | C—H | 2 | 208-211 |
| 1-1-015b | CF₃ | H | Me | C—H | C—H | C—I | C—H | 0 | 202-205 |
| 1-1-016a | CF₃ | H | Me | C—H | C—H | C—Br | C—H | 2 | 205-206 |
| 1-1-016b | CF₃ | H | Me | C—H | C—H | C—Br | C—H | 0 | 204-206 |
| 1-1-016c | CF₃ | H | Me | C—H | C—H | C—Br | C—H | 1 | *5 |
| 1-1-017a | CF₃ | H | Me | C—H | C—H | C—Me | C—H | 2 | 136-138 |
| 1-1-018a | CF₃ | H | Me | C—H | C—H | C—CN | C—H | 2 | 253-255 |
| 1-1-019a | CF₃ | H | Me | C—H | C—H | C—CO₂H | C—H | 2 | 210-214 |
| 1-1-020a | CF₃ | H | Me | C—H | C—CF₃ | C—H | C—Cl | 2 | 192-195 |
| 1-1-020b | CF₃ | H | Me | C—H | C—CF₃ | C—H | C—Cl | 0 | 138-144 |
| 1-1-021b | CF₃ | H | Me | C—H | C—CF₃ | C—H | C—SEt | 0 | 190-192 |
| 1-1-022a | CF₃ | H | Me | C—H | C—CF₃ | C—H | C—SO₂Et | 2 | *1 |
| 1-1-023a | CF₃ | H | Me | C—H | C—Br | C—CF₃ | C—H | 2 | 226-228 |
| 1-1-023b | CF₃ | H | Me | C—H | C—Br | C—CF₃ | C—H | 0 | 214-215 |
| 1-1-023c | CF₃ | H | Me | C—H | C—Br | C—CF₃ | C—H | 1 | 198-200 |
| 1-1-024a | CF₃ | H | Me | C—H | C—Me | C—CF₃ | C—H | 2 | 247-250 |
| 1-1-025b | CF₃ | H | Me | C—Me | C—H | C—Me | C—H | 0 | 156-158 |
| 1-1-025c | CF₃ | H | Me | C—Me | C—H | C—Me | C—H | 1 | *2 |
| 1-1-026a | I | H | Me | C—H | C—H | C—CF₃ | C—H | 2 | 202-205 |
| 1-1-026b | I | H | Me | C—H | C—H | C—CF₃ | C—H | 0 | 230-233 |
| 1-1-027a | SCF₃ | H | Me | C—H | C—H | C—CF₃ | C—H | 2 | 220-223 |
| 1-1-027b | SCF₃ | H | Me | C—H | C—H | C—CF₃ | C—H | 0 | 209-210 |
| 1-1-028b | Z1 | H | Me | C—H | C—H | C—CF₃ | C—H | 0 | 94-96 |
| 1-1-029a | CF₃ | H | Me | C—H | C—CF₃ | N | C—H | 2 | 234-236 |
| 1-1-029b | CF₃ | H | Me | C—H | C—CF₃ | N | C—H | 0 | 220-222 |
| 1-1-030a | H | CF₃ | Me | C—H | C—H | C—CF₃ | C—H | 2 | 217-219 |
| 1-1-030b | H | CF₃ | Me | C—H | C—H | C—CF₃ | C—H | 0 | 163-165 |
| 1-1-030c | H | CF₃ | Me | C—H | C—H | C—CF₃ | C—H | 1 | 190-200 |
| 1-1-031b | H | CF₃ | H | C—H | C—H | C—CF₃ | C—H | 0 | *5 |
| 1-1-032a | CF₃ | H | Et | C—H | C—H | C—CF₃ | C—H | 2 | 215-217 |
| 1-1-032b | CF₃ | H | Et | C—H | C—H | C—CF₃ | C—H | 0 | 199-202 |
| 1-1-033a | CF₃ | H | Me | C—H | C—H | C—CO₂Me | C—H | 2 | 199-202 |
| 1-1-034a | CF₃ | H | Me | C—H | C—H | C—CO₂Et | C—H | 2 | 192-194 |
| 1-1-035a | CF₃ | H | Me | C—H | C—H | C—CONMe₂ | C—H | 2 | 155-157 |
| 1-1-036a | CF₃ | H | Me | C—H | C—SMe | C—CF₃ | C—H | 2 | 192-202 |
| 1-1-037a | CF₃ | H | Me | C—H | C—Z1 | C—CF₃ | C—H | 2 | 77-79 |
| 1-1-038a | CF₃ | H | Me | C—H | C—SO₂Me | C—CF₃ | C—H | 2 | *1 |
| 1-1-039a | CF₃ | H | Me | C—H | C—SOMe | C—CF₃ | C—H | 2 | 220-223 |
| 1-1-040a | CF₃ | H | Me | C—CF₃ | C—H | C—H | C—H | 2 | 196-200 |
| 1-1-040b | CF₃ | H | Me | C—CF₃ | C—H | C—H | C—H | 0 | 131-133 |
| 1-1-040c | CF₃ | H | Me | C—CF₃ | C—H | C—H | C—H | 1 | 175-178 |
| 1-1-041a | CF₃ | H | Me | C—H | C—H | C—Z1 | C—H | 2 | 75-77 |
| 1-1-042a | CF₃ | H | Me | C—H | C—H | C—SMe | C—H | 2 | 194-196 |
| 1-1-043a | CF₃ | H | Me | C—H | C—H | C—SOMe | C—H | 2 | 226-228 |
| 1-1-044a | CF₃ | H | Me | C—H | C—H | C—SO₂Me | C—H | 2 | 290-292 |
| 1-1-045a | CF₃ | H | Me | C—H | C—CF₂CF₃ | C—H | C—H | 2 | 208-210 |
| 1-1-045b | CF₃ | H | Me | C—H | C—CF₂CF₃ | C—H | C—H | 0 | 165-167 |
| 1-1-046a | CF₃ | H | Me | C—H | C—Cl | C—Cl | C—H | 2 | 224-225 |
| 1-1-047a | CF₃ | H | Me | C—H | C—I | C—Cl | C—H | 2 | 268-270 |
| 1-1-047b | CF₃ | H | Me | C—H | C—I | C—Cl | C—H | 0 | 239-243 |
| 1-1-048a | CF₃ | H | Me | C—H | C—I | C—Me | C—H | 2 | 231-234 |
| 1-1-048b | CF₃ | H | Me | C—H | C—I | C—Me | C—H | 0 | *1 |
| 1-1-049a | CF₃ | H | Me | C—H | C—I | C—CF₃ | C—H | 2 | 240-243 |
| 1-1-049b | CF₃ | H | Me | C—H | C—I | C—CF₃ | C—H | 0 | 222-225 |
| 1-1-050a | CF₃ | H | Me | C—H | C—I | C—CN | C—H | 2 | 290-297 |
| 1-1-050b | CF₃ | H | Me | C—H | C—I | C—CN | C—H | 0 | 284-290 |

TABLE 6-continued (1-A-A)

| NO. | R³ | R⁴ | A¹ᵃ | G₁ | G₂ | G₃ | G₄ | n | m. p. |
|---|---|---|---|---|---|---|---|---|---|
| 1-1-051a | CF₃ | H | Me | C—H | C—I | C—F | C—H | 2 | *1 |
| 1-1-051b | CF₃ | H | Me | C—H | C—I | C—F | C—H | 0 | *1 |
| 1-1-052a | CF₃ | H | Me | C—H | C—I | C—OMe | C—H | 2 | 251-253 |
| 1-1-052b | CF₃ | H | Me | C—H | C—I | C—OMe | C—H | 0 | 240-244 |
| 1-1-053a | CF₃ | H | Me | C—H | C—I | C—H | N | 2 | 292-295 |
| 1-1-053b | CF₃ | H | Me | C—H | C—I | C—H | N | 0 | 275-278 |
| 1-1-054a | CF₃ | H | Me | C—H | C—CF₃ | C—H | N | 2 | 244-248 |
| 1-1-054b | CF₃ | H | Me | C—H | C—CF₃ | C—H | N | 0 | 220-222 |
| 1-1-055a | CF₃ | H | Me | C—H | N | C—CF₃ | C—H | 2 | 238-240 |
| 1-1-055b | CF₃ | H | Me | C—H | N | C—CF₃ | C—H | 0 | 198-200 |
| 1-1-056a | CF₃ | H | Me | C—H | C—I | N | C—H | 2 | 205-210 |
| 1-1-057a | CF₃ | H | Me | N | C—H | C—CF₃ | C—H | 2 | *2 |
| 1-1-057b | CF₃ | H | Me | N | C—H | C—CF₃ | C—H | 0 | *2 |
| 1-1-057c | CF₃ | H | Me | N | C—H | C—CF₃ | C—H | 1 | *2 |
| 1-1-058a | CF₃ | H | Me | C—H | C—Cl | C—H | C—Me | 2 | 198-200 |
| 1-1-058b | CF₃ | H | Me | C—H | C—Cl | C—H | C—Me | 0 | 199-202 |
| 1-1-059a | CF₃ | H | Me | C—H | C—Cl | C—H | C—Cl | 2 | 220-224 |
| 1-1-059b | CF₃ | H | Me | C—H | C—Cl | C—H | C—Cl | 0 | 222-225 |
| 1-1-060a | CF₃ | H | Me | C—H | C—F | C—H | C—F | 2 | 190-192 |
| 1-1-060b | CF₃ | H | Me | C—H | C—F | C—H | C—F | 0 | 181-185 |
| 1-1-061a | CF₃ | H | Me | C—H | C—I | C—H | C—I | 2 | 277-279 |
| 1-1-061b | CF₃ | H | Me | C—H | C—I | C—H | C—I | 0 | 267-270 |
| 1-1-062a | CF₃ | H | Me | C—H | C—I | C—H | C—Cl | 2 | 240-243 |
| 1-1-062b | CF₃ | H | Me | C—H | C—I | C—H | C—Cl | 0 | 248-251 |
| 1-1-063a | CF₃ | H | Me | C—H | C—Br | C—H | C—F | 2 | 229-231 |
| 1-1-063b | CF₃ | H | Me | C—H | C—Br | C—H | C—F | 0 | 202-205 |
| 1-1-064a | CF₃ | H | Me | C—H | C—I | C—H | C—OMe | 2 | 239-241 |
| 1-1-065a | CF₃ | H | Me | C—H | C—I | C—H | C—OEt | 2 | 220-221 |
| 1-1-066a | CF₃ | H | Me | C—H | C—I | C—H | C—CF₃ | 2 | 271-273 |
| 1-1-066b | CF₃ | H | Me | C—H | C—I | C—H | C—CF₃ | 0 | 222-225 |
| 1-1-067a | CF₃ | H | Me | C—H | C—I | C—H | C—CN | 2 | 253-256 |
| 1-1-067b | CF₃ | H | Me | C—H | C—I | C—H | C—CN | 0 | 298-300 |
| 1-1-068a | CF₃ | H | Me | C—H | C—I | C—H | C—NMe₂ | 2 | 202-203 |
| 1-1-069a | CF₃ | H | Me | C—H | C—Cl | C—H | C—CF₃ | 2 | 218-220 |
| 1-1-069b | CF₃ | H | Me | C—H | C—Cl | C—H | C—CF₃ | 0 | 201-203 |
| 1-1-070a | CF₃ | H | Me | C—H | C—CF₃ | C—H | C—F | 2 | 195-196 |
| 1-1-070b | CF₃ | H | Me | C—H | C—CF₃ | C—H | C—F | 0 | 169-171 |
| 1-1-071a | CF₃ | H | Me | C—H | C—CF₃ | C—H | C—I | 2 | 240-243 |
| 1-1-071b | CF₃ | H | Me | C—H | C—CF₃ | C—H | C—I | 0 | 227-229 |
| 1-1-072a | CF₃ | H | Me | C—H | C—I | C—H | C—Me | 2 | 204-206 |
| 1-1-072b | CF₃ | H | Me | C—H | C—I | C—H | C—Me | 0 | 214-216 |
| 1-1-072c | CF₃ | H | Me | C—H | C—I | C—H | C—Me | 1 | *5 |
| 1-1-073a | CF₃ | H | Me | C—H | C—Me | C—H | C—Cl | 2 | 233-236 |
| 1-1-073b | CF₃ | H | Me | C—H | C—Me | C—H | C—Cl | 0 | 213-218 |
| 1-1-074a | CF₃ | H | Me | C—H | C—I | C—H | C—F | 2 | 222-226 |
| 1-1-074b | CF₃ | H | Me | C—H | C—I | C—H | C—F | 0 | 232-236 |
| 1-1-075a | CF₃ | H | Me | C—H | C—SMe | C—H | C—SMe | 2 | 205-214 |
| 1-1-076a | CF₃ | H | Me | C—H | C—CF₃ | C—H | C—Br | 2 | 219-220 |
| 1-1-077a | CF₃ | H | Me | C—H | C—H | C—H | C—CF₃ | 2 | 199-202 |
| 1-1-077b | CF₃ | H | Me | C—H | C—H | C—H | C—CF₃ | 0 | 195-197 |
| 1-1-078a | CF₃ | H | He | C—H | C—Cl | C—Cl | C—Cl | 2 | *1 |
| 1-1-078b | CF₃ | H | Me | C—H | C—Cl | C—Cl | C—Cl | 0 | *1 |
| 1-1-079a | CF₃ | H | Me | C—H | C—Ph | C—H | C—H | 2 | 220-221 |
| 1-1-080a | CF₃ | H | Me | C—H | C—Z2 | C—H | C—H | 2 | 235-238 |
| 1-1-081a | CF₃ | H | Me | C—H | C—Z3 | C—H | C—H | 2 | 204-207 |
| 1-1-082a | CF₃ | H | Me | C—H | C—Z4 | C—H | C—H | 2 | 227-229 |
| 1-1-083a | CF₃ | H | Me | C—H | C—Z5 | C—H | C—H | 2 | 187-189 |
| 1-1-084a | CF₃ | H | Me | C—H | C—Z6 | C—H | C—H | 2 | 217-220 |
| 1-1-085a | CF₃ | H | Me | C—H | C—Z7 | C—H | C—H | 2 | 213-215 |
| 1-1-086a | CF₃ | H | Me | C—H | C—Z8 | C—H | C—H | 2 | 224-228 |
| 1-1-087a | CF₃ | H | Me | C—H | C—Z9 | C—H | C—H | 2 | 231-233 |
| 1-1-088a | CF₃ | H | Me | C—H | C—Z10 | C—H | C—H | 2 | 213-214 |
| 1-1-089a | CF₃ | H | Me | C—H | C—Z11 | C—H | C—H | 2 | 175-178 |
| 1-1-090a | CF₃ | H | Me | C—H | C—Z12 | C—H | C—H | 2 | 201-204 |
| 1-1-091a | CF₃ | H | Me | C—H | C—Z13 | C—H | C—H | 2 | 197-200 |
| 1-1-092a | Cl | H | Me | C—H | C—CF₃ | C—H | C—H | 2 | 181-183 |

TABLE 6-continued (1-A-A)

| NO. | R³ | R⁴ | A¹ᵃ | G₁ | G₂ | G₃ | G₄ | n | m. p. |
|---|---|---|---|---|---|---|---|---|---|
| 1-1-092b | Cl | H | Me | C—H | C—CF₃ | C—H | C—H | 0 | 224-228 |
| 1-1-093a | CF₂CF₃ | H | Me | C—H | C—Cl | C—H | C—H | 2 | 185-187 |
| 1-1-093b | CF₂CF₃ | H | Me | C—H | C—Cl | C—H | C—H | 0 | 169-171 |
| 1-1-094a | CF₂CF₃ | H | Me | C—H | C—I | C—H | C—H | 2 | 207-208 |
| 1-1-094b | CF₂CF₃ | H | Me | C—H | C—I | C—H | C—H | 0 | 225-230 |
| 1-1-094c | CF₂CF₃ | H | Me | C—H | C—I | C—H | C—H | 1 | 220-223 |
| 1-1-095a | CF₃ | H | Me | C—H | C—SMe | C—H | C—H | 2 | 198-200 |
| 1-1-096a | CF₃ | H | Me | C—H | C—SOMe | C—H | C—H | 2 | 230-232 |
| 1-1-097a | CF₃ | H | Me | C—H | C—SO₂Me | C—H | C—H | 2 | 225-230 |
| 1-1-098a | CF₃ | H | Me | C—H | C—SCH₂CF₃ | C—H | C—H | 2 | 229-233 |
| 1-1-099a | CF₂CF₃ | H | Me | C—H | C—SMe | C—H | C—H | 2 | 175-181 |
| 1-1-100a | CF₃ | H | Me | C—H | C—Z14 | C—H | C—H | 2 | 215-216 |
| 1-1-101a | CF₃ | H | Me | C—H | C—H | C—NO₂ | C—H | 2 | 230-232 |
| 1-1-101b | CF₃ | H | Me | C—H | C—H | C—NO₂ | C—H | 0 | 231-233 |
| 1-1-102a | H | H | Me | C—H | C—H | C—CF₃ | C—H | 2 | 180-183 |
| 1-1-102b | H | H | Me | C—H | C—H | C—CF₃ | C—H | 0 | 182-184 |
| 1-1-103a | CF₂CF₃ | H | Me | C—H | C—H | C—CF₃ | C—H | 2 | 229-232 |
| 1-1-103b | CF₂CF₃ | H | Me | C—H | C—H | C—CF₃ | C—H | 0 | 186-188 |
| 1-1-104a | CF₃ | H | Me | C—H | C—Z15 | C—CF₃ | C—H | 2 | *5 |
| 1-1-105a | CF₃ | H | Me | C—H | C—CF₃ | C—H | C—CN | 2 | 238-241 |
| 1-1-105a | CF₃ | H | Me | C—H | C—CF₃ | C—H | C—CN | 0 | 187-190 |
| 1-1-105a | CF₃ | H | Me | C—H | C—CF₃ | C—H | C—CN | 1 | 152-155 |
| 1-1-106a | CF₃ | H | Me | C—H | C—H | C—CHF₂ | C—H | 2 | 164-165 |
| 1-1-106b | CF₃ | H | Me | C—H | C—H | C—CHF₂ | C—H | 0 | 191-193 |
| 1-1-106c | CF₃ | H | Me | C—H | C—H | C—CHF₂ | C—H | 1 | 191-194 |
| 1-1-107a | CF₃ | H | Me | C—H | C—NH₂ | C—H | C—H | 2 | *2 |
| 1-1-108a | CF₃ | H | Me | C—H | C—Z16 | C—H | C—H | 2 | *2 |
| 1-1-109a | CF₃ | H | Me | C—H | C—Br | C—F | C—H | 2 | 240-242 |
| 1-1-109b | CF₃ | H | Me | C—H | C—Br | C—F | C—H | 0 | 250-253 |
| 1-1-110a | CF₃ | H | Me | C—H | C—Br | C—Cl | C—H | 2 | 238-242 |
| 1-1-110c | CF₃ | H | Me | C—H | C—Br | C—Cl | C—H | 1 | 298-300 |
| 1-1-111a | CF₃ | H | Me | C—H | C—Br | C—CN | C—H | 2 | 255-268 |
| 1-1-111b | CF₃ | H | Me | C—H | C—Br | C—CN | C—H | 0 | 246-248 |
| 1-1-112a | CF₃ | H | Me | C—H | C—Br | C—H | C—Cl | 2 | 220-221 |
| 1-1-112b | CF₃ | H | Me | C—H | C—Br | C—H | C—Cl | 0 | 223-226 |
| 1-1-113a | CF₃ | H | Me | C—H | C—F | C—H | C—Cl | 2 | 171-175 |
| 1-1-113b | CF₃ | H | Me | C—H | C—F | C—H | C—Cl | 0 | 204-208 |
| 1-1-114a | CF₃ | H | Me | C—H | C—Cl | C—I | C—H | 2 | 238-241 |
| 1-1-114b | CF₃ | H | Me | C—H | C—Cl | C—I | C—H | 0 | *1 |
| 1-1-115a | CF₃ | H | Me | C—H | C—Cl | C—Br | C—H | 2 | 220-224 |
| 1-1-115b | CF₃ | H | Me | C—H | C—Cl | C—Br | C—H | 0 | *1 |
| 1-1-116a | CF₃ | H | Me | C—H | C—Cl | C—SMe | C—H | 2 | 248-251 |
| 1-1-117a | CF₃ | H | Me | C—H | C—Cl | C—SOMe | C—H | 2 | 254-256 |
| 1-1-118a | CF₃ | H | Me | C—H | C—Cl | C—H | C—Br | 2 | 219-223 |
| 1-1-118b | CF₃ | H | Me | C—H | C—Cl | C—H | C—Br | 0 | 233-235 |
| 1-1-118c | CF₃ | H | Me | C—H | C—Cl | C—H | C—Br | 1 | *5 |
| 1-1-119b | CF₃ | H | Me | C—H | C—Cl | C—Me | C—Cl | 0 | 230-232 |
| 1-1-119c | CF₃ | H | Me | C—H | C—Cl | C—Me | C—Cl | 1 | *5 |
| 1-1-120c | CF₃ | H | Me | C—H | C—H | N | C—H | 1 | *5 |
| 1-1-121a | CF₃ | H | Me | C—H | C—F | C—I | C—H | 2 | 243-245 |
| 1-1-122a | SOCF₃ | H | Me | C—H | C—H | C—CF₃ | C—H | 2 | 218-219 |
| 1-1-123a | SO2CF₃ | H | Me | C—H | C—H | C—CF₃ | C—H | 2 | 241-243 |

TABLE 7

(1-A-B)

| No. | R³ | A⁵ | G₁ | G₂ | G₃ | G₄ | n | m.p. |
|---|---|---|---|---|---|---|---|---|
| 1-2-001a | SO₂CF₃ | C—H | C—H | C—CF₃ | C—H | C—H | 2 | *1 |
| 1-2-002a | SOCF₃ | C—H | C—H | C—CF₃ | C—H | C—H | 2 | *1 |
| 1-2-003b | SCF₃ | C—H | C—H | C—CF₃ | C—H | C—H | 0 | *1 |
| 1-2-004a | CF₃ | N | C—H | C—H | C—CF₃ | C—H | 2 | 244-246 |
| 1-2-004b | CF₃ | N | C—H | C—H | C—CF₃ | C—H | 0 | 159-161 |
| 1-2-004c | CF₃ | N | C—H | C—H | C—CF₃ | C—H | 1 | 175-177 |
| 1-2-005a | SCF₃ | C—H | C—H | C—H | C—CF₃ | C—H | 2 | 217-219 |
| 1-2-006a | SO₂CF₃ | C—H | C—H | C—H | C—CF₃ | C—H | 2 | 198-199 |

TABLE 8

(1-A-C)

| No. | R³ | R⁴ | R⁶ | G₁ | G₂ | G₃ | G₄ | n | m.p. |
|---|---|---|---|---|---|---|---|---|---|
| 1-3-001a | CF₃ | H | H | C—H | C—H | C—CF₃ | C—H | 2 | 235-237 |
| 1-3-002a | CF₃ | Me | H | C—H | C—H | C—CF₃ | C—H | 2 | 218-223 |
| 1-3-003a | CF₂CF₃ | Me | H | C—H | C—H | C—CF₃ | C—H | 2 | 218-222 |
| 1-3-004a | CF₂CF₃ | H | H | C—H | C—H | C—CF₃ | C—H | 2 | 228-232 |
| 1-3-005a | CF₃ | H | H | C—H | C—CF₃ | C—H | C—H | 2 | 165-168 |
| 1-3-006a | CF₃ | Me | H | C—H | C—CF₃ | C—H | C—H | 2 | 207-213 |
| 1-3-007a | CF₂CF₃ | Me | H | C—H | C—CF₃ | C—H | C—H | 2 | 224-226 |
| 1-3-008a | CF₂CF₃ | H | H | C—H | C—CF₃ | C—H | C—H | 2 | 233-239 |
| 1-3-009a | CF₂CF₃ | H | I | C—H | C—CF₃ | C—H | C—H | 2 | 196-198 |
| 1-3-010a | CF₂CF₃ | H | Br | C—H | C—CF₃ | C—H | C—H | 2 | 200-205 |
| 1-3-011a | CF₂CF₃ | H | Me | C—H | C—CF₃ | C—H | C—H | 2 | 223-225 |
| 1-3-012a | CF₃ | H | H | C—H | C—I | C—H | C—H | 2 | *1 |
| 1-3-013a | CF₂CF₃ | H | I | C—H | C—H | C—CF₃ | C—H | 2 | 254-258 |
| 1-3-014a | CF₂CF₃ | H | Me | C—H | C—H | C—CF₃ | C—H | 2 | 277-279 |

TABLE 9

(1-A-D)

| No. | R³ | G₁ | G₂ | G₃ | G₄ | n | m.p. |
|---|---|---|---|---|---|---|---|
| 1-4-001a | CF₃ | C—H | C—H | C—CF₃ | C—H | 2 | 214-218 |
| 1-4-002a | CF₃ | C—H | C—CF₃ | C—H | C—H | 2 | 235-238 |
| 1-4-003a | CF₃ | C—H | C—I | C—H | C—H | 2 | 253-258 |
| 1-4-003b | CF₃ | C—H | C—I | C—H | C—H | 0 | 220-225 |

TABLE 10

(1-A-E)

| No. | R³ | R⁴ | G₁ | G₂ | G₃ | G₄ | n | m.p. |
|---|---|---|---|---|---|---|---|---|
| 1-5-001a | CF₃ | H | C—H | C—H | C—CF, | C—H | 2 | 142-144 |
| 1-5-002a | CF₃ | H | C—H | C—CF₃ | C—H | C—H | 2 | 245-248 |
| 1-5-003a | H | CF₃ | C—H | C—H | C—CF₃ | C—H | 2 | 175-177 |
| 1-5-004a | H | CF₃ | C—H | C—CF₃ | C—H | C—H | 2 | 138-143 |

TABLE 11

(1-A-G)

| No. | R⁴ | G₁ | G₂ | G₃ | G₄ | n | m.p. |
|---|---|---|---|---|---|---|---|
| 1-6-001a | CF₃ | C—H | C—H | C—CF₃ | C—H | 2 | 200-202 |
| 1-6-002a | CF₃ | C—H | C—CF₃ | C—H | C—H | 2 | 266-270 |

TABLE 12

(1-A-G)

| No. | R³ | R⁴ | R¹ᵃ | G₁ | G₂ | G₃ | G₄ | n | m.p. |
|---|---|---|---|---|---|---|---|---|---|
| 1-7-001a | CF₃ | H | Me | C—H | C—H | C—CF₃ | C—H | 2 | 190-200 |
| 1-7-001b | CF₃ | H | Me | C—H | C—H | C—CF₃ | C—H | 0 | 164-166 |

TABLE 13

(1-A-H)

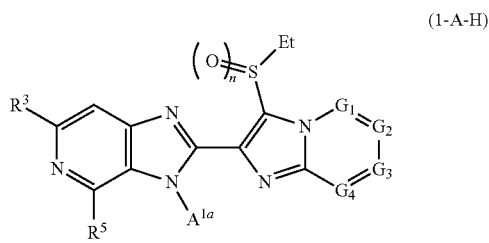

| No. | R³ | R⁵ | A¹ᵃ | G₁ | G₂ | G₃ | G₄ | n | m. p. |
|---|---|---|---|---|---|---|---|---|---|
| 1-8-001b | CF₃ | H | H | C—H | C—CF₃ | C—H | C—H | 0 | 233-235 |
| 1-8-002a | CF₃ | H | Me | C—H | C—CF₃ | C—H | C—H | 2 | 253-256 |
| 1-8-002b | CF₃ | H | Me | C—H | C—CF₃ | C—H | C—H | 0 | 226-228 |
| 1-8-003a | CF₃ | Me | Me | C—H | C—CF₃ | C—H | C—H | 2 | 200-205 |
| 1-8-003b | CF₃ | Me | Me | C—H | C—CF₃ | C—H | C—H | 0 | 169-171 |
| 1-8-004b | CF₃ | H | H | C—H | C—H | C—CF₃ | C—H | 0 | 96-98 |
| 1-8-005a | CF₃ | H | Me | C—H | C—H | C—CF₃ | C—H | 2 | 245-247 |
| 1-8-005b | CF₃ | H | Me | C—H | C—H | C—CF₃ | C—H | 0 | 217-219 |
| 1-8-006a | CF₃ | H | Me | C—H | C—H | C—Cl | C—H | 2 | 217-219 |
| 1-8-006b | CF₃ | H | Me | C—H | C—H | C—Cl | C—H | 0 | 215-217 |
| 1-8-007a | CF₃ | H | Me | C—H | C—I | C—H | C—H | 2 | *1 |
| 1-8-007b | CF₃ | H | Me | C—H | C—I | C—H | C—H | 0 | 280-282 |
| 1-8-008a | CF₃ | H | Me | C—H | C—I | C—H | C—F | 2 | 294-298 |
| 1-8-008b | CF₃ | H | Me | C—H | C—I | C—H | C—F | 0 | *1 |
| 1-8-009a | CF₃ | H | Me | C—H | C—I | C—H | C—OEt | 2 | 257-259 |
| 1-8-010a | CF₃ | H | Me | C—H | C—H | C—I | C—H | 2 | 235-237 |
| 1-8-011a | CF₃ | H | Me | C—H | C—Br | C—H | C—F | 2 | 266-268 |
| 1-8-012b | CF₃ | H | H | C—H | C—H | C—Cl | C—H | 0 | *1 |
| 1-8-013a | CF₃ | H | Me | C—H | C—Br | C—H | C—H | 2 | 270-272 |
| 1-8-013b | CF₃ | H | Me | C—H | C—Br | C—H | C—H | 0 | 240-242 |
| 1-8-013c | CF₃ | H | Me | C—H | C—Br | C—H | C—H | 1 | 238-240 |
| 1-8-014a | CF₃ | H | Me | C—H | C—I | C—CN | C—H | 2 | 280-284 |
| 1-8-014b | CF₃ | H | Me | C—H | C—I | C—CN | C—H | 0 | 248-253 |
| 1-8-015a | CF₃ | H | Me | C—H | C—I | C—F | C—H | 2 | 294-297 |
| 1-8-015b | CF₃ | H | Me | C—H | C—I | C—F | C—H | 0 | 259-263 |
| 1-8-016a | CF₃ | H | Me | C—H | C—Cl | C—H | C—H | 2 | 239-241 |
| 1-8-016b | CF₃ | H | Me | C—H | C—Cl | C—H | C—H | 0 | 238-242 |

TABLE 14

(1-A-I)

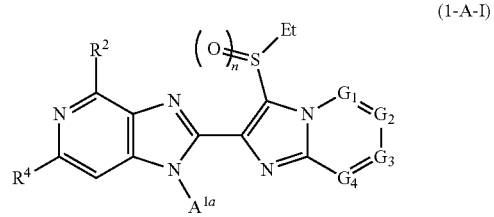

| No. | R² | R⁴ | A¹ᵃ | G₁ | G₂ | G₃ | G₄ | n | m. p. |
|---|---|---|---|---|---|---|---|---|---|
| 1-9-001a | H | CF₃ | Me | C—H | C—CF₃ | C—H | C—H | 2 | 269-271 |
| 1-9-001b | H | CF₃ | Me | C—H | C—CF₃ | C—H | C—H | 0 | 230-232 |
| 1-9-002a | H | CF₃ | Me | C—H | C—H | C—CF₃ | C—H | 2 | 185-187 |
| 1-9-002b | H | CF₃ | Me | C—H | C—H | C—CF₃ | C—H | 0 | 175-177 |
| 1-9-003a | H | CF₃ | Me | C—H | C—H | C—Cl | C—H | 2 | 200-202 |
| 1-9-003b | H | CF₃ | Me | C—H | C—H | C—Cl | C—H | 0 | 187-188 |

TABLE 15

(1-A-J)

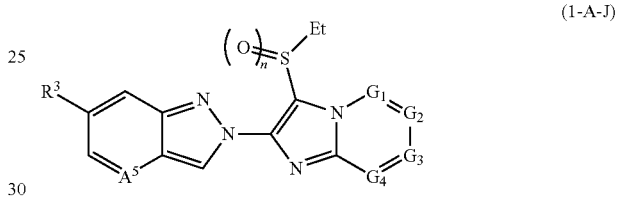

| No. | R³ | A⁵ | G₁ | G₂ | G₃ | G₄ | n | m. p. |
|---|---|---|---|---|---|---|---|---|
| 1-10-001a | CF₃ | C—H | C—H | C—H | C—CF₃ | C—H | 2 | 206-209 |
| 1-10-001b | CF₃ | C—H | C—H | C—H | C—CF₃ | C—H | 0 | 126-130 |
| 1-10-001c | CF₃ | C—H | C—H | C—H | C—CF₃ | C—H | 1 | 184-188 |
| 1-10-002a | CF₃ | N | C—H | C—H | C—CF₃ | C—H | 2 | 245-247 |
| 1-10-002b | CF₃ | N | C—H | C—H | C—CF₃ | C—H | 0 | 161-163 |
| 1-10-002c | CF₃ | N | C—H | C—H | C—CF₃ | C—H | 1 | *1 |
| 1-10-003a | CF₃ | N | C—H | C—I | C—H | C—H | 2 | 260-265 |
| 1-10-003b | CF₃ | N | C—H | C—I | C—H | C—H | 0 | 249-251 |

TABLE 16

(1-A-K)

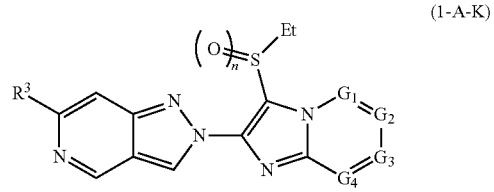

| No. | R³ | G₁ | G₂ | G₃ | G₄ | n | m. p. |
|---|---|---|---|---|---|---|---|
| 1-11-001a | CF₃ | C—H | C—H | C—CF₃ | C—H | 2 | 230-233 |
| 1-11-001b | CF₃ | C—H | C—H | C—CF₃ | C—H | 0 | 183-185 |
| 1-11-001c | CF₃ | C—H | C—H | C—CF₃ | C—H | 1 | 189-192 |
| 1-11-002a | CF₃ | C—H | C—H | C—I | C—H | 2 | 231-233 |
| 1-11-003a | CF₃ | C—H | C—I | C—H | C—H | 2 | 276-283 |
| 1-11-003b | CF₃ | C—H | C—I | C—H | C-H | 0 | *5 |
| 1-11-004a | CF₃ | C—H | C—CF₃ | C—H | C—H | 2 | 225-227 |
| 1-11-004b | CF₃ | C—H | C—CF₃ | C—H | C—H | 0 | 185-187 |
| 1-11-004c | CF₃ | C—H | C—CF₃ | C—H | C—H | 1 | 195-198 |
| 1-11-005a | CF₃ | C—H | C—Br | C—H | C—F | 2 | 254-256 |
| 1-11-005b | CF₃ | C—H | C—Br | C—H | C—F | 0 | 199-201 |
| 1-11-006a | CF₃ | C—H | C—I | C—H | C—F | 2 | 283-286 |
| 1-11-006b | CF₃ | C—H | C—I | C—H | C—F | 0 | 258-260 |
| 1-11-007a | CF₃ | C—H | C—Br | C—H | C—H | 2 | 250-255 |
| 1-11-007b | CF₃ | C—H | C—Br | C—H | C—H | 0 | 249-251 |
| 1-11-007c | CF₃ | C—H | C—Br | C—H | C—H | 1 | 198-202 |

TABLE 17

(1-A-L)

| No. | R⁷ | A⁸ | G₁ | G₂ | G₃ | G₄ | n | m.p. |
|---|---|---|---|---|---|---|---|---|
| 1-12-001a | CF₃ | C—H | C—H | C—CF₃ | C—H | C—H | 2 | 219-220 |
| 1-12-002a | CF₂CF₃ | C—H | C—H | C—CF₃ | C—H | C—H | 2 | 188-194 |
| 1-12-003a | CF₂CF₃ | C—Me | C—H | C—CF₃ | C—H | C—H | 2 | 182-186 |
| 1-12-004a | CF₃ | C—H | C—H | C—H | C—CF₃ | C—H | 2 | 198-200 |
| 1-12-005a | CF₂CF₃ | C—Me | C—H | C—H | C—CF₃ | C—H | 2 | 233-236 |
| 1-12-006a | CF₃ | N | C—H | C—CF₃ | C—H | C—H | 2 | 204-207 |
| 1-12-007a | CF₂CF₃ | N | C—H | C—CF₃ | C—H | C—H | 2 | 194-196 |
| 1-12-008a | CF₃ | N | C—H | C—H | C—CF₃ | C—H | 2 | 153-155 |
| 1-12-009a | CF₃ | N | C—H | C—I | C—H | C—H | 2 | *1 |

TABLE 18

(1-A-M)

| No. | R³ | A⁵ | G₁ | G₂ | G₃ | G₄ | n | m.p. |
|---|---|---|---|---|---|---|---|---|
| 1-13-001a | CF₃ | N | C—H | C—H | C—CF₃ | C—H | 2 | 243-245 |
| 1-13-001b | CF₃ | N | C—H | C—H | C—CF₃ | C—H | 0 | 150-160 |

TABLE 19

(1-A-N)

| No. | R³ | R⁴ | A¹ᵃ | G₁ | G₂ | G₃ | G₄ | n | m.p. |
|---|---|---|---|---|---|---|---|---|---|
| 1-14-001a | CF₃ | H | Me | C—H | C—H | C—CF₃ | C—H | 2 | *5 |

TABLE 20

(1-A-O)

| No. | R² | R³ | R⁴ | R⁵ | A¹ᵃ | Y2 | Y3 | n | m.p. |
|---|---|---|---|---|---|---|---|---|---|
| 1-15-001b | H | CF₃ | H | Br | H | H | CF₃ | 0 | 139-145 |
| 1-15-002a | Br | H | CF₃ | H | Me | H | CF₃ | 2 | 236-239 |
| 1-15-002b | Br | H | CF₃ | H | Me | H | CF₃ | 0 | 205-208 |
| 1-15-003a | H | CF₃ | H | Br | Me | H | CF₃ | 2 | 206-209 |

TABLE 21

(1-A-P)

| No. | R³ | A¹ᵃ | G₁ | G₂ | G₃ | G₄ | n | m.p. |
|---|---|---|---|---|---|---|---|---|
| 1-16-001a | CF₃ | Me | C—H | C—CF₃ | C—H | C—H | 2 | 274-276 |
| 1-16-001b | CF₃ | Me | C—H | C—CF₃ | C—H | C—H | 0 | 240-242 |

TABLE 22

(1-A-Q)

| No. | R³ | R⁴ | R⁶ | G₁ | G₂ | G₃ | G₄ | n | m.p. |
|---|---|---|---|---|---|---|---|---|---|
| 1-17-001a | H | CF₃ | Br | C—H | C—I | C—H | C—H | 2 | 255-260 |

TABLE 23

(1-B-A)

| No. | R³ | A¹ᵃ | G₅ | Y6 | n | m.p. |
|---|---|---|---|---|---|---|
| 2-1-001a | CF₃ | Me | C—H | CF₃ | 2 | 249-251 |
| 2-1-001b | CF₃ | Me | C—H | CF₃ | 0 | 200-203 |
| 2-1-002a | CF₃ | Me | N | CF₃ | 2 | 231-234 |
| 2-1-002b | CF₃ | Me | N | CF₃ | 0 | *1 |

TABLE 24

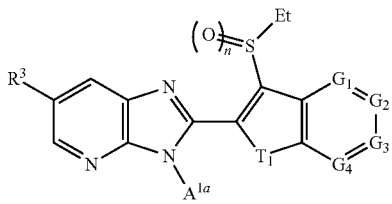

(1-C-A)

| No. | R³ | A¹ᵃ | T₁ | G₁ | G₂ | G₃ | G₄ | n | m.p. |
|---|---|---|---|---|---|---|---|---|---|
| 3-1-001a | CF₃ | Me | N—Me | C—H | C—CF₃ | C—H | C—H | 2 | 143-146 |
| 3-1-001b | CF₃ | Me | N—Me | C—H | C—CF₃ | C—H | C—H | 0 | 153-155 |
| 3-1-001c | CF₃ | Me | N—Me | C—H | C—CF₃ | C—H | C—H | 1 | 123-126 |
| 3-1-002a | CF₃ | Me | S | C—H | C—CF₃ | C—H | C—H | 2 | 70-75 |
| 3-1-002b | CF₃ | Me | S | C—H | C—CF₃ | C—H | C—H | 0 | 120-122 |
| 3-1-002c | CF₃ | Me | S | C—H | C—CF₃ | C—H | C—H | 1 | 195-197 |

TABLE 25

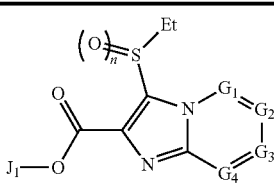

| No. | J₁ | G₁ | G₂ | G₃ | G₄ | n | m.p. |
|---|---|---|---|---|---|---|---|
| i-1-001 | Et | C—H | C—CF₃ | C—H | C—H | 0 | 76-78 |
| i-1-002 | H | C—H | C—CF₃ | C—H | C—H | 0 | 200-201 |
| i-1-003 | Et | C—H | C—H | C—CF₃ | C—H | 0 | 50-52 |
| i-1-004 | H | C—H | C—H | C—CF₃ | C—H | 0 | 163-171 |
| i-1-005 | Et | C—H | C—Cl | C—H | C—H | 0 | 63-64 |
| i-1-006 | H | C—H | C—Cl | C—H | C—H | 0 | 178-170 |
| i-1-007 | Et | C—H | C—F | C—H | C—H | 0 | 30-31 |
| i-1-008 | H | C—H | C—F | C—H | C—H | 0 | 165-168 |
| i-1-009 | Et | C—H | C—I | C—H | C—H | 0 | 110-112 |
| i-1-010 | H | C—H | C—I | C—H | C—H | 0 | 214-215 |
| i-1-011 | H | C—H | C—Br | C—H | C—H | 0 | 170-173 |
| i-1-012 | Et | C—H | C—OMe | C—H | C—H | 0 | *2 |
| i-1-013 | H | C—H | C—OMe | C—H | C—H | 0 | 180-182 |
| i-1-014 | Et | C—H | C—NO₂ | C—H | C—H | 0 | 95-97 |
| i-1-015 | H | C—H | C—NO₂ | C—H | C—H | 0 | 188-190 |
| i-1-016 | Et | C—H | C—H | C—Cl | C—H | 0 | 70-71 |
| i-1-017 | H | C—H | C—H | C—Cl | C—H | 0 | 210-212 |
| i-1-018 | Et | C—H | C—H | C—F | C—H | 0 | 74-76 |
| i-1-019 | H | C—H | C—H | C—F | C—H | 0 | 243-244 |
| i-1-020 | Et | C—H | C—H | C—I | C—H | 0 | *2 |
| i-1-021 | H | C—H | C—H | C—I | C—H | 0 | 175-178 |
| i-1-022 | H | C—H | C—H | C—Br | C—H | 0 | 150-152 |
| i-1-023 | Et | C—H | C—CF₃ | C—H | C—Cl | 0 | 138-140 |
| i-1-024 | H | C—H | C—I | C—H | C—Cl | 0 | 212-220 |

TABLE 25-continued

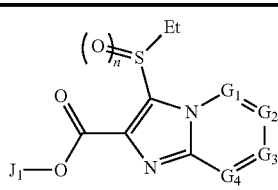

| No. | J₁ | G₁ | G₂ | G₃ | G₄ | n | m.p. |
|---|---|---|---|---|---|---|---|
| i-1-025 | Et | C—H | C—I | C—H | C—Cl | 0 | *2 |
| i-1-026 | Et | C—H | C—I | C—H | C—F | 0 | 173-175 |
| i-1-027 | H | C—H | C—I | C—H | C—F | 0 | 189-190 |
| i-1-028 | H | C—H | C—CF₃ | N | C—H | 0 | 175-178 |

TABLE 26

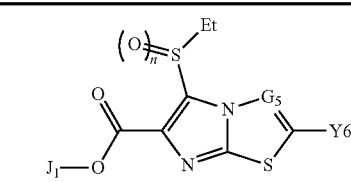

| No. | J₁ | G₆ | Y6 | n | m.p. |
|---|---|---|---|---|---|
| i-2-001 | Et | C—H | CF₃ | 0 | 41-43 |
| i-2-002 | H | C—H | CF₃ | 0 | 176-178 |

TABLE 27

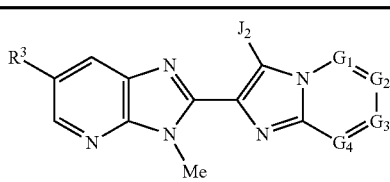

| No. | R³ | J₂ | G₁ | G₂ | G₃ | G₄ | m.p. |
|---|---|---|---|---|---|---|---|
| i-3-001 | CF₃ | H | C—H | C—Br | C—CF₃ | C—H | 220-225 |
| i-3-002 | CF₃ | H | C—Me | C—H | C—Me | C—H | 219-221 |
| i-3-003 | CF₃ | H | C—CF₃ | C—H | C—H | C—H | 180-183 |
| i-3-004 | CF₃ | H | C—H | C—CF₂CF₃ | C—H | C—H | 208-210 |
| i-3-005 | CF₃ | H | C—H | C—Cl | C—Cl | C—H | 245-248 |

TABLE 27-continued

| No. | R³ | J₂ | G₁ | G₂ | G₃ | G₄ | m.p. |
|---|---|---|---|---|---|---|---|
| i-3-006 | CF₃ | I | C—H | C—Cl | C—Cl | C—H | *5 |
| i-3-007 | CF₃ | H | C—H | C—I | C—Me | C—H | >250 |
| i-3-008 | CF₃ | Cl | C—H | C—I | C—Me | C—H | >250 |
| i-3-009 | CF₃ | H | C—H | C—I | C—CF₃ | C—H | 180-184 |
| i-3-010 | CF₃ | H | C—H | C—I | C—CN | C—H | 284-285 |
| i-3-011 | CF₃ | H | C—H | C—I | C—F | C—H | >250 |
| i-3-012 | CF₃ | H | C—H | C—I | C—OMe | C—H | >300 |
| i-3-013 | CF₃ | H | C—H | C—Cl | C—H | C—Me | 237-239 |
| i-3-014 | CF₃ | H | C—H | C—Cl | C—H | C—Cl | 265-266 |
| i-3-015 | CF₃ | H | C—H | C—F | C—H | C—F | >250 |
| i-3-016 | CF₃ | Cl | C—H | C—F | C—H | C—F | 239-242 |
| i-3-017 | CF₃ | H | C—H | C—I | C—H | C—I | >300 |
| i-3-018 | CF₃ | H | C—H | C—Br | C—H | C—F | >300 |
| i-3-019 | CF₃ | Cl | C—H | C—Br | C—H | C—F | 244-246 |
| i-3-020 | CF₃ | H | C—H | C—I | C—H | C—CN | 284-285 |
| i-3-021 | CF₃ | H | C—H | C—Cl | C—H | C—CF₃ | 252-257 |
| i-3-022 | CF₃ | H | C—H | C—CF₃ | C—H | C—F | 288-289 |
| i-3-023 | CF₃ | Cl | C—H | C—CF₃ | C—H | C—F | 255-256 |
| i-3-024 | CF₃ | H | C—H | C—CF₃ | C—H | C—I | >250 |
| i-3-025 | CF₃ | H | C—H | C—I | C—H | C—Me | 257-260 |
| i-3-026 | CF₃ | H | C—H | C—Me | C—H | C—Cl | >250 |
| i-3-027 | CF₃ | Cl | C—H | C—Me | C—H | C—Cl | *5 |
| i-3-028 | CF₃ | H | C—H | C—I | C—H | C—F | >250 |
| i-3-029 | CF₃ | H | C—H | C—H | C—H | C—CF₃ | 198-201 |
| i-3-030 | CF₃ | H | C—H | C—Cl | C—Cl | C—Cl | *5 |
| i-3-031 | CF₃ | Cl | C—H | C—Cl | C—Cl | C—Cl | >250 |
| i-3-032 | CF₃ | H | C—H | C—H | C—NO₂ | C—H | 150-151 |
| i-3-033 | CF₃ | H | C—H | C—I | C—H | N | 280-285 |
| i-3-034 | CF₃ | Cl | C—H | C—I | C—H | N | 250-255 |
| i-3-035 | CF₃ | H | C—H | C—CF₃ | C—H | N | 283-285 |
| i-3-036 | CF₃ | H | C—H | C—CF₃ | C—H | N | 260-265 |
| i-3-037 | CF₃ | H | C—H | N | C—CF₃ | C—H | 257-260 |
| i-3-038 | CF₃ | Br | C—H | N | C—CF₃ | C—H | 254-259 |
| i-3-039 | CF₃ | H | C—H | C—I | N | C—H | 256-259 |

TABLE 28

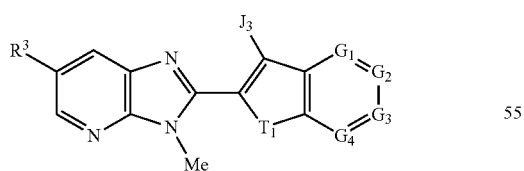

| No. | R³ | J₃ | T₁ | G₁ | G₂ | G₃ | G₄ | m.p. |
|---|---|---|---|---|---|---|---|---|
| i-4-001 | CF₃ | H | N—Me | C—H | C—CF₃ | C—H | C—H | 200-202 |
| i-4-002 | CF₃ | I | N—Me | C—H | C—CF₃ | C—H | C—H | 165-167 |
| i-4-003 | CF₃ | H | S | C—H | C—CF₃ | C—H | C—H | 191-193 |
| i-4-004 | CF₃ | Cl | S | C—H | C—CF₃ | C—H | C—H | 158-160 |

TABLE 29

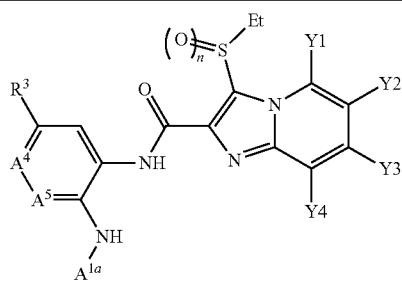

| No. | $R^3$ | $A_{1a}$ | $A^4$ | $A^5$ | Y1 | Y2 | Y3 | Y4 | n | m.p. |
|---|---|---|---|---|---|---|---|---|---|---|
| i-5-001 | $CF_3$ | Me | C—H | N | H | I | H | Cl | 0 | 208-217 |
| i-5-002 | $CF_3$ | Me | C—H | N | H | I | H | OEt | 2 | 230-239 |
| i-5-003 | $CF_3$ | Me | C—H | N | H | H | $CF_3$ | H | 0 | 135-140 |
| i-5-004 | I | Me | C—H | N | H | H | $CF_3$ | H | 0 | 194-195 |
| i-5-005 | $CF_3$ | Me | C—H | N | $CF_3$ | H | H | H | 0 | *2 |
| i-5-006 | $CF_3$ | Me | C—H | N | H | I | H | H | 0 | 90-92 |
| i-5-007 | $CF_3$ | Me | C—H | N | H | I | Cl | H | 0 | 203-205 |
| i-5-008 | H | Me | C—H | N | H | H | $CF_3$ | H | 0 | 125-127 |
| i-5-009 | $CF_3$ | H | C—H | C—Br | H | H | $CF_3$ | H | 0 | 70-72 |
| i-5-010 | Cl | Me | C—H | N | H | $CF_3$ | H | H | 0 | 75-80 |

TABLE 30

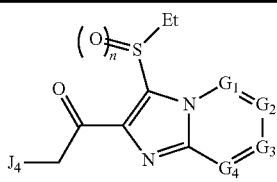

| No. | $J_4$ | $G_1$ | $G_2$ | $G_3$ | $G_4$ | n | m.p. |
|---|---|---|---|---|---|---|---|
| i-6-001 | H | C—H | C—H | C—$CF_3$ | C—H | 0 | 60-64 |
| i-6-002 | H | C—H | C—H | C—$CF_3$ | C—H | 2 | 135-138 |
| i-6-003 | Br | C—H | C—H | C—$CF_3$ | C—H | 2 | 122-123 |
| i-6-004 | H | C—H | C—$CF_3$ | C—H | C—H | 0 | 73-75 |
| i-6-005 | H | C—H | C—$CF_3$ | C—H | C—H | 2 | 125-127 |
| i-6-006 | Br | C—H | C—$CF_3$ | C—H | C—H | 2 | 83-85 |
| i-6-007 | H | C—H | C—I | C—H | C—H | 0 | 147-149 |
| i-6-008 | H | C—H | C—I | C—H | C—H | 2 | 110-133 |
| i-6-009 | Br | C—H | C—I | C—H | C—H | 2 | 162-164 |

TABLE 31

| No. | $G_1$ | $G_2$ | $G_3$ | $G_4$ | n | m.p. |
|---|---|---|---|---|---|---|
| i-7-001 | C—H | C—H | C—$CF_3$ | C—H | 0 | *2 |
| i-7-002 | C—H | C—I | C—H | C—H | 0 | 123-129 |
| i-7-003 | C—H | C—H | C—I | C—H | 0 | *2 |
| i-7-004 | C—H | C—$CF_3$ | C—H | C—H | 0 | *2 |
| i-7-005 | C—H | C—Br | C—H | C—F | 0 | *2 |
| i-7-006 | C—I | C—H | C—H | C—F | 0 | 150-153 |
| i-7-007 | C—H | C—H | C—H | C—H | 0 | 88-92 |

TABLE 32

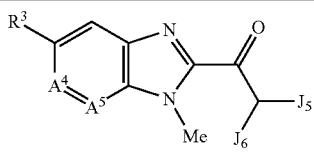

| No. | $R^3$ | $A^4$ | $A^5$ | $J_5$ | $J_6$ | m.p. |
|---|---|---|---|---|---|---|
| i-8-001 | $CF_3$ | C—H | N | H | H | 106-108 |
| i-8-002 | $CF_3$ | C—H | N | Br | H | 90-91 |
| i-8-003 | $CF_3$ | C—H | N | SEt | H | 67-69 |
| i-8-004 | $CF_3$ | C—H | N | SEt | Br | *2 |
| i-8-005 | $CF_3$ | N | C—H | H | H | 136-140 |
| i-8-006 | $CF_3$ | N | C—H | Br | H | 127-131 |
| i-8-007 | $CF_3$ | N | C—H | SEt | H | 90-93 |
| i-8-008 | $CF_3$ | N | C—H | SEt | Br | *2 |

$^1$H-NMR data of the compounds of the present invention and intermediates thereof are shown in Table 33. The proton nuclear magnetic resonance chemical shift values were measured by using $Me_4Si$ (tetramethylsilane) as a standard substance in deuterated chloroform solvent at 300 MHz (ECX300 or ECP300, manufactured by JEOL Ltd.).

Reference symbols in the proton nuclear magnetic resonance chemical shift values have the following meanings.

s: Singlet, brs: broad singlet, d: doublet, dd: double doublet, t: triplet, q: quartet, m: multiplet.

TABLE 33

| No. | $^1$H NMR ($CDCl_3$, $Me_4Si$, 300 MHz). |
|---|---|
| 1-1-001a | δ 9.68-9.63 (m, 1H), 8.76 (s, 1H), 8.35 (s, 1H), 7.95 (d, J = 9.5 Hz, 1H), 7.71 (d, J = 9.5 Hz, 1H), 4.17 (s, 3H), 4.12 (q, J = 7.2 Hz, 2H), 1.26 (t, J = 7.2 Hz, 3H). |

TABLE 33-continued

| No. | $^1$H NMR (CDCl$_3$, Me$_4$Si, 300 MHz). |
|---|---|
| 1-1-001b | δ 9.05-8.95 (m, 1H), 8.72 (s, 1H), 8.40 (s, 1H), 7.82 (d, J = 9.7 Hz, 1H), 7.52 (dd, J = 9.7, 1.9 Hz, 1H), 4.31 (s, 3H), 3.14 (q, J = 7.4 Hz, 2H), 1.22 (t, J = 7.4 Hz, 3H). |
| 1-1-001c | δ 9.95-9.90 (m, 1H), 8.72 (d, J = 1.4 Hz, 1H), 8.31 (d, J = 1.4 Hz), 7.86 (d, J = 9.5 Hz, 1H), 7.57 (dd, J = 9.5, 2.0 Hz, 1H), 4.44 (s, 3H), 3.80-3.50 (m, 2H), 1.57 (t, J = 7.5 Hz, 3H). |
| 1-1-003a | δ 9.82 (s, 1H), 8.75 (d, J = 1.2 Hz, 1H), 8.35 (d, J = 1.2 Hz, 1H), 7.79 (d, J = 9.6 Hz, 1H), 7.54 (dd, J = 9.6, 1.8 Hz, 1H), 4.15 (s, 3H), 4.04 (q, J = 7.5 Hz, 2H), 1.46 (t, J = 7.5 Hz, 3H). |
| 1-1-003b | δ 8.71 (s, 1H), 8.68 (d, J = 1.2 Hz, 1H), 8.39 (s, 1H), 7.66 (d, J = 9.6 Hz, 1H), 7.35 (d, J = 9.6 Hz, 1.8 Hz, 1H), 4.29 (s, 3H), 3.09 (q, J = 7.5 Hz, 2H), 1.21 (t, J = 7.5 Hz, 3H). |
| 1-1-003c | δ 9.53 (d, J = 1.2 Hz, 1H), 8.71 (d, J = 1.2 Hz, 1H), 8.30 (d, J = 1.2 Hz, 1H), 7.70 (d, J = 9.6 Hz, 1H), 7.40 (dd, J = 9.6, 1.8 Hz, 1H), 4.41 (s, 3H), 3.80-3.50 (m, 2H), 1.56 (t, J = 7.5 Hz, 3H). |
| 1-1-004a | δ 9.26-9.22 (m, 1H), 8.74 (d, J = 1.4 Hz, 1H), 8.33 (d, J = 1.4 Hz, 1H), 7.85-7.78 (m, 1H), 7.57-7.44 (m, 1H), 4.15 (s, 3H), 4.04 (q, J = 7.5 Hz, 2H), 1.45 (t, J = 7.5 Hz, 3H). |
| 1-1-004b | δ 8.70 (d, J = 1.2 Hz, 1H), 8.60-8.55 (m, 1H), 8.37 (d, J = 1.2 Hz, 1H), 7.73-7.65 (m, 1H), 7.35-7.25 (m, 1H), 4.29 (s, 3H), 3.09 (q, J = 7.4 Hz, 2H), 1.20 (t, J = 7.4 Hz, 3H). |
| 1-1-004c | δ 9.47-9.43 (m, 1H), 8.71 (dd, J = 1.8, 0.6 Hz, 1H), 8.30 (d, J = 1.7 Hz, 1H), 7.77-7.70 (m, 1H), 7.40-7.32 (m, 1H), 4.42 (s, 3H), 3.80-3.45 (m, 2H), 1.55 (t, J = 7.5 Hz, 3H). |
| 1-1-005a | δ 9.49 (s, 1H), 8.75 (s, 1H), 8.35 (s, 1H), 7.75 (dd, J = 9.3, 1.2 Hz, 1H), 7.61 (d, J = 9.3 Hz, 1H), 4.13 (s, 3H), 4.01 (q, J = 7.2 Hz, 2H), 1.46 (t, J = 7.2 Hz, 3H), |
| 1-1-005b | δ 8.91-8.88 (m, 1H), 8.73-8.70 (m, 1H), 8.41-8.39 (m, 1H), 7.56 (dd, J = 9.3, 1.8 Hz, 1H), 7.50 (d, J = 9.3 Hz, 1H), 4.29 (s, 3H), 3.08 (q, J = 7.2 Hz, 2H), 1.21 (t, J = 7.2 Hz, 3H). |
| 1-1-005c | δ 9.72 (s, 1H), 8.71 (d, J = 1.2 Hz, 1H), 8.30 (d, J = 1.2 Hz, 1H), 7.61 (d, J = 9.6 Hz, 1H), 7.54 (d, J = 9.6 Hz, 1H), 4.41 (s, 3H), 3.75-3.49 (m, 2H), 1.56 (t, J = 7.5 Hz, 3H). |
| 1-1-006a | δ 9.41 (s, 1H), 8.75 (s, 1H), 8.34 (s, 1H), 7.72 (d, J = 9.6 Hz, 1H), 7.64 (dd, J = 9.6, 1.8 Hz, 1H), 4.14 (s, 3H), 4.04 (q, J = 7.5 Hz, 2H), 1.46 (t, J = 7.5 Hz, 3H). |
| 1-1-006b | δ 8.78 (s, 1H), 8.71 (s, 1H), 8.42-8.36 (m, 1H), 7.70-7.55 (m, 1H). 7.50-7.40 (m, 1H), 4.29 (s, 3H), 3.09 (q, J = 7.5 Hz, 2H), 1.21 (t, J = 7.5 Hz, 3H). |
| 1-1-007a | δ 8.80 (d, J = 2.1 Hz, 1H), 8.73 (s, 1H), 8.33 (d, J = 0.9 Hz, 1H), 7.70 (d, J = 9.9 Hz, 1H), 7.33 (dd, J = 9.9, 2.1 Hz, 1H), 4.12 (s, 3H), 3.99 (q, J = 7.2 Hz, 2H). 3.93 (s, 3H). 1.44 (t, J = 7.2 Hz, 3H). |
| 1-1-007b | δ 8.72-8.68 (m, 1H), 8.37 (d, J = 2.1 Hz, 1H), 8.16 (d, J = 2.1 Hz, 1H), 7.60 (d, J = 9.6 Hz, 1H), 7.16 (dd, J = 9.6, 2.1 Hz, 1H), 4.29 (s, 3H), 3.94 (s, 3H), 3.06 (q, J = 7.2 Hz, 2H), 1.20 (t, J = 7.2 Hz, 3H). |
| 1-1-008a | δ 10.34 (dd, J = 2.1, 0.6 Hz, 1H), 8.77 (d, J = 1.2 Hz, 1H), 8.36 (d, J = 1.2 Hz, 1H), 8.33 (dd, J = 9.9, 2.1 Hz, 1H), 7.93 (dd, J = 9.9, 0.6 Hz, 1H), 4.20 (s, 3H), 4.16 (q, J = 7.2 Hz, 2H), 1.50 (t, J = 7.2 Hz, 3H). |
| 1-1-008b | δ 9.73 (d, J = 2.4 Hz, 1H), 8.73 (d, J = 2.4 Hz, 1H), 8.40 (d, J = 2.4 Hz, 1H), 8.14 (dd, J = 9.9, 2.4 Hz, 1H), 7.79 (d, J = 9.9 Hz, 1H), 4.33 (s, 3H), 3.20 (q, J = 7.2 Hz, 2H), 1.25 (t, J = 7.2 Hz, 3H). |
| 1-1-009a | δ 9.00 (s, 1H), 8.74 (d, J = 1.2 Hz, 1H), 8.33 (d, J = 1.2 Hz, 1H), 7.73 (d, J = 9.3 Hz, 1H), 7.42 (dd, J = 9.3, 1.2 Hz, 1H), 4.11 (s, 3H), 3.94 (q, J = 7.5 Hz, 2H), 2.47 (s, 3H). 1.44 (t, J = 7.5 Hz, 3H). |
| 1-1-010a | δ 9.26 (d, J = 1.2 Hz, 1H), 8.74 (d, J = 1.5 Hz, 1H), 8.33 (d, J = 1.5 Hz, 1H), 7.75 (d, J = 9.0 Hz, 1H), 7.60 (dd, J = 9.0, 1.8 Hz, 1H), 4.14 (s, 3H), 4.07-3.96 (m, 4H), 3.23 (t, J = 7.2 Hz, 2H), 2.69 (t, J = 7.2 Hz, 2H), 1.65-1.22 (m, 12H), 0.90 (t, J = 7.5 Hz, 6H). |
| 1-1-011a | δ 9.61 (s, 1H), 8.75 (d, J = 1.2 Hz, 1H), 8.35 (d, J = 1.2 Hz, 1H), 7.87 (dd, J = 9.6, 0.9 Hz, 1H), 7.74 (dd, J = 9.6, 1.2 Hz, 1H), 4.17 (s, 3H), 4.08 (q, J = 7.5 Hz, 2H), 1.46 (t, J = 7.5 Hz, 3H). |
| 1-1-012a | δ 9.24 (d, J = 7.2 Hz, 1H), 8.75 (d, J = 1.4 Hz, 1H), 8.35 (d, J = 1.4 Hz, 1H), 7.84 (d, J = 9.2 Hz, 1H), 7.62-7.54 (m, 1H), 7.21-7.13 (m, 1H), 4.15 (s, 3H), 3.99 (q, J = 7.4 Hz, 2H), 1.45 (t, J = 7.4 Hz, 3H). |
| 1-1-012b | δ 8.71 (s, 1H), 8.66 (d, J = 6.8 Hz, 1H), 8.39 (s, 1H), 7.72 (d, J = 8.9 Hz, 1H), 7.43-7.35 (m, 1H), 7.08-7.01 (m, 1H), 4.31 (s, 3H), 3.06 (q, J = 7.4 Hz, 2H), 1.20 (t, J = 7.4 Hz, 3H). |
| 1-1-013a | δ 9.18 (d, J = 7.4 Hz, 1H), 8.74 (s, 1H), 8.33 (d, J = 1.2 Hz, 1H), 7.85-7.80 (m, 1H), 7.15-7.10 (m, 1H), 4.14 (s, 3H), 4.03 (q, J = 7.4 Hz, 2H), 1.43 (t, J = 7.4 Hz, 3H). |
| 1-1-013b | δ 8.70 (d, J = 1.6 Hz, 1H), 8.57 (d, J = 7.4 Hz, 1H), 8.37 (s, 1H), 7.71 (d, J = 1.6 Hz, 1H), 7.02 (dd, J = 7.4, 1.6 Hz, 1H), 4.28 (s, 3H), 3.07 (q, J = 7.5 Hz, 2H), 1.19 (t, J = 7.5 Hz, 3H). |
| 1-1-013c | δ 9.40 (dd, J = 7.4, 0.8 Hz, 1H), 8.75-8.65 (m, 1H), 8.35-8.25 (m, 1H), 7.76 (dd, J = 2.2, 0.8 Hz, 1H), 6.97 (dd, J = 7.4, 2.2 Hz, 1H), 4.41 (s, 3H), 3.75-3.45 (m, 2H), 1.53 (t, J = 7.4 Hz, 3H). |
| 1-1-014a | δ 9.27-9.22 (m, 1H), 8.75-8.73 (m, 1H), 8.35-8.32 (m, 1H), 7.48-7.42 (m, 1H), 7.07-6.99 (m, 1H), 4.14 (s, 3H), 4.02 (q, J = 7.4 Hz, 2H), 1.44 (t, J = 7.4 Hz, 3H). |
| 1-1-014b | δ 8.70 (dd, J = 2.0, 1.2 Hz, 1H), 8.66-8.58 (m, 1H), 8.37 (d, J = 1.2 Hz, 1H), 7.34 (dd, J = 8.9, 2.4 Hz, 1H), 6.95-6.87 (m, 1H), 4.28 (s, 3H), 3.06 (q, J = 7.4 Hz, 2H), 1.19 (t, J = 7.4 Hz, 3H). |

TABLE 33-continued

| No. | $^1$H NMR (CDCl$_3$, Me$_4$Si, 300 MHz). |
|---|---|
| 1-1-014c | δ 9.50-9.43 (m, 1H), 8.73-8.69 (m, 1H), 8.30 (d, J-1.4 Hz, 1H), 7.38 (dd, J-9.2, 2.4 Hz, 1H), 6.93-6.83 (m, 1H), 4.41 (s, 3H), 3.75-3.45 (m, 2H), 1.54 (t, J = 7.3 Hz, 3H). |
| 1-1-015a | δ 8.99 (dd, J = 7.5, 0.6 Hz, 1H), 8.75 (d, J = 1.2 Hz, 1H), 8.33 (d, J = 1.2 Hz, 1H), 8.30-8.26 (m, 1H), 7.38 (dd, J = 7.2, 1.2 Hz, 1H), 4.13 (s, 3H), 4.02 (q, J = 7.6 Hz, 2H), 1.43 (t, J = 7.5 Hz, 3H). |
| 1-1-015b | δ 8.87 (d, J = 1.2 Hz, 1H), 8.82 (s, 1H), 8.48 (s, 1H), 8.41 (d, J = 7.2 Hz, 1H), 7.51 (d, J = 7.2 Hz, 1H), 4.38 (s, 3H), 3.14 (q, J = 7.5 Hz, 2H), 1.25 (t, J = 7.5 Hz, 3H). |
| 1-1-016a | δ 9.11 (dd, J = 7.5, 0.9 Hz, 1H), 8.75-8.72 (m, 1H), 8.33 (d, J = 1.2 Hz, 1H), 8.02-8.00 (m, 1H), 7.24-7.22 (m, 1H), 4.14 (s, 3H), 4.03 (q, J = 7.5 Hz, 2H), 1.43 (t, J = 7.5 Hz, 3H). |
| 1-1-016b | δ 8.71 (s, 1H), 8.52 (d, J = 7.5 Hz, 1H), 8.39 (s, 1H), 7.93-7.89 (m, 1H), 7.13 (dd, J = 7.5, 1.8 Hz, 1H), 4.29 (s, 3H), 3.07 (q, J = 7.5 Hz, 2H), 1.19 (t, J = 7.5 Hz, 3H). |
| 1-1-016c | δ 9.35 (d, J = 7.5 Hz, 1H), 8.72 (s, 1H), 8.31 (d, J = 2.1 Hz, 1H), 7.96 (dd, J = 2.1, 0.6 Hz, 1H), 7.09 (dd, J = 7.5, 2.1 Hz, 1H), 4.41 (s, 3H), 3.75-3.45 (m, 2H), 1.53 (t, J = 7.5 Hz, 3H). |
| 1-1-017a | δ 9.08 (d, J = 7.2 Hz, 1H), 8.74 (d, J = 1.5 Hz, 1H), 8.33 (d, J = 1.5 Hz, 1H), 7.59 (s, 1H), 6.99 (dd, J = 7.2, 1.8 Hz, 1H), 4.12 (s, 3H), 3.95 (q, J = 7.5 Hz, 2H), 2.53 (s, 3H), 1.42 (t, J = 7.5 Hz, 3H). |
| 1-1-018a | δ 9.41 (dd, J = 7.5, 0.9 Hz, 1H), 8.77 (d, J = 0.9 Hz, 1H), 8.36 (d, J = 0.9 Hz, 1H), 8.25-8.22 (m, 1H), 7.29 (dd, J = 7.5, 1.5 Hz, 1H), 4.19 (s, 3H), 4.14 (q, J = 7.5 Hz, 2H), 1.46 (t, J = 7.5 Hz, 3H). |
| 1-1-020a | δ 9.61-9.59 (m, 1H), 8.78-8.75 (m, 1H), 8.35 (d, J = 1.5 Hz, 7.78 (d, J = 1.5 Hz, 1H), 4.22 (s, 3H), 4.14 (q, J = 7.4 Hz, 2H), 1.47 (t, J = 7.4 Hz, 3H). |
| 1-1-020b | δ 8.95 (d, J = 1.4 Hz, 1H), 8.73 (d, J = 2.0 Hz, 1H), 8.39 (d, J = 2.0 Hz, 1H), 7.60 (d, J = 1.4 Hz, 1H), 4.36 (s, 3H), 3.18 (q, J = 7.4 Hz, 2H), 1.23 (t, J = 7.4 Hz, 3H). |
| 1-1-021b | δ 8.82-8.76 (m, 1H), 8.71 (d, J = 2.0 Hz, 1H), 8.38 (d, J = 2.0 Hz, 1H), 7.19 (d, J = 1.4 Hz, 1H), 4.35 (s, 2H), 3.24 (q, J = 7.4 Hz, 2H), 3.15 (q, J = 7.4 Hz, 2H), 1.49 (t, J = 7.4 Hz, 3H), 1.22 (t, J = 7.4 Hz, 3H). |
| 1-1-022a | δ 9.92-9.87 (m, 1H), 8.79 (d, J = 2.0 Hz, 1H), 8.44 (d, J = 2.0 Hz, 1H), 8.37 (d, J = 1.2 Hz, 1H), 4.22 (s, 3H), 4.22 (q, J = 7.4 Hz, 2H), 3.79 (q, J = 7.4 Hz, 2H), 1.50 (t, J = 7.4 Hz, 3H), 1.40 (t, J = 7.5 Hz, 3H). |
| 1-1-023c | δ 9.85 (s, 1H), 8.74 (d, J = 1.4 Hz, 1H), 8.32 (d, J = 1.4 Hz, 1H), 8.17 (s, 1H), 4.44 (s, 3H), 3.82-3.51 (m, 2H), 1.58 (t, J = 7.3 Hz, 3H). |
| 1-1-024a | δ 9.16 (s, 1H), 8.76 (d, J = 1.2 Hz, 1H), 8.35 (d, J = 1.2 Hz, 1H), 8.14 (s, 1H), 4.15 (s, 3H), 4.07 (q, J = 7.5 Hz, 2H), 2.57 (s, 3H), 1.46 (t, J = 7.5 Hz, 3H). |
| 1-1-025b | δ 8.71 (d, J = 1.5 Hz, 1H), 8.37 (d, J = 1.5 Hz, 1H), 7.38 (s, 1H), 6.55 (s, 1H), 4.13 (s, 3H), 3.15 (s, 3H), 2.91 (q, J = 7.5 Hz, 2H), 2.41 (s, 3H), 1.11 (t, J = 7.5 Hz, 3H). |
| 1-1-025c | δ 8.74-8.72 (m, 1H), 8.34 (d, J = 1.2 Hz, 1H), 7.45 (s, 1H), 6.75 (s, 1H), 4.10 (s, 3H), 3.88-3.72 (m, 1H), 3.67-3.52 (m, 1H), 3.02 (s, 3H), 2.48 (s, 3H), 1.42 (t J = 7.5 Hz, 3H). |
| 1-1-026a | δ 9.41 (d, J = 7.5 Hz, 1H), 8.66 (d, J = 1.7 Hz, 1H), 8.43 (d, J = 1.7 Hz, 1H), 8.16-8.12 (m, 1H), 7.31 (dd, J = 7.5, 1.7 Hz, 1H), 4.12 (s, 3H), 4.10 (q, J = 7.4 Hz, 2H), 1.45 (t, J = 7.4 Hz, 3H). |
| 1-1-030a | δ 9.42 (d, J = 7.3 Hz, 1H), 8.22 (d, J = 7.8 Hz, 1H), 8.17 (s, 1H), 7.70 (d, J = 7.8 Hz, 1H), 7.32 (dd, J = 7.3, 1.9 Hz, 1H), 4.19 (s, 3H), 4.11 (q, J = 7.4 Hz, 2H), 1.46 (t, J = 7.4 Hz, 3H). |
| 1-1-030c | δ 9.63 (d, J = 7.5 Hz, 1H), 8.18 (d, J = 8.5 Hz, 1H), 8.10 (s, 1H), 7.63 (d, J = 8.5 Hz, 1H), 7.16 (dd, J = 7.5, 1.7 Hz, 1H), 4.45 (s, 3H), 3.81-3.45 (m, 2H), 1.56 (t, J = 7.5 Hz, 3H). |
| 1-1-032a | δ 9.40 (d, J-7.5 Hz, 1H), 8.77-8.74 (m, 1H), 8.35 (d, J-1.8 Hz, 1H), 8.18-8.14 (m, 1H), 7.32 (dd, J = 7.5, 1.8 Hz, 1H), 4.71 (q, J = 7.5 Hz, 2H), 4.09 (q, J = 7.5 Hz, 2H), 1.50 (t, J = 7.5 Hz, 3H), 1.46 (t, J = 7.5 Hz, 3H). |
| 1-1-032b | δ 8.77 (d, J = 7.5 Hz, 1H, 8.73-8.70 (m, 1H), 8.42-8.38 (d, J = 1.8 Hz, 1H), 8.07-8.03 (m, 1H), 7.20 (dd, J = 7.5, 1.5 Hz, 1H), 4.96 (q, J = 7.5 Hz, 2H), 3.13 (q, J = 7.5 Hz, 2H), 1.50 (t, J = 7.5 Hz, 3H), 1.20 (t, J = 7.5 Hz, 3H). |
| 1-1-033a | δ 9. 29 (dd, J = 7.2, 1.2 Hz, 1H), 8.77-8.72 (m, 1H), 8.53-8.48 (m, 1H), 8.36-8.32 (m, 1H), 7.71 (dd, J = 7.2, 1.8 Hz, 1H), 4.17 (s, 3H), 4.06 (q, J = 7.5 Hz, 2H), 4.03 (s, 3H), 1.45 (t, J = 7.5 Hz, 3H). |
| 1-1-034a | δ 9.30 (dd, J = 7.5, 1.2 Hz, 1H), 8.78-8.74 (m, 1H), 8.55-8.50 (m, 1H), 8.36 8.34 (m, 1H), 7.72 (dd, J = 7.5, 1.8 Hz, 1H), 4.49 (q, J = 7.5 Hz, 2H), 4.17 (s, 3H), 4.07 (q, J = 7.5 Hz, 2H), 1.47 (t, J = 7.5 Hz, 3H), 1.45 (t, J = 7.5 Hz, 3H). |
| 1-1-035a | δ 9.27 (dd, J = 7.5, 0.9 Hz, 1H), 8.77-8.74 (m, 1H), 8.36-8.32 (m, 1H), 7.86-7.83 (m, 1H), 7.22 (dd, J = 7.5, 1.8 Hz, 1H), 4.15 (s, 3H), 4.03 (q, J = 7.5 Hz, 2H), 3.18 (s, 3H), 3.13 (s, 3H), 1.44 (t, J = 7.5 Hz, 3H). |
| 1-1-036a | δ 9.26 (s, 1H), 8.77 (d, J = 1.4 Hz, 1H), 8.36 (d, J = 1.4 Hz, 1H), 8.17 (s, 1H), 4.18 (s, 3H), 4.14 (q, J = 7.5 Hz, 2H), 2.63 (s, 3H), 1.48 (t, J = 7.5 Hz, 3H). |
| 1-1-037a | δ 9.46 (s, 1H), 8.76 (d, J = 1.2 Hz, 1H), 8.36 (d, J = 1.2 Hz, 1H), 8.19 (s, 1H), 4.18 (s, 3H), 4.13 (q, J = 7.4 Hz, 2H), 4.03 (dd, J = 5.7, 2.0 Hz, 2H), 3.25 (t, J = 7.0 Hz, 2H), 2.73 (t, J = 7.0 Hz, 2H), 1.48 (t, J = 7.4 Hz, 3H), 1.42-1.23 (m, 9H), 0.89 (t, J = 7.4 Hz, 6H). |
| 1-1-038a | δ 10.24 (s, 1H), 8.80 (s, 1H), 8.39 (s, 1H), 8.36 (s, 1H), 4.23 (s, 3H), 4.20 (q, J = 7.5 Hz, 2H), 3.36 (s, 3H), 1.52 (t, J = 7.5 Hz, 3H). |
| 1-1-039a | δ 10.02 (s, 1H), 8.78 (d, J = 1.4 Hz, 1H), 8.38 (s, 1H), 8.23 (s, 1H), 4.30-3.97 (m, 2H), 4.20 (s, 3H), 2.98 (s, 3H), 1.51 (t, J = 7.5 Hz, 3H). |

TABLE 33-continued

| No. | $^1$H NMR (CDCl$_3$, Me$_4$Si, 300 MHz). |
|---|---|
| 1-1-040a | δ 8.77 (s, 1H), 8.34 (s, 1H), 8.07 (dd, J = 7.7, 2.6 Hz, 1H), 7.74-7.65 (m, 2H), 4.11 (s, 3H), 4.03 (q, J = 7.5 Hz, 2H), 1.51 (t, J = 7.5 Hz, 3H). |
| 1-1-040b | δ 8.76-8.73 (m, 1H), 8.42-8.37 (m, 1H), 7.96 (d, J = 9.2 Hz, 1H), 7.59 (d, J = 7.5 Hz, 1H), 7.47-7.38 (m, 1H), 4.15 (s, 3H), 2.95 (q, J = 7.4 Hz, 2H), 1.11 (t, J = 7.4 Hz, 3H). |
| 1-1-040c | δ 8.74 (d, J = 1.4 Hz, 1H), 8.36 (d, J = 1.4 Hz, 1H), 8.05 (d, J = 8.5 Hz, 1H), 7.64 (d, J = 7.5 Hz, 1H), 7.59-7.52 (m, 1H), 4.61-4.48 (m, 1H), 3.95 (s, 3H), 3.41-3.26 (m, 1H), 1.48 (t, J = 7.5 Hz, 3H). |
| 1-1-041a | δ 9.04 (d, J = 7.5 Hz, 1H), 8.74 (s, 1H), 8.33 (s, 1H), 7.52 (d, J = 1.5 Hz, 1H), 6.97 (dd, J = 7.5, 1.5 Hz, 1H), 4.13 (s, 3H), 4.06 (dd, J = 5.7, 2.0 Hz, 2H), 3.99 (q, J = 7.5 Hz, 2H), 3.36 (t, J = 7.2 Hz, 2H), 2.80 (t, J = 7.2 Hz, 2H), 1.49-1.22 (m, 12H), 0.89 (t, J = 7.5 Hz, 6H). |
| 1-1-042a | δ 9.02 (d, J = 7.5 Hz, 1H), 8.76-8.73 (m, 1H), 8.35-8.32 (m, 1H), 7.42-7.40 (m 1H), 6.97 (dd, J = 7.5, 2.1 Hz, 1H), 4.13 (s, 3H), 3.97 (q, J = 7.5 Hz, 2H), 2.61 (s, 3H), 1.42 (t, J = 7.5 Hz, 3H). |
| 1-1-043a | δ 9.41 (dd, J = 7.5, 0.6 Hz, 1H), 8.76 (d, J = 1.5 Hz, 1H), 8.35 (d, J = 1.8 Hz, 1H), 8.21 (d, J = 1.8 Hz, 1H), 7.29 (dd, J = 7.5, 1.8 Hz, 1H), 4.18 (s, 3H), 4.10 (q, J = 7.5 Hz, 2H), 2.88 (s, 3H), 1.46 (t, J = 7.5 Hz, 3H). |
| 1-1-044a | δ 9.49 (dd, J = 7.5, 1.2 Hz, 1H), 8.77 (d, J = 1.5 Hz, 1H), 8.50-8.46 (m, 1H), 8.37-8.34 (m, 1H), 7.57 (dd, J = 7.5, 1.2 Hz, 1H), 4.20 (s, 3H), 4.14 (q, J = 7.5 Hz, 2H), 3.20 (s, 3H), 1.47 (t, J = 7.5 Hz, 3H). |
| 1-1-045a | δ 9.63 (d, J = 0.6 Hz, 1H), 8.75-8.79 (m, 1H), 8.38-8.35 (m, 1H), 7.96 (dd, J = 9.3, 0.6 Hz, 1H), 7.69 (dd, J = 9.3, 1.2 Hz, 1H), 4.18 (s, 3H), 4.11 (q, J = 7.5 Hz, 2H), 1.46 (t, J = 7.5 Hz, 3H). |
| 1-1-045b | δ 8.99 (s, 1H), 8.73 (d, J = 0.6 Hz, 1H), 8.40 (d, J = 1.2 Hz, 1H), 7.83 (d, J = 9.3 Hz, 1H), 7.50 (d, J = 9.3 Hz, 1H), 4.32 (s, 3H), 3.14 (q, J = 7.5 Hz, 2H), 1.22 (t, J = 7.5 Hz, 3H). |
| 1-1-046a | δ 9.43 (s, 1H), 8.77-8.74 (m, 1H), 8.36-8.33 (m, 1H), 7.96 (s, 1H), 4.15 (s, 3H), 4.08 (q, J = 7.4 Hz, 2H), 1.46 (t, J = 7.4 Hz, 3H). |
| 1-1-047a | δ 9.64 (s, 1H), 8.76 (s, 1H), 8.35 (s, 1H), 7.98 (s, 1H), 4.15 (s, 3H), 4.07 (q, J = 7.4 Hz, 2H), 1.47 (t, J = 7.4 Hz, 3H). |
| 1-1-047b | δ 8.88 (d, J = 0.7 Hz, 1H), 8.57 (d, J = 1.0 Hz, 1H), 8.24 (d, J = 1.0 Hz, 1H), 7.75 (d, J = 0.7 Hz, 1H), 4.15 (s, 3H), 2.97 (q, J = 7.4 Hz, 2H), 1.08 (t, J = 7.4 Hz, 3H), |
| 1-1-048a | δ 9.55 (s, 1H), 8.75 (d, J = 1.0 Hz, 1H), 8.34 (d, J = 1.0 Hz, 1H), 7.71 (s, 1H), 4.13 (s, 3H), 4.00 (q, J = 7.5 Hz, 2H), 2.61 (s, 3H), 1.45 (t, J = 7.5 Hz, 3H). |
| 1-1-048b | δ 8.96 (s, 1H), 8.70 (s, 1H), 8.38 (s, 1H), 7.60 (s, 1H), 4.28 (s, 3H), 3.06 (q, J = 7.5 Hz, 2H), 2.57 (s, 3H), 1.20 (t, J = 7.5 Hz, 3H). |
| 1-1-049a | δ 9.76 (s, 1H), 8.77 (s, 1H), 8.36 (s, 1H), 8.20 (s, 1H), 4.17 (s, 3H), 4.13 (q, J = 7.5 Hz, 2H), 1.48 (t, J = 7.5 Hz, 3H). |
| 1-1-049b | δ 9.09 (s, 1H), 8.72 (s, 1H), 8.40 (s, 1H), 8.09 (s, 1H), 4.31 (s, 3H), 3.16 (q, J = 7.5 Hz, 2H), 1.23 (t, J = 7.5 Hz, 3H). |
| 1-1-50a | δ 9.70 (s, 1H), 8.79-8.76 (m, 1H), 8.38-8.35 (m, 1H), 8.20 (s, 1H), 4.18 (s, 3H), 4.16 (q, J = 7.4 Hz, 2H), 1.48 (t, J = 7.4 Hz, 3H). |
| 1-1-050b | δ 9.04 (s, 1H), 8.76-8.73 (m, 1H), 8.43-8.39 (m, 1H), 8.11 (s, 1H), 4.33 (s, 3H), 3.20 (q, J = 7.5 Hz, 2H), 1.24 (t, J = 7.5 Hz, 3H). |
| 1-1-051a | δ 9.58 (d, J = 5.8 Hz, 1H), 8.76 (d, J = 1.0 Hz, 1H), 8.35 (d, J = 1.0 Hz, 1H), 7.50 (dd, J = 7.2, 0.7 Hz, 1H), 4.15 (s, 3H), 4.06 (q, J = 7.5 Hz, 2H), 1.47 (t, J = 7.5 Hz, 3H). |
| 1-1-051b | δ 8.93 (d, J = 6.1 Hz, 1H), 8.73-8.70 (m, 1H), 8.40-8.38 (m, 1H), 7.40 (d, J = 7.8 Hz, 1H), 4.29 (s, 3H), 3.09 (q, J = 7.4 Hz, 2H), 1.22 (t, J = 7.4 Hz, 3H). |
| 1-1-052a | δ 9.45 (s, 1H), 8.74 (d, J = 1.0 Hz, 1H), 8.34 (d, J = 1.0 Hz, 1H), 7.04 (s, 1H), 4.13 (s, 3H), 4.05 (s, 3H), 3.98 (q, J = 7.4 Hz, 2H), 1.45 (t, J = 7.4 Hz, 3H). |
| 1-1-052b | δ 8.86 (s, 1H), 8.70 (d, J = 1.4 Hz, 1H), 8.37 (d, J = 1.4 Hz, 1H), 6.96 (s, 1H), 4.28 (s, 3H), 4.01 (s, 3H), 3.05 (q, J = 7.5 Hz, 2H), 1.20 (t, J = 7.5 Hz, 3H). |
| 1-1-053a | δ 9.81 (d, J = 2.4 Hz, 1H), 8.91 (d, J = 2.4 Hz, 1H), 8.78-8.75 (m, 1H), 8.35 (d, J = 1.5 Hz, 1H), 4.26 (s, 3H), 4.21 (q, J = 7.5 Hz, 2H), 1.48 (t, J = 7.5 Hz, 3H). |
| 1-1-053b | δ 9.14 (d, J = 2.4 Hz, 1H), 8.76 (d, J = 2.4 Hz, 1H), 8.75-8.71 (m, 1H), 8.39 (d, J = 1.5 Hz, 1H), 4.39 (s, 3H), 3.19 (q, J = 7.5 Hz, 2H), 1.24 (t, J = 7.5 Hz, 3H). |
| 1-1-056a | δ 9.49 (d, J = 1.5 Hz, 1H), 9.14 (d, J = 1.5 Hz, 1H), 8.78 (s, 1H), 8.37 (s, 1H), 4.22 (s, 3H), 4.18 (q, J = 7.5 Hz, 2H), 1.48 (t, J = 7.5 Hz, 3H). |
| 1-1-058a | δ 9.14 (s, 1H), 8.74 (s, 1H), 8.33 (s, 1H), 7.35 (s, 1H), 4.15 (s, 3H), 3.96 (q, J = 7.4 Hz, 2H), 2.70 (s, 3H), 1.43 (t, J = 7.4 Hz, 3H). |
| 1-1-058b | δ 8.75-8.65 (m, 1H), 8.55-8.50 (m, 1H), 8.40-8.35 (m, 1H), 7.20-7.15 (m, 1H), 4.30 (s, 3H), 3.05 (q, J = 7.4 Hz, 2H), 2.68 (s, 3H), 1.19 (t, J = 7.4 Hz, 3H), |
| 1-1-059a | δ 9.28 (d, J = 1.6 Hz, 1H), 8.75 (d, J = 1.6 Hz, 1H), 8.34 (d, J = 1.6 Hz, 1H), 7.65 (d, J = 1.6 Hz, 1H), 4.19 (s, 3H), 4.08 (q, J = 7.4 Hz, 2H), 1.46 (t, J = 7.4 Hz, 3H), |
| 1-1-059b | δ 8.75-8.70 (m, 1H), 8.63 (d, J = 1.6 Hz, 1H), 8.40-8.35 (m, 1H), 7.46 (d, J = 1.6 Hz, 1H), 4.34 (s, 3H), 3.13 (q, J = 7.4 Hz, 2H), 1.22 (t, J = 7.4 Hz, 3H). |
| 1-1-060a | δ 9.18-9.14 (m, 1H), 8.78-8.75 (m, 1H), 8.37-8.34 (m, 1H), 7.33-7.24 (m, 1H), 4.19 (s, 3H), 4.11 (q, J = 7.4 Hz, 2H), 1.47 (t, J = 7.4 Hz, 3H). |
| 1-1-060b | δ 8.75-8.71 (m, 1H), 8.50-8.46 (m, 1H), 8.43-8.38 (m, 1H), 7.15-7.05 (m, 1H), 4.33 (s, 3H), 3.14 (q, J = 7.4 Hz, 2H), 1.22 (t, J = 7.4 Hz, 3H). |
| 1-1-061a | δ 9.50 (d, J = 1.4 Hz, 1H), 8.76 (d, J = 1.4 Hz, 1H), 8.35 (d, J = 1.4 Hz, 1H), 8.25 (d, J = 1.4 Hz, 1H), 4.21 (s, 3H), 4.08 (q, J = 7.4 Hz, 2H), 1.46 (t, J = 7.4 Hz, 3H). |
| 1-1-061b | δ 8.86 (d, J = 1.4 Hz, 1H), 8.72 (d, J = 1.0 Hz, 1H), 8.39 (d, J = 1.0 Hz, 1H), 8.05 (d, J = 1.4 Hz, 1H), 4.38 (s, 3H), 3.14 (q, J = 7.4 Hz, 2H), 1.22 (t, J = 7.4 Hz, 3H). |
| 1-1-062a | δ 9.45 (d, J = 1.4 Hz, 1H), 8.78-8.75 (m, 1H), 8.36-8.33 (m, 1H), 7.85 (d, J = 1.4 Hz, 1H), 4.19 (s, 3H), 4.07 (q, J = 7.5 Hz, 2H), 1.47 (t, J = 7.5 Hz, 3H). |

TABLE 33-continued

| No. | $^1$H NMR (CDCl$_3$, Me$_4$Si, 300 MHz). |
|---|---|
| 1-1-062b | δ 8.82 (d, J = 1.4 Hz, 1H), 8.72 (d, J = 1.0 Hz, 1H), 8.39 (d, J = 1.0 Hz, 1H), 7.66 (d, J = 1.4 Hz, 1H), 4.34 (s, 3H), 3.13 (q, J = 7.4 Hz, 2H), 1.23 (t, J = 7.4 Hz, 3H). |
| 1-1-063a | δ 9.30-9.25 (m, 1H), 8.80-8.70 (m, 1H), 8.40-8.30 (m, 1H), 7.42 (dd, J = 8.9, 1.5 Hz, 1H), 4.18 (s, 3H), 4.10 (q, J = 7.4 Hz, 2H), 1.47 (t, J = 7.4 Hz, 3H), |
| 1-1-063b | δ 8.75-8.70 (m, 1H), 8.65-8.60 (m, 1H), 8.40-8.35 (m, 1H), 7.23 (dd, J = 9.2, 1.5 Hz, 1H), 4.33 (s, 3H), 3.14 (q, J = 7.4 Hz, 2H), 1.22 (t, J = 7.4 Hz, 3H). |
| 1-1-064a | δ 9.08 (d, J = 1.2 Hz, 1H), 8.74 (d, J = 1.2 Hz, 1H), 8.33 (d, J = 1.2 Hz, 1H), 7.03 (d, J = 1.2 Hz, 1H), 4.11 (s, 3H), 4.10 (s, 3H), 3.97 (q, J = 7.4 Hz, 2H), 1.45 (t, J = 7.4 Hz, 3H). |
| 1-1-065a | δ 9.05 (d, J = 1.2 Hz, 1H), 8.73 (d, J = 1.5 Hz, 1H), 8.32 (d, J = 1.5 Hz, 1H), 7.02 (d, J = 1.2 Hz, 1H), 4.31 (q, J = 7.0 Hz, 2H), 4.09 (s, 3H), 3.93 (q, 7.4 Hz, 2H), 1.60 (t, J = 7.0 Hz, 3H), 1.43 (t, J = 7.4 Hz, 3H). |
| 1-1-066 | δ 9.75-9.70 (m, 1H), 8.60-8.70 (m, 1H), 8.40-8.30 (m, 1H), 8.10-8.00 (m, 1H), 4.20 (s, 3H), 4.17 (q, J = 7.4 Hz, 2H), 1.48 (t, J = 7.4 Hz, 3H). |
| 1-1-067 | δ 9.74 (d, J = 1.5 Hz, 1H), 8.78 (d, J = 1.8 Hz, 1H), 8.36 (d, J = 1.8 Hz, 1H), 8.14 (d, J = 1.5 Hz, 1H), 4.25 (s, 3H), 4.19 (q, J = 7.5 Hz, 2H), 1.48 (t, J = 7.5 Hz, 3H). |
| 1-1-067b | δ 9.08 (d, J = 1.7 Hz, 1H), 8.76-8.73 (m, 1H), 8.42-8.39 (m, 1H), 7.96 (d, J = 17 Hz, 1H), 4.40 (s, 3H), 3.20 (q, J = 7.4 Hz, 2H), 1.25 (t, J = 7.4 Hz, 3H). |
| 1-1-068a | δ 8.92-8.89 (m, 1H), 8.75-8.72 (m, 1H), 8.34-8.32 (m, 1H), 6.74-6.71 (m, 1H), 4.10 (s, 3H), 3.93 (q, J = 7.2 Hz, 2H), 3.30 (s, 6H), 1.43 (t, J = 7.2 Hz, 3H). |
| 1-1-069a | δ 9.60-9.50 (m, 1H), 8.80-8.70 (m, 1H), 8.40-8.30 (m, 1H), 7.90-7.85 (m, 1H), 4.21 (s, 3H), 4.18 (q, J = 7.4 Hz, 2H), 1.48 (t, J = 7.4 Hz, 3H). |
| 1-1-069b | δ 8.90-8.80 (m, 1H), 8.75-8.70 (m, 1H), 8.40-8.35 (m, 1H), 7.70-7.65 (m, 1H), 4.35 (s, 3H), 3.19 (q, J = 7.4 Hz, 2H), 1.24 (t, J = 7.4 Hz, 3H). |
| 1-1-070a | δ 9.55-9.50 (m, 1H), 8.80-8.75 (m, 1H), 8.40-8.30 (m, 1H), 7.43 (dd, J = 9.0, 1.6 Hz, 1H), 4.21 (s, 3H), 4.16 (q, J = 7.4 Hz, 2H), 1.48 (t, J = 7.4 Hz, 3H). |
| 1-1-070b | δ 8.90-8.85 (m, 1H), 8.75-8.70 (m, 1H), 8.45-8.35 (m, 1H), 7.22 (d, J = 1.2 Hz 1H), 4.35 (s, 3H), 3.19 (q, J = 7.4 Hz, 2H), 1.24 (t, J = 7.4 Hz, 3H). |
| 1-1-071a | δ 9.68 (s, 1H), 8.77 (d, J = 1.4 Hz, 1H), 8.36 (d, J = 1.4 Hz, 1H), 8.18 (d, J = 1.4 Hz, 1H), 4.25 (s, 3H), 4.15 (q, J = 7.3 Hz, 2H), 1.48 (t, J = 7.3 Hz, 3H). |
| 1-1-071b | δ 9.03-8.99 (m, 1H), 8.76-8.72 (m, 1H), 8.43-8.39 (m, 1H), 8.00 (d, J = 1.4 Hz 1H), 4.40 (s, 3H), 3.19 (q, J = 7.4 Hz, 2H), 1.24 (t, J = 7.4 Hz, 3H). |
| 1-1-072a | δ 9.33 (s, 1H), 8.74 (s, 1H), 8.34 (s, 1H), 7.58 (s, 1H), 4.13 (s, 3H), 3.95 (q, J = 7.5 Hz, 2H), 2.67 (s, 3H), 1.43 (t, J = 7.5 Hz, 3H). |
| 1-1-072b | δ 8.74 (s, 1H), 8.73 (s, 1H), 8.45 (s, 1H), 7.40 (s, 1H), 4.31 (s, 3H), 3.05 (q, J = 7.5 Hz, 2H), 2.65 (s, 3H), 1.19 (t, J = 7.5 Hz, 3H). |
| 1-1-072c | δ 9.57 (s, 1H), 8.71 (d, J = 1.5 Hz, 1H), 8.30 (d, J = 1.5 Hz, 1H), 7.46-7.42 (m, 1H), 4.44 (s, 3H), 3.75-3.40 (m, 2H), 2.65 (s, 3H), 1.54 (t, J = 7.5 Hz, 3H). |
| 1-1-073a | δ 9.00-8.90 (m, 1H), 8.75-8.70 (m, 1H), 8.35-8.30 (m, 1H), 7.51 (d, J = 1.2 Hz 1H), 4.15 (s, 3H), 4.00 (q, J = 7.4 Hz, 2H), 2.47 (d, J = 0.8 Hz, 3H), 1.44 (t, J = 7.4 Hz, 3H). |
| 1-1-073b | δ 8.75-8.65 (m, 1H), 8.40-8.30 (m, 2H), 7.33 (d, J = 1.2 Hz, 1H), 4.32 (s, 3H) 3.07 (q, J = 7.4 Hz, 2H), 2.45 (d, J = 0.8 Hz, 3H), 1.19 (t, J = 7.4 Hz, 3H). |
| 1-1-074a | δ 9.34 (s, 1H), 8.77-8.75 (m, 1H), 8.36-8.34 (m, 1H), 7.52 (dd, J = 8.7, 1.2 Hz, 1H), 4.18 (s, 3H), 4.09 (q, J = 7.5 Hz, 2H), 1.47 (t, J = 7.5 Hz, 3H). |
| 1-1-074b | δ 8.74-8.71 (m, 2H), 8.42-8.38 (m, 1H), 7.36-7.30 (m, 1H), 4.33 (s, 3H), 3.14 (q, J = 7.4 Hz, 2H), 1.23 (t, J = 7.4 Hz, 3H). |
| 1-1-075a | δ 8.84 (d, J = 1.5 Hz, 1H), 8.75-8.73 (m, 1H), 8.34-8.32 (m, 1H), 7.12 (d, J = 1.5 Hz, 1H), 4.16 (s, 3H), 4.02 (q, J = 7.5 Hz, 2H), 2.65 (s, 3H), 2.59 (s, 3H), 1.44 (t J = 7.5 Hz, 3H). |
| 1-1-076a | δ 9.70-9.60 (m, 1H), 8.80-8.75 (m, 1H), 8.40-8.30 (m, 1H), 8.00-7.95 (m, 1H), 4.22 (s, 3H), 4.14 (q, J = 7.4 Hz, 2H), 1.47 (t, J = 7.4 Hz, 3H). |
| 1-1-077a | δ 9.47 (d, J = 7.2 Hz, 1H), 8.76 (d, J = 1.2 Hz, 1H), 8.35 (d, J = 1.2 Hz, 1H), 7.90 (d, J = 7.2 Hz, 1H), 7.30-7.20 (m, 1H), 4.21 (s, 3H), 4.14 (q, J = 7.5 Hz, 2H), 1.46 (t, J = 7.5 Hz, 3H). |
| 1-1-077b | δ 8.83 (d, J = 7.5 Hz, 1H), 8.71 (s, 1H), 8.39 (s, 1H), 7.72 (d, J = 6.6 Hz, 1H), 7.10 (t, J = 6.6 Hz, 1H), 4.36 (s, 3H), 3.15 (q, J = 7.5 Hz, 2H), 1.22 (t, J = 7.5 Hz, 3H), |
| 1-1-078a | δ 9.41 (s, 1H), 8.78-8.76 (m, 1H), 8.37-8.34 (m, 1H), 4.21 (s, 3H), 4.12 (q, J = 7.4 Hz, 2H), 1.47 (t, J = 7.4 Hz, 3H). |
| 1-1-078b | δ 8.74 (d, J = 0.7 Hz, 1H), 8.74-8.72 (m, 1H), 8.41-8.38 (m, 1H), 4.36 (s, 3H) 3.16 (q, J = 7.5 Hz, 2H), 1.23 (t, J = 7.5 Hz, 3H). |
| 1-1-079a | δ 9.41 (s, 1H), 8.75 (s, 1H), 8.34 (s, 1H), 7.94-7.80 (m, 2H), 7.68-7.60 (m, 2H), 7.58-7.42 (m, 3H), 4.15 (s, 3H), 3.99 (q, J = 7.5 Hz, 2H), 1.46 (t, J = 7.5 Hz, 3H), |
| 1-1-080a | δ 9.41 (s, 1H), 8.75 (d, J = 1.8 Hz, 1H), 8.35 (d, J = 1.8 Hz, 1H), 7.95-7.75 (m, 2H), 7.70-7.25 (m, 4H), 4.15 (s, 3H), 4.00 (q, J = 7.5 Hz, 2H), 1.47 (t, J = 7.5 Hz, 3H), |
| 1-1-081a | δ 9.43 (s, 1H), 8.75 (d, J = 1.8 Hz, 1H), 8.35 (d, J = 1.8 Hz, 1H), 7.95-7.75 (m, 2H), 7.60-7.15 (m, 4H), 4.16 (s, 3H), 4.02 (q, J = 7.5 Hz, 2H), 1.47 (t, J = 7.5 Hz, 3H), |
| 1-1-082a | δ 9.40-9.36 (m, 1H), 8.75 (d, J = 1.8 Hz, 1H), 8.35 (d, J = 1.8 Hz, 1H), 7.95-7.75 (m, 2H), 7.70-7.55 (m, 2H), 7.25-7.20 (m, 2H), 4.16 (s, 3H), 4.02 (q, J = 7.5 Hz, 2H), 1.46 (t, J = 7.5 Hz, 3H). |
| 1-1-083a | δ 9.20 (s, 1H), 8.75 (s, 1H), 8.34 (s, 1H), 8.01 (s, 1H), 7.90-7.80 (m, 2H), 7.70-7.30 (m, 3H), 4.16 (s, 3H), 3.98 (q, J = 7.5 Hz, 2H), 1.43 (t, J = 7.5 Hz, 3H). |
| 1-1-084a | δ 9.47 (s, 1H), 8.76 (s, 1H), 8.36 (s, 1H), 7.95-7.30 (m, 6H), 4.17 (s, 3H), 4.05 (q, J = 7.5 Hz, 2H), 1.47 (t, J = 7.5 Hz, 3H). |
| 1-1-085a | δ 9.49 (s, 1H), 8.76 (s, 1H), 8.36 (s, 1H), 7.94 (d, J = 9.6 Hz, 1H), 7.85-7.35 (m, 5H), 4.17 (s, 3H), 4.05 (q, J = 7.5 Hz, 2H), 1.47 (t, J = 7.5 Hz, 3H). |

TABLE 33-continued

| No. | $^1$H NMR (CDCl$_3$, Me$_4$Si, 300 MHz). |
|---|---|
| 1-1-086a | δ 9.47 (s, 1H), 8.92 (s, 1H), 8.80-8.70 (m, 2H), 8.36 (s, 1H), 7.97 (s, 1H), 7.94 (s, 1H), 7.80 (dd, J = 9.6, 1.8 Hz, 1H), 7.55-7.43 (m, 1H), 4.17 (s, 3H), 4.05 (q, J = 7.5 Hz, 2H), 1.48 (t, J = 7.5 Hz, 3H). |
| 1-1-087a | δ 9.56 (s, 1H), 8.82-8.74 (m, 3H), 8.36 (s, 1H), 7.96 (d, J = 9.6 Hz, 1H), 7.84 (d, J = 9.6 Hz, 1H), 7.65-7.53 (m, 2H) 4.18 (s, 3H), 4.08 (q, J = 7.5 Hz, 2H), 1.48 (t, J = 7.5 Hz, 3H). |
| 1-1-088a | δ 9.45 (s, 1H), 8.75 (s, 1H), 8.34 (s, 1H), 7.85-7.80 (m, 2H), 7.65-7.40 (m, 3H), 4.15 (s, 3H), 4.01 (q, J = 7.5 Hz, 2H), 1.46 (t, J = 7.5 Hz, 3H). |
| 1-1-089a | δ 9.34 (d, J = 0.9 Hz, 1H), 8.75 (s, 1H), 8.34 (s, 1H), 7.74 (d, J = 9.6 Hz, 1H), 7.56 (dd, J = 9.6, 1.8 Hz, 1H), 4.14 (s, 3H), 4.01 (q, J = 7.5 Hz, 2H), 1.46 (t, J = 7.5 Hz, 3H), 0.30 (s, 9H). |
| 1-1-090a | δ 9.22 (s, 1H), 8.75-8.72 (m, 1H), 8.34-8.31 (m, 1H), 7.70 (d, J = 9.3 Hz, 1H) 7.49 (dd, J = 9.3, 1.8 Hz, 1H), 4.12 (s, 3H), 3.97 (q, J = 7.5 Hz, 2H), 1.44 (t, J = 7.5 Hz, 3H), 1.00-0.80 (m, 5H). |
| 1-1-091a | δ 9.24 (s, 1H), 8.74 (s, 1H), 8.34 (s, 1H), 7.77 (d, J = 1.5 Hz, 2H), 5.56 (s, 1H), 5.32 (s, 1H), 4.13 (s, 3H), 3.99 (q, J = 7.5 Hz, 2H), 2.24 (s, 3H) 1.45 (t, J = 7.5 Hz, 3H). |
| 1-1-092a | δ 9.65 (s, 1H), 8.45 (d, J = 2.0 Hz, 1H), 8.10 (d, J = 2.0 Hz, 1H), 7.94 (d, J = 9.2 Hz, 1H), 7.71 (d, J = 9.2 Hz, 1H), 4.13 (s, 3H), 4.10 (q, J = 7.3 Hz, 2H), 1.47 (t, J = 7.3 Hz, 3H). |
| 1-1-092b | δ 9.03-8.99 (m, 1H), 8.41 (d, J = 2.4 Hz, 1H), 8.14 (d, J = 2.4 Hz, 1H), 7.82 (d, J = 9.5 Hz, 1H), 7.52 (d, J = 9.5 Hz, 1H), 4.26 (s, 3H), 3.11 (q, J = 7.4 Hz, 2H), 1.21 (t, J = 7.4 Hz, 3H). |
| 1-1-093a | δ 9.34-9.32 (m, 1H), 8.71-8.69 (m, 1H), 8.33-8.31 (m, 1H), 7.79 (dd, J = 9.5, 1.0 Hz, 1H), 7.55 (dd, J = 9.5, 1.9 Hz, 1H), 4.16 (s, 3H), 4.06 (q, J = 7.4 Hz, 2H), 1.47 (t J = 7.4 Hz, 3H). |
| 1-1-093b | δ 8.69 (dd, J = 2.0, 1.0 Hz, 1H), 8.66 (d, J = 1.7 Hz, 1H), 8.37 (d, J = 1.7 Hz, 1H), 7.67 (dd, J = 9.5, 1.0 Hz, 1H), 7.36 (dd, J = 9.5, 2.0 Hz, 1H), 4.32 (s, 3H), 3.12 (q, J = 7.5 Hz, 2H), 1.23 (t, J = 7.5 Hz, 3H). |
| 1-1-094a | δ 9.50 (dd, J = 1.5, 0.9 Hz, 1H), 8.70 (d, J = 2.0 Hz, 1H), 8.32 (d, J = 2.0 Hz, 1H), 7.76 (d, J = 9.4, 1.5 Hz, 1H), 7.61 (dd, J = 9.4, 0.9 Hz, 1H), 4.15 (s, 3H), 4.05 (q, J = 7.4 Hz, 2H), 1.47 (t, J = 7.4 Hz, 3H). |
| 1-1-094b | δ 8.91-8.89 (m, 1H), 8.67-8.65 (m, 1H), 8.37-8.35 (m, 1H), 7.56 (dd, J = 9.4, 1.5 Hz, 1H), 7.50 (dd, J = 9.4, 0.9 Hz, 1H), 4.31 (s, 3H), 3.11 (q, J = 7.3 Hz, 2H), 1.23 (t J = 7.3 Hz, 3H). |
| 1-1-094c | δ 9.74-9.72 (m, 1H), 8.68-8.66 (m, 1H), 8.29-8.27 (m, 1H), 7.62 (dd, J = 9.4, 1.7 Hz, 1H), 7.55 (dd, J = 9.4, 0.9 Hz, 1H), 4.43 (s, 3H), 3.75-3.64 (m, 1H), 3.63-3.49 (m, 1H), 1.57 (t, J = 7.5 Hz, 3H). |
| 1-1-095a | δ 9.05 (d, J = 1.2 Hz, 1H), 8.74 (d, J = 0.9 Hz, 1H), 8.33 (d, J = 1.5 Hz, 1H), 7.73 (dd, J = 9.3, 0.6 Hz, 1H), 7.50 (dd, J = 9.3, 1.5 Hz, 1H), 4.13 (s, 3H), 4.00 (q, J = 7.2 Hz, 2H), 2.59 (s, 3H) 1.45 (t, J = 7.2 Hz, 3H). |
| 1-1-096a | δ 9.57 (s, 1H), 8.77 (s, 1H), 8.36 (s, 1H), 8.00 (d, J = 9.6 Hz, 1H), 7.81 (dd, J = 9.6, 1.8 Hz, 1H), 4.18 (s, 3H), 4.18-4.00 (m, 2H), 2.91 (s, 3H), 1.47 (t, J = 7.2 Hz, 3H). |
| 1-1-097a | δ 9.93 (s, 1H), 8.77 (s, 1H), 8.37 (s, 1H), 8.02-7.90 (m, 2H), 4.19 (s, 3H), 4.12 (q, J = 7.5 Hz, 2H), 3.23 (s, 3H), 1.49 (t, J = 7.5 Hz, 3H). |
| 1-1-098a | δ 9.48-9.46 (m, 1H), 8.76 (d, J = 1.4 Hz, 1H), 8.35 (d, J = 1.4 Hz, 1H), 7.81 (dd J = 9.4, 0.9 Hz, 1H), 7.67 (dd, J = 9.4, 1.7 Hz, 1H), 4.15 (s, 3H), 4.04 (q, J = 7.4 Hz, 2H), 3.47 (q, J = 18.7 Hz, 2H), 1.46 (t, J = 7.4 Hz, 3H). |
| 1-1-099a | δ 9.07 (dd, J = 1.7, 0.9 Hz, 1H), 8.69 (d, J = 1.7 Hz, 1H), 8.31 (d, J = 1.7 Hz, 1H), 7.74 (dd, J = 9.4, 0.9 Hz, 1H), 7.51 (dd, J = 9.4, 1.7 Hz, 1H), 4.15 (s, 3H), 4.02 (q, J = 7.3 Hz, 2H), 2.60 (s, 3H), 1.46 (t, J = 7.3 Hz, 3H). |
| 1-1-100a | δ 9.47 (s, 1H), 8.73 (d, J = 1.5 Hz, 1H), 8.33 (d, J = 1.5 Hz, 1H), 7.74 (d, J = 9.6 Hz, 1H), 7.58 (d, J = 9.6 Hz, 1H), 6.60 (brs, 1H), 4.11 (s, 3H), 3.93 (q, J = 7.5 Hz, 2H), 1.56 (s, 9H) 1.45 (t, J = 7.5 Hz, 3H). |
| 1-1-101a | δ 9.47 (d, J = 2.1 Hz, 1H), 8.80-8.77 (m, 1H), 8.75 (d, J = 1.5 Hz, 1H), 8.39-8.35 (m, 1H), 7.95 (dd, J = 7.8, 2.4 Hz, 1H), 4.21 (s, 3H), 4.17 (q, J = 7.5 Hz, 2H) 1.47 (t, J = 7.5 Hz, 3H). |
| 1-1-101b | δ 8.82-8.72 (m, 2H), 8.70-8.66 (m, 1H), 8.40 (d, J = 2.1 Hz, 1H), 7.85 (dd, J = 7.5, 2.1 Hz, 1H), 4.35 (s, 3H), 3.21 (q, J = 7.5 Hz, 2H), 1.22 (t, J = 7.5 Hz, 3H). |
| 1-1-102a | δ 9.42 (d, J = 7.5 Hz, 1H), 8.50 (dd, J = 4.8, 1.4 Hz, 1H), 8.16-8.13 (m, 1H), 8.10 (dd, J = 7.5, 1.4 Hz, 1H), 7.33-7.28 (m, 2H), 4.15 (s, 3H), 4.14 (q, J = 7.3 Hz, 2H), 1.45 (t, J = 7.3 Hz, 3H). |
| 1-1-102b | δ 8.76 (d, J = 7.2 Hz, 1H), 8.47 (dd, J = 4.8, 1.4 Hz, 1H), 8.16 (dd, J = 8.2, 1.4 Hz, 1H), 8.04 (s, 1H), 7.29 (dd, J = 8.2, 4.8 Hz, 1H), 7.19 (dd, J = 7.2, 1.7 Hz, 1H), 4.28 (s, 3H), 3.11 (q, J = 7.4 Hz, 2H), 1.19 (t, J = 7.4 Hz, 3H). |
| 1-1-103a | δ 9.42 (d = 7.5 Hz, 1H), 8.72 (d, J = 1.7 Hz, 1H), 8.33 (d, J = 1.7 Hz, 1H), 8.17-8.15 (m, 1H), 7.33 (dd, J = 7.5, 1.7 Hz, 1H), 4.19 (s, 3H) 4.13 (q, J = 7.5 Hz, 2H), 1.47 (t, J = 7.5 Hz, 3H). |
| 1-1-103b | δ 8.78 (d, J = 7.2 Hz, 1H), 8.68 (d, J = 1.7 Hz, 1H), 8.38 (d, J = 1.7 Hz, 1H), 8.05 (s, 1H), 7.21 (dd, J = 7.2, 1.7 Hz, 1H), 4.34 (s, 3H), 3.16 (q, J = 7.4 Hz, 2H), 1.23 (t, J = 7.4 Hz, 3H). |
| 1-1-104a | δ 10.35 (s, 1H), 8.77 (s, 1H), 8.39-8.35 (m, 1H), 8.22 (s, 1H), 8.06-8.02 (m 1H), 7.96-7.90 (m, 2H), 7.07-7.62 (m, 1H), 7.62-7.54 (m, 2H), 4.16 (s, 3H), 4.06 (q, J = 7.7 Hz, 2H), 1.54 (t, J = 7.7 Hz, 3H). |
| 1-1-105a | δ 9.92-9.89 (m, 1H), 8.81-8.78 (m, 1H), 8.38 (d, J = 1.5 Hz, 1H), 8.12 (d, J = 1.5 Hz, 1H), 4.29 (s, 3H), 4.12 (q, J = 7.1 Hz, 2H), 1.26 (t, J = 7.1 Hz, 3H). |

TABLE 33-continued

| No. | ¹H NMR (CDCl₃, Me₄Si, 300 MHz). |
|---|---|
| 1-1-105b | δ 9.22-9.19 (m, 1H), 8.76 (d, J = 1.4 Hz, 1H), 8.42 (d, J = 1.4 Hz, 1H), 7.96 (d, J = 1.4 Hz, 1H), 4.42 (s, 3H), 3.26 (q, J = 7.3 Hz, 2H), 1.26 (t, J = 7.3 Hz, 3H). |
| 1-1-105c | δ 10.22-10.19 (m, 1H), 8.78-8.76 (m, 1H), 8.34 (d, J = 1.7 Hz, 1H), 8.00 (d, J = 1.7 Hz, 1H), 4.51 (s, 3H), 3.81-3.57 (m, 2H), 1.58 (t, J = 7.7 Hz, 3H). |
| 1-1-106a | δ 9.36 (dd, J = 7.5, 0.7 Hz, 1H), 8.76 (d, J = 1.0 Hz, 1H), 8.36 (d, J = 1.7 Hz, 1H), 8.00-7.97 (m, 1H), 7.32-7.27 (m, 1H), 6.79 (t, J = 55.5 Hz, 1H), 4.17 (s, 3H), 4.07 (q, J = 7.5 Hz, 2H), 1.46 (t, J = 7.5 Hz, 3H). |
| 1-1-106b | δ 8.75 (dd, J = 7.2, 0.7 Hz, 1H), 8.72 (dd, J = 2.0, 0.7 Hz, 1H), 8.40 (d, J = 2.0 Hz, 1H), 7.88-7.85 (m, 1H), 7.18 (dd, J = 7.2, 2.0 Hz, 1H), 6.76 (t, J = 55.7 Hz, 1H), 4.32 (s, 3H), 3.12 (q, J = 7.4 Hz, 2H), 1.21 (t, J = 7.4 Hz, 3H). |
| 1-1-106c | δ 9.56 (d, J = 7.4 Hz, 1H), 8.72 (d, J = 1.8 Hz, 1H), 8.32 (d, J = 1.8 Hz, 1H), 7.93-7.90 (m, 1H), 7.11 (dd, J = 7.4, 1.5 Hz, 1H), 6.75 (t, J = 55.7 Hz, 1H), 4.43 (s, 3H), 3.80-3.64 (m, 1H), 3.63-3.47 (m, 1H), 1.55 (t, J = 7.5 Hz, 3H). |
| 1-1-107a | δ 8.73 (d, J = 1.4 Hz, 1H), 8.65-8.63 (m, 1H), 8.32 (d, J = 2.0 Hz, 1H), 7.64 (d, J-9.5 Hz, 1H), 7.13 (dd, J-9.5, 2.0 Hz, 1H), 4.11 (s, 3H), 3.92 (q, J = 7.4 Hz, 2H), 3.83 (brs, 2H), 1.43 (t, J-7.4 Hz, 3H). |
| 1-1-108a | δ 9.72 (s, 1H), 8.76 (d, J-2.0 Hz, 1H), 8.35 (d, J-2.0 Hz, 1H), 7.80 (d J = 9.5 Hz, 1H), 7.71 (d, J = 9.5 Hz, 1H), 4.14 (s, 3H), 3.99 (q, J = 7.5 Hz, 2H), 1.45 (t, J = 7.5 Hz, 3H) (No peek of proton of NH was observed). |
| 1-1-109a | δ 9.49 (dd, J = 6.5, 0.7 Hz, 1H), 8.80-8.70 (m, 1H), 8.35-8.30 (m, 1H) 7.53 (dd, J = 7.7, 0.7 Hz, 1H), 4.14 (s, 3H), 4.07 (q, J = 7.4 Hz, 2H), 1.46 (t, J = 7.4 Hz, 3H). |
| 1-1-109b | δ 6.83 (d, J = 6.5 Hz, 1H), 8.75-8.65 (m, 1H), 8.40-8.35 (m, 1H), 7.44 (d, J = 8.5 Hz, 1H), 4.28 (s, 3H), 3.09 (q, J = 7.5 Hz, 2H), 1.21 (t, J = 7.5 Hz, 3H). |
| 1-1-110a | δ 9.52 (s, 1H), 8.75 (d, J-2.0 Hz, 1H), 8.34 (d, J-2.0 Hz, 1H), 7.95 (s 1H), 4.15 (s, 3H), 4.07 (q, J = 7.4 Hz, 2H), 1.46 (t, J = 7.4 Hz, 3H). |
| 1-1-110c | δ 9.78 (d, J = 0.7 Hz, 1H), 8.75-8.70 (m, 1H), 8.35-8.25 (m, 1H), 7.90 (d, J = 0.7 Hz, 1H), 4.40 (s, 3H), 3.75-3.45 (m, 2H), 1.55 (t, J = 7.3 Hz, 3H). |
| 1-1-111a | δ 9.60 (d, J = 0.7 Hz, 1H), 8.80-8.75 (m, 1H), 8.40-8.30 (m, 1H), 8.23 (d, J = 0.7 Hz, 1H), 4.18 (s, 3H), 4.17 (q, J = 7.5 Hz, 2H), 1.48 (t, J = 7.5 Hz, 3H). |
| 1-1-111b | δ 8.93 (d, J = 0.7 Hz, 1H), 8.75-8.70 (m, 1H), 8.40-8.35 (m, 1H), 8.17 (d, J = 0.7 Hz, 1H), 4.32 (s, 3H), 3.20 (q, J = 7.4 Hz, 2H), 1.23 (t, J = 7.4 Hz, 3H). |
| 1-1-112a | δ 9.37 (d, J = 1.5 Hz, 1H), 8.80-8.70 (m, 1H), 8.40-8.30 (m, 1H), 7.75 (d, J = 1.5 Hz, 1H), 4.18 (s, 3H), 4.07 (q, J = 7.4 Hz, 2H), 1.46 (t, J = 7.4 Hz, 3H). |
| 1-1-112b | δ 8.75-8.70 (m, 2H), 8.45-8.30 (m, 1H), 7.56 (d, J = 1.5 Hz, 1H), 4.34 (s, 3H), 3.13 (q, J = 7.5 Hz, 2H), 1.22 (t, J = 7.5 Hz, 3H). |
| 1-1-113a | δ 9.24 (dd, J = 4.4, 2.0 Hz, 1H), 8.80-8.70 (m, 1H), 8.35-8.30 (m, 1H) 7.61 (dd, J = 7.7, 2.0 Hz, 1H), 4.19 (s, 3H), 4.08 (q, J = 7.4 Hz, 2H), 1.45 (t, J = 7.4 Hz, 3H). |
| 1-1-113b | δ 8.75-8.65 (m, 1H), 8.55 (dd, J = 3.7, 2.4 Hz, 1H), 8.40-8.35 (m, 1H) 7.43 (dd, J = 7.8, 2.4 Hz, 1H), 4.34 (s, 3H), 3.12 (q, J = 7.4 Hz, 2H), 1.21 (t, J = 7.4 Hz, 3H). |
| 1-1-114a | δ 9.39 (s, 1H), 8.75 (d, J = 1.8 Hz, 1H), 8.43 (s, 1H), 8.34 (d, J = 1.8 Hz 1H) 4.14 (s, 3H), 4.07 (q, J = 7.5 Hz, 2H), 1.45 (t, J = 7.5 Hz, 3H). |
| 1-1-114b | δ 8.76 (d, J = 0.7 Hz, 1H), 8.73-8.71 (m, 1H), 8.40-8.38 (m, 1H), 8.31 (d, J = 0.7 Hz, 1H), 4.29 (s, 3H), 9, 3.12 (d, J = 7.4 Hz, 2H), 1.21 (t, J = 7.4 Hz, 3H). |
| 1-1-115a | δ 9.42 (d, J = 0.6 Hz, 1H), 8.75 (dd, J = 1.8, 0.6 Hz, 1H), 8.34 (dd, J = 1.8, 0.6 Hz, 1H), 8.17 (d, J = 0.6 Hz, 1H), 4.15 (s, 3H), 4.08 (q, J = 7.5 Hz, 2H), 1.46 (t, J = 7.5 Hz, 3H). |
| 1-1-115b | δ 8.77 (d, J = 0.7 Hz, 1H), 8.73-8.71 (m, 1H), 8.40-8.38 (m, 1H), 8.06 (d, J = 0.7 Hz, 1H), 4.30 (s, 3H), 3.12 (q, J = 7.4 Hz, 2H), 1.22 (t, J = 7.4 Hz, 3H). |
| 1-1-116a | δ 9.24 (s, 1H), 8.75 (d, J = 2.0 Hz, 1H), 8.34 (d, J = 2.0 Hz, 1H), 7.40 (s, 1H), 4.15 (s, 3H), 4.03 (q, J = 7.4 Hz, 2H), 2.62 (s, 3H), 1.46 (t, J = 7.4 Hz, 3H). |
| 1-1-117a | δ 9.42 (s, 1H), 8.80-8.75 (m, 1H), 8.44 (s, 1H), 8.39-8.32 (m, 1H), 4.21 (s. 3H), 4.13 (q, J = 7.3 Hz, 2H), 3.00 (s, 3H), 1.49 (t, J = 7.3 Hz, 3H). |
| 1-1-118a | δ 9.33 (d, J = 1.7 Hz, 1H), 8.80-8.70 (m, 1H), 8.35-8.30 (m, 1H), 7.83 (d, J = 1.7 Hz, 1H), 4.19 (s, 3H), 4.07 (q, J = 7.4 Hz, 2H), 1.45 (t, J = 7.4 Hz, 3H). |
| 1-1-118b | δ 8.75-8.70 (m, 1H), 8.67 (d, J = 1.7 Hz, 1H), 8.40-8.35 (m, 1H), 7.64 (d, J = 1.7 Hz, 1H), 4.35 (s, 3H), 3.13 (q, J = 7.4 Hz, 2H), 1.21 (t, J = 7.4 Hz, 3H). |
| 1-1-118c | δ 9.57 (d, J = 1.7 Hz, 1H), 8.75-8.70 (m, 1H), 8.35-8.25 (m, 1H), 7.70 (d, J = 1.7 Hz, 1H), 4.47 (s, 3H), 3.75-3.50 (m, 2H), 1.55 (t, J = 7.5 Hz, 3H). |
| 1-1-119b | δ 8.75-8.65 (m, 1H), 8.63 (s, 1H), 8.40-8.30 (m, 1H), 4.33 (s, 3H), 3.10 (q, J = 7.4 Hz, 2H), 2.63 (s, 3H), 1.20 (t, J = 7.4 Hz, 3H). |
| 1-1-119c | δ 9.52 (s, 1H), 8.75-8.70 (m, 1H), 8.35-8.25 (m, 1H), 4.46 (s, 3H), 3.75-3.45 (m, 2H), 2.63 (s, 3H), 1.54 (t, J = 7.3 Hz, 3H). |
| 1-1-120c | δ 9.37 (d, J = 4.8 Hz, 1H), 9.30-9.25 (m, 1H), 8.75-8.70 (m, 1H), 8.35-8.30 (m, 1H), 8.04 (d, J = 4.8 Hz, 1H), 4.46 (s, 3H), 3.80-3.50 (m, 2H), 1.55 (t, J = 7.3 Hz, 3H). |

TABLE 33-continued

| No. | $^1$H NMR (CDCl$_3$, Me$_4$Si, 300 MHz). |
|---|---|
| 1-1-121a | δ 9. 22 (d, J = 3.7 Hz, 1H), 8.80-8.70 (m, 1H), 8.35-8.30 (m, 2H), 4.15 (s, 3H), 4.07 (q, J = 7. 4 Hz, 2H), 1.44 (t, J = 7. 4 Hz, 3H). |
| 1-1-122a | δ 9.12 (d, J = 7.5 Hz, 1H), 8.79 (d, J = 2.0 Hz, 1H), 8.60 (d, J = 2.0 Hz, 1H), 8.19-8.15 (m, 1H), 7.34 (dd, J = 7.5, 1.7 Hz, 1H), 4.21 (s, 3H), 4.12 (q, J = 7.5 Hz, 2H), 1.48 (t, J = 7.5 Hz, 3H). |
| 1-1-123a | δ 9.42 (d, J = 7.5 Hz, 1H), 9.08 (d, J = 2.0 Hz, 1H), 8.72 (d, J = 2.0 Hz, 1H, 8.19-8.16 (m, 1H), 7.35 (dd, J = 7.5, 1.7 Hz, 1H), 4.24 (s, 3H), 4.10 (q, J = 7.4 Hz, 2H), 1.49 (t, J = 7.4 Hz, 3H). |
| 1-2-004a | δ 9.46 (d, J = 7.5 Hz, 1H), 8.80 (d, J = 1.4 Hz, 1H), 8.47 (d, J = 2.0 Hz, 1H), 8.20 (s, 1H), 7.35 (dd, J = 7.5, 2.0 Hz, 1H), 4.00 (q, J = 7.4 Hz, 2H), 1.48 (t J = 7.4 Hz, 3H). |
| 1-2-004b | δ 8.78-8.72 (m, 2H), 8.43 (d, J = 2.0 Hz, 1H), 8.09 (s, 1H), 7.23 (dd, J = 7.3, 2.0 Hz, 1H), 3.10 (q, J = 7.4 Hz, 2H), 1.27 (t, J = 7.4 Hz, 3H). |
| 1-2-004c | δ 9.54 (d, J = 7.5 Hz, 1H), 8.75 (d, J = 1.4 Hz, 1H), 8.40 (d, J = 1.4 Hz, 1H), 8.13 (s, 1H), 7.20 (dd, J = 7.5, 1.4 Hz, 1H), 3.66-3.39 (m, 2H), 1.50 (t, J = 7.5 Hz, 3H). |
| 1-2-005a | δ 9.50 (d, J = 7.4 Hz, 1H), 8.25-8.20 (m, 1H), 8.20-8.10 (m, 1H), 7.80-7.70 (m, 2H), 7.31 (dd, J = 7.4, 1.8 Hz, 1H), 4.08 (q, J = 7.4 Hz, 2H), 1.45 (t J = 7.4 Hz, 3H). |
| 1-2-006a | δ 9.49 (d, J = 7.4 Hz, 1H), 8.65-8.60 (m, 1H), 8.20-8.10 (m, 2H), 7.98 (d, J = 8.6 Hz, 1H), 7.34 (dd, J = 7.4, 1.8 Hz, 1H), 4.06 (q, J = 7.4 Hz, 2H), 1.47 (t, J = 7.4 Hz, 3H). |
| 1-3-002a | δ 9.41 (d, J = 7.5 Hz, 1H), 8.44 (s, 1H), 8.10-8.07 (m, 1H), 7.91 (s, 1H), 7.27-7.23 (m, 1H), 3.84 (q, J = 7.4 Hz, 2H), 2.99 (s, 3H), 1.36 (t, J = 7.4 Hz 3H). |
| 1-3-003a | δ 9.41 (d, J = 7.5 Hz, 1H), 8.44 (s, 1H), 8.09-8.07 (m, 1H), 7.95 (s, 1H), 7.27-7.22 (m, 1H), 3.87 (q, J = 7.4 Hz, 2H), 2.98 (s, 3H), 1.37 (t, J = 7.4 Hz, 3H). |
| 1-3-004a | δ 9.39 (d, J = 7.5 Hz, 1H), 9.20 (s, 1H), 8.63 (s, 1H), 8.12-8.08 (m 1H), 8.05 (s, 1H), 7.25 (dd, J = 7.5, 1.8 Hz, 1H), 3.75 (q, J = 7.4 Hz, 2H), 1.35 (J = 7.5 Hz, 3H). |
| 1-3-005a | δ 9.63 (s, 1H), 9.19 (s, 1H), 8.65 (s, 1H), 8.01 (s, 1H), 7.93 (d J = 9.3 Hz, 1H), 7.66 (dd, J = 9.3, 1.5 Hz, 1H), 3.69 (q, J = 7.5 Hz, 2H), 1.34 (t J = 7.5 Hz, 3H). |
| 1-3-006a | δ 9.66 (s, 1H), 8.46 (s, 1H), 7.94-7.86 (m, 2H), 7.65 (dd, J = 9.3 1.5 Hz, 1H), 3.82 (q, J = 7.5 Hz, 2H), 2.98 (s, 3H), 1.37 (t, J = 7.5 Hz, 3H). |
| 1-3-009a | δ 9.61 (s, 1H), 9.23 (s, 1H), 7.96 (d, J = 9.6 Hz, 1H), 7.94 (s, 1H) 7.68 (d, J = 9.6 Hz, 1H), 4.00 (q, J = 7.5 Hz, 2H), 1.45 (t, J = 7.5 Hz, 3H). |
| 1-3-011a | δ 9.65 (s, 1H), 8.98 (s, 1H), 7.96 (d, J = 1.5 Hz, 1H), 7.88 (d, J = 9.3H 1H), 7.64 (dd, J = 9.3, 1.5 Hz, 1H), 4.09 (q, J = 7.5 Hz, 2H), 2.94 (s, 3H), 1.44 (t J = 7.5 Hz, 3H). |
| 1-3-012a | δ 9.46-9.44 (m, 1H), 9.24 (d, J = 0.7 Hz, 1H), 8.67 (s, 1H), 7.99 (s 1H), 7.71 (dd, J = 9.5, 1.7 Hz, 1H), 7.61 (dd, J = 9.5, 0.7 Hz, 1H), 3.63 (q J = 7.3 Hz, 2H), 1.33 (t, J = 7.3 Hz, 3H). |
| 1-3-013a | δ 9.40-9.30 (m, 1H), 9.25-9.15 (m, 1H), 8.20-8.15 (m, 1H) 7.95-7.90 (m, 1H), 7.30-7.20 (m, 1H), 3.99 (q, J = 7.5 Hz, 2H), 1.43 (t, J = 7.5H 3H). |
| 1-3-014a | δ 9.41 (d, J = 7.5 Hz, 1H), 8.99 (s, 1H), 8.09 (s, 1H), 7.97 (d, J = 1.5H 1H), 7.30-7.20 (m, 1H), 4.10 (q, J = 7.5 Hz, 2H), 2.94 (s, 3H), 1.43 (t, J = 7.5 Hz 3H). |
| 1-4-002a | δ 9.65 (s, 1H), 8.94 (s, 1H), 8.57 (d, J = 2.1 Hz, 1H), 8.31 (s, 1H) 7.91 (d, J-9.3 Hz, 1H), 7.64 (dd, J-9.3, 2.1 Hz, 1H), 3.76 (q, J-7.5 Hz, 2H) 1.36 (t, J = 7.5 Hz, 3H). |
| 1-4-003a | δ 9.48 (dd, J = 1.7, 1.0 Hz, 1H), 8.94 (s, 1H), 8.56 (d, J = 2.0 Hz, 1H) 8.31-8.29 (m, 1H), 7.69 (dd, J = 9.4, 1.7 Hz, 1H), 7.60 (dd, J = 9.4, 1.0 Hz, 1H) 3.69 (q, J = 7.4 Hz, 2H), 1.34 (t, J = 7.4 Hz, 3H). |
| 1-4-003b | δ 9.05-9.00 (m, 1H), 8.80-8.70 (m, 1H), 8.55-8.50 (m, 1H) 8.30-8.25 (m, 1H), 7.55-7.45 (m, 2H), 2.86 (q, J-7.4 Hz, 2H), 1.20 (t, J-7.4H 3H). |
| 1-5-001a | δ 9.39 (d, J = 7.4 Hz, 1H), 8.54 (s, 1H), 8.30 (d, J = 7.4 Hz, 1H), 8.07 (1H), 8.01 (s, 1H), 7.21 (dd, J = 7.4, 1.7 Hz, 1H), 7.04 (dd, J = 7.4, 1.7 Hz, 1H), 3.75 (q, J = 7.5 Hz, 2H), 1.31 (t, J = 7.5 Hz, 3H). |
| 1-5-003a | δ 9.38 (d, J = 7.5 Hz, 1H), 8.59 (s, 2H), 8.10 (s, 1H), 7.82 (d, J = 9.5H 1H), 7.40 (dd, J = 9.5, 2.0 Hz, 1H), 7.22 (dd, J = 7.5, 2.0 Hz, 1H), 3.66 (q J = 7.4 Hz, 2H), 1.31 (t, J = 7.4 Hz, 3H). |
| 1-5-004a | δ 9.64 (s, 1H), 8.61 (s, 1H), 8.59 (s, 1H), 7.91 (d, J = 9.6 Hz, 1H) 7.80 (d, J = 9.6 Hz, 1H), 7.63 (dd, J = 9.6, 1.8 Hz, 1H), 7.39 (dd, J = 9.6, 1.8 Hz 1H), 3.64 (q, J = 7.5 Hz, 2H), 1.31 (t, J = 7.5 Hz, 3H). |
| 1-6-001a | δ 9.38 (d, J = 7.5 Hz, 1H), 9.24 (s, 1H), 8.66 (s, 1H), 8.62 (s, 1H) 8.13-8.08 (m, 1H), 7.26 (dd, J = 7.5, 1.9 Hz, 1H), 3.74 (q, J = 7.4 Hz, 2H), 1.35 (J = 7.4 Hz, 3H). |
| 1-6-002a | δ 0.63 (s, 1H), 9.24 (s, 1H), 8.68 (s, 1H), 8.62 (s, 1H), 7.93 (d J = 9.3 Hz, 1H), 7.66 (dd, J = 9.3, 1.8 Hz, 1H), 3.70 (q, J = 7.5 Hz, 2H), 1.35 (t J = 7.5 Hz, 3H). |
| 1-7-001a | δ 9.42 (d, J = 7.5 Hz, 1H), 8.15 (d, J = 1.7 Hz, 1H), 7.96 (d, J = 8.2 Hz 1H), 7.75 (d, J = 8.2 Hz, 1H), 7.32 (dd, J = 7.5, 1.7 Hz, 1H), 4.23 (q, J = 7.4 Hz 2H), 4.14 (s, 3H), 1.46 (t, J = 7.4 Hz, 3H). |

TABLE 33-continued

| No. | $^1$H NMR (CDCl$_3$, Me$_4$Si, 300 MHz). |
|---|---|
| 1-8-002a | δ 9.63 (s, 1H), 9.00 (s, 1H), 8.15 (s, 1H), 7.95 (d, J = 9.6 Hz, 1H), 7.73 (dd, J = 9.6, 1.5 Hz, 1H), 4.19 (s, 3H), 4.06 (q, J = 7.5 Hz, 2H), 1.47 (t, J = 7.5 Hz, 3H). |
| 1-8-002b | δ 9.03 (s, 1H), 8.97 (s, 1H), 8.20 (s, 1H), 7.82 (d, J = 9.6 Hz, 1H), 7.54 (dd, J = 9.6, 1.5 Hz, 1H), 4.36 (s, 3H), 3.15 (q, J = 7.5 Hz, 2H), 1.23 (t, J = 7.5 Hz, 3H). |
| 1-8-006a | δ 9.17 (d, J = 7.5 Hz, 1H), 8.99 (s, 1H), 8.14 (s, 1H), 7.84 (d, J = 2.4 Hz 1H), 7.15 (dd, J = 7.5, 2.4 Hz, 1H), 4.17 (s, 3H), 3.99 (q, J = 7.5 Hz, 2H), 1.43 (t J = 7.5 Hz, 3H). |
| 1-8-006b | δ 8.95 (s, 1H), 8.59 (d, J = 7.5 Hz, 1H), 8.19 (s, 1H), 7.74-7.71 (m, 1H), 7.03 (dd, J = 7.5, 2.1 Hz, 1H), 4.33 (s, 3H), 3.09 (q, J = 7.5 Hz, 2H), 1.19 (t J = 7.5 Hz, 3H). |
| 1-8-007a | δ 9.47 (s, 1H), 8.98 (s, 1H), 8.14 (s, 1H), 7.76 (dd, J = 9.3, 1.2 Hz, 1H), 7.61 (d, J = 9.3 Hz, 1H), 4.15 (s, 3H), 3.98 (q, J = 7.5 Hz, 2H), 1.45 (t, J-7.5 Hz, 3H). |
| 1-8-007b | δ 8.95 (s, 1H), 8.90 (s, 1H), 8.19 (s, 1H), 7.57 (dd, J = 9.3, 1.2 Hz, 1H), 7.50 (d, J = 9.3 Hz, 1H), 4.33 (s, 3H), 3.10 (q, J = 7.5 Hz, 2H), 1.21 (t, J = 7.5 Hz, 3H). |
| 1-8-008a | δ 9.32-9.31 (m, 1H), 8.99 (s, 1H), 8.14 (d, J = 1.2 Hz, 1H), 7.53 (dd, J = 8.3, 1.2 Hz, 1H), 4.19 (s, 3H), 4.05 (q, J = 7.5 Hz, 2H), 1.46 (t, J = 7.5 Hz, 3H). |
| 1-8-009a | δ 8.88 (d, J = 1.4 Hz, 1H), 8.85 (s, 1H), 7.99-7.97 (m, 1H), 6.94 (d, J = 1.4 Hz, 1H), 4.20 (q, J-7.0 Hz, 2H), 3.99 (s, 3H), 3.76 (q, J-7.4 Hz, 2H), 1.47 (t, J = 7.0 Hz, 3H), 1.30 (t, J = 7.4 Hz, 3H). |
| 1-8-010a | δ 9.00-8.90 (m, 2H), 8.30-8.25 (m, 1H), 8.15-8.10 (m, 1H), 7.40 (dd, J = 7.4, 1.6 Hz, 1H), 4.15 (s, 3H), 3.98 (q, J = 7.4 Hz, 2H), 1.43 (t, J = 7.4 Hz, 3H). |
| 1-8-011a | δ 9.25-9.20 (m, 1H), 9.00-8.95 (m, 1H), 8.15-8.10 (m, 1H), 7.43 (dd, J = 8.6, 1.6 Hz, 1H), 4.20 (s, 3H), 4.12 (q, J = 7.4 Hz, 2H), 1.47 (t, J = 7.4 Hz, 3H). |
| 1-8-013a | δ 9.39 (dd, J = 1. 7. 0. 7 Hz, 1H), 8.99 (s, 1H), 8.14 (d, J = 0.7 Hz, 1H), 7.74 (dd, J = 9.5, 0.7 Hz, 1H), 7.66 (dd, J = 9.5, 1.7 Hz, 1 Hz), 4.17 (s, 3H), 4.01 (q, J = 7.5 Hz, 2H), 1.47 (t, J = 7.5 Hz, 3H). |
| 1-8-013b | δ 8.95 (s, 1H), 8.80 (dd, J = 9.5, 2.0 Hz, 1H), 8.19 (d, J = 0.9 Hz, 1H), 7.62 (dd, J = 9.5, 0.9 Hz, 1H), 7.46 (dd, J = 9.5, 2.0 Hz, 1H), 4.36 (s, 3H), 3.11 (q, J = 7.4 Hz, 2H), 1.22 (t, J = 7.4 Hz, 3H). |
| 1-8-013c | δ 9.65 (dd, J = 1.9, 0.9 Hz, 1H), 8.97 (s, 1H), 8.10 (d, J = 0.9 Hz, 1H), 7.66 (dd, J = 9.5, 0.9 Hz, 1H), 7.52 (dd, J = 9.7, 1.9 Hz, 1H), 4.49 (s, 3H), 3.77-3.64 (m, 1H), 3.63-3.52 (m, 1H), 1.58 (t, J = 7.3 Hz, 3H). |
| 1-8-014a | δ 9.68 (s, 1H), 9.02 (s, 1H), 8.20 (s, 1H), 8.15 (s, 1H), 4.20 (s, 3H), 4.12 (q, J = 7.2 Hz, 2H), 1.48 (t, J = 7.2 Hz, 3H). |
| 1-8-014b | δ 9.04 (s, 1H), 9.00 (s, 1H), 8.18 (s, 1H), 8.13 (s, 1H), 4.37 (s, 3H), 3.19 (q, J = 7.3 Hz, 2H), 1.23 (t, J = 7.3 Hz, 3H). |
| 1-8-015a | δ 9.55 (d, J = 6.1 Hz, 1H), 9.00 (s, 1H), 8.14 (s, 1H), 7.52 (d, J = 7.4 Hz, 1H), 4.18 (s, 3H), 4.03 (q, J = 7.4 Hz, 2H), 1.46 (t, J = 7.4 Hz, 3H). |
| 1-8-015b | δ 8.96-8.92 (m, 2H), 8.19-8.18 (m, 1H), 7.40 (d, J = 8.2 Hz, 1H), 4.34 (s, 3H), 3.11 (q, J = 7.4 Hz, 2H), 1.22 (t, J = 7.3 Hz, 3H). |
| 1-8-016a | δ 9.29 (d, J = 2.0 Hz, 1H), 9.00-8.95 (m, 1H), 8.15-8.10 (m, 1H), 7.78 (d, J = 9.5 Hz, 1H), 7.55 (dd, J = 9.5, 2.0 Hz, 1H), 4.16 (s, 3H, 4.00 (q, J = 7.4 Hz, 2H), 1.45 (t, J = 7.4 Hz, 3H). |
| 1-8-016b | δ 8.95-8.90 (m, 1H), 8.68 (d, J = 2.0 Hz, 1H), 8.20-8.15 (m, 1H), 7.66 (d, J = 9.4 Hz, 1H), 7.36 (dd, J = 9.4, 2.0 Hz, 1H), 4.34 (s, 3H), 3.10 (q, J = 7.4 Hz, 2H), 1.21 (t, J = 7.4 Hz, 3H). |
| 1-9-001a | δ 9.63 (s, 1H), 9.21 (s, 1H), 7.95 (d, J = 9.6 Hz, 1H), 7.85 (s, 1H), 7.72 (d, J = 9.6 Hz, 1H), 4.11 (s, 3H), 4.06 (q, J = 7.5 Hz, 2H), 1.47 (t, J = 7.5 Hz, 3H). |
| 1-9-001b | δ 9.26 (s, 1H), 9.03 (s, 1H), 7.83 (s, 1H), 7.82 (d, J = 9.6 Hz, 1H), 7.54 (d, J = 9.6 Hz, 1H), 4.29 (s, 3H), 3.16 (q, J = 7.5 Hz, 2H), 1.23 (t, J = 7.5 Hz, 3H). |
| 1-9-002a | δ 9.39 (d, J = 7.8 Hz, 1H), 9.20 (s, 1H), 8.14 (s, 1H), 7.85 (s, 1H), 7.32 (dd, J = 7.8, 1.5 Hz, 1H), 4.12 (s, 3H), 4.07 (q, J = 7.5 Hz, 2H), 1.46 (t, J = 7.5 Hz, 3H). |
| 1-9-002b | δ 9.25 (s, 1H), 8.77 (d, J = 7.2 Hz, 1H), 8.04 (s, 1H), 7.82 (s, 1H), 7.20 (dd, J = 7.2, 1.2 Hz, 1H), 4.29 (s, 3H), 3.16 (q, J = 7.5 Hz, 2H), 1.22 (t, J = 7.5 Hz, 3H). |
| 1-9-003a | δ 9.19 (s, 1H), 9.17 (d, J = 7.5 Hz, 1H), 7.85-7.81 (m, 2H), 7.14 (dd, J = 7.5, 2.4 Hz, 1H), 4.08 (s, 3H), 4.00 (q, J = 7.5 Hz, 2H), 1.44 (t, J = 7.5 Hz, 3H). |
| 1-9-003b | δ 9.24 (s, 1H), 8.59 (dd, J = 7.2, 0.6 Hz, 1H), 7.81 (s, 1H), 7.73-7.69 (m, 1H), 7.03 (dd, J = 7.2, 1.8 Hz, 1H), 4.26 (s, 3H), 3.10 (q, J = 7.5 Hz 2H), 1.20 (t, J = 7.5 Hz, 3H). |
| 1-10-001a | δ 9.44 (d, J = 7.2 Hz, 1H), 8.86 (d, J = 0.7 Hz, 1H), 8.12-8.04 (m, 2H), 7.87 (d, J = 8.9 Hz, 1H), 7.33-7.28 (m, 2H), 4.08 (s, 3H), 1.47 (t, J = 7.5 Hz, 3H). |
| 1-10-001b | δ 9.08 (d, J = 0.7 Hz, 1H), 8.75 (d, J = 7.2 Hz, 1H), 8.20-8.17 (m, 1H), 8.00-7.97 (m, 1H), 7.87 (d, J = 8.9 Hz, 1H), 7.29 (dd, J = 8.9, 1.4 Hz, 1H), 7.22 (dd, J = 7.2, 1.9 Hz, 1H), 3.00 (q, J = 7.4 Hz, 2H), 1.20 (t, J = 7.4 Hz, 3H). |

TABLE 33-continued

| No. | $^1$H NMR (CDCl$_3$, Me$_4$Si, 300 MHz). |
|---|---|
| 1-10-001c | δ 9.57 (d, J = 7.2 Hz, 1H), 8.99 (d, J = 1.0 Hz, 1H), 8.09-8.05 (m, 1H), 8.01 7.97 (m, 1H), 7.87 (d, J = 8.9 Hz, 1H), 7.31 (dd, J = 8.9, 1.4 Hz, 1H), 7.16 (dd, J = 7.2, 1.9 Hz, 1H), 3.73-3.46 (m, 2H), 1.55 (t, J = 7.5 Hz, 3H). |
| 1-10-002c | δ 9.57 (d, J = 7.4 Hz, 1H), 9.30 (d, J = 0.9 Hz, 1H), 8.85 (d, J = 1.5 Hz, 1H), 8.44-8.41 (m, 1H), 8.05-8.02 (m, 1H), 7.19 (dd, J = 7.4, 2.3 Hz, 1H), 3.70-3.43 (m, 2H), 1.55 (t, J = 7.4 Hz, 3H). |
| 1-10-003a | δ 9.52-9.50 (m, 1H), 9.13-9.12 (m, 1H), 8.86-8.84 (m, 1H), 8.45-8.43 (m, 1H), 7.80 (dd, J = 9.2, 1.5 Hz, 1H), 7.58 (dd, J = 9.2, 0.9 Hz, 1H), 3.97 (q, J = 7.5 Hz, 2H), 1.48 (t, J = 7.5 Hz, 3H). |
| 1-10-003b | δ 9.40 (s, 1H), 8.86-8.85 (m, 1H), 8.83 (d, J = 2.1 Hz, 1H), 8.50-8.48 (m, 1H), 7.62 (dd, J = 9.2, 1.5 Hz, 1H), 7.51 (d, J = 9.2 Hz, 1H), 2.94 (q J = 7.4 Hz, 2H), 1.20 (t, J = 7.4 Hz, 3H). |
| 1-11-001c | δ 9.58 (d, J = 7.4 Hz, 1H), 9.38 (s, 1H), 9.23 (d, J = 0.9 Hz, 1H), 8.06 (s, 1H), 8.04-8.01 (m, 1H), 7.25-7.17 (m, 1H), 3.75-3.45 (m, 2H), 1.53 (t J = 7.4 Hz, 3H). |
| 1-11-002a | δ 9.40-9.35 (m, 1H), 9.05-9.00 (m, 1H), 8.99 (d, J = 7.4 Hz, 1H), 8.25-8.20 (m, 1H), 8.10-8.05 (m, 1H), 7.43 (dd, J = 7.4, 1.8 Hz, 1H), 3.95 (q, J = 7.4 Hz, 2H), 1.44 (t, J = 7.4 Hz, 3H). |
| 1-11-003a | δ 9.51-9.48 (m, 1H), 9.38 (s, 1H), 9.03-9.01 (m, 1H), 8.07 (s, 1H), 7.81 (dd, J = 9.3, 1.7 Hz, 1H), 7.58 (d, J = 9.3 Hz, 1H), 3.95 (q, J = 7.4 Hz, 2H), 1.47 (t, J = 7.4 Hz, 3H). |
| 1-13-003b | δ 9.36 (s, 1H), 9.27 (s, 1H), 8.87-8.85 (m, 1H), 8.13 (s, 1H), 7.62 (dd, J = 9.2, 0.9 Hz, 1H), 7.49 (d, J = 9.2 Hz, 1H), 2.97 (q, J = 7.4 Hz, 2H), 1.20 (t, J = 7.4 Hz, 3H). |
| 1-11-004a | δ 9.69-9.66 (m, 1H), 9.40 (d, J-1.0 Hz, 1H), 9.08 (d, J-1.0 Hz, 1H), 8.09 (s, 1H), 7.93 (d, J = 9.5 Hz, 1H), 7.78 (dd, J = 9.5, 1.7 Hz, 1H), 4.03 (q, J = 7.5 Hz, 2H), 1.50 (t, J = 7.5 Hz, 3H). |
| 1-11-004b | δ 9.38 (dd, J = 1.4, 0.7 Hz, 1H), 9.30 (d, J = 1.0 Hz, 1H), 9.02-8.99 (m 1H), 8.15 (s, 1H), 7.85-7.80 (m, 1H), 7.60 (dd, J = 9.3, 1.7 Hz, 1H), 3.03 (q, J = 7.4 Hz, 2H), 1.23 (t, J = 7.4 Hz, 3H). |
| 1-11-004c | δ 9.87-9.85 (m, 1H), 9.38 (s, 1H), 9.23 (d, J = 1.0 Hz, 1H), 8.05 (s, 1H), 7.83 (d, J = 9.5 Hz, 1H), 7.64 (dd, J = 9.5, 1.7 Hz, 1H), 3.72-3.47 (m, 2H), 1.57 (t, J = 7.5 Hz, 3H). |
| 1-11-005a | δ 9.40-9.35 (m, 1H), 9.30-9.25 (m, 1H), 9.10-9.05 (m, 1H), 8.06 (s, 1H), 7.48 (dd, J = 8.6, 1.6 Hz, 1H), 4.02 (q, J = 7.4 Hz, 2H), 1.49 (t, J = 7.4 Hz, 3H). |
| 1-11-005b | δ 9.40-9.30 (m, 1H), 9.25 (d, J = 1.0 Hz, 1H), 8.65-8.60 (m, 1H), 8.15-8.10 (m, 1H), 7.30 (dd, J = 8.9, 1.7 Hz, 1H), 3.04 (q, J = 7.4 Hz, 2H), 1.23 (t J = 7.4 Hz, 3H). |
| 1-11-006a | δ 9.39-9.37 (m, 1H), 9.35 (s, 1H), 9.08 (d, J = 1.4 Hz, 1H) 8.07 (s, 1H), 7.58 (dd, J = 8.2, 1.4 Hz, 1H), 4.03 (q, J = 7.5 Hz, 2H), 1.50 (t, J = 7.5 Hz, 3H). |
| 1-11-006b | δ 9.36 (s, 1H), 9.27 (s, 1H), 8.72 (d, J-1.4 Hz, 1H), 8.14 (s, 1H), 7.40 (dd, J = 8.9, 1.4 Hz, 1H), 3.05 (q, J = 7.5 Hz, 2H), 1.23 (t, J = 7.5 Hz, 3H). |
| 1-11-007a | δ 9.42-9.41 (m, 1H), 9.39-9.37 (m, 1H), 9.03 (d, J = 1.0 Hz, 1H), 8.08 (s, 1H), 7.71-7.69 (m, 2H), 3.96 (q, J = 7.5 Hz, 2H), 1.48 (t, J = 7.5 Hz, 3H). |
| 1-11-007b | δ 9.38-9.36 (m, 1H), 9.27 (d, J = 1.0 Hz, 1H), 8.77 (d, J = 1.0 Hz, 1H), 8.14 (s, 1H), 7.61 (d, J = 9.5 Hz, 1H), 7.52 (dd, J = 9.5, 1.9 Hz, 1H), 2.98 (q, J = 7.4 Hz, 2H), 1.22 (t, J = 7.4 Hz, 3H). |
| 1-11-007c | δ 9.58 (d, J = 1.0 Hz, 1H), 9.37 (s, 1H), 9.19 (s, 1H), 8.05 (s, 1H), 7.62 (d, J = 9.5 Hz, 1H), 7.56 (dd, J = 9.5, 1.4 Hz, 1H), 3.71-3.44 (m, 2H), 1.56 (t J = 7.3 Hz, 3H). |
| 1-12-002a | δ 9.59 (s, 1H), 8.45 (s, 1H), 7.94-7.92 (m, 1H), 7.86 (d, J = 9.6 Hz, 1H), 7.61 (dd, J = 9.6, 2.1 Hz, 1H), 3.60 (q, J = 7.5 Hz, 2H), 1.31 (t, J = 7.5 Hz, 3H). |
| 1-12-003a | δ 9.62 (s, 1H), 8.30 (s, 1H), 7.85 (d, J = 9.6 Hz, 1H), 7.61 (dd, J = 9.6 1.5 Hz, 1H), 3.69 (q, J = 7.5 Hz, 2H), 2.61 (s, 3H), 1.32 (t, J = 7.5 Hz, 3H). |
| 1-12-004a | δ 9.35 (d, J = 7.5 Hz, 1H), 8.42 (s, 1H), 8.04 (s, 1H), 7.96 (d, J = 1.7 Hz, 1H), 7.20 (dd, J = 7.5, 1.7 Hz, 1H), 3.62 (q, J = 7.4 Hz, 2H), 1.30 (t, J = 7.4 Hz, 3H). |
| 1-12-005a | δ 9.37 (d, J = 7.5 Hz, 1H), 8.28 (s, 1H), 8.04-8.02 (m, 1H), 7.20 (dd, J = 7.5, 1.9 Hz, 1H), 3.72 (q, J = 7.4 Hz, 2H), 2.63 (s, 3H), 1.32 (t, J = 7.4 Hz, 3H). |
| 1-12-006a | δ 9.61 (s, 1H), 8.78 (s, 1H), 7.87 (d, J = 9.6 Hz, 1H), 7.63 (dd, J = 9.6 1.8 Hz, 1H), 3.63 (q, J = 7.5 Hz, 2H), 1.33 (t, J = 7.5 Hz, 3H). |
| 1-12-007a | δ 9.60 (s, 1H), 8.81 (s, 1H), 7.87 (d, J = 9.6 Hz, 1H), 7.63 (dd, J = 9.6 1.8 Hz, 1H), 3.62 (q, J = 7.5 Hz, 2H), 1.33 (t, J = 7.5 Hz, 3H). |
| 1-12-008a | δ 9.35 (d, J = 7.5 Hz, 1H), 8.77 (s, 1H), 8.08-8.04 (m, 1H), 7.22 (dd, J = 7.5, 1.9 Hz, 1H), 3.64 (q, J = 7.4 Hz, 2H), 1.32 (t, J = 7.4 Hz, 3H). |
| 1-12-009a | δ 9.43 (dd, J = 1.5, 0.9 Hz, 1H), 8.77 (s, 1H), 7.67 (dd, J = 9.4, 1.5 Hz 1H), 7.56 (dd, J-9.4, 0.9 Hz, 1H), 3.56 (q, J-7.5 Hz, 2H), 1.32 (t, J-7.5 Hz, 3H). |
| 1-15-002a | δ 9.43 (d, J = 7.5 Hz, 1H), 8.15-8.12 (m, 1H), 7.79 (s, 1H), 7.73 (s, 1H), 7.31 (dd, J = 7.5, 1.9 Hz, 1H), 4.27 (q, J = 7.4 Hz, 2H), 4.14 (s, 3H), 1.50 (t J = 7.4 Hz, 3H). |
| 1-15-002b | δ 8.79 (d, J = 7.4 Hz, 1H), 8.02 (s, 1H), 7.77 (s, 1H), 7.70 (s, 1H), 7.19 (dd, J = 7.4, 1.7 Hz, 1H), 4.26 (s, 3H), 3.35 (q, J = 7.4 Hz, 2H), 1.29 (t, J = 7.4 Hz, 3H). |

TABLE 33-continued

| No. | $^1$H NMR (CDCl$_3$, Me$_4$Si, 300 MHz). |
|---|---|
| 1-15-003a | δ 9.35 (d, J = 7.5 Hz, 1H), 8.15 (s, 1H), 8.04 (s, 1H), 7.76 (s, 1H), 7.36-7.29 (m, 1H), 4.31 (s, 3H), 3.98 (q, J = 7.4 Hz, 2H), 1.44 (t, J = 7.4 Hz, 3H). |
| 1-17-001a | δ 9.46 (s, 1H), 8.85-8.81 (m, 1H), 8.78 (d, J = 2.4 Hz, 1H), 7.70 (dd, J = 9.6, 1.5 Hz, 1H), 7.62 (d, J = 9.3 Hz, 1H), 4.05 (q, J = 7.5 Hz, 2H), 1.45 (t, J = 7.5 Hz, 3H). |
| 2-1-001a | δ 8.76-8.73 (m, 1H), 8.71-8.67 (m, 1H), 8.35-8.32 (m, 1H), 4.22 (s, 3H), 4.19 (q, J = 7.4 Hz, 2H), 1.45 (t, J = 7.4 Hz, 3H). |
| 2-1-001b | δ 8.66-8.64 (m, 1H), 8.36-8.34 (m, 1H), 8.11-8.09 (m, 1H), 4.24 (s, 3H), 3.14 (q, J = 7.4 Hz, 2H), 1.25 (t, J = 7.4 Hz, 3H). |
| 3-1-001c | δ 8.83 (d, J = 1.4 Hz, 1H), 8.57 (brs, 1H), 8.41 (d, J = 1.7 Hz, 1H), 7.72 (dd, J = 8.9, 1.4 Hz, 1H), 7.63 (d, J = 8.9 Hz, 1H), 4.00 (s, 3H), 3.82 (s, 3H), 3.41-3.09 (m, 2H), 1.19 (t, J = 7.3 Hz, 3H). |
| 3-1-002c | δ 9.16 (s, 1H), 8.78 (s, 1H), 8.36 (s, 1H), 8.10 (d, J = 8.6 Hz, 1H), 7.79 (d, J = 8.6 Hz, 1H), 4.12 (s, 3H), 3.64-3.46 (m, 2H), 1.49 (t, J = 7.5 Hz, 3H). |
| i-1-012 | δ 8.03 (d, J = 1.8 Hz, 1H), 7.58 (d, J = 9.9 Hz, 1H), 7.40 (d, J = 2.4 Hz, 1H), 4.48 (q, J-7.2 Hz, 2H), 3.89 (s, 3H), 2.94 (q, J-7.2 Hz, 2H), 1.46 (t, J = 7.5 Hz, 3H), 1.19 (t, J = 7.5 Hz, 3H). |
| i-1-020 | δ 8.29 (d, J = 6.6 Hz, 1H), 8.10 (d, J = 0.9 Hz, 1H), 7.217 (dd, J = 7.2, 1.5 Hz, 1H), 4.49 (q, J = 7.2 Hz, 2H), 2.93 (q, J = 7.2 Hz, 2H), 1.47 (t, J = 7.5 Hz, 3H), 1.18 (t, J = 7.5 Hz, 3H). |
| i-1-025 | δ 8.73 (d, J = 1.4 Hz, 1H), 7.62 (d, J = 1.4 Hz, 1H), 4.51 (q, J = 7.0 Hz, 2H), 2.97 (q, J = 7.4 Hz, 2H), 1.37 (t, J = 7.0 Hz, 3H), 1.21 (t, J = 7.4 Hz, 3H), |
| i-5-005 | δ 9.13 (brs, 1H), 8.37 (s, 1H), 7.91 (s, 1H), 7.87 (d, J = 8.9 Hz, 1H), 7.58 (d, J = 6.8 Hz, 1H), 7.46-7.40 (m, 1H), 5.24 (brs, 1H), 3.10 (d, J = 4.8 Hz, 3H), 3.06 (q, J = 7.5 Hz, 2H), 1.27 (t, J = 7.5 Hz, 3H). |
| i-7-003 | δ 7.95 (d, J = 7.0 Hz, 1H), 7.69 (s, 1H), 7.04 (d, J = 7.0 Hz, 1H), 4.35 (brs, 2H), 2.58 (q, J = 7.4 Hz, 2H), 1.19 (t, J = 7.4 Hz, 3H). |
| i-7-004 | δ 8.56 (s, 1H), 7.42 (d, J = 9.2 Hz, 1H), 7.32 (dd, J = 9.2, 1.7 Hz, 1H), 4.42 (brs, 2H), 2.65 (q, J = 7.3 Hz, 2H), 1.24 (t, J -7.3 Hz, 3H). |
| i-7-005 | δ 8.17 (d, J = 1.6 Hz, 1H), 7.04 (dd, J = 9.4, 1.6 Hz, 1H), 4.38 (brs, 2H), 2.63 (q, J = 7.4 Hz, 2H), 1.22 (t, J = 7.4 Hz, 3H). |

Now, usefulness of the compounds of the present invention as pesticides will be described in detail by referring to the following Test Examples, but the present invention is by no means restricted thereto.

Test Example 1: Insecticidal Test on *Nilaparvata lugens*

10% emulsifiable concentrates (or 10% wettable powders) of compounds of the present invention were diluted with water containing a spreader to obtain 500 ppm solutions. Rice sheaths were soaked in the solutions for about 10 seconds. After the soaking, the rice sheaths were dried in air and put in test tubes. In each tube, five 3rd-instar larvae of *Nilaparvata lugens* were released, and the tubes were capped with sponge and placed in an incubator at 25° C. 6 Days after, dead insects in the test tubes were counted, and the mortality (%) (the number of dead insects÷the number of released insects×100) was calculated. The test was carried out in duplicate.

Among the compounds tested, the following compounds showed a mortality of at least 90%.

Compounds Nos. 1-1-001a, 1-1-002a, 1-1-005a, 1-1-006a, 1-1-009a, 1-1-015a, 1-1-020a, 1-1-023a, 1-1-024a, 1-1-035a, 1-1-036a, 1-1-038a, 1-1-039a, 1-1-040a, 1-1-042a, 1-1-043a, 1-1-044a, 1-1-049a, 1-1-052a, 1-1-057a, 1-1-057c, 1-1-058a, 1-1-064a, 1-1-072a, 1-1-074a, 1-1-095a, 1-1-096a, 1-1-097a, 1-1-099a, 1-1-100a, 1-1-105a, 1-1-106a, 1-1-116a, 1-1-117a, 1-1-122a, 1-1-123a, 1-2-001a, 1-2-002a, 1-3-001a, 1-3-003a, 1-3-005a, 1-3-007a, 1-4-002a, 1-5-002a, 1-8-002a, 1-8-005a, 1-8-010a, 1-9-002a, 1-11-001a, 1-11-001b, 1-11-002a, 1-11-003a, 1-11-004a, 1-11004b, 1-12-003a, 1-12-004a, 1-12-006a, 1-12-007a, 1-12-008a, 1-12-009a, 1-14-001a, 1-16-001a, 1-16-001 b, 2-1-001a and 3-1-002a of the present invention.

Test Example 2: Insecticidal Test on *Plutella xylostella*

10% emulsifiable concentrates (or 10% wettable powders) of compounds of the present invention were diluted with water containing a spreader to obtain 500 ppm solutions. Leaves of cabbage were soaked in the solutions for about 10 seconds. After the soaking, the leaves were dried in air and placed in dishes. In each dish, five 3rd-instar larvae of *Plutella xylostella* were released, and the dishes were covered with lids and placed in an incubator at 25° C. 6 Days after, dead insects in the dishes were counted, and the mortality was calculated by using the same equation as in Test Example 1. The test was carried out in duplicate.

Among the compounds tested, the following compounds showed a mortality of at least 90%.

Compounds Nos. 1-1-001a, 1-1-001b, 1-1-001c, 1-1-002a, 1-1-002b, 1-1-003a, 1-1-003c, 1-1-004a, 1-1-005a, 1-1-005c, 1-1-006a, 1-1-007a, 1-1-008a, 1-1-009a, 1-1-0l1a, 1-1-012a, 1-1-012b, 1-1-013a, 1-1-013b, 1-1-013c, 1-1-014a, 1-1-014b, 1-1-014c, 1-1-015a, 1-1-015b, 1-1-016a, 1-1-016b, 1-1-016c, 1-1-017a, 1-1-018a, 1-1-019a, 1-1-020a, 1-1-020b, 1-1-021 b, 1-1-022a, 1-1-023a, 1-1-023b, 1-1-023c, 1-1-024a, 1-1-026a, 1-1-027a, 1-1-027b, 1-1-029a, 1-1-030a, 1-1-030b, 1-1-030c, 1-1-032a, 1-1-033a, 1-1-034a, 1-1-035a, 1-1-036a, 1-1-037a, 1-1-038a, 1-1-039a, 1-1-040a, 1-1-040c, 1-1-041a, 1-1-042a, 1-1-043a, 1-1-044a, 1-1-045a, 1-1-045b, 1-1-046a, 1-1-047a, 1-1-048a, 1-1-049a, 1-1-049b, 1-1-050a, 1-1-050b, 1-1-051a, 1-1-051b, 1-1-052a, 1-1-052b, 1-1-053a, 1-1-054a, 1-1-055a, 1-1-056a, 1-1-057a, 1-1-057c, 1-1-058a, 1-1-058b, 1-1-059a, 1-1-060a, 1-1-060b, 1-1-061a, 1-1-062a, 1-1-063a, 1-1-063b, 1-1-064a, 1-1-065a, 1-1-066a, 1-1-067a, 1-1-068a, 1-1-069a, 1-1-069b, 1-1-070a, 1-1-070b, 1-1-071a, 1-1-072a, 1-1-072b, 1-1-072c, 1-1-073b, 1-1-074a, 1-1-076a, 1-1-077a, 1-1-077b, 1-1-080a, 1-1-081a, 1-1-

082a, 1-1-083a, 1-1-084a, 1-1-085a, 1-1-086a, 1-1-087a, 1-1-088a, 1-1-089a, 1-1-090a, 1-1-091a, 1-1-092a, 1-1-093a, 1-1-093b, 1-1-094a, 1-1-094b, 1-1-094c, 1-1-095a, 1-1-096a, 1-1-097a, 1-1-099a, 1-1-100a, 1-1-101a, 1-1-10b, 1-1-103a, 1-1-103b, 1-1-104a, 1-1-105a, 1-1-105b, 1-1-105c, 1-1-106a, 1-1-106b, 1-1-106c, 1-1-107a, 1-1-108a, 1-1-109a, 1-1-109b, 1-1-111a, 1-1-110c, 1-1-111a, 1-1-112a, 1-1-112b, 1-1-113a, 1-1-113b, 120c, 1-1-121a, 1-1-122a, 1-1-123a, 1-2-001a, 1-2-002a, 1-2-004a, 1-2-004b, 1-2-004c, 1-2-005a, 1-2-006a, 1-3-001a, 1-3-002a, 1-3-003a, 1-3-004a, 1-3-005a, 1-3-006a, 1-3-007a, 1-3-008a, 1-3-009a, 1-010a, 1-3-011a, 1-3-012a, 1-3-013a, 1-3-014a, 1-4-001a, 1-4-002a, 1-003a, 1-003b, 1-5-001a, 1-5-002a, 1-5-003a, 1-5-004a, 1-6-001a, 1-6-002a, 1-7-001a, 1-8-002b, 1-8-002a, 1-8-002b, 198-003a, 1-8-003b, 1-8-004b, 1-8-005a, 1-005b, 1-006a, 1-8-006b, 1-8-007a, 1-008a, 1-8-009a, 1-8-010a, 1-8-011a, 1-8-013a, 1-8-013b, 1-8-014a, 1-8-014b, 1-8-015a, 1-8-105b, 1-9-002a, 1-9-002b, 1-9-003a, 1-9-003b, 1-10-001a, 1-10-001b, 1-10-001c, 1-10-002a, 1-10-002b, 1-10-002c, 1-10-003a, 1-11-001a, 1-11-001b, 1-11-001c, 1-11-002a, 1-11-003a, 1-11-003b, 1-11-04a, 1-11-004b, 1-11-004c, 1-11-005a, 1-11-005b, 1-11-006a, 1-11-006b, 1-11-007a, 1-11-007b, 1-11-007c, 1-12-001a, 1-12-002a, 1-12-003a, 1-12-004a, 1-12-005a, 1-12-006a, 1-12-007a, 1-12-008a, 1-12-009a, 1-13-001a, 1-14-001a, 1-15-002a, 1-15-003a, 1-16-001a, 1-16-001b, 2-1-001a, 2-1-001b, 2-1-002a, 3-1-001a, 3-1-001b, 3-1-001c, 3-1-002a, 3-1-002b and 3-1-002c of the present invention.

Test Example 3: Insecticidal Test on *Spodoptera litura*

10% emulsifiable concentrates (or 10% wettable powders) of compounds of the present invention were diluted with water containing a spreader to obtain 500 ppm solutions. Leaves of cabbage were soaked in the solutions for about 10 seconds. After the soaking, the leaves were dried in air and placed in dishes. In each dish, five 3rd-instar larvae of *Spodoptera litura* were released, and the dishes were covered with lids and placed in an incubator at 25° C. 6 Days after, dead insects in the dishes were counted, and the mortality was calculated by using the same equation as in Test Example 1. The test was carried out in duplicate.

Among the compounds tested, the following compounds showed a mortality of at least 90%.

Compounds Nos. 1-1-001a, 1-1-001b, 1-1-001c, 1-1-002a, 1-1-002b, 1-1-003a, 1-1-004a, 1-1-005a, 1-1-005c, 1-1-006a, 1-1-007a, 1-1-009a, 1-1-011a, 1-1-012a, 1-1-013a, 1-1-013b, 1-1-013c, 1-1-014a, 1-1-014c, 1-1-015a, 1-1-015b, 1-1-016a, 1-1-016b, 1-1-016c, 1-1-017a, 1-1-018a, 1-1-019a, 1-1-020a, 1-1-020b, 1-1-023a, 1-1-023b, 1-1-023c, 1-1-024a, 1-1-026a, 1-1-027a, 1-1-027b, 1-1-029a, 1-1-030a, 1-1-030b, 1-1-030c, 1-1-032a, 1-1-033a, 1-1-034a, 1-1-036a, 1-1-037a, 1-1038a, 1-1-039a, 1-1-040a, 1-1-040c, 1-1-041a, 1-1-042a, 1-1-043a, 1-1-044a, 1-1-045a, 1-1-045b, 1-1-046a, 1-1-047a, 1-1-048a, 1-1-049a, 1-1-049b, 1-1-050a, 1-1-051a, 1-1-051b, 1-1-052a, 1-1-053a, 1-1-056a, 1-1-057a, 1-1-057c, 1-1-058a, 1-1-059a, 1-1-060a, 1-1-061a, 1-1-062a, 1-1-063a, 1-1-064a, 1-1-065a, 1-1-066a, 1-1-067a, 1-1-068a, 1-1-069a, 1-1-070a, 1-1-070b, 1-1-071a, 1-1-072a, 1-1-072b, 1-1-072c, 1-1-074a, 1-1-076a, 1-1-077a, 1-1-077b, 1-1-080a, 1-1-081a, 1-1-082a, 1-1-083a, 1-1-084a, 1-1-085a, 1-1-087a, 1-1-089a, 1-1-090a, 1-1-091a, 1-1-092a, 1-1-093a, 1-1-093b, 1-1-094a, 1-1-094b, 1-1-094c, 1-1-095a, 1-1-096a, 1-1-097a, 1-1-099a, 1-1-100a, 1-1-101a, 1-1-103a, 1-1-103b, 1-1-104a, 1-1-105a, 1-1-105b, 1-1-106a, 1-1-109a, 1-1-110a, 1-1-110c, 1-1-111a, 1-1-112a, 1-1-113a, 1-1-114a, 1-1-114b, 1-1-115a, 1-1-115b, 1-1-118a, 1-1-122a, 1-1-123a, 1-2-001a, 1-2-002a, 1-2-004a, 1-2-004b, 1-2-004c, 1-2-005a, 1-2-006a, 1-3-001a, 1-3-002a, 1-3-003a, 1-3-004a, 1-3-005a, 1-3-006a, 1-3-007a, 1-3-008a, 1-3-009a, 1-3-010a, 1-3-011a, 1-3-012a, 1-3-013a, 1-3-014a, 1-4-001a, 1-4-002a, 1-4-003a, 1-4-003b, 1-5-001a, 1-5-002a, 1-5-003a, 1-5-004a, 1-6-001a, 1-6-002a, 1-7-001a, 1-a, 1-82a, 1-8-002b, 1-8-003a, 1-8-003b, 1-8-005a, 1-8-005b, 1-8-006a, 1-8-006b, 1-8-007a, 1-8-008a, 1-8-009a, 1-8-010a, 1-8-011a, 1-8-013a, 1-8-013b, 1-8-014a, 1-8-015a, 1-9-002a, 1-9-002b, 1-9-003a, 1-10-001a, 1-10-001b, 1-10-001c, 1-10-002a, 1-10-002b, 1-10-002c, 1-10-003a, 1-11-001a, 1-11-001b, 1-11-001c, 1-11-002a, 1-11-003a, 1-11-004a, 1-11-004b, 1-11-004c, 1-11-005a, 1-11-005b, 1-11-006a, 1-11-007a, 1-11-007b, 1-11-007c, 1-12-001a, 1-12-002a, 1-12-003a, 1-12-004a, 1-12-005a, 1-12-006a, 1-12-007a, 1-12-008a, 1-12-009a, 1-13-001a, 1-14-001a, 1-15-003a, 1-16-001a, 2-1-001a, 2-1-001b, 3-1-001a, 3-1-001c, 3-1-002a, 3-1-002b and 3-1-002c of the present invention.

Test Example 4: Insecticidal Activity on *Frankliniella occidentalis*

In styrol cups having an inner diameter of 7 cm, wet filter paper was laid, kidney bean leaves cut into a 3 cm square were laid on the paper, and each leaf was inoculated with 20 larvae of *Frankliniella occidentalis*. 10% emulsifiable concentrates (or 10% wettable powders) of compounds of the present invention were diluted with water containing a spreader to obtain 500 ppm solutions. 2.5 ml of the solutions were sprayed from a rotary spray tower into the styrol cups (2.5 mg/cm$^2$).

2 Days after, dead insects were counted, and insect damage on kidney bean leaves was examined. The mortality was calculated by using the same equation as in Test Example 1.

The insect damage degree was evaluated as follows. 1: 0 to 20% insect damage, 2: 20 to 50% insect damage, 3: 50 to 70% insect damage, and 4: 70% or higher insect damge. The test was carried out in duplicate.

Among the compounds tested, the following compounds showed a mortality of at least 50% and an insect damage degree of 2 or higher.

Compounds Nos. 1-1-001a, 1-1-002b, 1-1-003a, 1-1-005a, 1-1-006a, 1-1-023c, 1-1-035a, 1-1-036a, 1-1-038a, 1-1-039a, 1-1-042a, 1-1-043a, 1-1-049a, 1-1-050a, 1-1-051a, 1-1-052a, 1-1-052b, 1-1-053a, 1-1-054b, 1-1-055b, 1-1-056a, 1-1-057a, 1-1-057c, 1-1-061a, 1-1-062a, 1-1-063a, 1-1-064a, 1-1-067a, 1-1-068a, 1-1-069b, 1-1-070a, 1-1-071a, 1-1-072a, 1-1-074a, 1-1-076a, 1-1-080a, 1-1-081a, 1-1-082a, 1-1-087a, 1-1-089a, 1-1-090a, 1-1-093a, 1-1-095a, 1-1-096a, 1-1-097a, 1-1-099a, 1-1-105a, 1-1-106b, 1-1-109a, 1-1-110a, 1-1-112a, 1-1-114a, 1-1-115a, 1-1-117a, 1-1-120c, 1-1-122a, 1-1-123a, 1-2-006a, 1-3-012a, 1-4-003a, 1-8-007a, 1-8-008a, 1-8-011a, 1-8-013a, 1-8-014a, 1-8-015a, 1-9-002a, 1-9-003a, 1-10-003a, 1-11-003a, 1-11-004a, 1-11-006a, 1-11-007a, 1-11-007c, 1-12-009a, 2-1-002a, 3-1-001a, 3-1-001b, 3-1-001c and 3-1-002a of the present invention.

Test Example 5: Insecticidal Test on *Myzus persicae*

Wet absorbent cotton was laid on glass dishes having an inner diameter of 3 cm, and covered with leaves of cabbage cut into circles of the same diameter, and 4 apterous adults of *Myzus persicae* were released. After a day, 10% emulsifiable concentrates (or 10% wettable powders) of compounds of the present invention were diluted with water containing a spreader to obtain 500 ppm solutions. The solutions were sprayed from a rotary spray tower (2.5 mg/cm$^2$), and the dishes were covered with lids and placed in an incubator at 25° C. 6 Days after, dead insects were counted, and the mortality was calculated by using the same equation as in Test Example 1. The test was carried out in duplicate.

Among the compounds tested, the following compounds showed a mortality of at least 90%.

Compounds Nos. 1-1-001a, 1-1-002a, 1-1-002b, 1-1-003a, 1-1-004a, 1-1-004b, 1-1-004c, 1-1-005a, 1-1-006a, 1-1-007a, 1-1-009a, 1-1-011a, 1-1-012a, 1-1-012b, 1-1-013a, 1-1-013c, 1-1-014a, 1-1-014c, 1-1-015a, 1-1-015b, 1-1-016c, 1-1-017a, 1-1-018a, 1-1-019a, 1-1-020a, 1-1-023a, 1-1-024a, 1-1-025c, 1-1-026a, 1-1-027a, 1-1-032a, 1-1-033a, 1-1-034a, 1-1-035a, 1-1-036a, 1-1-037a, 1-1-038a, 1-1-039a, 1-1-040b, 1-1-040c, 1-1-041a, 1-1-042a, 1-1-043a, 1-1-044a, 1-1-045b, 1-1-046a, 1-1-047a, 1-1-048a, 1-1-049a, 1-1-049b, 1-1-050a, 1-1-051a, 1-1-052a, 1-1-053a, 1-1-056a, 1-1-057a, 1-1-057c, 1-1-058a, 1-1-059a, 1-1-060a, 1-1-061a, 1-1-062a, 1-1-063a, 1-1-064a, 1-1-065a, 1-1-066a, 1-1-067a, 1-1-068a, 1-1-071a, 1-1-072a, 1-1-073b, 1-1-074a, 1-1-077a, 1-1-077b, 1-1-080a, 1-1-082a, 1-1-086a, 1-1-087a, 1-1-090a, 1-1-091a, 1-1-093a, 1-1-093b, 1-1-095a, 1-1-096a, 1-1-097a, 1-1-099a, 1-1-100a, 1-1-101a, 1-1-102a, 1-1-105a, 1-1-106a, 1-1-106b, 1-1-106c, 1-1-107a, 1-1-108a, 1-1-109a, 1-1-110a, 1-1-112a, 1-1-113a, 1-1-115a, 1-1-116a, 1-1-117a, 1-1-118a, 1-1-120c, 1-1-121a, 1-1-122a, 1-1-123a, 1-2-001a, 1-2-002a, 1-3-001a, 1-3-002a, 1-3-003a, 1-3-004a, 1-3-005a, 1-3-006a, 1-3-007a, 1-3-009a, 1-3-010a, 1a, 1-3-011a, 1-3-012a, 1-4-001a, 1-4-002a, 1-4-003a, 1-5-001a, 1-5-002a, 1-5-003a, 1-5-004a, 1-6-001a, 1-6-002a, 1-8-002a, 1-002b, 1-003a, 1-003b, 1-8-004b, 1-8-005a, 1-8-006a, 1-8-008a, 1-8-010a, 1-8-013a, 1-8-014a, 1-8-015b, 1-9-002a, 1-9-003a, 1-10-001a, 1-10-001b, 1-10-002a, 1-10-002b, 1-10-002c, 1-10-003a, 1-11-001a, 1-11-001b, 1-11-002a, 1-11-003a, 1-11-004a, 1-11-007a, 1-11-007b, 1-11-007c, 1-12-001a, 1-12-002a, 1-12-003a, 1-12-004a, 1-12-005a, 1-12-006a, 1-12-007a, 1-12-008a, 1-14-001a, 1-15-003a, 1-16-001a, 1-17-001a, 2-1-001a, 2-1-002a, 3-1-001a, 3-1-001c and 3-1-002a of the present invention.

Test Example 6: Insecticidal Test on *Bemisia argentifolii*

In styrol cups having an inner diameter of 7 cm, wet filter paper was laid, and kidney bean leaves cut to 3 cm were laid on the paper. 10% emulsifiable concentrates (or 10% wettable powders) of compounds of the present invention were diluted with water containing a spreader to obtain 500 ppm solutions, and 2.5 ml of the solutions were sprayed from a rotary spray tower into the styrol cups (2.5 mg/cm$^2$). The leaves were dried in air, and adults of *Bemisia argentifolii* were released in the cups, and the cups were covered with lids and placed in an incubator at 25° C. 5 Days after, dead insects were counted, and the mortality was calculated by using the same equation as in Test Example 1. The test was carried out in duplicate.

Among the compounds tested, the following compounds showed a mortality of at least 90%.

Compounds Nos. 1-1-035a, 1-1-036a, 1-1-043a, 1-1-049a, 1-1-047a, 1-1-094a, 1-1-095a, 1-1-096a, 1-1-099a, 1-3-001a, 1-14-001a and 3-1-002a of the present invention.

Test Example 7: Soil Irrigation Test on *Myzus persicae*

10% emulsifiable concentrates of compounds of the present invention were diluted with tap water to obtain 500 ppm solutions.

The soil around the bases of cabbage seedlings (at the 2.5-leaf stage) planted in plastic cups was irrigated with 10 ml of the solutions. After the irrigation, the cabbage seedlings were placed in a greenhouse. One day after the irrigation, adults of *Myzus persicae* were released at a ratio of 20 insects per seedling, and the seedlings were left in the greenhouse. 6 Days after the release of the insects, living insects were counted, and the control value was calculated from the following equation.

Control value (%)={1−(Cb×Tai)/(Cai×Tb)}×100

Cb: the number of insects in a non-treated plot before treatment

Cai: the final number of living insects in a non-treated plot

Tb: the number of insects in a treated plot before treatment

Tai: the final number of living insects in a treated plot

Among the compounds tested, the following compounds showed a control value of at least 90%.

Compounds Nos. 1-1-001a, 1-1-002a, 1-1-003a, 1-1-004a, 1-1-005a, 1-1-006a, 1-1-012a, 1-1-013a, 1-1-014a, 1-1-016a, 1-1-017a, 1-1-018a, 1-1-029a, 1-1-032a, 1-1-035a, 1-1-039a, 1-1-042a, 1-1-043a, 1-1-049a, 1-1-057a, 1-1-058a, 1-1-060a, 1-1-074a, 1-1-093a, 1-1-097a, 1-1-106a, 1-1-112a, 1-1-113a, 1-1-122a, 1-8-002a, 1-8-003a, 1-8-005a, 1-8-006a, 1-8-010a, 1-8-013a, 1-9-002a, 1-12-008a, 1-14-001a, 1-16-001a and 2-1-002a of the present invention.

Test Example 8: Systemic Insecticidal Test on *Nilaparvata lugens*

10% emulsifiable concentrates of compounds of the present invention were diluted with tap water to obtain 20 ppm solutions, and root of rice plug seedlings (at the 2-leaf stage) were dipped in the solutions. 7 Days after, the rice seedlings were picked and put in test tubes, and in each tube, five 3rd-instar larvae of *Nilaparvata lugens* were released, and the tubes were capped with sponge and placed in an incubator at 25° C. 6 Days after the release of the insects, dead insects were counted, and the mortality (%) (the number of dead insects÷the number of released insects×100) was calculated. The test was carried out in duplicate.

Among the compounds tested, the following compounds showed a mortality of at least 90%.

Compounds Nos. 1-1-001a, 1-1-001b, 1-1-002a, 1-1-005a, 1-1-006a, 1-1-013a, 1-1-014a, 1-1-017a, 1-1-018a, 1-1-020a, 1-1-030a, 1-1-032a, 1-1-035a, 1-1-036a, 1-1-038a, 1-1-039a, 1-1-042a, 1-1-043a, 1-1-044a, 1-1-049a, 1-1-052a, 1-1-057a, 1-1-057c, 1-1-058a, 1-1-067a, 1-1-070a, 1-1-072a, 1-1-074a, 1-1-076a, 1-1-077a, 1-1-092a, 1-1-093a, 1-1-095a, 1-1-096a, 1-1-097a, 1-1-099a, 1-1-105a, 1-1-106a, 1-1-107a, 1-1-109a, 1-1-111a, 1-1-113a, 1-1-117a, 1-1-122a, 1-2-002a, 1-3-001a, 1-3-005a, 1-3-007a, 1-8-002a, 1-8-005a, 1-8-006a, 1-8-008a, 1-8-010a, 1-8-013a, 1-9-002a, 1-11-001a, 1-11-002a, 1-11-003a, 1-11-

004a, 1-11-007a, 1-12-006a, 1-12-008a, 1-12-009a, 1-14-001a, 1-16-001a, 2-1-002a and 3-1-002b of the present invention.

Test Example 9: Soil Irrigation Test on *Plutella xylostella*

10% emulsifiable concentrates of compounds of the present invention were diluted with tap water to obtain 500 ppm solutions.

The soil around the bases of cabbage seedlings (at the 2.5-leaf stage) planted in plastic cups was irrigated with 10 ml of the solutions. After the irrigation, the cabbage seedlings were placed in a greenhouse. 5 Days after the irrigation, leaves of cabbage were picked and placed in dishes. In each dish, five 3rd-instar larvae of *Plutella xylostella* were released, and the dishes were covered with lids and placed in an incubator at 25° C. 6 Days after, dead insects in the dishes were counted, and the mortality was calculated by using the same equation as in Test Example 1. The test was carried out in duplicate.

Among the compounds tested, the following compounds showed a control value of at least 90%.
Compounds Nos. 1-1-001a, 1-1-001c, 1-1-002a, 1-103a, 1-1-004a, 1-1-005a, 1-1-006a, 1-1-013a, 1-1-014a, 1-1-015a, 1-1-016a, 1-1-018a, 1-1-029a, 1-1-030a, 1-1-039a, 1-1-042a, 1-1-043a, 1-1-049a, 1-1-050a, 1-1-052a, 1-1056a, 1-1-057a, 1-1-058a, 1-1-059a, 1-1-060a, 1-1-063a, 1-1-069a, 1-1-070a, 1-1-074a, 1-1-076a, 1-1-077a, 1-1-080a, 1-1-082a, 1-1-090a, 1-1-093a, 1-1-096a, 1-1-097a, 1-1-099a, 1-1-103a, 1-1-103b, 1-1-105a, 1-1-106a, 1-1-107a, 1-1-109a, 1-1-111a, 1-1-112a, 1-1-113a, 1-1-117a, 1-1-122a, 1-3-001a, 1-3-004a, 1-3-013a, 1-3-014a, 1-4-001a, 1-8-002a, 1-8-003a, 1-8-005a, 1-8-006a, 1-8-007a, 1-8-008a, 1-8-010a, 1-8-013a, 1-9-002a, 1-10-002a, 1-11-001a, 1-11-002a, 1-11-003a, 1-11-004a, 1-11-007a, 1-12-008a, 1-12-009a, 1-14-001a, 1-16-001a and 2-1-002a of the present invention.

Test Example 10: Test on the Effect of Seed Treatment on *Aphis glycines*

2.4 mg of compounds of the present invention were diluted with 97.6 µl of acetone. Four soybean seeds were put in each 50 ml plastic tube, and the solutions of compounds of the present invention were poured onto the seeds and stirred until the acetone evaporated completely so that the seeds were evenly coated with the compounds. The treated seeds were sown in pots, 4 seeds per pot, and placed in a greenhouse. After the primary leaf folded out, two adults of *Aphis glycines* were released per seedling. 7 Days after the release of the insects, living insects were counted, and the control value was calculated from the following equation.

Control value (%)={1−(Cb×Tai)/(Cai×Tb)}×100 wherein
Cb: the number of insects in a non-treated plot before treatment
Cai: the final number of living insects in a non-treated plot
Tb: the number of insects in a treated plot before treatment
Tai: the final number of living insects in a treated plot
Among the compounds tested, the following compounds showed a control value of at least 90%.
Compounds Nos. 1-1-001a, 1-1-002a, 1-1-003a, 1-1-004a, 1-1-005a, 1-1-006a, 1-1-012a, 1-1-013a, 1-1-014a, 1-1-016a, 1-1-017a, 1-1-018a, 1-1-029a, 1-1-032a, 1-1-035a, 1-1-039a, 1-1-042a, 1-1-043a, 1-1-049a, 1-1-057a, 1-1-058a, 1-1-060a, 1-1-074a, 1-1-093a, 1-1-097a, 1-1-106a, 1-1-112a, 1-1-113a, 1-1-122a, 1-3-001a, 1-8-002a, 1-8-003a, 1-8-005a, 1-8-006a, 1-8-010a, 1-8-013a, 1-9-002a, 1-12-008a, 1-14-001a and 1-16-001a of the present invention.

Test Example 11: Test on the Effect on *Rhipicephalus sanguineus*

3.5 mg of compounds of the present invention were diluted with 3.5 ml of acetone to obtain 1,000 ppm solutions. 350 µl of the solutions were applied to the bottoms and the side walls of glass containers with an inner wall surface area of 35 cm$^2$, and acetone was volatilized to prepare thin films of the compounds on the inner walls of the glass containers. Since the inner wall surface area of each glass container was 35 cm$^2$, the application dose was 10 µg/cm$^2$.

To each glass container, five protonymphs (male and female) of *Rhipiceohalus sanguineus* were released, and the containers were covered with lids and placed in an incubator at 25° C. 4 Days after the release of the ticks, dead ticks were counted, and the mortality was calculated by using the same equation as in Test Example 1.

Among the compounds tested, the following compounds showed a mortality of at least 50%.
Compounds Nos. 1-1-001a, 1-1-001b, 1-1-002a, 1-1-003a, 1-1-003b, 1-1-003c, 1-1-004a, 1-1-004b, 1-1-004c, 1-1-005a, 1-1-005b, 1-1-006a, 1-1-006b, 1-1-010a, 1-1-011a, 1-1-012a, 1-1-013a, 1-1-014a, 1-1-014b, 1-1-016a, 1-1-016c, 1-1-017a, 1-1-018a, 1-1-020a, 1-1-022a, 1-1-023c, 1-1-026a, 1-1-023c, 1-1-027b, 1-1-035a, 1-1-039a, 1-1-040a, 1-1-042a, 1-1-043a, 1-1-045a, 1-1-046a, 1-1-047a, 1-1-049a, 1-1-051a, 1-1-052b, 1-1-053a, 1-1-055a, 1-1-057a, 1-1-057c, 1-1-059b, 1-1-060a, 1-1-062a, 1-1-063a, 1-1-065a, 1-1-067a, 1-1-068a, 1-1-071a, 1-1-072a, 1-1-072b, 1-1-075a, 1-1-080a, 1-1-083a, 1-1-088a, 1-1-093a, 1-1-093b, 1-1-094a, 1-1-094b, 1-1-095a, 1-1-096a, 1-1-099a, 1-1-103a, 1-1-105a, 1-1-105b, 1-1-105c, 1-1-106a, 1-1-106b, 1-1-106c, 1-107a, 1-1-108a, 1-1-109a, 1-1-110a, 1-1-110c, 1-1-111a, 1-1-111b, 1-1-112a, 1-1-113a, 1-1-114a, 1-1-114b, 1-1-115a, 1-1-115b, 1-1-116a, 1-1-118b, 1-1-118c, 1-1-120c, 1-3-004a, 1-3-005a, 1-3-011a, 1-3-013a, 1-3-014a, 1-5-001a, 1-6-001a, 1-8-002a, 1-8-005a, 1-8-006a, 1-8-006b, 1-8-008a, 1-8-010a, 1-8-011a, 1-8-013a, 1-8-014a, 1-8-014b, 1-8-015b, 1-9-002a, 1-9-002b, 1-9-003a, 1-10-002c, 1-11-004a, 1-11-004c, 1-11-005a, 1-11-006a, 1-11-007c, 1-12-004a, 1-12-007a, 1-15-003a, 1-16-001a, 3-1-002a, 3-1-002b and 3-1-002c of the present invention.

Test Example 12: Test on the Effect on *Ctenocephalides felis*

3.5 mg of compounds of the present invention were diluted with 3.5 ml of acetone to obtain 1,000 ppm solutions. 350 µl of the solutions were applied to the bottoms and the side walls of glass containers with an inner wall surface area of 35 cm$^2$, and acetone was volatilized to prepare thin films of the compounds on the inner walls of the glass containers. Since the inner wall surface area of each glass container was 35 cm$^2$, the application dose was 10 µg/cm$^2$.

To each glass container, five adults (male and female) of *Ctenocephalides felis* were released, and the containers were covered with lids and placed in an incubator at 25° C. 4 Days after the release of the fleas, dead fleas were counted, and the mortality was calculated by using the same equation as in Test Example 1.

Among the compounds tested, the following compounds showed a mortality of at least 50%.

Compounds Nos. 1-1-001a, 1-1-001b, 1-1-001c, 1-1-002a, 1-1-002b, 1-1-003a, 1-1-003b, 1-1-003c, 1-1-004a, 1-1-004b, 1-1-004c, 1-1-005a, 1-1-005b, 1-1-005c, 1-1-006a, 1-1-007a, 1-1-009a, 1-1-012a, 1-1-013a, 1-1-013b, 1-1-013c, 1-1-014a, 1-1-014c, 1-1-015a, 1-1-015b, 1-1-016a, 1-1-016b, 1-1-016c, 1-1-017a, 1-1-018a, 1-1-019a, 1-1-020a, 1-1-023a, 1-1-023b, 1-1-023c, 1-1-024a, 1-1-025c, 1-1-026a, 1-1-027a, 1-1-027b, 1-1-029a, 1-1-030a, 1-1-032a, 1-1-033a, 1-1-034a, 1-1-035a, 1-1-036a, 1-1-037a, 1-1-039a, 1-1-040c, 1-1-041a, 1-1-042a, 1-1-043a, 1-1-044a, 1-1-045a, 1-1-046a, 1-1-047a, 1-1-047b, 1-1-048a, 1-1-048b, 1-1-049a, 1-1-050a, 1-1-050b, 1-1-051a, 1-1-051b, 1-1-052a, 1-1-052b, 1-1-053a, 1-1-054b, 1-1-055a, 1-1-056a, 1-1-057a, 1-1-057c, 1-1-058a, 1-1-058b, 1-1-059b, 1-1-060a, 1-1-060b, 1-1-061a, 1-1-062a, 1-1-062b, 1-1-063a, 1-1-063b, 1-1-064a, 1-1-065a, 1-1-066a, 1-1-066b, 1-1-067a, 1-1-067b, 1-1-068a, 1-1-069a, 1-1-070a, 1-1-071a, 1-1-072a, 1-1-072b, 1-1-072c, 1-1-073b, 1-1-074a, 1-1-074b, 1-1-075a, 1-1-076a, 1-1-077a, 1-1-077b, 1-1-080a, 1-1-081a, 1-1-082a, 1-1-084a, 1-1-085a, 1-1-086a, 1-1-087a, 1-1-088a, 1-1-089a, 1-1-090a, 1-1-091a, 1-1-092a, 1-1-093a, 1-1-093b, 1-1-094a, 1-1-094b, 1-1-094c, 1-1-095a, 1-1-096a, 1-1-097a, 1-1-099a, 1-1-101a, 1-1-102a, 1-1-103a, 1-1-103b, 1-1-104a, 1-1-105a, 1-1-105b, 1-1-105c, 1-1-106a, 1-1-106b, 1-1-106c, 1-1-107a, 1-1-108a, 1-1-109a, 1-1-110a, 1-1-110c, 1-1-111a, 1-1-111b, 1-1-112a, 1-1-113a, 1-1-114a, 1-1-114b, 1-1-115a, 1-1-115b, 1-1-116a, 1-1-117a, 1-1-118a, 1-1-118b, 1-1-119c, 1-1-122a, 1-1-123a, 1-2-001a, 1-3-001a, 1-3-002a, 1-3-003a, 1-3-004a, 1-3-005a, 1-3-006a, 1-3-007a, 1-3-008a, 1-3-009a, 1-3-010a, 1-3-011a, 1-3-012a, 1-3-013a, 1-3-014a, 1-4-001a, 1-4-002a, 1-4-003a, 1-4-003b, 1-5-001a, 1-5-002a, 1-5-003a, 1-5-004a, 1-8-002a, 1-8-002b, 1-8-003a, 1-8-004b, 1-8-005a, 1-8-006a, 1-8-006b, 1-8-007a, 1-8-007b, 1-8-008a, 1-8-009a, 1-8-010a, 1-8-011a, 1-8-013a, 1-8-013c, 1-8-014a, 1-8-014b, 1-9-002a, 1-9-002b, 1-9-003a, 1-9-003b, 1-10-001b, 1-10-002a, 1-10-002b, 1-10-002c, 1-10-003a, 1-11-001a, 1-11-001b, 1-11-001c, 1-11-003a, 1-11-004a, 1-11-004c, 1-11-005b, 1-11-006a, 1-11-007b, 1-11-007c, 1-12-001a, 1-12-002a, 1-12-003a, 1-12-006a, 1-12-007a, 1-12-008a, 1-12-009a, 1-14-001a, 1-15-003a, 1-16-001a, 1-16-001b, 1-17-001a, 2-1-001a, 3-1-001a, 3-1-001b, 3-1-001c, 3-1-002a, 3-1-002b and 3-1-002c of the present invention.

Test Example 13: Test on the Parasiticidal Effect by Rat Oral Administration on *Rhipicephalus sanguineus*

5 mg of compounds of the present invention were dissolved in 5 ml of olive oil to prepare administration solutions. The solutions were orally administered to rats in a dose of 10 ml/kg body weight by a feeding tube. The oral administration was repeated twice in each group. 1 Hour after the administration, 50 protonymphs (male and female) of *Rhipicephalus sanguineus* were released for each rat. 3 Days after the release of the ticks, the number of ticks parasitic on the rats were counted, and the parasiticidal degree was calculated from the following equation.

Parasiticidal degree (%)=100×(1−the number of parasitic ticks on administered group/the number of parasitic ticks on non-administered group)

Among the compounds tested, the following compounds showed a parasiticidal deree of at least 70%.

Compounds Nos. 1-1-001a, 1-1-002a, 1-1-003a, 1-1-006a, 1-1-016a, 1-1-096a, 1-1-103a, 1-3-011a and 1-9-002a of the present invention.

INDUSTRIAL APPLICABILITY

The compounds of the present invention are very useful compounds which are excellent in pesticidal activities and have little harmful effect on non-target organisms such as mammals, fishes and beneficial insects.

The entire disclosures of Japanese Patent Application No. 2015-025604 filed on Feb. 12, 2015 and Japanese Patent Application No. 2015-133816 filed on Jul. 2, 2015 including specifications, claims and summaries are incorporated herein by reference in their entireties.

The invention claimed is:

1. A condensed heterocyclic compound represented by the following formula or its salt or an N-oxide thereof:

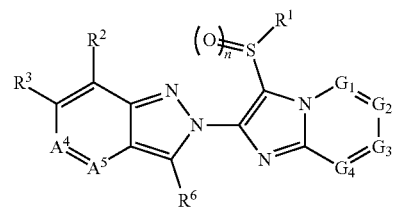

wherein:

$G_1$ is $C(Y1)$;

$G_2$ is $C(Y2)$;

$G_3$ is $C(Y3)$;

$G_4$ is $C(Y4)$;

$A^4$ is a nitrogen atom or $C(R^4)$;

$A^5$ is a nitrogen atom or $C(R^5)$;

$R^1$ is $C_1$-$C_6$ alkyl, $C_1$-$C_6$ haloalkyl, $(C_1$-$C_6)$ alkyl optionally substituted with $R^{1a}$, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_3$-$C_6$ cycloalkyl $(C_1$-$C_6)$ alkyl, $C_3$-$C_6$ halocycloalkyl $(C_1$-$C_6)$ alkyl or hydroxy $(C_1$-$C_6)$ alkyl;

$R^{1a}$ is $C_1$-$C_8$ alkoxy, $C_1$-$C_8$ haloalkoxy, $C_1$-$C_8$ alkoxycarbonyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or cyano;

$R^2$ is a hydrogen atom, a halogen atom, $C_1$-$C_6$ alkyl, $C_1$-$C_6$ haloalkyl, $C_1$-$C_8$ alkoxy, $C_1$-$C_8$ haloalkoxy, $C_3$-$C_6$ cycloalkyl, $C_3$-$C_6$ halocycloalkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —$C(O)R^{20a}$, —$C(O)OH$, hydroxy, —$NH_2$, —$NHR^{20g}$, —$N(R^{20h})R^{20g}$, mercapto, cyano or nitro;

$R^3$ is a hydrogen atom, a halogen atom, $C_1$-$C_6$ alkyl, $C_1$-$C_6$ haloalkyl, $C_2$-$C_6$ haloalkenyl, $C_2$-$C_6$ haloalkynyl, $C_1$-$C_8$ alkoxy, $C_1$-$C_8$ haloalkoxy, $C_3$-$C_6$ cycloalkyl, $C_3$-$C_6$ halocycloalkyl, $C_1$-$C_6$ alkylthio, $C_1$-$C_6$ haloalkylthio, $(C_1$-$C_6)$ alkylthio optionally substituted with $R^{3a}$, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —$C(O)$ $R^{30a}$, —C(O)OH, hydroxy, —OC(O)$R^{30c}$, —OS(O)$_2$$R^{30f}$, —NH$_2$, —NHR$^{30g}$, —N(R$^{30h}$)R$^{30g}$, mercapto, —SC(O)R$^{30i}$, —SF$_5$, cyano, nitro, phenyl, phenyl optionally substituted with R$^{3b}$, heterocyclyl or heterocyclyl optionally substituted with R$^{3b}$;

$R^{3a}$ is C$_1$-C$_8$ alkoxycarbonyl;

$R^{3b}$ is a halogen atom, a C$_1$-C$_6$ alkyl, C$_1$-C$_6$ haloalkyl, C$_1$-C$_8$ alkoxy, C$_1$-C$_8$ haloalkoxy, cyano or nitro;

$R^4$ is a hydrogen atom, a halogen atom, C$_1$-C$_6$ alkyl, C$_1$-C$_6$ haloalkyl, C$_2$-C$_6$ haloalkenyl, C$_2$-C$_6$ haloalkynyl, C$_1$-C$_8$ alkoxy, C$_1$-C$_8$ haloalkoxy, C$_3$-C$_6$ cycloalkyl, C$_3$-C$_6$ halocycloalkyl, C$_1$-C$_6$ alkylthio, C$_1$-C$_6$ haloalkylthio, (C$_1$-C$_6$) alkylthio optionally substituted with R$^{4a}$, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, —C(O)R$^{40a}$, —C(O)OH, hydroxy, —OC(O)R$^{40e}$, —OS(O)$_2$R$^{40f}$, —NH$_2$, —NHR$^{40g}$, —N(R$^{4h}$)R$^{40g}$, mercapto, —SC(O)R$^{40i}$, —SF$_5$, cyano, nitro, phenyl, phenyl optionally substituted with R$^{4b}$, heterocyclyl or heterocyclyl optionally substituted with R$^{4b}$;

$R^{4a}$ is C$_1$-C$_8$ alkoxycarbonyl;

$R^{4b}$ is a halogen atom, C$_1$-C$_6$ alkyl, C$_1$-C$_6$ haloalkyl, C$_1$-C$_8$ alkoxy, C$_1$-C$_8$ haloalkoxy, cyano or nitro;

$R^5$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_3$-C$_6$ cycloalkyl, C$_3$-C$_6$ halocycloalkyl, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, —C(O)R$^{50a}$, —C(O)OH, hydroxy, —NH$_2$, —NHR$^{50g}$, —N(R$^{50h}$)R$^{50g}$, mercapto, cyano or nitro;

$R^6$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_3$-C$_6$ cycloalkyl, C$_3$-C$_6$ halocycloalkyl, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, —C(O)R$^{60a}$, —C(O)OH, hydroxy, —NH$_2$, —NHR$^{60g}$, —N(R$^{60h}$)R$^{60g}$, mercapto, cyano or nitro;

each of Y1, Y2, Y3 and Y4 is independently a hydrogen atom, a halogen atom, C$_1$-C$_6$ alkyl, C$_1$-C$_6$ haloalkyl, (C$_1$-C$_6$) alkyl optionally substituted with Y$^a$, (C$_1$-C$_6$) haloalkyl optionally substituted with Y$^a$, C$_2$-C$_6$ alkenyl, C$_2$-C$_6$ haloalkenyl, (C$_2$-C$_6$) alkenyl optionally substituted with Y$^a$, C$_2$-C$_6$ alkynyl, C$_2$-C$_6$ haloalkynyl, (C$_2$-C$_6$) alkynyl optionally substituted with Y$^b$, C$_1$-C$_8$ alkoxy, C$_1$-C$_8$ haloalkoxy, (C$_1$-C$_8$) alkoxy optionally substituted with Y$^a$, C$_2$-C$_6$ alkenyloxy, C$_2$-C$_6$ haloalkenyloxy, (C$_2$-C$_6$) alkenyloxy optionally substituted with Y$^a$, C$_2$-C$_6$ alkynyloxy, C$_2$-C$_6$ haloalkynyloxy, (C$_2$-C$_6$) alkynyloxy optionally substituted with Y$^a$, C$_3$-C$_6$ cycloalkyl, C$_3$-C$_6$ halocycloalkyl, C$_3$-C$_6$ cycloalkyl (C$_1$-C$_6$) alkyl, C$_3$-C$_6$ halocycloalkyl (C$_1$-C$_6$) alkyl, C$_1$-C$_6$ alkylthio, C$_1$-C$_6$ haloalkylthio, (C$_1$-C$_6$) alkylthio optionally substituted with Y$^a$, C$_2$-C$_6$ alkenylthio, C$_2$-C$_6$ haloalkenylthio, C$_2$-C$_6$ alkynylthio, C$_2$-C$_6$ haloalkynylthio, C$_1$-C$_6$ alkylsulfinyl, C$_1$-C$_6$ haloalkylsulfinyl, (C$_1$-C$_6$) alkylsulfinyl optionally substituted with Y$^a$, C$_2$-C$_6$ alkenylsulfinyl, C$_2$-C$_6$ haloalkenylsulfinyl, C$_2$-C$_6$ alkynylsulfinyl, C$_2$-C$_6$ haloalkynylsulfinyl, C$_1$-C$_6$ alkylsulfonyl, C$_1$-C$_6$ haloalkylsulfonyl, (C$_1$-C$_6$) alkylsulfonyl optionally substituted with Y$^a$, C$_2$-C$_6$ alkenylsulfonyl, C$_2$-C$_6$ haloalkenylsulfonyl, C$_2$-C$_6$ alkynylsulfonyl, C$_2$-C$_6$ haloalkynylsulfonyl, —C(O)R$^{90a}$, —C(O)NHR$^{90b}$, —C(O)N(R$^{90c}$)R$^{90b}$, —C(=NOR$^{90d}$)R$^{90a}$, —C(O)NH$_2$, hydroxy, —OC(O)R$^{90e}$, —OS(O)$_2$R$^{90f}$, —NH$_2$, —NHR$^{90g}$, —N(R$^{90h}$)R$^{90g}$, mercapto, —SC(O)R$^{90i}$, —S(O)$_2$NHR$^{90j}$, —S(O)$_2$N(R$^{90k}$)R$^{90j}$, —SF$_5$, cyano, nitro, phenyl, phenyl optionally substituted with Y$^c$, heterocyclyl or heterocyclyl optionally substituted with Y$^c$;

Y$^a$ is C$_1$-C$_8$ alkoxy, C$_1$-C$_8$ haloalkoxy, C$_1$-C$_8$ alkoxycarbonyl, C$_1$-C$_8$ haloalkoxycarbonyl, C$_1$-C$_6$ alkylcarbonyl, C$_1$-C$_6$ haloalkylcarbonyl, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, hydroxy or cyano;

Y$^b$ is C$_1$-C$_6$ alkyl, C$_3$-C$_6$ cycloalkyl, trimethylsilyl or phenyl;

Y$^c$ is a halogen atom, C$_1$-C$_6$ alkyl, C$_1$-C$_6$ haloalkyl, C$_1$-C$_8$ alkoxy, C$_1$-C$_8$ haloalkoxy, cyano or nitro;

each of R$^{20a}$, R$^{30a}$, R$^{30e}$, R$^{40a}$, R$^{40e}$, R$^{50a}$, R$^{60a}$ and R$^{90a}$ is independently a hydrogen atom, C$_1$-C$_6$ alkyl, C$_1$-C$_6$ haloalkyl, C$_1$-C$_8$ alkoxy or C$_1$-C$_8$ haloalkoxy;

each of R$^{20g}$, R$^{20h}$, R$^{30f}$, R$^{30g}$, R$^{30h}$, R$^{30i}$, R$^{40f}$, R$^{40g}$, R$^{40h}$, R$^{40i}$, R$^{50g}$, R$^{50h}$, R$^{60g}$, R$^{60h}$, R$^{90b}$, R$^{90c}$, R$^{90i}$, R$^{90j}$ and R$^{90k}$ is independently C$_1$-C$_6$ alkyl or C$_1$-C$_6$ haloalkyl;

R$^{90d}$ is a hydrogen atom, C$_1$-C$_6$ alkyl or C$_1$-C$_6$ haloalkyl;

R$^{90e}$ is a hydrogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylamino, C$_1$-C$_6$ haloalkylamino, di(C$_1$-C$_6$) alkylamino or di(C$_1$-C$_6$) haloalkylamino;

R$^{90f}$ is C$_1$-C$_6$ alkyl, C$_1$-C$_6$ haloalkyl, C$_1$-C$_6$ alkylamino, C$_1$-C$_6$ haloalkylamino, di(C$_1$-C$_6$) alkylamino or di(C$_1$-C$_6$) haloalkylamino;

each of R$^{90g}$ and R$^{90h}$ is independently C$_1$-C$_6$ alkyl, C$_1$-C$_6$ haloalkyl, C$_1$-C$_6$ alkylcarbonyl, C$_1$-C$_6$ haloalkylcarbonyl, C$_1$-C$_8$ alkoxycarbonyl, C$_1$-C$_8$ haloalkoxycarbonyl, C$_1$-C$_6$ alkylaminocarbonyl, C$_1$-C$_6$ haloalkylaminocarbonyl, C$_1$-C$_6$ alkylaminothiocarbonyl, C$_1$-C$_6$ haloalkylaminothiocarbonyl, phenylcarbonyl, C$_1$-C$_6$ alkylsulfonyl, C$_1$-C$_6$ haloalkylsulfonyl, C$_1$-C$_6$ alkylaminosulfonyl or di(C$_1$-C$_6$) alkylaminosulfonyl; and n is an integer of 0, 1 or 2.

2. The condensed heterocyclic compound or its salt or an N-oxide thereof according to claim 1, wherein:

R$^1$ is C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_2$-C$_6$ haloalkynyl, C$_3$-C$_6$ cycloalkyl (C$_1$-C$_6$) alkyl or C$_3$-C$_6$ halocycloalkyl (C$_1$-C$_6$) alkyl;

R$^2$ is a hydrogen atom, a halogen atom, C$_1$-C$_6$ alkyl or C$_1$-C$_6$ haloalkyl;

R$^3$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, (C$_1$-C$_6$) alkylthio optionally substituted with R$^{3a}$, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl;

R$^4$ is a hydrogen atom, a halogen atom, C$_1$-C$_6$ alkyl, C$_1$-C$_6$ haloalkyl, C$_1$-C$_8$ alkoxy, C$_1$-C$_8$ haloalkoxy, C$_1$-C$_6$ alkylthio, C$_1$-C$_6$ haloalkylthio, (C$_1$-C$_6$) alkylthio optionally substituted with R$^{4a}$, C$_1$-C$_6$ alkylsulfinyl, C$_1$-C$_6$ haloalkylsulfinyl, C$_1$-C$_6$ alkylsulfonyl or C$_1$-C$_6$ haloalkylsulfonyl;

each of R$^5$ and R$^6$ is independently a hydrogen atom, a halogen atom, C$_1$-C$_6$ alkyl or C$_1$-C$_6$ haloalkyl;

each of Y1, Y2, Y3 and Y4 is independently a hydrogen atom, a halogen atom, C$_1$-C$_6$ alkyl, C$_1$-C$_6$ haloalkyl, C$_2$-C$_6$ alkenyl, C$_2$-C$_6$ alkynyl, (C$_2$-C$_6$) alkynyl optionally substituted with Y$^b$, C$_1$-C$_8$ alkoxy, C$_1$-C$_8$ haloalkoxy, C$_1$-C$_6$ alkylthio, C$_1$-C$_6$ haloalkylthio, (C$_1$-C$_6$) alkylthio optionally substituted with Y$^a$, C$_1$-C$_6$ alkylsulfinyl, C$_1$-C$_6$ haloalkylsulfinyl, C$_1$-C$_6$ alkylsulfonyl, $C_1$-$C_6$ haloalkylsulfonyl, —C(O)$R^{90a}$, —C(O)NH$R^{90b}$, —C(O)N($R^{90c}$)$R^{9b}$, —C(O)OH, hydroxy, —OC(O)$R^{90e}$, —OS(O)$_2R^{90f}$, —NH$_2$, —NHR$^{90g}$, —N($R^{90h}$)$R^{90g}$, mercapto, —SC(O)$R^{90i}$, —S(O)$_2$NHR$^{90j}$, —S(O)$_2$N($R^{90k}$)$R^{90j}$, —SF$_5$, cyano, nitro, phenyl, phenyl optionally substituted with $Y^c$, heterocyclyl or heterocyclyl optionally substituted with $Y^c$; and $Y^a$ is $C_1$-$C_8$ alkoxycarbonyl.

3. The condensed heterocyclic compound or its salt or an N-oxide thereof according to claim 2, wherein:
$A^4$ and $A^5$ are not nitrogen atoms at the same time;
$R^1$ is $C_1$-$C_6$ alkyl;
$R^2$ is a hydrogen atom;
$R^3$ is a hydrogen atom, a halogen atom, $C_1$-$C_6$ haloalkyl, $C_1$-$C_6$ haloalkylthio, ($C_1$-$C_6$)alkylthio optionally substituted with $R^{3a}$, $C_1$-$C_6$ haloalkylsulfinyl or $C_1$-$C_6$ haloalkylsulfonyl; and
$R^4$ is a hydrogen atom, a halogen atom, $C_1$-$C_6$ haloalkyl, $C_1$-$C_6$ haloalkylthio, ($C_1$-$C_6$) alkylthio optionally substituted with $R^{4a}$, $C_1$-$C_6$ haloalkylsulfinyl or $C_1$-$C_6$ haloalkylsulfonyl.

4. The condensed heterocyclic compound or its salt or an N-oxide thereof according to claim 3, wherein:
$A^4$ is a nitrogen atom;
$A^5$ is C($R^5$);
$R^3$ is $C_1$-$C_6$ haloalkyl;
$R^5$ is a hydrogen atom;
$R^6$ is a hydrogen atom;
Y1 is a hydrogen atom;
each of Y2 and Y3 is independently a hydrogen atom, a halogen atom or $C_1$-$C_6$ haloalkyl; and
Y4 is a hydrogen atom or a halogen atom.

5. The condensed heterocyclic compound or its salt or an N-oxide thereof according to claim 2, wherein:
$R^2$ is a hydrogen atom;
$R^3$ is $C_1$-$C_6$ haloalkyl, $C_1$-$C_6$ haloalkylthio, $C_1$-$C_6$ haloalkylsulfinyl or $C_1$-$C_6$ haloalkylsulfonyl;
$R^4$ is a hydrogen atom;
$R^5$ is a hydrogen atom or $C_1$-$C_6$ alkyl;
$R^6$ is a hydrogen atom;
each of Y1 and Y4 is a hydrogen atom; and
each of Y2 and Y3 is independently a hydrogen atom or $C_1$-$C_6$ haloalkyl.

6. The condensed heterocyclic compound or its salt or an N-oxide thereof according to claim 1, wherein:
$A^4$ is a nitrogen atom;
$A^5$ is C($R^5$); and
n is 2.

7. The condensed heterocyclic compound or its salt or an N-oxide thereof according to claim 6, wherein:
each of Y1, Y2 and Y4 is a hydrogen atom;
Y3 is $C_1$-$C_6$ haloalkyl;
each of $R^2$, $R^5$ and $R^6$ is a hydrogen atom; and
$R^3$ is a $C_1$-$C_6$ haloalkyl.

8. An agricultural chemical composition, comprising:
the condensed heterocyclic compound of claim 1 or its salt or N-oxide as an active ingredient; and
an agriculturally acceptable diluent.

* * * * *